United States Patent
Bergeron et al.

(10) Patent No.: US 10,787,446 B2
(45) Date of Patent: Sep. 29, 2020

(54) THERAPEUTIC COMPOUNDS AND METHODS OF USE THEREOF

(71) Applicants: GENENTECH, INC., South San Francisco, CA (US); XENON PHARMACEUTICALS INC., Burnaby (CA)

(72) Inventors: Philippe Bergeron, South San Francisco, CA (US); Kristen Burford, Burnaby (CA); Sultan Chowdhury, Burnaby (CA); Christoph Martin Dehnhardt, Burnaby (CA); Thilo Focken, Burnaby (CA); Michael Edward Grimwood, Burnaby (CA); Abid Hasan, Burnaby (CA); Kwong Wah Lai, Shanghai (CN); Zhiguo Liu, Shanghai (CN); Steven McKerrall, South San Francisco, CA (US); Teresa Phuongtram Nguyen, South San Francisco, CA (US); Brian Safina, South San Francisco, CA (US); Daniel Sutherlin, South San Francisco, CA (US); Tao Wang, Shanghai (CN)

(73) Assignees: GENENTECH, INC., South San Francisco, CA (US); XENON PHARMACEUTICALS INC., Burnaby, BC (CA)

( * ) Notice: Subject to any disclaimer, the term of this patent is extended or adjusted under 35 U.S.C. 154(b) by 0 days.

(21) Appl. No.: 15/939,112

(22) Filed: Mar. 28, 2018

(65) Prior Publication Data
US 2018/0291014 A1 Oct. 11, 2018

Related U.S. Application Data

(63) Continuation of application No. PCT/US2016/054011, filed on Sep. 27, 2016.
(Continued)

(30) Foreign Application Priority Data
Aug. 25, 2016 (WO) ................ PCT/CN2016/096659

(51) Int. Cl.
*C07D 405/14* (2006.01)
*C07D 417/12* (2006.01)
(Continued)

(52) U.S. Cl.
CPC ............ *C07D 417/12* (2013.01); *A61P 17/04* (2018.01); *C07D 401/12* (2013.01);
(Continued)

(58) Field of Classification Search
CPC ... C07D 405/14; C07D 417/12; C07D 417/14
See application file for complete search history.

(56) References Cited

U.S. PATENT DOCUMENTS

| 3,705,185 A | 12/1972 | Moore et al. |
| 5,096,771 A | 3/1992 | Walles et al. |

(Continued)

FOREIGN PATENT DOCUMENTS

| CN | 101466665 A | 6/2009 |
| CN | 101643458 A | 2/2010 |

(Continued)

OTHER PUBLICATIONS

Chemical Abstracts Registry No. 73081-64-8, indexed in the Registry file on STN CAS Online Nov. 16, 1984. (Year: 1984).*
(Continued)

*Primary Examiner* — Laura L Stockton
(74) *Attorney, Agent, or Firm* — Viksnins Harris Padys Malen LLP

(57) ABSTRACT

The invention provides a compound of formula:

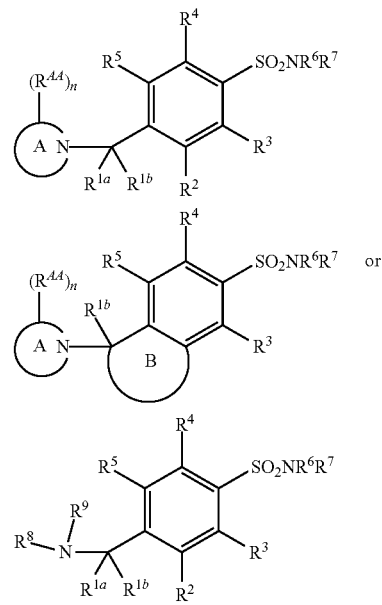

or a salt thereof, wherein the variables $R^{AA}$, n, ring A, ring B, $R^{1a}$, $R^{1b}$, $R^2$, $R^3$, $R^4$, $R^5$, $R^6$, $R^7$, $R^8$, and $R^9$ have the meaning as described herein, and compositions containing such compounds and methods for using such compounds and compositions.

26 Claims, No Drawings

Related U.S. Application Data

(60) Provisional application No. 62/298,817, filed on Feb. 23, 2016, provisional application No. 62/233,863, filed on Sep. 28, 2015.

(51) Int. Cl.
  *C07D 417/14* (2006.01)
  *A61P 17/04* (2006.01)
  *C07D 401/12* (2006.01)
  *C07D 491/107* (2006.01)

(52) U.S. Cl.
  CPC ......... *C07D 405/14* (2013.01); *C07D 417/14* (2013.01); *C07D 491/107* (2013.01)

(56) References Cited

U.S. PATENT DOCUMENTS

| | | | |
|---|---|---|---|
| 5,171,748 | A | 12/1992 | Roberts et al. |
| 5,573,653 | A | 11/1996 | Bandlish |
| 5,580,982 | A | 12/1996 | O'Malley et al. |
| 5,753,653 | A | 5/1998 | Bender et al. |
| 7,262,304 | B2 | 8/2007 | Ueno et al. |
| 7,291,638 | B2 | 11/2007 | Lee et al. |
| 7,858,639 | B2 | 12/2010 | Sun et al. |
| 8,153,814 | B2 | 4/2012 | Beaudoin et al. |
| 8,193,194 | B2 | 6/2012 | Martinborough et al. |
| 8,642,660 | B2 | 2/2014 | Goldfarb |
| 8,889,741 | B2 | 11/2014 | Shinozuka et al. |
| 8,933,236 | B2 | 1/2015 | Chowdhury et al. |
| 8,952,169 | B2 | 2/2015 | Andrez et al. |
| 9,102,621 | B2 | 8/2015 | Brown et al. |
| 2006/0069093 | A1 | 3/2006 | Scarborough et al. |
| 2007/0088015 | A1 | 4/2007 | Silva et al. |
| 2008/0161303 | A1 | 7/2008 | Zhang et al. |
| 2008/0261978 | A1* | 10/2008 | Clark ............... C07C 237/30 514/235.8 |
| 2008/0312286 | A1 | 12/2008 | Pinkerton et al. |
| 2009/0012103 | A1 | 1/2009 | Abelman et al. |
| 2010/0179137 | A1 | 7/2010 | Kamikubo et al. |
| 2010/0197655 | A1 | 8/2010 | Beaudoin et al. |
| 2010/0286110 | A1 | 11/2010 | Fyfe et al. |
| 2011/0092703 | A1 | 4/2011 | Sakuma et al. |
| 2012/0004714 | A1 | 1/2012 | Kleve et al. |
| 2012/0010182 | A1 | 1/2012 | Brown et al. |
| 2012/0010183 | A1 | 1/2012 | Bell et al. |
| 2012/0010207 | A1 | 1/2012 | Bell et al. |
| 2012/0196869 | A1 | 8/2012 | Hadida Ruah et al. |
| 2013/0317000 | A1 | 11/2013 | Chowdhury et al. |
| 2013/0324525 | A1 | 12/2013 | Abelman et al. |
| 2013/0338111 | A1 | 12/2013 | Beaudoin et al. |
| 2014/0213616 | A1 | 7/2014 | Hadida-Ruah et al. |
| 2014/0296266 | A1 | 10/2014 | Hu et al. |
| 2015/0252038 | A2 | 9/2015 | Andrez et al. |
| 2015/0291514 | A1 | 10/2015 | Brown et al. |
| 2016/0340309 | A1 | 11/2016 | Chowdhury et al. |
| 2020/0017469 | A1* | 1/2020 | Sutherlin et al. .... C07D 401/14 |

FOREIGN PATENT DOCUMENTS

| | | |
|---|---|---|
| EP | 0179619 B1 | 9/1990 |
| EP | 0516392 A2 | 12/1992 |
| EP | 2184278 A1 | 5/2010 |
| JP | S59140445 A | 8/1984 |
| WO | 1990008128 A1 | 7/1990 |
| WO | 1990009997 A1 | 9/1990 |
| WO | 1996037490 A1 | 11/1996 |
| WO | 2000039077 A2 | 7/2000 |
| WO | 2003059882 A1 | 7/2003 |
| WO | 2004014913 A2 | 2/2004 |
| WO | 2004052869 A1 | 6/2004 |
| WO | 2004092145 A1 | 10/2004 |
| WO | 2005013914 A2 | 2/2005 |
| WO | 2005032488 A2 | 4/2005 |
| WO | 2006015158 A1 | 2/2006 |
| WO | 2006020830 A2 | 2/2006 |
| WO | 2006020830 A3 | 2/2006 |
| WO | 2006039212 A2 | 4/2006 |
| WO | 2006121097 A1 | 11/2006 |
| WO | 2006122014 A2 | 11/2006 |
| WO | 2006122800 A1 | 11/2006 |
| WO | 2007030582 A3 | 3/2007 |
| WO | 2007045572 A1 | 4/2007 |
| WO | 2007062078 A2 | 5/2007 |
| WO | 2007067994 A1 | 6/2007 |
| WO | 2007120647 A2 | 10/2007 |
| WO | 2008094602 A2 | 8/2008 |
| WO | 2008097991 A1 | 8/2008 |
| WO | 2008118758 A1 | 10/2008 |
| WO | 2009010784 A1 | 1/2009 |
| WO | 2009012242 A3 | 1/2009 |
| WO | 2009157399 A1 | 12/2009 |
| WO | 2010022055 A2 | 2/2010 |
| WO | 2010079443 A1 | 7/2010 |
| WO | 2010137351 A1 | 12/2010 |
| WO | 2011014462 A1 | 2/2011 |
| WO | 2011016234 A1 | 2/2011 |
| WO | 2011037192 A1 | 2/2011 |
| WO | 2011059042 A1 | 5/2011 |
| WO | 2011063001 A1 | 5/2011 |
| WO | 2011088201 A1 | 7/2011 |
| WO | 2011100433 A1 | 8/2011 |
| WO | 2011153588 A1 | 12/2011 |
| WO | 2012004664 A2 | 1/2012 |
| WO | 2012004706 A2 | 1/2012 |
| WO | 2012004706 A3 | 1/2012 |
| WO | 2012004714 A2 | 1/2012 |
| WO | 2012007836 A1 | 1/2012 |
| WO | 2012007861 A1 | 1/2012 |
| WO | 2012007868 A2 | 1/2012 |
| WO | 2012007869 A2 | 1/2012 |
| WO | 2012007877 A2 | 1/2012 |
| WO | 2012007883 A1 | 1/2012 |
| WO | 2012035023 A1 | 3/2012 |
| WO | 2012039657 A1 | 3/2012 |
| WO | 2012085650 A1 | 6/2012 |
| WO | 2012095781 A1 | 7/2012 |
| WO | 2013025883 A1 | 2/2013 |
| WO | 2013056232 A2 | 4/2013 |
| WO | 2013063459 A1 | 5/2013 |
| WO | 2013064983 A1 | 5/2013 |
| WO | 2013064984 A1 | 5/2013 |
| WO | 2013072758 A1 | 5/2013 |
| WO | 2013086229 A1 | 6/2013 |
| WO | 2013088315 A1 | 6/2013 |
| WO | 2013102826 A1 | 7/2013 |
| WO | 2013118805 A1 | 8/2013 |
| WO | 2013118854 A1 | 8/2013 |
| WO | 2013122897 A1 | 8/2013 |
| WO | 2013134518 A1 | 9/2013 |
| WO | 2013146969 A1 | 10/2013 |
| WO | 2013177224 A1 | 11/2013 |
| WO | 2014008458 A2 | 1/2014 |
| WO | 2014014050 A1 | 1/2014 |
| WO | 2014066490 A1 | 5/2014 |
| WO | 2014066491 A1 | 5/2014 |
| WO | 2014096941 A1 | 6/2014 |
| WO | 2014144545 A2 | 9/2014 |
| WO | 2014151472 A1 | 9/2014 |
| WO | 2014153037 A1 | 9/2014 |
| WO | 2015051043 A1 | 4/2015 |
| WO | 2015078374 A1 | 6/2015 |

OTHER PUBLICATIONS

Chemical Abstracts Registry No. 901923-07-7, indexed in the Registry file on STN CAS Online Aug. 16, 2006. (Year: 2006).*
Chemical Abstracts Registry No. 1622686-06-9, indexed in the Registry file on STN CAS Online Sep. 12, 2014. (Year: 2014).*
Estacion, et al., "A sodium channel gene SCN9A polymorphism that increases nociceptor excitability", Ann Neurol 66 (6), 862-866 (2009).
Federal Register, vol. 76(27), 7162-7175, Slide 1, 64-67 (2011).

(56) References Cited

OTHER PUBLICATIONS

File Caplus, Registry No. 1333872-40-4, entered STN: Sep. 29, 2011.
Fishman, et al., "Intravenous lidocaine for treatment-resistant pruritus", American J. of Medicine 102, 584-585 (1997).
Fraser, et al., "Voltage-gated sodium channel expression and potentiation of human breast cancer metastasis", Clin. Cancer Res. 11(15), 5381-5389 (2005).
Goldberg, et al., "Loss-of-function mutations in the Nav1.7 gene underlie congenital indifference to pain in multiple human populations", Clin. Genet. 71, 311-319 (2007).
Goldin, et al., "Nomenclature of Voltage-Gated Sodium Channels", Neuron vol. 28, 365-368 (2000).
Gould, et al., "Development of inflammatory hypersensitivity and augmentation of sodium channels in rat dorsal root ganglia", Brain Res. 824 (2), 296-299 (1999).
Hains, et al., "Upregulation of sodium channel Nav1.3 and functional involvement in neuronal hyperexcitability associated with central neuropathic pain after spinal cord injury", J. Neurosci. 23 (26), 8881-8892 (2003).
Hayes, et al., "Na(V)1.7 Paint Control: A Novel Target", Neurosurgery 73, N16 (2013).
Ikoma, et al., "Neuronal sensitization for histamine-induced itch in lesional skin of patients with atopic dermatitis", Arch. Dermatol. 139, 1445-1458 (2003).
Ikoma, et al., "The neurobiology of itch", Nature Reviews Neuroscience 7, 535-547 (2006).
Ikuma, et al., "Preparation of 3-substituted proline derivatives as FXIa inhibitors", CA159:371450 (2013).
Kis-Toth, et al., "Voltage-gated sodium channel NaV1.7 maintains the membrane potential and regulates the 45 activation and chemokine-induced migration of a monocyte-derived dendritic cell subset", J. Immunology 187, 1273-1280 (2011).
Klugbauer, et al., "Structure and functional expression of a new member of the tetrodotoxin-sensitive voltage-activated sodium channel family from human neuroendocrine cells", Embo J. 14 (6), 1084-1090 (1995).
Kuo, et al., "Application of CoMFA and CoMSIA 3D-QSAR and Docking Studies in Optimization of Mercaptobenzenesulfonamides as HIV-1 Integrase Inhibitors", Journal of Medicinal Chemistry. American Chemical Society. US. vol. 47. No. 2, 385-399 (2003).
Kutt, et al., "A Comprehensive Self-Consistent Spectrophotometric Acidity Scale of Neutral Bronsted Acids in Acetonitrile", J. Org. Chern. 71, 2829-2838 (2006).
Lai, et al., "Inhibition of neuropathic pain by decreased expression of the tetrodotoxin-resistant sodium channel, NaV1.8", Pain 95 (1-2), 143-152 (2002).
Lai, et al. "The role of voltage-gated sodium channels in neuropathic pain", Current Opinion in Neurobiology 13, 291-297 (2003).
Lamoureux, et al., "Use of the adamantane structure in medicinal chemistry", Curr Med Chem 17(26), 2967-2978 (2010).
Lee, et al., "A monoclonal antibody that targets a NaV1.7 channel voltage sensor for pain and itch relief", Cell 157(6), 1393-1404 (2014).
Leeman, et al., "Preparation of 4-benzimidazolylmethoxy-3-halophenylmethoxybenzoates and analogs as tRNA synthestase inhibitors", CA 133:350214 (2000).
Li, et al., "Recent advances in the structure-activity relationship study of small-molecule sodium channel blockers with analgesic effects", Acta Pharmaceutica Sinica, vol. 44, (2), 101-108 (2009). [English Translation.].
Liu, et al. "Mutations in cardiac sodium channels: clinical implications", Am. J. Pharmacogenomics 3(3), 173-179 (2003).
Mao, et al., "Systemic lidocaine for neuropathic pain relief", Pain 87, 7-17 (2000).
Massah, et al., "Synthesis. In vitro antibacterial and carbonic anyydrase II inhibitory activities of N-acylsulfonamides 2 using silica sulfuric acid as an efficient catalyst under both solvent-free and heterogeneous conditions", Bioorganic & Medicinal Chemistry 16, 5465-5472 (2008).

Meisler, et al., "Sodium channel gene family: epilepsy mutations, gene interactions and modifier effects", The Journal of Physiology 588.11, 1841-1848 (2010).
Morinville, et al., "Distribution of the voltage-gated sodium channel NaV1.7 in the rat: expression in the autonomic and endocrine systems", J. Comparative Neurology 504, 680-689 (2007).
Oaklander, et al., "Intractable post-herpetic itch and cutaneous deafferentation after facial singles", Pain 96,9-12 (2002).
Patani, et al., "Bioisosterism: A Rational Approach in Drug Design", Chem Rev 96, 3147-3176 (1996).
Patent Cooperation Treaty, International Searching Authority, Search Report and Written Opinion for PCT/US2016/054011, 17 pages, dated Mar. 8, 2017.
Priest, et al., "Contribution of the tetrodotoxin-resistant voltage-gated sodium channel NaV1.9 to sensory transmission and nociceptive behavior", Proc Nail Acad Sci 102 (26) 9382-9387 (2005).
Priest, "Future potential and status of selective sodium channel blockers for the treatment of pain", Current Opinion in Drug Discovery and Development, 12(5), 682-692 (2009).
Prodrug, Dictionary 1-2, Internet (2002).
Pubchem, Compound Summary for CID 14280666, N-(1,2-benzoxazol-3-yl) methanesulfonamide, https://pubchem.ncbi_nim.nih.gov/summary/summary.cgi?cid=14280666, 3 pages (2007).
Raymond, et al., "Expression of alternatively spliced sodium channel alpha-subunit genes. Unique splicing patterns are observed in dorsal root ganglia", J. Biol. Chem. 279(44), 46234-46241 (2004).
Reich, et al., "Design and synthesis of novel 6,7-imidazotetrahydroquinoline inhibitors of thymidylate synthase using terative protein crystal structure analysis", Journal of Medicinal Chemistry 35 (5), 847-858 (1992).
Reid-Mooring, et al., "Benzenesulfonamides: a unique class of chemokine receptor type 4 inhibitors", ChemMedchem 8(4), 622-632 (2013).
Reimann, et al., "Pain perception is altered by a nucleotide polymorphism in SCN9A", Proc. Nail. Acad. Sci. 107, 5148-5153 (2010).
Roberts, et al., "Molybdenum-Mediated Carbonylaiton of Aryl Halides with Nucleophiles Using Microwave Irradiation", Organic Letters, vol. 12 (19), 4280-4283 (2010).
Roberts, et al., "Novel Aryl and Heteroaryl Acyl Sulfamide Synthesis via Microwave-Assisted Palladium-Catalyzed Carbonylation", Organic Letters, vol. 12 (6), 1264-1267 (2010).
Ruan, et al., "Sodium channel mutations and arrhythmias", Nature Reviews Cardiology, 6, 337-348 (2009).
Rugiero, et al., "Selective Expression of a Persistent Tetrodotoxin-Resistant Na+ Current and NaV1.9 Subunit in Myenteric Sensory Neurons", J. Neurosci 23 (7), 2715-2725 (2003).
Sakuma, et al., "Preparation of piperazine", CA150:260220 (2009).
Sangameswaran, et al., "A novel tetrodotoxin-sensitive, voltage-gated sodium channel expressed in rat and human dorsal root ganglia", J. Bioi. Chem. 272 (23), 14805-14809 (1997).
Sato, et al., "The voltage-sensitive sodium channel is a bell-shaped molecule with several cavities", Nature 409, 1047-1051 (2001).
Schmelz, et al., "Itch and pain", Neuroscience and Biobehaviorial Reviews, 34, 171-176 (2010).
Seddon, "Pseudopolymorph: A Polemic", Crystal Growth and Design vol. 4(6), 1087 (2004).
Silos-Santiago, "Drugs in Clinical Development for Neuropathic Pain", presented at First World Conference Abdominal and Pelvic Pain, Amsterdam, pp. 1-23 (Jun. 6, 2013).
Smith, et al., "Sodium channel protein expression enhances the invasiveness of rat and human prostate cancer cells" FEBS Letters, 423, 19-24 (1998).
Amaya, et al., "The voltage-gated sodium channel Na(v)1.9 is an effector of peripheral inflammatory pain hypersensitivity", J. Neurosci 26 (50), 12852-12860 (2006).
Arcangeli, et al., "Targeting Ion Channels in Cancer: A Novel Frontier in AntineoplasticTherapy", Current Medicinal, Chemistry 16, 66-93 (2009).
Bach, et al., "A novel series of piperazinyl-pyridine ureas as antagonists of the purinergic P2712 receptor", Bioorganic & Medicinal Chemistry Letters 21, 2877-2881 (2011).

(56) References Cited

OTHER PUBLICATIONS

Banks, et al., "The Reaction of N-Aikylhydroxamic Acids with Sulphinyl Chlorides", J. Chem. Soc. Perkin Trans. II, 1211-1216 (1986).
Bean, et al., "Lidocaine Block of Cardiac Sodium Channels", J. Gen. Physiol. 81, 613-642 (1983).
Binder, et al., "Disease Mechanisms in Neuropathic Itch", Nature Clinical Practice Neurology 4(6), 329-337 (2008).
Black, et al., "Changes in the expression of tetrodotoxin-sensitive sodium channels within dorsal root ganglia neurons in inflammatory pain", Pain 108 (3), 237-247 (2004).
Blair, et al., "Roles of tetrodotoxin (TIX)-sensitive Na+ current, TIX-resistant Na+ current, and Ca2+ current in the action potentials of nociceptive sensory neurons", J. Neurosci 22, 10277-10290 (2002).
Brackenbury, et al., "Activity-dependent regulation of voltage-gated Na+ channel expression in Mat-LyLu rat prostate cancer cell line", J. Physiol 573.2, 343-356 (2006).
Braga, et al., "Making crystals from crystals: a green route to crystal engineering and polymorphism", Chern Commun J Roy Soc Chern, 3635-3645 (2005).
Caldwell, et al., "Sodium channel Na(v)1.6 is localized at nodes of ranvier, dendrites, and synapses", Proc. Nail. Acad. Sci. 97(10), 5616-5620 (2000).
CAS Registry, Nos. 1027529-26-5, 1027209-51-3 and 1026292-79-4, 1 page (2015).
Catron, et al., "Preparation of 4-[4-[2-phenylcclohexen -1-en-1-yl)methyl]piperazin-1-ui]-N-(phenylsulfonyl) 13 benzamides and 4-[4-[(2-phenylcyclohexen-1-en-1-yl)methylipiperazin-1-71]-N-(3-pyridylsulfonlyl) benzamides", CAPLUS 2012:637301, 156:638098, 2 pages (2012).
Catterall, "From ionic currents to molecular mechanisms: the structure and function of voltage-gated sodium channels", Neuron 26 (1), 13-25 (2000).
Catterall, "Molecular mechanisms of gating and drug block of sodium channels", Novartis Foundation Symposium 241, 206-225 (2002).
Catterall, "Structural biology: A 3D view of sodium channels", Nature, vol. 409, 988-990 (2001).
Cestele, et al., "Molecular mechanisms of neurotoxin action on voltage-gated sodium channels", Biochimie vol. 82 (9-1 0), 883-892 (2000).
Chan, et al., "Rh(II)-Catalyzed Intermolecular Oxidative Sulfamidalion of Aldehydes: A Mild Efficient Synthesis of N-Sulfonylcarboxamides", J. Am. Chern. Soc., 129, 14106-14107 (2007).
Chemical Abstract Service, STN Registry Database No. 891026-77-0 [entered STN: Jul. 9, 2006].
Chemical Abstract Service, STN Registry Database No. 892698-09-8 [entered STN: Jul. 14, 2006].
Chemical ABSTRACTS_4, XP002744146, Database accession No. 1294599-14-6 Abstract, (May 15, 2011).
Chemical ABSTRACTS_1, XP002744143, Database accession No. 1321299-48-2 Abstract (Aug. 22, 2011).
Chemical ABSTRACTS_10, XP002744152, Database accession No. 1288553-28-5 Abstract (May 1, 2011).
Chemical ABSTRACTS_11, XP002744153, Database accession No. 1278399-39-5 Abstract (Apr. 11, 2011).
Chemical Abstracts_12, XP002744154, Database accession No. 1297052-59-5 Abstract (May 19, 2011).
Chemical Abstracts_13, XP002744155, Database accession No. 1277490-84-2 Abstract (Apr. 10, 2011).
Chemical Abstracts_2, XP002744144, Database accession No. 1320435-32-2 Abstract (Aug. 22, 2011).
Chemical Abstracts_3, XP002744145, Database accession No. 1319619-74-3 Abstract (Aug. 18, 2011).
Chemical Abstracts_6, XP002744148, Database accession No. 1051172-94-1 Abstract (Sep. 21, 2008).
Chemical Abstracts_5, XP002744147, Database accession No. 1051238-85-7 Abstract (Sep. 21, 2008).
Chemical Abstracts_7, XP002744149, Database accession No. 1301192-24-4 (May 26, 2011).
Chemical Abstracts_8, XP002744150, Database accession No. 1299653-84-1 Abstract (May 24, 2011).
Chemical ABstracts_9, XP002744151, Database accession No. 299214-10-0 (May 24, 2011).
Chioni, et al., "A novel adhesion molecule in human breast cancer cell lines: Voltage-gated Na+ channel β1 subunit", Int'l J. Biochem. Cell Biol. 41, 1216-1227 (2009).
Chung, et al., "Sodium channels and neuropathic pain", Novartis Foundation Symposium 261, 19-31 (2004).
Clare, et al., "Voltage-gated sodium channels as therapeutic targets", Drug Discovery Today 5(11), 506-520 (2000).
Cox, et al., "An SCN9A channelopathy causes congenital inability to experience pain", Nature 444, 894-898 (2006).
Daeniker, et al., "234. Uber bicyclische Sulfonamide", Helvetica Chimica ACTA, vol. 45 (6), 1972-1981 (1962). [English Translation.].
Database Reaxys, XP002692384, Accession No. XRN: 6729065, 6731122, 1 page, (D. Bertoia et al., ""Base 24 promoted ring-opening reactions of 2-p-lolyl-5,6-dihydro-1, 4,3-oxathiazine 4,4-dioxides, Gazella Chimica Ilaliana, vol. 118 (6), 435-440 (1988).
Deng, et al., "Dynamic 1-15 Receptor-Based Pharmacophore Model Development and Its Application in Designing Novel HIV-1 Integrase Inhibitors", Journal of Medicinal Chemistry. vol. 48. No. 5, 1496-1505 (2005), Supporting Information, S1-S14. XP055285519. DOI: 10.1021jjm049410e (2005).
Devor, et al., "Na+ Channellmmunolocalization in Peripheral Mammalian Axons and Changes following Nerve Injury and Neuroma Formation", J. Neurosci. 13 (5), 1976-1992 (1993).
Dib-Hajj, et al., "Genetics and Molecular Pathophysiology of NaV1. 7-related Pain Syndromes", Advances in Genetics 63,85-110 (2008).
Dib-Hajj, et al., "NaN, a novel voltage-gated Na channel, is expressed preferentially in peripheral sensory neurons and down-regulated after axotomy", Proc. Natl. Acad. Sci. 95 (15), 8963-8968 (1998).
Dib-Hajj, et al., "The Na(V)1.7 sodium channel: from molecule to man", Nature Reviews Neuroscience 14, 49-62 (2013).
Dickore, "Synthese und reaktionen von 1.3.4-oxathiazolin-3-dioxyden", Justus Liebigs Annalen Der Chemie, vol. 671, 135-146, XP055053742, Compounds IVa, IVb, IVd, V, VI (1964). [English Translation.].
Diss, et al., "A potential novel marker for human prostate cancer: voltage-gated sodium channel expression in vivo", Prostate Cancer and Prostatic Diseases 8, 266-273 (2005).
Diss, et al., "Expression profiles of voltage-gated sodium channel a-subunit genes in rat and human prostate cancer cell lines", The Prostate 48, 165-178 (2001).
Diss, et al., "Identification and characterization of the promoter region of the NaV1.7 voltage-gated sodium channel gene (SCN9A)", Mol. Cell. Neurosci. 37, 537-547 (2008).
Dong, et al., "Small interfering RNA-mediated selective knock-down of Na(V)1.8 tetrodotoxin-resistant sodium channel reverses mechanical allodynia in neuropathic rats", Neuroscience 146, 812-821 (2007).
England, et al., "Isoform-selective voltage-gated Na(+) channel modulators as next-generation analgesics", Future Med Chem 2 (5), 775-790 (2010).
Tamaoka, "Paramyotonia congenita and skeletal sodium channelopathy", Intern. Med. 42 (9), 769-770 (2003).
Tanelian, et al., "Neuropathic pain can be relieved by drugs that are use-dependent sodium channel blockers: lidocaine, carbamazepine and mexileline", Anesthesiology, 74(5), 949-951 (1991).
Termin, et al., "Recent Advances in Voltage-Gated Sodium Channel Blockers: Therapeutic Potential as Drug Targets in the CNS", Annual Reports in Medicinal Chemistry 43, 43-60 (2008).
Toledo-Aral, et al., "Identification of PN1, a predominant voltage-dependent sodium channel expressed principally in peripheral neurons", Proc. Nail. Acad. Sci. 94 (4), 1527-1532 (1997).
Villamil, et al., "Efficacy of lidocaine in the treatment of pruritus in patients with chronic chlolestatic liver disease", Am. J. Med, 118, 1160-1163 (2005).

(56) References Cited

OTHER PUBLICATIONS

Vippagunta, et al., "Crystal Solids", Adv Drug Del Rev vol. 48, 3-26 (2001).
Wallace, et al., "Efficacy of oral mexileline for neuropathic pain with allodynia: a double-blind, placebo-controlled, crossover study", Reg. Anesth. Pain Med. 25 (5), 459-467 (2000).
Wolff, "Burger's Medicinal Chemistry and Drug Discovery", Fifth Edition, vol. 1: Principles and Practice, 975-977 (1995).
Wood, et al., "Voltage-gated sodium channels and pain pathways", J. Neurobiol. 61(1 ), 55-71 (2004).
Xiao, et al., "C-fiber spontaneous discharge evoked by chronic inflammation is suppressed by a long-term infusion of lidocaine yielding nanogram per milliliter plasma levels", Pain, 137,218-228 (2008).
Yang, et al., "Mutations in SCN9A, encoding a sodium channel alpha subunit, in patients with primary erythermalgia", J. Med. Genet. 41 (3), 171-174 (2004).
Yu, et al., "Reduced sodium current in GABAergic interneurons in a mouse model of severe myoclonic epilepsy in infancy", Nat Neurosci 9, 1142-1149 (2006).
Yu, et al., "Sodium Channel β4. a New Disulfide-Linked Auxiliary Subunit with Similarity to β2", J. Neurosci. 23(20), 7577-7585 (2003).
Yu, et al., "The VGL-chanome: a protein superfamily specialized for electrical signaling and ionic homeostasis", Sci. STKE 253, re15, 17 pages (2004).
Zhao, et al., "Voltage-gated sodium channel expression in rat and human epidermal keratinocytes: evidence for a role in pain", Pain, 139, 90-105 (2008).
Zuliani, et al., "Sodium channel blockers for neuropathic pain", Expert Opinion Ther Patents 20(6), 755-779 (2010).

\* cited by examiner

THERAPEUTIC COMPOUNDS AND METHODS OF USE THEREOF

PRIORITY APPLICATIONS

This application is a continuation of International Application No. PCT/US2016/054011 filed 27 Sep. 2016, which claims priority to International Application No. PCT/CN2016/096659, filed 25 Aug. 2016; which claims the benefit of U.S. Provisional Application No. 62/298,817, filed 23 Feb. 2016 and U.S. Provisional Application No. 62/233,863, filed 28 Sep. 2015. The entire content of the applications referenced above are hereby incorporated by reference herein.

The present invention relates to organic compounds useful for therapy in a mammal, and in particular to inhibitors of sodium channel (e.g., NaV1.7) that are useful for treating sodium channel-mediated diseases or conditions, such as pain, as well as other diseases and conditions associated with the modulation of sodium channels.

Voltage-gated sodium channels are transmembrane proteins that initiate action potentials in nerve, muscle and other electrically excitable cells, and are a necessary component of normal sensation, emotions, thoughts and movements (Catterall, W. A., Nature (2001), Vol. 409, pp. 988-990). These channels consist of a highly processed alpha subunit that is associated with auxiliary beta subunits. The pore-forming alpha subunit is sufficient for channel function, but the kinetics and voltage dependence of channel gating are in part modified by the beta subunits (Goldin et al., Neuron (2000), Vol. 28, pp. 365-368). Electrophysiological recording, biochemical purification, and molecular cloning have identified ten different sodium channel alpha subunits and four beta subunits (Yu, F. H., et al., Sci. STKE (2004), 253; and Yu, F. H., et al., Neurosci. (2003), 20:7577-85).

The sodium channel family of proteins has been extensively studied and shown to be involved in a number of vital body functions. Research in this area has identified variants of the alpha subunits that result in major changes in channel function and activities, which can ultimately lead to major pathophysiological conditions. The members of this family of proteins are denoted NaV1.1 to NaV1.9.

NaV1.7 is a tetrodotoxin-sensitive voltage-gated sodium channel encoded by the gene SCN9A. Human NaV1.7 was first cloned from neuroendocrine cells (Klugbauer, N., et al., 1995 EMBO J., 14 (6): 1084-90.) and rat NaV1.7 was cloned from a pheochromocytoma PC12 cell line (Toledo-Aral, J. J., et al., Proc. Natl. Acad. Sci. USA (1997), 94:1527-1532) and from rat dorsal root ganglia (Sangameswaran, L., et al., (1997), J. Biol. Chem., 272 (23): 14805-9). NaV1.7 is expressed primarily in the peripheral nervous system, especially nociceptors and olfactory neurons and sympathetic neurons. The inhibition, or blocking, of NaV1.7 has been shown to result in analgesic activity. Knockout of NaV1.7 expression in a subset of sensory neurons that are predominantly nociceptive results in resistance to inflammatory pain (Nassar, et al., op. cit.). Likewise, loss of function mutations in humans results in congenital indifference to pain (CIP), in which the individuals are resistant to both inflammatory and neuropathic pain (Cox, J. J., et al., Nature (2006); 444:894-898; Goldberg, Y. P., et al., Clin. Genet. (2007); 71:311-319). Conversely, gain of function mutations in NaV1.7 have been established in two human heritable pain conditions, primary erythromelalgia and familial rectal pain, (Yang, Y., et al., J. Med. Genet. (2004), 41(3):171-4). In addition, a single nucleotide polymorphism (R1150W) that has very subtle effects on the time- and voltage-dependence of channel gating has large effects on pain perception (Estacion, M., et al., 2009. Ann Neurol 66: 862-6; Reimann, F., et al., Proc Natl Acad Sci USA (2010), 107: 5148-53). About 10% of the patients with a variety of pain conditions have the allele conferring greater sensitivity to pain and thus might be more likely to respond to block of NaV1.7. Because NaV1.7 is expressed in both sensory and sympathetic neurons, one might expect that enhanced pain perception would be accompanied by cardiovascular abnormalities such as hypertension, but no correlation has been reported. Thus, both the CIP mutations and SNP analysis suggest that human pain responses are more sensitive to changes in NaV1.7 currents than are perturbations of autonomic function.

Sodium channel blockers have been shown to be useful in the treatment of pain, (see, e.g., Wood, J. N., et al., J. Neurobiol. (2004), 61(1), 55-71. Genetic and functional studies have provided evidence to support that activity of NaV1.7 as a major contributor to pain signalling in mammals. (See Hajj, et al. Nature Reviews Neuroscience; 2013, vol 14, 49-62; and Lee, et al. Cell; 2014, vol 157; 1-12). Presently, there are a limited number of effective sodium channel blockers for the treatment of pain with a minimum of adverse side effects which are currently in the clinic. Thus there remains a need for selective voltage-gated sodium channel modulators (e.g., modulators of NaV1.7) that can provide a greater therapeutic index for treatment.

SUMMARY OF THE INVENTION

In one aspect the present invention provides novel compounds having sodium channel blocking activity that are useful for the treatment of pain.

In a first embodiment (Embodiment 1; abbreviated as "E1") the invention provides for a compound of formula (I):

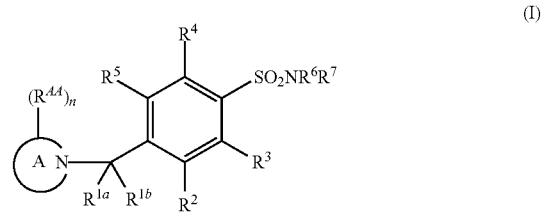

or a salt thereof; wherein,
each $R^{AA}$ is independently selected from the group consisting of F, Cl, Br, I, —CN, —C(=O)OR$^{A1}$, —SO$_2$R$^{A1}$, —OR$^{A1}$, —(X$^{RA}$)-(3-15 membered carbocyclyl), —(X$^{RA}$)-(6-12 membered aryl), —(X$^{RA}$)-(5-12 membered heteroaryl), and —R$^{A2}$, wherein said 3-15 membered carbocyclyl, 6-12 membered aryl, and 5-12 membered heteroaryl of R$^{AA}$ is optionally substituted with from 1 to 5 substituents R$^b$ independently selected from the group consisting of F, Cl, Br, I, C$_{1-4}$ alkyl, C$_{1-4}$ haloalkyl, amino, C$_{1-4}$ alkylamino, di(C$_{1-4}$alkyl)amino, and C$_{1-4}$(halo)alkoxy; R$^{A1}$ is selected from the group consisting of hydrogen, C$_{1-8}$ alkyl, C$_{2-8}$ alkenyl, C$_{1-8}$ haloalkyl, C$_{3-8}$ cycloalkyl, phenyl and benzyl; R$^{A2}$ is selected from the group consisting of C$_{1-8}$ alkyl that is optionally substituted with one or more substituents selected from oxo (=O), fluoro, hydroxy, amino, C$_{1-4}$ alkylamino and di(C$_{1-4}$alkyl)amino; X$^{RA}$ is selected from the group consisting of absent, —C(=O)—, and C$_{1-4}$ alkylene; wherein any C$_{1-4}$ alkylene, of X$^{RA}$ is optionally substituted with 1 to 3 substituents selected from the group consisting of C$_{1-4}$ alkyl, C$_{1-4}$ haloalkyl, and phenyl that is optionally substituted with 1 to 5 substituents selected from, F, Cl, Br, I, —NH$_2$, —OH, —CN, —NO$_2$, C$_{1-4}$ alkyl, C$_{1-4}$ haloalkyl, C$_{1-4}$ alkoxy, C$_{1-4}$(halo)alkoxy, C$_{1-4}$ alkylamino and C$_{1-4}$ dialkylamino; ring "A" is a 5-12 membered heteroaryl, or a 3-15 membered heterocyclyl;

R$^{1a}$ is H or C$_{1-4}$ alkyl;

R$^{1b}$ is H or C$_{1-4}$ alkyl;

R$^2$ is selected from the group consisting of H, F, Cl, Br, I, —CN, C$_{1-8}$ alkyl, C$_{3-8}$ cycloalkyl, C$_{1-8}$ haloalkyl and C$_{1-8}$ alkoxy;

R$^3$, R$^4$, and R$^5$ are each independently selected from the group consisting of H, F, Cl, Br, I, —CN, C$_{1-8}$ alkyl, C$_{3-8}$ cycloalkyl, C$_{1-8}$ haloalkyl and C$_{1-8}$ alkoxy;

R$^6$ is selected from the group consisting of H, C$_{1-8}$ alkyl, C$_{3-8}$ cycloalkyl, aryl, and aryl(C$_{1-4}$ alkyl);

and R$^7$ is selected from the group consisting of C$_{1-8}$ alkyl, 3-15 membered heterocyclyl, 5-12 membered heteroaryl, —C(O)N(R$^c$)$_2$ and —C(=NCN)N(R$^c$)$_2$; or R$^6$ and R$^7$, together with the nitrogen to which they are attached, form a 3-15 membered heterocyclyl or 5-12 membered heteroaryl; wherein any C$_{1-8}$ alkyl, C$_{3-8}$ cycloalkyl, aryl, aralkyl, 3-15 membered heterocyclyl, and 5-12 membered heteroaryl is optionally substituted with one or more groups R$^d$ that are independently selected from the group consisting of F, Cl, Br, I, —NH$_2$, —OH, —CN, —NO$_2$, C$_{1-4}$ alkyl, C$_{1-4}$ haloalkyl, C$_{1-4}$ alkoxy, C$_{1-4}$(halo)alkoxy, C$_{1-4}$ alkylamino and C$_{1-4}$ dialkylamino; each R$^c$ is independently selected from the group consisting of hydrogen, C$_{1-8}$ alkyl, C$_{3-8}$ cycloalkyl, phenyl and benzyl; and n is 0, 1, 2, 3, 4, 5, or 6.

In a second embodiment (Embodiment 2; abbreviated as "E2") the invention provides for a compound of formula Ix:

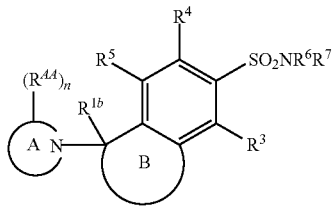

(Ix)

or a salt thereof; wherein, each R$^{AA}$ is independently selected from the group consisting of F, Cl, Br, I, —CN, —C(=O)OR$^{A1}$, —SO$_2$R$^{A1}$, —OR$^{A1}$, —(X$^{RA}$)-(3-15 membered carbocyclyl), —(X$^{RA}$)-(6-12 membered aryl), —(X$^{RA}$)-(5-12 membered heteroaryl), and —R$^{A2}$, wherein said 3-15 membered carbocyclyl, 6-12 membered aryl, and 5-12 membered heteroaryl of R$^{AA}$ is optionally substituted with from 1 to 5 substituents R$^b$ independently selected from the group consisting of F, Cl, Br, I, C$_{1-4}$ alkyl, C$_{1-4}$ haloalkyl, amino, C$_{1-4}$ alkylamino, di(C$_{1-4}$alkyl)amino, C$_{1-4}$(halo)alkoxy, and —C(O)N(R$^c$)$_2$;

R$^{A1}$ is selected from the group consisting of hydrogen, C$_{1-8}$ alkyl, C$_{2-8}$ alkenyl, C$_{1-8}$ haloalkyl, C$_{3-8}$ cycloalkyl, phenyl and benzyl; R$^{A2}$ is selected from the group consisting of C$_{1-8}$ alkyl that is optionally substituted with one or more substituents selected from oxo (=O), fluoro, hydroxy, amino, C$_{1-4}$ alkylamino and di(C$_{1-4}$alkyl)amino; X$^{RA}$ is selected from the group consisting of absent, —C(=O)—, and C$_{1-4}$ alkylene; wherein any C$_{1-4}$ alkylene, of X$^{RA}$ is optionally substituted with 1 to 3 substituents selected from the group consisting of C$_{1-4}$ alkyl, C$_{1-4}$ haloalkyl, and phenyl that is optionally substituted with 1 to 5 substituents selected from, F, Cl, Br, I, —NH$_2$, —OH, —CN, —NO$_2$, C$_{1-4}$ alkyl, C$_{1-4}$ haloalkyl, C$_{1-4}$ alkoxy, C$_{1-4}$(halo)alkoxy, C$_{1-4}$ alkylamino and C$_{1-4}$ dialkylamino;

ring "A" is a 5-12 membered heteroaryl, or a 3-15 membered heterocyclyl;

Ring B is a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from C$_{1-4}$ alkyl, halo, and haloC$_{1-4}$ alkyl;

R$^{1b}$ is H or C$_{1-4}$ alkyl;

R$^3$, R$^4$, and R$^5$ are each independently selected from the group consisting of H, F, Cl, Br, I, —CN, C$_{1-8}$ alkyl, C$_{3-8}$ cycloalkyl, C$_{1-8}$ haloalkyl and C$_{1-8}$ alkoxy;

R$^6$ is selected from the group consisting of H, C$_{1-8}$ alkyl, C$_{3-8}$ cycloalkyl, aryl, and aryl(C$_{1-4}$ alkyl);

and R$^7$ is selected from the group consisting of C$_{1-8}$ alkyl, 3-15 membered heterocyclyl, 5-12 membered heteroaryl, —C(O)N(R$^c$)$_2$ and —C(=NCN)N(R$^c$)$_2$; or R$^6$ and R$^7$, together with the nitrogen to which they are attached, form a 3-15 membered heterocyclyl or 5-12 membered heteroaryl; wherein any C$_{1-8}$ alkyl, C$_{3-8}$ cycloalkyl, aryl, aralkyl, 3-15 membered heterocyclyl, and 5-12 membered heteroaryl is optionally substituted with one or more groups R$^d$ that are independently selected from the group consisting of F, Cl, Br, I, —NH$_2$, —OH, —CN, —NO$_2$, C$_{1-4}$ alkyl, C$_{1-4}$ haloalkyl, C$_{1-4}$ alkoxy, C$_{1-4}$(halo)alkoxy, C$_{1-4}$ alkylamino and C$_{1-4}$ dialkylamino; each R$^c$ is independently selected from the group consisting of hydrogen, C$_{1-8}$ alkyl, C$_{3-8}$ cycloalkyl, phenyl and benzyl; and n is 0, 1, 2, 3, 4, 5, or 6.

In a third embodiment (Embodiment 3; abbreviated as "E3") the invention provides for a compound of formula (II):

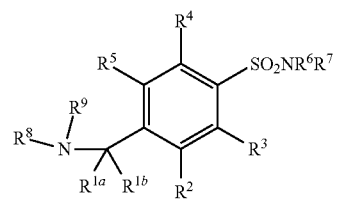

(II)

or a salt thereof; wherein,

R$^{1a}$ is H or C$_{1-4}$ alkyl; or R$^{1a}$ and R$^2$ taken together with the atoms to which they are attached form a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from C$_{1-4}$ alkyl, halo, and haloC$_{1-4}$ alkyl;

R$^{1b}$ is H or C$_{1-4}$ alkyl;

R$^2$ is selected from the group consisting of H, F, Cl, Br, I, —CN, C$_{1-8}$ alkyl, C$_{3-8}$ cycloalkyl, C$_{1-8}$ haloalkyl and C$_{1-8}$ alkoxy; or R$^2$ and R$^{1a}$ taken together with the atoms to which they are attached form a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from C$_{1-4}$ alkyl, halo, and haloC$_{1-4}$ alkyl;

R$^3$, R$^4$, and R$^5$ are each independently selected from the group consisting of H, F, Cl, Br, I, —CN, C$_{1-8}$ alkyl, C$_{3-8}$ cycloalkyl, C$_{1-8}$ haloalkyl and C$_{1-8}$ alkoxy;

$R^6$ is selected from the group consisting of H, $C_{1-8}$ alkyl, $C_{3-8}$ cycloalkyl, aryl, and aryl($C_{1-4}$ alkyl);

and $R^7$ is selected from the group consisting of $C_{1-8}$ alkyl, 3-15 membered heterocyclyl, 5-12 membered heteroaryl, —C(O)N($R^c$)$_2$ and —C(=NCN)N($R^c$)$_2$; or $R^6$ and $R^7$, together with the nitrogen to which they are attached, form a 3-15 membered heterocyclyl or 5-12 membered heteroaryl; wherein any $C_{1-8}$ alkyl, $C_{3-8}$ cycloalkyl, aryl, aralkyl, 3-15 membered heterocyclyl, and 5-12 membered heteroaryl is optionally substituted with one or more groups $R^d$ that are independently selected from the group consisting of F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino; each $R^c$ is independently selected from the group consisting of hydrogen, $C_{1-8}$ alkyl, $C_{3-8}$ cycloalkyl, phenyl and benzyl;

$R^8$ is selected from the group consisting of H, $C_{1-8}$ alkyl, $C_{3-8}$ cycloalkyl, aryl, and aryl($C_{1-4}$ alkyl); and $R^9$ is selected from the group consisting of H, $C_{1-8}$ alkyl, $C_{3-8}$ cycloalkyl, aryl, and aryl($C_{1-4}$ alkyl), wherein any $C_{1-8}$ alkyl, $C_{3-8}$ cycloalkyl, aryl, and aryl($C_{1-4}$ alkyl) is optionally substituted with one or more halo.

Further embodiments of the compounds of the invention are described below.

E4. A compound of formula (I) of E1:

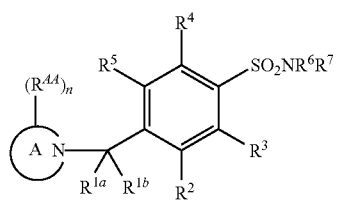

(I)

or a salt thereof; wherein, each $R^{AA}$ is independently selected from the group consisting of F, Cl, Br, I, —CN, —OR$^{A1}$, —(X$^{RA}$)-(3-15 membered carbocyclyl), —(X$^{RA}$)-(6-12 membered aryl), —(X$^{RA}$)-(5-12 membered heteroaryl), and —R$^{A2}$, wherein said (3-15 membered carbocyclyl), 6-12 membered aryl, and 5-12 membered heteroaryl of $R^{AA}$ is optionally substituted with from 1 to 5 substituents $R^b$ independently selected from the group consisting of F, Cl, Br, I, $C_{1-4}$ alkyl, $C_{1-4}$ haloalkyl, amino, $C_{1-4}$ alkylamino and di($C_{1-4}$alkyl)amino, and $C_{1-4}$ (halo)alkoxy; $R^{A1}$ is selected from the group consisting of hydrogen, $C_{1-8}$ alkyl, $C_{2-8}$ alkenyl, $C_{1-8}$ haloalkyl, $C_{3-8}$ cycloalkyl, phenyl and benzyl; $R^{A2}$ is selected from the group consisting of $C_{1-8}$ alkyl that is optionally substituted with one or more substituents selected from oxo (=O), fluoro, hydroxy, amino, $C_{1-4}$ alkylamino and di($C_{1-4}$alkyl) amino; $X^{RA}$ is selected from the group consisting of absent, —C(=O)—, and $C_{1-4}$ alkylene; wherein any $C_{1-4}$ alkylene, of $X^{RA}$ is optionally substituted with 1 to 3 substituents selected from the group consisting of $C_{1-4}$ alkyl, $C_{1-4}$ haloalkyl, and phenyl that is optionally substituted with 1 to 5 substituents selected from, F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$ (halo)alkoxy, $C_{1-4}$ alkylamino and $C_{1-4}$ dialkylamino;

ring "A" is a 5-12 membered heteroaryl, or a 3-15 membered heterocyclyl;

$R^{1a}$ is H or $C_{1-4}$ alkyl;

$R^{1b}$ is H or $C_{1-4}$ alkyl;

$R^2$ is selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy;

$R^3$, $R^4$, and $R^5$ are each independently selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy;

$R^6$ is selected from the group consisting of H, $C_{1-8}$ alkyl, $C_{3-8}$ cycloalkyl, aryl, and aryl($C_{1-4}$ alkyl);

and $R^7$ is selected from the group consisting of $C_{1-8}$ alkyl, 3-15 membered heterocyclyl, 5-12 membered heteroaryl, —C(O)N($R^c$)$_2$ and —C(=NCN)N($R^c$)$_2$; or $R^6$ and $R^7$, together with the nitrogen to which they are attached, form a 3-15 membered heterocyclyl or 5-12 membered heteroaryl; wherein any $C_{1-8}$ alkyl, $C_{3-8}$ cycloalkyl, aryl, aralkyl, 3-15 membered heterocyclyl, and 5-12 membered heteroaryl is optionally substituted with one of more groups $R^d$ that are independently selected from the group consisting of F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino; each $R^c$ is independently selected from the group consisting of hydrogen, $C_{1-8}$ alkyl, $C_{3-8}$ cycloalkyl, phenyl and benzyl; and n is 0, 1, 2, 3, 4, 5, or 6.

E5. A compound of formula Ix of E2:

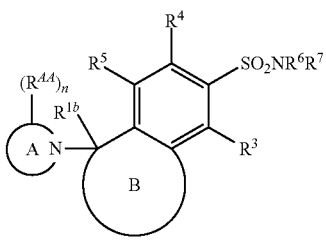

(Ix)

or a salt thereof; wherein, each $R^{AA}$ is independently selected from the group consisting of F, Cl, Br, I, —CN, —OR$^{A1}$, —(X$^{RA}$)-(3-15 membered carbocyclyl), —(X$^{RA}$)-(6-12 membered aryl), —(X$^{RA}$)-(5-12 membered heteroaryl), and —R$^{A2}$, wherein said (3-15 membered carbocyclyl), 6-12 membered aryl, and 5-12 membered heteroaryl of $R^{AA}$ is optionally substituted with from 1 to 5 substituents $R^b$ independently selected from the group consisting of F, Cl, Br, I, $C_{1-4}$ alkyl, $C_{1-4}$ haloalkyl, amino, $C_{1-4}$ alkylamino and di($C_{1-4}$alkyl)amino, and $C_{1-4}$ (halo)alkoxy; $R^{A1}$ is selected from the group consisting of hydrogen, $C_{1-8}$ alkyl, $C_{2-8}$ alkenyl, $C_{1-8}$ haloalkyl, $C_{3-8}$ cycloalkyl, phenyl and benzyl; $R^{A2}$ is selected from the group consisting of $C_{1-8}$ alkyl that is optionally substituted with one or more substituents selected from oxo (=O), fluoro, hydroxy, amino, $C_{1-4}$ alkylamino and di($C_{1-4}$alkyl) amino; $X^{RA}$ is selected from the group consisting of absent, —C(=O)—, and $C_{1-4}$ alkylene; wherein any $C_{1-4}$ alkylene, of $X^{RA}$ is optionally substituted with 1 to 3 substituents selected from the group consisting of $C_{1-4}$ alkyl, $C_{1-4}$ haloalkyl, and phenyl that is optionally substituted with 1 to 5 substituents selected from, F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$ (halo)alkoxy, $C_{1-4}$ alkylamino and $C_{1-4}$ dialkylamino;

ring "A" is a 5-12 membered heteroaryl, or a 3-15 membered heterocyclyl;

Ring B is a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from $C_{1-4}$ alkyl, halo, and halo$C_{1-4}$ alkyl;

$R^{1b}$ is H or $C_{1-4}$ alkyl;

$R^3$, $R^4$, and $R^5$ are each independently selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy;

$R^6$ is selected from the group consisting of H, $C_{1-8}$ alkyl, $C_{3-8}$ cycloalkyl, aryl, and aryl($C_{1-4}$ alkyl);

and $R^7$ is selected from the group consisting of $C_{1-8}$ alkyl, 3-15 membered heterocyclyl, 5-12 membered heteroaryl, —C(O)N($R^c$)$_2$ and —C(=NCN)N($R^c$)$_2$; or $R^6$ and $R^7$, together with the nitrogen to which they are attached, form a 3-15 membered heterocyclyl or 5-12 membered heteroaryl; wherein any $C_{1-8}$ alkyl, $C_{3-8}$ cycloalkyl, aryl, aralkyl, 3-15 membered heterocyclyl, and 5-12 membered heteroaryl is optionally substituted with one of more groups $R^d$ that are independently selected from the group consisting of F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino; each $R^c$ is independently selected from the group consisting of hydrogen, $C_{1-8}$ alkyl, $C_{3-8}$ cycloalkyl, phenyl and benzyl; and n is 0, 1, 2, 3, 4, 5, or 6.

E6. A compound of formula (II) of E3:

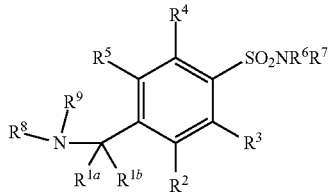

(II)

or a salt thereof; wherein, $R^{1a}$ is H or $C_{1-4}$ alkyl; or $R^{1a}$ and $R^2$ taken together with the atoms to which they are attached form a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from $C_{1-4}$ alkyl, halo, and halo$C_{1-4}$ alkyl;

$R^{1b}$ is H or $C_{1-4}$ alkyl;

$R^2$ is selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy; or $R^2$ and $R^{1a}$ taken together with the atoms to which they are attached form a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from $C_{1-4}$ alkyl, halo, and halo$C_{1-4}$ alkyl;

$R^3$, $R^4$, and $R^5$ are each independently selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy;

$R^6$ is selected from the group consisting of H, $C_{1-8}$ alkyl, $C_{3-8}$ cycloalkyl, aryl, and aryl($C_{1-4}$ alkyl);

and $R^7$ is selected from the group consisting of $C_{1-8}$ alkyl, 3-15 membered heterocyclyl, 5-12 membered heteroaryl, —C(O)N($R^c$)$_2$ and —C(=NCN)N($R^c$)$_2$; or $R^6$ and $R^7$, together with the nitrogen to which they are attached, form a 3-15 membered heterocyclyl or 5-12 membered heteroaryl; wherein any $C_{1-8}$ alkyl, $C_{3-8}$ cycloalkyl, aryl, aralkyl, 3-15 membered heterocyclyl, and 5-12 membered heteroaryl is optionally substituted with one of more groups $R^d$ that are independently selected from the group consisting of F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino; each $R^c$ is independently selected from the group consisting of hydrogen, $C_{1-8}$ alkyl, $C_{3-8}$ cycloalkyl, phenyl and benzyl;

$R^8$ is selected from the group consisting of H, $C_{1-8}$ alkyl, $C_{3-8}$ cycloalkyl, aryl, and aryl($C_{1-4}$ alkyl); and $R^9$ is selected from the group consisting of H, $C_{1-8}$ alkyl, $C_{3-8}$ cycloalkyl, aryl, and aryl($C_{1-4}$ alkyl).

E7. A compound of formula I:

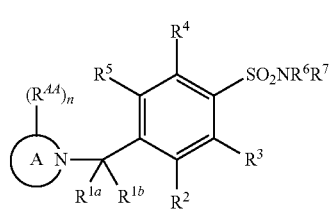

(I)

or a salt thereof; wherein, each $R^{AA}$ is independently selected from the group consisting of F, Cl, Br, I, —CN, —OR$^{A1}$, —(X$^{RA}$)-(3-15 membered carbocyclyl), —(X$^{RA}$)-(6-12 membered aryl), —(X$^{RA}$)-(5-12 membered heteroaryl), and —R$^{A2}$, wherein said (3-15 membered carbocyclyl), 6-12 membered aryl, and 5-12 membered heteroaryl of $R^{AA}$ is optionally substituted with from 1 to 5 substitutents $R^b$ independently selected from the group consisting of F, Cl, Br, I, $C_{1-4}$ alkyl, $C_{1-4}$ haloalkyl, amino, $C_{1-4}$ alkylamino and di($C_{1-4}$alkyl)amino, and $C_{1-4}$ (halo)alkoxy; $R^{A1}$ is selected from the group consisting of hydrogen, $C_{1-8}$ alkyl, $C_{2-8}$ alkenyl, $C_{1-8}$ haloalkyl, $C_{3-8}$ cycloalkyl, phenyl and benzyl; $R^{A2}$ is selected from the group consisting of $C_{1-8}$ alkyl that is optionally substituted with one or more substituents selected from oxo (=O), fluoro, hydroxy, amino, $C_{1-4}$ alkylamino and di($C_{1-4}$alkyl)amino; $X^{RA}$ is selected from the group consisting of absent, —C(=O)—, and $C_{1-4}$ alkylene; wherein any $C_{1-4}$ alkylene, of $X^{RA}$ is optionally substituted with 1 to 3 substituents selected from the group consisting of $C_{1-4}$ alkyl, $C_{1-4}$ haloalkyl, and phenyl that is optionally substituted with 1 to 5 substitutents selected from, F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$ (halo)alkoxy, $C_{1-4}$ alkylamino and $C_{1-4}$ dialkylamino;

ring "A" is a 5-12 membered heteroaryl, or a 3-15 membered heterocyclyl;

$R^{1a}$ is H or $C_{1-4}$ alkyl; or $R^{1a}$ and $R^2$ taken together with the atoms to which they are attached form a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from $C_{1-4}$ alkyl, halo, and halo$C_{1-4}$ alkyl;

$R^{1b}$ is H or $C_{1-4}$ alkyl;

$R^2$ is selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy; or $R^2$ and $R^{1a}$ taken together with the atoms to which they are attached form a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from $C_{1-4}$ alkyl, halo, and halo$C_{1-4}$ alkyl;

$R^3$, $R^4$, and $R^5$ are each independently selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy;

$R^6$ is selected from the group consisting of H, $C_{1-8}$ alkyl, $C_{3-8}$ cycloalkyl, aryl, and aryl($C_{1-4}$ alkyl);

and $R^7$ is selected from the group consisting of $C_{1-8}$ alkyl, 3-15 membered heterocyclyl, 5-12 membered heteroaryl, —C(O)N($R^c$)$_2$ and —C(=NCN)N($R^c$)$_2$; or $R^6$ and $R^7$, together with the nitrogen to which they are attached, form a 3-15 membered heterocyclyl or 5-12 membered heteroaryl; wherein any $C_{1-8}$ alkyl, $C_{3-8}$ cycloalkyl, aryl, aralkyl, 3-15 membered heterocyclyl, and 5-12 membered heteroaryl is optionally substituted with one of more groups $R^d$ that are independently selected from the group consisting of F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino; each $R^c$ is independently selected from the group consisting of hydrogen, $C_{1-8}$ alkyl, $C_{3-8}$ cycloalkyl, phenyl and benzyl; and n is 0, 1, 2, 3, 4, 5, or 6.

E8. The compound of E7 or a salt thereof; wherein, each $R^{AA}$ is independently selected from the group consisting of F, Cl, Br, I, —CN, —OR$^{A1}$, —(X$^{RA}$)-(3-15 membered carbocyclyl), —(X$^{RA}$)-(6-12 membered aryl), —(X$^{RA}$)-(5-12 membered heteroaryl), and —R$^{A2}$, wherein said (3-15 membered carbocyclyl), 6-12 membered aryl, and 5-12 membered heteroaryl of $R^{AA}$ is optionally substituted with from 1 to 5 substitutents $R^b$ independently selected from the group consisting of F, Cl, Br, I, $C_{1-4}$ alkyl, $C_{1-4}$ haloalkyl, amino, $C_{1-4}$ alkylamino and di($C_{1-4}$alkyl)amino, and $C_{1-4}$ (halo)alkoxy; $R^{A1}$ is selected from the group consisting of hydrogen, $C_{1-8}$ alkyl, $C_{2-8}$ alkenyl, $C_{1-8}$ haloalkyl, $C_{3-8}$ cycloalkyl, phenyl and benzyl; $R^{A2}$ is selected from the group consisting of $C_{1-8}$ alkyl that is optionally substituted with one or more substituents selected from oxo (=O), fluoro, amino, $C_{1-4}$ alkylamino and di($C_{1-4}$alkyl)amino; $X^{RA}$ is selected from the group consisting of absent, —C(=O)—, and $C_{1-4}$ alkylene; wherein any $C_{1-4}$ alkylene, of $X^{RA}$ is optionally substituted with 1 to 3 substituents selected from the group consisting of $C_{1-4}$ alkyl, $C_{1-4}$ haloalkyl, and phenyl that is optionally substituted with 1 to 5 substitutents selected from, F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino;

ring "A" is a 5-12 membered heteroaryl, or a 3-15 membered heterocyclyl;

$R^{1a}$ is H or $C_{1-4}$ alkyl; or $R^{1a}$ and $R^2$ taken together with the atoms to which they are attached form a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from $C_{1-4}$ alkyl, halo, and halo$C_{1-4}$ alkyl;

$R^{1b}$ is H or $C_{1-4}$ alkyl;

$R^2$ is selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy; or $R^2$ and $R^{1a}$ taken together with the atoms to which they are attached form a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from $C_{1-4}$ alkyl, halo, and halo$C_{1-4}$ alkyl;

$R^3$, $R^4$, and $R^5$ are each independently selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy;

$R^6$ is selected from the group consisting of H, $C_{1-8}$ alkyl, $C_{3-8}$ cycloalkyl, aryl, and aryl($C_{1-4}$ alkyl);

and $R^7$ is selected from the group consisting of $C_{1-8}$ alkyl, 3-15 membered heterocyclyl, 5-12 membered heteroaryl, —C(O)N($R^c$)$_2$ and —C(=NCN)N($R^c$)$_2$; or $R^6$ and $R^7$, together with the nitrogen to which they are attached, form a 3-15 membered heterocyclyl or 5-12 membered heteroaryl; wherein any $C_{1-8}$ alkyl, $C_{3-8}$ cycloalkyl, aryl, aralkyl, 3-15 membered heterocyclyl, and 5-12 membered heteroaryl is optionally substituted with one of more groups $R^d$ that are independently selected from the group consisting of F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino; each $R^c$ is independently selected from the group consisting of hydrogen, $C_{1-8}$ alkyl, $C_{3-8}$ cycloalkyl, phenyl and benzyl; and n is 0, 1, 2, 3, 4, 5, or 6.

E9. The compound of E7 or E8 wherein ring "A" is a 3-15 membered heterocyclyl; or a salt thereof.

E10. The compound of E2, E5 or E8 which is a compound of formula Ib:

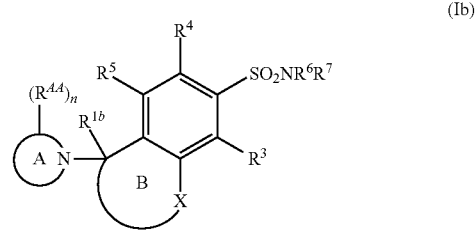

wherein the ring B, including X, is a 5, 6, or 7 membered carbocyclyl or a 5, 6, or 7 membered heterocyclyl; or a salt thereof.

E11. The compound of E10 wherein X is O, S, SO, or SO$_2$; or a salt thereof.

E12. The compound of E10 which is a compound of formula Ic:

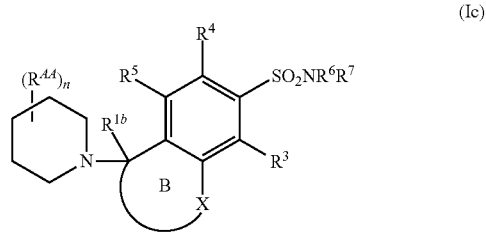

or a salt thereof.

E13. The compound of E10 which is a compound of formula Id:

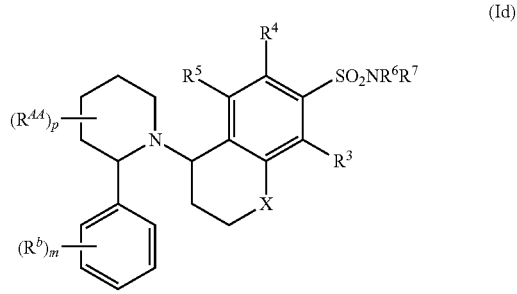

wherein X is O, S, SO, or SO$_2$; m is 0, 1, 2, 3, 4 or 5; and p is 0, 1, 2, 3, 4, or 5; or a salt thereof.

E14. The compound of E10 which is a compound of formula Ie:

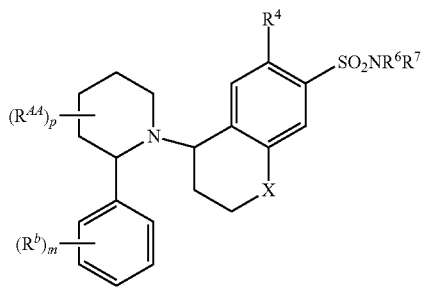

(Ie)

or a salt thereof.

E15. The compound of E1, E4, E7, or E8 wherein $R^{1a}$ is H or $C_{1-4}$ alkyl; $R^{1b}$ is H or $C_{1-4}$ alkyl; and $R^2$ is selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy; or a salt thereof.

E16. The compound of E1, E4, E7, or E8 which is a compound of formula If:

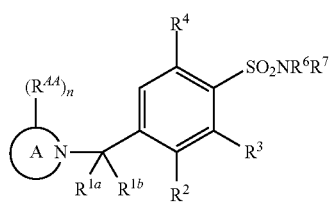

(If)

or a salt thereof.

E17. The compound of E1, E4, E7, or E8 which is a compound of formula Ig

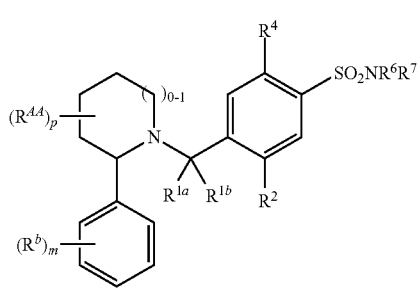

(Ig)

wherein m is 0, 1, 2, 3, 4 or 5; and p is 0, 1, 2, 3, 4, or 5; or a salt thereof.

E18. The compound of E2, E5, E7, or E8 which is a compound of formula Ih:

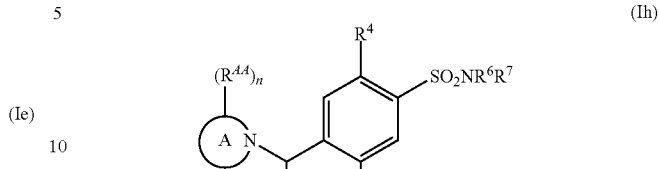

(Ih)

or a salt thereof.

E19. The compound of E2, E5, E7, or E8 which is a compound of formula Ij:

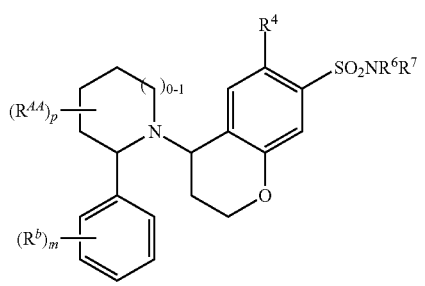

(Ij)

wherein m is 0, 1, 2, 3, 4 or 5; and p is 0, 1, 2, 3, 4, or 5; or a salt thereof.

E20. The compound of E1, E3, E4, E6, E7, E16, or E17 wherein $R^2$ is F; or a salt thereof.

E21. The compound of any one of E1-E20 wherein $R^4$ is F; or a salt thereof.

E22. The compound of any one of E1-E21 wherein $R^6$ is H; or a salt thereof.

E23. The compound of any one of E1-E22 wherein $R^7$ is a 5-12 membered heteroaryl; or a salt thereof.

E24. The compound of any one of E1-E23 wherein $R^7$ is 1,2,4-thiadiazol-5-yl; or a salt thereof.

E25. The compound of E2, E5, or E8 which is a compound of formula Ir:

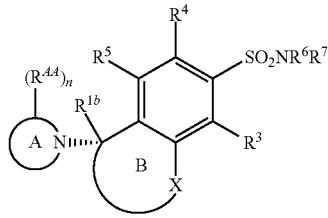

(Ir)

wherein the ring B, including X, is a 5, 6, or 7 membered carbocyclyl or a 5, 6, or 7 membered heterocyclyl; or a salt thereof.

E26. The compound of any one of E1, E2, E4, E5, E7-E11, E16, E18 and E20-E25 wherein the group
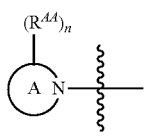
is selected from the group consisting of:
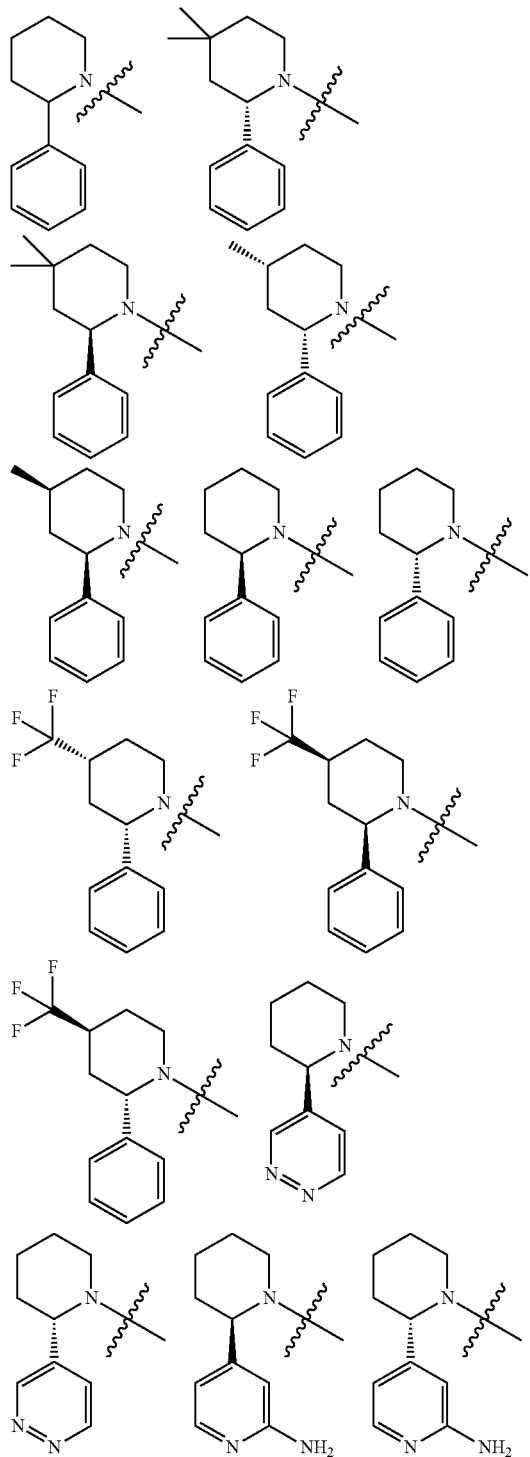
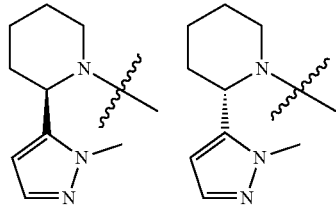
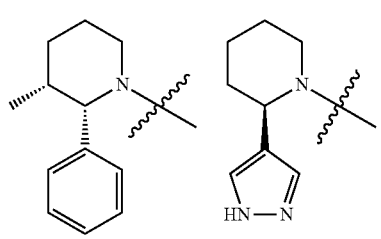
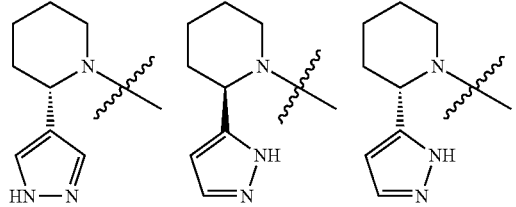
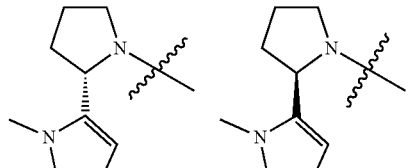
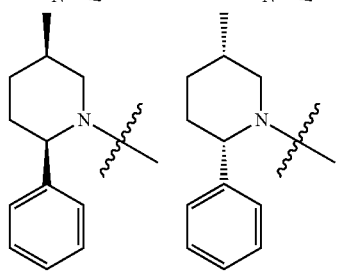
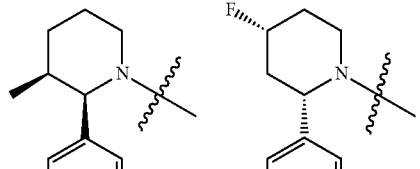
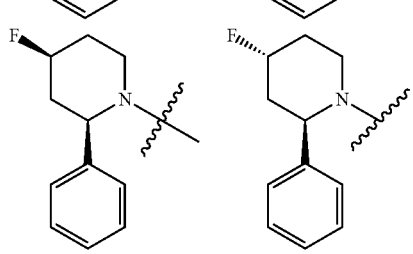

-continued
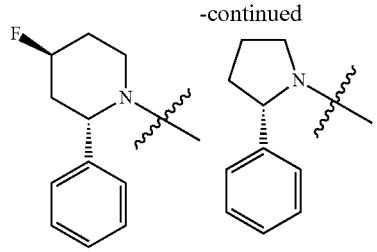
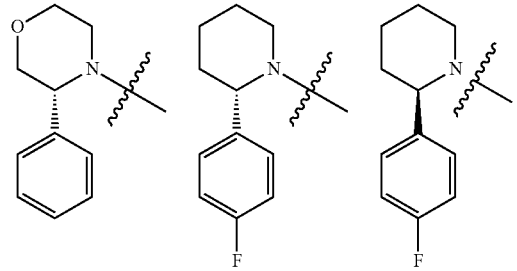
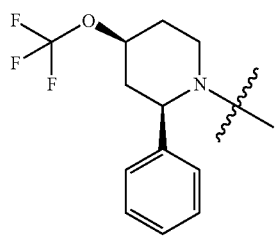
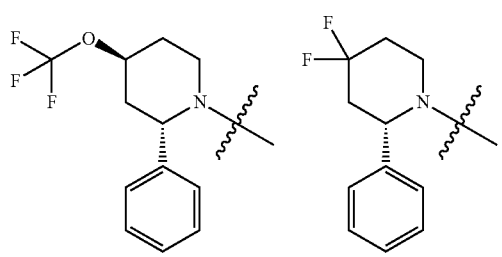
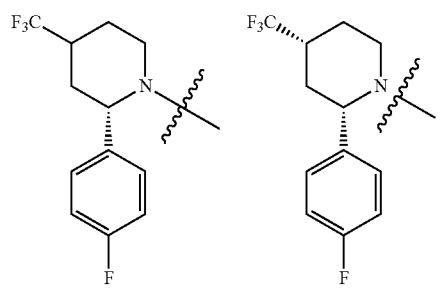
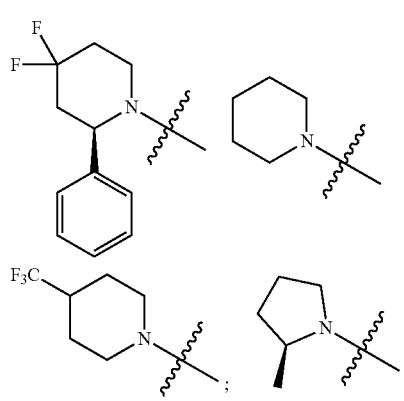
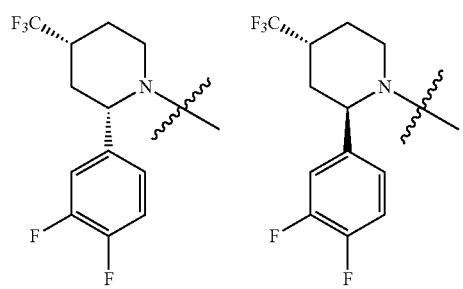
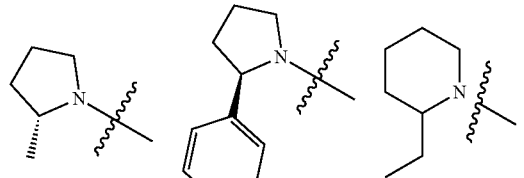
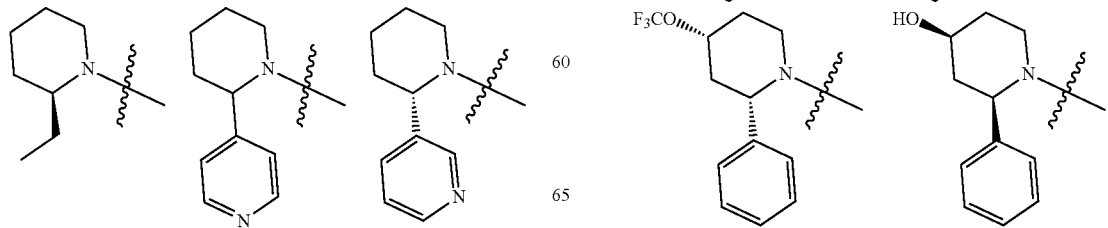

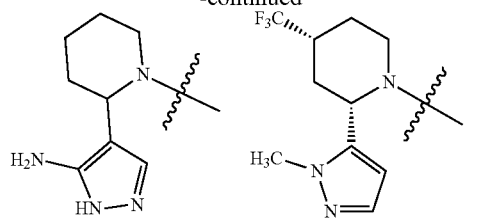
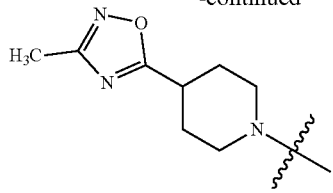
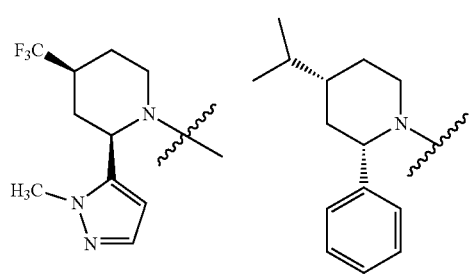
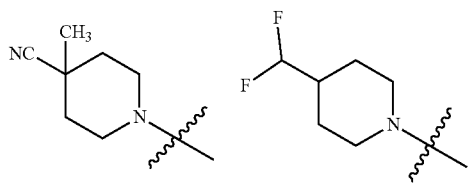
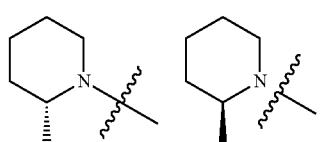
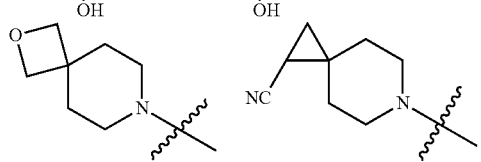
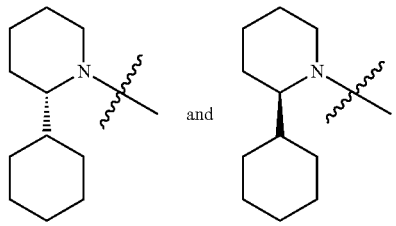
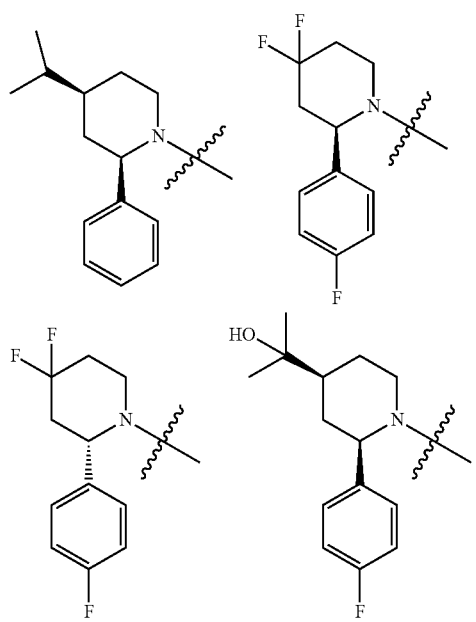
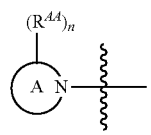
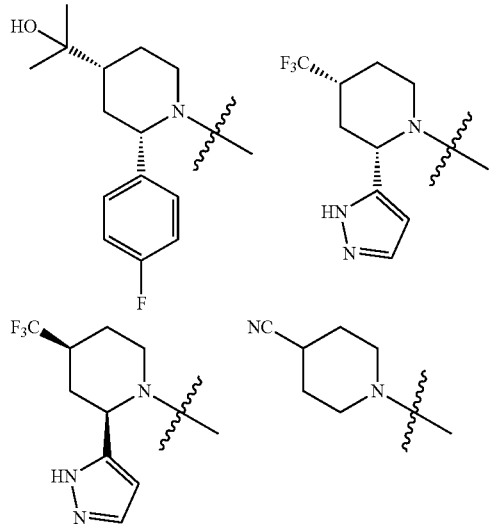
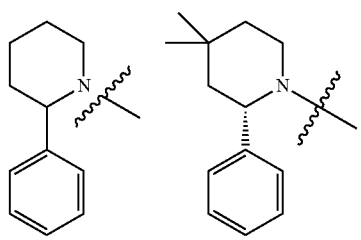
or a salt thereof.
E27. The compound of any one of E1, E2, E4, E5, E7-E11, E16, E18 and E20-E25 wherein the group
$$\underset{A}{\bigcirc}\!\!-\!\!N\!\!-\!\!\!\!\!\!\!\!\!\!\!\!\overset{(R^{AA})_n}{\phantom{|}}$$
is selected from the group consisting of:

-continued
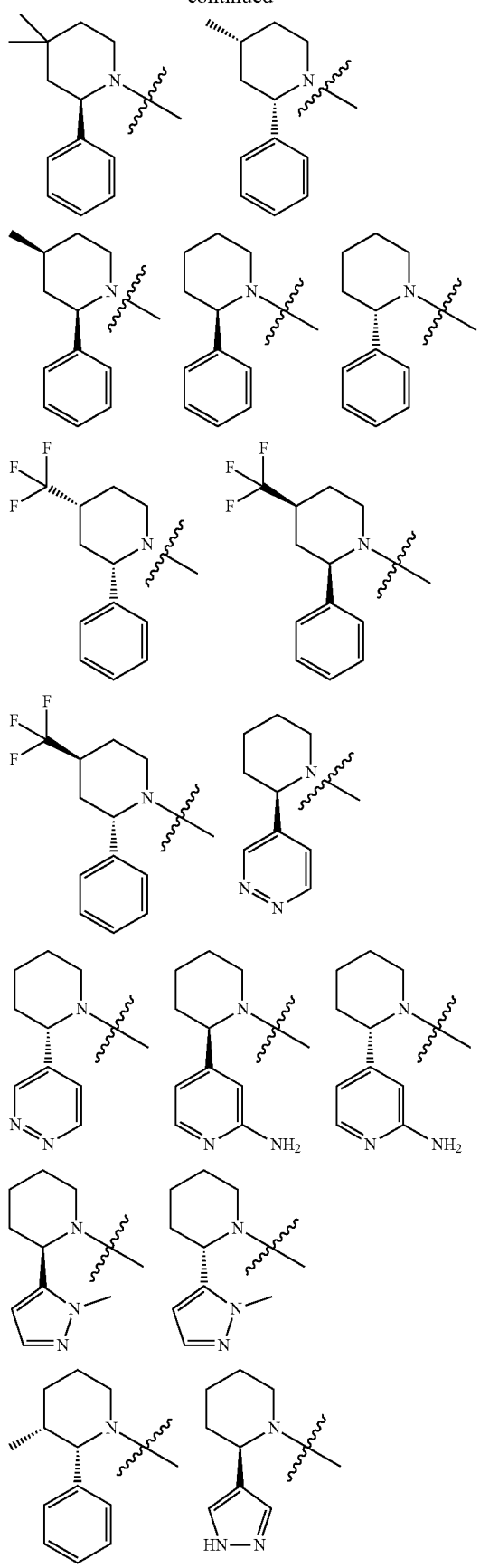
-continued
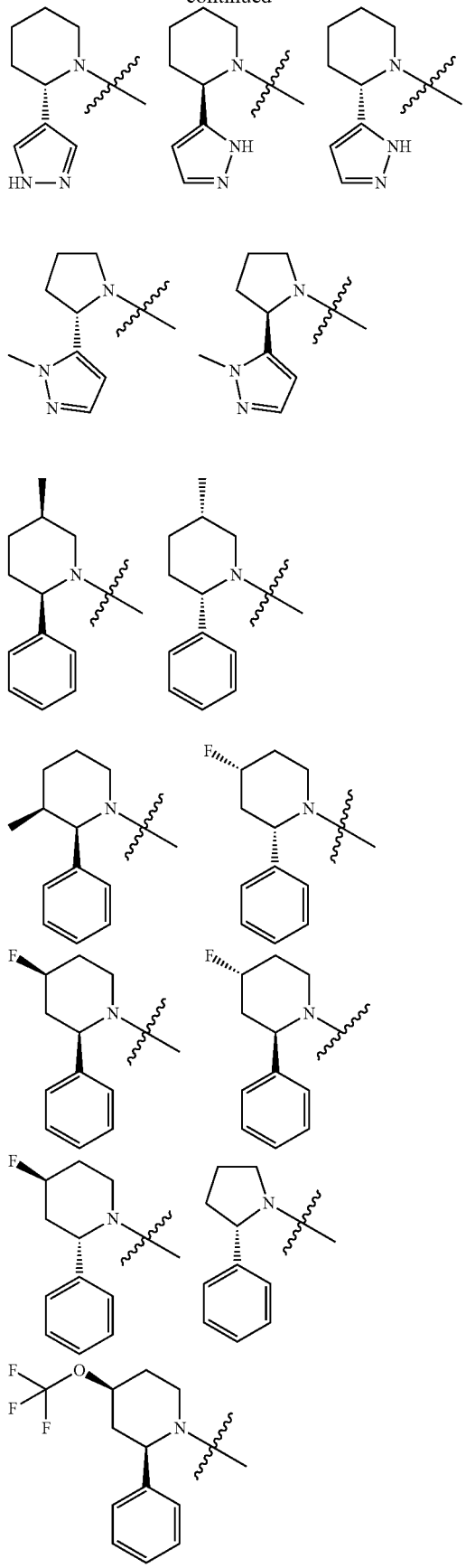

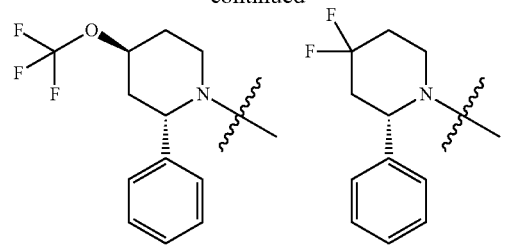
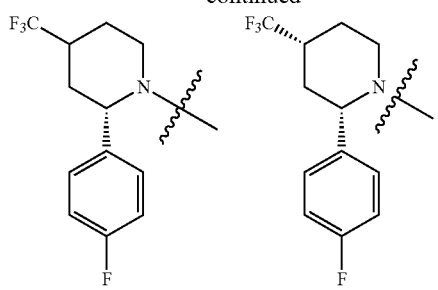
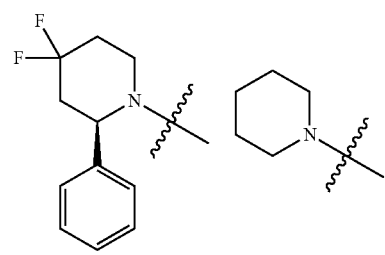
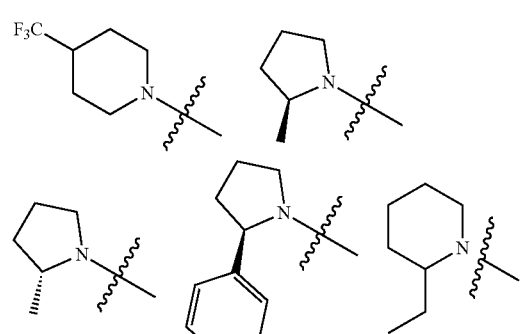

-continued
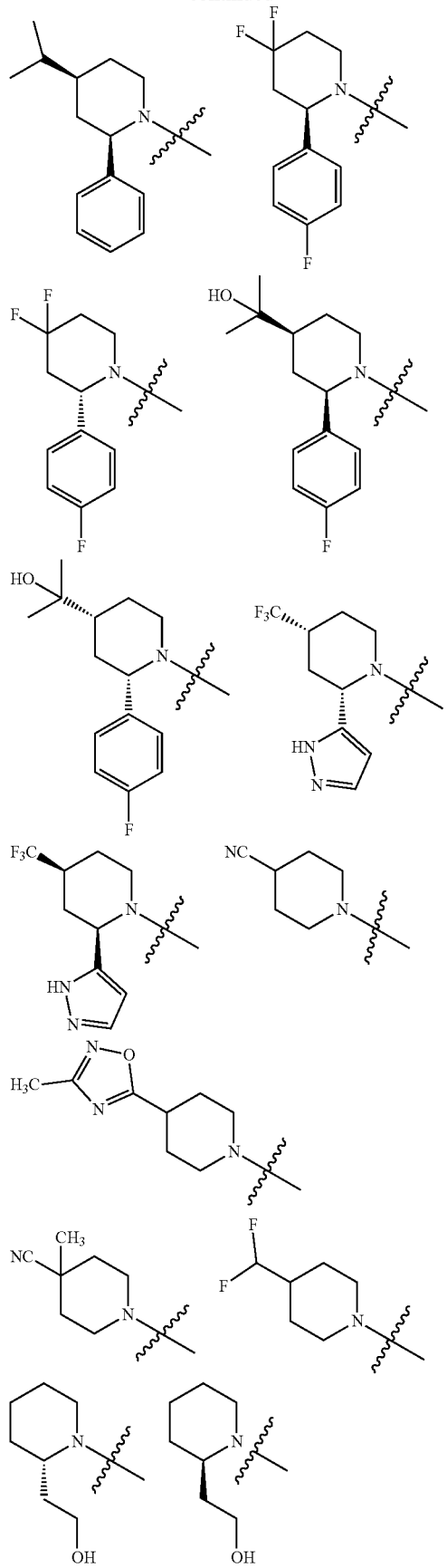
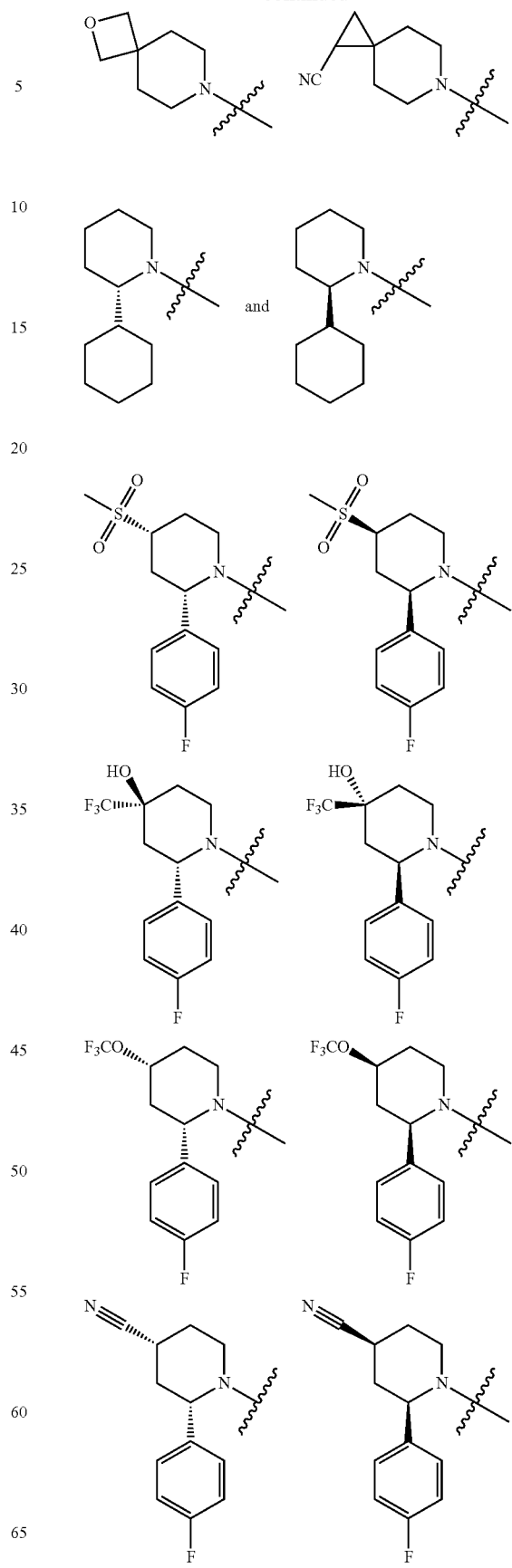

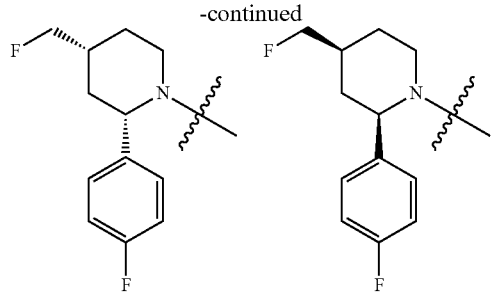
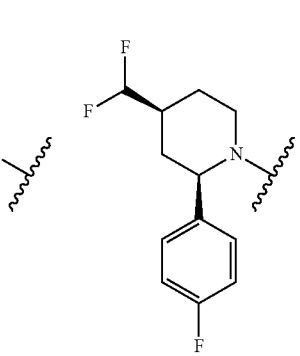
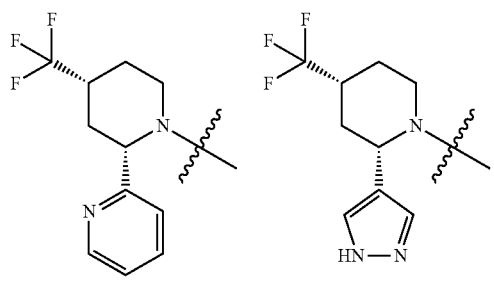
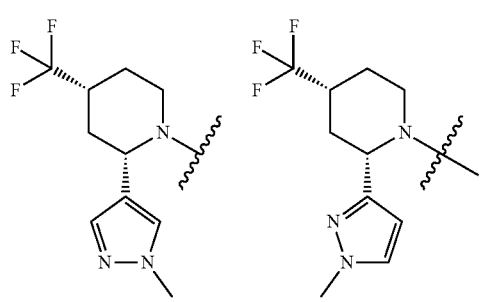
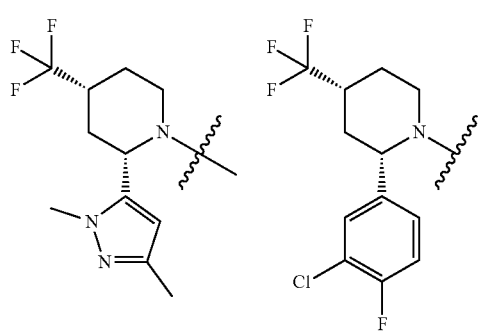
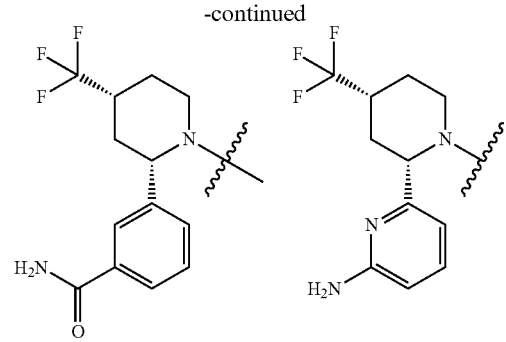
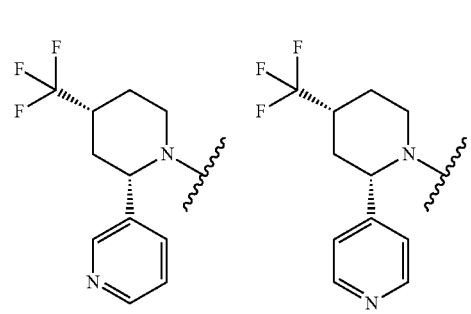
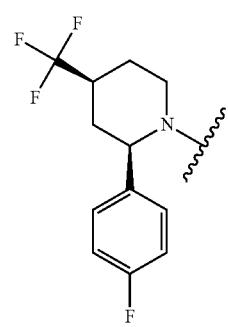
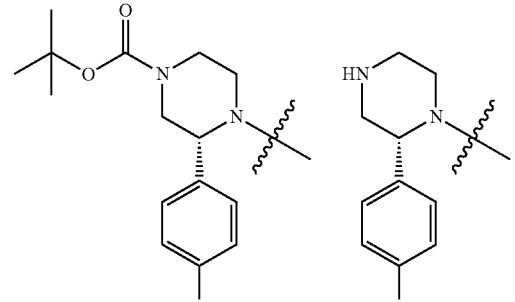
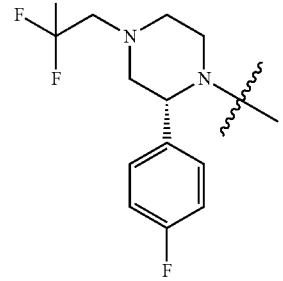

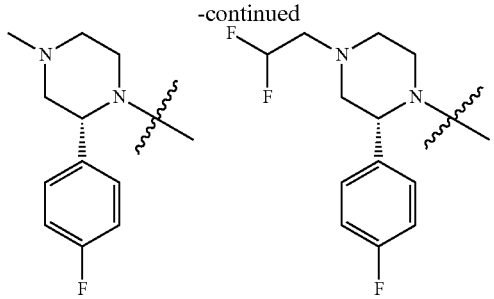

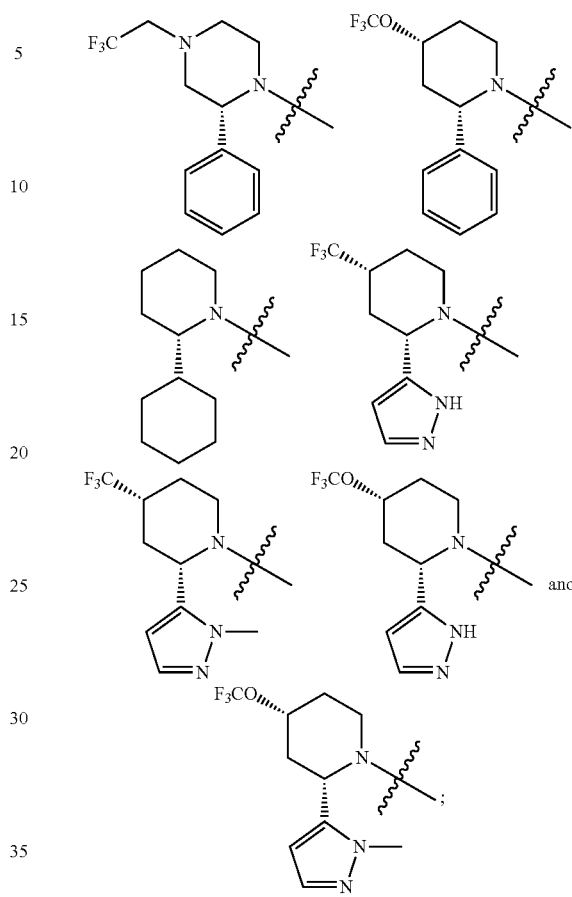

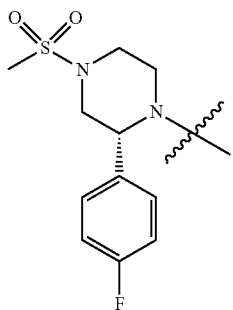

E28. The compound of any one of E1, E2, E4, E5, E7-E11, E16, E18 and E20-E25 wherein the group is selected from the group consisting of:

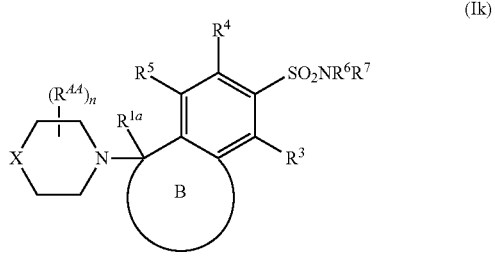

for a salt thereof.

E29. The compound of E2 or E5 which is a compound of formula Ik:

$$\text{(Ik)}$$

or a salt thereof; wherein, each $R^{AA}$ is independently selected from the group consisting of F, Cl, Br, I, —CN, —OR$^{A1}$, —(X$^{RA}$)-(3-15 membered carbocyclyl), —(X$^{RA}$)-(6-12 membered aryl), —(X$^{RA}$)-(5-12 membered heteroaryl), and —R$^{A2}$, wherein said (3-15 membered carbocyclyl), 6-12 membered aryl, and 5-12 membered heteroaryl of R$^{AA}$ is optionally substituted with from 1 to 5 substitutents R$^b$ independently selected from the group consisting of F, Cl, Br, I, C$_{1-4}$ alkyl, C$_{1-4}$ haloalkyl, amino, C$_{1-4}$ alkylamino and di(C$_{1-4}$alkyl)amino, and C$_{1-4}$ (halo)alkoxy; R$^{A1}$ is selected from the group consisting of hydrogen, C$_{1-8}$ alkyl, C$_{2-8}$ alkenyl, C$_{1-8}$ haloalkyl, C$_{3-8}$ cycloalkyl, phenyl and benzyl; R$^{A2}$ is selected from the group consisting of $C_{1-8}$ alkyl that is optionally substituted with one or more substituents selected from oxo (=O), fluoro, hydroxy, amino, $C_{1-4}$ alkylamino and di($C_{1-4}$alkyl)amino; $X^{RA}$ is selected from the group consisting of absent, —C(=O)—, and $C_{1-4}$ alkylene; wherein any $C_{1-4}$ alkylene, of $X^{RA}$ is optionally substituted with 1 to 3 substituents selected from the group consisting of $C_{1-4}$ alkyl, $C_{1-4}$ haloalkyl, and phenyl that is optionally substituted with 1 to 5 substitutents selected from, F, Cl, Br, I, —$NH_2$, —OH, —CN, —$NO_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino;

ring "A" is a 5-12 membered heteroaryl, or a 3-15 membered heterocyclyl;

Ring B is a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from $C_{1-4}$ alkyl, halo, and halo$C_{1-4}$ alkyl;

$R^{1b}$ is H or $C_{1-4}$ alkyl;

$R^3$, $R^4$, and $R^5$ are each independently selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy;

$R^6$ is selected from the group consisting of H, $C_{1-8}$ alkyl, $C_{3-8}$ cycloalkyl, aryl, and aryl($C_{1-4}$ alkyl);

and $R^7$ is selected from the group consisting of $C_{1-8}$ alkyl, 3-15 membered heterocyclyl, 5-12 membered heteroaryl, —C(O)N($R^c$)$_2$ and —C(=NCN)N($R^c$)$_2$; or $R^6$ and $R^7$, together with the nitrogen to which they are attached, form a 3-15 membered heterocyclyl or 5-12 membered heteroaryl; wherein any $C_{1-8}$ alkyl, $C_{3-8}$ cycloalkyl, aryl, aralkyl, 3-15 membered heterocyclyl, and 5-12 membered heteroaryl is optionally substituted with one of more groups $R^d$ that are independently selected from the group consisting of F, Cl, Br, I, —$NH_2$, —OH, —CN, —$NO_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino; each $R^c$ is independently selected from the group consisting of hydrogen, $C_{1-8}$ alkyl, $C_{3-8}$ cycloalkyl, phenyl and benzyl;

n is 0, 1, 2, 3, 4, 5, or 6; and

X is $CH_2$, $NR^{42}$, S, or O.

E30. The compound of E2 or E5 which is a compound of formula Im:

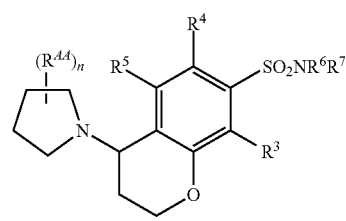

(Im)

or a salt thereof.

E31. The compound of E2 or E5 which is a compound of formula In:

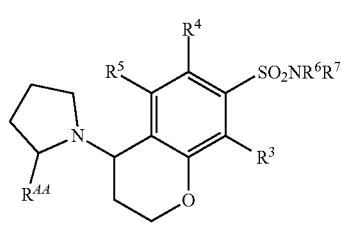

(In)

or a salt thereof.

E32. The compound of E2 or E5 which is a compound of formula Io:

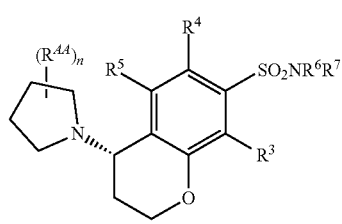

(Io)

or a salt thereof.

E33. The compound of E2 or E5 which is a compound of formula In:

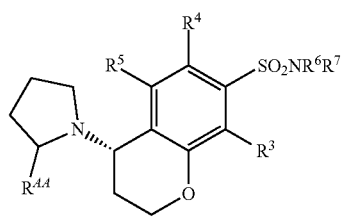

(Ip)

or a salt thereof.

E34. The compound of any one of E28-E33 wherein $R^{AA}$ is phenyl.

E35. The compound of any one of E28-E33 wherein $R^{AA}$ is 1-methyl-1H-pyrazol-5-yl.

E36. The compound of E2, E5, or E8 which is a compound of formula Is:

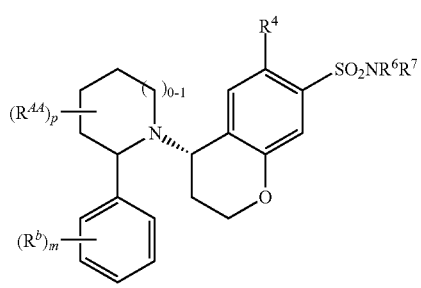

(Is)

wherein m is 0, 1, 2, 3, 4 or 5; and p is 0, 1, 2, 3, 4, or 5; or a salt thereof.

E37. The compound of E16 or E17 wherein $R^2$ is selected from the group consisting of F, Cl, Br, I, —CN, $C_{1-8}$ alkyl, $C_{3-8}$ cycloalkyl, $C_{1-8}$ haloalkyl and $C_{1-8}$ alkoxy; and $R^4$ is selected from the group consisting of F, Cl, Br, I, —CN, $C_{1-8}$ alkyl, $C_{3-8}$ cycloalkyl, $C_{1-8}$ haloalkyl and $C_{1-8}$ alkoxy.

E38. The compound of E16, E17, or E37 wherein $R^{1a}$ is H; and $R^{1b}$ is H.

E39. A compound selected from the group consisting of:

-continued

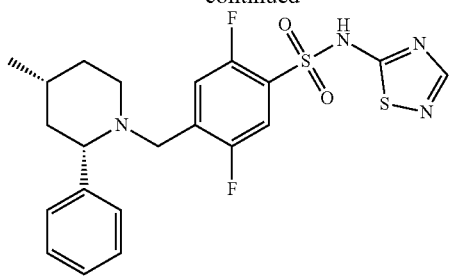

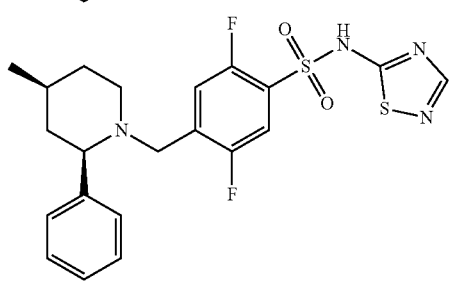

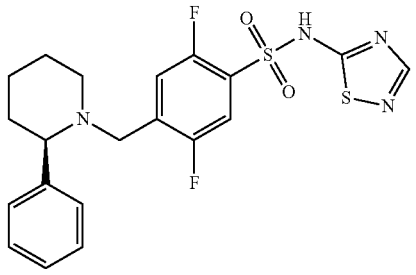

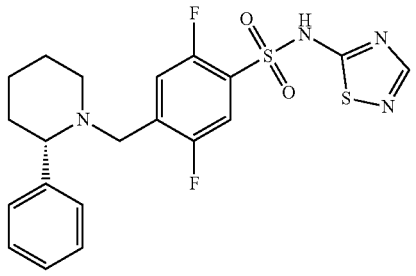

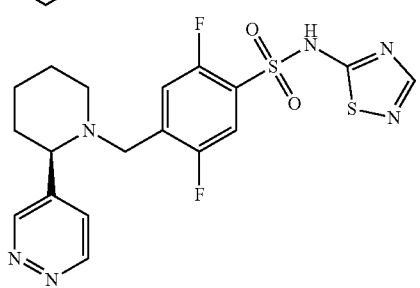

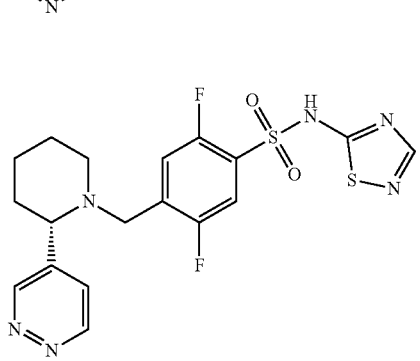

33
-continued
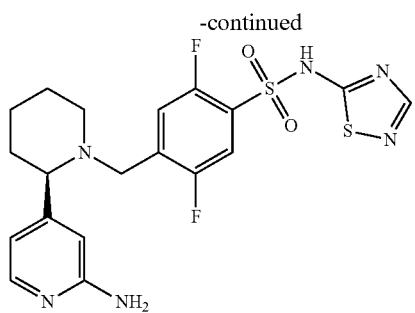
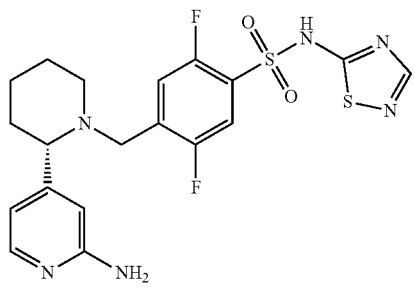
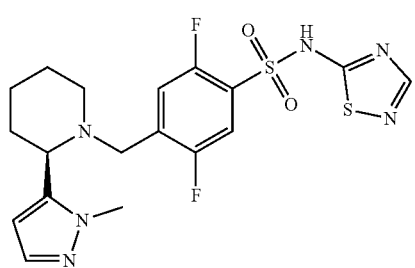
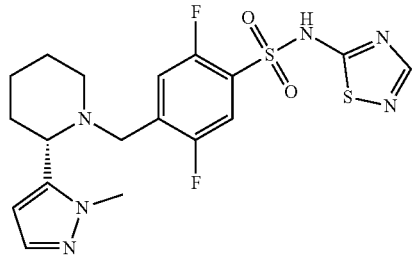
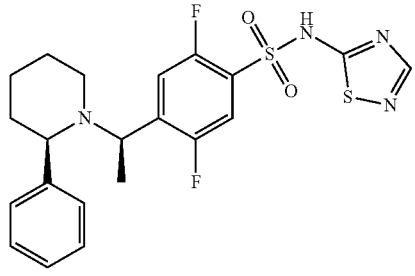
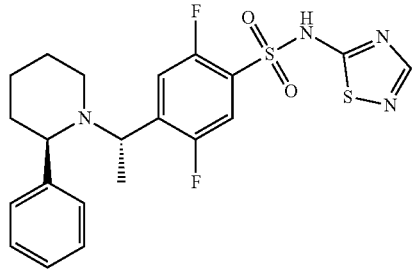
34
-continued
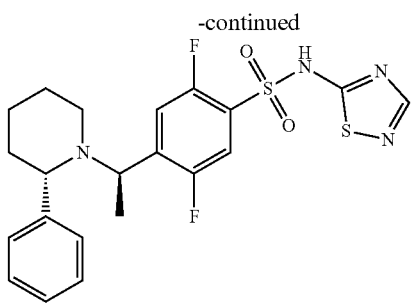
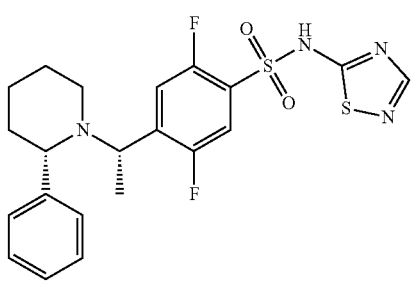
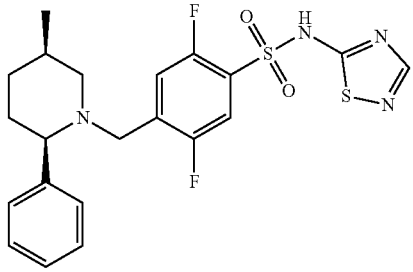
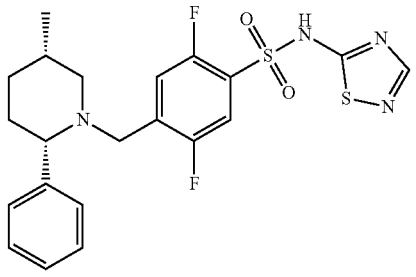
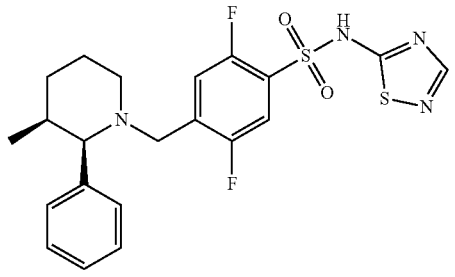
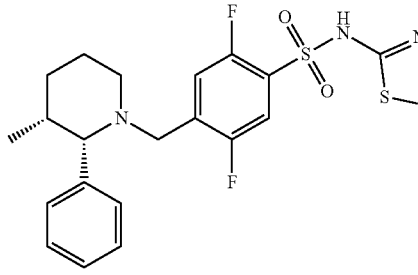

35
-continued
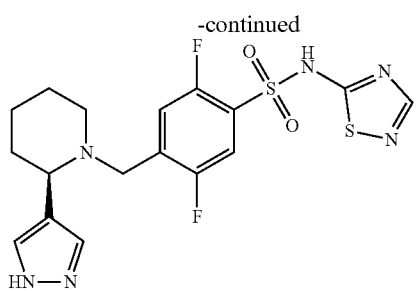
36
-continued
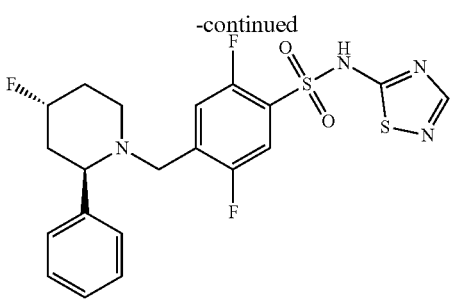
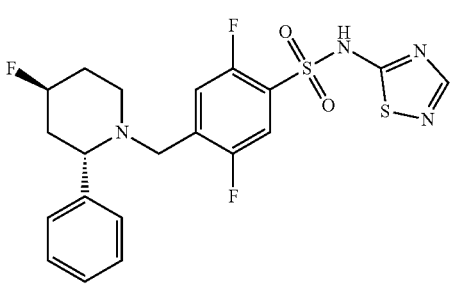
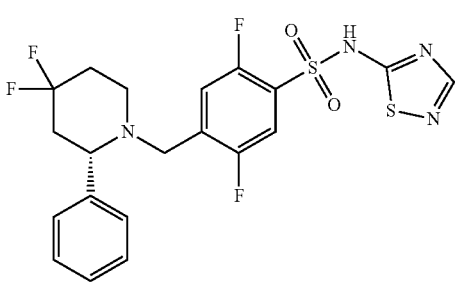
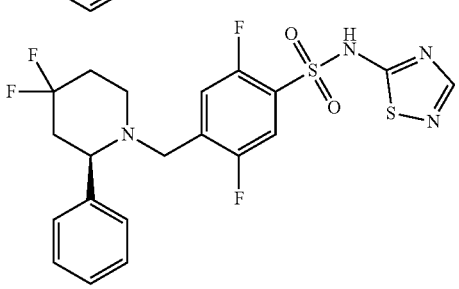
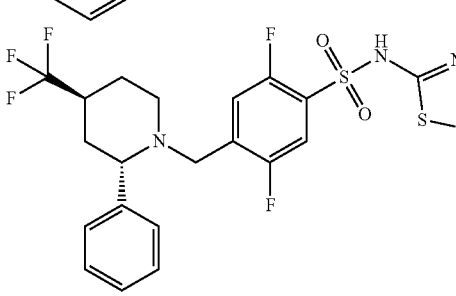
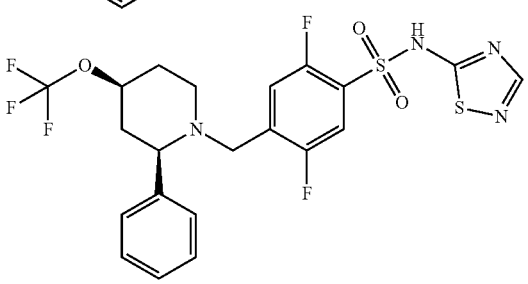

-continued
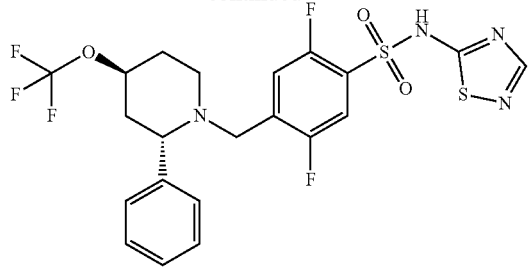
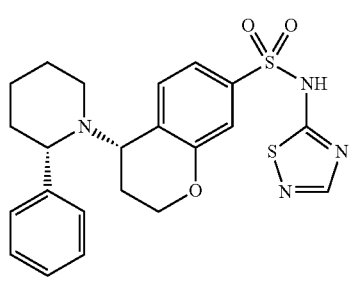
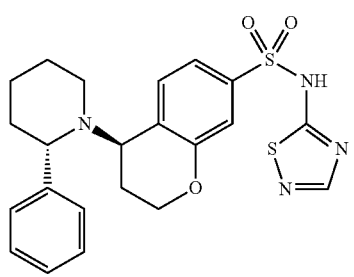
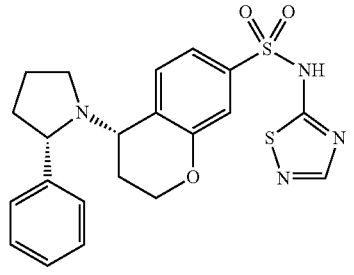
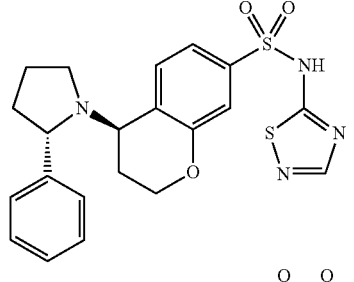
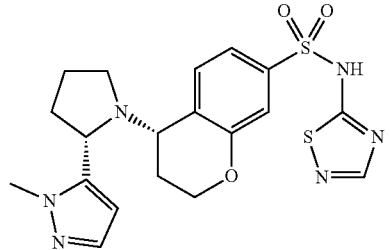
-continued
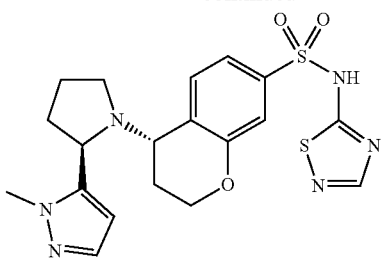
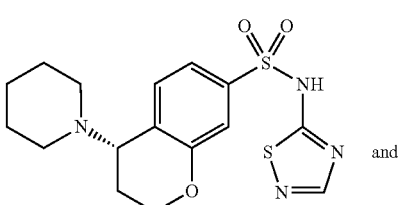
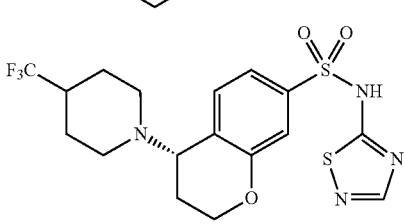
and
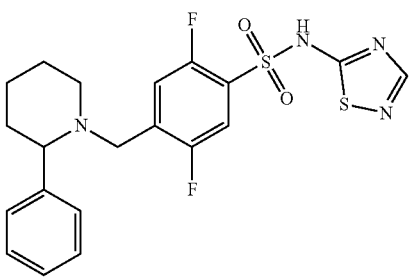
and salts thereof.
E40. The compound of E1 selected from the group consisting of:
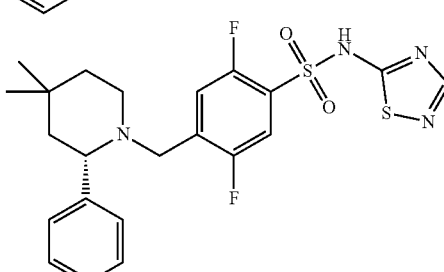
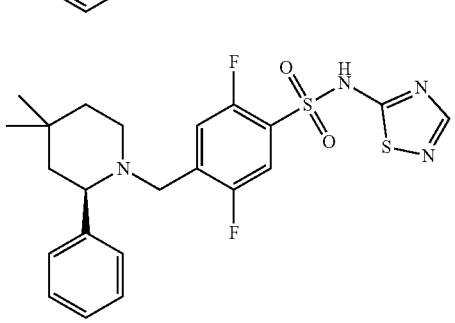

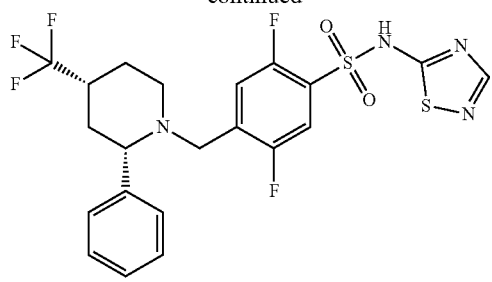
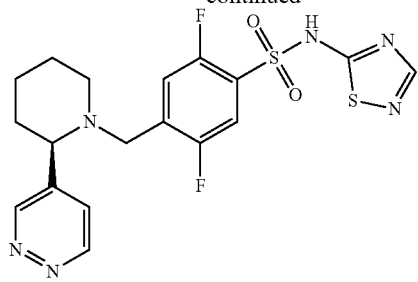
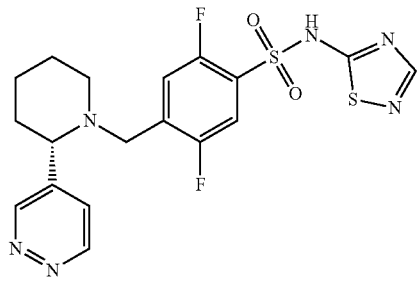
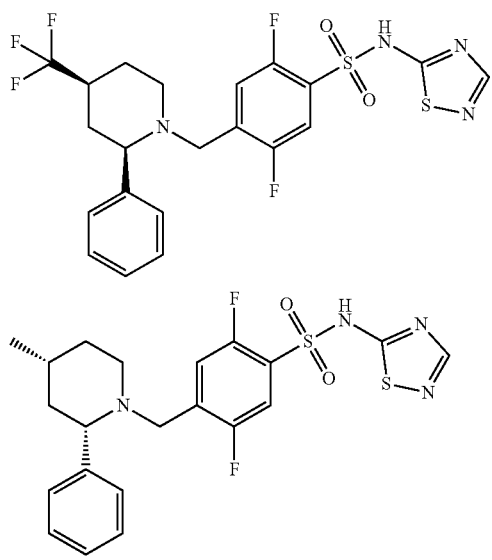
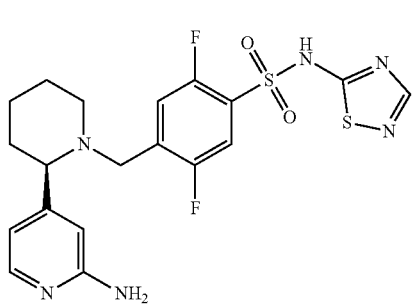
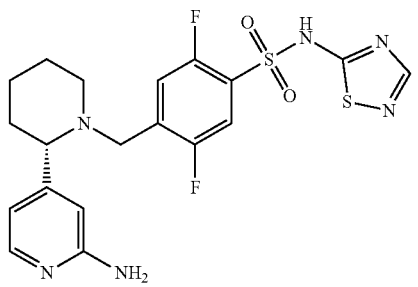
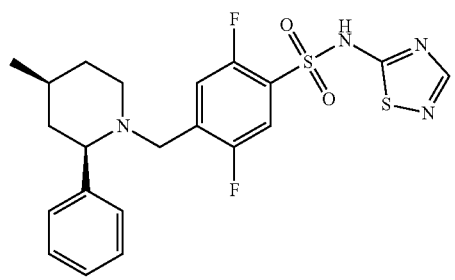
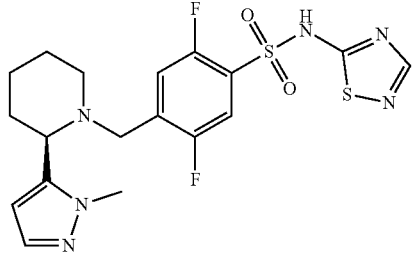
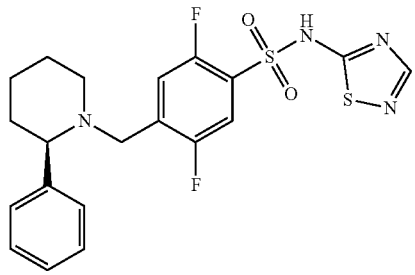
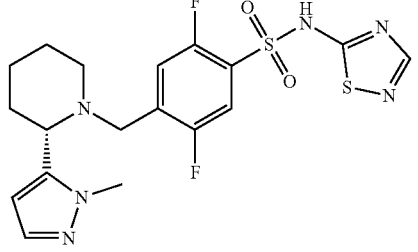
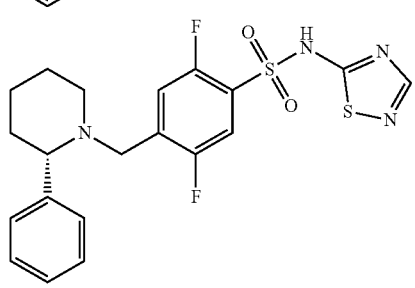

-continued
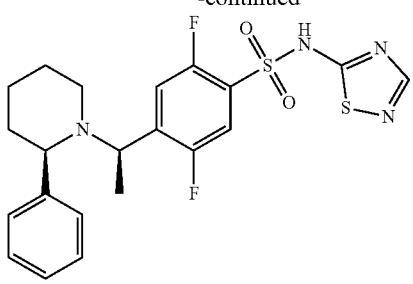
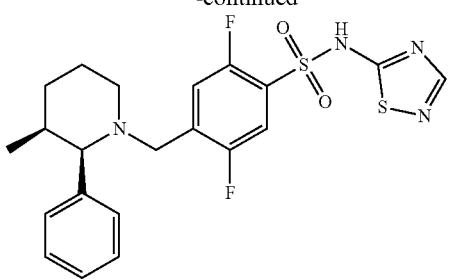
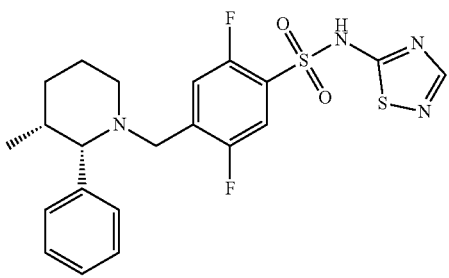
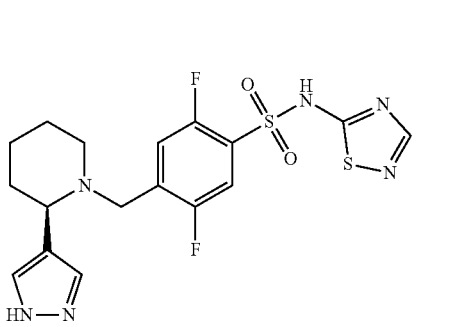
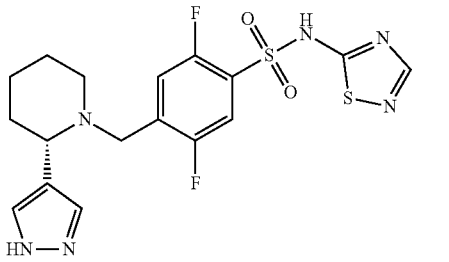
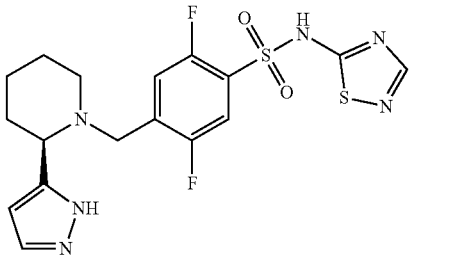
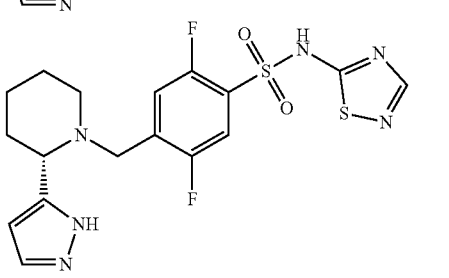

-continued
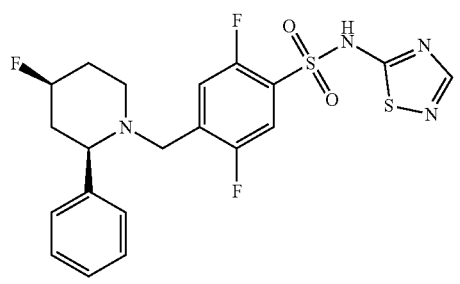
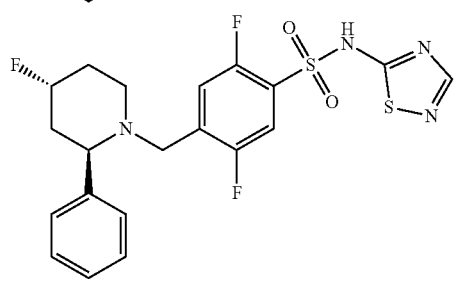
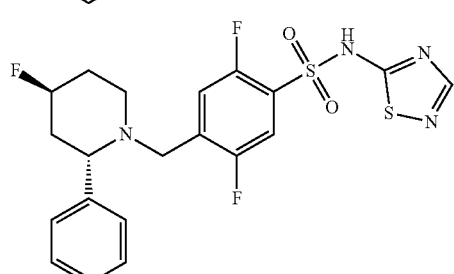
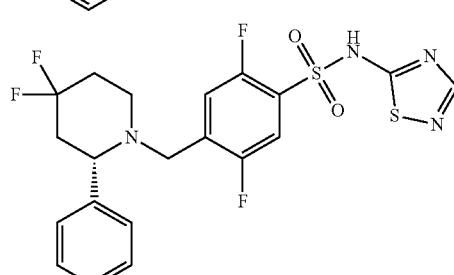
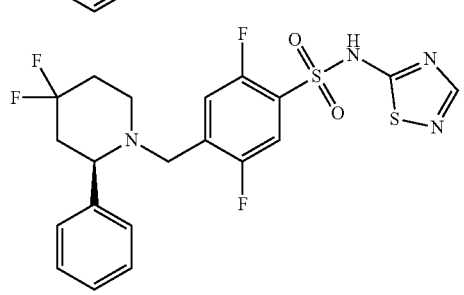
-continued
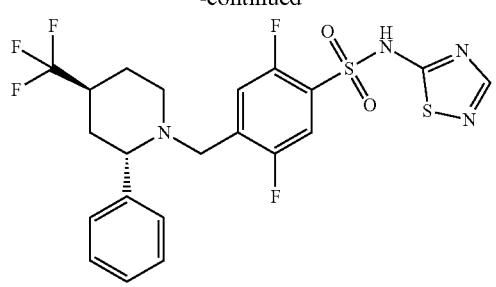
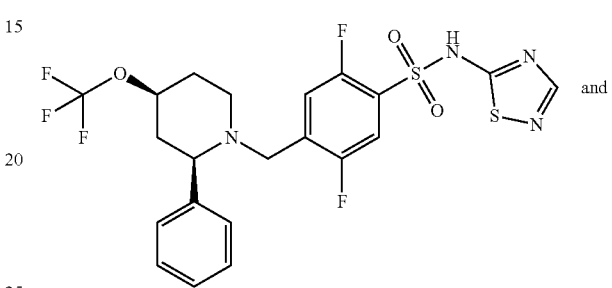 and
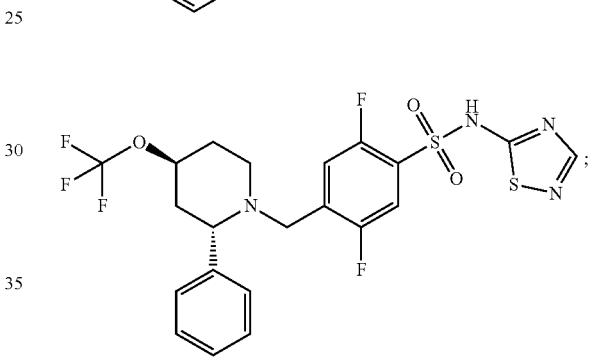;
and salts thereof.
E41. The compound of E2 selected from the group consisting of:
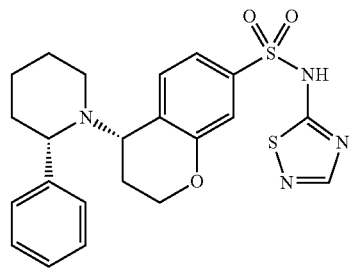
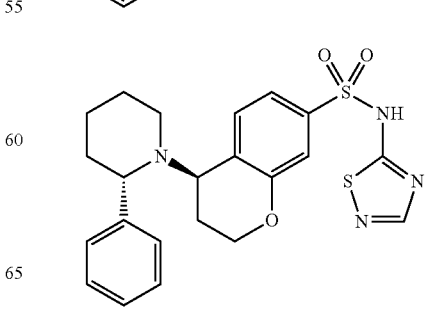

-continued
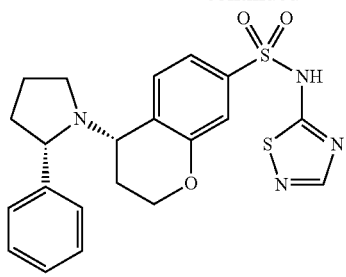
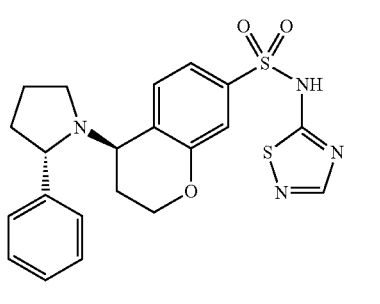
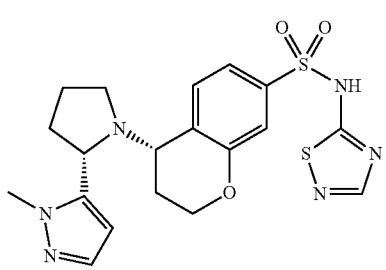
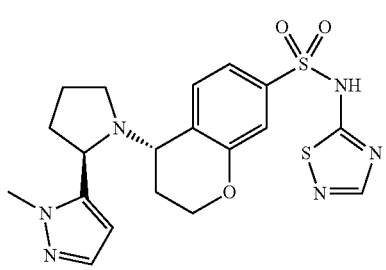
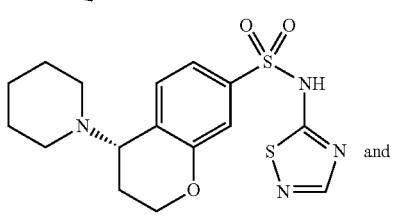 and
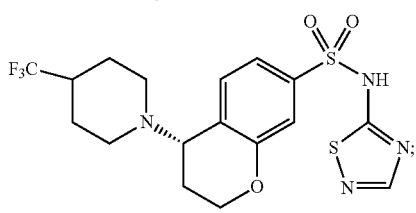
and salts thereof.
E42. The compound of E2 selected from the group consisting of:
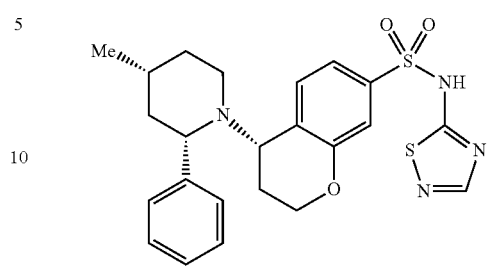
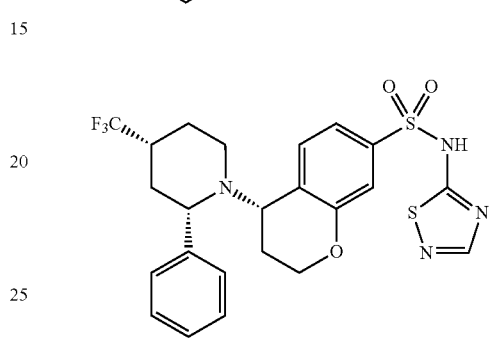
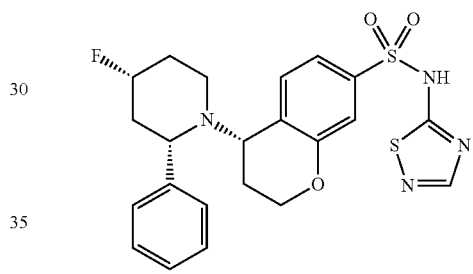
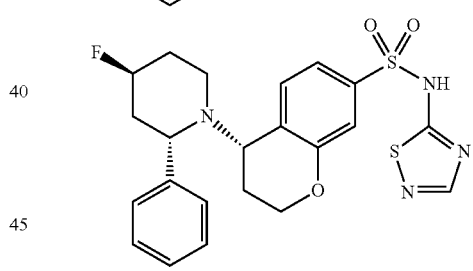
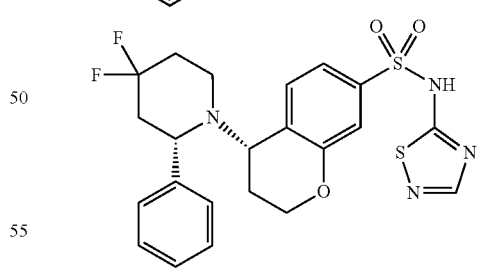
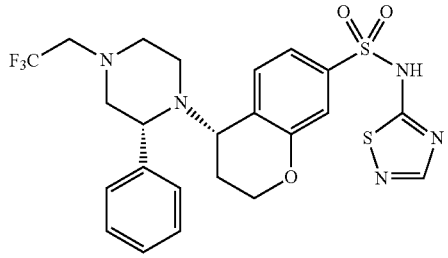

47
-continued
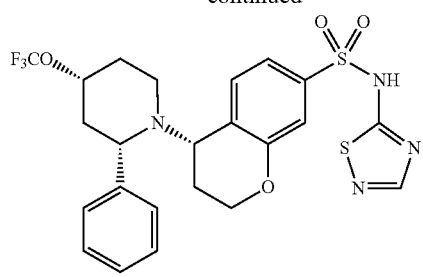
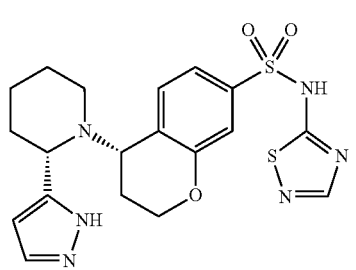
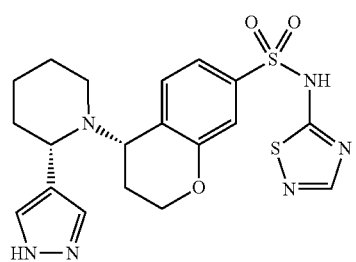
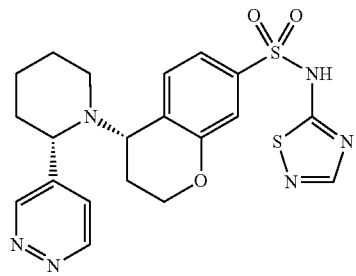
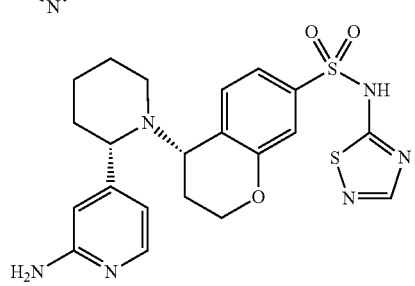
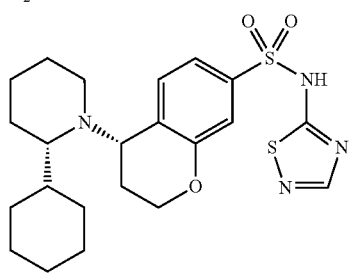
48
-continued
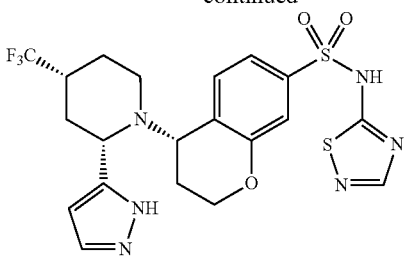
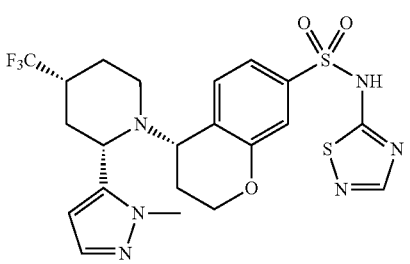
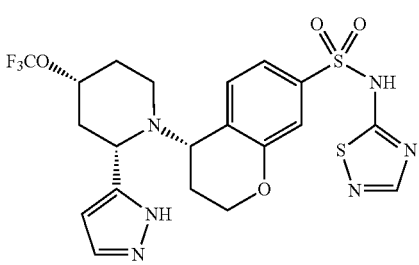
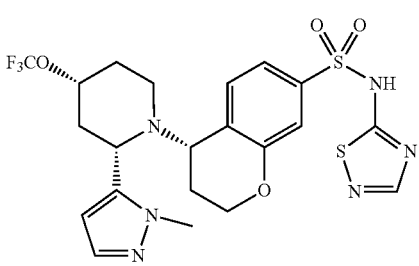
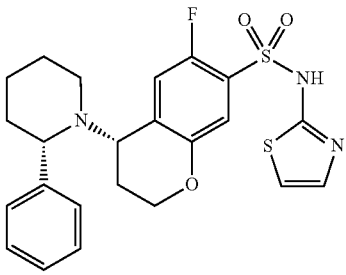
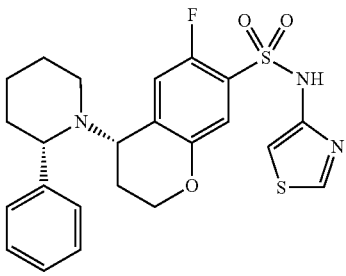

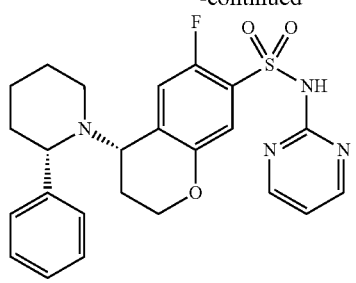
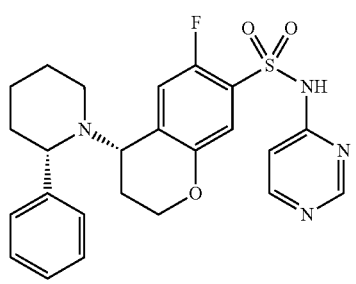
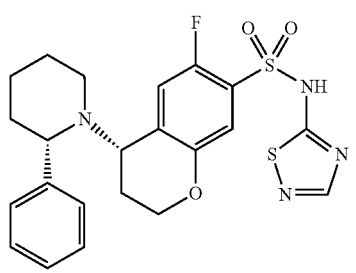
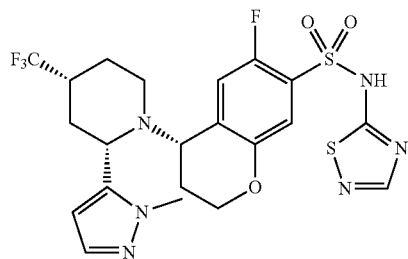
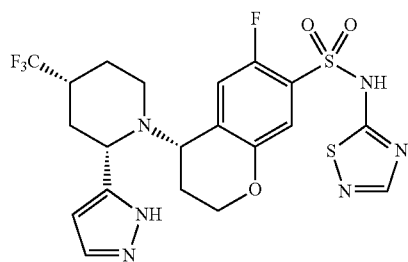
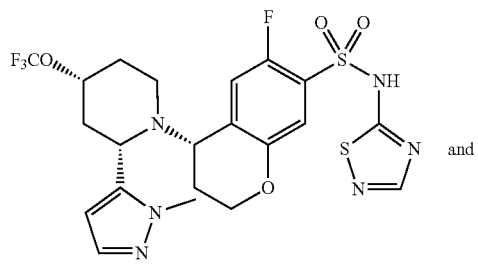 and
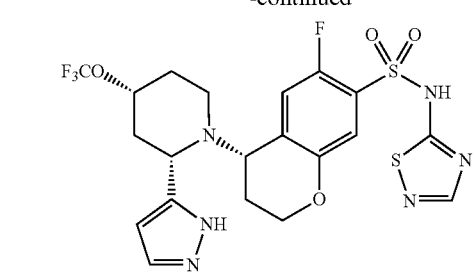
and salts thereof.
E43. The compound selected from the group consisting of:
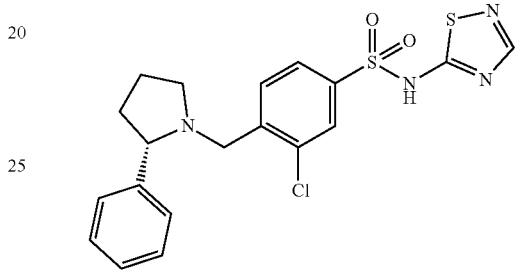
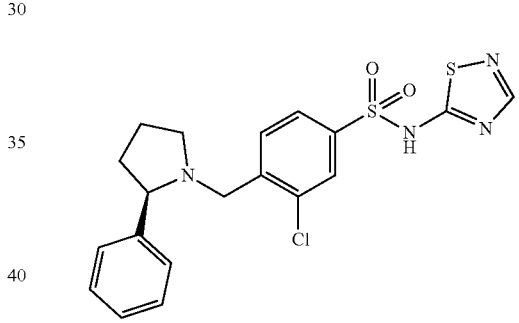
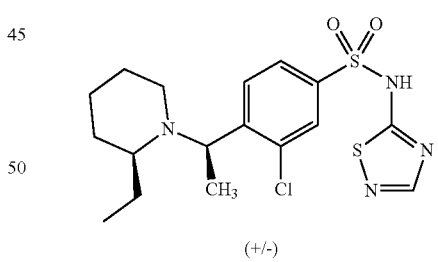
(+/−)
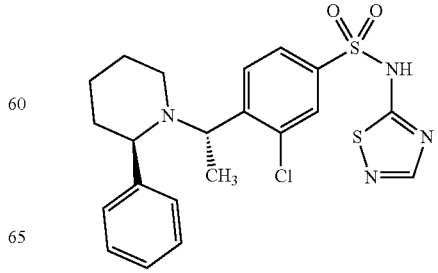

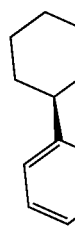
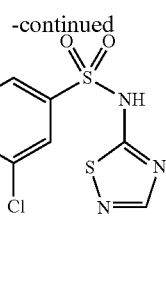
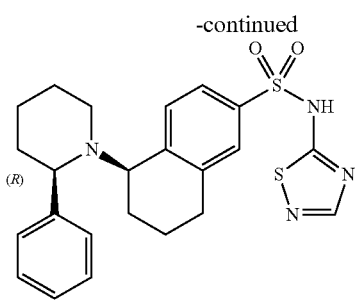
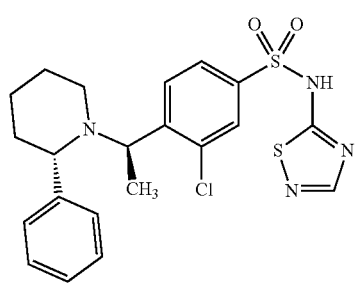
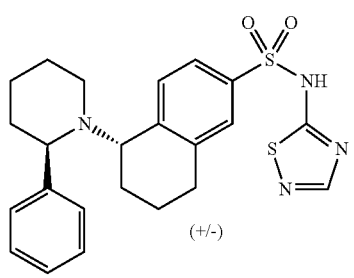
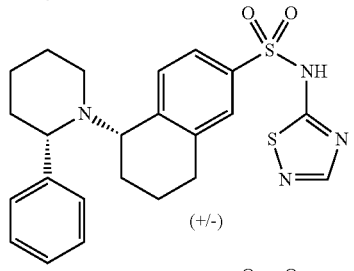
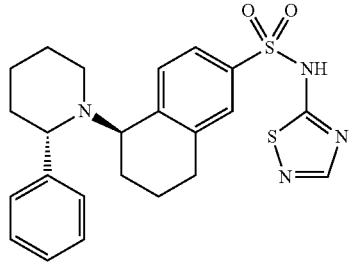
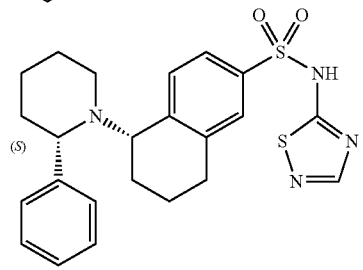
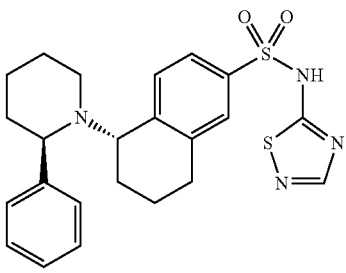
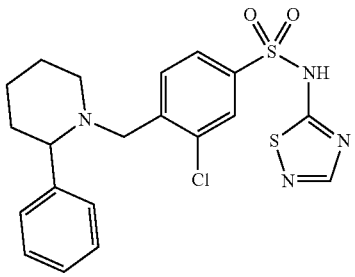
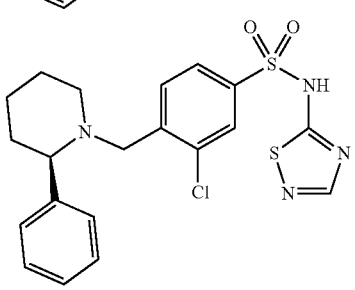
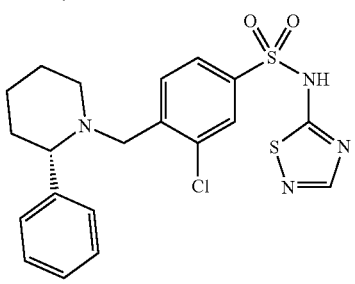
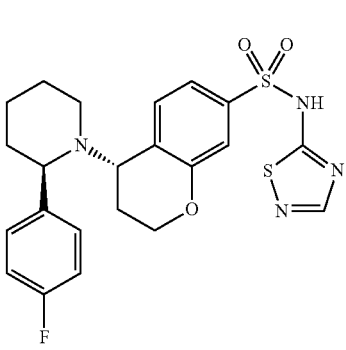

53
-continued
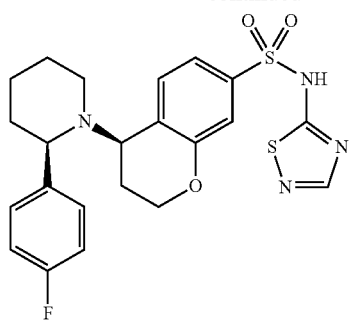
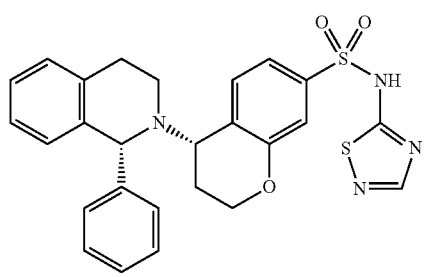
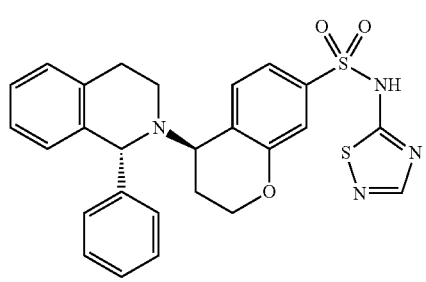
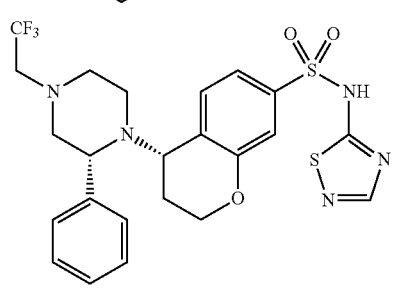
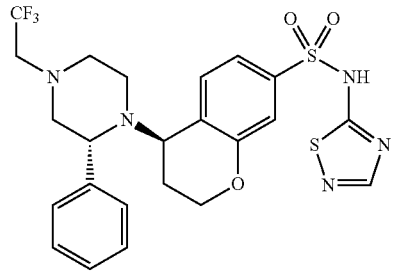
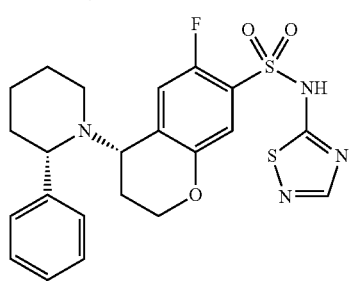
54
-continued
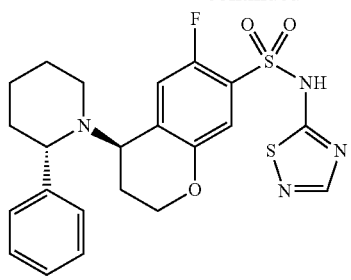
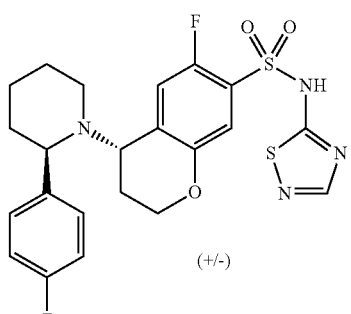
(+/-)
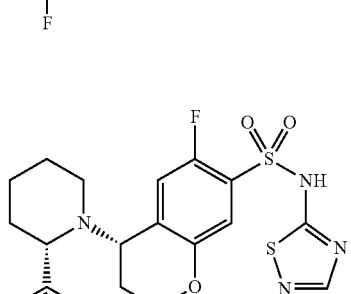
(+/-)
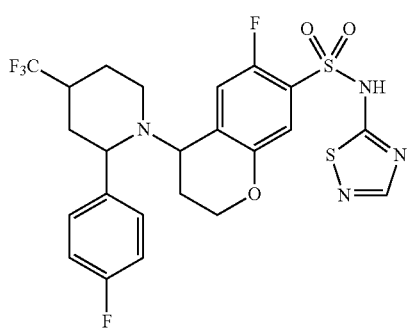
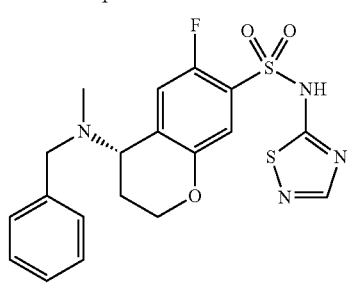

55
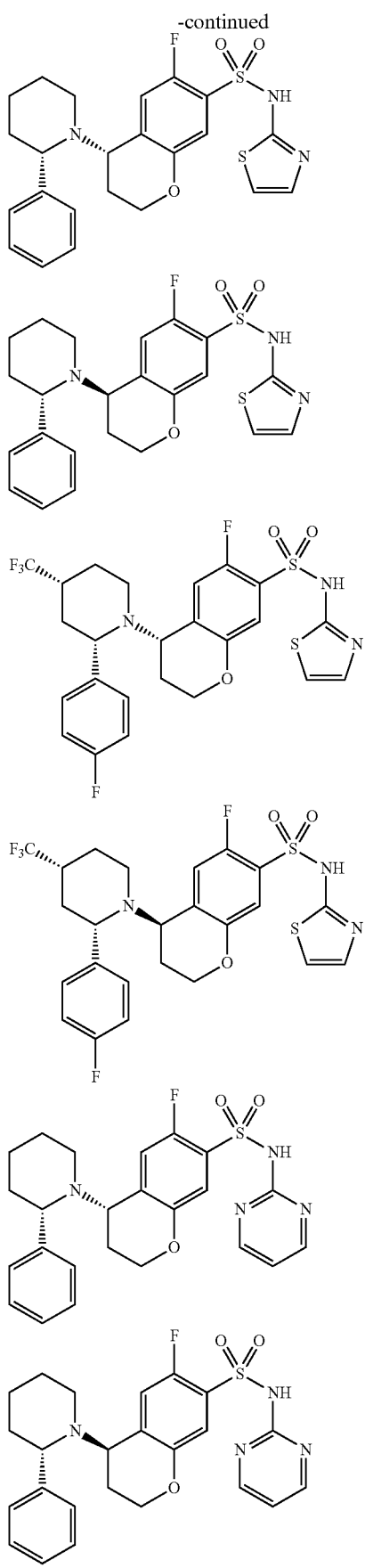
56
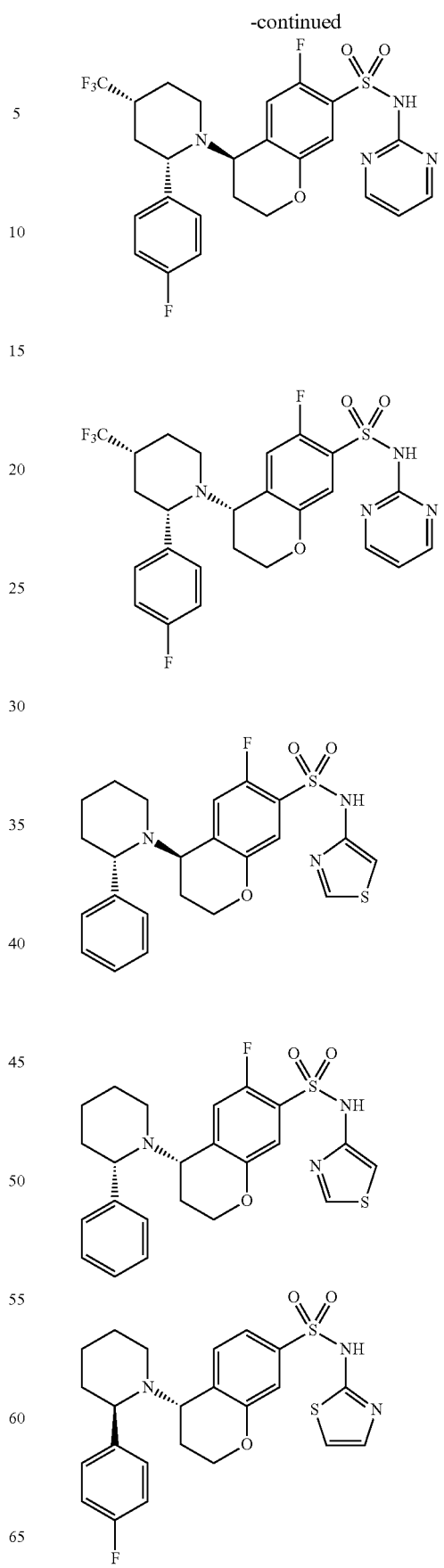

57
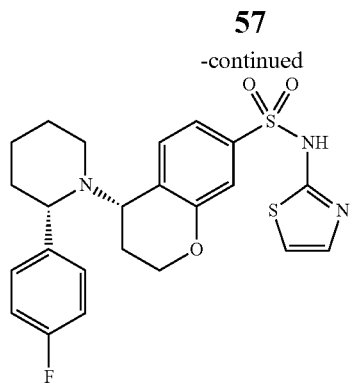
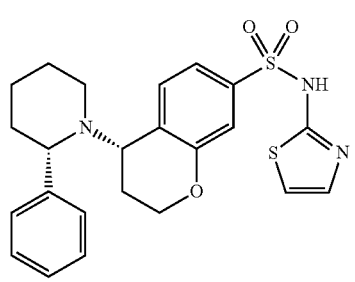
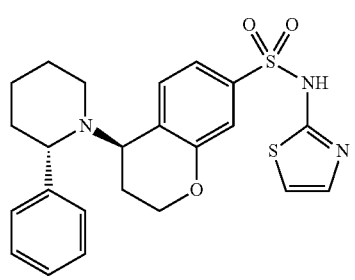
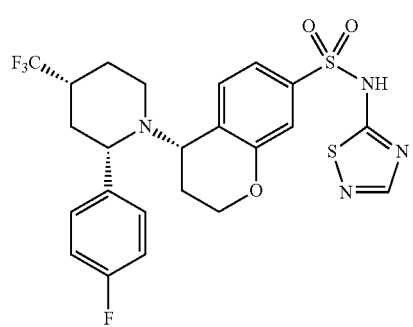
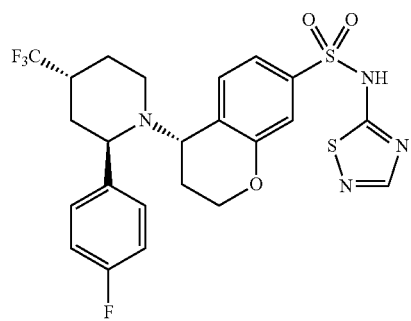
58
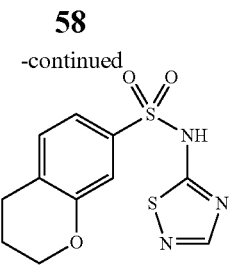
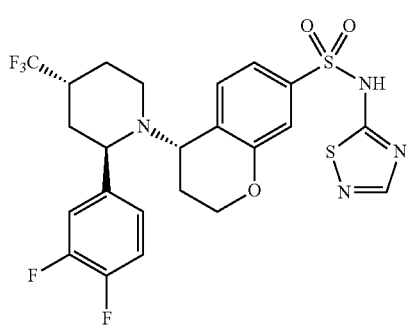
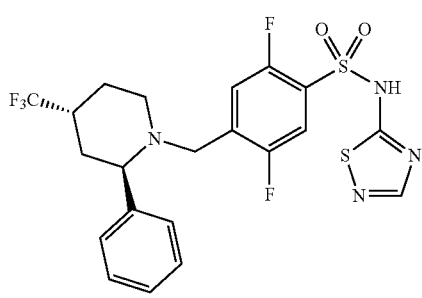
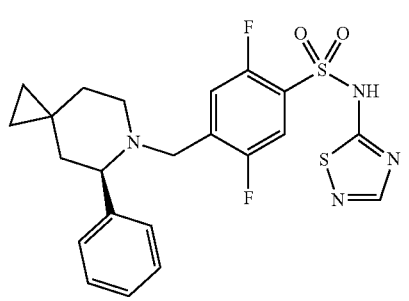
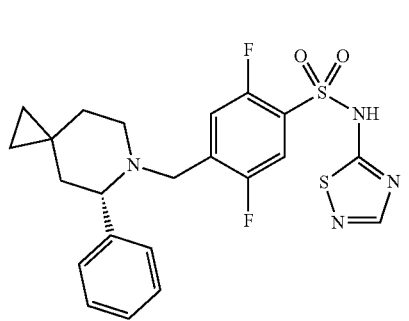

59
-continued
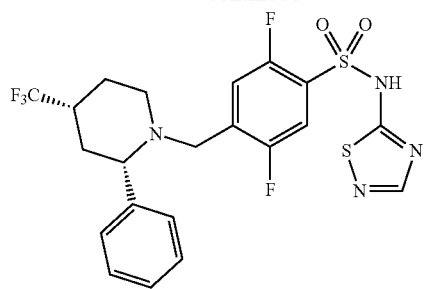
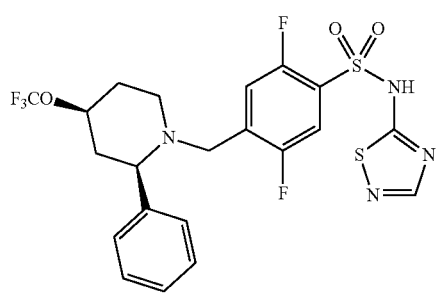
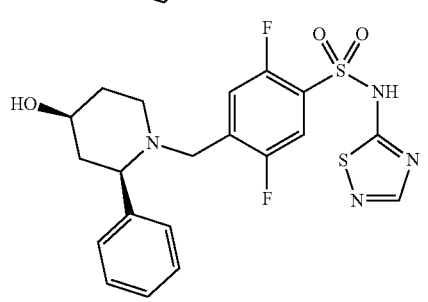
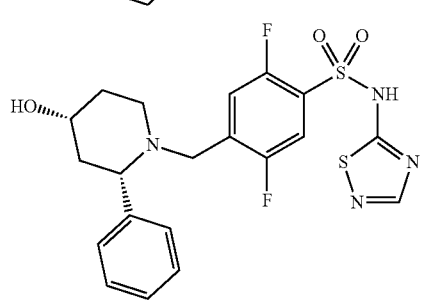
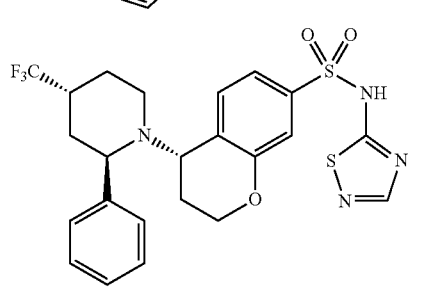
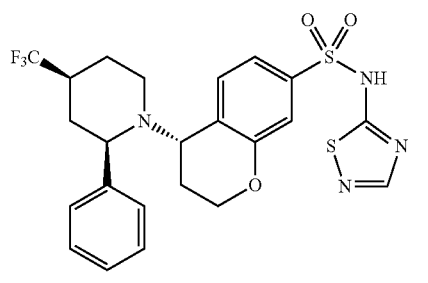
60
-continued
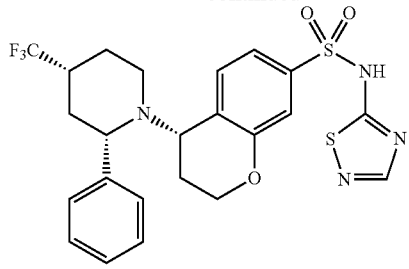
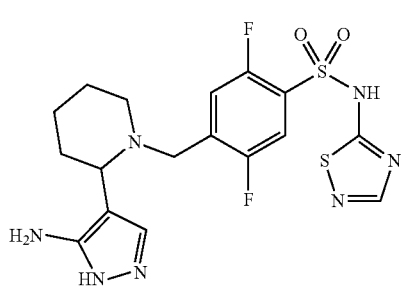
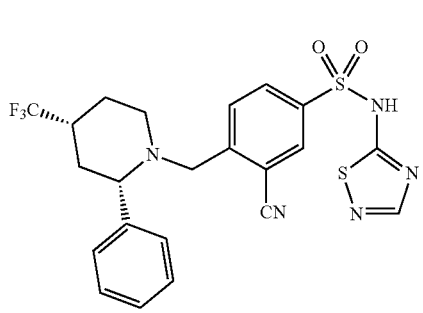
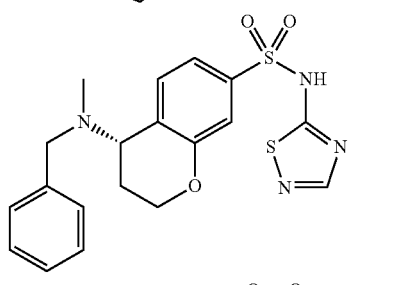
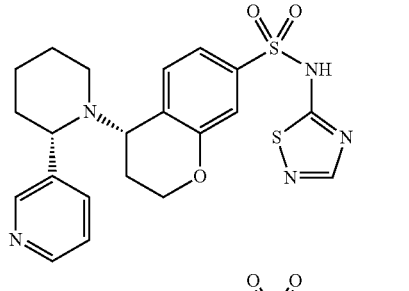
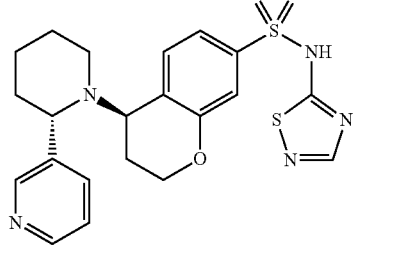

61
-continued
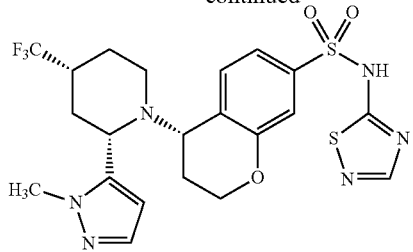
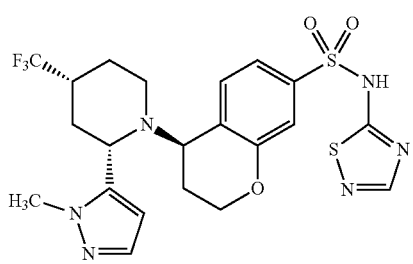
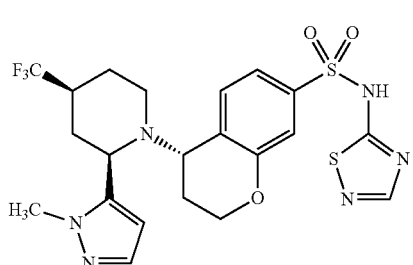
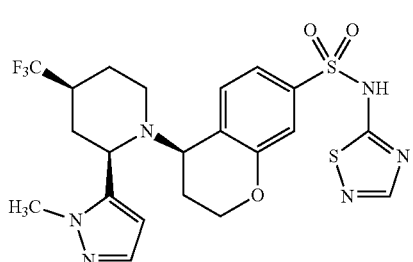
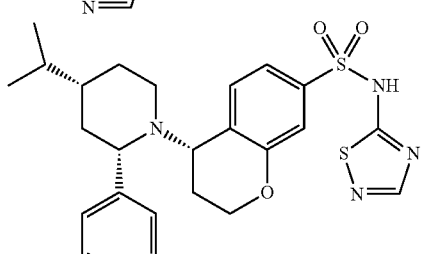
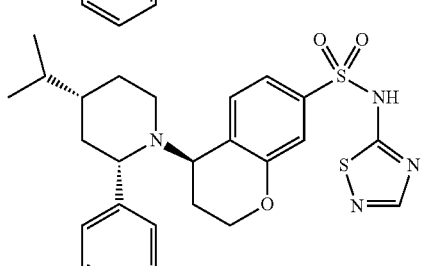
62
-continued
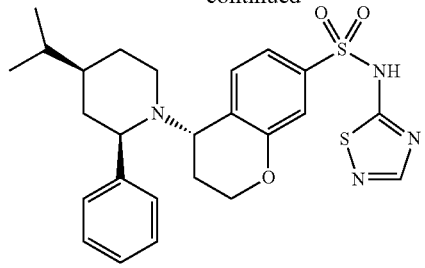
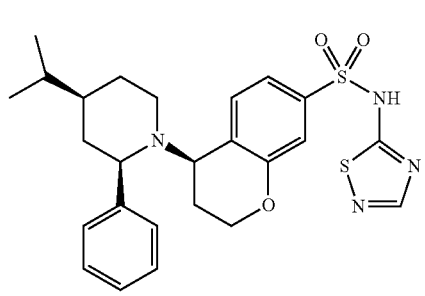
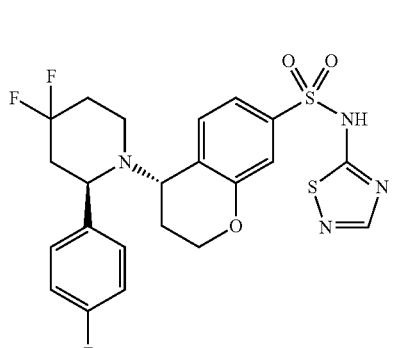
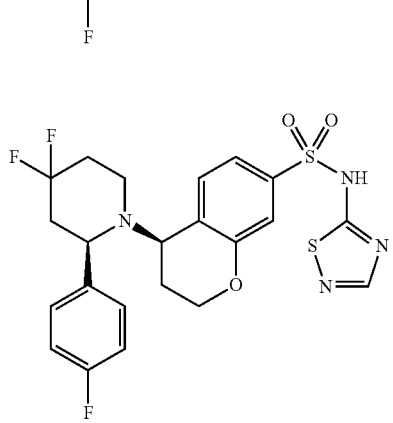
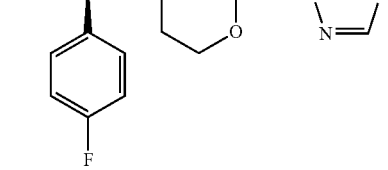
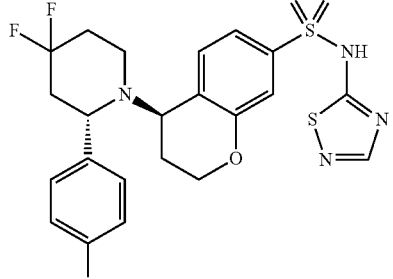

63
-continued
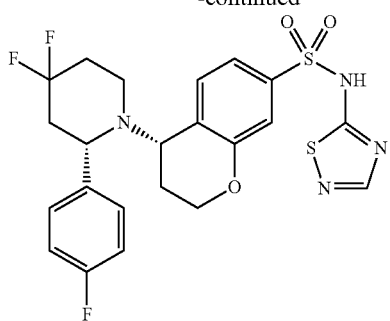
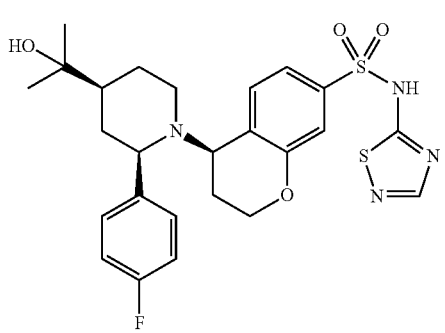
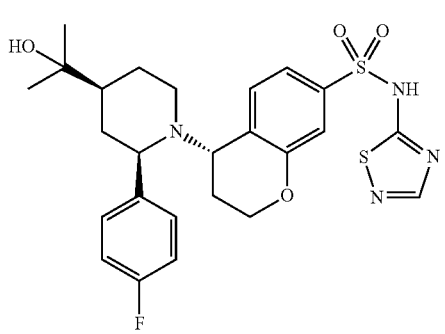
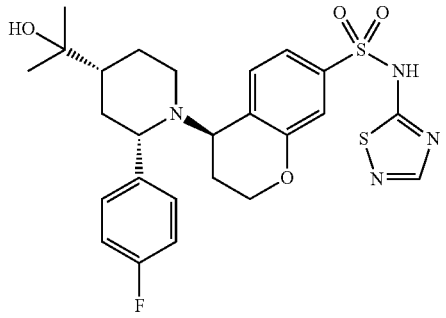
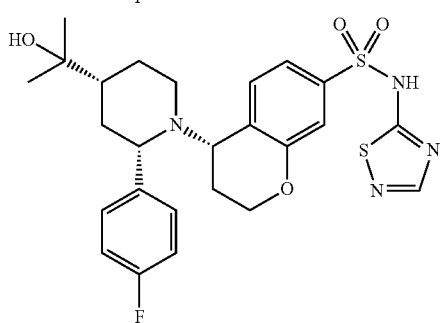
64
-continued
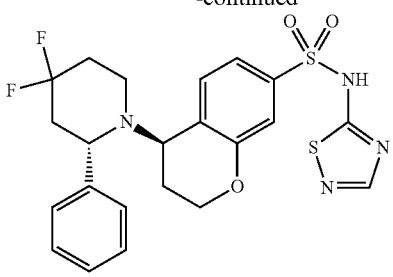
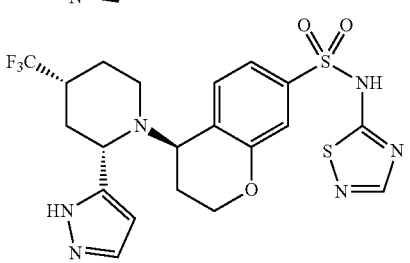

65
-continued
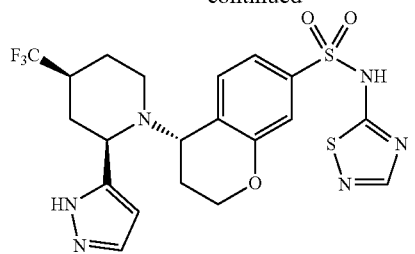
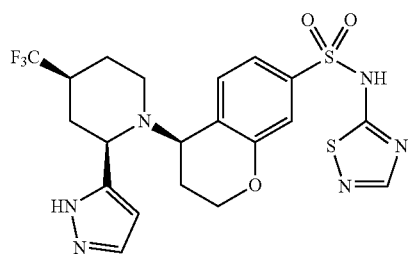
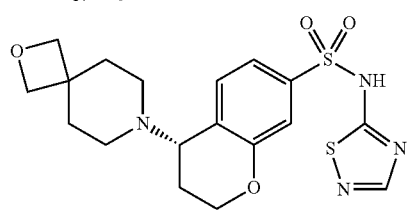
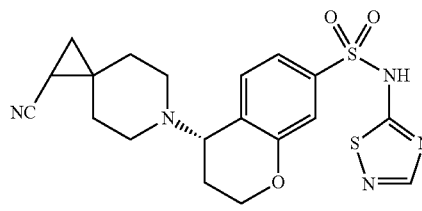
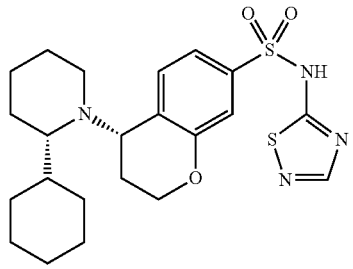
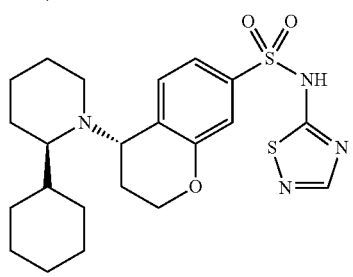
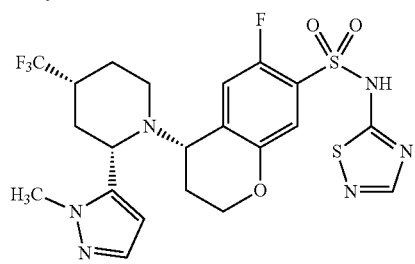
66
-continued
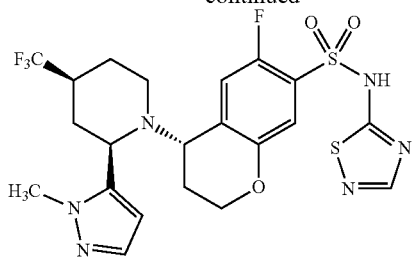
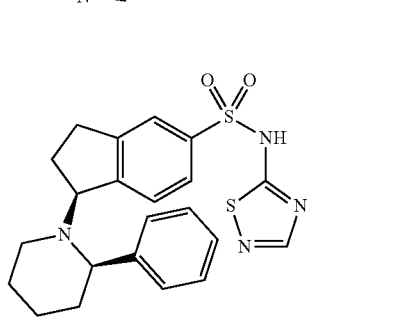
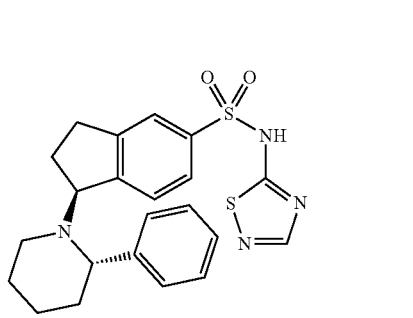
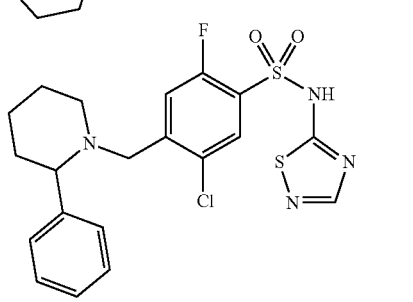
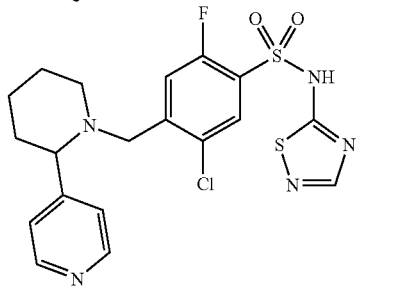
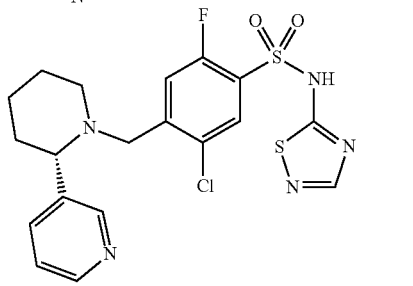

67
-continued
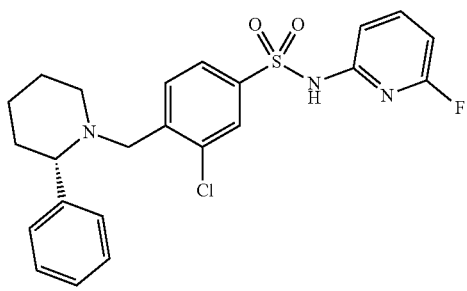
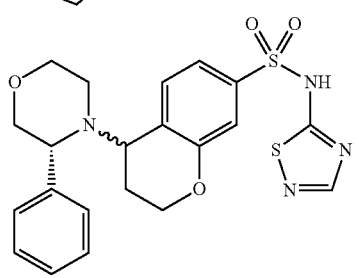
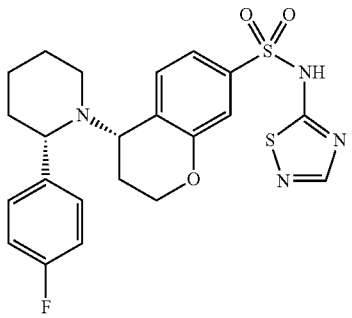
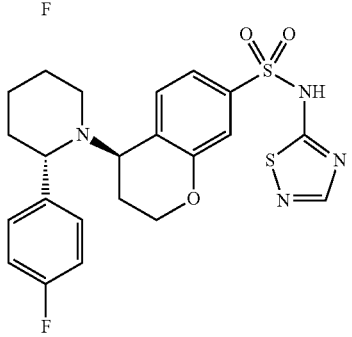
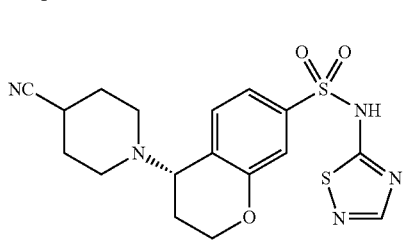
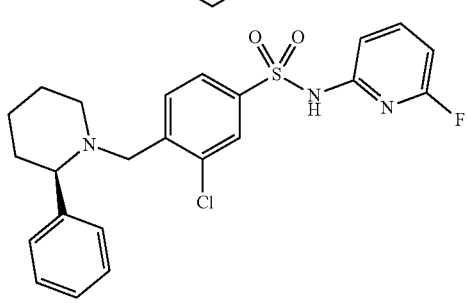
68
-continued
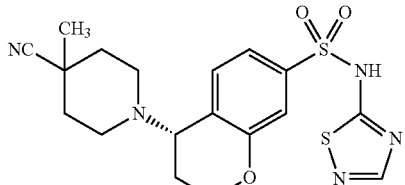
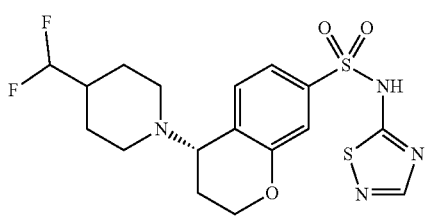
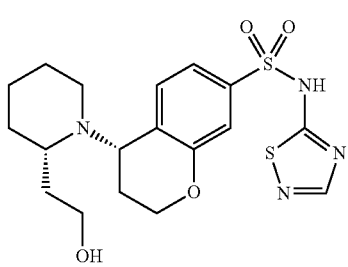
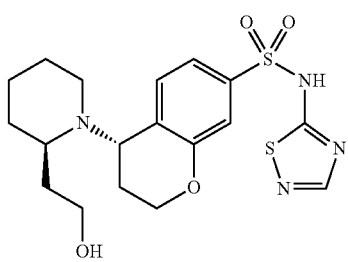
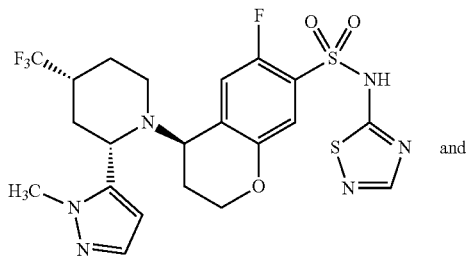 and
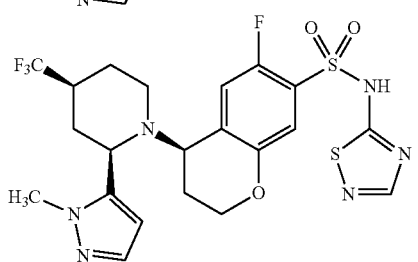
and salts thereof.

E44. The compound of E1 selected from the group consisting of:
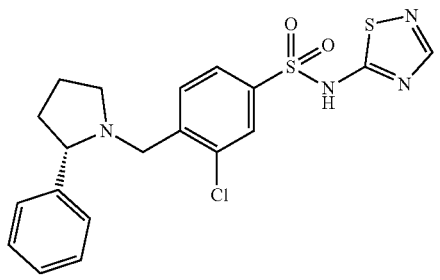
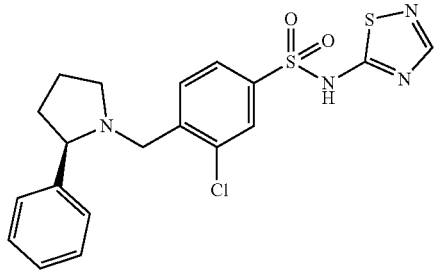
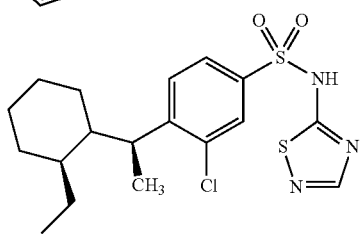
(+/−)
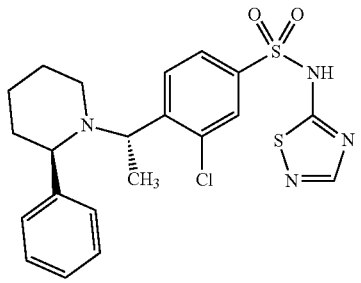
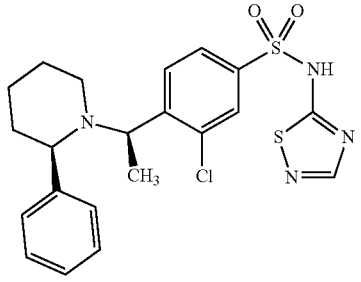
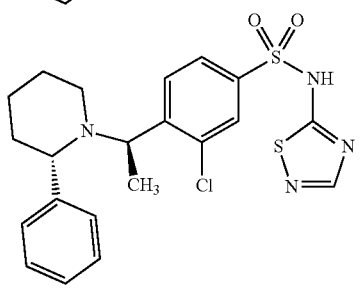
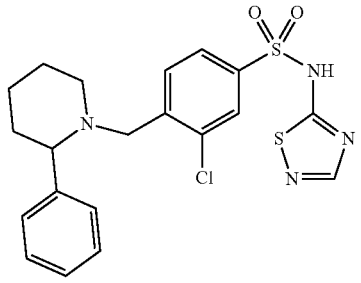
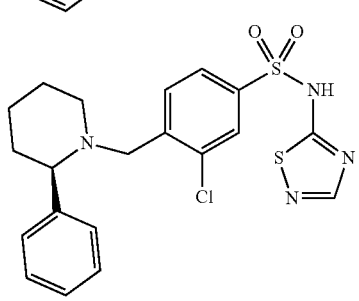
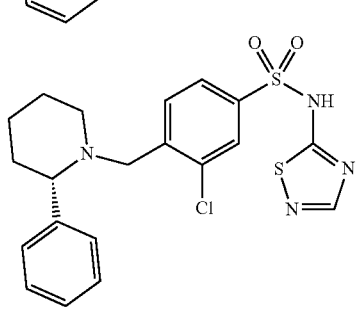
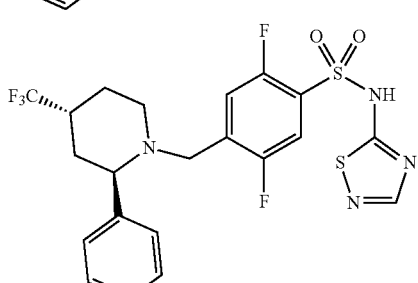
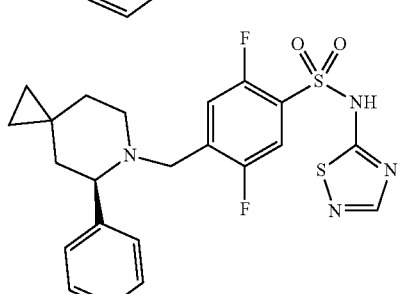
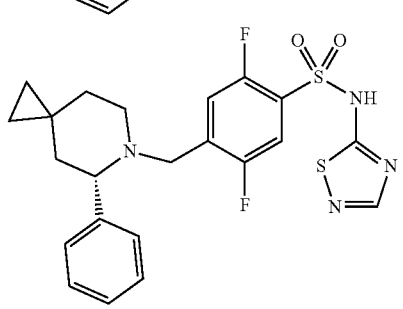

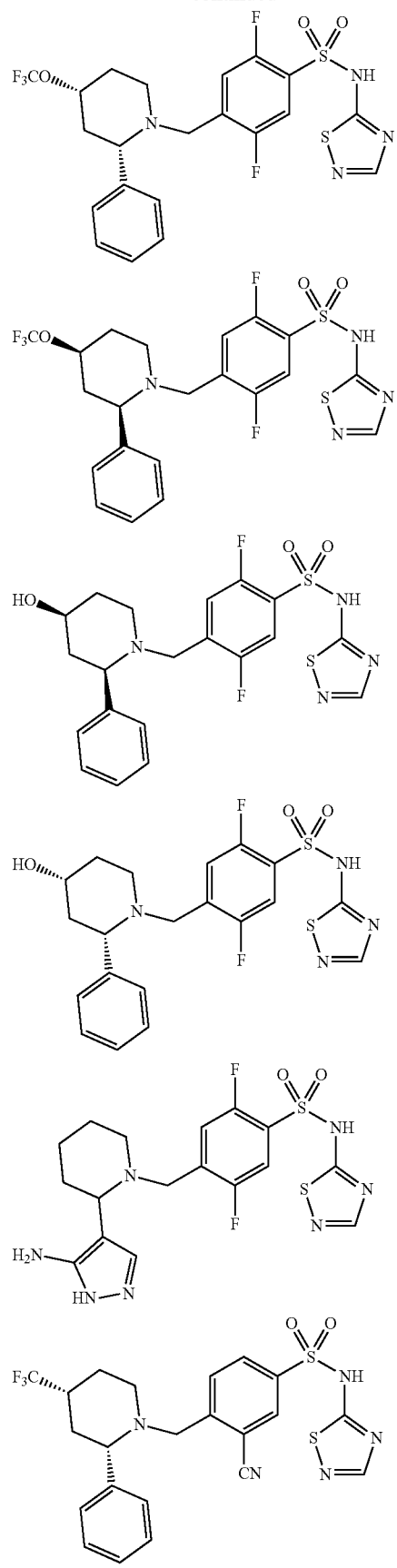 [SMILES: O=S(=O)(Nc1ncns1)c1cc(F)c(CN2CC[C@@H](OC(F)(F)F)C[C@H]2c2ccccc2)cc1F ; O=S(=O)(Nc1ncns1)c1cc(F)c(CN2CC[C@H](OC(F)(F)F)C[C@@H]2c2ccccc2)cc1F ; O=S(=O)(Nc1ncns1)c1cc(F)c(CN2CC[C@H](O)C[C@@H]2c2ccccc2)cc1F ; O=S(=O)(Nc1ncns1)c1cc(F)c(CN2CC[C@@H](O)C[C@H]2c2ccccc2)cc1F ; Nc1[nH]ncc1C1CCCCN1Cc1cc(F)c(S(=O)(=O)Nc2ncns2)cc1F ; N#Cc1cc(S(=O)(=O)Nc2ncns2)ccc1CN1CC[C@@H](C(F)(F)F)C[C@H]1c1ccccc1]
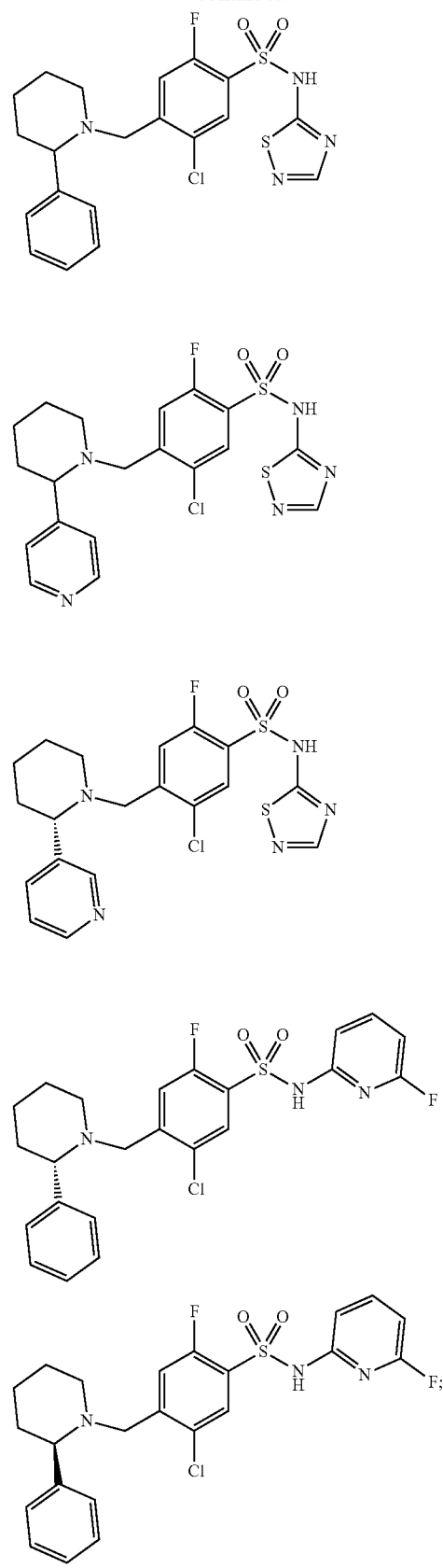
and salts thereof.

E45. The compound of E2 selected the group consisting of:
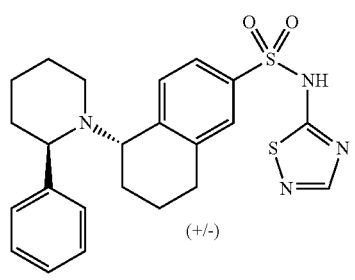
(+/-)
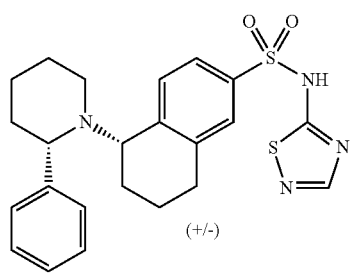
(+/-)
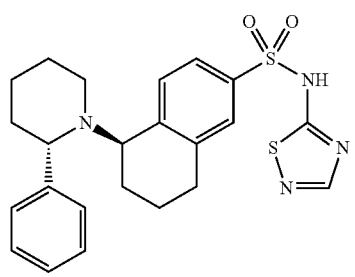
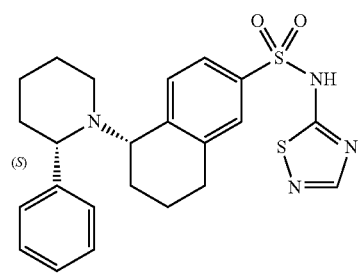
(S)
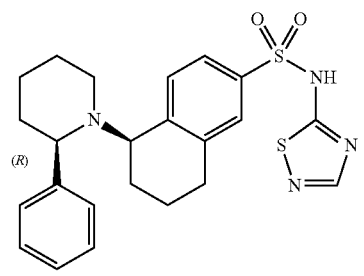
(R)
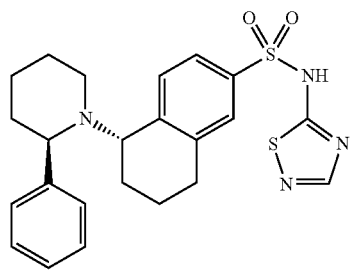
-continued
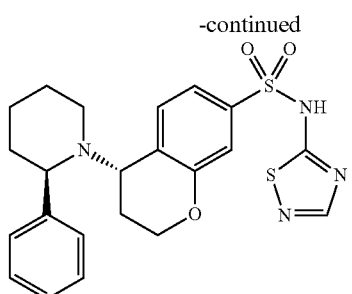
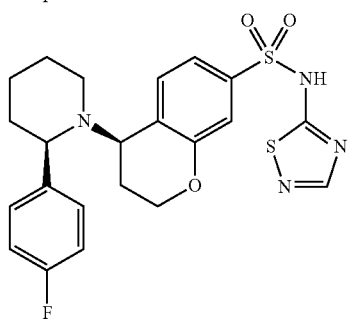
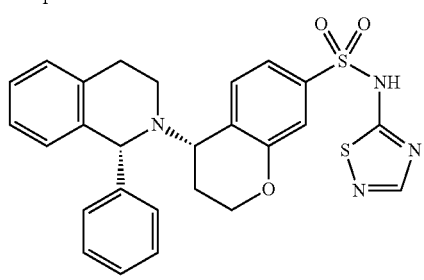
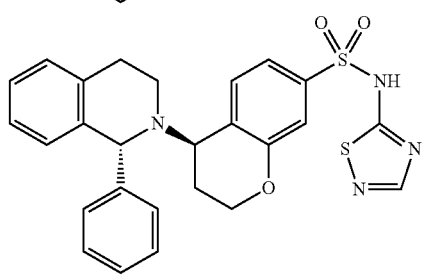
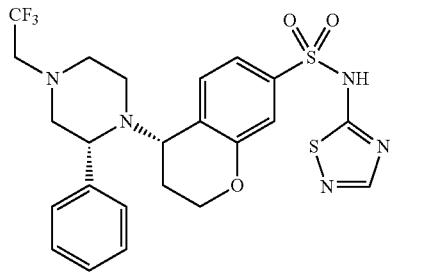
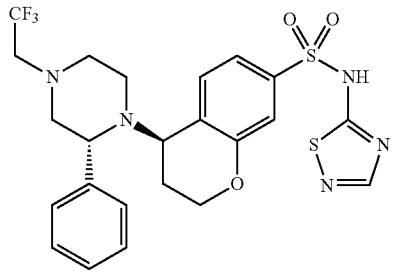

75
-continued
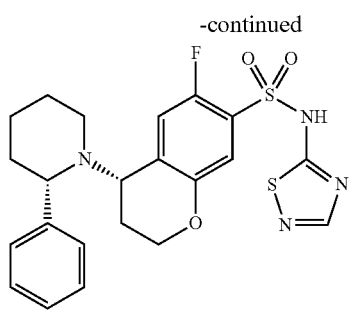
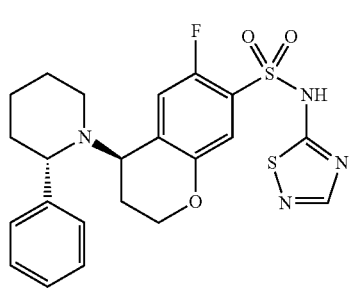
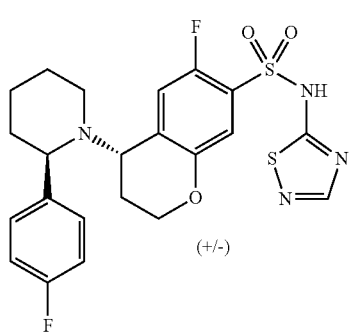
(+/-)
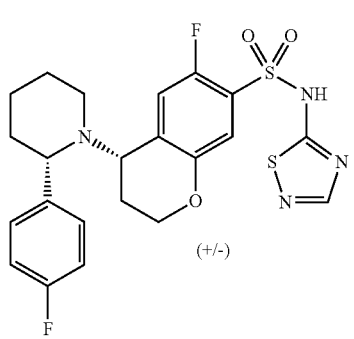
(+/-)
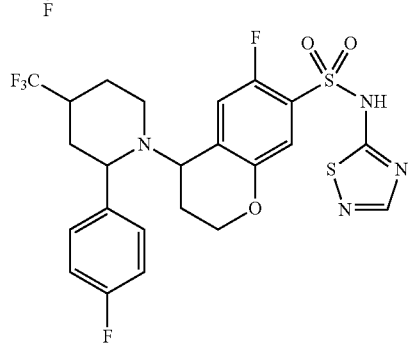
76
-continued
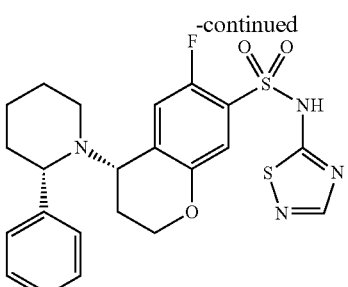
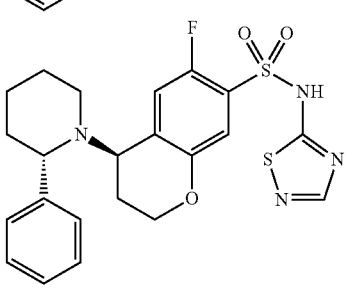
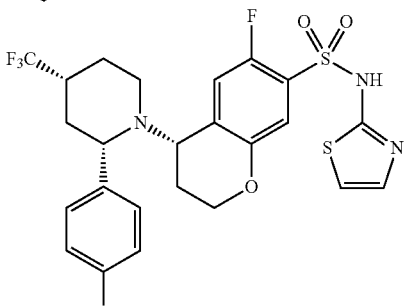
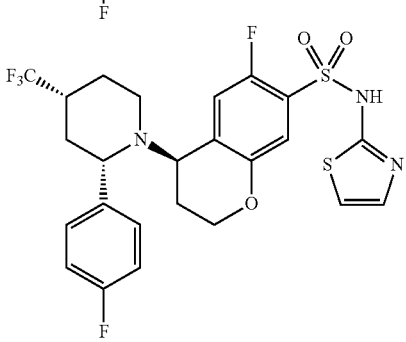
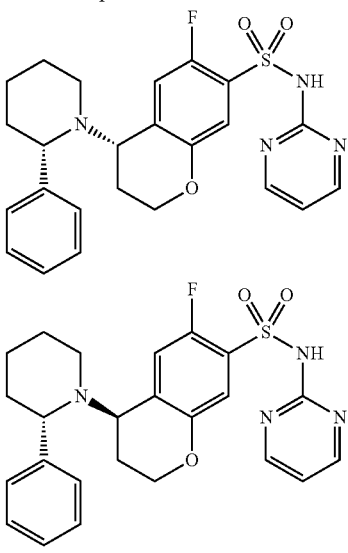

77
-continued
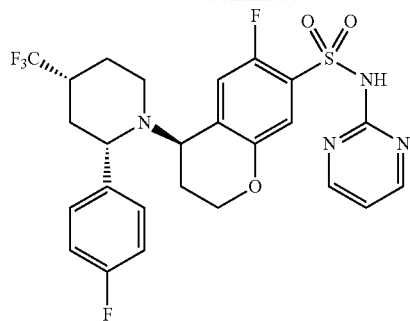
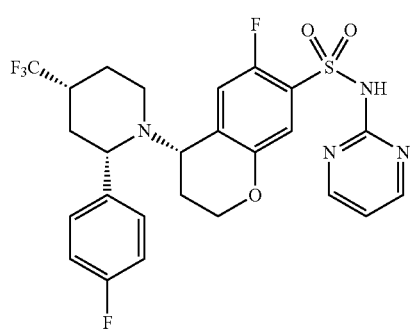
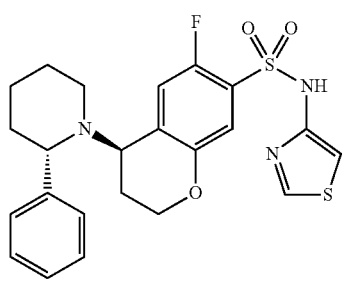
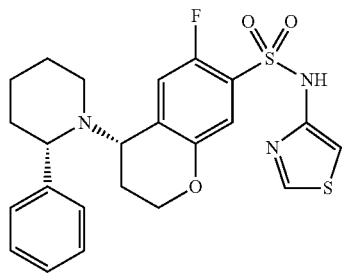
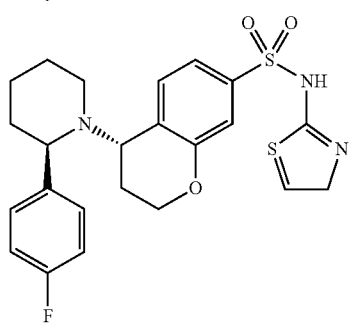
78
-continued
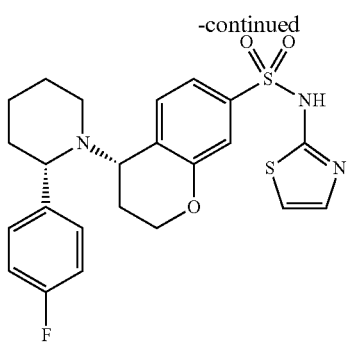
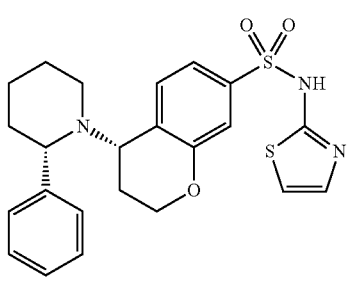
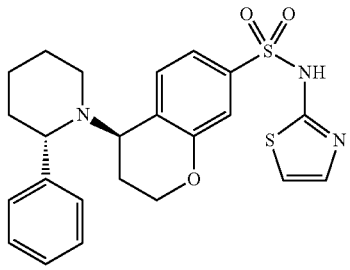
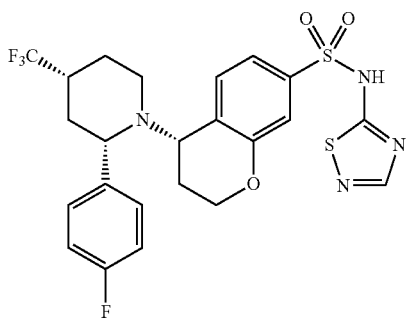
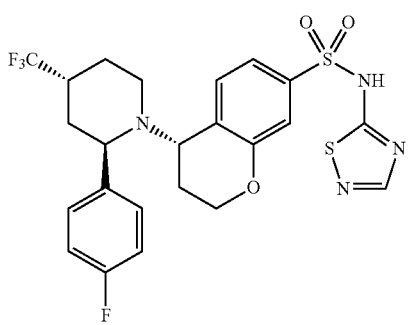

79
-continued
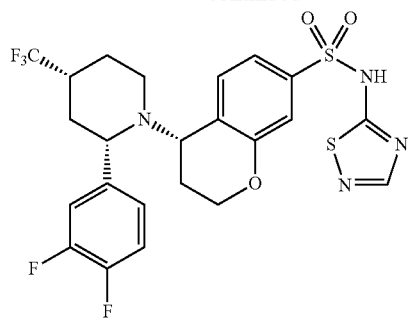
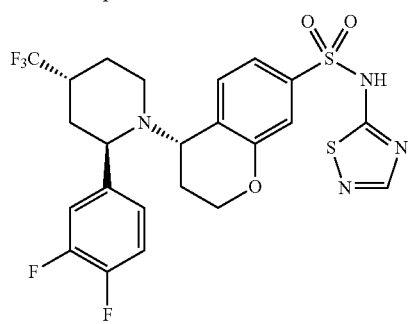
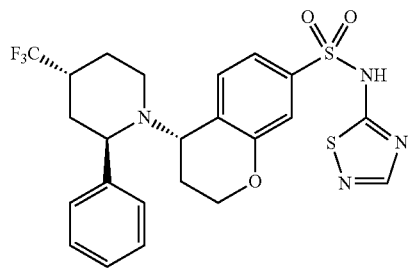
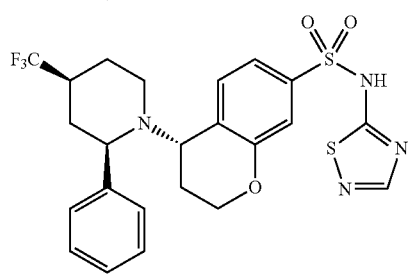
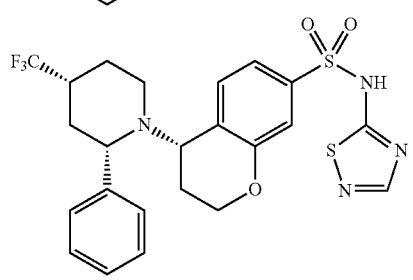
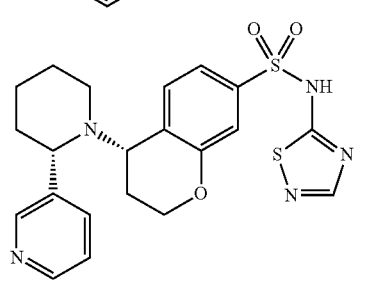
80
-continued
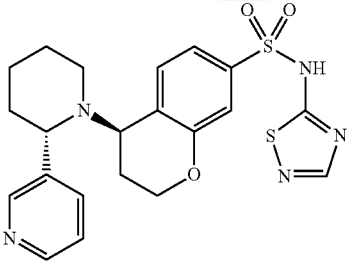
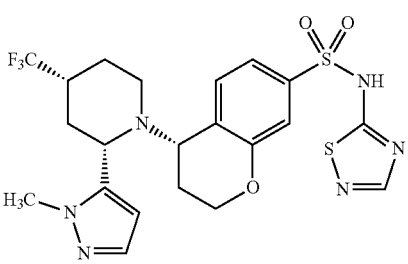
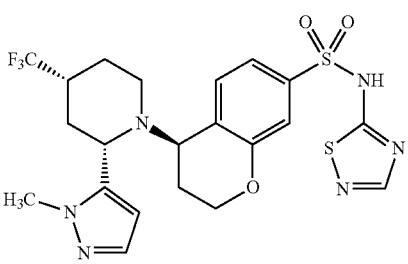
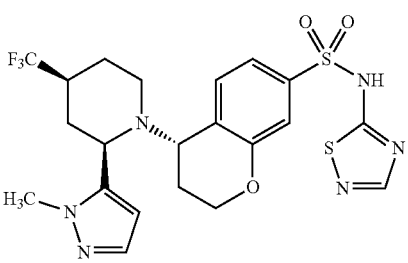
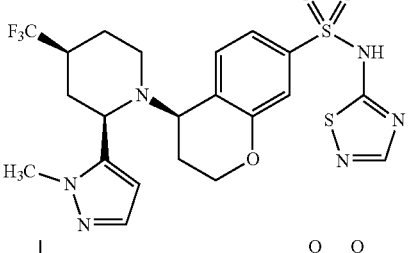
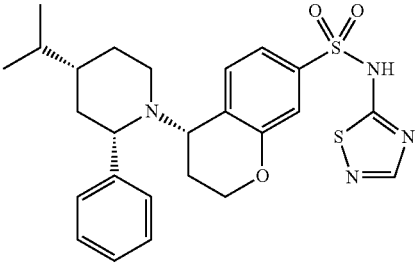

81
-continued
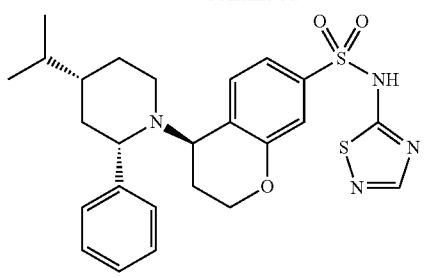
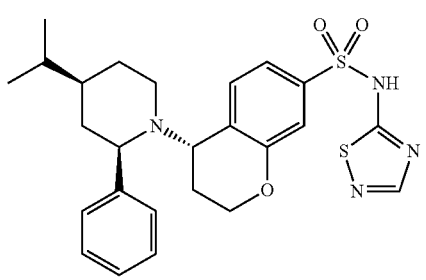
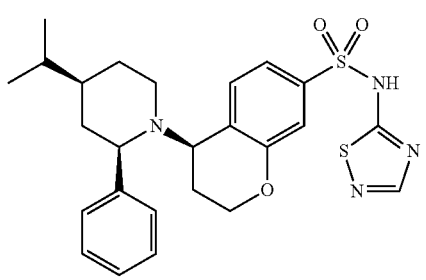
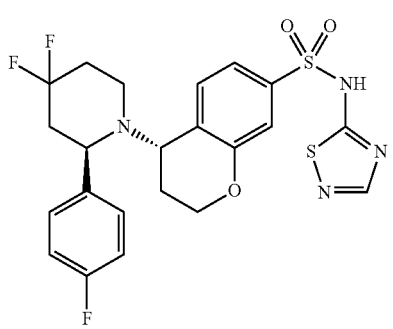
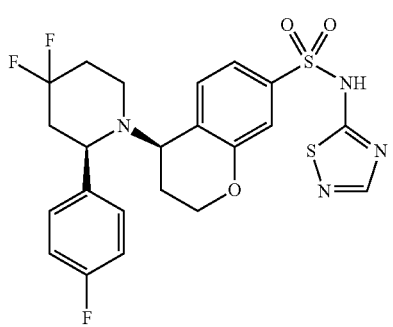
82
-continued
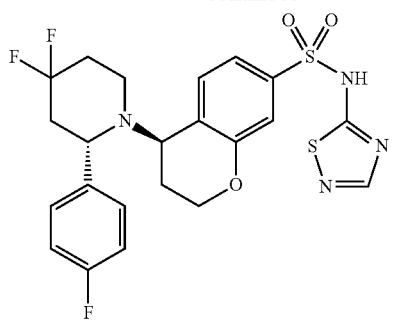
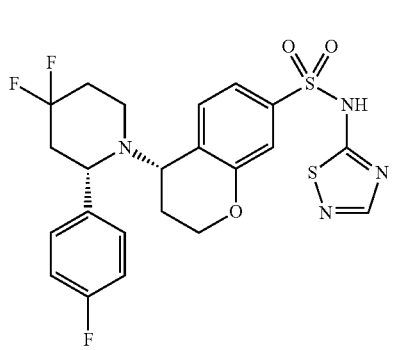
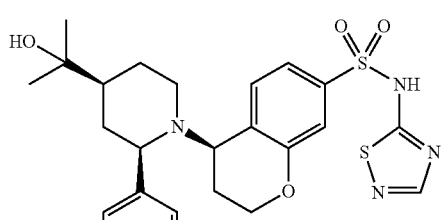
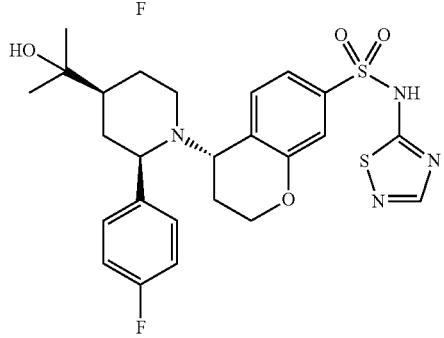
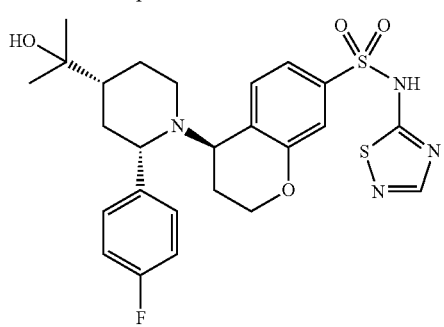

83
-continued
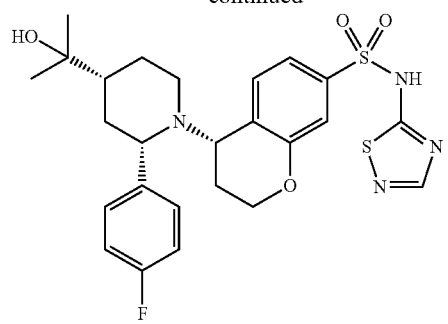
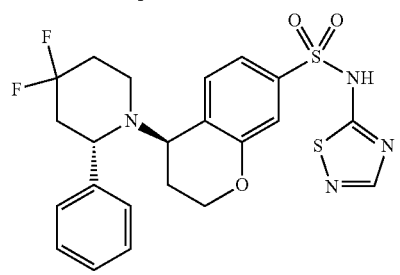
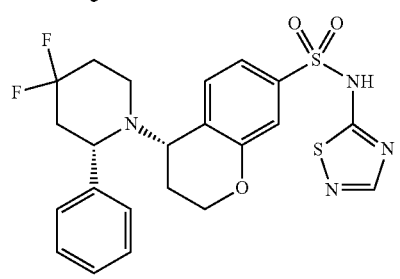
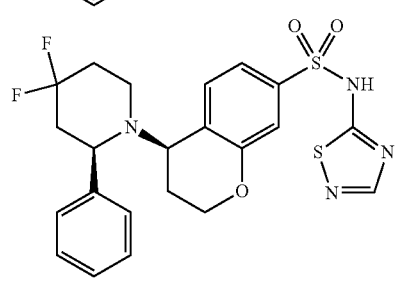
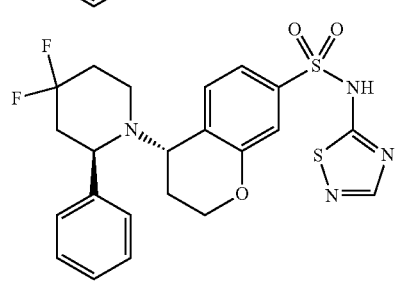
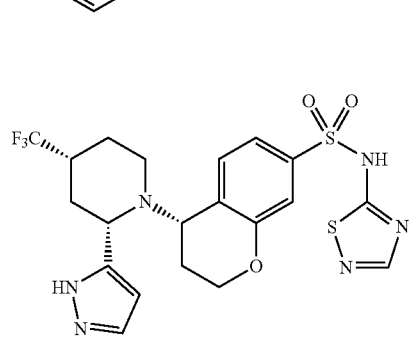
84
-continued
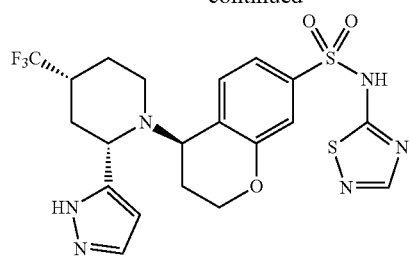
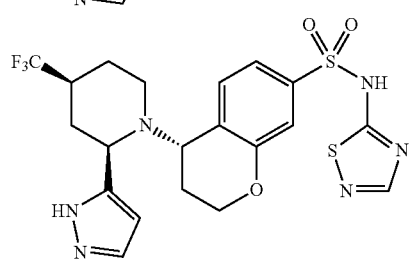
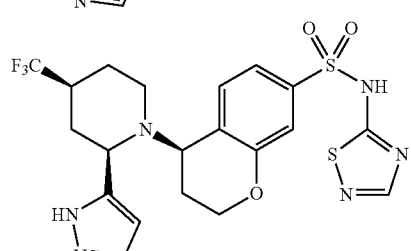
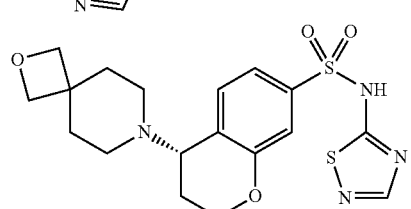
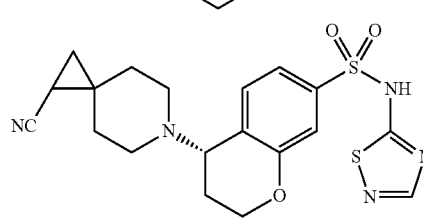
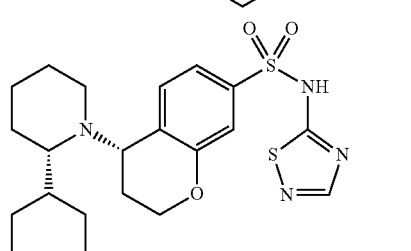
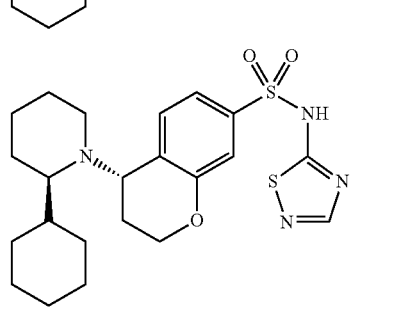

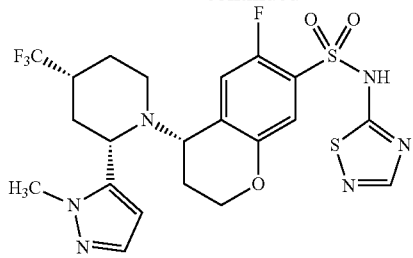

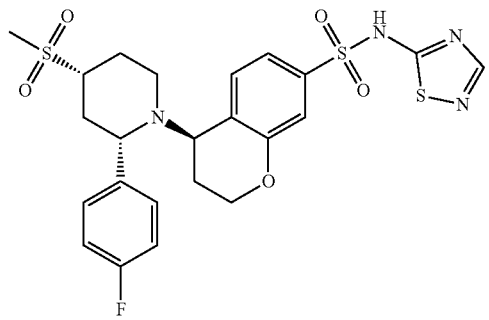
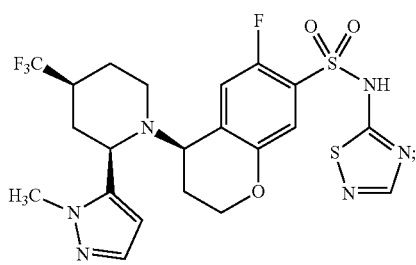 [SMILES: Cn1nccc1[C@H]1C[C@@H](C(F)(F)F)CCN1[C@@H]1CCOc2cc(S(=O)(=O)Nc3ncns3)c(F)cc21]
and salts thereof.
E46. A compound of E3 selected from the group consisting of:
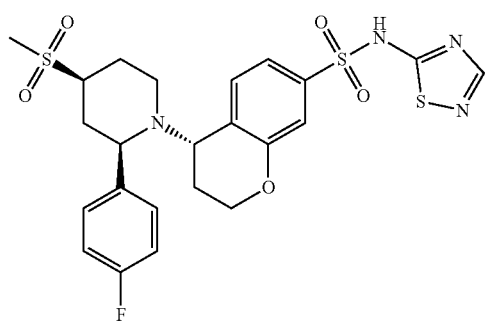
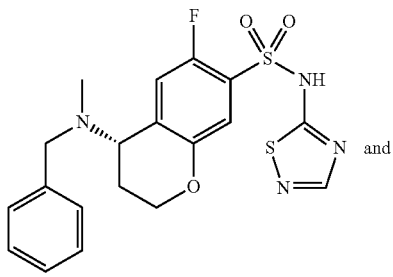
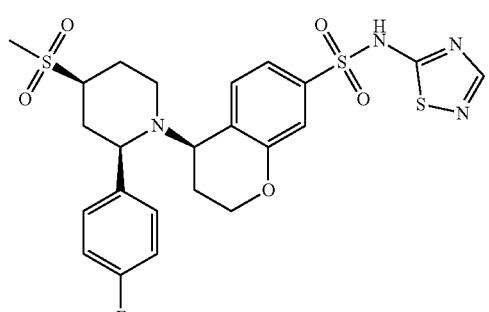
and
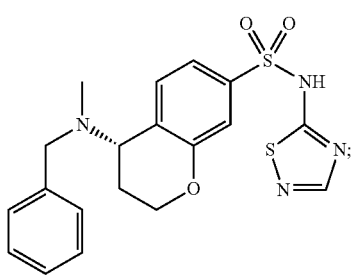
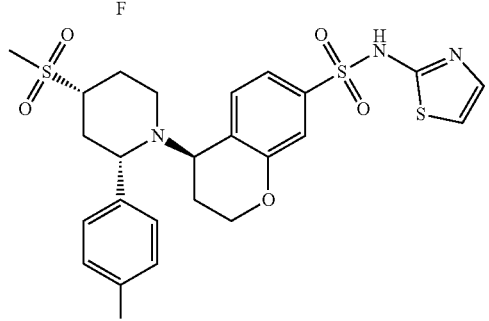
and salts thereof.
E47. A compound of selected from the group consisting of:
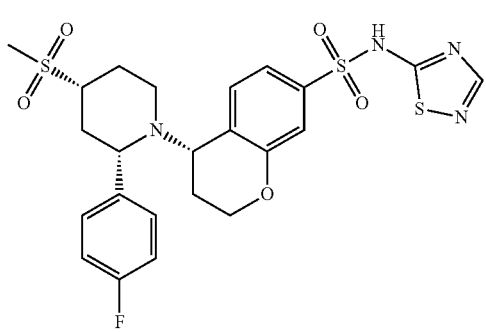
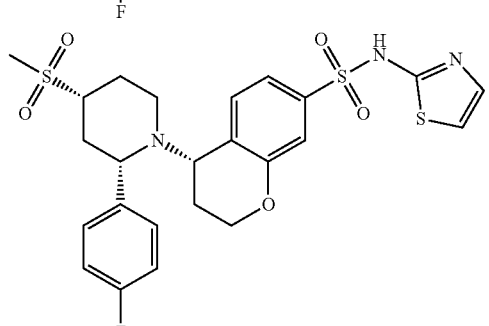

89
-continued
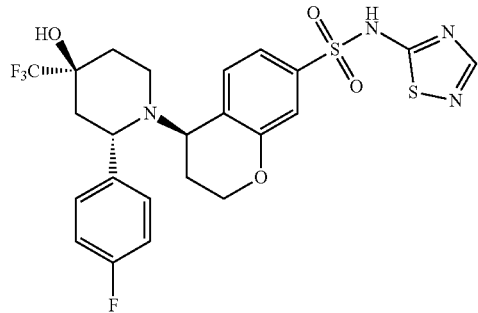
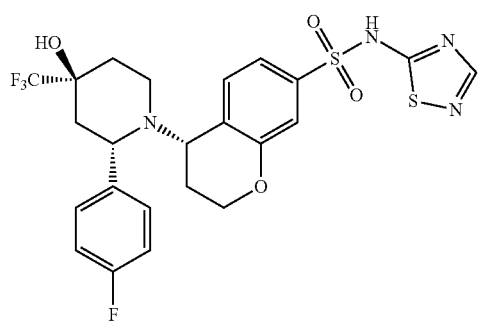
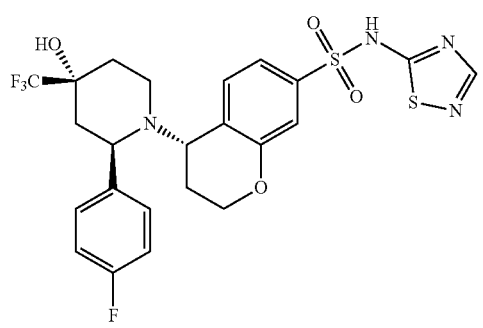
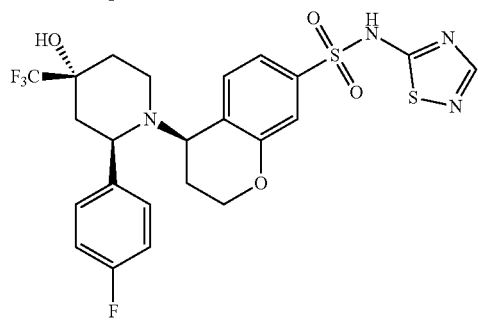
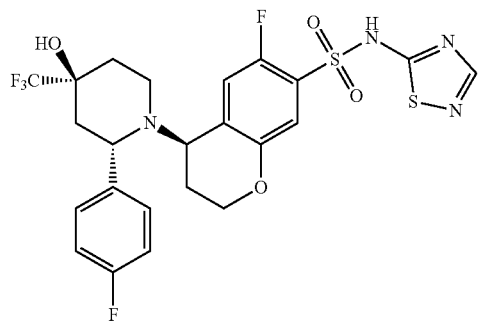
90
-continued
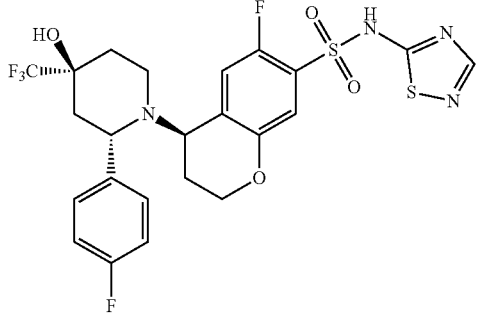
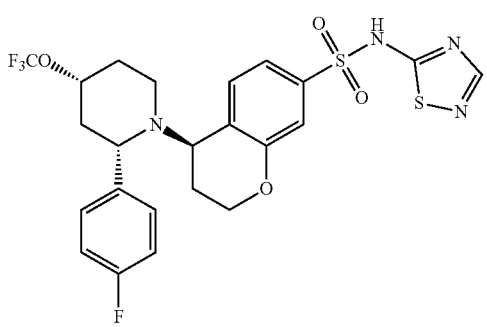
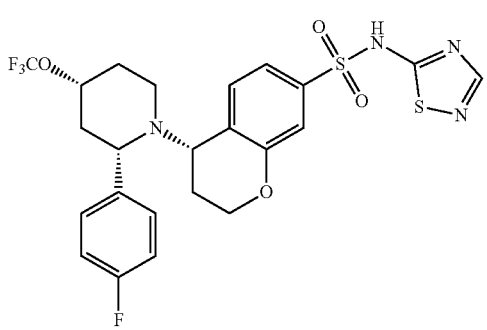
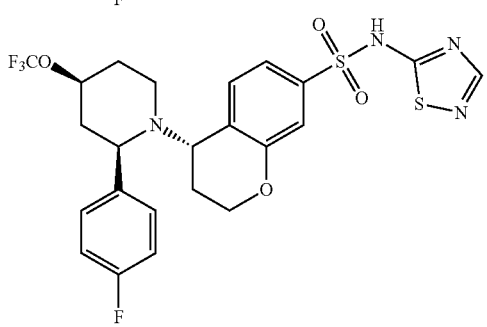
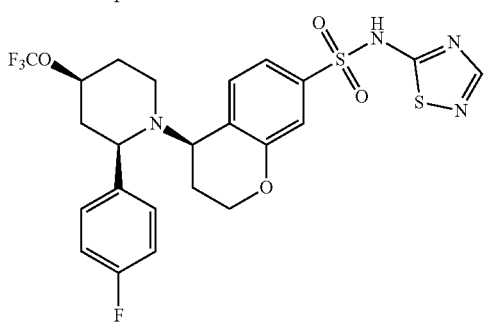

91
-continued
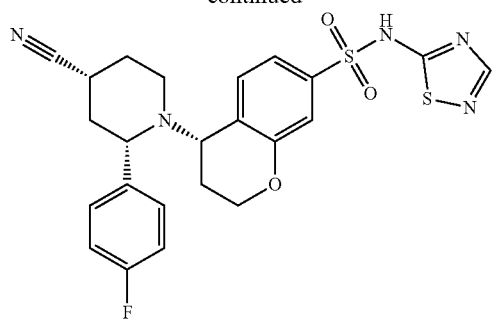
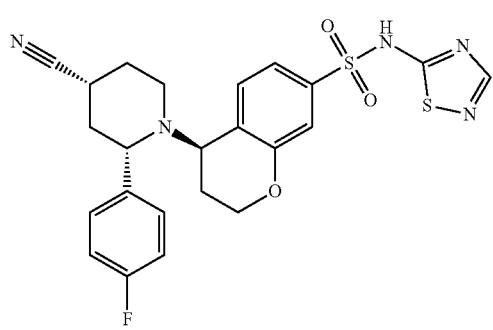
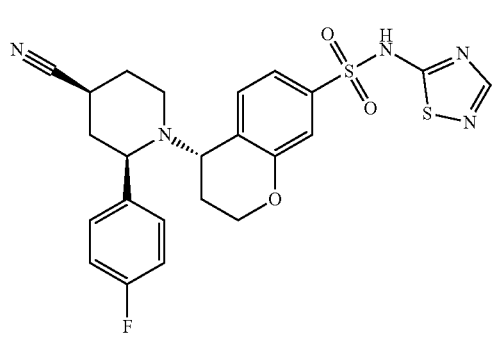
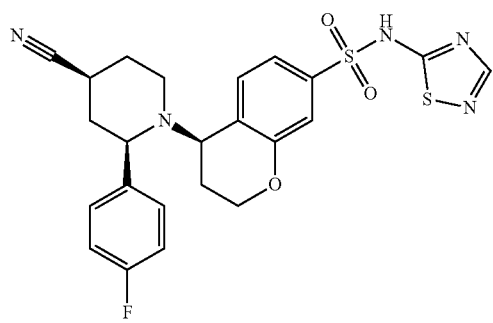
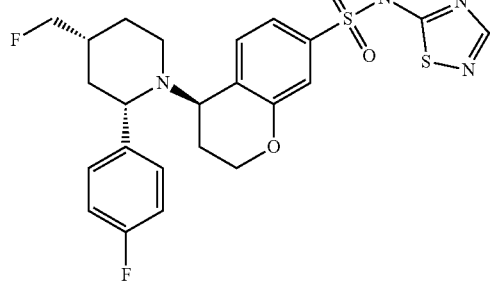
92
-continued
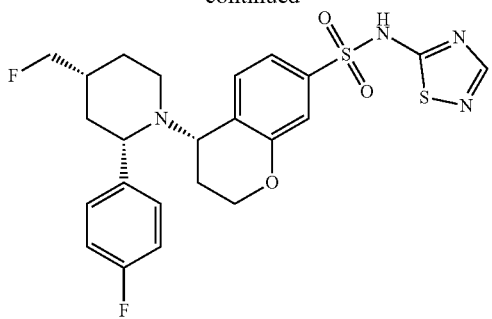
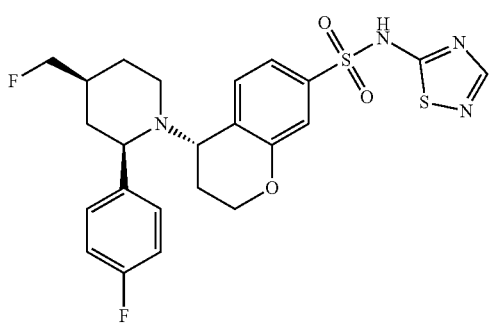
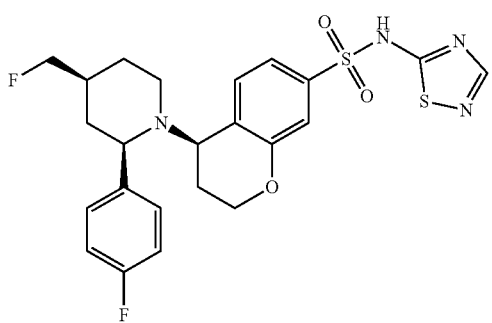
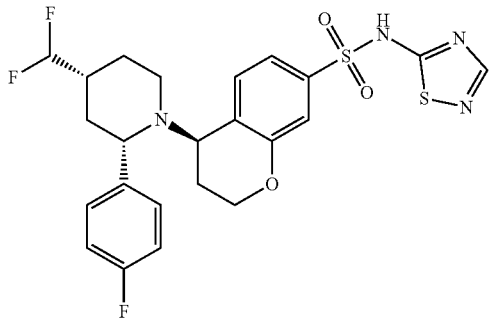
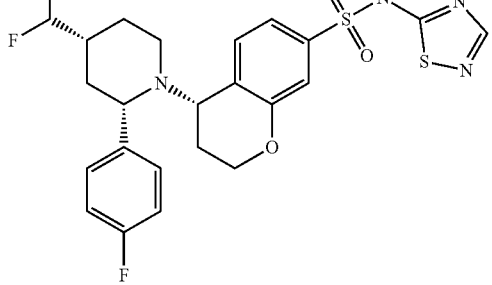

93
-continued
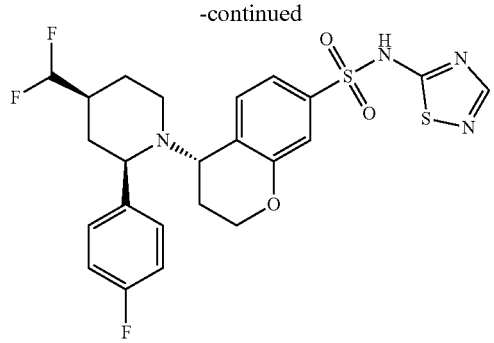
94
-continued
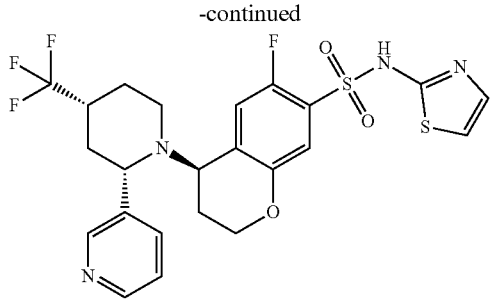
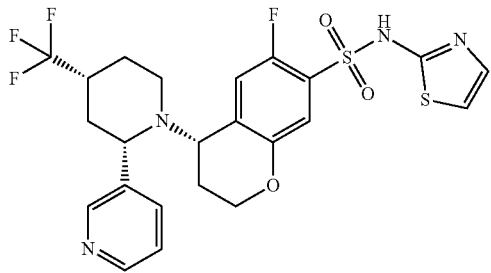
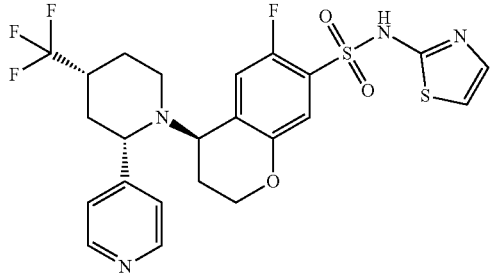
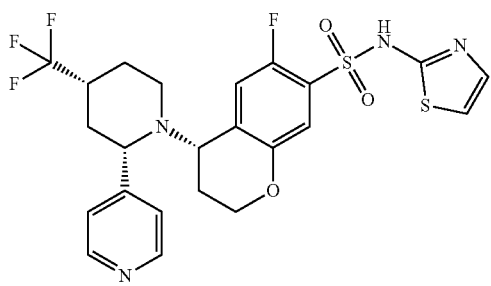
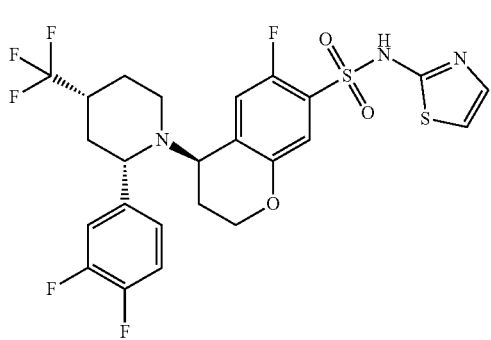

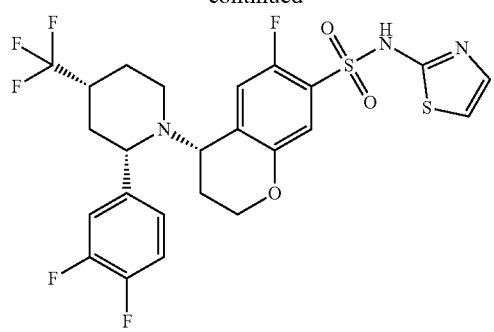
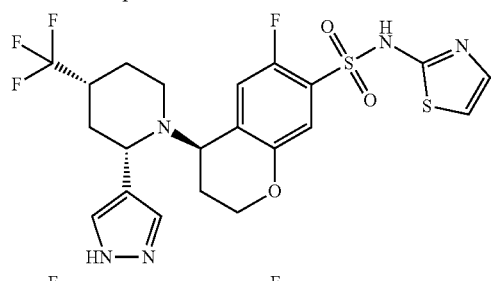
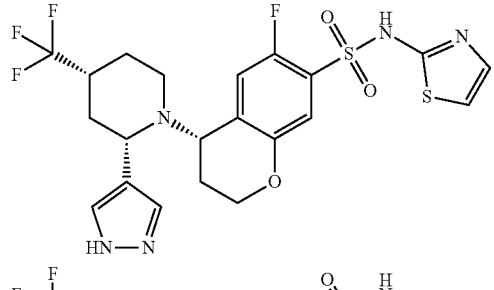
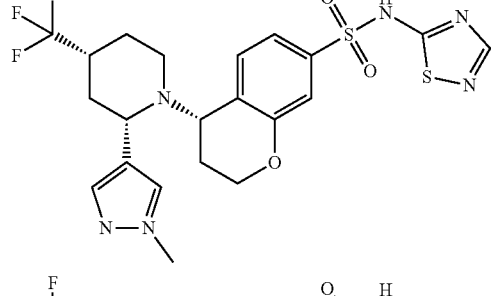
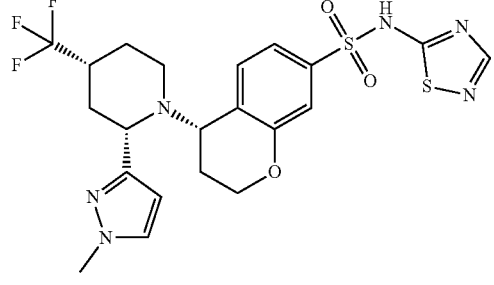
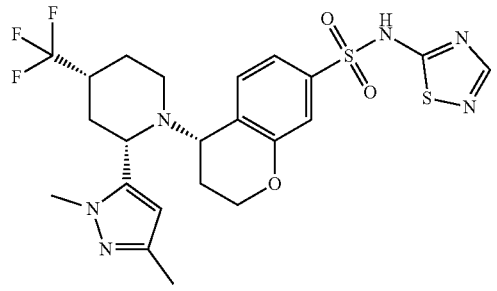
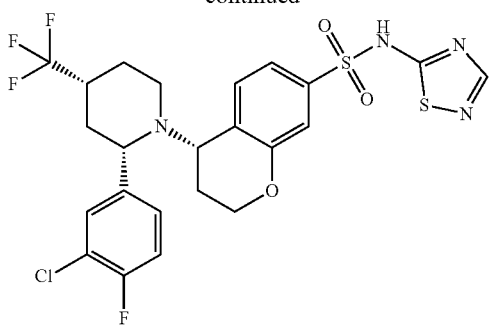
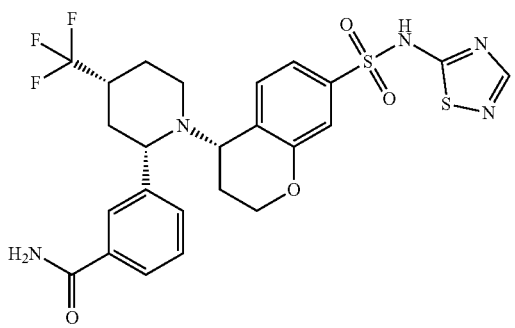
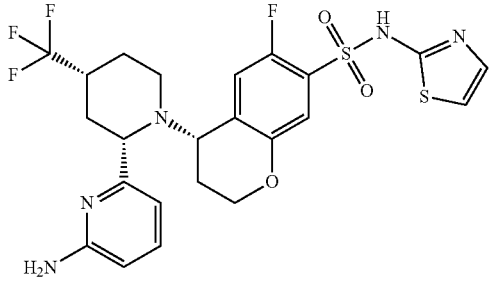
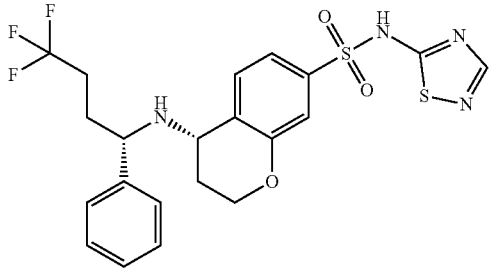
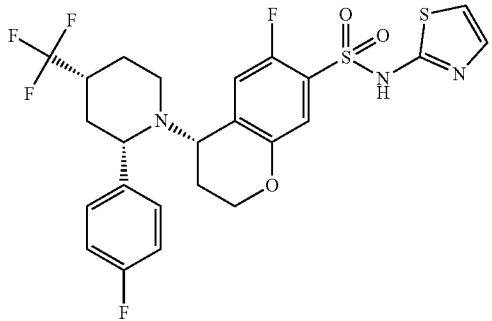

97
-continued
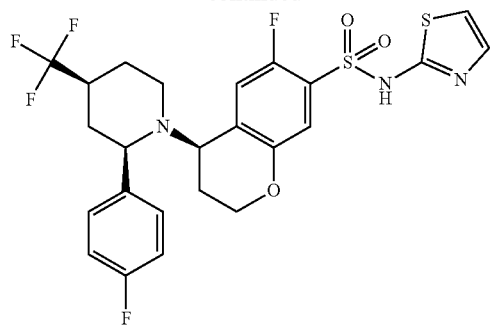
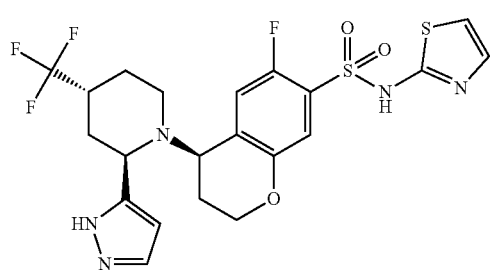
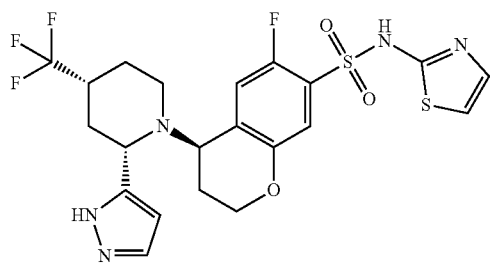
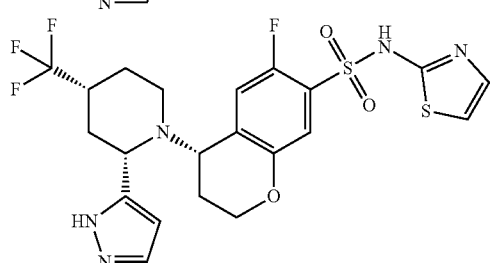
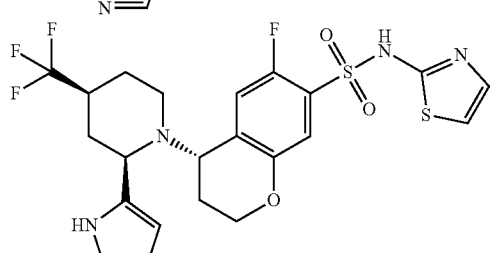
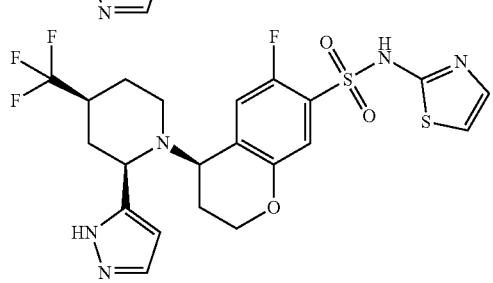
98
-continued
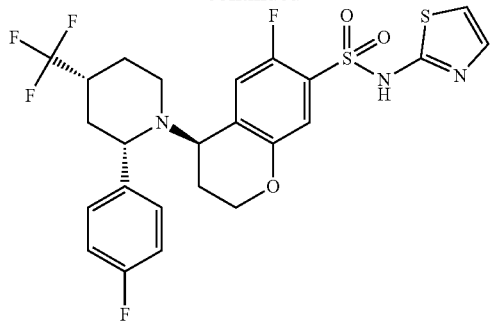
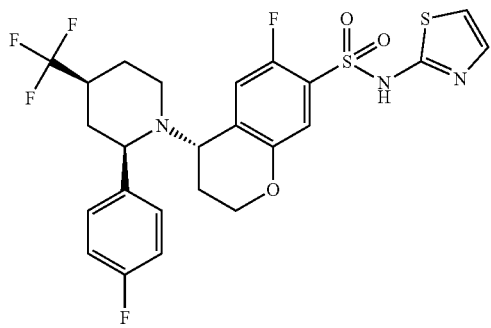
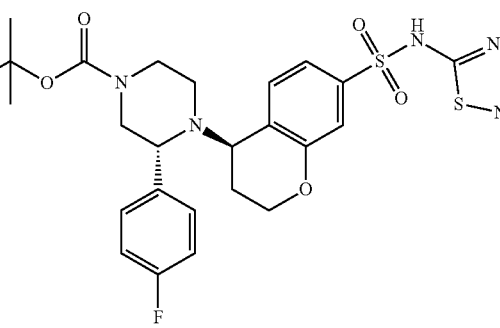
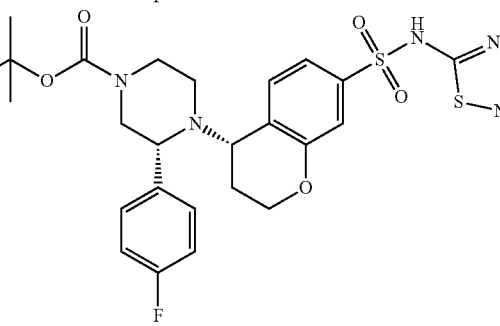
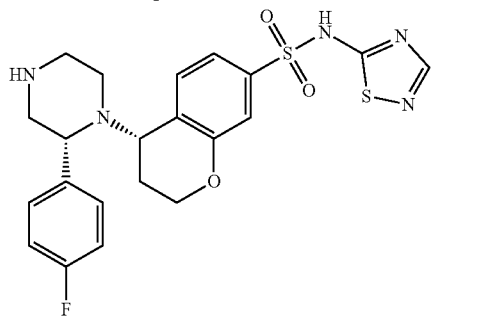

99
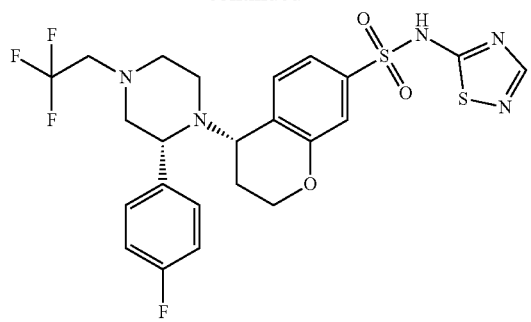
100
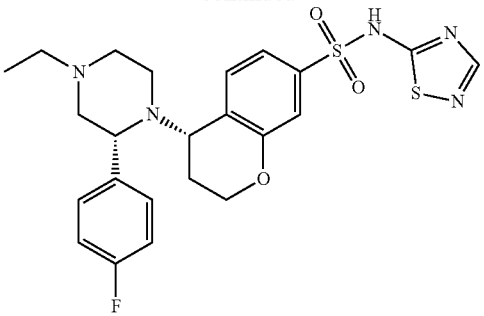

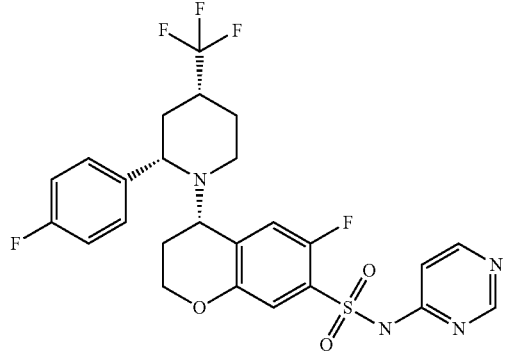
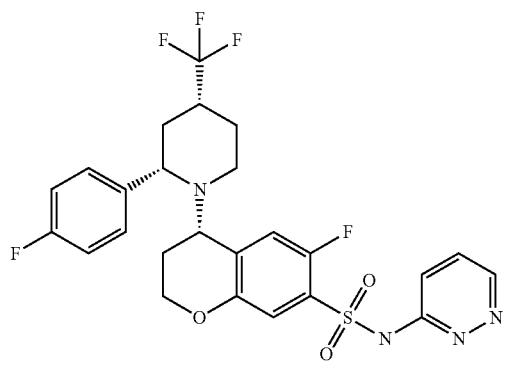
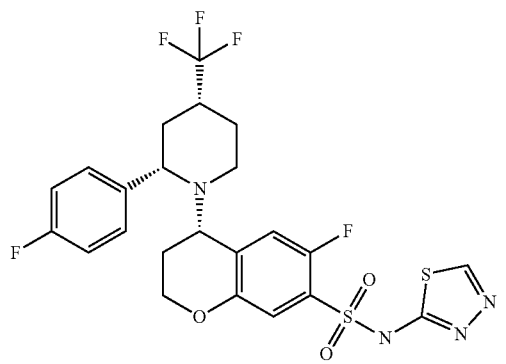
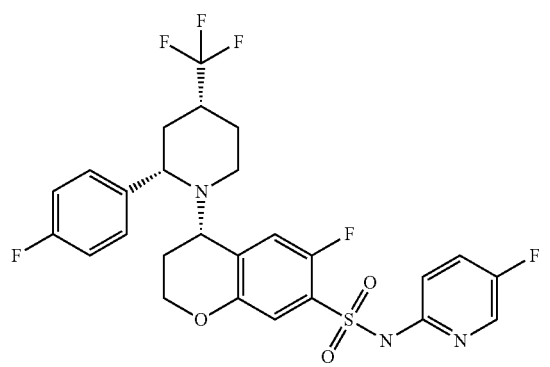
and
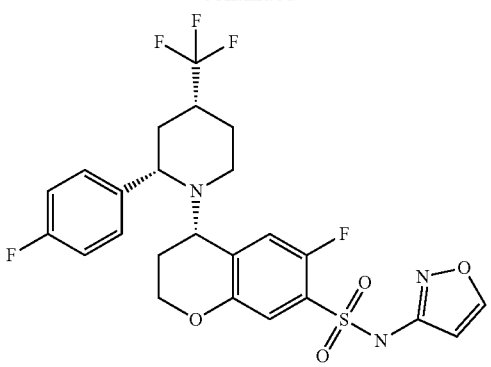
and salts thereof.
E48. A compound of E2 selected from the group consisting of:
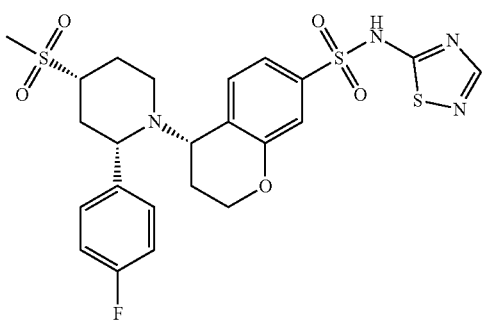
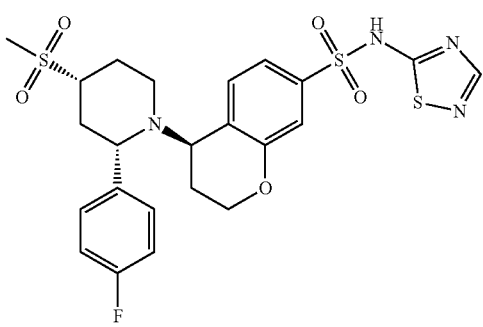
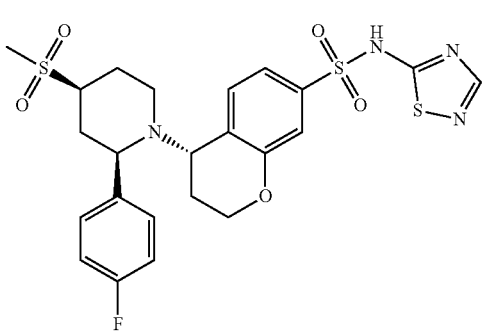

-continued
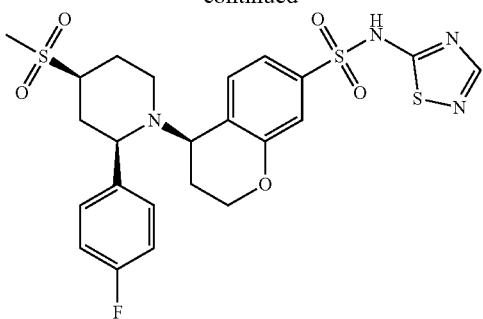
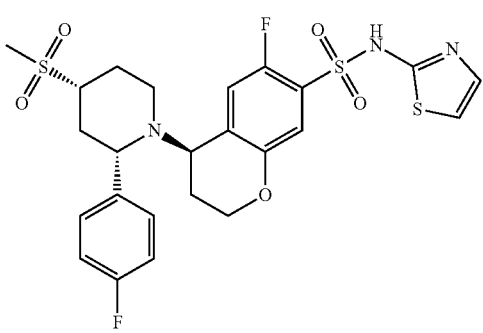
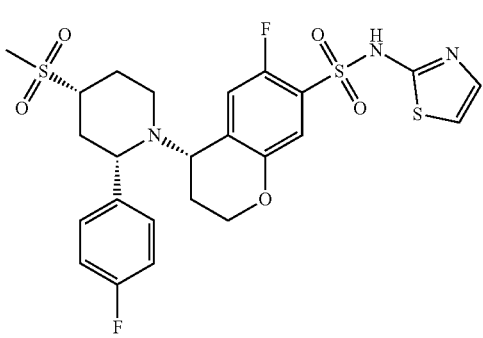
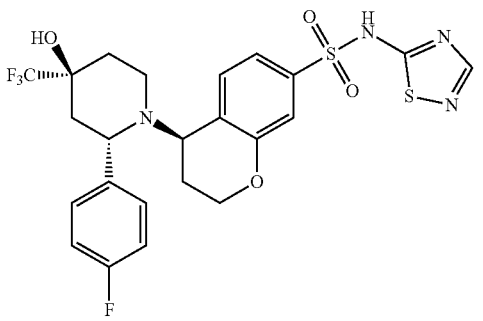
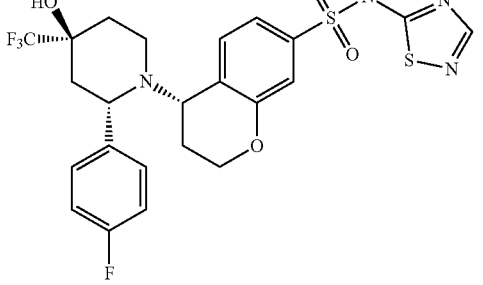
-continued
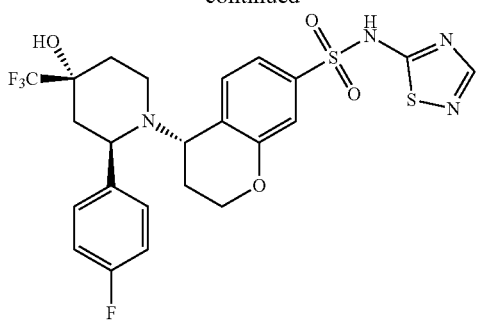
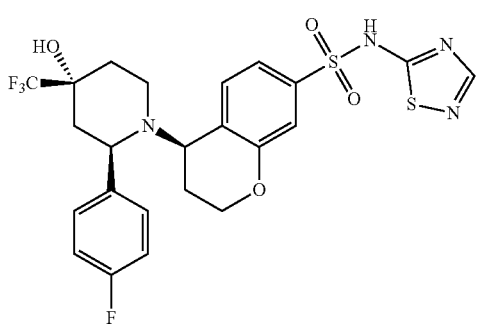
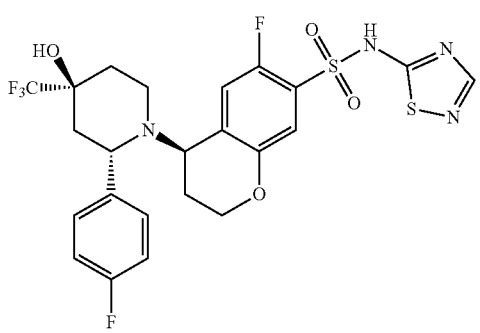
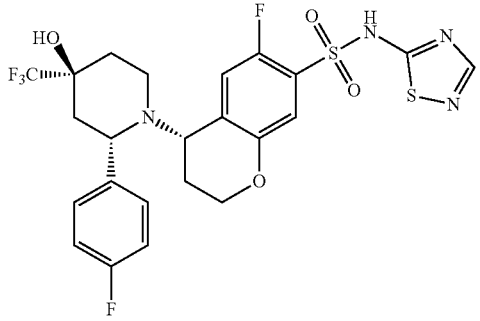
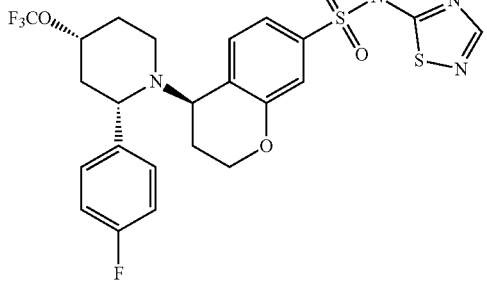

105
-continued
106
-continued
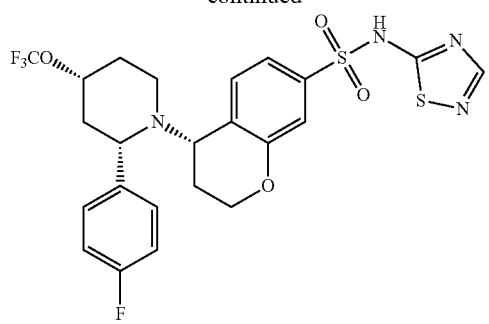
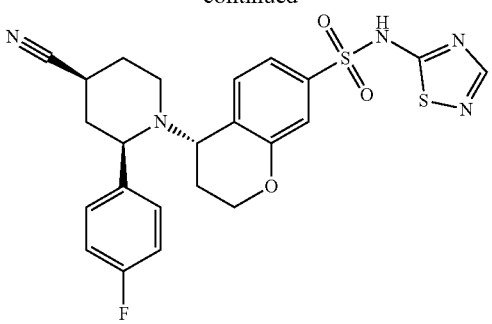

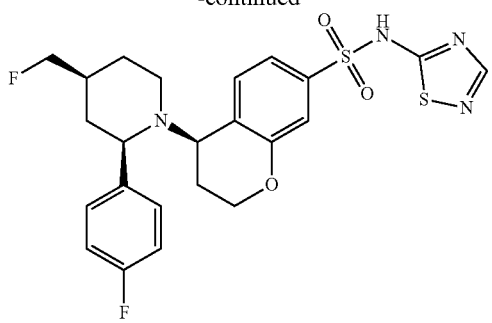
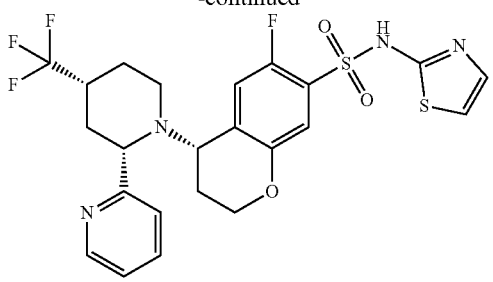

109
-continued
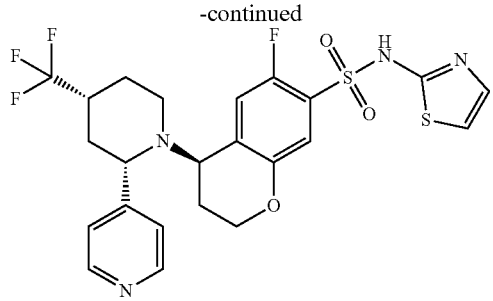
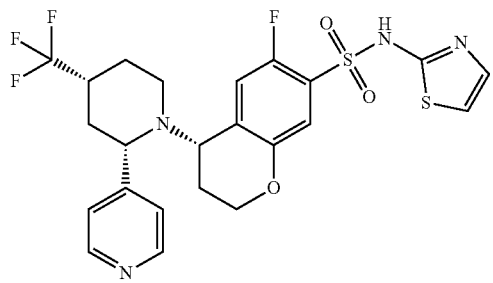
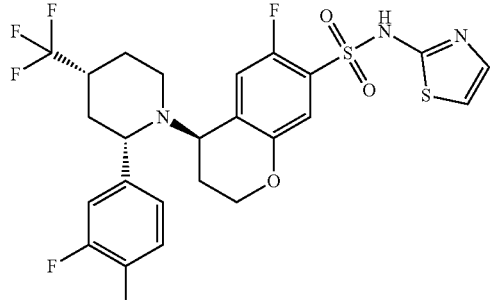
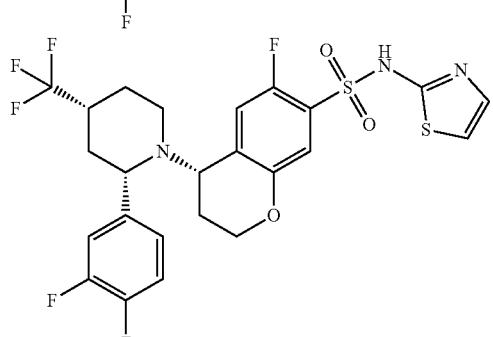
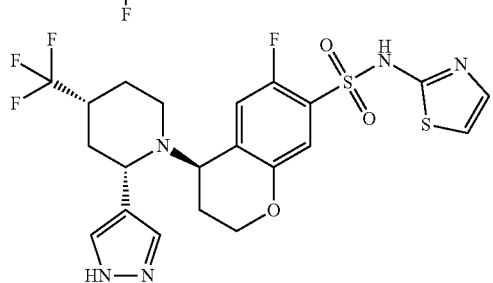
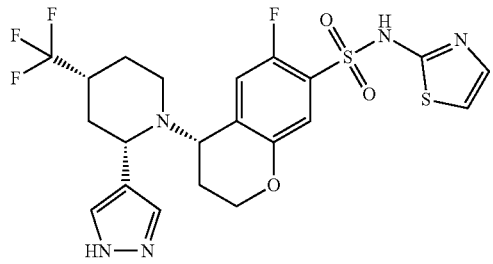
110
-continued
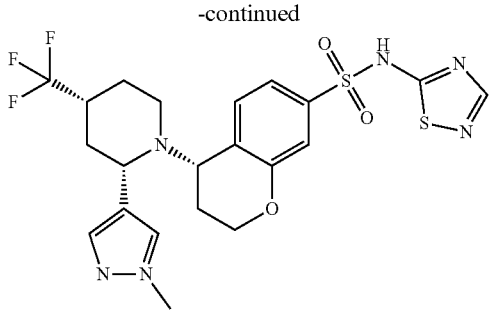
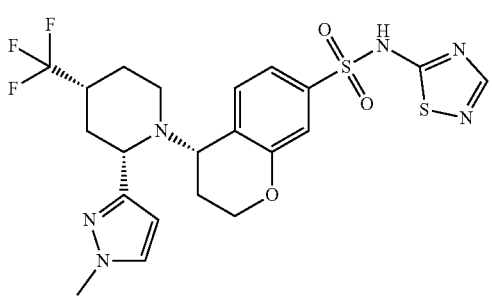
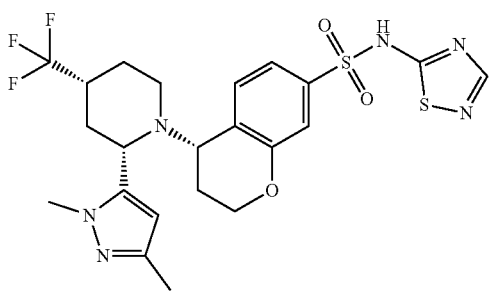
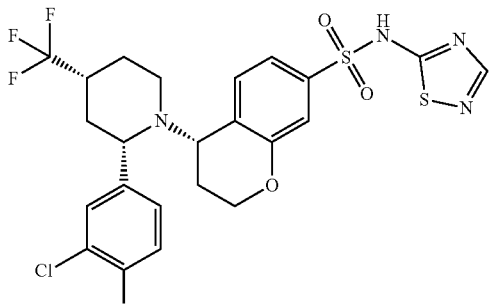
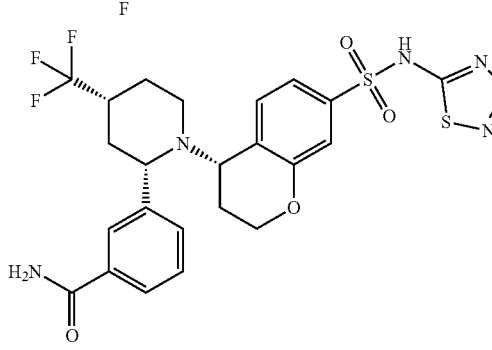

111
-continued
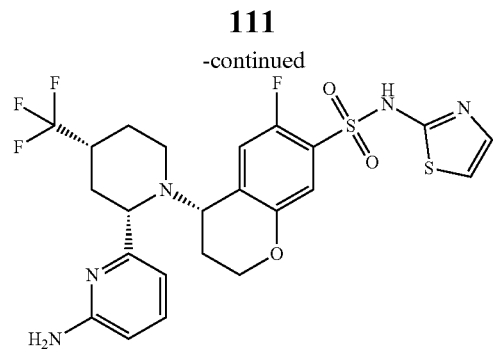
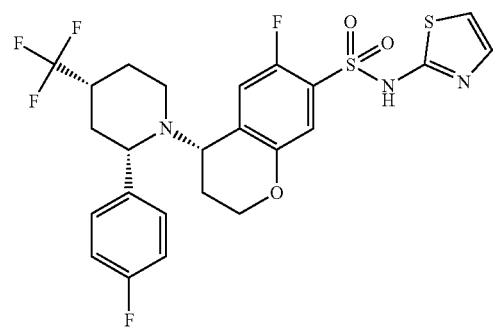
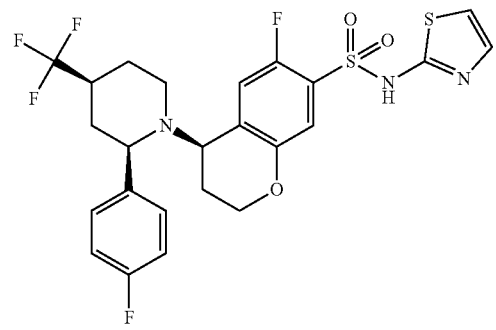
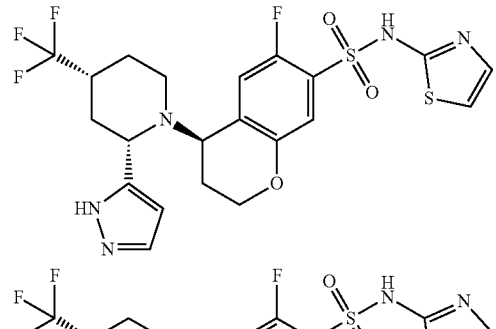
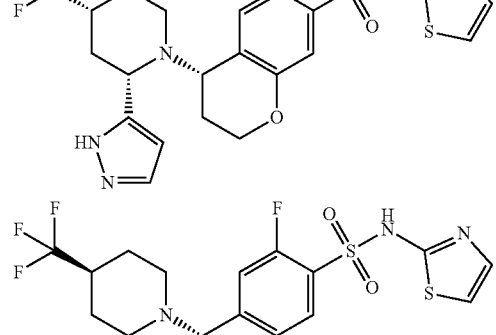
112
-continued
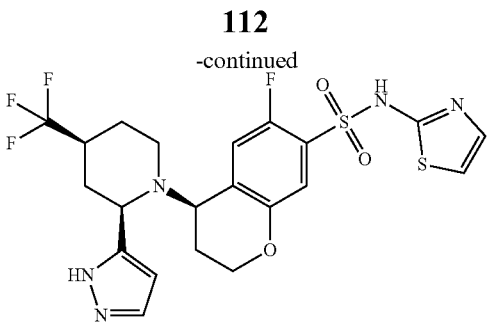
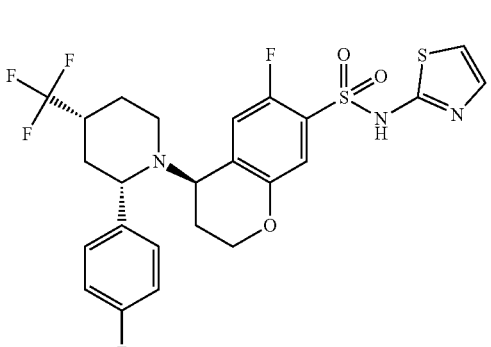
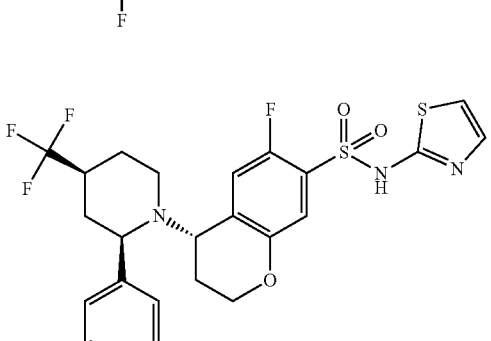
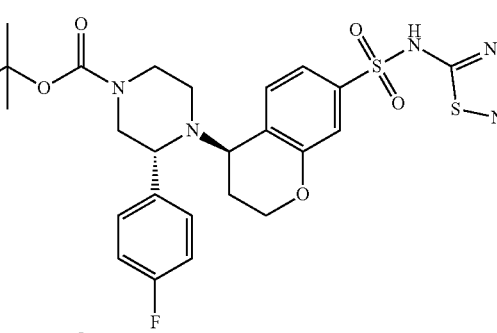
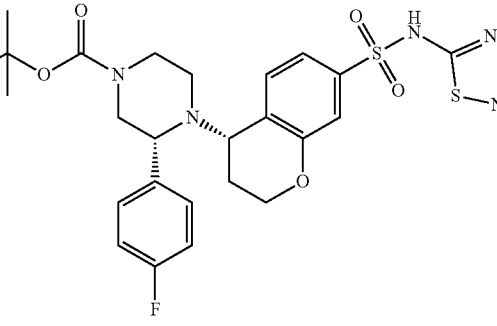

113
-continued
114
-continued
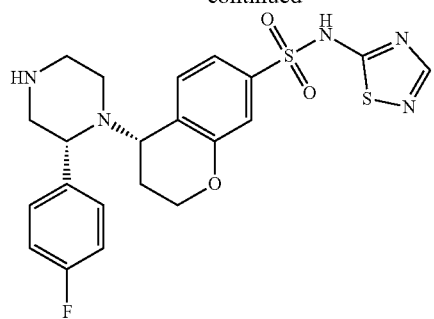
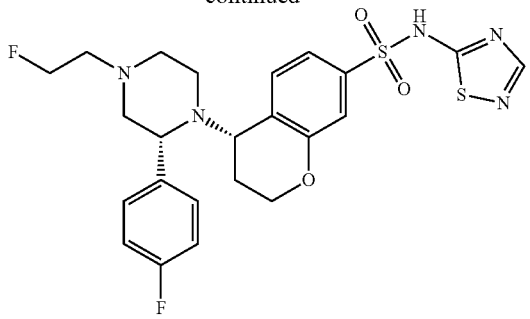

115
-continued
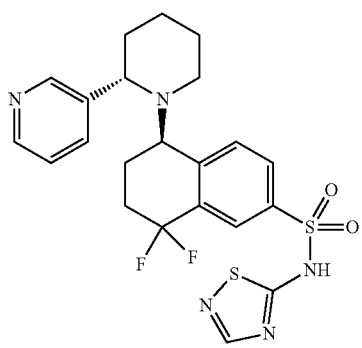
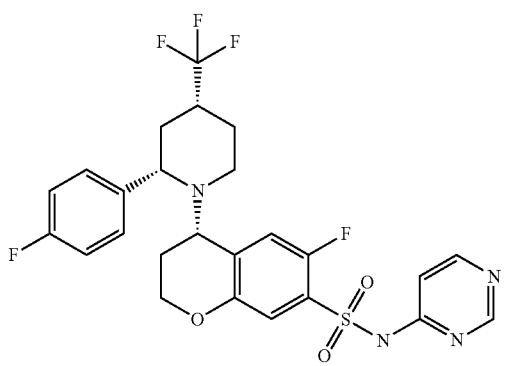
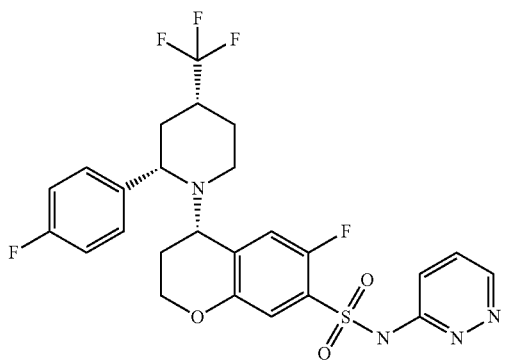
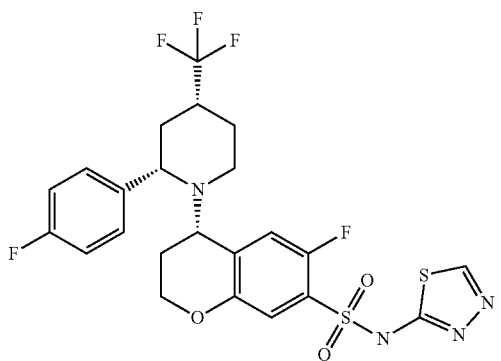
116
-continued
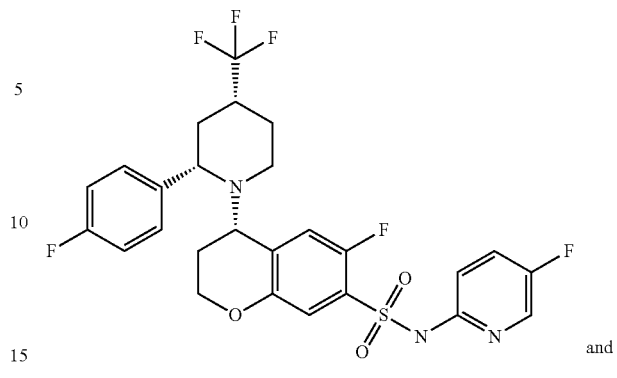
and
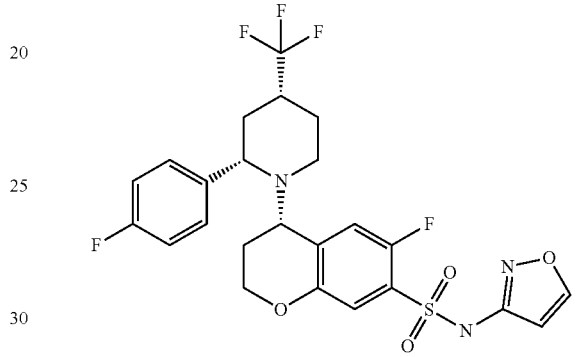
and salts thereof.
E49. A compound of E3 which is:
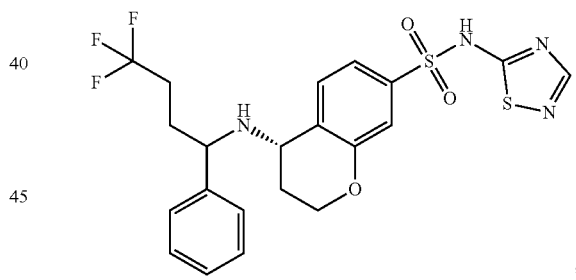
;
Or a salt thereof.
E50. The compound of E1, E2, E5, E6, E7 or E8, excluding:
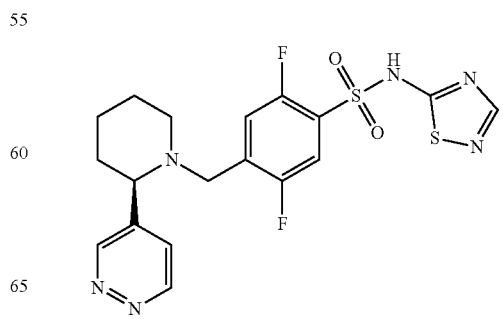

117
-continued
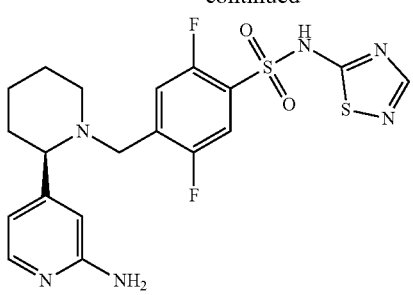
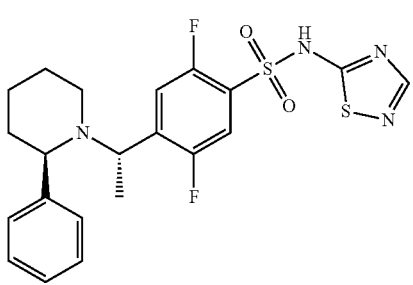
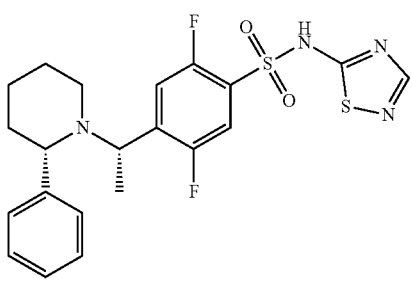
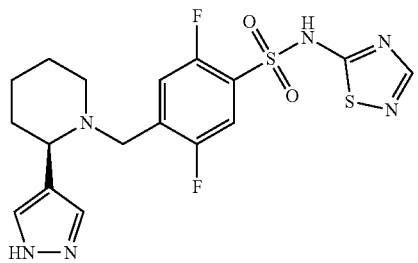
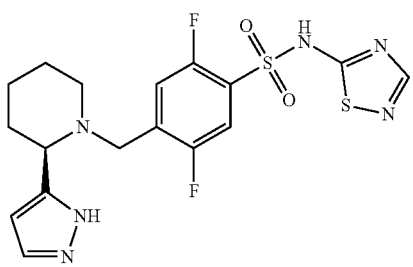
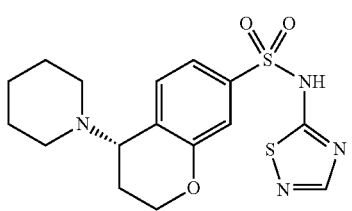
118
-continued
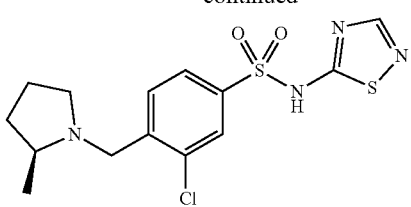
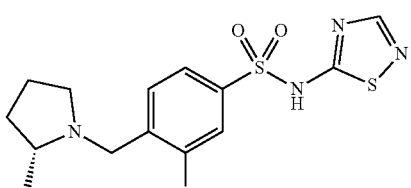
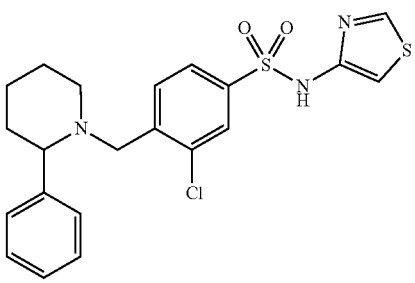
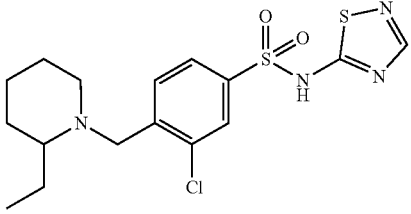
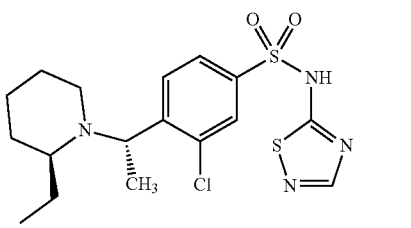
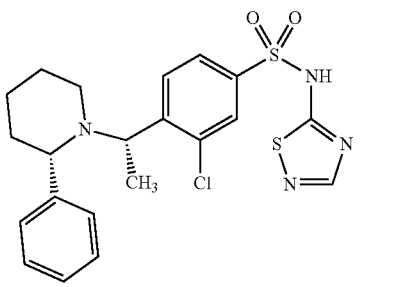
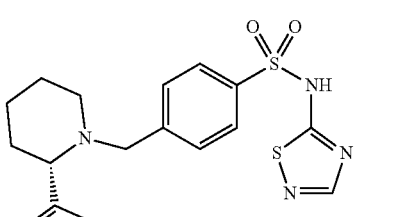

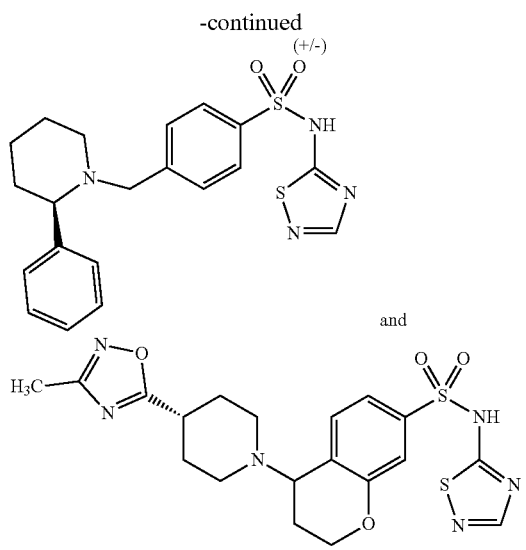

and salts thereof.

In another aspect the present invention provides for a pharmaceutical composition comprising a compound of formula I or a pharmaceutically acceptable salt thereof, and a pharmaceutically acceptable excipient.

In another aspect the present invention provides for a method of treating a disease or condition in a mammal selected from the group consisting of pain, depression, cardiovascular diseases, respiratory diseases, and psychiatric diseases, and combinations thereof, wherein the method comprises administering to the mammal in need thereof a therapeutically effective amount of a compound of formula I, or a pharmaceutically acceptable salt thereof. In another aspect of the present invention said disease or condition is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof. In another aspect of the present invention said disease or condition is selected from the group consisting of pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions cause by stroke or neural trauma, tach-arrhythmias, atrial fibrillation and ventricular fibrillation.

In another aspect the present invention provides for a method of treating pain in a mammal by the inhibition of ion flux through a voltage-dependent sodium channel in the mammal, wherein the method comprises administering to the mammal in need thereof a therapeutically effective amount of a compound of formula I, or a pharmaceutically acceptable salt thereof.

In another aspect the present invention provides for a method of decreasing ion flux through a voltage-dependent sodium channel in a cell in a mammal, wherein the method comprises contacting the cell with a compound of formula I, or a pharmaceutically acceptable salt thereof.

In another aspect the present invention provides for a method of treating pruritus in a mammal, wherein the method comprises administering to the mammal in need thereof a therapeutically effective amount of a compound of formula I, or a pharmaceutically acceptable salt thereof.

In another aspect the present invention provides for a method of treating cancer in a mammal, wherein the method comprises administering to the mammal in need thereof a therapeutically effective amount a compound of formula I, or a pharmaceutically acceptable salt thereof.

In another aspect the present invention provides for a method of treating, but not preventing, pain in a mammal, wherein the method comprises administering to the mammal in need thereof a therapeutically effective amount of a compound of formula I, or a pharmaceutically acceptable salt thereof. In another aspect of the present invention the pain is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof. In another aspect the present invention the pain is associated with a disease or condition selected from the group consisting of HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions cause by stroke or neural trauma, tach-arrhythmias, atrial fibrillation and ventricular fibrillation.

In another aspect the present invention provides for a method for the treatment or prophylaxis of pain, depression, cardiovascular disease, respiratory disease, or psychiatric disease, or a combinations thereof, in an animal which method comprises administering an effective amount of a compound of formula I, or a pharmaceutically acceptable salt thereof.

In another aspect the present invention provides for a compound of formula I, or a pharmaceutically acceptable salt thereof for the use as a medicament for the treatment of diseases and disorders selected from the group consisting of pain, depression, cardiovascular diseases, respiratory diseases, and psychiatric diseases, or a combination thereof.

In another aspect the present invention provides for the use of a compound of formula I, or a pharmaceutically acceptable salt thereof for the manufacture of a medicament for the treatment of diseases and disorders selected from the group consisting of pain, depression, cardiovascular diseases, respiratory diseases, and psychiatric diseases, or a combination thereof.

In another aspect the present invention provides for the invention as described herein.

DETAILED DESCRIPTION OF THE INVENTION

Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include —$CH_2$—$CH_2$—O—$CH_3$, —$CH_2$—$CH_2$—O—$CF_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH=N($CH_3$)—$CH_3$. Up to two heteroatoms can be consecutive, such as, for example, —$CH_2$—NH—$OCH_3$ and —$CH_2$—O—Si($CH_3$)$_3$.

The term "alkylene" by itself or as part of another substituent means a divalent radical derived from an alkane (including branched alkane), as exemplified by —$CH_2CH_2CH_2CH_2$— and —CH($CH_2$)$CH_2CH_2$—. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)C $H_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio", are used in their conventional sense, and refer to those alkyl groups attached to the remainder of the molecule via an oxygen atom ("oxy"), an amino group ("amino") or thio group. Additionally, for dialkylamino groups, the alkyl portions can be the same or different.

The term "acyl" means a group ($C_{1-6}$ alkyl)-C(=O)—.

The terms "halo" or "halogen," by themselves or as part of another substituent, mean, unless otherwise stated, a fluorine, chlorine, bromine, or iodine atom. The term "(halo)alkyl" is meant to include both a "alkyl" and "haloalkyl" substituent. Additionally, the term "haloalkyl," is meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, naphthyl, 1, 2, 3, 4-tetrahydronaphthyl, anthracenyl, and the like.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e., ($C_3$-$C_7$)carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocycles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2] octane, etc). The "carbocycle" or "carbocyclyl" can also be optionally substituted with one or more (e.g., 1, 2 or 3) oxo groups. In one embodiment the term carbocycle includes a $C_{3-15}$ carbocycle. In one embodiment the term carbocycle includes a $C_{6-15}$ carbocycle. In one embodiment the term carbocycle includes a $C_{3-8}$ carbocycle. In one embodiment the term carbocycle includes a $C_{3-6}$ carbocycle. In one embodiment the term carbocycle includes a $C_{3-8}$ carbocycle. Non-limiting examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, bicyclo[2.2.1]heptane, pinane, adamantane, norborene, spirocyclic $C_{5-12}$ alkane, and 1-cyclohex-3-enyl.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). In one embodiment the term heterocycle includes a $C_{2-20}$ heterocycle. In one embodiment the term heterocycle includes a $C_{2-7}$ heterocycle. In one embodiment the term heterocycle includes a $C_{2-5}$ heterocycle. In one embodiment the term heterocycle includes a $C_{2-4}$ heterocycle. In one embodiment the term heterocycle includes a 3-15 membered heterocycle. In one embodiment the term heterocycle includes a 3-8 membered heterocycle. In one embodiment the term heterocycle includes a 3-6 membered heterocycle. In one embodiment the term heterocycle includes a 4-6 membered heterocycle. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrahydrothiophene, quinuclidine, tropane, 2-azaspiro[3.3]heptane, (1R,5S)-3-azabicyclo[3.2.1]octane, (1 s,4s)-2-azabicyclo[2.2.2]octane, (1R,4R)-2-oxa-5-azabicyclo[2.2.2]octane and pyrrolidin-2-one.

The term "heterocyclyloxy" as used herein refers to a group (heterocyclyl)-O—, wherein the term heterocyclyl has the meaning defined herein.

The term "alkoxycarbonyl" as used herein refers to a group (alkyl)-O—C(=O)—, wherein the term alkyl has the meaning defined herein.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line " $\sim$ " that intersects a bond in a chemical structure indicates the point of attachment of the bond that the wavy bond intersects in the chemical structure to the remainder of a molecule.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process.

The terms "racemic mixture" and "racemate" refer to an equimolar mixture of two enantiomeric species, devoid of optical activity.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 97% the absolute stereoisomer depicted. In another embodiment, the compound may be at least 98% the absolute stereoisomer depicted. In another embodiment, the compound may be at least 99% the absolute stereoisomer depicted.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenyl sulfonylethyl, cyanoethyl, 2-(trimethylsilyl) ethyl, 2-(trimethyl silyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})$alkyl$)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

Compounds

In one aspect the present invention provides for compounds of Formula I and its embodiments as described hereinbove.

In another embodiment, the compound is selected from compounds of formula I as described in the Examples herein and salts thereof.

Synthesis of Compounds

Compounds of formula (I) may be prepared by the process illustrated in the schemes below.

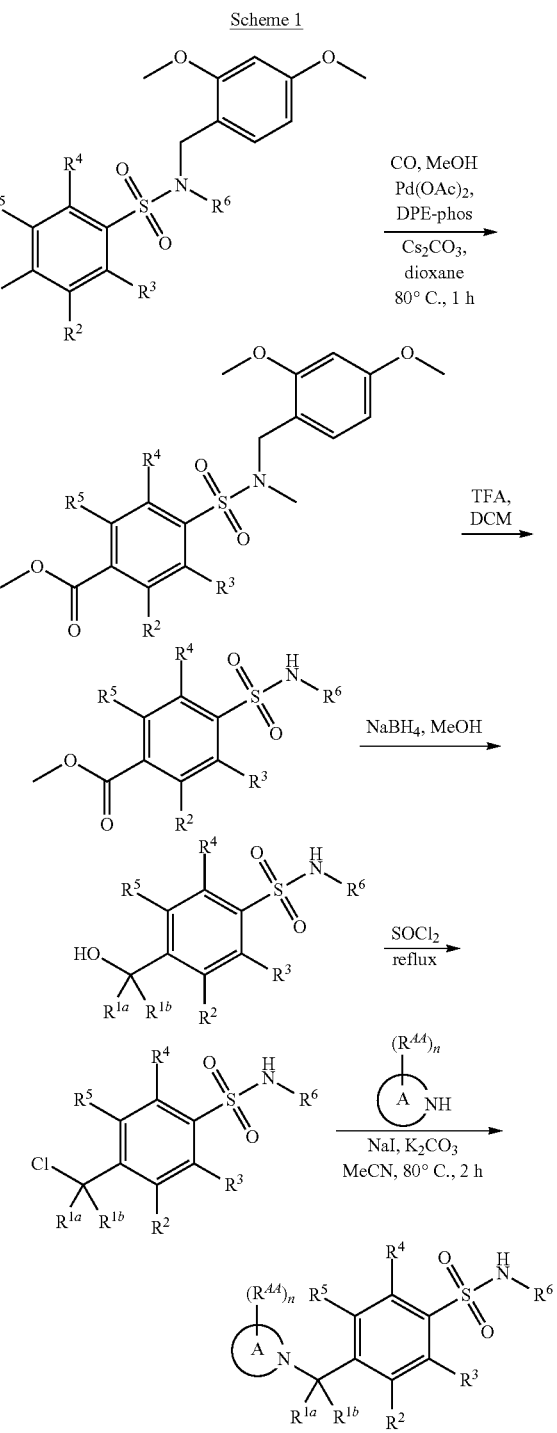

Scheme 1

Scheme 2

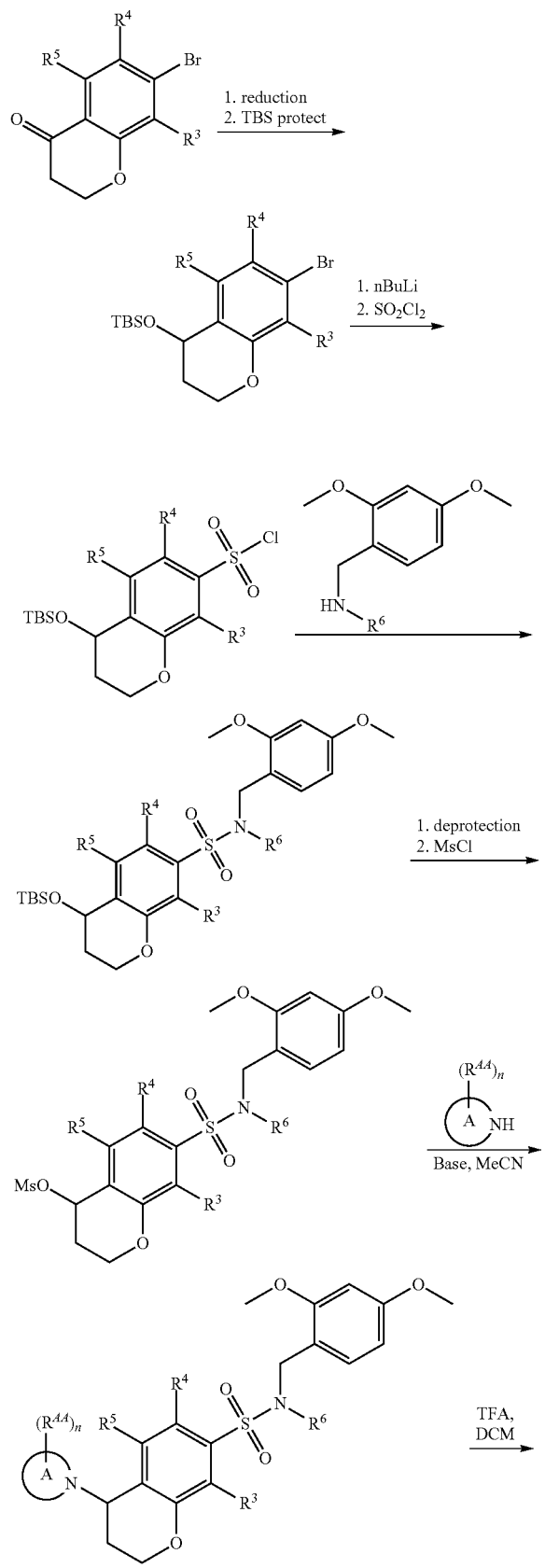

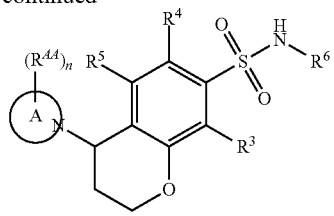

Pharmaceutical Compositions and Administration

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of formula I or and embodiment thereof and at least one pharmaceutically acceptable carrier, diluent or excipient. The compositions of the invention can be used to selectively inhibit NaV1.7 in patients (e.g, humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of formula I or an embodiment thereof, and its stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of formula I or its embodiments and compositions comprising compounds of formula I or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit NaV1.7 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response.

The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of formula I or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) $21^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

Formulations of a compound of the invention (e.g., compound of formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

In one aspect of topical applications, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

Aqueous suspensions of a compound of the invention (e.g., compound of formula I or an embodiment thereof) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/02043 54) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

A compound of formula I (or an embodiment thereof) used in the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. A compound of formula I (or an embodiment thereof) need not be, but is optionally formulated with one or more agent currently used to prevent or treat the disorder in question. The effective amount of such other agents depends on the amount of a compound of the invention present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of formula I (or an embodiment thereof) (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 µg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 µg kg to 100 mg/kg or more, depending on the factors mentioned above. For repeated administrations over several days or longer, depending on the condition, the treatment would generally be sustained until a desired suppression of disease symptoms occurs. One exemplary dosage of a compound of formula I (or an embodiment thereof) would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 µg kg to 1 mg/kg, about 1 µg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

Indications and Methods of Treatment

The compounds of the invention modulate, preferably inhibit, ion flux through a voltage-dependent sodium channel in a mammal, (e.g, a human). Any such modulation, whether it be partial or complete inhibition or prevention of ion flux, is sometimes referred to herein as "blocking" and corresponding compounds as "blockers" or "inhibitors". In general, the compounds of the invention modulate the activity of a sodium channel downwards by inhibiting the voltage-dependent activity of the sodium channel, and/or reduce or prevent sodium ion flux across a cell membrane by preventing sodium channel activity such as ion flux.

Accordingly, the compounds of the invention are sodium channel blockers and are therefore useful for treating diseases and conditions in mammals, for example humans, and other organisms, including all those diseases and conditions which are the result of aberrant voltage-dependent sodium channel biological activity or which may be ameliorated by modulation of voltage-dependent sodium channel biological activity. In particular, the compounds of the invention, i.e., the compounds of formula (I) and embodiments and (or stereoisomers, geometric isomers, tautomers, solvates, metabolites, isotopes, pharmaceutically acceptable salts, or prodrugs thereof), are useful for treating diseases and conditions in mammals, for example humans, which are the result of aberrant voltage-dependent NaV1.7 biological activity or which may be ameliorated by the modulation, preferably the inhibition, of NaV1.7 biological activity. In certain aspects, the compounds of the invention selectively inhibit NaV1.7 over NaV1.5.

As defined herein, a sodium channel-mediated disease or condition refers to a disease or condition in a mammal, preferably a human, which is ameliorated upon modulation of the sodium channel and includes, but is not limited to, pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome.

In one aspect, the present invention relates to compounds, pharmaceutical compositions and methods of using the compounds and pharmaceutical compositions for the treatment of sodium channel-mediated diseases in mammals, preferably humans and preferably diseases and conditions related to pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome, by administering to a mammal, for example a human, in need of such treatment an effective amount of a sodium channel blocker modulating, especially inhibiting, agent.

A sodium channel-mediated disease or condition also includes pain associated with HIV, HIV treatment induced neuropathy, trigeminal neuralgia, glossopharyngeal neuralgia, neuropathy secondary to metastatic infiltration, adiposis dolorosa, thalamic lesions, hypertension, autoimmune disease, asthma, drug addiction (e.g., opiate, benzodiazepine, amphetamine, cocaine, alcohol, butane inhalation), Alzheimer, dementia, age-related memory impairment, Korsakoff syndrome, restenosis, urinary dysfunction, incontinence, Parkinson's disease, cerebrovascular ischemia, neurosis, gastrointestinal disease, sickle cell anemia, transplant rejection, heart failure, myocardial infarction, reperfusion injury, intermittant claudication, angina, convulsion, respiratory disorders, cerebral or myocardial ischemias, long-QT syndrome, Catecholeminergic polymorphic ventricular tachycardia, ophthalmic diseases, spasticity, spastic paraplegia, myopathies, myasthenia gravis, paramyotonia congentia, hyperkalemic periodic paralysis, hypokalemic periodic paralysis, alopecia, anxiety disorders, psychotic disorders, mania, paranoia, seasonal affective disorder, panic disorder, obsessive compulsive disorder (OCD), phobias, autism, Aspergers Syndrome, Retts syndrome, disintegrative disorder, attention deficit disorder, aggressivity, impulse control disorders, thrombosis, pre clampsia, congestive cardiac failure, cardiac arrest, Freidrich's ataxia, Spinocerebellear ataxia, myelopathy, radiculopathy, systemic lupus erythamatosis, granulomatous disease, olivo-ponto-cerebellar atrophy, spinocerebellar ataxia, episodic ataxia, myokymia, progressive pallidal atrophy, progressive supranuclear palsy and spasticity, traumatic brain injury, cerebral oedema, hydrocephalus injury, spinal cord injury, anorexia nervosa, bulimia, Prader-Willi syndrome, obesity, optic neuritis, cataract, retinal haemorrhage, ischaemic retinopathy, retinitis pigmentosa, acute and chronic glaucoma, macular degeneration, retinal artery occlusion, Chorea, Huntington's chorea, cerebral edema, proctitis, post-herpetic neuralgia, eudynia, heat sensitivity, sarcoidosis, irritable bowel syndrome, Tourette syndrome, Lesch-Nyhan Syndrome, Brugado syndrome, Liddle syndrome, Crohns disease, multiple sclerosis and the pain associated with multiple sclerosis (MS), amyotrophic lateral sclerosis (ALS), disseminated sclerosis, diabetic neuropathy, peripheral neuropathy, charcot marie tooth syndrome, arthritic, rheumatoid arthritis, osteoarthritis, chondrocalcinosis, atherosclerosis, paroxysmal dystonia, myasthenia syndromes, myotonia, myotonic dystrophy, muscular dystrophy, malignant hyperthermia, cystic fibrosis, pseudoaldosteronism, rhabdomyolysis, mental handicap, hypothyroidism, bipolar depression, anxiety, schizophrenia, sodium channel toxin related illnesses, familial erythromelalgia, primary erythromelalgia, rectal pain, cancer, epilepsy, partial and general tonic seizures, febrile seizures, absence seizures (petit mal), myoclonic seizures, atonic seizures, clonic seizures, Lennox Gastaut, West Syndome (infantile spasms), multiresistant seizures, seizure prophylaxis (antiepileptogenic), familial Mediterranean fever syndrome, gout, restless leg syndrome, arrhythmias, fibromyalgia, neuroprotection under ischaemic conditions caused by stroke or neural trauma, tachy-arrhythmias, atrial fibrillation and ventricular fibrillation and as a general or local anaesthetic.

As used herein, the term "pain" refers to all categories of pain and is recognized to include, but is not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, chronic regional pain syndrome (CRPS), reflex sympathetic dystrophy, brachial plexus avulsion, neurogenic bladder, acute pain (e.g., musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV pain, post-herpetic pain, non-cardiac chest pain, irritable bowel syndrome and pain associated with bowel disorders and dyspepsia, and combinations thereof.

Furthermore, sodium channel blockers have clinical uses in addition to pain. The present invention therefore also relates to compounds, pharmaceutical compositions and methods of using the compounds and pharmaceutical compositions for the treatment of diseases or conditions such as cancer and pruritus (itch).

Pruritus, commonly known as itch, is a common dermatological condition. While the exact causes of pruritus are complex and incompletely understood, there has long been evidence that itch involves sensory neurons, especially C fibers, similar to those that mediate pain (Schmelz, M., et al., J. Neurosci. (1997), 17: 8003-8). In particular, it is believed that sodium influx through voltage-gated sodium channels is essential for the propagation of itch sensation from the skin. Transmission of the itch impulses results in the unpleasant sensation that elicits the desire or reflex to scratch.

Multiple causes and electrical pathways for eliciting itch are known. In humans, pruritus can be elicited by histamine or PAR-2 agonists such as mucunain that activate distinct populations of C fibers (Namer, B., et al., J. Neurophysiol. (2008), 100: 2062-9). A variety of neurotrophic peptides are known to mediate itch in animal models (Wang, H., and Yosipovitch, G., International Journal of Dermatology (2010), 49: 1-11). Itch can also be elicited by opioids, evidence of distinct pharmacology from that of pain responses.

There exists a complex interaction between itch and pain responses that arises in part from the overlapping sensory input from the skin (Ikoma, A., et al., Arch. Dermatol. (2003), 139: 1475-8) and also from the diverse etiology of both pain and pruritus. Pain responses can exacerbate itching by enhancing central sensitization or lead to inhibition of painful scratching. Particularly severe forms of chronic itch occur when pain responses are absent, as in the case of post-herpetic itch (Oaklander, A. L., et al., Pain (2002), 96: 9-12).

The compounds of the invention can also be useful for treating pruritus. The rationale for treating itch with inhibitors of voltage-gated sodium channels, especially NaV1.7, is as follows:

The propagation of electrical activity in the C fibers that sense pruritinergic stimulants requires sodium entry through voltage-gated sodium channels.

NaV1.7 is expressed in the C fibers and kerotinocytes in human skin (Zhao, P., et al., Pain (2008), 139: 90-105).

A gain of function mutation of NaV1.7 (L858F) that causes erythromelalgia also causes chronic itch (Li, Y., et al., Clinical and Experimental Dermatology (2009), 34: e313-e4).

Chronic itch can be alleviated with treatment by sodium channel blockers, such as the local anesthetic lidocaine (Oaklander, A. L., et al., Pain (2002), 96: 9-12; Villamil, A. G., et al., The American Journal of Medicine (2005), 118: 1160-3). In these reports, lidocaine was effective when administered either intravenously or topically (a Lidoderm patch). Lidocaine can have multiple activities at the plasma concentrations achieved when administered systemically, but when administered topically, the plasma concentrations are only about 1 μM (Center for Drug Evaluation and Research NDA 20-612). At these concentrations, lidocaine is selective for sodium channel block and inhibits spontaneous electrical activity in C fibers and pain responses in animal models (Xiao, W. H., and Bennett, G. J. Pain (2008), 137: 218-28). The types of itch or skin irritation, include, but are not limited to:

psoriatic pruritus, itch due to hemodyalisis, aguagenic pruritus, and itching caused by skin disorders (e.g., contact dermatitis), systemic disorders, neuropathy, psychogenic factors or a mixture thereof;

itch caused by allergic reactions, insect bites, hypersensitivity (e.g., dry skin, acne, eczema, psoriasis), inflammatory conditions or injury;

itch associated with vulvar vestibulitis; and skin irritation or inflammatory effect from administration of another therapeutic such as, for example, antibiotics, antivirals and antihistamines.

The compounds of the invention are also useful in treating certain cancers, such as hormone sensitive cancers, such as prostate cancer (adenocarcinoma), breast cancer, ovarian cancer, testicular cancer and thyroid neoplasia, in a mammal, preferably a human. The voltage gated sodium channels have been demonstrated to be expressed in prostate and breast cancer cells. Up-regulation of neonatal NaV1.5 occurs as an integral part of the metastatic process in human breast cancer and could serve both as a novel marker of the metastatic phenotype and a therapeutic target (Clin. Cancer Res. (2005), August 1; 11(15): 5381-9). Functional expression of voltage-gated sodium channel alpha-subunits, specifically NaV1.7, is associated with strong metastatic potential in prostate cancer (CaP) in vitro. Voltage-gated sodium channel alpha-subunits immunostaining, using antibodies specific to the sodium channel alpha subunit was evident in prostatic tissues and markedly stronger in CaP vs non-CaP patients (Prostate Cancer Prostatic Dis., 2005; 8(3):266-73). See also Diss, J. K. J., et al., Mol. Cell. Neurosci. (2008), 37:537-547 and Kis-Toth, K., et al., The Journal of Immunology (2011), 187:1273-1280.

In consideration of the above, in one embodiment, the present invention provides a method for treating a mammal for, or protecting a mammal from developing, a sodium channel-mediated disease, especially pain, comprising administering to the mammal, especially a human, in need thereof, a therapeutically effective amount of a compound of the invention or a pharmaceutical composition comprising a therapeutically effective amount of a compound of the invention wherein the compound modulates the activity of one or more voltage-dependent sodium channels.

In another embodiment of the invention is a method of treating a disease or a condition in a mammal, preferably a human, wherein the disease or condition is selected from the group consisting of pain, depression, cardiovascular diseases, respiratory diseases, and psychiatric diseases, and combinations thereof, and wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is wherein the disease or condition is selected from the group consisting of acute pain, chronic pain, neuropathic pain, inflammatory pain, visceral pain, cancer pain, chemotherapy pain, trauma pain, surgical pain, post surgical pain, childbirth pain, labor pain, neurogenic bladder, ulcerative colitis, persistent pain, peripherally mediated pain, centrally mediated pain, chronic headache, migraine headache, sinus headache, tension headache, phantom limb pain, peripheral nerve injury, and combinations thereof.

Another embodiment of this embodiment is wherein the disease or condition is selected from the group consisting of pain associated with HIV, HIV treatment induced neuropathy, trigeminal neuralgia, post herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions caused by stroke or neural trauma, tachy arrhythmias, atrial fibrillation and ventricular fibrillation.

Another embodiment of the invention is a method of treating, but not preventing, pain in a mammal, wherein the method comprises administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is a method wherein the pain is selected from the group consisting of neuropathic pain, inflammatory pain, visceral pain, cancer pain, chemotherapy pain, trauma pain, surgical pain, post surgical pain, childbirth pain, labor pain, dental pain, chronic pain, persistent pain, peripherally mediated pain, centrally mediated pain, chronic headache, migraine headache, sinus headache, tension headache, phantom limb pain, peripheral nerve injury, trigeminal neuralgia, post herpetic neuralgia, eudynia, familial erythromelalgia, primary erythromelalgia, familial rectal pain or fibromyalgia, and combinations thereof.

Another embodiment of this embodiment is a method wherein the pain is associated with a disease or condition selected from HIV, HIV treatment induced neuropathy, heat sensitivity, tosarcoidosis, irritable bowel syndrome, Crohns disease, multiple sclerosis, amyotrophic lateral sclerosis, diabetic neuropathy, peripheral neuropathy, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, neurogenic bladder, ulcerative colitis, cancer, epilepsy, partial and general tonic seizures, restless leg syndrome, arrhythmias, ischaemic conditions caused by stroke or neural trauma, tachy arrhythmias, atrial fibrillation and ventricular fibrillation.

Another embodiment of the invention is the method of treating pain in a mammal, preferably a human, by the inhibition of ion flux through a voltage dependent sodium channel in the mammal, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating pruritus in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating cancer in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of decreasing ion flux through a voltage dependent sodium channel in a cell in a mammal, wherein the method comprises contacting the cell with an embodiment of a compound of the invention, as set forth above, as a stereoisomer, enantiomer or tautomer thereof or mixtures thereof, or a pharmaceutically acceptable salt, solvate or prodrug thereof.

Another embodiment of the invention is the method of selectively inhibiting a first voltage-gated sodium channel over a second voltage-gated sodium channel in a mammal, wherein the method comprises administering to the mammal an inhibitory amount of a compound of formula (I), or an embodiment of a compound of formula (I).

Another embodiment of the invention is the method of selectively inhibiting NaV1.7 in a mammal or a mammalian cell as compared to NaV1.5, wherein the method comprises administering to the mammal in need thereof an inhibitory amount of a compound of formula (I) or an embodiment of an embodiment thereof.

For each of the above embodiments described related to treating diseases and conditions in a mammal, the present invention also contemplates relatedly a compound of formula I or an embodiment thereof for the use as a medicament in the treatment of such diseases and conditions.

For each of the above embodiments described related to treating diseases and conditions in a mammal, the present invention also contemplates relatedly the use of a compound of formula I or an embodiment thereof for the manufacture of a medicament for the treatment of such diseases and conditions.

Another embodiment of the invention is a method of using the compounds of formula (I) as standards or controls in in vitro or in vivo assays in determining the efficacy of test compounds in modulating voltage-dependent sodium channels.

In another embodiment of the invention, the compounds of formula (I) are isotopically-labeled by having one or more atoms therein replaced by an atom having a different atomic mass or mass number. Such isotopically-labeled (i.e., radiolabelled) compounds of formula (I) are considered to be within the scope of this invention. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These isotopically-labeled compounds would be useful to help determine or measure the effectiveness of the compounds, by characterizing, for example, the site or mode of action on the sodium channels, or binding affinity to pharmacologically important site of action on the sodium channels, particularly NaV1.7. Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e., $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Testing Compounds

The assessment of the compounds of the invention in mediating, especially inhibiting, the sodium channel ion flux can be determined using the assays described hereinbelow. Alternatively, the assessment of the compounds in treating conditions and diseases in humans may be established in industry standard animal models for demonstrating the efficacy of compounds in treating pain. Animal models of human neuropathic pain conditions have been developed that result in reproducible sensory deficits (allodynia, hyperalgesia, and spontaneous pain) over a sustained period of time that can be evaluated by sensory testing. By establishing the degree of mechanical, chemical, and temperature induced allodynia and hyperalgesia present, several physio-pathological conditions observed in humans can be modeled allowing the evaluation of pharmacotherapies.

In rat models of peripheral nerve injury, ectopic activity in the injured nerve corresponds to the behavioural signs of pain. In these models, intravenous application of the sodium channel blocker and local anesthetic lidocaine can suppress the ectopic activity and reverse the tactile allodynia at concentrations that do not affect general behaviour and motor function (Mao, J. and Chen, L. L, Pain (2000), 87:7-17). Allometric scaling of the doses effective in these rat models, translates into doses similar to those shown to be efficacious in humans (Tanelian, D. L. and Brose, W. G., Anesthesiology (1991), 74(5):949-951). Furthermore, Lidoderm®, lidocaine applied in the form of a dermal patch, is currently an FDA approved treatment for post-herpetic neuralgia (Devers, A. and Glaler, B. S., Clin. J. Pain (2000), 16(3):205-8).

The present invention readily affords many different means for identification of sodium channel modulating agents that are useful as therapeutic agents. Identification of modulators of sodium channel can be assessed using a variety of in vitro and in vivo assays, e.g., measuring current, measuring membrane potential, measuring ion flux, (e.g., sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., J. General Physiology (1983), 83:613-642, and Leuwer, M., et al., Br. J. Pharmacol (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive 22[Na] and 14[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Life Technologies, or Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

Modulating agents so identified are then tested in a variety of in vivo models so as to determine if they alleviate pain, especially chronic pain or other conditions such as cancer and pruritus (itch) with minimal adverse events. The assays described below in the Biological Assays Section are useful in assessing the biological activity of the instant compounds.

Typically, the efficacy of a compound of the invention is expressed by its IC50 value ("Inhibitory Concentration— 50%"), which is the measure of the amount of compound required to achieve 50% inhibition of the activity of the target sodium channel over a specific time period.

For example, representative compounds of the present invention have demonstrated IC50's ranging from less than 100 nanomolar to less than 10 micromolar in the patch voltage clamp NaV1.7 electrophysiology assay described herein.

In another aspect of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting NaV1.1, NaV1.2, NaV1.3, NaV1.4, NaV1.5, NaV1.6, NaV1.7, NaV1.8, or NaV1.9 activity, preferably NaV1.7 activity, in a biological sample or a mammal, preferably a human, which method comprises administering to the mammal, preferably a human, or contacting said biological sample with a compound of formula (I) or a pharmaceutical composition comprising a compound of formula (I). The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of NaV1.1, NaV1.2, NaV1.3, NaV1.4, NaV1.5, NaV1.6, NaV1.7, NaV1.8, or NaV1.9 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention (or stereoisomers, geometric isomers, tautomers, solvates, metabolites, isotopes, pharmaceutically acceptable salts, or prodrugs thereof) and/or the pharmaceutical compositions described herein which comprise a pharmaceutically acceptable excipient and one or more compounds of the invention, can be used in the preparation of a medicament for the treatment of sodium channel-mediated disease or condition in a mammal.

Combination Therapy

The compounds of the invention may be usefully combined with one or more other compounds of the invention or one or more other therapeutic agent or as any combination thereof, in the treatment of sodium channel-mediated diseases and conditions. For example, a compound of the invention may be administered simultaneously, sequentially or separately in combination with other therapeutic agents, including, but not limited to:

opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetomeniphen, salicylates (e.g., aspirin);

nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, valproate, topiramate, gabapentin and pregabalin;

antidepressants such as tricyclic antidepressants, e.g., amitriptyline, clomipramine, despramine, imipramine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., (αR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

coal-tar analgesics, in particular paracetamol;

serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g., maprotiline, lofepramine, mirtazepine, oxaprotiline, fezolamine, tomoxetine, mianserin, buprorion, buprorion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT3 antagonists such as ondansetron;

metabotropic glutamate receptor (mGluR) antagonists;

local anaesthetic such as mexiletine and lidocaine;

corticosteroid such as dexamethasone;

antiarrhythimics, e.g., mexiletine and phenytoin;

muscarinic antagonists, e.g., tolterodine, propiverine, tropsium t chloride, darifenacin, solifenacin, temiverine and ipratropium;

cannabinoids;

vanilloid receptor agonists (e.g., resinferatoxin) or antagonists (e.g., capsazepine);

sedatives, e.g., glutethimide, meprobamate, methaqualone, and dichloralphenazone;

anxiolytics such as benzodiazepines, antidepressants such as mirtazapine, topical agents (e.g., lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

5-HT receptor agonists/antagonists;

PDEV inhibitors;

Tramadol®;

cholinergic (nicotinc) analgesics;

alpha-2-delta ligands;

prostaglandin E2 subtype antagonists;

leukotriene B4 antagonists;

5-lipoxygenase inhibitors; and

5-HT3 antagonists.

Sodium channel-mediated diseases and conditions that may be treated and/or prevented using such combinations include but not limited to, pain, central and peripherally mediated, acute, chronic, neuropathic as well as other diseases with associated pain and other central nervous disorders such as epilepsy, anxiety, depression and bipolar disease; or cardiovascular disorders such as arrhythmias, atrial fibrillation and ventricular fibrillation; neuromuscular disorders such as restless leg syndrome and muscle paralysis or tetanus; neuroprotection against stroke, neural trauma and multiple sclerosis; and channelopathies such as erythromyalgia and familial rectal pain syndrome.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

The invention will be more fully understood by reference to the following examples. They should not, however, be construed as limiting the scope of the invention.

EXAMPLES

These examples serve to provide guidance to a skilled artisan to prepare and use the compounds, compositions and methods of the invention. While particular embodiments of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering group, by utilizing other suitable reagents known in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celcius. Commerically available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. $^1$H NMR spectra were obtained in deuterated $CDCl_3$, $d_6$-DMSO, $CH_3OD$ or $d_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, ar reported in Hz (Hertz).

All abbreviations used to describe reagents, reaction conditions or equipment are intended to be consistent with the definitions set forth in the "List of standard abbreviates and acronyms".

The chemical names of discrete compounds of the invention were obtained using the structure naming feature of ChemDraw naming program.

LCMS Analytical Methods

Final compounds were analyzed using three different LC/MS conditions, with UV detector monitoring at 214 nm and 254 nm, and mass spectrometry scanning 110-800 amu in ESI+ ionization mode.

LC/MS Method A (8.0 min LC-MS Run): XBridge C18 column (4.6×50 mm, 3.5 m, 40° C.); mobile phase: A=10 mM ammonium hydrogen carbonate in water, B=acetonitrile; gradient: 0.0-8.0 min, 5%-95% B; flow rate=1.2 mL/min.

LC/MS Method B (8.0 min LC-MS Run): XBridge C18 column (4.6×50 mm, 3.5 m, 40° C.); mobile phase: A=0.1% ammonia in water, B=acetonitrile; gradient: 0.0-8.0 min, 5%-95% B; flow rate=1.2 mL/min.

LC/MS Method C (8.0 min LC-MS Run): XBridge C18 column (4.6×50 mm, 3.5 m, 40° C.); mobile phase: A=0.1% TFA in water, B=acetonitrile; gradient: 0.0-8.0 min, 5%-95% B; flow rate=1.2 mL/min.

LC/MS Method D: Agilent SB C18, 2.1×30 mm, 1.8 μm; mobile phase: A water (0.05% TFA), B $CH_3CN$ (0.05% TFA); gradient: 3% B (0.3 min), followed by 3-95% B (6.5 min), 95% B (1.5 min); flow rate: 0.4 mL/min; oven temperature 25° C.

LC/MS Method E: Acquity BEH C18, 2.1×50 mm, 1.8 μm; mobile phase: A water (0.1% FA), B $CH_3CN$ (0.1% FA); gradient: 3% B (0.4 min), followed by 3-95% B (7.5 min), 95% B (0.5 min); flow rate: 0.5 mL/min; oven temperature 25° C.

Abbreviations

MeCN Acetonitrile
EtOAc Ethyl acetate
DCE Dichloroethane
DCM Dichloromethane
DIPEA Diisopropylethylamine
DEA Diethylamine
DMAP 4-dimethylaminopyridine
DMF N,N-Dimethylformamide
DMSO Dimethyl sulfoxide
FA Formic acid
IPA Isopropyl alcohol
TFA Trifluoroacetic acid
EDCI 1-Ethyl-3-(3-dimethylaminopropyl)carbodiimide hydrochloride
HCl Hydrochloric acid
HPLC High Pressure Liquid Chromatography
LCMS Liquid Chromatography Mass Spectrometry
MeOH Methanol
NMP N-methyl-2-pyrrolidone
RPHPLC Reverse phase high pressure liquid chromatography
RT Retention time
SFC Supercritical Fluid Chromatography
THF Tetrahydrofuran
TEA Triethylamine Example 1

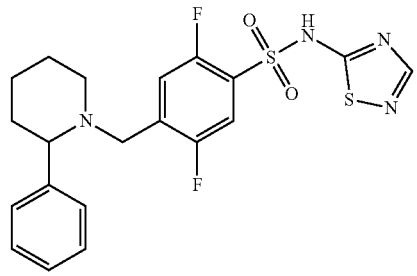 [SMILES: O=S(=O)(Nc1ncns1)c1cc(F)c(CN2CCCCC2c2ccccc2)cc1F]

2,5-difluoro-4-((2-phenylpiperidin-1-yl)methyl)-N-(1,2,4-thiadiazol-5-yl)benzenesulfonamide

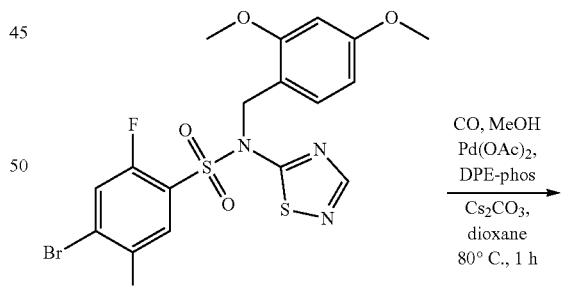

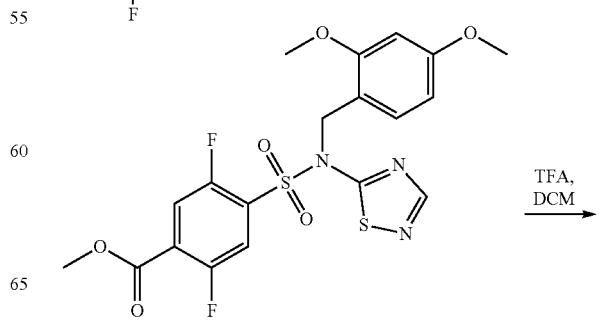

-continued

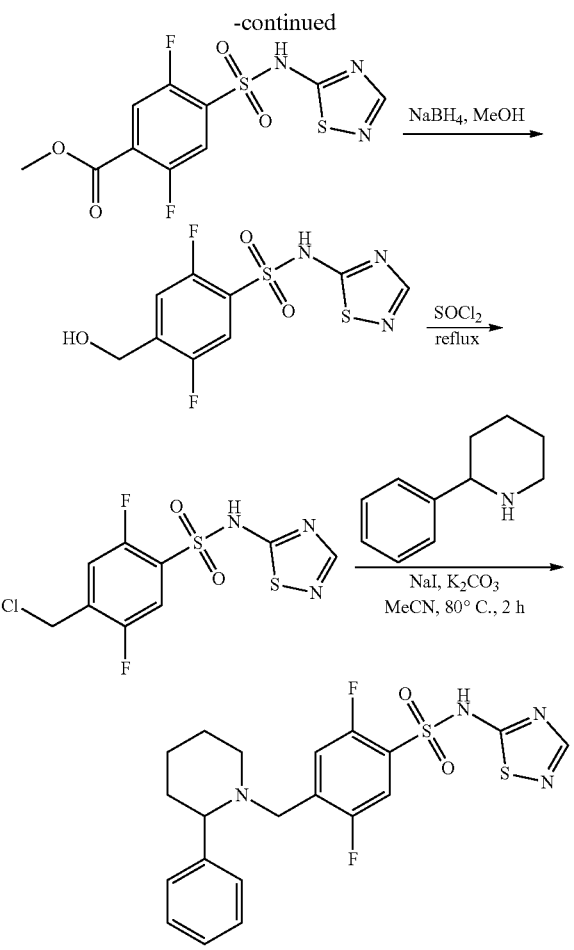

Step 1

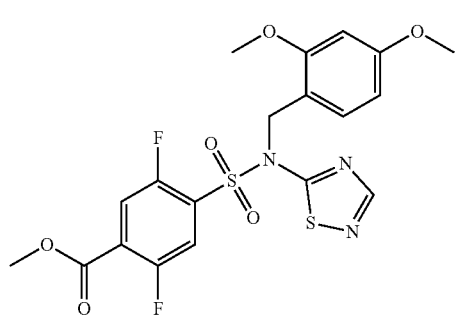

Methyl 4-(N-(2,4-dimethoxybenzyl)-N-(1,2,4-thiadiazol-5-yl)sulfamoyl)-2,5-difluorobenzoate A mixture of 4-bromo-N-[(2,4-dimethoxyphenyl)methyl]-2,5-difluoro-N-(1,2,4-thiadiazol-5-yl)benzenesulfonamide (500 mg, 0.99 mmol), oxydi-2,1-phenylene)bis(diphenylphosphine (125 mg, 0.23 mmol), cesium carbonate (643 mg, 1.98 mmol) and palladium diacetate (25 mg, 0.11 mmol) in MeOH (1.25 mL) and 1,4-dioxane (25 mL) were stirred under CO atmosphere at 80° C. for 1 h. The reaction mixture was cooled to room temperature, filtered and concentrated. The residue was purified by silica gel chromatography (eluting with 50% EtOAc in petroleum ether) to afford the desired product (300 mg, 62.6%) as a white solid. LCMS (ESI) m/z: 508.1 [M+Na]$^+$.

Step 2

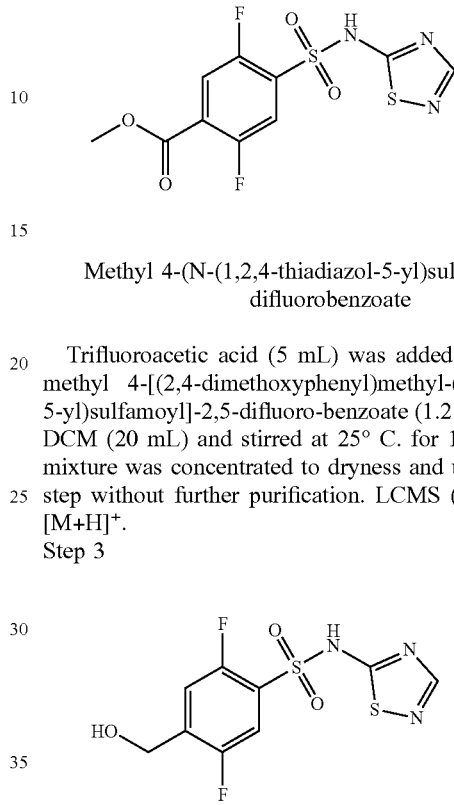

Methyl 4-(N-(1,2,4-thiadiazol-5-yl)sulfamoyl)-2,5-difluorobenzoate

Trifluoroacetic acid (5 mL) was added to a solution of methyl 4-[(2,4-dimethoxyphenyl)methyl-(1,2,4-thiadiazol-5-yl)sulfamoyl]-2,5-difluoro-benzoate (1.2 g, 2.47 mmol) in DCM (20 mL) and stirred at 25° C. for 1 h. The reaction mixture was concentrated to dryness and used for the next step without further purification. LCMS (ESI) m/z: 336.1 [M+H]$^+$.

Step 3

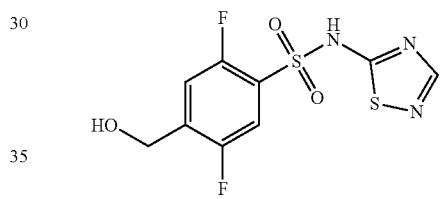

2,5-difluoro-4-(hydroxymethyl)-N-(1,2,4-thiadiazol-5-yl)benzenesulfonamide

To a solution of methyl 2,5-difluoro-4-(1,2,4-thiadiazol-5-ylsulfamoyl)benzoate (820 mg, 2.45 mmol) in MeOH (50 mL) was added sodium borohydride (929 mg, 24.5 mmol). The reaction mixture was stirred at 25° C. for 2 h and concentrated to dryness. The crude was purified by Combiflash (20-50% MeCN in 0.1% FA) to afford the desired product (500 mg, 66.5%) as a white solid. LCMS (ESI) m/z: 308.0 [M+H]$^+$.

Step 4

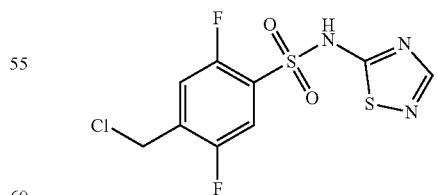

4-(Chloromethyl)-2,5-difluoro-N-(1,2,4-thiadiazol-5-yl)benzenesulfonamide

A solution of 2,5-difluoro-4-(hydroxymethyl)-N-(1,2,4-thiadiazol-5-yl)benzenesulfonamide (200 mg, 0.65 mmol) in Step 5

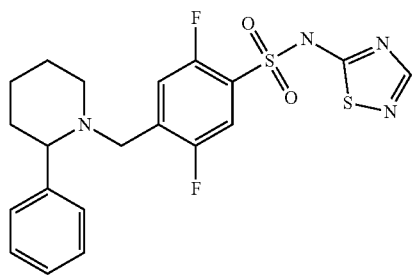 [SMILES: O=S(=O)(Nc1ncns1)c1cc(F)c(CN2CCCCC2c2ccccc2)cc1F]

2,5-difluoro-4-((2-phenylpiperidin-1-yl)methyl)-N-(1,2,4-thiadiazol-5-yl)benzenesulfonamide A mixture of 4-(chloromethyl)-2,5-difluoro-N-(1,2,4-thiadiazol-5-yl)benzenesulfonamide (100 mg, 0.31 mmol), 2-phenylpiperidine hydrochloride (70 mg, 0.36 mmol), sodium iodide (70 mg, 0.46 mmol) and potassium carbonate (130 mg, 0.94 mmol) in MeCN (5 mL) was stirred at 80° C. under $N_2$ for 2 h. The reaction mixture was concentrated to dryness, diluted with DMF (4 mL) and filtered. The filtrate was purified by Prep-HPLC (30-50% MeCN in 0.05% FA) to afford the desired product (90 mg, 65.1%) as a white solid. LCMS (ESI) Method C: RT=4.09 min, m/z: 451.1 [M+H]$^+$. $^1$H NMR (400 MHz, DMSO-d$_6$) δ: 8.10 (s, 1H), 7.48-7.28 (m, 7H), 3.67 (s, 2H), 3.15-3.09 (m, 3H), 1.78-1.43 (m, 6H).

Example 2

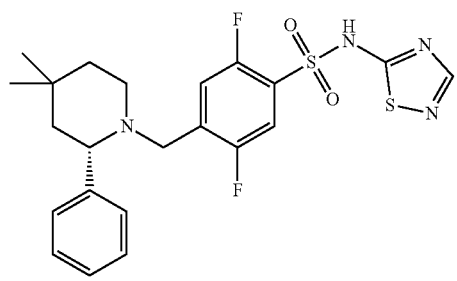 [SMILES: CC1(C)CCN(Cc2cc(F)c(S(=O)(=O)Nc3ncns3)cc2F)[C@H](c2ccccc2)C1]

(S)-4-((4,4-dimethyl-2-phenylpiperidin-1-yl)methyl)-2,5-difluoro-N-(1,2,4-thiadiazol-5-yl)benzenesulfonamide

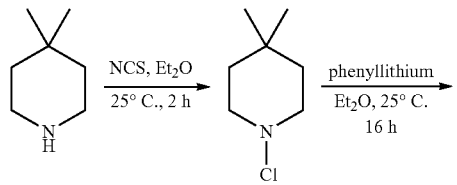

thionyl chloride (15 mL) was stirred at 90° C. for 16 h. The reaction mixture was concentrated to afford a white solid (200 mg, 94%) and used in next step without further purification. LCMS (ESI) m/z: 326.0 [M+H]$^+$.

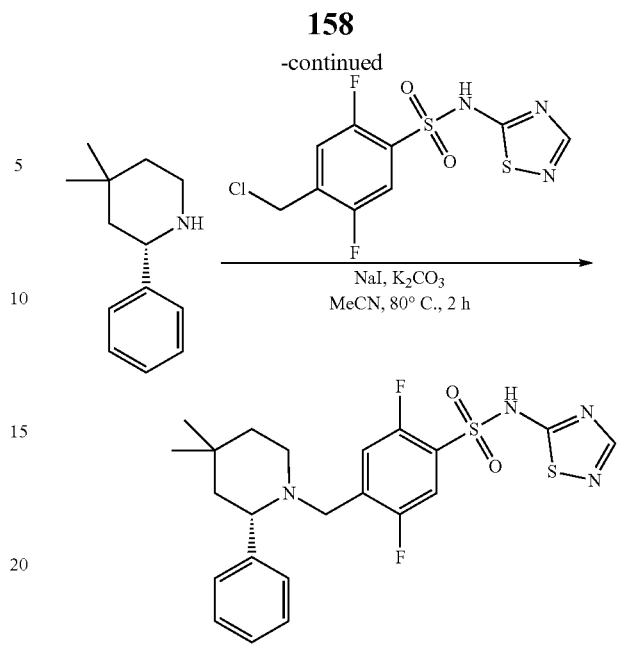

Step 1

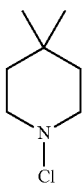

1-Chloro-4,4-dimethylpiperidine

To a solution of 4,4-dimethylpiperidine (2.2 g, 19.5 mmol) in dry ethyl ether (40 mL) was added N-chlorosuccinimide (3.4 g, 23.4 mmol) and the solution was stirred at room temperature for 2 h. The reaction mixture was filtered, washed with water (20 mL) and dried over anhydrous magnesium sulfate. The solution was used in the next step directly.

Step 2

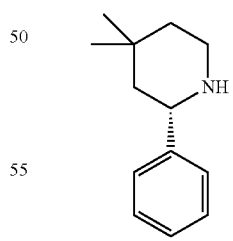

(S)-4,4-dimethyl-2-phenylpiperidine

To the above solution of 1-chloro-4,4-dimethylpiperidine in ethyl ether was added dropwise phenyllithium (11.7 mL, 23.4 mmol) at room temperature. After addition completed, the solution was stirred at room temperature for 16 h. The reaction was quenched with water (40 mL), extracted with ethyl ether (40 mL), dried over anhydrous magnesium sulfate and concentrated. The crude was purified by Combiflash (eluting with 0~8% MeCN in 4% NH₄HCO₃) to afford target product as a yellow oil (280 mg, 8% in two steps). The enantiomer was separated by chiral SFC from the racemate. The second eluting fraction was arbitrarily assigned as (S)-4,4-dimethyl-2-phenylpiperidine (40 mg, 0.21 mmol). Chiral HPLC (column: AS-H, 4.6×250 mm, 5 μm; mobile Phase: A: supercritical CO₂, B: MeOH (0.2% ammonia), A:B=85:15; flow: 3.0 mL/min; column temperature: 39.9° C.; RT=2.45 min). LCMS (ESI) m/z: 190.1 [M+H]⁺.

Step 3

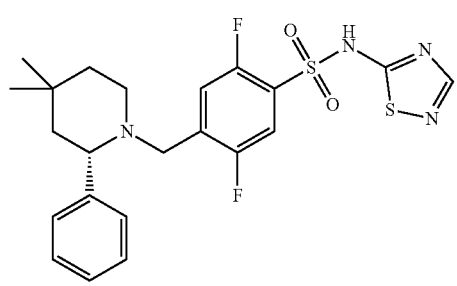 [SMILES: CC1(C)CCN(Cc2cc(F)c(S(=O)(=O)Nc3ncns3)cc2F)[C@H](c2ccccc2)C1]

(S)-4-((4,4-dimethyl-2-phenylpiperidin-1-yl)methyl)-2,5-difluoro-N-(1,2,4-thiadiazol-5-yl)benzenesulfonamide The compound was synthesized as for step 5 of Example 1. LCMS (ESI) Method C: RT=5.23 min, m/z 479.0 [M+H]⁺. ¹H NMR (400 MHz, DMSO-d₆) δ 8.12 (s, 1H), 7.49-7.33 (m, 7H), 3.48-3.46 (m, 1H), 3.37-3.35 (m, 2H), 3.27-3.25 (m, 2H), 1.62-1.41 (m, 4H), 1.08 (s, 3H), 0.94 (s, 3H).

Example 3

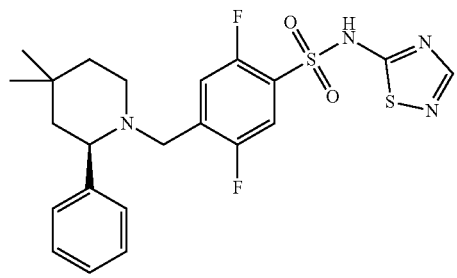 [SMILES: CC1(C)CCN(Cc2cc(F)c(S(=O)(=O)Nc3ncns3)cc2F)[C@@H](c2ccccc2)C1]

(R)-4-((4,4-dimethyl-2-phenylpiperidin-1-yl)methyl)-2,5-difluoro-N-(1,2,4-thiadiazol-5-yl)benzenesulfonamide The compound was synthesized as for Example 2. The enantiomer was arbitrarily assigned as (R)-4-((4,4-dimethyl-2-phenylpiperidin-1-yl)methyl)-2,5-difluoro-N-(1,2,4-thiadiazol-5-yl)benzenesulfonamide. LCMS (ESI) Method C: RT=5.21 min, m/z 479.0 [M+H]⁺. ¹H NMR (400 MHz, DMSO-d₆) δ 8.12 (s, 1H), 7.49-7.33 (m, 7H), 3.48-3.46 (m, 1H), 3.37-3.35 (m, 2H), 3.27-3.25 (m, 2H), 1.62-1.41 (m, 4H), 1.08 (s, 3H), 0.94 (s, 3H).

Example 4

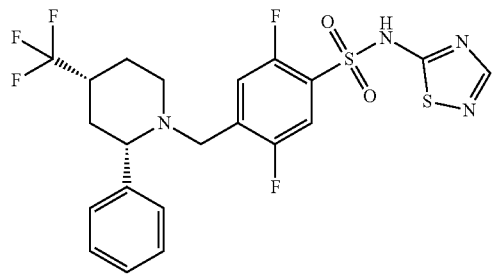 [SMILES: O=S(=O)(Nc1ncns1)c1cc(F)c(CN2CC[C@@H](C(F)(F)F)C[C@H]2c2ccccc2)cc1F]

2,5-Difluoro-4-(((2S,4R)-2-phenyl-4-(trifluoromethyl)piperidin-1-yl)methyl)-N-(1,2,4-thiadiazol-5-yl)benzenesulfonamide

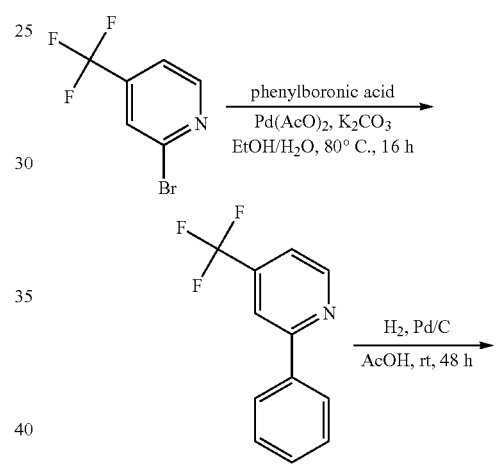

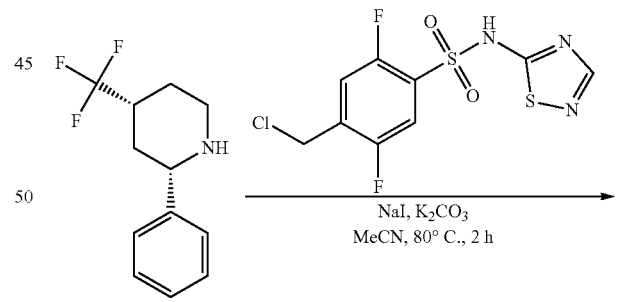

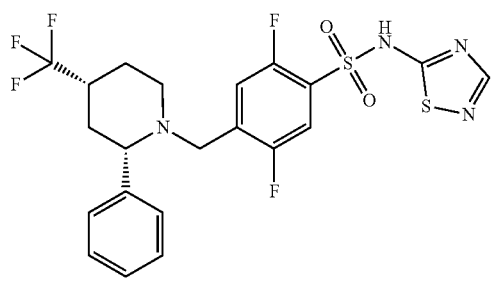

Step 1

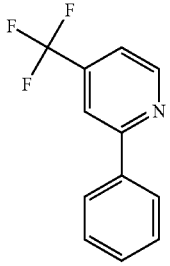 [SMILES: FC(F)(F)c1ccnc(-c2ccccc2)c1]

2-Phenyl-4-(trifluoromethyl)pyridine

To a mixture of 2-bromo-4-(trifluoromethyl)pyridine (2.0 g, 8.85 mmol), phenylboronic acid (1.1 g, 9.02 mmol) in ethanol (40 mL) and water (10 mL) was added palladium diacetate (0.1 g, 0.45 mmol) and potassium carbonate (3.66 g, 26.5 mmol) under $N_2$ atmosphere. The reaction mixture was stirred at 80° C. for 16 h, then filtered and concentrated in vacuo. The crude was purified by flash chromatography (eluting with 10% EtOAc in petroleum ether) to afford the desired compound (1.38 g, 69.8%) as a yellow oil. LCMS (ESI): m/z 224.1 [M+H]$^+$.

Step 2

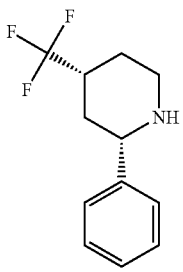

(2S,4R)-2-phenyl-4-(trifluoromethyl)piperidine

A mixture of 2-phenyl-4-(trifluoromethyl)pyridine (500 mg, 2.24 mmol) and Pd/C (10%) (50 mg, 2.24 mmol) in acetic acid (20 mL) was stirred under hydrogen atmosphere at 25° C. for 48 h. The reaction mixture was filtered, diluted with EtOAc (20 mL), and concentrated in vacuo. The residue was purified by Combiflash chromatography (eluting with 0~20% MeCN in 0.1% FA). The enantiomer was separated by chiral SFC from the racemate. The second eluting fraction was arbitrarily assigned as (2S,4R)-2-phenyl-4-(trifluoromethyl)piperidine (70 mg, 0.29 mmol, 13.1%). Chiral HPLC (column: AD-H, 4.6×250 mm, 5 μm; mobile Phase: A: supercritical $CO_2$, B: MeOH (0.2% Ammonia), A:B=90:10; flow: 3.0 mL/min; column temperature: 40.3° C.; RT=1.97 min). LCMS (ESI) m/z: 230.1 [M+H]$^+$.

Step 3

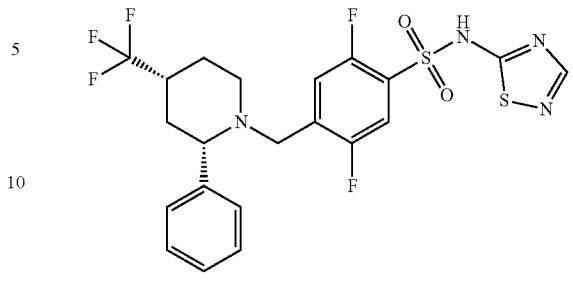

2,5-Difluoro-4-(((2S,4R)-2-phenyl-4-(trifluoromethyl)piperidin-1-yl)methyl)-N-(1,2,4-thiadiazol-5-yl)benzenesulfonamide The compound was synthesized as for step 5 of Example 1. LCMS (ESI) Method A: RT=4.77 min, m/z 519.2 [M+H]$^+$. $^1$H NMR (400 MHz, DMSO-$d_6$) δ 8.20 (s, 1H), 7.45-7.24 (m, 7H), 3.52-3.48 (m, 2H), 3.18-3.15 (m, 1H), 2.96-2.93 (m, 1H), 2.61-2.54 (m, 1H), 2.25-2.18 (m, 1H), 1.87-1.84 (m, 2H), 1.61-1.55 (m, 2H).

Example 5

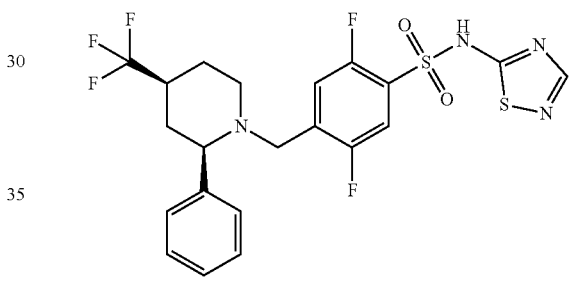

2,5-Difluoro-4-(((2R,4S)-2-phenyl-4-(trifluoromethyl)piperidin-1-yl)methyl)-N-(1,2,4-thiadiazol-5-yl)benzenesulfonamide The compound was synthesized as for Example 4. The enantiomer was arbitrarily assigned as 2,5-Difluoro-4-(((2R,4S)-2-phenyl-4-(trifluoromethyl)piperidin-1-yl)methyl)-N-(1,2,4-thiadiazol-5-yl)benzenesulfonamide. LCMS (ESI) Method A: RT=4.76 min, m/z 519.1 [M+H]$^+$. $^1$H NMR (400 MHz, DMSO-$d_6$) δ 8.44 (s, 1H), 7.53-7.27 (m, 7H), 3.56-3.51 (m, 2H), 3.14-3.12 (m, 2H), 2.58-2.57 (m, 1H), 2.45 (m, 1H), 1.90-1.84 (m, 2H), 1.64-1.62 (m, 2H).

Example 6

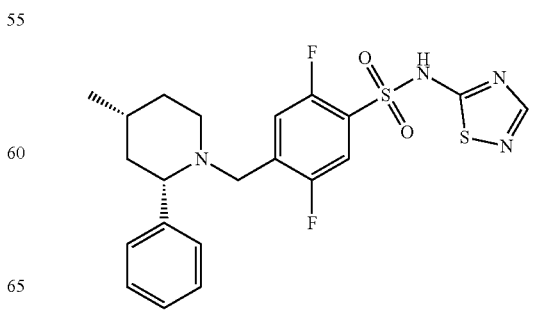

2,5-Difluoro-4-(((2S,4R)-4-methyl-2-phenylpiperidin-1-yl)methyl)-N-(1,2,4-thiadiazol-5-yl)benzenesulfonamide The compound was synthesized as for Example 4. The enantiomer was arbitrarily assigned as 2,5-difluoro-4-(((2S,4R)-4-methyl-2-phenylpiperidin-1-yl)methyl)-N-(1,2,4-thiadiazol-5-yl)benzenesulfonamide. LCMS (ESI) Method C: RT=4.17 min, m/z 465.1 [M+H]$^+$. $^1$H NMR (400 MHz, DMSO-d$_6$) δ 8.13 (s, 1H), 7.49-7.31 (m, 7H), 3.70-3.60 (m, 3H), 3.13 (m, 2H), 1.81-1.70 (m, 3H), 1.35-1.33 (m, 2H), 0.90 (d, J=6.0 Hz, 3H).

Example 7

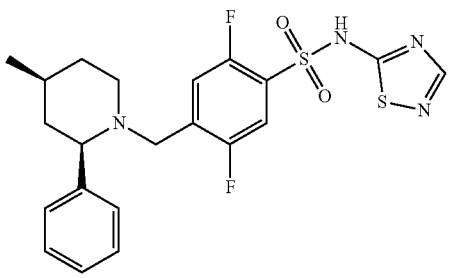 [SMILES: C[C@H]1CCN(Cc2cc(F)c(S(=O)(=O)Nc3ncns3)cc2F)[C@@H](c2ccccc2)C1]

2,5-Difluoro-4-(((2R,4S)-4-methyl-2-phenylpiperidin-1-yl)methyl)-N-(1,2,4-thiadiazol-5-yl)benzenesulfonamide The compound was synthesized as for Example 4. The enantiomer was arbitrarily assigned as 2,5-difluoro-4-(((2R,4S)-4-methyl-2-phenylpiperidin-1-yl)methyl)-N-(1,2,4-thiadiazol-5-yl)benzenesulfonamide. LCMS (ESI) Method C: RT=4.17 min, m/z 465.1 [M+H]$^+$. $^1$H NMR (400 MHz, DMSO-d$_6$) δ 8.13 (s, 1H), 7.49-7.31 (m, 7H), 3.70-3.50 (m, 3H), 3.13 (m, 2H), 1.81-1.70 (m, 3H), 1.35-1.33 (m, 2H), 0.91 (d, J=6.0 Hz, 3H).

Example 8

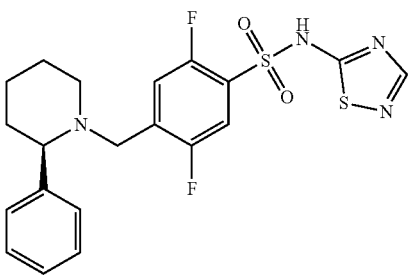 [SMILES: O=S(=O)(Nc1ncns1)c1cc(F)c(CN2CCCC[C@@H]2c2ccccc2)cc1F]

(R)-2,5-difluoro-4-((2-phenylpiperidin-1-yl)methyl)-N-(1,2,4-thiadiazol-5-yl)benzenesulfonamide The compound was synthesized as for Example 1. The enantiomer was arbitrarily assigned as (R)-2,5-difluoro-4-((2-phenylpiperidin-1-yl)methyl)-N-(1,2,4-thiadiazol-5-yl)benzenesulfonamide. LCMS (ESI) Method C: RT=3.84 min, m/z 451.1 [M+H]$^+$. $^1$H NMR (400 MHz, DMSO-d$_6$) δ 12.7 (brs, 1H), 7.95 (s, 1H), 7.48-7.24 (m, 7H), 3.51-3.47 (m, 1H), 3.23-3.15 (m, 2H), 2.95-2.86 (m, 1H), 2.33-2.31 (m, 1H), 1.75-1.56 (m, 5H), 1.44-1.35 (m, 1H).

Example 9

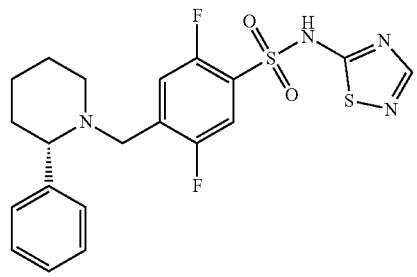 [SMILES: O=S(=O)(Nc1ncns1)c1cc(F)c(CN2CCCC[C@H]2c2ccccc2)cc1F]

(S)-2,5-difluoro-4-((2-phenylpiperidin-1-yl)methyl)-N-(1,2,4-thiadiazol-5-yl)benzenesulfonamide The compound was synthesized as for Example 1. The enantiomer was arbitrarily assigned as (S)-2,5-difluoro-4-((2-phenylpiperidin-1-yl)methyl)-N-(1,2,4-thiadiazol-5-yl)benzenesulfonamide. LCMS (ESI) Method C: RT=3.87 min, m/z 451.1 [M+H]$^+$. $^1$H NMR (400 MHz, DMSO-d$_6$) δ 12.7 (brs, 1H), 7.90 (s, 1H), 7.40-7.19 (m, 7H), 3.47-3.43 (m, 1H), 3.25-3.20 (m, 2H), 3.08-3.04 (m, 1H), 2.84-2.81 (m, 1H), 1.74-1.39 (m, 5H), 1.36-1.33 (m, 1H).

Example 10

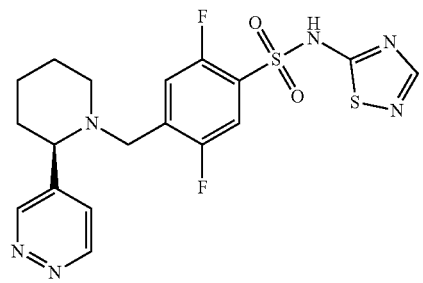 [SMILES: O=S(=O)(Nc1ncns1)c1cc(F)c(CN2CCCC[C@@H]2c2ccnnc2)cc1F]

(R)-2,5-difluoro-4-((2-(pyridazin-4-yl)piperidin-1-yl)methyl)-N-(1,2,4-thiadiazol-5-yl)benzenesulfonamide

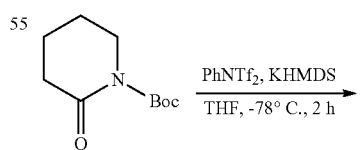

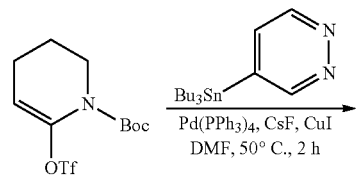

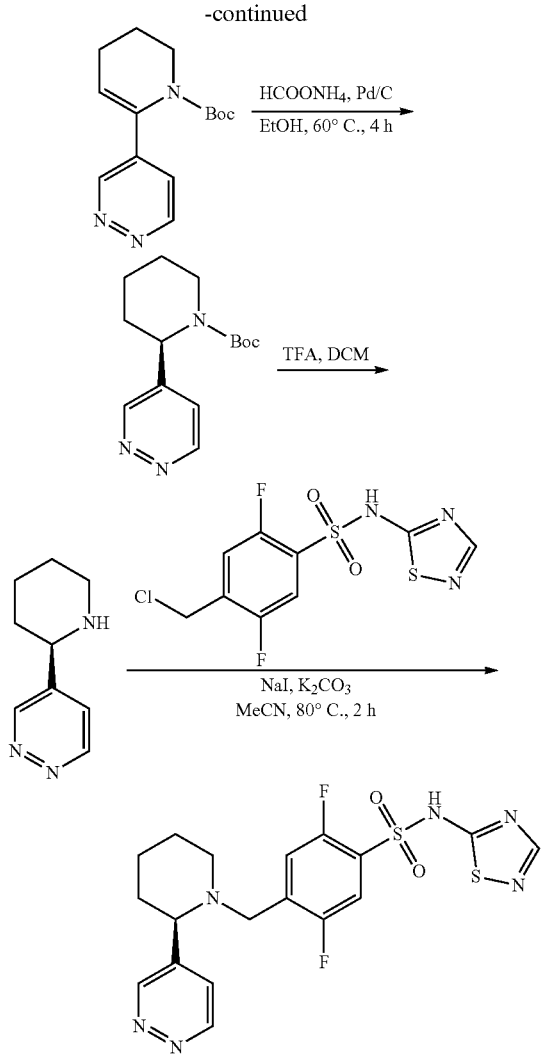

Step 1

Tert-butyl 6-(((trifluoromethyl)sulfonyl)oxy)-3,4-dihydropyridine-1(2H)-carboxylate To a solution of tert-butyl 2-oxopiperidine-1-carboxylate (1.0 g, 5 mmol) in dry THF (20 mL) was added dropwised potassium bis(trimethylsilyl)amide in THF (3 mL, 6 mmol) at −78° C. After 1 h, 1,1,1-trifluoro-N-phenyl-N-(trifluoromethylsulfonyl)methanesulfonamide (3.6 g, 10 mmol) in dry THF (20 mL) was slowly added at −78° C. The resulting mixture was stirred for 1 h, quenched by sat. ammonia chloride (20 mL) and EtOAc (40 mL), extracted with EtOAc (30 mL×3), dried over anhydrous sodium sulfate and concentrated. The crude was purified by silica gel chromatography (eluting with 0~30% EtOAc in petroleum ether) to afford desired product as a pale yellow solid (1.1 g, 66%). LCMS m/z: 276.0 [M−55]⁺.

Step 2

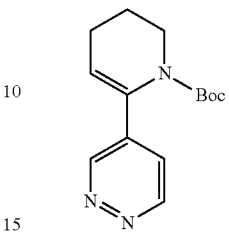

Tert-butyl 6-(pyridazin-4-yl)-3,4-dihydropyridine-1(2H)-carboxylate

A mixture of tert-butyl 6-(trifluoromethylsulfonyloxy)-3,4-dihydropyridine-1(2H)-carboxylate (500 mg, 1.5 mmol), 4-(tributylstannyl)pyridazine (666 mg, 1.8 mmol), cesium fluoride (186 mg, 3.0 mol) and tetrakis(triphenylphosphine)palladium (140 mg, 0.12 mmol) in dry DMF (20 mL) was stirred at 60° C. for 2 h. The reaction mixture was quenched with water (30 mL), extracted with EtOAc (50 mL), dried over anhydrous sodium sulfate and concentrated. The crude was purified by Combiflash (eluting with 0~35% MeCN in 4% NH₄HCO₃) to afford desired product as a yellow oil (160 mg, 40%). LCMS m/z: 262.0 [M+H]⁺.

Step 3

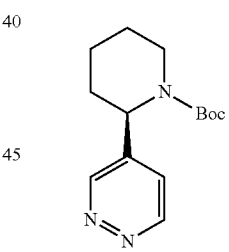

Tert-butyl (R)-2-(pyridazin-4-yl)piperidine-1-carboxylate

A mixture of tert-butyl 6-(pyridazin-4-yl)-3,4-dihydropyridine-1(2H)-carboxylate (160 mg, 0.6 mmol), ammonium formate (380 mg, 6 mmol) and Pd/C (30 mg, 10%) in EtOH (20 mL) was stirred at 50° C. for 4 h. The reaction mixture was filtered and concentrated. The enantiomer was separated by chiral SFC from the crude racemate. The first eluting fraction was arbitrarily assigned as tert-butyl (R)-2-(pyridazin-4-yl)piperidine-1-carboxylate (60 mg, 37%). Chiral HPLC (column: OZ-H, 4.6×250 mm, 5 μm; mobile Phase: A: supercritical CO₂, B: MeOH (0.2% ammonia), A:B=70:30; flow: 3.0 mL/min; column temperature: 40.1° C.; RT=2.43 min). LCMS m/z: 264.0 [M+H]⁺.

Step 4

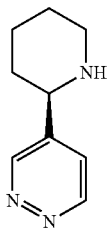

(R)-4-(piperidin-2-yl)pyridazine

A solution of tert-butyl (R)-2-(pyridazin-4-yl)piperidine-1-carboxylate (60 mg, 0.23 mmol) in trifluoroacetic acid (10 mL) and DCM (15 mL) was stirred at room temperature for 1 h.

The solvents were removed under reduced pressure and the crude was used in the next step without further purification. LCMS m/z: 164.0 [M+H]$^+$.

Step 5

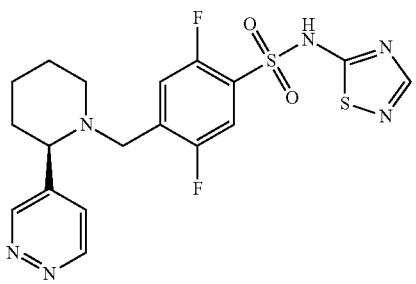 [SMILES: O=S(=O)(Nc1ncns1)c1cc(F)c(CN2CCCC[C@@H]2c2ccnnc2)cc1F]

(R)-2,5-difluoro-4-((2-(pyridazin-4-yl)piperidin-1-yl)methyl)-N-(1,2,4-thiadiazol-5-yl)benzenesulfonamide The compound was synthesized as for step 5 of Example 1. LCMS (ESI) Method A: RT=4.06 min, m/z 453.1 [M+H]$^+$. $^1$H NMR (400 MHz, DMSO-d$_6$) δ 9.29 (s, 1H), 9.12 (brs, 1H), 8.03 (s, 1H), 7.82 (brs, 1H), 7.51-7.47 (m, 1H), 7.37-7.34 (m, 1H), 3.49-3.43 (m, 2H), 3.28-3.26 (m, 1H), 3.01-2.98 (m, 1H), 2.21-2.18 (m, 1H), 1.84-1.81 (m, 2H), 1.71-1.60 (m, 4H).

Example 11

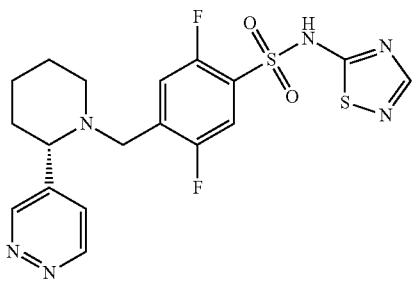 [SMILES: O=S(=O)(Nc1ncns1)c1cc(F)c(CN2CCCC[C@H]2c2ccnnc2)cc1F]

(S)-2,5-difluoro-4-((2-(pyridazin-4-yl)piperidin-1-yl)methyl)-N-(1,2,4-thiadiazol-5-yl)benzenesulfonamide The compound was synthesized as for Example 10. The enantiomer was arbitrarily assigned as (S)-2,5-difluoro-4-((2-(pyridazin-4-yl)piperidin-1-yl)methyl)-N-(1,2,4-thiadiazol-5-yl)benzenesulfonamide. LCMS (ESI) Method A: RT=4.09 min, m/z 453.1 [M+H]$^+$. $^1$H NMR (400 MHz, DMSO-d$_6$) δ 9.30 (s, 1H), 9.12 (brs, 1H), 7.97 (s, 1H), 7.83 (brs, 1H), 7.52-7.49 (m, 1H), 7.34-7.32 (m, 1H), 3.49-3.43 (m, 2H), 3.27-3.26 (m, 1H), 2.99-2.96 (m, 1H), 2.19-2.16 (m, 1H), 1.84-1.81 (m, 2H), 1.70-1.55 (m, 4H).

Example 12

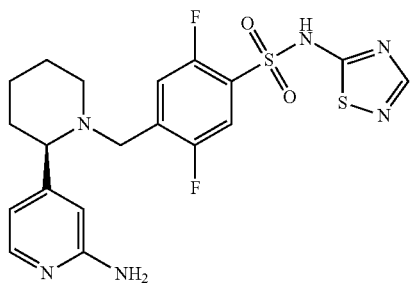

(R)-4-((2-(2-aminopyridin-4-yl)piperidin-1-yl)methyl)-2,5-difluoro-N-(1,2,4-thiadiazol-5-yl)benzenesulfonamide

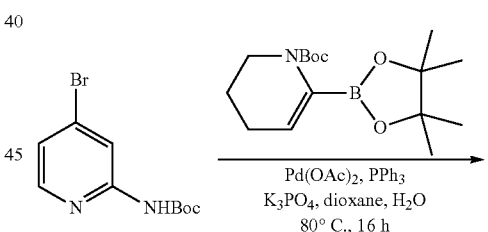

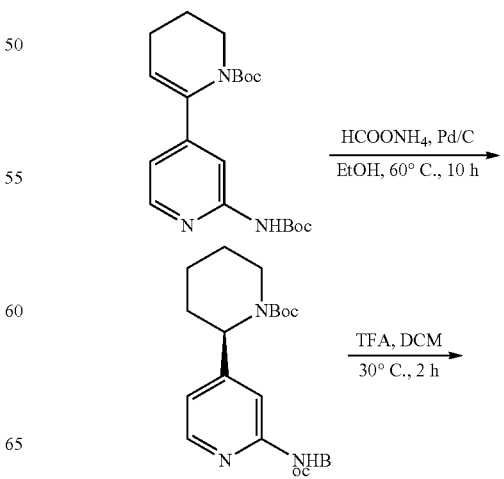

169

-continued

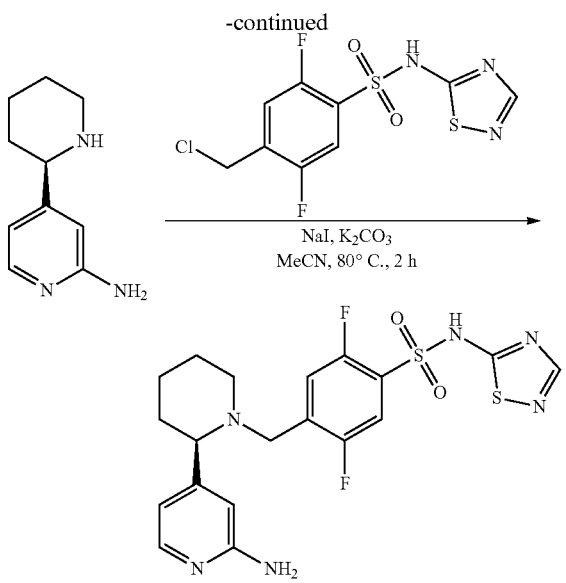

Step 1

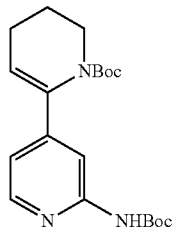 [SMILES: CC(C)(C)OC(=O)Nc1cc(C2=CCCCN2C(=O)OC(C)(C)C)ccn1]

Tert-butyl 2'-((tert-butoxycarbonyl)amino)-5,6-di-hydro-[2,4'-bipyridine]-1(4H)-carboxylate A mixture of tert-butyl 4-bromopyridin-2-ylcarbamate (1.0 g, 3.7 mmol), tert-butyl 6-(4,4,5,5-tetramethyl-1,3,2-dioxaborolan-2-yl)-3,4-dihydropyridine-1(2H)-carboxylate (1.1 g, 3.7 mml), palladium acetate (66 mg, 0.3 mmol), triphenylphosphine (94 mg, 0.36 mmol) and potassium phosphate (2.4 g, 11.1 mmol) in 1,4-dioxane (20 mL) and water (1 mL) was stirred under N₂ at 80° C. for 16 h. The reaction mixture was quenched with water (30 mL) and EtOAc (30 mL), extracted with EtOAc (20 mL×2), dried over anhydrous sodium sulfate and concentrated. The crude was purified by Combiflash (eluting with 0~35% MeCN in 4% NH₄HCO₃) to afford desired product as a white solid (320 mg, 24%). LCMS m/z: 376.0 [M+H]⁺.

Step 2

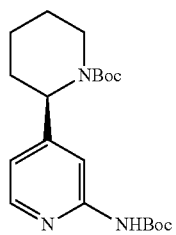 [SMILES: CC(C)(C)OC(=O)Nc1cc([C@H]2CCCCN2C(=O)OC(C)(C)C)ccn1]

170

Tert-butyl (R)-2-(2-((tert-butoxycarbonyl)amino)pyridin-4-yl)piperidine-1-carboxylate The compound was synthesized as for step 3 of Example 10. The enantiomer was separated by chiral SFC from the crude racemate. The first eluting fraction was arbitrarily assigned as tert-butyl (R)-2-(2-((tert-butoxycarbonyl)amino)pyridin-4-yl)piperidine-1-carboxylate. Chiral HPLC (column: (R,R)-Whelk-O1, 4.6×250 mm, 5 rpm; mobile Phase: A: supercritical $CO_2$, B: MeOH (0.2% ammonia), A:B=85:15; flow: 3.0 mL/min; column temperature: 39.9° C.; RT=2.88 min). LCMS m/z: 378.0 [M+H]⁺.

Step 3

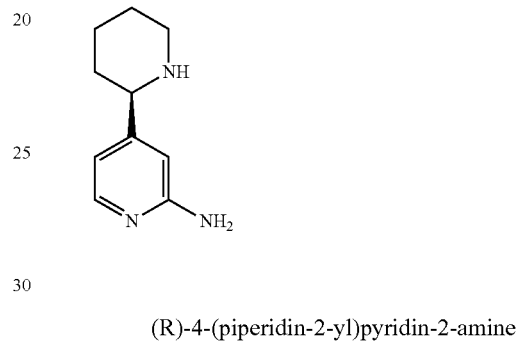

(R)-4-(piperidin-2-yl)pyridin-2-amine

The compound was synthesized as for step 4 of Example 10. LCMS m/z: 178.0 [M+H]⁺.

Step 4

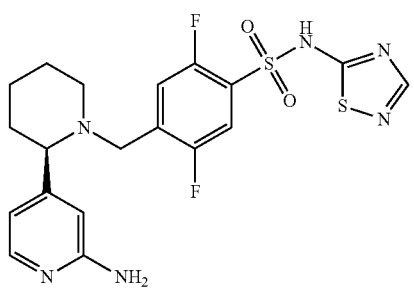 [SMILES: Nc1cc([C@H]2CCCCN2Cc2cc(F)c(S(=O)(=O)Nc3ncns3)cc2F)ccn1]

(R)-4-((2-(2-aminopyridin-4-yl)piperidin-1-yl)methyl)-2,5-difluoro-N-(1,2,4-thiadiazol-5-yl)benzenesulfonamide The compound was synthesized as for step 5 of Example 1. LCMS (ESI) Method C: RT=4.02 min, m/z 467.0 [M+H]⁺. ¹H NMR (400 MHz, DMSO-d₆) δ 7.90 (s, 1H), 7.83 (d, J=5.6 Hz, 1H), 7.40-7.29 (m, 2H), 6.82-6.80 (m, 2H), 6.71-6.70 (m, 2H), 3.47-3.44 (m, 1H), 3.16-3.10 (m, 2H), 2.80-2.78 (m, 1H), 2.02-1.98 (m, 1H), 1.73-1.67 (m, 2H), 1.48-1.30 (m, 4H).

Example 13

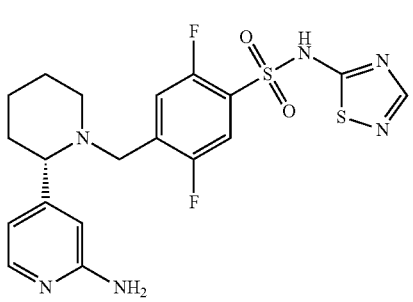

(S)-4-((2-(2-aminopyridin-4-yl)piperidin-1-yl)methyl)-2,5-difluoro-N-(1,2,4-thiadiazol-5-yl)benzenesulfonamide The compound was synthesized as for Example 12. The enantiomer was arbitrarily assigned as (S)-4-((2-(2-aminopyridin-4-yl)piperidin-1-yl)methyl)-2,5-difluoro-N-(1,2,4-thiadiazol-5-yl)benzenesulfonamide. LCMS (ESI) Method C: RT=3.93 min, m/z 467.0 [M+H]$^+$. $^1$H NMR (400 MHz, DMSO-d$_6$) δ 7.90 (s, 1H), 7.83 (d, J=6.0 Hz, 1H), 7.40-7.30 (m, 2H), 6.82-6.79 (m, 2H), 6.61-6.60 (m, 2H), 3.47-3.44 (m, 1H), 3.12-3.08 (m, 2H), 2.81-2.79 (m, 1H), 2.02-1.98 (m, 1H), 1.73-1.67 (m, 2H), 1.48-1.30 (m, 4H).

Example 14

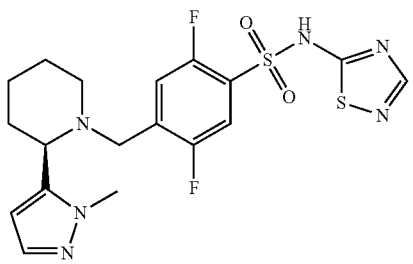 [SMILES: Cn1nccc1[C@H]1CCCCN1Cc1cc(F)c(S(=O)(=O)Nc2ncns2)cc1F]

(R)-2,5-difluoro-4-((2-(1-methyl-1H-pyrazol-5-yl)piperidin-1-yl)methyl)-N-(1,2,4-thiadiazol-5-yl)benzenesulfonamide The compound was synthesized as for Example 1. The enantiomer was arbitrarily assigned as (R)-2,5-difluoro-4-((2-(1-methyl-1H-pyrazol-5-yl)piperidin-1-yl)methyl)-N-(1,2,4-thiadiazol-5-yl)benzenesulfonamide. LCMS (ESI) Method A: RT=4.45 min, m/z 455.0 [M+H]$^+$. $^1$H NMR (400 MHz, DMSO-d$_6$) δ 8.25 (s, 1H), 7.53-7.50 (m, 1H), 7.37-7.29 (m, 2H), 6.32 (s, 1H), 3.86 (s, 3H), 3.60-3.44 (m, 3H), 3.00-2.95 (m, 1H), 1.85-1.38 (m, 7H).

Example 15

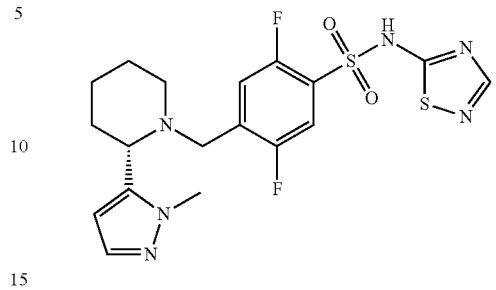

(S)-2,5-difluoro-4-((2-(1-methyl-1H-pyrazol-5-yl)piperidin-1-yl)methyl)-N-(1,2,4-thiadiazol-5-yl)benzenesulfonamide The compound was synthesized as for Example 1. The enantiomer was arbitrarily assigned as (S)-2,5-difluoro-4-((2-(1-methyl-1H-pyrazol-5-yl)piperidin-1-yl)methyl)-N-(1,2,4-thiadiazol-5-yl)benzenesulfonamide. LCMS (ESI) Method A: RT=4.40 min, m/z 455.0 [M+H]$^+$. $^1$H NMR (400 MHz, DMSO-d$_6$) δ 8.19 (s, 1H), 7.51-7.47 (m, 1H), 7.36 (s, 1H), 7.31-7.27 (s, 1H), 6.29 (s, 1H), 3.86 (s, 3H), 3.59-3.45 (m, 3H), 2.98-2.92 (m, 1H), 1.77-1.44 (m, 7H).

Example 16

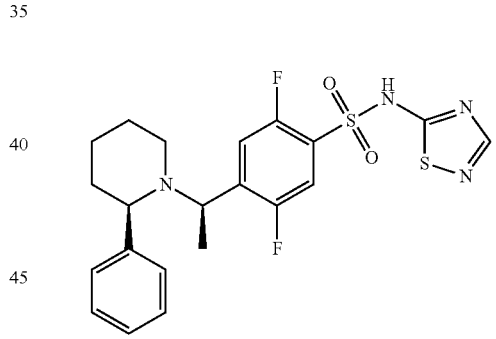

2,5-Difluoro-4-((R)-1-((R)-2-phenylpiperidin-1-yl)ethyl)-N-(1,2,4-thiadiazol-5-yl)benzenesulfonamide

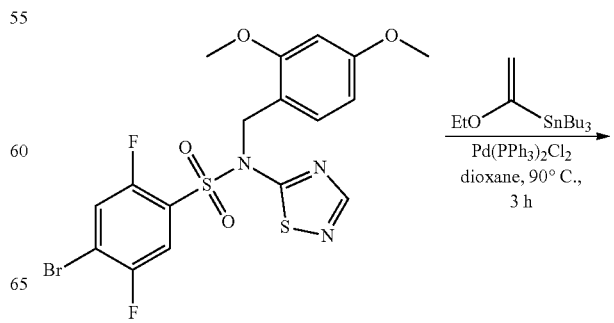

173
-continued

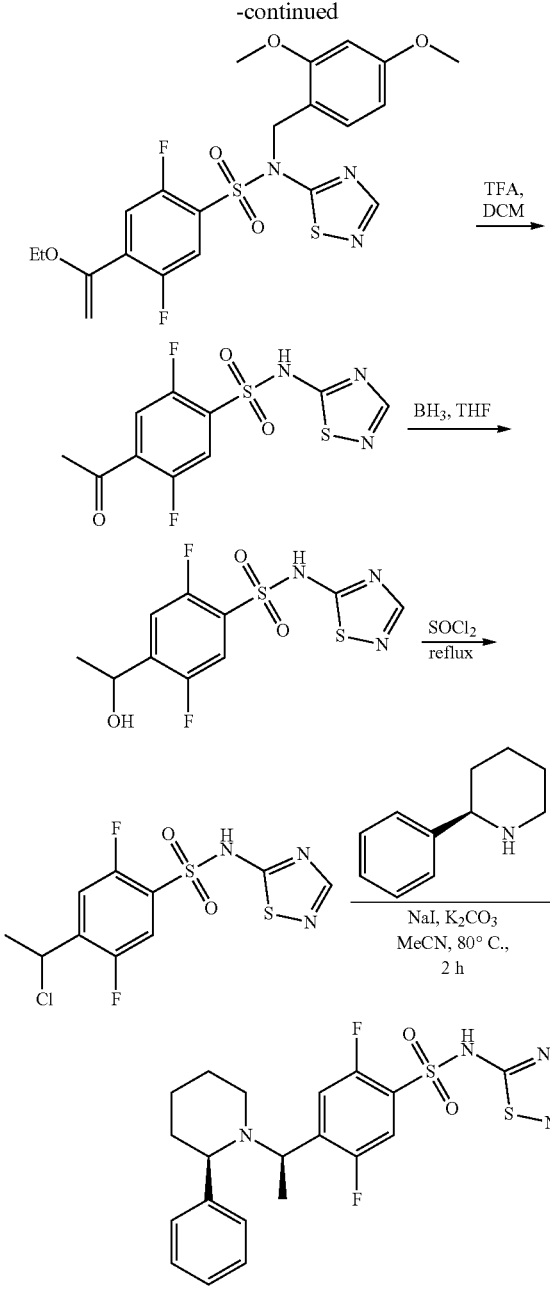

Step 1

N-(2,4-dimethoxybenzyl)-4-(1-ethoxyvinyl)-2,5-difluoro-N-(1,2,4-thiadiazol-5-yl)benzenesulfonamide To a mixture of 4-bromo-N-[(2,4-dimethoxyphenyl)methyl]-2,5-difluoro-N-(1,2,4-thiadiazol-5-yl)benzenesulfonamide (5.0 g, 9.87 mmol) and dichlorobis(triphenylphosphine)-palladium(II) (1.04 g, 1.48 mmol) in 1,4-dioxane (100 mL) was added tributyl(1-ethoxyvinyl)tin (4.3 g, 11.8 mmol). The reaction mixture was stirred at 90° C. under $N_2$ for 4 h and concentrated to dryness. The residue was purified by silica gel chromatography (eluting with 50% EtOAc in petroleum ether) to afford the target compound (4.0 g, 81.4%) as a light yellow solid. LCMS (ESI) m/z: 520.1 [M+Na]⁺.

Step 2

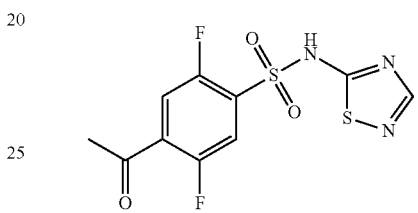

4-acetyl-2,5-difluoro-N-(1,2,4-thiadiazol-5-yl)benzenesulfonamide

To a solution of N-[(2,4-dimethoxyphenyl)methyl]-4-(1-ethoxyvinyl)-2,5-difluoro-N-(1,2,4-thiadiazol-5-yl)benzenesulfonamide (900 mg, 1.81 mmol) in DCM (20 mL) was added trifluoroacetic acid (5 mL) and stirred at room temperature for 1 h. The reaction mixture was concentrated to dryness and the crude product was used in the next step without further purification. LCMS (ESI) m/z: 320.1 [M+H]⁺.

Step 3

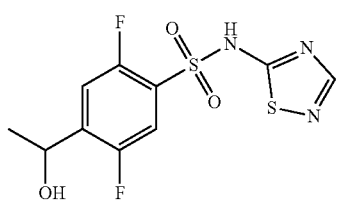

2,5-difluoro-4-(1-hydroxyethyl)-N-(1,2,4-thiadiazol-5-yl)benzenesulfonamide

4-Acetyl-2,5-difluoro-N-(1,2,4-thiadiazol-5-yl)benzenesulfonamide (500 mg, 1.57 mmol) was dissolved in borane-tetrahydrofuran complex (10 mL, 10 mmol) at 0° C. The reaction mixture was stirred at 25° C. for 1 h, quenched by MeOH (10 mL) and concentrated to dryness. The crude was purified by Combiflash (20-50% MeCN in 0.1% FA) to afford the desired product (130 mg, 25.8%) as a white solid. LCMS (ESI) m/z: 322.0 [M+H]⁺.

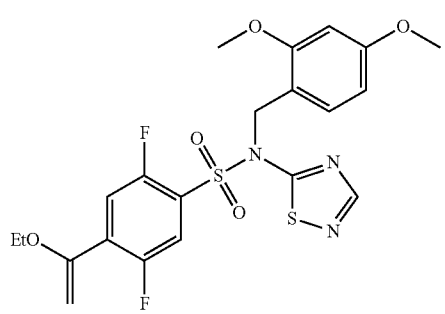 [SMILES: C=C(OCC)c1cc(F)c(S(=O)(=O)N(Cc2ccc(OC)cc2OC)c2ncns2)cc1F]

Step 4

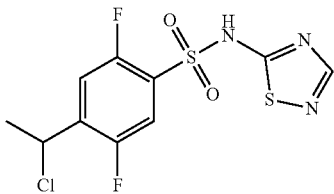 [SMILES: CC(Cl)c1cc(F)c(S(=O)(=O)Nc2ncns2)cc1F]

4-(1-chloroethyl)-2,5-difluoro-N-(1,2,4-thiadiazol-5-yl)benzenesulfonamide

A solution of 2,5-difluoro-4-(1-hydroxyethyl)-N-(1,2,4-thiadiazol-5-yl)benzenesulfonamide (130 mg, 0.40 mmol) in thionyl chloride (5 mL) was stirred at 90° C. for 16 h. The reaction mixture was concentrated and the crude product was used in the next step without further purification. LCMS (ESI) m/z: 340.1 [M+H]$^+$.

Step 5

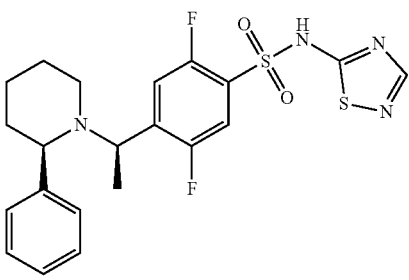 [SMILES: C[C@H](c1cc(F)c(S(=O)(=O)Nc2ncns2)cc1F)N1CCCC[C@@H]1c1ccccc1]

2,5-difluoro-4-((R)-1-((R)-2-phenylpiperidin-1-yl)ethyl)-N-(1,2,4-thiadiazol-5-yl)benzenesulfonamide The compound was synthesized as for step 5 of Example 1. The stereoisomer was separated by chiral SFC from the racemate. The first eluting fraction was arbitrarily assigned as 2,5-difluoro-4-((R)-1-((R)-2-phenylpiperidin-1-yl)ethyl)-N-(1,2,4-thiadiazol-5-yl)benzenesulfonamide. Chiral HPLC (column: OZ-H, 4.6×250 mm, 5 μm; mobile Phase: A: supercritical CO$_2$, B: MeOH (0.2% ammonia), A:B=70:30; flow: 3 mL/min; column temperature: 40° C.; RT=3.89 min). LCMS (ESI) Method C: RT=4.41 min, m/z: 465.1 [M+H]$^+$. $^1$H NMR (400 MHz, DMSO-d$_6$) δ: 8.17 (s, 1H), 7.51-7.31 (m, 7H), 4.33-4.34 (m, 1H), 3.48-3.23 (m, 3H), 1.74-1.34 (m, 9H).

Example 17

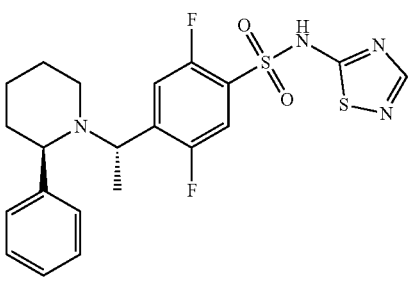 [SMILES: C[C@@H](c1cc(F)c(S(=O)(=O)Nc2ncns2)cc1F)N1CCCC[C@@H]1c1ccccc1]

2,5-Difluoro-4-((S)-1-((R)-2-phenylpiperidin-1-yl)ethyl)-N-(1,2,4-thiadiazol-5-yl)benzenesulfonamide The compound was synthesized as for Example 16. The stereoisomer was arbitrarily assigned as 2,5-difluoro-4-((S)-1-((R)-2-phenylpiperidin-1-yl)ethyl)-N-(1,2,4-thiadiazol-5-yl)benzenesulfonamide. LCMS (ESI) Method C: RT=4.28 min, m/z: 465.1 [M+H]$^+$. $^1$H NMR (400 MHz, DMSO-d$_6$) δ: 8.02 (s, 1H), 7.56-7.49 (m, 7H), 4.60-4.34 (m, 2H), 3.38-3.23 (m, 2H), 2.08-1.46 (m, 9H).

Example 18

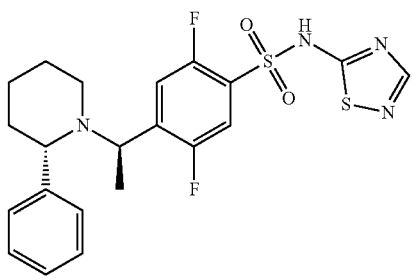 [SMILES: C[C@H](c1cc(F)c(S(=O)(=O)Nc2ncns2)cc1F)N1CCCC[C@H]1c1ccccc1]

2,5-Difluoro-4-((R)-1-((S)-2-phenylpiperidin-1-yl)ethyl)-N-(1,2,4-thiadiazol-5-yl)benzenesulfonamide The compound was synthesized as for Example 16. The stereoisomer was arbitrarily assigned as 2,5-difluoro-4-((R)-1-((S)-2-phenylpiperidin-1-yl)ethyl)-N-(1,2,4-thiadiazol-5-yl)benzenesulfonamide. LCMS (ESI) Method C: RT=4.28 min, m/z: 465.1 [M+H]$^+$. $^1$H NMR (400 MHz, DMSO-d$_6$) δ: 7.89 (s, 1H), 7.41-7.21 (m, 7H), 3.94-3.92 (m, 1H), 3.45-3.23 (m, 1H), 2.58-2.56 (m, 1H), 2.34-2.27 (m, 1H), 1.70-1.51 (m, 4H), 1.37-1.14 (m, 2H), 1.13 (d, J=6.8 Hz, 3H).

Example 19

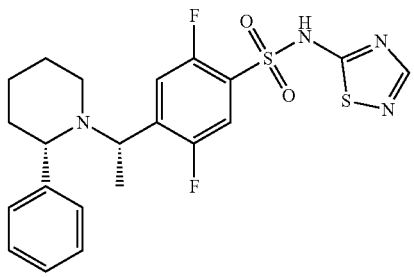 [SMILES: C[C@@H](c1cc(F)c(S(=O)(=O)Nc2ncns2)cc1F)N1CCCC[C@H]1c1ccccc1]

2,5-Difluoro-4-((S)-1-((S)-2-phenylpiperidin-1-yl)ethyl)-N-(1,2,4-thiadiazol-5-yl)benzenesulfonamide The compound was synthesized as for Example 16. The stereoisomer was arbitrarily assigned as 2,5-difluoro-4-((S)-1-((S)-2-phenylpiperidin-1-yl)ethyl)-N-(1,2,4-thiadiazol-5-yl)benzenesulfonamide. LCMS (ESI) Method C: RT=4.32 min, m/z: 465.1 [M+H]$^+$. $^1$H NMR (400 MHz, DMSO-d$_6$) δ: 7.89 (s, 1H), 7.38-7.10 (m, 7H), 4.05-4.04 (m, 1H), 3.44-3.34 (m, 3H), 1.63-1.56 (m, 5H), 1.28 (d, J=6.8 Hz, 3H), 1.13-1.12 (m, 1H).

Example 20

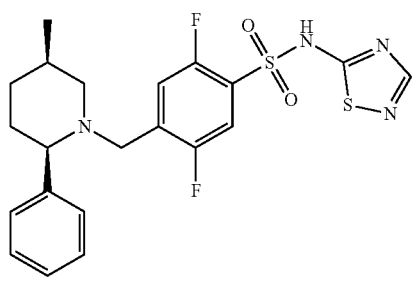 [SMILES: C[C@@H]1CC[C@H](c2ccccc2)N(Cc2cc(F)c(S(=O)(=O)Nc3ncns3)cc2F)C1]

2,5-Difluoro-4-(((2R,5R)-5-methyl-2-phenylpiperidin-1-yl)methyl)-N-(1,2,4-thiadiazol-5-yl)benzenesulfonamide The compound was synthesized as for Example 4. The enantiomer was arbitrarily assigned as 2,5-difluoro-4-(((2R,5R)-5-methyl-2-phenylpiperidin-1-yl)methyl)-N-(1,2,4-thiadiazol-5-yl)benzenesulfonamide. LCMS (ESI) Method C: RT=4.04 min, m/z 465.1 [M+H]$^+$. $^1$H NMR (400 MHz, DMSO-d$_6$) δ 8.14 (s, 1H), 7.47-7.30 (m, 7H), 3.64-3.60 (m, 2H), 3.17-3.10 (m, 3H), 1.78-1.76 (m, 4H), 1.14-1.13 (m, 1H), 0.86 (d, J=6.0 Hz, 3H).

Example 21

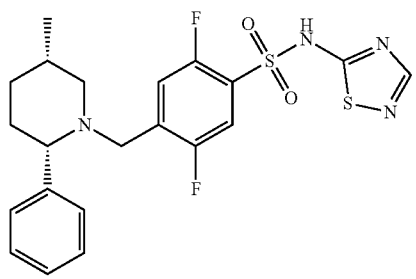 [SMILES: C[C@H]1CC[C@@H](c2ccccc2)N(Cc2cc(F)c(S(=O)(=O)Nc3ncns3)cc2F)C1]

2,5-Difluoro-4-(((2S,5S)-5-methyl-2-phenylpiperidin-1-yl)methyl)-N-(1,2,4-thiadiazol-5-yl)benzenesulfonamide The compound was synthesized as for Example 4. The enantiomer was arbitrarily assigned as 2,5-difluoro-4-(((2S,5S)-5-methyl-2-phenylpiperidin-1-yl)methyl)-N-(1,2,4-thiadiazol-5-yl)benzenesulfonamide. LCMS (ESI) Method C: RT=4.05 min, m/z 465.1 [M+H]$^+$. $^1$H NMR (400 MHz, DMSO-d$_6$) δ 8.17 (s, 1H), 7.50-7.31 (m, 7H), 3.69-3.67 (m, 2H), 3.17-3.16 (m, 3H), 1.80-1.77 (m, 4H), 1.20-1.15 (m, 1H), 0.86 (d, J=6.4 Hz, 3H).

Example 22

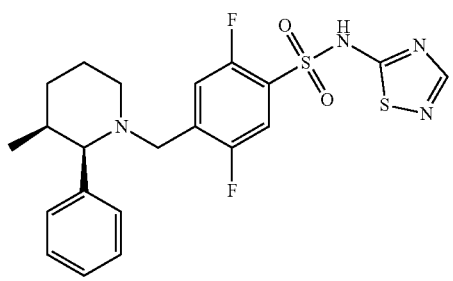 [SMILES: C[C@H]1CCCN(Cc2cc(F)c(S(=O)(=O)Nc3ncns3)cc2F)[C@H]1c1ccccc1]

2,5-Difluoro-4-(((2R,3S)-3-methyl-2-phenylpiperidin-1-yl)methyl)-N-(1,2,4-thiadiazol-5-yl)benzenesulfonamide The compound was synthesized as for Example 4. The enantiomer was arbitrarily assigned as 2,5-difluoro-4-(((2R,3S)-3-methyl-2-phenylpiperidin-1-yl)methyl)-N-(1,2,4-thiadiazol-5-yl)benzenesulfonamide. LCMS (ESI) Method C: RT=4.82 min, m/z 465.1 [M+H]$^+$. $^1$H NMR (400 MHz, DMSO-d$_6$) δ 8.18 (s, 1H), 7.51-7.28 (m, 7H), 3.75-3.68 (m, 1H), 3.45-3.38 (m, 3H), 3.07-2.95 (m, 1H), 2.00-1.91 (m, 1H), 1.81-1.42 (m, 4H), 0.79 (d, J=6.8 Hz, 3H).

Example 23

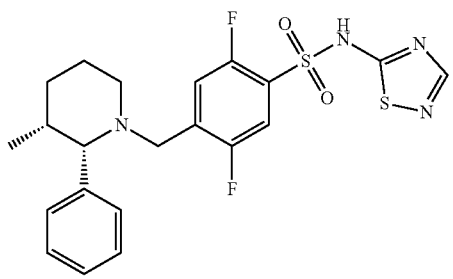 [SMILES: C[C@@H]1CCCN(Cc2cc(F)c(S(=O)(=O)Nc3ncns3)cc2F)[C@@H]1c1ccccc1]

2,5-Difluoro-4-(((2S,3R)-3-methyl-2-phenylpiperidin-1-yl)methyl)-N-(1,2,4-thiadiazol-5-yl)benzenesulfonamide The compound was synthesized as for Example 4. The enantiomer was arbitrarily assigned as 2,5-difluoro-4-(((2S,3R)-3-methyl-2-phenylpiperidin-1-yl)methyl)-N-(1,2,4-thiadiazol-5-yl)benzenesulfonamide. LCMS (ESI) Method C: RT=4.81 min, m/z 465.1 [M+H]$^+$. $^1$H NMR (400 MHz, DMSO-d$_6$) δ 8.24 (s, 1H), 7.55-7.31 (m, 7H), 3.79-3.71 (m, 1H), 3.49-3.39 (m, 3H), 3.09-3.01 (m, 1H), 2.05-1.95 (m, 1H), 1.80-1.47 (m, 4H), 0.79 (d, J=6.8 Hz, 3H).

Example 24

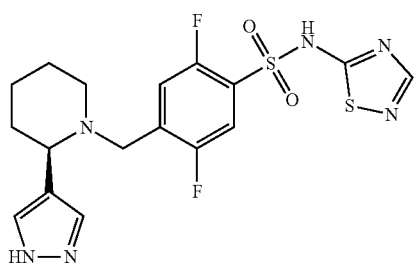 [SMILES: O=S(=O)(Nc1ncns1)c1cc(F)c(CN2CCCC[C@@H]2c2cn[nH]c2)cc1F]

(R)-4-((2-(1H-pyrazol-4-yl)piperidin-1-yl)methyl)-2,5-difluoro-N-(1,2,4-thiadiazol-5-yl)benzenesulfonamide The compound was synthesized as for Example 1. The enantiomer was arbitrarily assigned as (R)-4-((2-(1H-pyrazol-4-yl)piperidin-1-yl)methyl)-2,5-difluoro-N-(1,2,4-thiadiazol-5-yl)benzenesulfonamide. LCMS (ESI) Method C: RT=2.68 min, m/z 441.1 [M+H]$^+$. $^1$H NMR (400 MHz, DMSO-d$_6$) δ 12.63 (brs, 1H), 7.90 (s, 1H), 7.57-7.23 (m, 4H), 3.33-3.26 (m, 3H), 3.07-3.05 (m, 2H), 1.78-1.76 (m, 6H).

Example 25

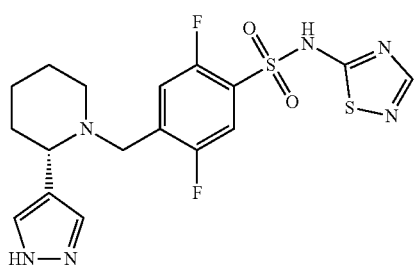 [SMILES: O=S(=O)(Nc1ncns1)c1cc(F)c(CN2CCCC[C@H]2c2cn[nH]c2)cc1F]

(S)-4-((2-(1H-pyrazol-4-yl)piperidin-1-yl)methyl)-2,5-difluoro-N-(1,2,4-thiadiazol-5-yl)benzenesulfonamide The compound was synthesized as for Example 1. The enantiomer was arbitrarily assigned as (S)-4-((2-(1H-pyrazol-4-yl)piperidin-1-yl)methyl)-2,5-difluoro-N-(1,2,4-thiadiazol-5-yl)benzenesulfonamide. LCMS (ESI) Method C: RT=2.64 min, m/z 441.1 [M+H]$^+$. $^1$H NMR (400 MHz, DMSO-d$_6$) δ 12.70 (brs, 1H), 7.89 (s, 1H), 7.58-7.22 (m, 4H), 3.40-3.38 (m, 3H), 3.07-3.06 (m, 2H), 1.72-1.68 (m, 6H).

Example 26

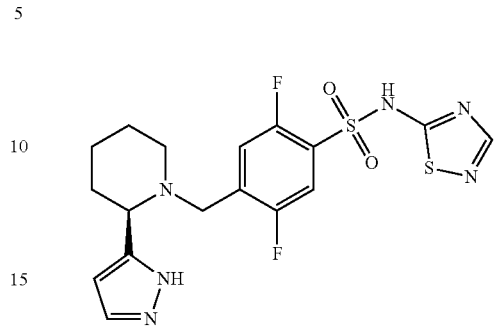

(R)-4-((2-(1H-pyrazol-5-yl)piperidin-1-yl)methyl)-2,5-difluoro-N-(1,2,4-thiadiazol-5-yl)benzenesulfonamide The compound was synthesized as for Example 1. The enantiomer was arbitrarily assigned as (R)-4-((2-(1H-pyrazol-5-yl)piperidin-1-yl)methyl)-2,5-difluoro-N-(1,2,4-thiadiazol-5-yl)benzenesulfonamide. LCMS (ESI) Method C: RT=2.87 min, m/z 441.1 [M+H]$^+$. $^1$H NMR (400 MHz, DMSO-d$_6$) δ 13.04 (brs, 1H), 7.98 (s, 1H), 7.75 (s, 1H), 7.49-7.45 (m, 1H), 7.32-7.28 (m, 1H), 6.38 (s, 1H), 4.12-3.67 (m, 3H), 3.15-3.14 (m, 1H), 1.89-1.71 (m, 6H), 1.50-1.49 (m, 1H).

Example 27

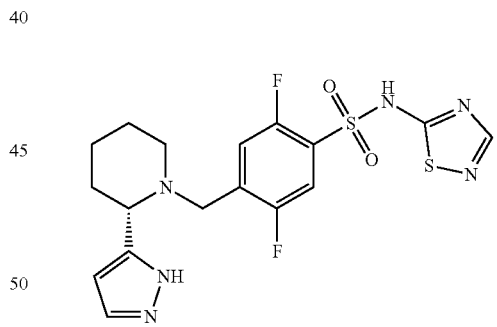

(S)-4-((2-(1H-pyrazol-5-yl)piperidin-1-yl)methyl)-2,5-difluoro-N-(1,2,4-thiadiazol-5-yl)benzenesulfonamide The compound was synthesized as for Example 1. The enantiomer was arbitrarily assigned as (S)-4-((2-(1H-pyrazol-5-yl)piperidin-1-yl)methyl)-2,5-difluoro-N-(1,2,4-thiadiazol-5-yl)benzenesulfonamide. LCMS (ESI) Method C: RT=2.88 min, m/z 441.1 [M+H]$^+$. $^1$H NMR (400 MHz, DMSO-d$_6$) δ 13.13 (brs, 1H), 8.01 (s, 1H), 7.77 (s, 1H), 7.51-7.47 (m, 1H), 7.32-7.28 (m, 1H), 6.40 (s, 1H), 4.40-3.74 (m, 3H), 3.18-3.01 (m, 1H), 1.92-1.52 (m, 7H).

Example 28

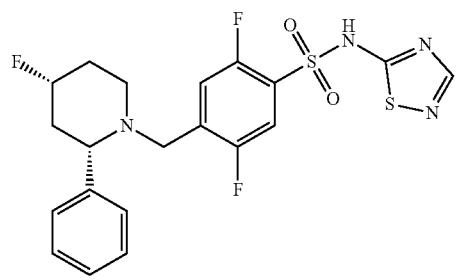 [SMILES: O=S(=O)(Nc1ncns1)c1cc(F)c(CN2CC[C@@H](F)C[C@H]2c2ccccc2)cc1F]

2,5-Difluoro-4-(((2S,4R)-4-fluoro-2-phenylpiperidin-1-yl)methyl)-N-(1,2,4-thiadiazol-5-yl)benzenesulfonamide

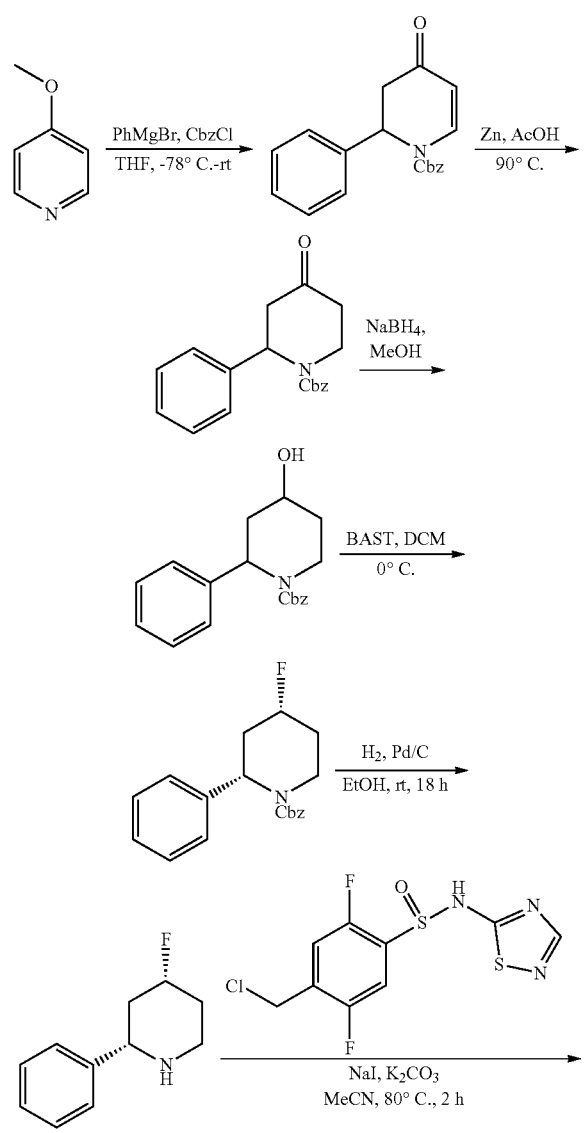

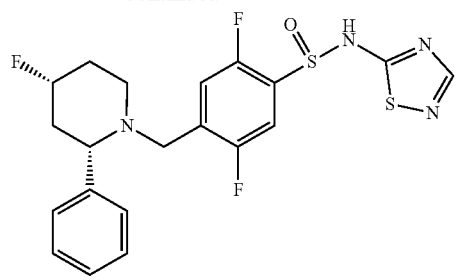

Step 1

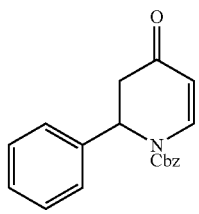 [SMILES: O=C1C=CN(C(=O)OCc2ccccc2)C(c2ccccc2)C1]

Benzyl 4-oxo-2-phenyl-3,4-dihydropyridine-1(2H)-carboxylate

To a solution of 4-methoxypyridine (10.0 g, 91.6 mmol) in THF (500 mL) was added dropwise benzyl chloroformate (15.6 g, 91.6 mmol) at −78° C. and stirred for 30 min. Then phenylmagnesiumbromide in THF (110 mL, 2M, 110 mmol) was added slowly to the mixture at −78° C. The mixture was stirred at −78° C. for 30 min, warmed up to room temperature and stirred for 30 min. Then it was quenched by HCl (2M, 400 mL) and the organic solvent was removed under reduced pressure. The residue was filtered to afford the desired product (28 g, 99.4%) as a white solid. LCMS (ESI) m/z: 330.1 [M+Na]$^+$.

Step 2

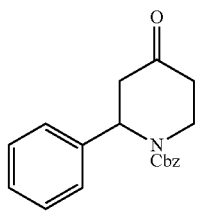 [SMILES: O=C1CCN(C(=O)OCc2ccccc2)C(c2ccccc2)C1]

Benzyl 4-oxo-2-phenylpiperidine-1-carboxylate

To a solution of benzyl 4-oxo-2-phenyl-2,3-dihydropyridine-1-carboxylate (4.0 g, 13.0 mmol) in acetic acid (30 mL) was slowly added zinc powder (21.1 g, 325.4 mmol). The reaction mixture was stirred at 90° C. for 2 h, filtered and concentrated in vacuo. The crude was purified by silica gel chromatography (eluting with 10% EtOAc in petroleum ether) to afford the desired product (2.4 g, 59.6%) as a white solid. LCMS (ESI) m/z: 310.0 [M+H]$^+$.

Step 3

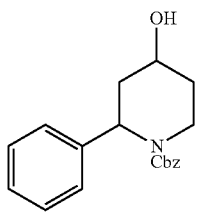 [SMILES: O=C(OCc1ccccc1)N1CCC(O)CC1c1ccccc1]

Benzyl 4-hydroxy-2-phenylpiperidine-1-carboxylate

To a solution of benzyl 4-oxo-2-phenyl-piperidine-1-carboxylate (3.1 g, 10.0 mmol) in MeOH (15 mL) was slowly added sodium borohydride (1.9 g, 50.1 mmol). The reaction mixture was stirred at room temperature for 1 h and concentrated in vacuo. The crude was purified by silica gel chromatography (eluting with 10% EtOAc in petroleum ether) to afford the desired product (3 g, 96.2%) as a white solid. LCMS (ESI) m/z: 312.0 [M+H]$^+$.

Step 4

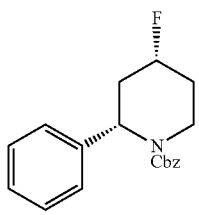 [SMILES: O=C(OCc1ccccc1)N1CC[C@@H](F)C[C@H]1c1ccccc1]

Benzyl (2S,4R)-4-fluoro-2-phenylpiperidine-1-carboxylate

Bis(2-methoxyethyl)aminosulfur trifluoride (6.63 g, 30.0 mmol) was added dropwise to a solution of benzyl 4-hydroxy-2-phenylpiperidine-1-carboxylate (3.1 g, 10.0 mmol) in DCM (100 mL) at 0° C. under argon. The reaction mixture was stirred at room temperature for 18 h, quenched with saturated sodium bicarbonate (1.0 L) and DCM (200 mL) at 0° C. The organic phase was dried over anhydrous sodium sulfate, filtered and concentrated. The residue was purified by silica gel chromatography (eluting with 20~30% EtOAc in petroleum ether) to afford cis-benzyl 4-fluoro-2-phenylpiperidine-1-carboxylate (360 mg, 11.5%) and trans-benzyl 4-fluoro-2-phenylpiperidine-1-carboxylate (300 mg, 9.6%).

The enantiomer was separated by chiral SFC from the cis-mixture. The first eluting fraction was arbitrarily assigned as benzyl (2S,4R)-4-fluoro-2-phenylpiperidine-1-carboxylate (160 mg). Chiral HPLC (column: AD-H, 4.6× 250 mm, 5 μm; mobile Phase: A: supercritical CO$_2$, B: MeOH (0.2% ammonia), A:B=80:20; flow: 3.0 mL/min; column temperature: 39.4° C.; RT=2.59 min). LCMS (ESI) m/z: 314.1 [M+H]$^+$.

Step 5

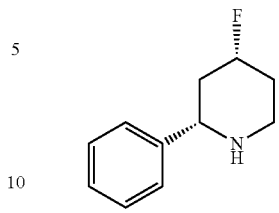

(2S,4R)-4-fluoro-2-phenylpiperidine

A mixture of benzyl (2 S,4R)-4-fluoro-2-phenylpiperidine-1-carboxylate (160 mg, 0.51 mmol) and Pd/C (10 mg, 10%) in EtOH (5.0 mL) was stirred under hydrogen atmosphere at room temperature for 18 h. The reaction mixture was filtered and the concentrated in vacuo to afford the desired product (80 mg, 87%) as yellow oil. LCMS (ESI) m/z: 180.1 [M+H]$^+$.

Step 6

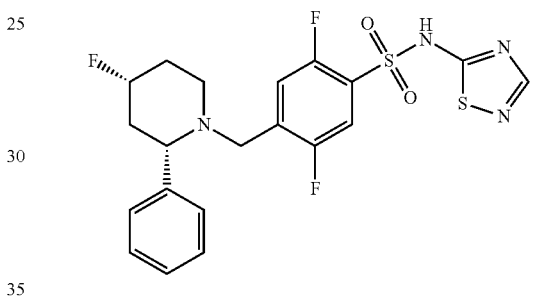

2,5-Difluoro-4-(((2S,4R)-4-fluoro-2-phenylpiperidin-1-yl)methyl)-N-(1,2,4-thiadiazol-5-yl)benzenesulfonamide The compound was synthesized as for step 5 of Example 1. LCMS (ESI) Method C: RT=4.86 min, m/z 469.0 [M+H]$^+$. $^1$H NMR (400 MHz, DMSO-d$_6$) δ 8.34 (s, 1H), 7.47-7.26 (m, 7H), 4.71-4.62 (m, 1H), 3.47-3.45 (m, 2H), 3.20-3.10 (m, 2H), 2.12-2.04 (m, 3H), 1.76-1.75 (m, 2H).

Example 29

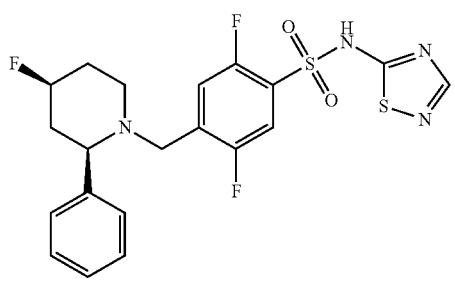 [SMILES: O=S(=O)(Nc1ncns1)c1cc(F)c(CN2CC[C@H](F)C[C@@H]2c2ccccc2)cc1F]

2,5-Difluoro-4-(((2R,4S)-4-fluoro-2-phenylpiperidin-1-yl)methyl)-N-(1,2,4-thiadiazol-5-yl)benzenesulfonamide The compound was synthesized as for Example 28. The enantiomer was arbitrarily assigned as 2,5-difluoro-4-(((2R, 4S)-4-fluoro-2-phenylpiperidin-1-yl)methyl)-N-(1,2,4-thia-diazol-5-yl)benzenesulfonamide. LCMS (ESI) Method C: RT=4.90 min, m/z 469.0 [M+H]$^+$. $^1$H NMR (400 MHz, DMSO-d$_6$) δ 8.34 (s, 1H), 7.43-7.25 (m, 7H), 4.71-4.62 (m, 1H), 3.48-3.45 (m, 2H), 3.10-2.90 (m, 2H), 2.12-2.10 (m, 3H), 1.76-1.74 (m, 2H).

Example 30

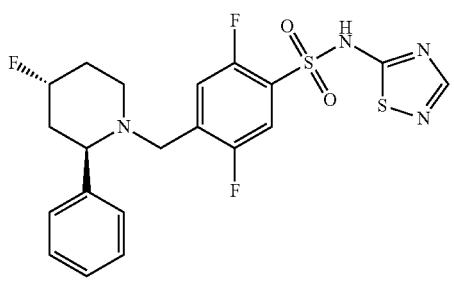

2,5-Difluoro-4-(((2R,4R)-4-fluoro-2-phenylpiperidin-1-yl)methyl)-N-(1,2,4-thiadiazol-5-yl)benzenesulfonamide The compound was synthesized as for Example 28. The enantiomer was arbitrarily assigned as 2,5-difluoro-4-(((2R,4R)-4-fluoro-2-phenylpiperidin-1-yl)methyl)-N-(1,2,4-thiadiazol-5-yl)benzenesulfonamide. LCMS (ESI) Method C: RT=4.32 min, m/z 469.1 [M+H]$^+$. $^1$H NMR (400 MHz, DMSO-d$_6$) δ 8.30 (s, 1H), 7.49-7.27 (m, 7H), 5.02-4.97 (m, 1H), 3.79-3.73 (m, 1H), 3.59-3.55 (m, 2H), 2.80-2.78 (m, 1H), 2.59-2.50 (m, 1H), 2.02-1.90 (m, 4H).

Example 31

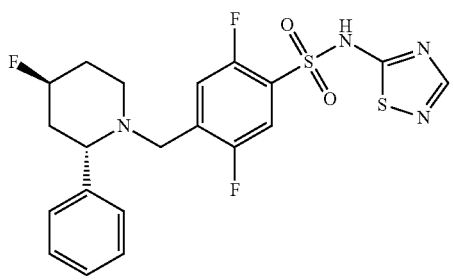 [SMILES: O=S(=O)(Nc1ncns1)c1cc(F)c(CN2CC[C@H](F)C[C@H]2c2ccccc2)cc1F]

2,5-Difluoro-4-(((2S,4S)-4-fluoro-2-phenylpiperidin-1-yl)methyl)-N-(1,2,4-thiadiazol-5-yl)benzenesulfonamide The compound was synthesized as for Example 28. The enantiomer was arbitrarily assigned as 2,5-difluoro-4-(((2S,4S)-4-fluoro-2-phenylpiperidin-1-yl)methyl)-N-(1,2,4-thiadiazol-5-yl)benzenesulfonamide. LCMS (ESI) Method C: RT=4.32 min, m/z 469.1 [M+H]$^+$. $^1$H NMR (400 MHz, DMSO-d$_6$) δ 8.25 (s, 1H), 7.47-7.24 (m, 7H), 5.02-4.96 (m, 1H), 3.72-3.70 (m, 1H), 3.57-3.53 (m, 2H), 2.75-2.73 (m, 1H), 2.53-2.50 (m, 1H), 2.00-1.86 (m, 4H).

Example 32

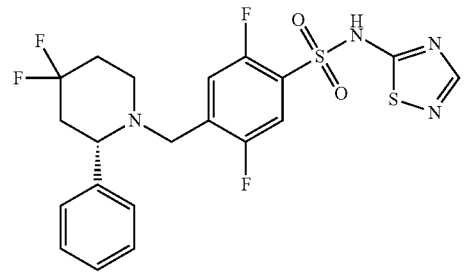 [SMILES: O=S(=O)(Nc1ncns1)c1cc(F)c(CN2CCC(F)(F)C[C@H]2c2ccccc2)cc1F]

(S)-4-((4,4-difluoro-2-phenylpiperidin-1-yl)methyl)-2,5-difluoro-N-(1,2,4-thiadiazol-5-yl)benzenesulfonamide

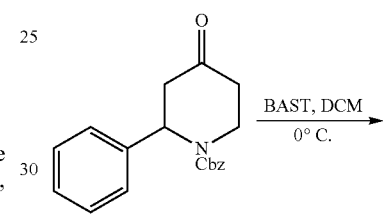

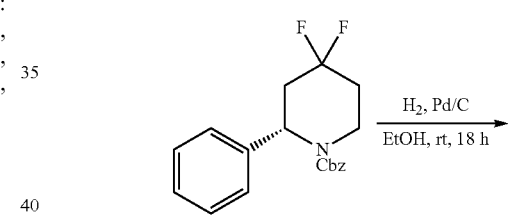

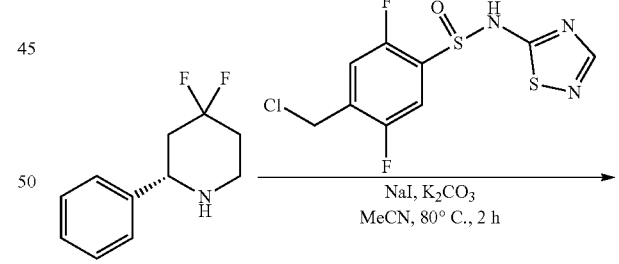

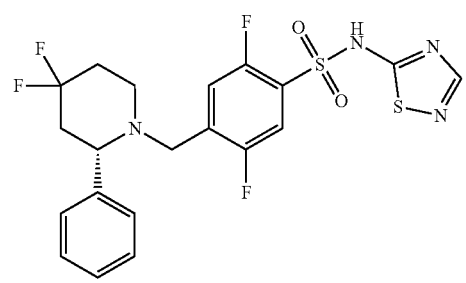

Step 1

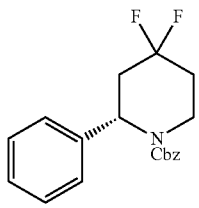 [SMILES: O=C(OCc1ccccc1)N1CCC(F)(F)C[C@H]1c1ccccc1]

Benzyl (S)-4,4-difluoro-2-phenylpiperidine-1-carboxylate

Bis(2-methoxyethyl)aminosulfur trifluoride (7.12 g, 32.2 mmol) was added dropwise to a solution of benzyl 4-oxo-2-phenylpiperidine-1-carboxylate (2.0 g, 6.45 mmol) in DCM (30 mL) at 0° C. under argon. The reaction mixture was stirred at room temperature for 18 h, quenched with saturated sodium bicarbonate (1.0 L) and DCM (200 mL) at 0° C. The organic phase was dried over anhydrous sodium sulfate, filtered and concentrated. The residue was purified by silica gel chromatography (eluting with 30% EtOAc in petroleum ether) to afford the racemate as a yellow oil. The enantiomer was separated by chiral SFC from the racemate. The first eluting fraction was arbitrarily assigned as benzyl (S)-4,4-difluoro-2-phenylpiperidine-1-carboxylate (320 mg, 14.9%). Chiral HPLC (column: AD-H, 4.6×250 mm, 5 μm; mobile Phase: A: supercritical $CO_2$, B: MeOH (0.2% ammonia), A:B=65:35; flow: 3.0 mL/min; column temperature: 40.1° C.; RT=2.02 min). LCMS (ESI) m/z: 332.1 $[M+H]^+$.

Step 2

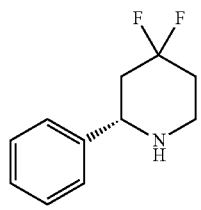 [SMILES: FC1(F)CCN[C@H](c2ccccc2)C1]

(S)-4,4-difluoro-2-phenylpiperidine

The compound was synthesized as for step 5 of Example 28. LCMS (ESI) m/z 198.1 $[M+H]^+$.

Step 3

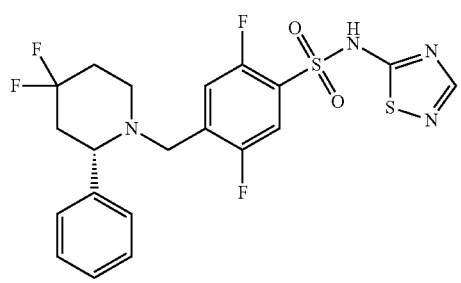 [SMILES: O=S(=O)(Nc1ncns1)c1cc(F)c(CN2CCC(F)(F)C[C@H]2c2ccccc2)cc1F]

(S)-4-((4,4-difluoro-2-phenylpiperidin-1-yl)methyl)-2,5-difluoro-N-(1,2,4-thiadiazol-5-yl)benzenesulfonamide The compound was synthesized as for step 5 of Example 1. LCMS (ESI) Method C: RT=5.59 min, m/z 487.0 $[M+H]^+$. $^1$H NMR (400 MHz, DMSO-$d_6$) δ 8.27 (s, 1H), 7.51-7.40 (m, 3H), 7.31-7.28 (m, 4H), 3.72-3.70 (m, 2H), 3.58-3.47 (m, 2H), 3.26-3.22 (m, 1H), 2.97-2.85 (m, 1H), 2.40-2.36 (m, 1H), 2.14-2.08 (m, 2H).

Example 33

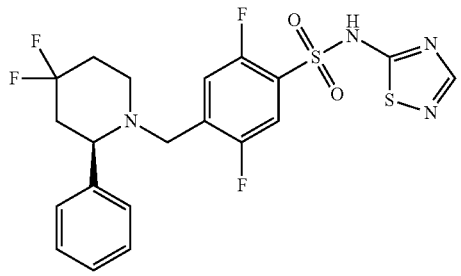 [SMILES: O=S(=O)(Nc1ncns1)c1cc(F)c(CN2CCC(F)(F)C[C@@H]2c2ccccc2)cc1F]

(R)-4-((4,4-difluoro-2-phenylpiperidin-1-yl)methyl)-2,5-difluoro-N-(1,2,4-thiadiazol-5-yl)benzenesulfonamide The compound was synthesized as for Example 32. The enantiomer was arbitrarily assigned as (R)-4-((4,4-difluoro-2-phenylpiperidin-1-yl)methyl)-2,5-difluoro-N-(1,2,4-thiadiazol-5-yl)benzenesulfonamide. LCMS (ESI) Method C: RT=5.63 min, m/z 487.0 $[M+H]^+$. $^1$H NMR (400 MHz, DMSO-$d_6$) δ 8.27 (s, 1H), 7.51-7.40 (m, 3H), 7.30-7.29 (m, 4H), 3.71-3.70 (m, 2H), 3.58-3.47 (m, 2H), 3.25-3.20 (m, 1H), 2.97-2.85 (m, 1H), 2.41-2.36 (m, 1H), 2.12-2.05 (m, 2H).

Example 34

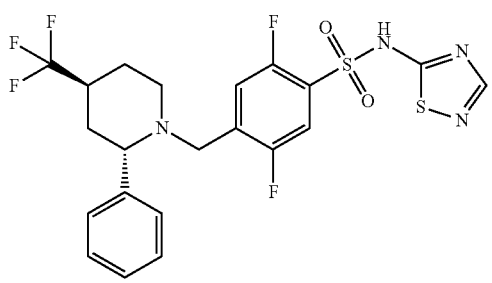 [SMILES: O=S(=O)(Nc1ncns1)c1cc(F)c(CN2CC[C@H](C(F)(F)F)C[C@H]2c2ccccc2)cc1F]

2,5-Difluoro-4-(((2S,4S)-2-phenyl-4-(trifluoromethyl)piperidin-1-yl)methyl)-N-(1,2,4-thiadiazol-5-yl)benzenesulfonamide

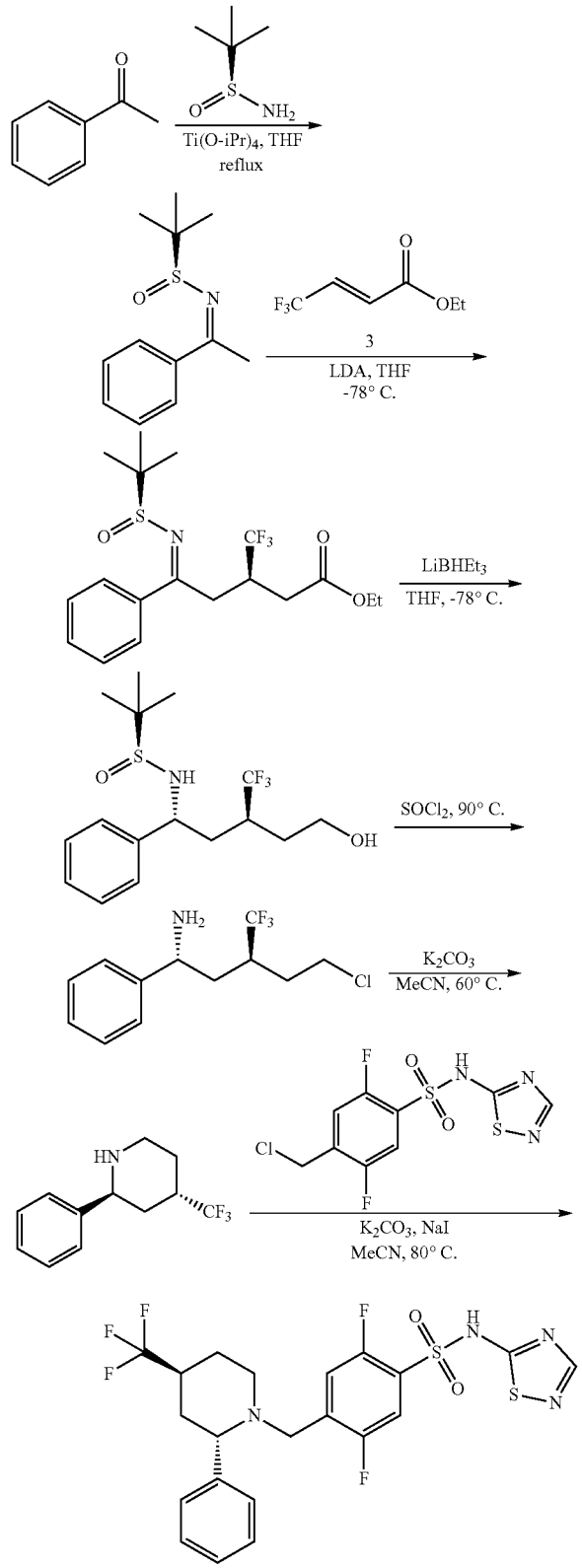

Step 1

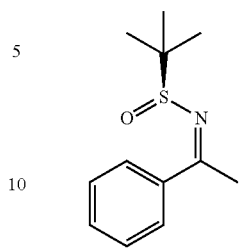

(S)-2-methyl-N-(1-phenylethylidene)propane-2-sulfinamide

To a mixture of (S)-2-methyl-2-propanesulfinamide (5.0 g, 41.3 mmol) and acetophenone (5.31 mL, 45.4 mmol) in THF was slowly added titanium isopropoxide (21.9 mL, 82.5 mmol) under $N_2$. The reaction mixture was stirred at 90° C. for 2 h and concentrated in vacuo. The crude was purified by chromatography (eluting with 10% EtOAc in petroleum ether) to afford the desired product (6.9 g, 74.8%). LCMS (ESI) m/z: 224.0 [M+H]⁺.

Step 2

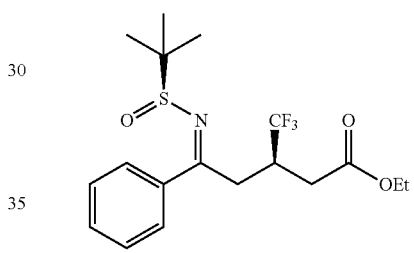

Ethyl (R)-5-(((S)-tert-butylsulfinyl)imino)-5-phenyl-3-(trifluoromethyl)pentanoate To a solution of (S)-2-methyl-N-(1-phenylethylidene)propane-2-sulfinamide (4.5 g, 20.2 mmol) in dry THF (50 mL) was slowly added lithium diisopropylamide in THF (25.2 mL, 2 M, 50.5 mmol) at −78° C. After 1 h, ethyl 4,4,4-trifluorocrotonate (5.09 g, 30.3 mmol) was added. The reaction mixture was stirred at −78° C. for 2 h, quenched with saturated ammonium chloride (50 mL), extracted with EtOAc (100 mL), dried over anhydrous sodium sulfate and concentrated. The crude was purified by chromatography (eluting with 50% EtOAc in petroleum ether) to afford the desired product (4.8 g, 60.6%). LCMS (ESI) m/z: 392.0 [M+H]⁺.

Step 3

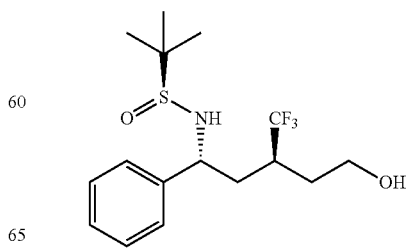

(S)—N-((1R,3R)-5-hydroxy-1-phenyl-3-(trifluoromethyl)pentyl)-2-methylpropane-2-sulfinamide To a solution of ethyl (R)-5-(((S)-tert-butylsulfinyl)imino)-5-phenyl-3-(trifluoromethyl)pentanoate (2.2 g, 5.62 mmol) in dry THF (30 mL) was slowly added lithium triethylborohydride in THF (14.1 mL, 1M, 14.1 mmol) at −78° C. under $N_2$. The reaction mixture was stirred at −78° C. for 1.5 h, quenched with water (15 mL), extracted with EtOAc (30 mL×3) and concentrated. The crude was purified by chromatography (eluting with 10% EtOAc in petroleum ether) to afford desired product (1.6 g, 81%). LCMS (ESI) m/z: 352 [M+H]⁺.

Step 4

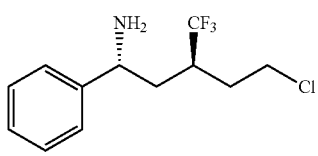 [SMILES: N[C@H](C[C@H](CCCl)C(F)(F)F)c1ccccc1]

(1R,3R)-5-chloro-1-phenyl-3-(trifluoromethyl)pentan-1-amine

A solution of (S)—N-((1R,3R)-5-hydroxy-1-phenyl-3-(trifluoromethyl)pentyl)-2-methylpropane-2-sulfinamide (150 mg, 0.43 mmol) in thionyl chloride (6 mL, 1.14 mmol) was stirred at 90° C. for 16 h. The reaction mixture was concentrated and the crude was used in next step directly without further purification. LCMS (ESI) m/z: 266 [M+H]⁺.

Step 5

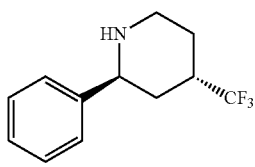 [SMILES: FC(F)(F)[C@H]1CCN[C@H](c2ccccc2)C1]

(2S,4S)-2-phenyl-4-(trifluoromethyl)piperidine

A mixture of (1R,3R)-5-chloro-1-phenyl-3-(trifluoromethyl)pentan-1-amine (150 mg, crude) and potassium carbonate (30.4 mg, 0.22 mmol) in MeCN (5 mL) was stirred at 60° C. for 16 h. The reaction mixture was quenched with water (5 mL) and EtOAc (25 mL), washed with saturated brine solution (10 mL), dried over anhydrous sodium sulfate and concentrated. The crude was purified by Combiflash (eluting with 0~40 MeCN in 0.05% TFA) to afford the desired product (31 mg, 31% in two steps). LCMS (ESI) m/z: 230 [M+H]⁺.

Step 5

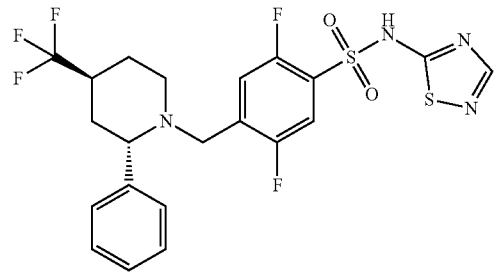 [SMILES: O=S(=O)(Nc1ncns1)c1cc(F)c(CN2CC[C@H](C(F)(F)F)C[C@H]2c2ccccc2)cc1F]

2,5-Difluoro-4-(((2S,4S)-2-phenyl-4-(trifluoromethyl)piperidin-yl)methyl)-N-(1,2,4-thiadiazol-5-yl)benzenesulfonamide The compound was synthesized as for step 5 of Example 1. LCMS (ESI) Method C: RT=5.50 min, m/z 487.0 [M+H]⁺. ¹H NMR (400 MHz, DMSO-d₆) δ 8.03 (s, 1H), 7.44-7.23 (m, 7H), 3.65-3.55 (m, 3H), 2.77-2.74 (m, 1H), 2.63-2.60 (m, 1H), 2.43-2.40 (m, 1H). 1.99-1.80 (m, 4H).

Example 35

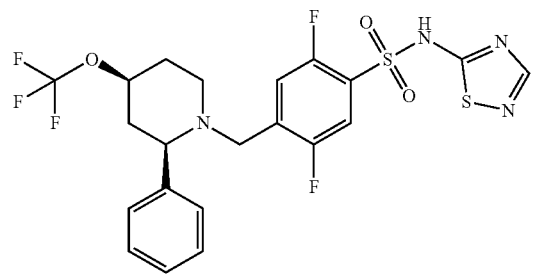 [SMILES: O=S(=O)(Nc1ncns1)c1cc(F)c(CN2CC[C@H](OC(F)(F)F)C[C@@H]2c2ccccc2)cc1F]

2,5-Difluoro-4-(((2R,4S)-2-phenyl-4-(trifluoromethoxy)piperidin-1-yl)methyl)-N-(1,2,4-thiadiazol-5-yl)benzenesulfonamide

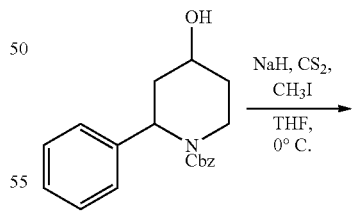

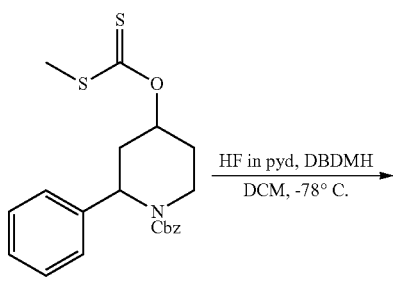

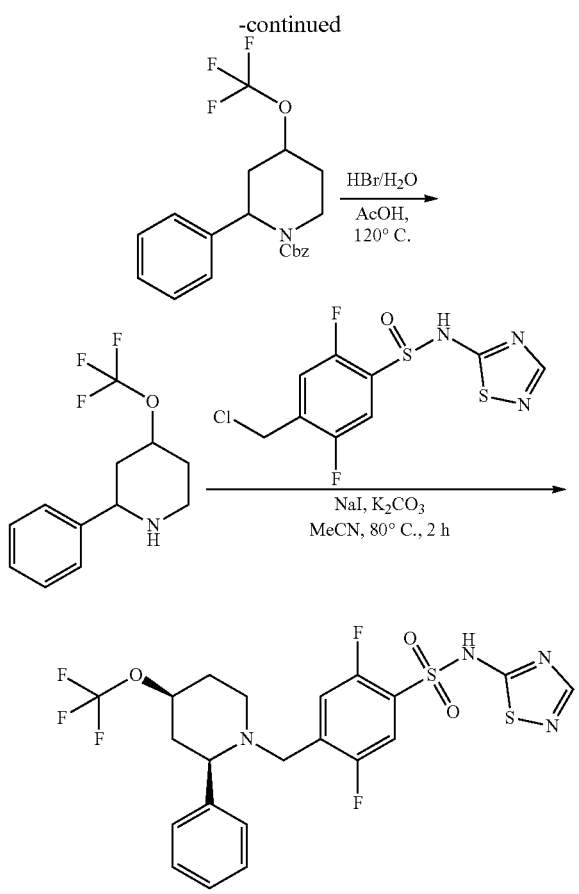

Step 1

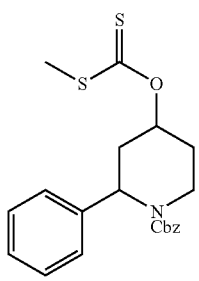 [SMILES: CSC(=S)OC1CCN(C(=O)OCc2ccccc2)C(c2ccccc2)C1]

Benzyl 4-(((methylthio)carbonothioyl)oxy)-2-phenylpiperidine-1-carboxylate

Into an ice-cooled suspension of sodium hydride (585 mg, 14.64 mmol) in THF (5.0 mL) was added dropwise a solution of benzyl 4-hydroxy-2-phenyl-piperidine-1-carboxylate (2.28 g, 7.32 mmol) in THF (10.0 mL) in 5 min. The mixture became dense after addition. A solution of carbon disulfide (836 mg, 10.98 mmol) in THF (5.0 mL) was added dropwise in 5 min and then the reaction mixture stirred at 0-5° C. for 15 min. The reaction mixture became clear and dark yellow, into which a solution of methyl iodide (1.35 g, 9.52 mmol) in THF (5.0 mL) was added dropwise in 2 min. Then the reaction mixture was stirred for 10 min at 0-5° C., quenched carefully with water (5.0 mL) and concentrated. The residue was diluted with EtOAc (100 mL), washed with water (50 mL), dried over anhydrous sodium sulfate, filtered and concentrated. The crude oil was purified by silica gel chromatography (eluting with 10% EtOAc in petroleum ether) to afford desired product (2.4 g, 81.6%) as a yellow oil. LCMS (ESI) m/z: 424.0 [M+Na]$^+$.

Step 2

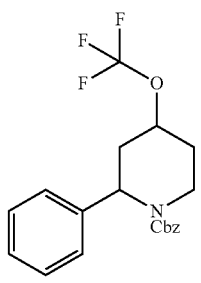 [SMILES: O=C(OCc1ccccc1)N1CCC(OC(F)(F)F)CC1c1ccccc1]

Benzyl 2-phenyl-4-(trifluoromethoxy)piperidine-1-carboxylate

To a solution of 1,3-dibromo-5,5-dimethylhydantoin (3.4 g, 11.95 mmol) in DCM (80 mL) was added pyridine hydrofluoride (12 mL, 133.2 mmol) at −78° C. and stirred for 10 min. Then benzyl 4-methyl sulfanylcarbothioyloxy-2-phenyl-piperidine-1-carboxylate (1.6 g, 3.98 mmol) in DCM (10 mL) was added at −78° C. and stirred at room temperature for 16 h. The reaction mixture was diluted with DCM (50 mL), washed with sodium carbonate (20×3 mL), dried over anhydrous sodium sulfate and concentrated. The crude product was used in the next step without further purification. LCMS (ESI) m/z: 380.2 [M+H]$^+$.

Step 3

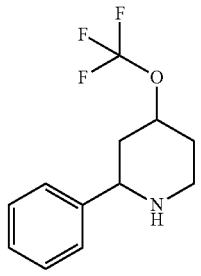 [SMILES: FC(F)(F)OC1CCNC(c2ccccc2)C1]

2-Phenyl-4-(trifluoromethoxy)piperidine

A mixture of benzyl 2-phenyl-4-(trifluoromethoxy)piperidine-1-carboxylate (1.5 g, 3.95 mmol) in hydrogen bromide (5 mL, 38%, 3.95 mmol) and acetic acid (20 mL) was stirred at 120° C. for 2 h. The reaction was concentrated to dryness and the crude was purified by combiflash (eluting with 30~40% MeCN in 0.1% FA) to afford the desired product (180 mg, 18.6%) as a yellow oil. LCMS (ESI) m/z: 246.2 [M+H]$^+$.

Step 4

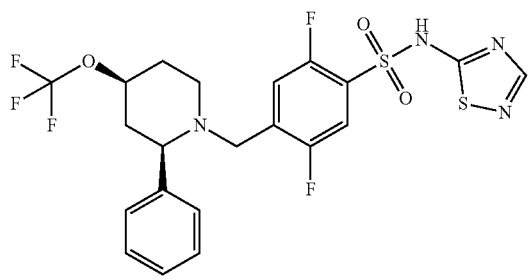 [SMILES: O=S(=O)(Nc1ncns1)c1cc(F)c(CN2CC[C@H](OC(F)(F)F)C[C@@H]2c2ccccc2)cc1F]

2,5-Difluoro-4-(((2R,4S)-2-phenyl-4-(trifluoromethoxy)piperidin-1-yl)methyl)-N-(1,2,4-thiadiazol-5-yl)benzenesulfonamide The compound was synthesized as for step 5 of Example 1. The cis-diastereoisomers were purified by Prep-HPLC (eluting with 30-50% MeCN in 0.5% FA). The second eluting fraction was arbitrarily assigned as 2,5-difluoro-4-(((2R,4S)-2-phenyl-4-(trifluoromethoxy)piperidin-1-yl)methyl)-N-(1,2,4-thiadiazol-5-yl)benzenesulfonamide. LCMS (ESI) Method C: RT=6.05 min, m/z 535.1 [M+H]$^+$. $^1$H NMR (400 MHz, DMSO-d$_6$) δ 8.16 (s, 1H), 7.44-7.23 (m, 7H), 4.53-4.51 (m, 1H), 3.50-3.47 (m, 2H), 3.13-3.10 (m, 1H), 2.89-2.87 (m, 1H), 2.25-2.22 (m, 1H), 2.07-2.01 (m, 2H), 1.83-1.75 (m, 2H).

Example 36

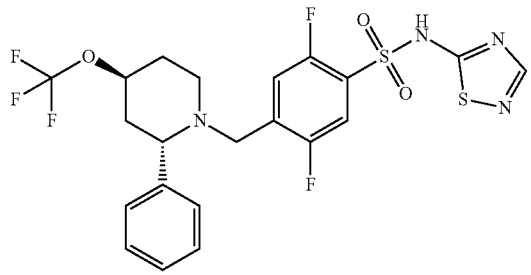 [SMILES: O=S(=O)(Nc1ncns1)c1cc(F)c(CN2CC[C@H](OC(F)(F)F)C[C@H]2c2ccccc2)cc1F]

2,5-Difluoro-4-(((2S,4S)-2-phenyl-4-(trifluoromethoxy)piperidin-1-yl)methyl)-N-(1,2,4-thiadiazol-5-yl)benzenesulfonamide The compound was synthesized as for Example 35. The trans-diastereoisomers were purified by Prep-HPLC (eluting with 30-50% MeCN in 0.5% FA), the first eluting fraction was arbitrarily assigned as 2,5-Difluoro-4-(((2 S,4S)-2-phenyl-4-(trifluoromethoxy)piperidin-1-yl)methyl)-N-(1,2,4-thiadiazol-5-yl)benzenesulfonamide. LCMS (ESI) Method C: RT=5.51 min, m/z 535.1 [M+H]$^+$. $^1$H NMR (400 MHz, DMSO-d$_6$) δ 8.22 (s, 1H), 7.46-7.23 (m, 7H), 4.78 (brs, 1H), 3.63-3.59 (m, 3H), 3.25-3.19 (m, 1H), 2.75-2.71 (m, 1H), 2.47-1.85 (m, 4H).

Example 37

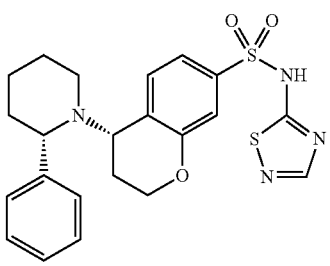 [SMILES: O=S(=O)(Nc1ncns1)c1ccc2c(c1)OCC[C@@H]2N1CCCC[C@H]1c1ccccc1]

(S)-4-((S)-2-phenylpiperidin-1-yl)-N-(1,2,4-thiadiazol-5-yl)chromane-7-sulfonamide

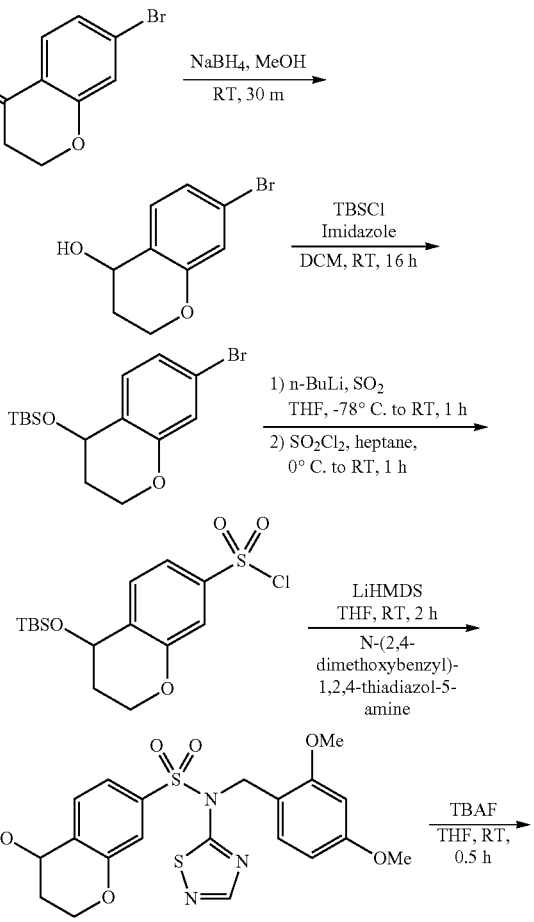

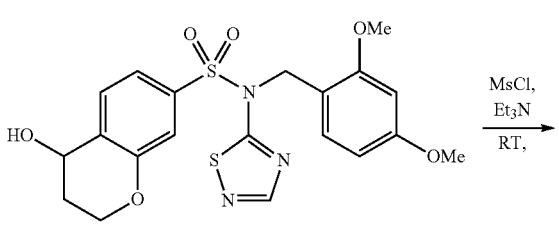

-continued

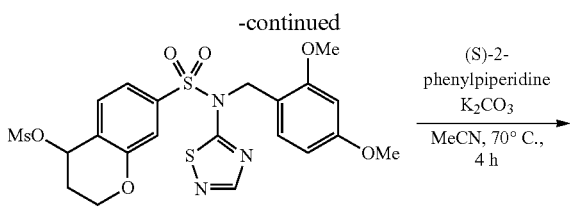

Step 2

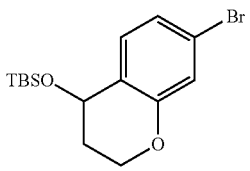 [SMILES: CC(C)(C)[Si](C)(C)OC1CCOc2cc(Br)ccc21]

((7-bromochroman-4-yl)oxy)(tert-butyl)dimethylsilane 7-bromochaoman-4-ol (8.80 mmol, crude), TBSCl (1.64 g, 10.5 mmol), and imidazole (1.80 g, 26.4 mmol) were stirred in DCM (17 mL) at r.t. After 16 h the reaction was quenched by the addition of water (100 mL) and DCM (100 mL). The organic layer was removed and the aqueous layer was extracted with DCM (2×100 mL). The combined organic fractions were dried with Na$_2$SO$_4$ and concentrated. The crude product was purified by column chromatography to provide ((7-bromochroman-4-yl)oxy)(tert-butyl)dimethylsilane (2.9 g, 96%). m/z 375.0 [M+MeOH+H]$^+$, 1H NMR (400 MHz, Chloroform-d) δ 7.05 (d, J=8.0 Hz, 1H), 7.02-6.94 (m, 2H), 4.74 (t, J=4.6 Hz, 1H), 4.31 (ddd, J=10.9, 9.6, 3.0 Hz, 1H), 4.20 (ddd, J=10.9, 5.7, 3.6 Hz, 1H), 2.11-1.88 (m, 2H), 0.90 (s, 9H), 0.15 (s, 3H), 0.13 (s, 3H).

Step 3

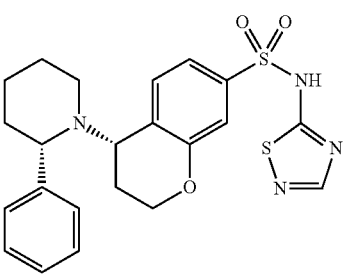

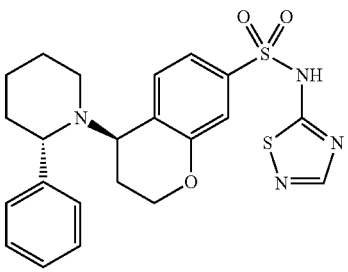

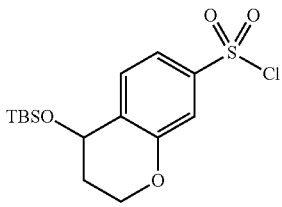 [SMILES: CC(C)(C)[Si](C)(C)OC1CCOc2cc(S(=O)(=O)Cl)ccc21]

4-((tert-butyldimethylsilyl)oxy)chromane-7-sulfonyl chloride n-Butyllithium (1.6 M in hexanes, 4.0 mL, 6.4 mmol) was added dropwise to a solution of ((7-bromochroman-4-yl)oxy)(tert-butyl)dimethylsilane (2.0 g, 5.8 mmol) in THF (30 mL) at −50° C. After 30 minutes, the solution was bubbled with SO$_2$ gas for 5 minutes. The reaction was stirred at −50° C. for an additional 15 minutes then warmed to r.t. over 1 hour. The reaction was concentrated. The crude product mixture was suspended in heptane (20 mL) and a solution of SO$_2$Cl$_2$ (0.47 mL, 5.8 mmol) in heptane (20 mL) was added dropwise at 0° C. After the addition was complete the reaction was warmed to r.t. and stirred for 1 hour. The reaction was concentrated and the crude mixture was suspended in benzene. The precipitates were removed by filtration and the organic layer was concentrated to provide crude 4-((tert-butyldimethylsilyl)oxy)chromane-7-sulfonyl chloride, which was used in the subsequent step immediately without further purification.

Step 1

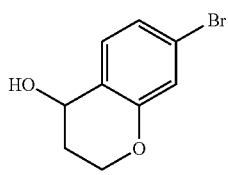

7-bromochroman-4-ol

NaBH$_4$ (166 mg, 4.40 mmol) was added to a solution of 7-bromochroman-4-one (2.00 g, 8.80 mmol) in MeOH (45 mL) at r.t. After 30 minutes, the reaction was quenched by the addition of 1% aqueous HCl (100 mL) and DCM (100 mL). The organic layer was removed and the aqueous layer was extracted with DCM (2×100 mL). The combined organic fractions were dried with Na$_2$SO$_4$ and concentrated. The crude product was used in the subsequent step without further purification.

Step 4

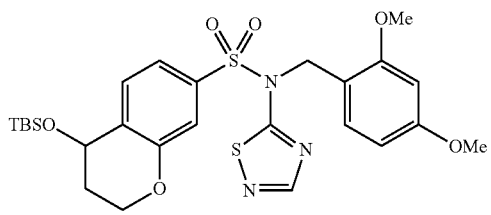 [SMILES: COc1ccc(CN(c2ncns2)S(=O)(=O)c2ccc3c(c2)OCCC3O[Si](C)(C)C(C)(C)C)c(OC)c1]

4-((tert-butyldimethylsilyl)oxy)-N-(2,4-dimethoxy-
benzyl)-N-(1,2,4-thiadiazol-5-yl)chromane-7-sulfo-
namide LiHMDS (1.0 M in THF, 7.0 mL, 7.0 mmol) was added dropwise to a solution of N-(2,4-dimethoxybenzyl)-1,2,4-thiadiazol-5-amine (1.5 g, 5.8 mmol) in THF (30 mL) at r.t. After 30 minutes a solution of 4-((tert-butyldimethylsilyl)oxy)chromane-7-sulfonyl chloride (5.8 mmol, crude) in THF (30 mL) was added. The reaction was stirred at r.t. for 2 hours. Water (100 mL) and iPrOAc (100 mL) were added, and the organic layer was removed. The aqueous layer was extracted with iPrOAc (2×100 mL). The combined organic fractions were dried with $Na_2SO_4$ and concentrated. The crude product was purified by column chromatography to give 4-((tert-butyldimethylsilyl)oxy)-N-(2,4-dimethoxyben-zyl)-N-(1,2,4-thiadiazol-5-yl)chromane-7-sulfonamide (1.6 g, 48%) as a white solid. m/z 600.2 [M+Na]$^+$, 1H NMR (400 MHz, Chloroform-d) δ 8.12 (s, 1H), 7.29-7.28 (m, 2H), 7.18-7.16 (m, 1H), 7.08 (dq, J=8.0, 0.7 Hz, 1H), 6.36-6.32 (m, 2H), 5.26-5.14 (m, 2H), 4.76 (dd, J=6.0, 4.3 Hz, 1H), 4.32 (ddd, J=11.5, 8.4, 3.3 Hz, 1H), 4.26-4.18 (m, 1H), 3.75 (s, 3H), 3.72 (s, 3H), 2.12-1.91 (m, 2H), 0.91 (s, 9H), 0.16 (s, 3H), 0.15 (s, 3H).

Step 5

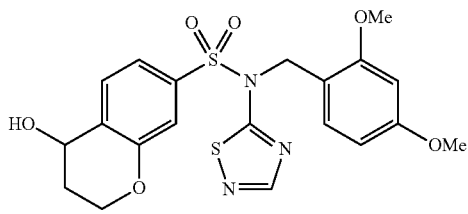 [SMILES: COc1ccc(CN(c2ncns2)S(=O)(=O)c2ccc3c(c2)OCCC3O)c(OC)c1]

N-(2,4-dimethoxybenzyl)-4-hydroxy-N-(1,2,4-thia-
diazol-5-yl)chromane-7-sulfonamide TBAF (1.0 M in THF, 0.83 mL, 0.83 mmol) was added dropwise to a solution of (R)-4-((tert-butyldimethylsilyl)oxy)-N-(2,4-dimethoxybenzyl)-N-(1,2,4-thiadiazol-5-yl)chromane-7-sulfonamide (400 mg, 0.69 mmol) in THF (1.4 mL) at r.t. After 30 minutes, water (25 mL) and DCM (25 mL) were added. The organic layer was removed and the aqueous layer was extracted with DCM (2×25 mL). The combined organic layers were dried with $Na_2SO_4$ and concentrated. The crude product was used without further purification in the subsequent step. m/z 486.1 [M+Na]$^+$, 1H NMR (400 MHz, Chloroform-d) δ 8.13 (d, J=1.1 Hz, 1H), 7.34 (d, J=8.2 Hz, 1H), 7.28 (dd, J=8.1, 1.8 Hz, 1H), 7.21 (d, J=1.8 Hz, 1H), 7.06 (d, J=8.2 Hz, 1H), 6.34-6.28 (m, 2H), 5.22 (dd, J=2.9, 0.9 Hz, 2H), 4.76 (q, J=4.9 Hz, 1H), 4.30-4.24 (m, 2H), 3.76 (s, 3H), 3.73 (s, 3H), 2.18-1.99 (m, 2H), 1.83 (d, J=5.5 Hz, 1H).

Step 6

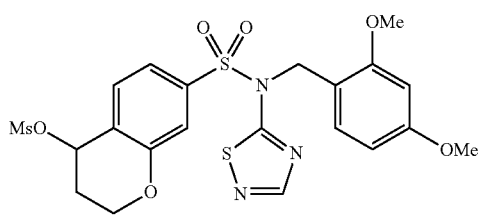 [SMILES: COc1ccc(CN(c2ncns2)S(=O)(=O)c2ccc3c(c2)OCCC3OS(C)(=O)=O)c(OC)c1]

7-(N-(2,4-dimethoxybenzyl)-N-(1,2,4-thiadiazol-5-
yl)sulfamoyl)chroman-4-yl methanesulfonate MsCl (107 μL, 1.40 mmol) was added dropwise to a solution of N-(2,4-dimethoxybenzyl)-4-hydroxy-N-(1,2,4-thiadiazol-5-yl)chromane-7-sulfonamide (0.69 mmol, crude) and TEA (290 μL, 2.00 mmol) in DCM (3.5 mL) at r.t. After 30 minutes the reaction was quenched by the addition of water (25 mL) and DCM (25 mL). The organic layer was removed and the aqueous layer was extracted with DCM (2×25 mL). The combined organic layers were dried with $Na_2SO_4$ and concentrated. The crude product was used without further purification in the subsequent step. 1H NMR (400 MHz, Chloroform-d) δ 8.15 (s, 1H), 7.43 (dt, J=8.2, 0.5 Hz, 1H), 7.32 (dd, J=8.2, 1.9 Hz, 1H), 7.25 (d, J=1.9 Hz, 1H), 7.09-7.06 (m, 1H), 6.33 (dd, J=8.3, 2.5 Hz, 1H), 6.31 (d, J=2.3 Hz, 1H), 5.78-5.74 (m, 1H), 5.24 (s, 2H), 4.37 (dtd, J=11.5, 4.1, 1.1 Hz, 1H), 4.27 (td, J=11.5, 2.7 Hz, 1H), 3.77 (s, 3H), 3.72 (s, 3H), 3.06 (s, 3H), 2.45-2.36 (m, 1H), 2.34-2.22 (m, 1H).

Step 7

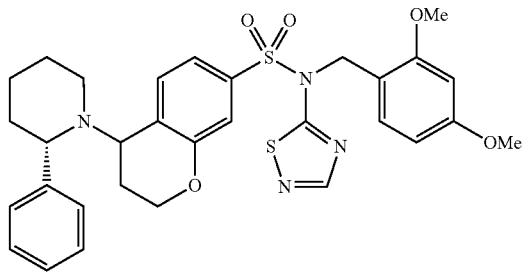 [SMILES: COc1ccc(CN(c2ncns2)S(=O)(=O)c2ccc3c(c2)OCCC3N2CCCC[C@H]2c2ccccc2)c(OC)c1]

N-(2,4-dimethoxybenzyl)-4-((S)-2-phenylpiperidin-
1-yl)-N-(1,2,4-thiadiazol-5-yl)chromane-7-sulfona-
mide 7-(N-(2,4-dimethoxybenzyl)-N-(1,2,4-thiadiazol-5-yl) sulfamoyl)chroman-4-yl methanesulfonate (0.69 mmol, crude), (S)-2-phenylpiperidine (170 mg, 1.04 mmol), and $K_2CO_3$ (287 mg, 2.07 mmol) were stirred in MeCN (3.5 mL) at 70° C. After 4 hours the reaction was diluted with DCM (10 mL), filtered, and concentrated. The crude mixture of diastereomers was carried on to the subsequent step.

Step 8

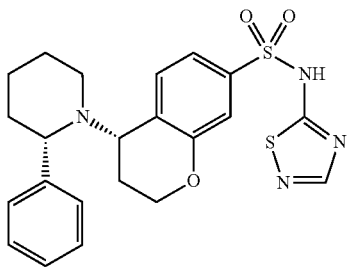 [SMILES: O=S(=O)(Nc1ncns1)c1ccc2c(c1)OCC[C@@H]2N1CCCC[C@H]1c1ccccc1]

(S)-4-((S)-2-phenylpiperidin-1-yl)-N-(1,2,4-thiadiazol-5-yl)chromane-7-sulfonamide Crude N-(2,4-dimethoxybenzyl)-4-((S)-2-phenylpiperidin-1-yl)-N-(1,2,4-thiadiazol-5-yl)chromane-7-sulfonamide (0.69 mmol, mixture of diastereomers) was dissolved in DCM (3.5 mL) and TFA (170 μL, 2.215 mmol) was added dropwise at r.t. After 1 hour, the reaction was concentrated to dryness. The crude product was purified by HPLC to provide (S)-4-((S)-2-phenylpiperidin-1-yl)-N-(1,2,4-thiadiazol-5-yl)chromane-7-sulfonamide as a white solid (12.6 mg, 4% over 4 steps). The stereochemistry was arbitrarily assigned at the chromane center. m/z 457.1 [M+H]$^+$, 1H NMR (400 MHz, DMSO-d6, broad peaks due to rotamers) δ 8.24 (s, 1H), 7.49 (s, 3H), 7.40-7.22 (m, 4H), 7.04 (s, 1H), 4.20 (dt, J=10.8, 4.9 Hz, 1H), 4.09-3.86 (m, 3H), 2.77 (s br, 2H), 2.03 (s, 1H), 1.94-1.49 (m, 6H), 1.39 (s, 1H).

Example 38

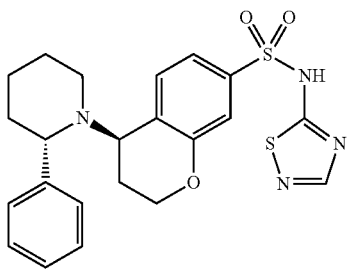 [SMILES: O=S(=O)(Nc1ncns1)c1ccc2c(c1)OCC[C@H]2N1CCCC[C@H]1c1ccccc1]

(R)-4-((S)-2-phenylpiperidin-1-yl)-N-(1,2,4-thiadiazol-5-yl)chromane-7-sulfonamide This compound was prepared in the same sequence as Example 37. The stereochemistry was arbitrarily assigned at the chromane center. m/z 457.1 [M+H]$^+$, 1H NMR (400 MHz, DMSO-d6) δ 8.31 (s, 1H), 7.78 (dd, J=8.2, 1.1 Hz, 1H), 7.45 (d, J=7.4 Hz, 2H), 7.38-7.28 (m, 3H), 7.28-7.21 (m, 1H), 7.01 (d, J=1.9 Hz, 1H), 4.24 (dt, J=11.2, 3.7 Hz, 1H), 3.82-3.55 (m, 3H), 2.24 (s, 1H), 1.99 (s, 1H), 1.77 (td, J=20.6, 20.2, 11.1 Hz, 3H), 1.68-1.27 (m, 5H).

Example 39

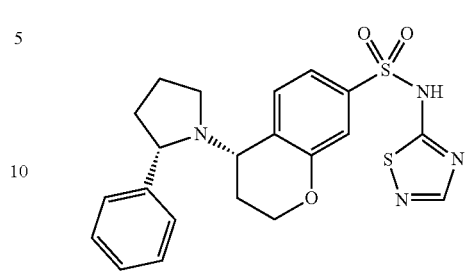

(S)-4-((S)-2-phenylpyrrolidin-1-yl)-N-(1,2,4-thiadiazol-5-yl)chromane-7-sulfonamide This compound was prepared as for Example 37. The stereochemistry was arbitrarily assigned at the chromane center. m/z 443.1 [M+H]$^+$, 1H NMR (400 MHz, DMSO-d6) δ 8.28 (s, 1H), 7.69 (dd, J=8.1, 1.1 Hz, 1H), 7.49-7.41 (m, 2H), 7.34-7.28 (m, 3H), 7.25-7.18 (m, 1H), 7.01 (d, J=1.9 Hz, 1H), 4.33 (dt, J=11.2, 3.8 Hz, 1H), 4.03 (td, J=10.7, 3.4 Hz, 1H), 3.97-3.85 (m, 1H), 3.84-3.69 (m, 1H), 2.72 (d, J=8.1 Hz, 1H), 2.18 (ddt, J=12.6, 7.9, 4.0 Hz, 1H), 2.10-1.91 (m, 2H), 1.92-1.50 (m, 4H).

Example 40

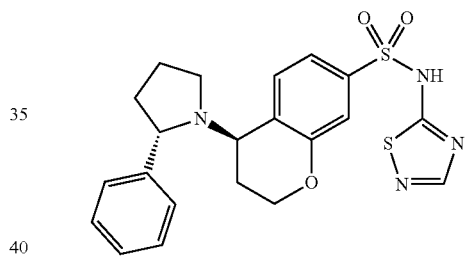

(R)-4-((S)-2-phenylpyrrolidin-1-yl)-N-(1,2,4-thiadiazol-5-yl)chromane-7-sulfonamide This compound was prepared as for Example 37. The stereochemistry was arbitrarily assigned at the chromane center. m/z 443.1 [M+H]$^+$, 1H NMR (400 MHz, DMSO-d6) δ 8.24 (s, 1H), 7.43-7.35 (m, 3H), 7.30 (t, J=7.6 Hz, 2H), 7.22 (t, J=7.4 Hz, 1H), 7.16 (dd, J=8.1, 1.9 Hz, 1H), 7.07 (d, J=1.9 Hz, 1H), 4.28 (s, 2H), 4.11 (d, J=11.7 Hz, 1H), 4.00 (dt, J=10.7, 4.6 Hz, 1H), 2.29 (s, 1H), 1.91 (s, 5H), 1.69 (s, 1H).

Example 41

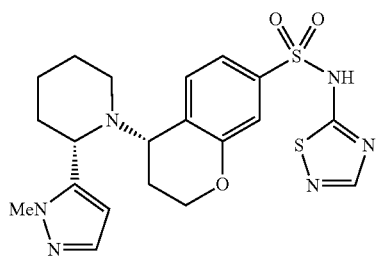 [SMILES: Cn1nccc1[C@@H]1CCCCN1[C@H]1CCOc2cc(S(=O)(=O)Nc3ncns3)ccc21]

203

(S)-4-((S)-2-(1-methyl-1H-pyrazol-5-yl)piperidin-1-yl)-N-(1,2,4-thiadiazol-5-yl)chromane-7-sulfonamide

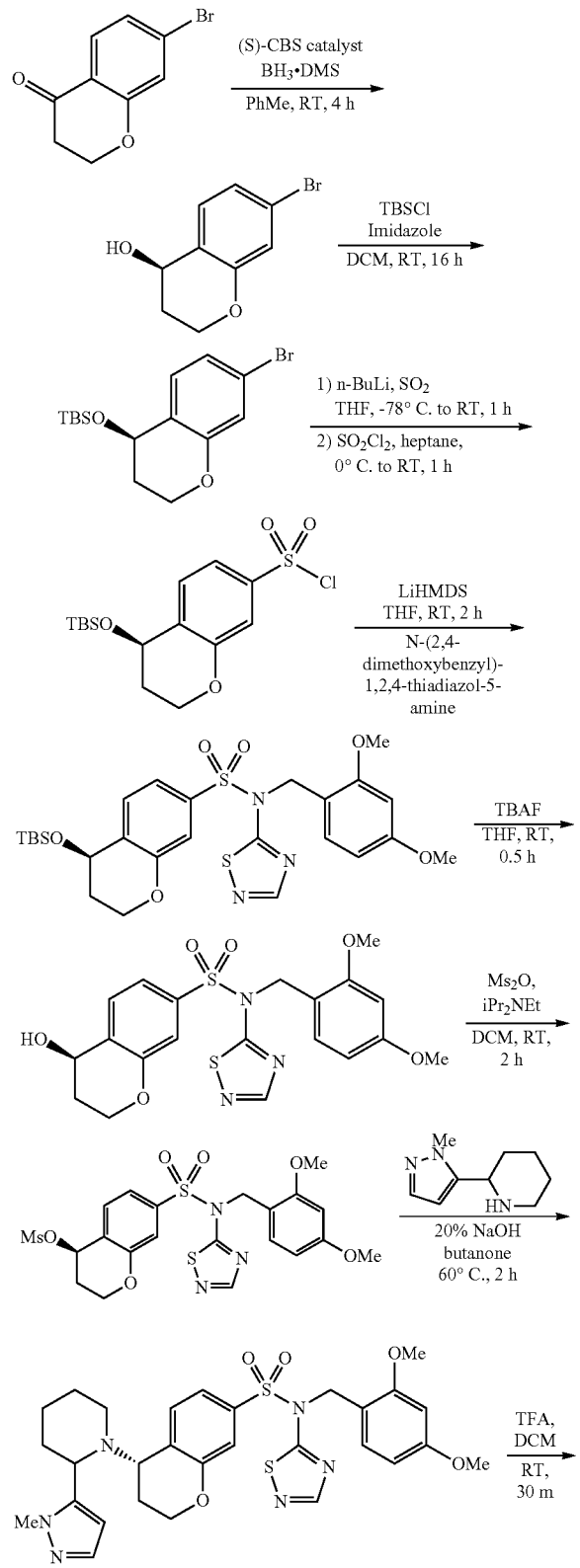

204

-continued

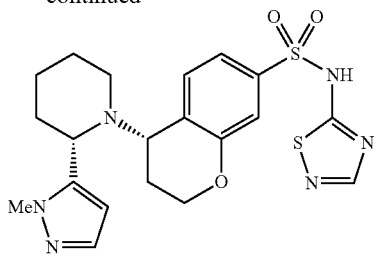

Step 1

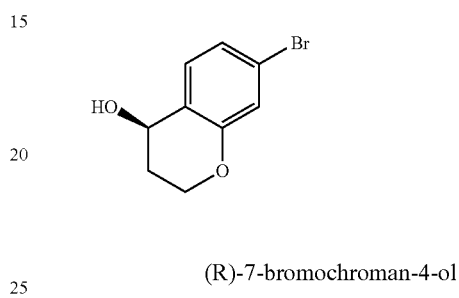

(R)-7-bromochroman-4-ol

A solution of 7-bromochroman-4-one (9.92 g, 43.7 mmol) in toluene (150 mL) was added dropwise over 2 hours to a stirring solution of α,α-Diphenyl-L-prolinol methylboronic acid cycl-amide ester (S-2-Methyl-CBS, 1.0 M solution in toluene, 4.37 mL, 4.37 mmol) and borane dimethylsulfide complex (4.07 mL, 43.7 mmol) in toluene (450 mL) at r.t. After 2 hours of additional stirring, the reaction was quenched by the dropwise addition of methanol (100 mL). 2M HCl (300 mL) and iPrOAc (300 mL) were added. The organic layer was separated and washed with 2M HCl (2×300 mL) and brine (400 mL). The enantiomeric purity of the crude product was determined to be 99.55:0.45 e.r. (99.1% e.e.) by Chiral SFC (AD column, 20% isocratic MeOH) and comparison with a racemic standard. The crude alcohol was used in the subsequent step without further purification.

Step 2

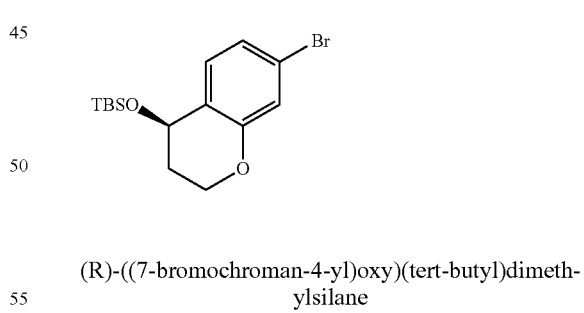

(R)-((7-bromochroman-4-yl)oxy)(tert-butyl)dimethylsilane (R)-7-bromochroman-4-ol (43.7 mmol, crude), TBSCl (8.83 g, 56.8 mmol), and imidazole (8.92 g, 131 mmol) were stirred in dichloromethane (87.4 mL) at r.t. After 16 hours, water (100 mL) was added and the organic layer was removed. The aqueous layer was extracted with DCM (2×100 mL). The combined organic layers were dried with $Na_2SO_4$ and concentrated. The crude product was purified by column chromatography to give (R)-((7-bromochroman-4-yl)oxy)(tert-butyl)-dimethylsilane as a white solid (12.2 g, 81% over 2 steps). m/z 375.0 [M+MeOH+H]$^+$, 1H NMR (400 MHz, Chloroform-d) δ 7.05 (d, J=8.0 Hz, 1H), 7.02-

6.94 (m, 2H), 4.74 (t, J=4.6 Hz, 1H), 4.31 (ddd, J=10.9, 9.6, 3.0 Hz, 1H), 4.20 (ddd, J=10.9, 5.7, 3.6 Hz, 1H), 2.11-1.88 (m, 2H), 0.90 (s, 9H), 0.15 (s, 3H), 0.13 (s, 3H).
Step 3

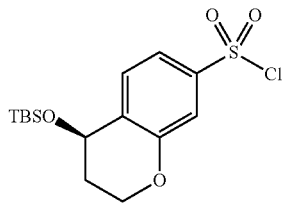 [SMILES: CC(C)(C)[Si](C)(C)O[C@@H]1CCOc2cc(S(=O)(=O)Cl)ccc21]

(R)-4-((tert-butyldimethylsilyl)oxy)chromane-7-sulfonyl chloride n-Butyllithium (1.6 M in hexanes, 25 mL, 39.7 mmol) was added dropwise to a solution of (R)-((7-bromochroman-4-yl)oxy)(tert-butyl)dimethylsilane (12.2 g, 36.1 mmol) in THF (180 mL) at −50° C. After 30 minutes, the reaction was bubbled with SO₂ gas for 20 minutes. The reaction was stirred at −50° C. for an additional 15 minutes then warmed to r.t. over 1 hour. The reaction was concentrated. The crude product mixture was suspended in heptane (260 mL) and a solution of SO₂Cl₂ (4.37 mL, 54.2 mmol) in heptane (10 mL) was added dropwise at 0° C. After the addition was complete the reaction was warmed to r.t. and stirred for 1 hour. The reaction was concentrated and the crude mixture was suspended in benzene. The precipitates were removed by filtration and the organic layer was concentrated to provide crude (R)-4-((tert-butyldimethylsilyl)-oxy)chromane-7-sulfonyl chloride, which was used in the subsequent step immediately without further purification.
Step 4

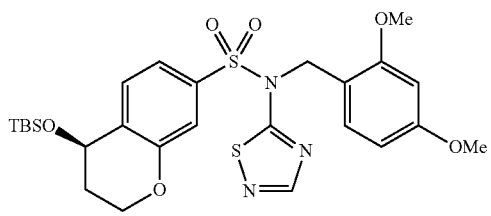 [SMILES: COc1ccc(CN(c2ncns2)S(=O)(=O)c2ccc3c(c2)OCC[C@H]3O[Si](C)(C)C(C)(C)C)c(OC)c1]

(R)-4-((tert-butyldimethylsilyl)oxy)-N-(2,4-dimethoxybenzyl)-N-(1,2,4-thiadiazol-5-yl)chromane-7-sulfonamide LiHMDS (1.0 M in THF, 43.3 mL, 43.3 mmol) was added dropwise to a solution of N-(2,4-dimethoxybenzyl)-1,2,4-thiadiazol-5-amine (9.08 g, 43.3 mmol) in THF (180 mL) at r.t. After 30 minutes a solution of (R)-4-((tert-butyldimethylsilyl)oxy)chromane-7-sulfonyl chloride (36.1 mmol, crude) in THF (180 mL) was added. The reaction was stirred at r.t. for 2 hours. Water (300 mL) and iPrOAc (300 mL) were added, and the organic layer was removed. The aqueous layer was extracted with iPrOAc (2×300 mL). The combined organic fractions were dried with Na₂SO₄ and concentrated. The crude product was purified by column chromatography to give (R)-4-((tert-butyldimethylsilyl)oxy)-N-(2,4-dimethoxybenzyl)-N-(1,2,4-thiadiazol-5-yl)chromane-7-sulfonamide (9.1 g, 44%) as a white solid. m/z 600.2 [M+Na]⁺, 1H NMR (400 MHz, Chloroform-d) δ 8.12 (s, 1H), 7.29-7.28 (m, 2H), 7.18-7.16 (m, 1H), 7.08 (dq, J=8.0, 0.7 Hz, 1H), 6.36-6.32 (m, 2H), 5.26-5.14 (m, 2H), 4.76 (dd, J=6.0, 4.3 Hz, 1H), 4.32 (ddd, J=11.5, 8.4, 3.3 Hz, 1H), 4.26-4.18 (m, 1H), 3.75 (s, 3H), 3.72 (s, 3H), 2.12-1.91 (m, 2H), 0.91 (s, 9H), 0.16 (s, 3H), 0.15 (s, 3H).
Step 5

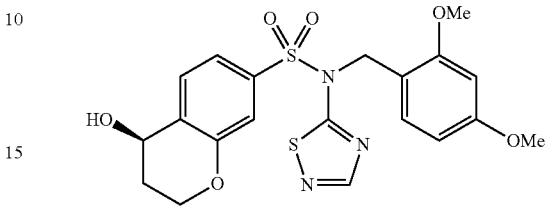

(R)—N-(2,4-dimethoxybenzyl)-4-hydroxy-N-(1,2,4-thiadiazol-5-yl)chromane-7-sulfonamide TBAF (1.0 M in THF, 17 mL, 17 mmol) was added dropwise to a solution of (R)-4-((tert-butyldimethylsilyl)oxy)-N-(2,4-dimethoxybenzyl)-N-(1,2,4-thiadiazol-5-yl)chromane-7-sulfonamide (9.1 g, 16 mmol) in THF (31 mL) at r.t. After 30 minutes, water (100 mL) and DCM (100 mL) were added. The organic layer was removed and the aqueous layer was extracted with DCM (2×100 mL). The combined organic layers were dried with Na₂SO₄ and concentrated. The crude product was purified by column chromatography to give (R)—N-(2,4-dimethoxybenzyl)-4-hydroxy-N-(1,2,4-thiadiazol-5-yl)chromane-7-sulfonamide (5.8 g, 79%) as a white solid. m/z 486.1 [M+Na]⁺, 1H NMR (400 MHz, Chloroform-d) δ 8.13 (d, J=1.1 Hz, 1H), 7.34 (d, J=8.2 Hz, 1H), 7.28 (dd, J=8.1, 1.8 Hz, 1H), 7.21 (d, J=1.8 Hz, 1H), 7.06 (d, J=8.2 Hz, 1H), 6.34-6.28 (m, 2H), 5.22 (dd, J=2.9, 0.9 Hz, 2H), 4.76 (q, J=4.9 Hz, 1H), 4.30-4.24 (m, 2H), 3.76 (s, 3H), 3.73 (s, 3H), 2.18-1.99 (m, 2H), 1.83 (d, J=5.5 Hz, 1H).
Step 6

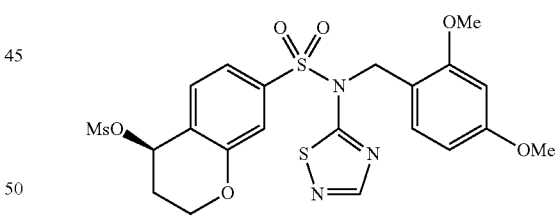

(R)-7-(N-(2,4-dimethoxybenzyl)-N-(1,2,4-thiadiazol-5-yl)sulfamoyl)chroman-4-yl methanesulfonate (R)—N-(2,4-dimethoxybenzyl)-4-hydroxy-N-(1,2,4-thiadiazol-5-yl)chromane-7-sulfonamide (50 mg, 0.10 mmol) was dissolved in DCM (0.6 mL). DIPEA (0.06 mL, 0.32 mmol) and Ms₂O (39 mg, 0.21 mmol) were added at r.t. The reaction was stirred at r.t. for 2 hours, then quenched by the addition of H₂O (1 mL) and DCM (1 mL). The organic layer was removed and the aqueous layer was extracted with DCM (2×1 mL). The combined organic layers were dried with Na₂SO₄ and concentrated. The crude mesylate was used in the subsequent step without further purification. 1H NMR (400 MHz, Chloroform-d) δ 8.15 (s, 1H), 7.43 (dt, J=8.2, 0.5 Hz, 1H), 7.32 (dd, J=8.2, 1.9 Hz, 1H), 7.25 (d, J=1.9 Hz, 1H), 7.09-7.06 (m, 1H), 6.33 (dd, J=8.3, 2.5 Hz, 1H), 6.31 (d, J=2.3 Hz, 1H), 5.78-5.74 (m, 1H), 5.24 (s, 2H), 4.37 (dtd, J=11.5, 4.1, 1.1 Hz, 1H), 4.27 (td, J=11.5, 2.7 Hz, 1H), 3.77 (s, 3H), 3.72 (s, 3H), 3.06 (s, 3H), 2.45-2.36 (m, 1H), 2.34-2.22 (m, 1H).

Step 7

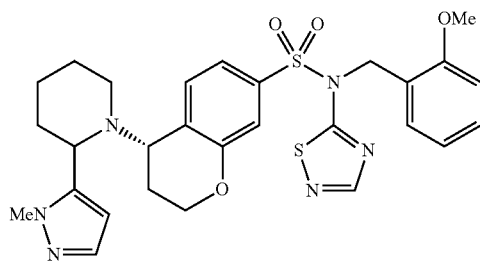

(4S)—N-(2,4-dimethoxybenzyl)-4-(2-(1-methyl-1H-pyrazol-5-yl)piperidin-1-yl)-N-(1,2,4-thiadiazol-5-yl)chromane-7-sulfonamide Crude (R)-7-(N-(2,4-dimethoxybenzyl)-N-(1,2,4-thiadiazol-5-yl)sulfamoyl)chroman-4-yl methanesulfonate (0.10 mmol) was dissolved in 2-butanone (0.6 mL). 2-(2-methyl-pyrazol-3-yl)piperidine (36 mg, 0.22 mmol) and NaOH (20% w/w solution in H₂O, 0.04 mL, 0.22 eq) were added. The mixture was heated to 60 C. After 1 hour, the reaction was diluted with iPrOAc (1 mL) and H₂O (1 mL). The organic layer was removed and the aqueous layer was extracted with iPrOAc (2×1 mL). The combined organic layers were dried with Na₂SO₄ and concentrated. The crude product was used in the subsequent step without further purification.

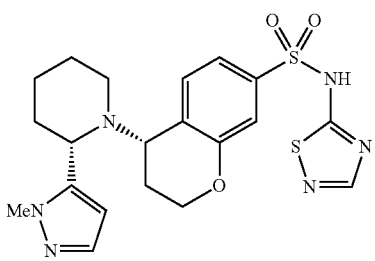 [SMILES: Cn1nccc1[C@@H]1CCCCN1[C@H]1CCOc2cc(S(=O)(=O)Nc3ncns3)ccc21]

(S)-4-((S)-2-(1-methyl-1H-pyrazol-5-yl)piperidin-1-yl)-N-(1,2,4-thiadiazol-5-yl)chromane-7-sulfonamide TFA (0.08 mL, 1.0 mmol) was added dropwise to a solution of crude (4S)—N-(2,4-dimethoxybenzyl)-4-(2-(1-methyl-1H-pyrazol-5-yl)piperidin-1-yl)-N-(1,2,4-thiadiazol-5-yl)chromane-7-sulfonamide in DCM (1 mL). After 30 minutes the reaction was diluted with DCM (2 mL) and TEA (0.5 mL). The mixture was concentrated and purified by LCMS to give the desired product as a white solid (2.1 mg, 4.2% over 3 steps). m/z 461.1 [M+H]⁺ 1H NMR (400 MHz, DMSO-d6) δ 8.26 (s, 1H), 7.70 (dd, J=8.2, 1.1 Hz, 1H), 7.32 (d, J=1.8 Hz, 1H), 7.29 (dd, J=8.1, 1.9 Hz, 1H), 7.03 (d, J=1.9 Hz, 1H), 6.24 (d, J=1.9 Hz, 1H), 4.26 (dt, J=11.2, 3.7 Hz, 1H), 4.02-3.81 (m, 5H), 3.66 (d, J=9.2 Hz, 1H), 2.47 (s, 1H), 2.21 (t, J=11.3 Hz, 1H), 2.06-1.93 (m, 1H), 1.90-1.66 (m, 4H), 1.64-1.24 (m, 3H).

Example 42

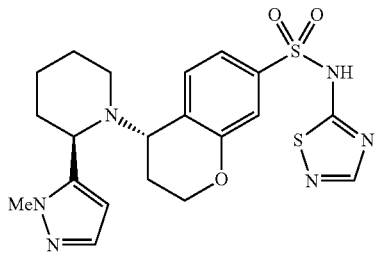 [SMILES: Cn1nccc1[C@H]1CCCCN1[C@H]1CCOc2cc(S(=O)(=O)Nc3ncns3)ccc21]

(S)-4-((R)-2-(1-methyl-1H-pyrazol-5-yl)piperidin-1-yl)-N-(1,2,4-thiadiazol-5-yl)chromane-7-sulfonamide This compound was prepared in the same sequence as Example 40. m/z 461.1 [M+H]⁺, 1H NMR (400 MHz, DMSO-d6) 8.15 (d, J=14.6 Hz, 1H), 7.44 (d, J=8.0 Hz, 1H), 7.34 (d, J=1.8 Hz, 1H), 7.25 (dd, J=7.8, 1.7 Hz, 1H), 7.03 (d, J=1.7 Hz, 1H), 6.36 (d, J=1.9 Hz, 1H), 4.31 (s, 1H), 4.18 (dt, J=11.2, 4.2 Hz, 1H), 4.01-3.81 (m, 5H), 2.75-2.60 (m, 1H), 2.20-2.01 (m, 1H), 1.97-1.76 (m, 2H), 1.75-1.58 (m, 2H), 1.58-1.35 (m, 4H).

Example 43

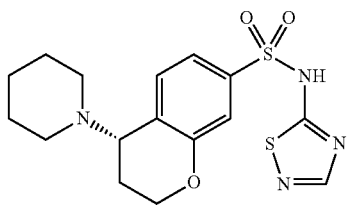 [SMILES: O=S(=O)(Nc1ncns1)c1ccc2c(c1)OCC[C@@H]2N1CCCCC1]

(S)-4-(piperidin-1-yl)-N-(1,2,4-thiadiazol-5-yl)chromane-7-sulfonamide

This compound was prepared as for Example 37. m/z 381.1 [M+H]⁺, 1H NMR (400 MHz, DMSO-d6) δ 7.94 (s, 1H), 7.55 (d, J=8.1 Hz, 1H), 7.29 (dd, J=8.0, 1.8 Hz, 1H), 7.13 (s, 1H), 4.39-4.26 (m, 1H), 4.23-4.18 (m, 1H), 2.87 (s, 4H), 2.26 (s, 1H), 2.09 (s, 1H), 1.65 (s, 4H), 1.48 (s, 2H), 1.25 (q, J=7.4, 6.6 Hz, 2H).

Example 44

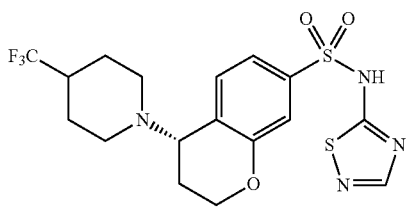 [SMILES: O=S(=O)(Nc1ncns1)c1ccc2c(c1)OCC[C@@H]2N1CCC(C(F)(F)F)CC1]

(S)—N-(1,2,4-thiadiazol-5-yl)-4-(4-(trifluoromethyl)piperidin-1-yl)chromane-7-sulfonamide This compound was prepared as for Example 37. m/z 449.1 [M+H]⁺, 1H NMR (400 MHz, DMSO-d6) δ 8.08 (s, 1H), 7.54 (d, J=8.1 Hz, 1H), 7.30-7.18 (m, 1H), 7.07 (d, J=2.0 Hz, 1H), 6.51 (s, 1H), 4.38-4.28 (m, 1H), 4.19-4.08 (m, 1H), 4.06-4.00 (m, 1H), 2.95 (d, J=11.7 Hz, 1H), 2.67-2.52 (m, 2H), 2.29 (s, 1H), 2.16 (s, 1H), 2.03-1.92 (m, 3H), 1.86 (dt, J=12.7, 3.2 Hz, 1H), 1.74 (d, J=11.4 Hz, 1H), 1.67-1.50 (m, 1H), 1.47-1.32 (m, 1H).

Example 45

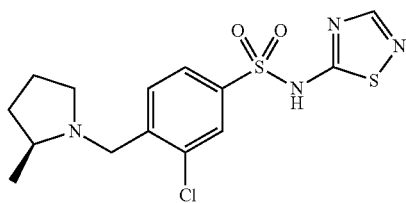 [SMILES: C[C@H]1CCCN1Cc1ccc(S(=O)(=O)Nc2ncns2)cc1Cl]

(S)-3-chloro-4-((2-methylpyrrolidin-1-yl)methyl)-N-(1,2,4-thiadiazol-5-yl)benzenesulfonamide Step 1

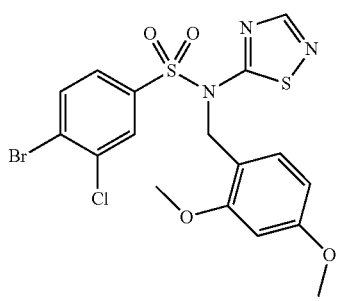 [SMILES: COc1ccc(CN(c2ncns2)S(=O)(=O)c2ccc(Br)c(Cl)c2)c(OC)c1]

4-bromo-3-chloro-N-(2,4-dimethoxybenzyl)-N-(1,2,4-thiadiazol-5-yl)benzenesulfonamide To a mixture of N-(2,4-dimethoxybenzyl)-1,2,4-thiadiazol-5-amine (prepared according to WO2010079443, 5.00 g, 19.90 mmol) in anhydrous THF (100 mL) was added a 1 M solution of lithium bis(trimethylsilyl)amide in THF (20.0 mL, 20.0 mmol) at 0° C. and the reaction mixture was stirred for 1 h. The reaction mixture was cooled to −78° C. and a solution of 4-bromo-3-chlorobenzenesulfonyl chloride (5.77 g, 19.90 mmol) in anhydrous THF (20 mL) was added. The reaction mixture was allowed to warm to ambient temperature, stirred for 2 h, and diluted with EtOAc (200 mL). The mixture was washed with saturated aqueous ammonium chloride (2×150 mL), brine (150 mL), dried over anhydrous sodium sulfate, and filtered. Concentration of the filtrate in vacuo and trituration of the residue in MeOH (50 mL) provided the title compound as a colorless solid (9.00 g, 90% yield). ¹H NMR (300 MHz, CDCl₃) δ 8.22 (s, 1H), 7.66-7.63 (m, 2H), 7.47 (dd, J=2.2, 8.5 Hz, 1H), 7.07 (d, J=8.4 Hz, 1H), 6.34 (dd, J=2.4, 8.4 Hz, 1H), 6.27 (d, J=2.4 Hz, 1H), 5.31 (s, 2H), 3.79 (s, 3H), 3.67 (s, 3H).

Step 2

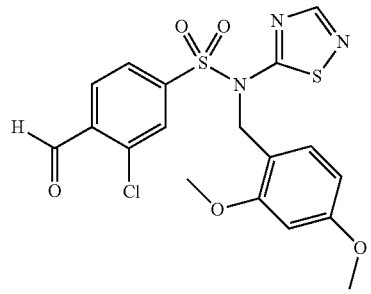 [SMILES: COc1ccc(CN(c2ncns2)S(=O)(=O)c2ccc(C=O)c(Cl)c2)c(OC)c1]

3-chloro-N-(2,4-dimethoxybenzyl)-4-formyl-N-(1,2,4-thiadiazol-5-yl)benzenesulfonamide To a solution of 4-bromo-3-chloro-N-(2,4-dimethoxybenzyl)-N-(1,2,4-thiadiazol-5-yl) benzenesulfonamide (1.22 g, 2.42 mmol) in anhydrous THF (25 mL) at 0° C. was added a 1.3 M solution of isopropylmagnesium chloride lithium chloride complex in THF (2.4 mL, 3.15 mmol). The resulting mixture was stirred for 40 minutes under an argon atmosphere, DMF (0.47 mL, 6.05 mmol) was added, and the reaction mixture was stirred for 1 h. The mixture was diluted with EtOAc (80 mL), washed with saturated aqueous ammonium chloride (2×60 mL), brine (2×60 mL), dried over anhydrous sodium sulfate, and filtered. Concentration of the filtrate in vacuo and purification by column chromatography (R_f=0.25 in 3:1 hexanes:EtOAc) provided the title compound as a colorless oil (0.66 g, 60% yield). ¹H NMR (300 MHz, CDCl₃) δ 10.45 (s, 1H), 8.23 (s, 1H), 7.90 (d, J=8.2 Hz, 1H), 7.74-7.69 (m, 1H), 7.67-7.63 (m, 1H), 7.11 (d, J=8.4 Hz, 1H), 6.37-6.24 (m, 1H), 6.20 (d, J=2.3 Hz, 1H), 5.33 (s, 2H), 3.76 (s, 3H), 3.63 (s, 3H).

Step 3

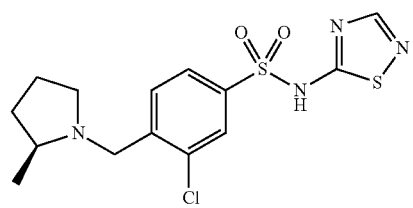 [SMILES: C[C@H]1CCCN1Cc1ccc(S(=O)(=O)Nc2ncns2)cc1Cl]

(S)-3-chloro-4-((2-methylpyrrolidin-1-yl)methyl)-N-(1,2,4-thiadiazol-5-yl)benzenesulfonamide To a mixture of 3-chloro-N-(2,4-dimethoxybenzyl)-4-formyl-N-(1,2,4-thiadiazol-5-yl) benzenesulfonamide (0.30 g, 0.66 mmol), (S)-2-methylpyrrolidine 4-methylbenzenesulfonic acid salt (0.34 g, 1.32 mmol), and potassium acetate (0.13 g, 1.32 mmol) in 1,2-dichloroethane (10 mL) was added sodium triacetoxyborohydride (0.28 g, 1.32 mmol). The resulting mixture was stirred for 24 h and then diluted with EtOAc (50 mL). The mixture was washed with saturated aqueous ammonium chloride (50 mL), brine (50 mL), dried over anhydrous sodium sulfate, filtered, and concentrated in vacuo. The residue was dissolved in DCM (20 mL) and TFA (5 mL) was added. The mixture was stirred for 40 minutes, concentrated in vacuo, quenched with MeOH (10 mL), filtered, and concentrated in vacuo. The residue was purified by reverse-phase HPLC (Gemini NX, C-18, 5 µm, 30×150 mm; mobile phase: A water (0.1% TFA), B CH$_3$CN (0.1% TFA); gradient: 15% B (2 min), followed by 15-55% B (8 min); flow rate: 60 mL/min) to provide the title compound as a trifluoroacetate salt as a colorless solid (0.11 g, 34% yield). MS (ES+) m/z: 373.0, 375.0 (M+1). $^1$H NMR (300 MHz, DMSO-d$_6$) δ 9.51 (br s, 1H), 8.42 (s, 1H), 7.90-7.81 (m, 3H), 6.21 (br s, 1H), 4.67 (d, J=13.5 Hz, 1H), 4.33 (d, J=13.5 Hz, 1H), 3.67-3.48 (m, 1H), 3.39-3.15 (m, 2H), 2.28-2.12 (m, 1H), 2.01-1.73 (m, 2H), 1.68-1.50 (m, 1H), 1.37 (d, J=6.5 Hz, 3H).

Example 46

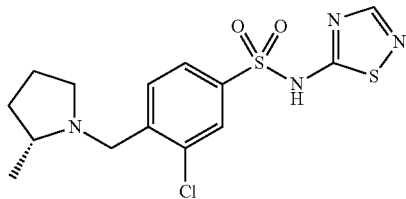 [SMILES: C[C@@H]1CCCN1Cc1ccc(S(=O)(=O)Nc2ncns2)cc1Cl]

(R)-3-chloro-4-((2-methylpyrrolidin-1-yl)methyl)-N-(1,2,4-thiadiazol-5-yl)benzenesulfonamide Following the procedure as described for Example 45, step 3 and making non-critical variations as required to replace (S)-2-methylpyrrolidine 4-methylbenzenesulfonic acid salt with (R)-2-methylpyrrolidine 4-methylbenzenesulfonic acid salt, the title compound was obtained as a trifluoroacetate salt as a colorless solid (0.10 g, 31% yield). MS (ES+) m/z: 373.0, 375.0 (M+1). $^1$H NMR (300 MHz, DMSO-d$_6$) δ 9.60 (br s, 2H), 8.43 (s, 1H), 7.89-7.80 (m, 3H), 4.67 (d, J=13.0 Hz, 1H), 4.34 (d, J=13.0 Hz, 1H), 3.69-3.47 (m, 1H), 3.40-3.14 (m, 2H), 2.28-2.11 (m, 1H), 2.00-1.72 (m, 2H), 1.68-1.49 (m, 1H), 1.37 (d, J=6.2 Hz, 3H).

Example 47

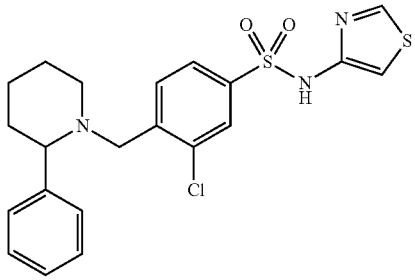 [SMILES: O=S(=O)(Nc1cscn1)c1ccc(CN2CCCCC2c2ccccc2)c(Cl)c1]

3-chloro-4-((2-phenylpiperidin-1-yl)methyl)-N-(thiazol-4-yl)benzenesulfonamide

Step 1

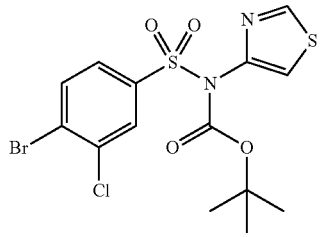 [SMILES: CC(C)(C)OC(=O)N(c1cscn1)S(=O)(=O)c1ccc(Br)c(Cl)c1]

tert-butyl ((4-bromo-3-chlorophenyl)sulfonyl)(thiazol-4-yl)carbamate

To a solution of tert-butyl thiazol-4-ylcarbamate (26.50 g, 132.33 mmol) in THF (300 mL) at −78° C., under nitrogen, was added 1 M solution of lithium bis(trimethylsilyl)amide in THF (185 mL, 185 mmol) dropwise. The mixture was warmed to 0° C. and stirred for 1 h. The mixture was added dropwise a solution of 4-bromo-3-chlorobenzenesulfonyl chloride (49.88 g, 172.03 mmol) in THF (200 mL) at −78° C. The resulting mixture was stirred at 20° C. for 3 h and then quenched with saturated aqueous sodium bicarbonate (100 mL) and water (300 mL). The mixture was extracted with EtOAc (3×300 mL) and the combined organic layers were washed with brine (100 mL), dried over anhydrous sodium sulfate, filtered, and the filtrate was concentrated in vacuo. The residue was triturated with MeOH (200 mL) to give the title compound as a colorless solid (35.00 g, 58% yield). MS (ES+) m/z: 476.9 (M+23). $^1$H NMR (300 MHz, CDCl$_3$) δ 8.82 (d, J=2.0 Hz, 1H), 8.25 (d, J=4.0 Hz, 1H), 7.95-7.89 (m, 1H), 7.87-7.83 (m, 1H), 7.58 (d, J=4.0 Hz, 1H), 1.38 (s, 9H).

Step 2

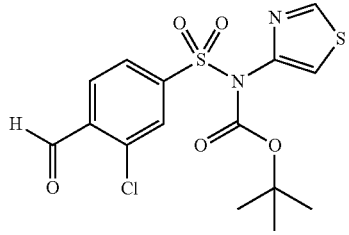 [SMILES: CC(C)(C)OC(=O)N(c1cscn1)S(=O)(=O)c1ccc(C=O)c(Cl)c1]

tert-butyl ((3-chloro-4-formylphenyl)sulfonyl)(thiazol-4-yl)carbamate

Following the procedure as described in Example 45, step 2 and making non-critical variations as required to replace 4-bromo-3-chloro-N-(2,4-dimethoxybenzyl)-N-(1,2,4-thiadiazol-5-yl)benzenesulfonamide with tert-butyl ((4-bromo-3-chlorophenyl)sulfonyl)(thiazol-4-yl)carbamate, the title compound was obtained as a colorless oil (0.58 g, 50% yield). MS (ES+) m/z: 303.0 (M-Boc+H), 305.0 (M-Boc+H). $^1$H NMR (300 MHz, CDCl$_3$) δ 10.55 (s, 1H), 8.83 (d, J=2.3 Hz, 1H), 8.30 (d, J=1.6 Hz, 1H), 8.20-8.16 (m, 1H), 8.10 (d, J=8.2 Hz, 1H), 7.65-7.50 (m, 1H), 1.36 (s, 9H).

Step 3

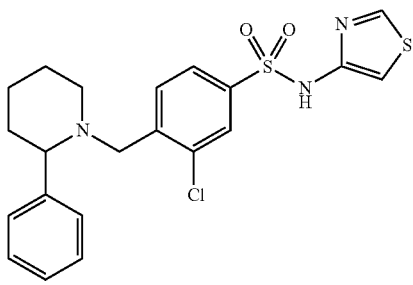 [SMILES: O=S(=O)(Nc1cscn1)c1ccc(CN2CCCCC2c2ccccc2)c(Cl)c1]

3-chloro-4-((2-phenylpiperidin-1-yl)methyl)-N-(thiazol-4-yl)benzenesulfonamide

To a mixture of tert-butyl ((3-chloro-4-formylphenyl)sulfonyl)(thiazol-4-yl)carbamate (0.20 g, 0.50 mmol), 2-phenylpiperidine hydrochloride (0.0.10 g, 0.50 mmol), and potassium acetate (0.10 g, 1.00 mmol) in 1,2-dichloroethane (10 mL) was added sodium triacetoxyborohydride (0.21 g, 1.00 mmol). The resulting mixture was stirred for 24 h and then diluted with EtOAc (50 mL). The mixture was washed with saturated aqueous ammonium chloride (50 mL), brine (50 mL), dried over anhydrous sodium sulfate, filtered, and concentrated in vacuo. The residue was dissolved in DCM (10 mL) and TFA (2 mL) was added. The mixture was stirred for 40 minutes and concentrated in vacuo. The residue was purified by reverse-phase HPLC (Gemini NX, C-18, 5 μm, 30×150 mm; mobile phase: A water (0.1% TFA), B CH$_3$CN (0.1% TFA); gradient: 15% B (2 min), followed by 15-55% B (8 min); flow rate: 60 mL/min) to provide the title compound as a trifluoroacetate salt as a colorless solid (0.12 g, 41% yield). MS (ES+) m/z: 448.0, 450.0 (M+1). $^1$H NMR (300 MHz, DMSO-d$_6$) δ 11.28 (br s, 1H), 9.47 (br s, 1H), 8.86 (d, J=2.1 Hz, 1H), 7.88-7.81 (m, 1H), 7.77 (dd, J=1.6, 7.9 Hz, 1H), 7.62-7.36 (m, 6H), 7.09 (d, J=2.0 Hz, 1H), 4.54-4.39 (m, 1H), 4.24-3.97 (m, 2H), 3.42-3.10 (m, 2H), 2.08-1.88 (m, 1H), 1.86-1.68 (m, 3H), 1.65-1.46 (m, 2H).

Example 48

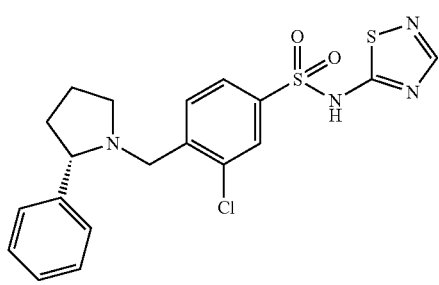 [SMILES: O=S(=O)(Nc1ncns1)c1ccc(CN2CCC[C@H]2c2ccccc2)c(Cl)c1]

(S)-3-chloro-4-((2-phenylpyrrolidin-1-yl)methyl)-N-(1,2,4-thiadiazol-5-yl)benzenesulfonamide Following the procedure as described for Example 45, step 3 and making non-critical variations as required to replace (S)-2-methylpyrrolidine 4-methylbenzenesulfonic acid salt with (S)-2-phenylpyrrolidine, the title compound was obtained as a trifluoroacetate salt as a colorless solid (0.10 g, 41% yield). MS (ES+) m/z: 435.1, 437.0 (M+1). $^1$H NMR (300 MHz, MeOD-d$_4$) δ 8.20 (s, 1H), 7.85-7.84 (m, 1H), 7.79 (dd, J=1.8, 8.0 Hz, 1H), 7.63 (d, J=8.0 Hz, 1H), 7.52-7.48 (m, 2H), 7.46-7.41 (m, 3H), 4.63-4.57 (m, 1H), 4.49 (d, J=13.4 Hz, 1H), 4.37 (d, J=13.4 Hz, 1H), 3.70-3.62 (m, 1H), 3.57-3.48 (m, 1H), 2.63-2.52 (m, 1H), 2.38-2.17 (m, 3H) (Note: Exchangeable protons not observed).

Example 49

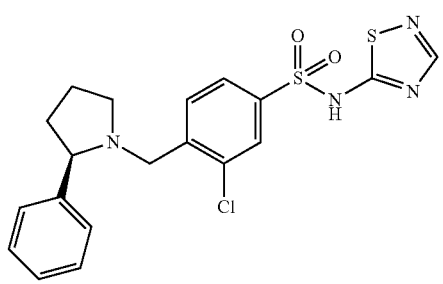 [SMILES: O=S(=O)(Nc1ncns1)c1ccc(CN2CCC[C@@H]2c2ccccc2)c(Cl)c1]

(R)-3-chloro-4-((2-phenylpyrrolidin-1-yl)methyl)-N-(1,2,4-thiadiazol-5-yl)benzenesulfonamide Following the procedure as described for Example 45, step 3 and making non-critical variations as required to replace (S)-2-methylpyrrolidine 4-methylbenzenesulfonic acid salt with (R)-2-phenylpyrrolidine, the title compound was obtained as a trifluoroacetate salt as a colorless solid (0.05 g, 23% yield). MS (ES+) m/z: 435.0, 437.0 (M+1). $^1$H NMR (300 MHz, MeOD-d$_4$) δ 8.23 (s, 1H), 7.85-7.84 (m, 1H), 7.79 (dd, J=1.8, 8.0 Hz, 1H), 7.64 (d, J=8.0 Hz, 1H), 7.52-7.48 (m, 2H), 7.46-7.41 (m, 3H), 4.62-4.59 (m, 1H), 4.50 (d, J=13.4 Hz, 1H), 4.39 (d, J=13.4 Hz, 1H), 3.71-3.65 (m, 1H), 3.58-3.49 (m, 1H), 2.64-2.54 (m, 1H), 2.36-2.18 (m, 3H) (Note: Exchangeable protons not observed).

Example 50

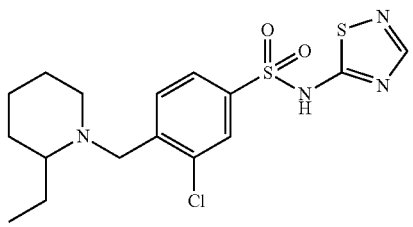 [SMILES: CCC1CCCCN1Cc1ccc(S(=O)(=O)Nc2ncns2)cc1Cl]

3-chloro-4-((2-ethylpiperidin-1-yl)methyl)-N-(1,2,4-thiadiazol-5-yl)benzenesulfonamide Following the procedure as described for Example 45, step 3 and making non-critical variations as required to replace (S)-2-methylpyrrolidine 4-methylbenzenesulfonic acid salt with 2-ethylpiperidine, the title compound was obtained as a trifluoroacetate salt as a colorless solid (0.02 g, 11% yield). MS (ES+) m/z: 401.1, 403.1 (M+1). $^1$H NMR (300 MHz, DMSO-d$_6$) δ 9.51 (br s, 1H), 9.21 (br s, 1H), 8.41

(s, 1H), 7.87-7.83 (m, 3H), 4.82-4.77 (m, 1H), 4.46-4.24 (m, 2H), 3.07-2.96 (m, 2H), 2.21-1.66 (m, 6H), 1.57-1.41 (m, 2H), 0.93 (t, J=7.2 Hz, 3H).

Example 51

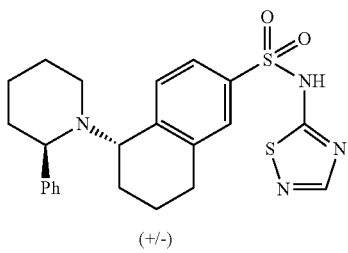

(±)

(±)-5-((R)-2-phenylpiperidin-1-yl)-N-(1,2,4-thiadiazol-5-yl)-5,6,7,8-tetrahydronaphthalene-2-sulfonamide (Stereochemistry Arbitrarily Assigned)

Step 1

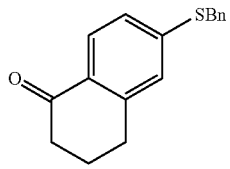

6-(benzylthio)-3,4-dihydronaphthalen-1(2H)-one

A solution of 6-bromo-3,4-dihydronaphthalen-1(2H)-one (4.30 g, 19.11 mmol) and DIPEA (6.6 mL, 38.22 mmol), in 1,4-dioxane (75 mL) was evacuated and backfilled with nitrogen three times. Tris(dibenzylideneacetone)dipalladium(0) (0.44 g, 0.48 mmol), 4,5-bis(diphenylphosphino)-9,9-dimethylxanthene (XantPhos, 0.55 g, 0.96 mmol), and benzenethiol (2.2 mL, 19.11 mmol) were added, the mixture was evacuated and backfilled with nitrogen two times and heated to reflux for 17 h. It was then cooled to ambient temperature and the solid was removed by filtration, washing with 1,4-dioxane (50 mL). The filtrate was concentrated in vacuo and purified by column chromatography eluting with a 5-50% gradient of ethyl acetate in hexanes to afford the title compound as an orange solid (4.65 g, 90% yield). $^1$H NMR (300 MHz, MeOD-d$_4$): δ 7.88-7.87 (m, 1H), 7.81-7.78 (m, 1H), 7.60-7.55 (m, 2H), 7.29-7.22 (m, 2H), 7.12 (d, J=4.6 Hz, 1H), 6.75-6.73 (m, 1H), 4.39 (s, 2H), 3.46-3.35 (m, 2H), 2.31-2.00 (m, 4H).
Step 2

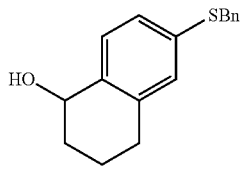

6-(benzylthio)-1,2,3,4-tetrahydronaphthalen-1-ol

To a solution of 6-(benzylthio)-3,4-dihydronaphthalen-1(2H)-one (3.93 g, 14.54 mmol) in THF (15 mL) and MeOH (15 mL) at ambient temperature was added sodium borohydride (0.55 g, 14.5 mmol) portionwise. The mixture was stirred for 18 h, then diluted with ethyl acetate (20 mL) and water (20 mL) and the layers were separated. The aqueous phase was extracted with ethyl acetate (3×20 mL) and the combined organic phases were washed with brine (20 mL), dried with anhydrous sodium sulfate, filtered, and concentrated in vacuo to afford the title compound as a colorless oil (3.96 g, quant. yield). $^1$H NMR (300 MHz, CDCl$_3$): δ 7.34-7.26 (m, 6H), 7.15 (dd, J=1.8, 8.1 Hz, 1H), 7.04 (s, 1H), 4.74 (t, J=4.8 Hz, 1H), 4.11 (s, 2H), 2.78-2.61 (m, 2H), 2.00-1.72 (m, 4H).
Step 3

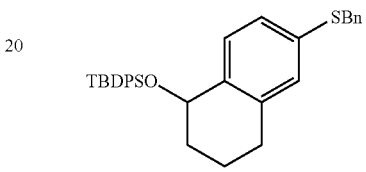

((6-(benzylthio)-1,2,3,4-tetrahydronaphthalen-1-yl)oxy)(tert-butyl)diphenylsilane To a solution of 6-(benzylthio)-1,2,3,4-tetrahydronaphthalen-1-ol (3.96 g, 14.5 mmol) in DCM (50 mL) was added tert-butyldiphenylsilylchloride (3.90 mL, 15.3 mmol), imidazole (1.48 g, 21.8 mmol) and DMAP (0.177 g, 1.45 mmol). The mixture was stirred for 17 h at ambient temperature. The solution was diluted with water (50 mL) and DCM (50 mL) and the layers were separated. The aqueous phase was extracted with DCM (3×30 mL) then the combined organic phases were washed with brine (30 mL), dried with anhydrous sodium sulfate, filtered, and concentrated in vacuo. The residue was purified by column chromatography eluting with a 6-50% gradient of ethyl acetate in hexanes. The product was dissolved in a minimum volume of acetonitrile and concentrated in vacuo three times to afford the title compound as a colorless oil (7.94 g, quant. yield, still containing a minor amount of ethyl acetate). $^1$H NMR (300 MHz, CDCl$_3$): δ 7.73 (dt, J=1.6, 6.0 Hz, 2H), 7.67-7.63 (m, 2H), 7.45-7.35 (m, 6H), 7.31 (dd, J=2.5, 6.3 Hz, 4H), 7.10 (d, J=8.7 Hz, 1H), 7.04-7.01 (m, 2H), 4.76-4.73 (m, 1H), 4.10 (s, 2H), 2.80-2.71 (m, 1H), 2.63-2.55 (m, 1H), 2.04-1.98 (m, 1H), 1.85-1.79 (m, 1H), 1.73-1.60 (m, 2H), 1.07 (s, 9H).

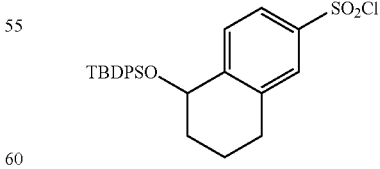

5-((tert-butyldiphenylsilyl)oxy)-5,6,7,8-tetrahydronaphthalene-2-sulfonyl chloride To a solution of ((6-(benzylthio)-1,2,3,4-tetrahydronaphthalen-1-yl)oxy)(tert-butyl)diphenylsilane (7.94 g, 14.54 mmol) in acetonitrile (100 mL) and water (3.6 mL) at 0° C. was added acetic acid (4.5 mL) then 1,3-dichloro-5,5-dimethylhydantoin (5.73 g, 29.08 mmol). After 1 h the mixture was diluted with ice water (100 mL) and ethyl acetate (50 mL). The resulting solid was removed by filtration and washed with water (50 mL) to afford the title compound as a colorless solid (4.54 g, 64% yield). The filtrate layers were separated and the aqueous phase extracted with ethyl acetate (3×50 mL). The combined organic phases were then washed with brine (50 mL), dried with anhydrous sodium sulfate, filtered, and concentrated in vacuo. The residue was purified by column chromatography eluting with a 6-50% gradient of ethyl acetate in hexanes. After concentration in vacuo an oil was obtained. With the addition of methanol (10 mL) and vigorous stirring at ambient temperature a solid precipitated and was collected by filtration to afford an additional amount of title compound (1.32 g, 18% yield; total 82% yield). $^1$H NMR (300 MHz; CDCl$_3$): δ 7.74-7.69 (m, 4H), 7.65-7.62 (m, 2H), 7.47-7.35 (m, 7H), 4.81-4.77 (m, 1H), 2.93-2.86 (m, 1H), 2.79-2.71 (m, 1H), 2.05-2.00 (m, 1H), 1.88-1.74 (m, 1H), 1.69-1.67 (m, 1H), 1.08 (s, 9H).

Step 5

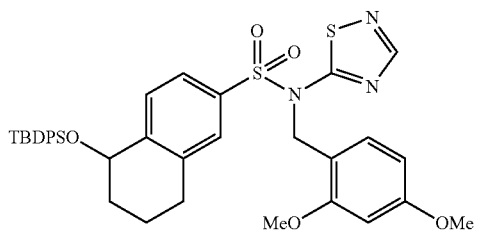

5-((tert-butyldiphenylsilyl)oxy)-N-(2,4-dimethoxybenzyl)-N-(1,2,4-thiadiazol-5-yl)-5,6,7,8-tetrahydronaphthalene-2-sulfonamide Following the procedure as described in Example 45, step 1 and making non-critical variations as required to replace 4-bromo-3-chlorobenzenesulfonyl chloride with 5-((tert-butyldiphenyl silyl)oxy)-5,6,7,8-tetrahydronaphthalene-2-sulfonyl chloride, the title compound was obtained following purification by column chromatography eluting with a 5-50% gradient of ethyl acetate in hexanes as a colorless solid (5.41 g, 83% yield). $^1$H NMR (300 MHz, CDCl$_3$): δ 8.15 (s, 1H), 7.71 (dd, J=1.6, 7.9 Hz, 2H), 7.62 (dd, J=1.4, 8.0 Hz, 2H), 7.53 (dd, J=2.0, 8.2 Hz, 1H), 7.46-7.32 (m, 8H), 7.05 (d, J=9.0 Hz, 1H), 6.34-6.30 (m, 2H), 5.24-5.13 (m, 2H), 4.74-4.70 (m, 1H), 3.73 (s, 3H), 3.71 (s, 3H) 2.79-2.69 (m, 1H), 2.62-2.52 (m, 1H), 1.99-1.91 (m, 1H), 1.81-1.72 (m, 2H), 1.65-1.55 (m, 1H), 1.07 (s, 9H).

Step 6

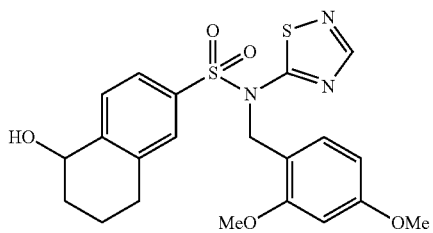 [SMILES: COc1ccc(CN(c2ncns2)S(=O)(=O)c2ccc3c(c2)CCCC3O)c(OC)c1]

N-(2,4-dimethoxybenzyl)-5-hydroxy-N-(1,2,4-thiadiazol-5-yl)-5,6,7,8-tetrahydronaphthalene-2-sulfonamide Following the procedure as described in Example 41, step 5 and making non-critical variations as required to replace (R)-4-((tert-butyldimethylsilyl)oxy)-N-(2,4-dimethoxybenzyl)-N-(1,2,4-thiadiazol-5-yl)chromane-7-sulfonamide with 5-((tert-butyldiphenylsilyl)oxy)-N-(2,4-dimethoxybenzyl)-N-(1,2,4-thiadiazol-5-yl)-5,6,7,8-tetrahydronaphthalene-2-sulfonamide, the title compound was obtained as a colorless solid (3.07 g, 86% yield). $^1$H NMR (300 MHz, CDCl$_3$): δ 8.13 (s, 1H), 7.60 (dd, J=2.0, 8.2 Hz, 1H), 7.52 (d, J=8.2 Hz, 1H), 7.41 (d, J=1.6 Hz, 1H), 7.03 (d, J=8.2 Hz, 1H), 6.33-6.28 (m, 2H), 5.20 (s, 2H), 4.74-4.72 (m, 1H), 3.75 (s, 3H), 3.70 (s, 3H), 2.80-2.60 (m, 2H), 2.08-1.73 (m, 4H).

Step 7

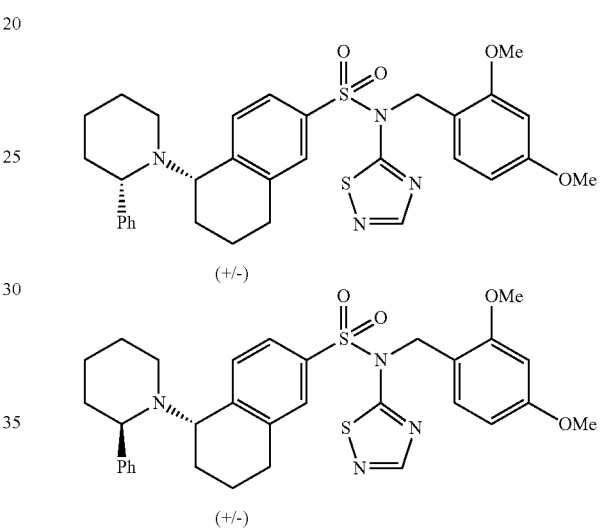

(±)-N-(2,4-dimethoxybenzyl)-5-((S)-2-phenylpiperidin-1-yl)-N-(1,2,4-thiadiazol-5-yl)-5,6,7,8-tetrahydronaphthalene-2-sulfonamide and (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide To a solution of N-(2,4-dimethoxybenzyl)-5-hydroxy-N-(1,2,4-thiadiazol-5-yl)-5,6,7,8-tetrahydronaphthalene-2-sulfonamide (0.200 g, 0.434 mmol) in tetrahydrofuran (2 mL) at −78° C., under a nitrogen atmosphere, was added triethylamine (0.24 mL, 1.7 mmol) and methanesulfonylchloride (0.070 mL, 0.87 mmol). The mixture was stirred for one hour at which time 2-phenylpiperidine (0.21 mL, 1.3 mmol) was added. The suspension was stirred for 17 h. The mixture was diluted with ethyl acetate (10 mL), saturated aqueous sodium bicarbonate (10 mL) and water (10 mL) and the layers were separated. The aqueous phase was extracted with ethyl acetate (3×10 mL) and the combined organic phases were washed with brine (10 mL), dried with anhydrous sodium sulfate, filtered, and concentrated in vacuo. The residue was purified by column chromatography eluting with a 6-75% gradient of ethyl acetate in hexanes to afford the two diastereomers of the title compound as mixtures of enantiomers.

Diastereomer 1: (±)-N-(2,4-dimethoxybenzyl)-5-((S)-2-phenylpiperidin-1-yl)-N-(1,2,4-thiadiazol-5-yl)-5,6,7,8-tetrahydronaphthalene-2-sulfonamide (Mixture of Enantiomers, Stereochemistry Arbitrarily Assigned)

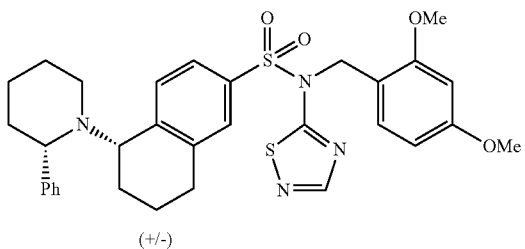 [SMILES: COc1ccc(CN(c2ncns2)S(=O)(=O)c2ccc3c(c2)CCC[C@@H]3N2CCCC[C@H]2c2ccccc2)c(OC)c1]

(+/-)

Colorless oil (0.059 g, 22% yield). MS (ES+) m/z 605.2 (M+1). $^1$H NMR (300 MHz, CDCl$_3$): δ 8.16 (d, J=0.6 Hz, 1H), 8.01 (d, J=8.4 Hz, 1H), 7.63 (dd, J=1.8, 8.4 Hz, 1H), 7.42 (d, J=7.6 Hz, 2H), 7.34-7.21 (m, 4H), 7.01 (d, J=9.2 Hz, 1H), 6.28-6.26 (m, 2H), 5.23 (s, 2H), 3.89-3.78 (m, 1H), 3.73 (s, 3H), 3.67 (s, 3H), 3.59 (dd, J=2.9, 10.7 Hz, 1H), 2.54-2.48 (m, 2H), 2.34-2.25 (m, 1H), 1.88-1.33 (m, 11H).

Diastereomer 2: (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide (Mixture of Enantiomers, Stereochemistry Arbitrarily Assigned)

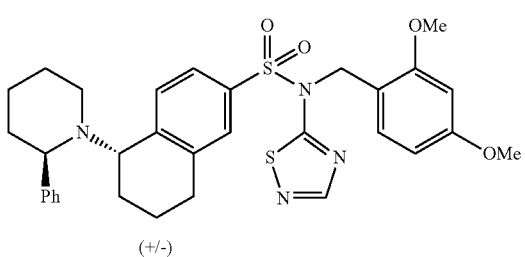 [SMILES: COc1ccc(CN(c2ncns2)S(=O)(=O)c2ccc3c(c2)CCC[C@@H]3N2CCCC[C@@H]2c2ccccc2)c(OC)c1]

(+/-)

Colorless oil (0.058 g, 22% yield). MS (ES+) m/z 605.2 (M+1). $^1$H NMR (300 MHz, CDCl$_3$): δ 8.14 (s, 1H), 7.57 (dd, J=1.9, 8.3 Hz, 1H), 7.39 (d, J=8.3 Hz, 2H), 7.34-7.32 (m, 2H), 7.28-7.16 (m, 3H), 7.02 (d, J=8.0 Hz, 1H), 6.33-6.29 (m, 2H), 5.18 (d, J=1.7 Hz, 2H), 3.86-3.75 (m, 3H), 3.73 (s, 3H), 3.72 (s, 3H), 3.49-3.46 (m, 4H), 2.69-2.63 (m, 1H), 2.49-2.44 (m, 2H), 1.87-1.66 (m, 4H), 1.62-1.53 (m, 2H), 1.39-1.21 (m, 1H), 1.05-1.00 (m, 1H), 0.90-0.83 (m, 1H).
Step 8

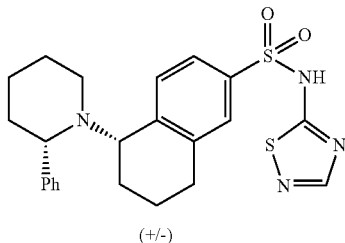 [SMILES: O=S(=O)(Nc1ncns1)c1ccc2c(c1)CCC[C@@H]2N1CCCC[C@H]1c1ccccc1]

(+/-)

(±)-5-((R)-2-phenylpiperidin-1-yl)-N-(1,2,4-thiadiazol-5-yl)-5,6,7,8-tetrahydronaphthalene-2-sulfonamide (Stereochemistry Arbitrarily Assigned)

A solution of (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide (0.058 g, 0.097 mmol) in dichloromethane (5 mL) and trifluoroacetic acid (1 mL) was stirred at ambient temperature for 2 h. Methanol (10 mL) was added, the suspension was filtered, and the filtrate was concentrated in vacuo. The residue was purified by reverse-phase HPLC eluting with a 20-80% gradient of acetonitrile in water containing 0.1% trifluoroacetic acid to afford the title compound as a trifluoroacetate salt as a colorless solid (0.017 g, 38% yield). MS (ES+) m/z 455.1 (M+1). $^1$H NMR (300 MHz, DMSO-d$_6$) δ 9.22 (br s, 1H), 8.53 (s, 1H), 7.73 (d, J=8.1 Hz, 1H), 7.69-7.64 (m, 3H), 7.52 (s, 1H), 7.40-7.36 (m, 2H), 7.33-7.27 (m, 1H), 4.76-4.63 (m, 1H), 4.63-4.49 (m, 1H), 3.33 (d, J=11.1 Hz, 1H), 2.88-2.56 (m, 3H), 2.24-1.83 (m, 6H), 1.84-1.70 (m, 2H), 1.67-1.47 (m, 2H) (Note: Exchangeable proton not observed).

Example 52

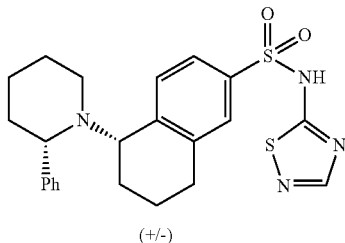 [SMILES: O=S(=O)(Nc1ncns1)c1ccc2c(c1)CCC[C@@H]2N1CCCC[C@H]1c1ccccc1]

(+/-)

(±)-5-((S)-2-phenylpiperidin-1-yl)-N-(1,2,4-thiadiazol-5-yl)-5,6,7,8-tetrahydronaphthalene-2-sulfonamide (Stereochemistry Arbitrarily Assigned)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (±)-N-(2,4-dimethoxybenzyl)-5-((S)-2-phenylpiperidin-1-yl)-N-(1,2,4-thiadiazol-5-yl)-5,6,7,8-tetrahydronaphthalene-2-sulfonamide, the title compound was obtained as a trifluoroacetate salt as a colorless solid (0.011 g, 25% yield). MS (ES+) m/z 455.1 (M+1). $^1$H NMR (300 MHz, CDCl$_3$) δ 8.10-7.90 (m, 2H), 7.50-7.39 (m, 3H), 7.28-7.17 (m, 4H), 4.69-4.55 (m, 1H), 4.11 (d, J=12.0 Hz, 1H), 3.20-2.07 (m, 2H), 3.03-2.90 (m, 2H), 2.80-2.53 (m, 4H), 2.43-2.11 (m, 2H), 2.07-1.91 (m, 3H), 1.83-1.70 (m, 1H), 1.66-1.50 (m, 2H).

Example 53

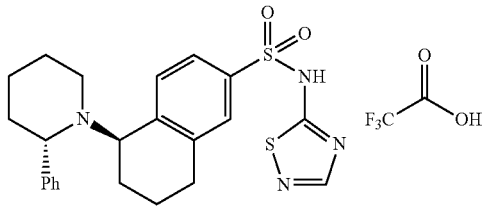

-continued

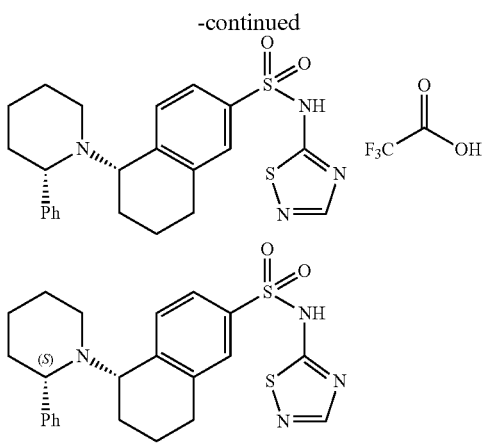

(R)-5-((S)-2-phenylpiperidin-1-yl)-N-(1,2,4-thiadiazol-5-yl)-5,6,7,8-tetrahydronaphthalene-2-sulfonamide trifluoroacetic Acid Salt, (S)-5-((S)-2-phenylpiperidin-1-yl)-N-(1,2,4-thiadiazol-5-yl)-5,6,7,8-tetrahydronaphthalene-2-sulfonamide trifluoroacetic Acid Salt, and (S)-5-((S)-2-phenylpiperidin-1-yl)-N-(1,2,4-thiadiazol-5-yl)-5,6,7,8-tetrahydronaphthalene-2-sulfonamide (Stereochemistry at Chromane Arbitrarily Assigned)

To a solution of N-(2,4-dimethoxybenzyl)-5-hydroxy-N-(1,2,4-thiadiazol-5-yl)-5,6,7,8-tetrahydronaphthalene-2-sulfonamide (0.500 g, 1.09 mmol) in tetrahydrofuran (5 mL) at −78° C., under a nitrogen atmosphere, was added triethylamine (0.60 mL, 4.3 mmol) and methanesulfonylchloride (0.17 mL, 2.2 mmol). The mixture was stirred for 1 h at which time (S)-2-phenylpiperidine (0.21 mL, 1.3 mmol) was added. The suspension was stirred for 17 h at ambient temperature. The mixture was diluted with ethyl acetate (10 mL), saturated aqueous sodium bicarbonate (10 mL) and water (10 mL) and the layers were separated. The aqueous phase was extracted with ethyl acetate (3×10 mL) and the combined organic phases were washed with brine (10 mL), dried with anhydrous sodium sulfate, filtered, and concentrated in vacuo. The residue was dissolved in dichloromethane (5 mL) and trifluoroacetic acid (1 mL) was added. The suspension was stirred at ambient temperature for 1.5 h. Methanol (10 mL) was added and the mixture filtered. The filtrate was concentrated in vacuo and a portion of the residue was purified by reverse-phase HPLC eluting with a 20-80% gradient of acetonitrile in water containing 0.1% trifluoroacetic acid to afford (S)-5-((S)-2-phenylpiperidin-1-yl)-N-(1,2,4-thiadiazol-5-yl)-5,6,7,8-tetrahydronaphthalene-2-sulfonamide trifluoroacetic acid salt and (S)-5-((S)-2-phenylpiperidin-1-yl)-N-(1,2,4-thiadiazol-5-yl)-5,6,7,8-tetrahydronaphthalene-2-sulfonamide trifluoroacetic acid salt. The remainder was purified by reverse-phase HPLC eluting with a 20-80% gradient of acetonitrile in water containing 0.1% ammonium hydroxide to afford (S)-5-((S)-2-phenylpiperidin-1-yl)-N-(1,2,4-thiadiazol-5-yl)-5,6,7,8-tetrahydronaphthalene-2-sulfonamide.

(R)-5-((S)-2-phenylpiperidin-1-yl)-N-(1,2,4-thiadiazol-5-yl)-5,6,7,8-tetrahydronaphthalene-2-sulfonamide trifluoroacetic acid salt (Stereochemistry at Chromane Arbitrarily Assigned)

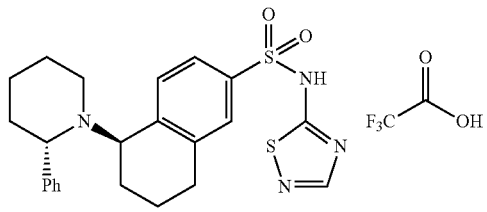

Colorless solid (0.025 g, 5% yield). MS (ES+) m/z 455.0 (M+1). $^1$H NMR (300 MHz, DMSO-$d_6$) δ 8.08 (s, 1H), 7.59-7.43 (m, 4H), 7.40 (s, 1H), 7.37-7.27 (m, 2H), 7.27-7.18 (m, 1H), 4.36-3.95 (m, 2H), 3.55-3.11 (m, 2H), 3.00-2.83 (m, 1H), 2.75-2.56 (m, 2H), 2.27-2.08 (m, 1H), 1.88-1.56 (m, 6H), 1.47-1.28 (m, 2H) (Note: Exchangeable proton not observed).

Example 54

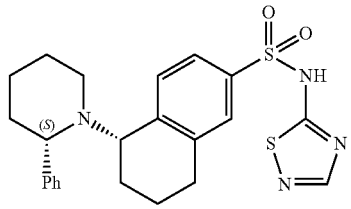

(S)-5-((S)-2-phenylpiperidin-1-yl)-N-(1,2,4-thiadiazol-5-yl)-5,6,7,8-tetrahydronaphthalene-2-sulfonamide (Stereochemistry at Chromane Arbitrarily Assigned)

This compound was prepared in the same sequence as Example 53. Colorless solid (0.017 g, 3% yield). MS (ES+) m/z 455.0 (M+1). $^1$H NMR (300 MHz, DMSO-$d_6$+TFA) δ 9.32 (br s, 1H), 8.05 (s, 1H), 7.90 (d, J=7.8 Hz, 1H), 7.55 (s, 1H), 7.47-7.36 (m, 3H), 7.31-7.22 (m, 3H), 4.61 (t, J=7.2 Hz, 1H), 4.14 (d, J=12.3 Hz, 1H), 3.17 (d, J=12.9 Hz, 1H), 3.09-2.95 (m, 1H), 2.83-2.68 (m, 2H), 2.65-2.49 (m, 1H), 2.37-2.25 (m, 1H), 2.23-2.12 (m, 1H), 2.10-1.91 (m, 4H), 1.89-1.75 (m, 1H), 1.68-1.41 (m, 2H) (Note: Exchangeable proton not observed).

Example 55

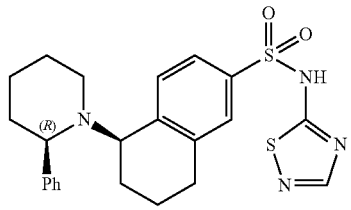

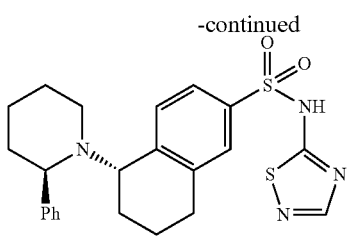

(R)-5-((R)-2-phenylpiperidin-1-yl)-N-(1,2,4-thiadiazol-5-yl)-5,6,7,8-tetrahydronaphthalene-2-sulfonamide and (S)-5-((R)-2-phenylpiperidin-1-yl)-N-(1,2,4-thiadiazol-5-yl)-5,6,7,8-tetrahydronaphthalene-2-sulfonamide (Sterochemistry at Chromane Arbitrarily Assigned)

Following the procedure as described in Example 53 and making non-critical variations as required to replace (S)-2-phenylpiperidine with (R)-2-phenylpiperidine, the title compounds were obtained as trifluoroacetate salts.

(R)-5-((R)-2-phenylpiperidin-1-yl)-N-(1,2,4-thiadiazol-5-yl)-5,6,7,8-tetrahydronaphthalene-2-sulfonamide (Sterochemistry at Chromane Arbitrarily Assigned)

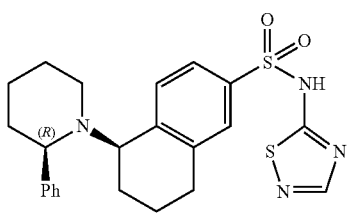

Colorless solid (0.045 g, 9% yield). MS (ES+) m/z 455.1 (M+1). $^1$H NMR (300 MHz, CDCl$_3$+2 drops TFA) δ 8.16 (s, 1H), 7.89-7.76 (m, 1H), 7.75-7.59 (m, 3H), 7.57-7.44 (m, 4H), 4.51-4.38 (m, 1H), 4.24-4.12 (m, 1H), 3.29-3.17 (m, 1H), 3.15-2.95 (m, 1H), 2.83-2.65 (m, 2H), 2.49-2.29 (m, 1H), 2.19-1.95 (m, 6H), 1.92-1.79 (m, 1H), 1.70-1.48 (m, 2H) (Note: Exchangeable proton not observed).

Example 56

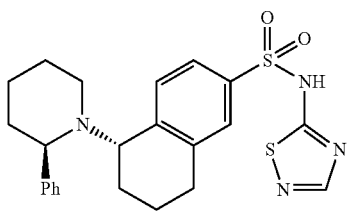 [SMILES: O=S(=O)(Nc1ncns1)c1ccc2c(c1)CCC[C@@H]2N1CCCC[C@@H]1c1ccccc1]

(S)-5-((R)-2-phenylpiperidin-1-yl)-N-(1,2,4-thiadiazol-5-yl)-5,6,7,8-tetrahydronaphthalene-2-sulfonamide (Sterochemistry at Chromane Arbitrarily Assigned)

This compound was prepared in the same sequence as Example 55. Colorless solid (0.027 g, 5% yield). MS (ES+) m/z 455.1 (M+1). $^1$H NMR (300 MHz, DMSO-d$_6$+2 drops TFA) δ 9.19 (br s, 1H), 8.49 (s, 1H), 7.74-7.58 (m, 4H), 7.48 (s, 1H), 7.41-7.32 (m, 2H), 7.29-7.22 (m, 1H), 4.72-4.58 (m, 1H), 4.55-4.46 (m, 1H), 3.30 (d, J=13.5 Hz, 1H), 2.83-2.51 (m, 2H), 2.17-1.65 (m, 9H), 1.59-1.41 (m, 2H).

Example 57

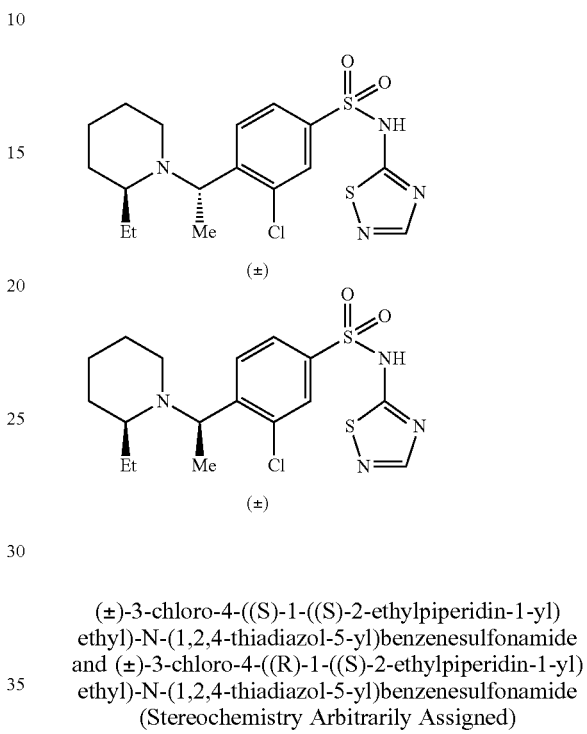

(±)-3-chloro-4-((S)-1-((S)-2-ethylpiperidin-1-yl)ethyl)-N-(1,2,4-thiadiazol-5-yl)benzenesulfonamide and (±)-3-chloro-4-((R)-1-((S)-2-ethylpiperidin-1-yl)ethyl)-N-(1,2,4-thiadiazol-5-yl)benzenesulfonamide (Stereochemistry Arbitrarily Assigned)

Step 1

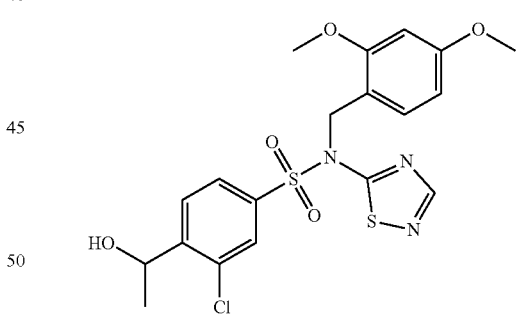

3-chloro-N-(2,4-dimethoxybenzyl)-4-(1-hydroxyethyl)-N-(1,2,4-thiadiazol-5-yl)benzenesulfonamide Following the procedure as described in Example 45, step 2 and making non-critical variations as required to replace DMF with acetaldehyde, the title compound was obtained as an off-white solid (4.8 g, 57% yield). $^1$H NMR (300 MHz, CDCl$_3$) δ 8.19 (s, 1H), 7.66-7.62 (m, 2H), 7.57-7.54 (m, 1H), 7.06 (d, J=8.4 Hz, 1H), 6.31 (dd, J=2.4, 8.4 Hz, 1H), 6.21 (d, J=2.4 Hz, 1H), 5.31-5.19 (m, 3H), 3.76 (s, 3H), 3.66 (s, 3H), 1.45 (d, J=6.4 Hz, 3H) (Note: 1 exchangeable proton not observed).

Step 2

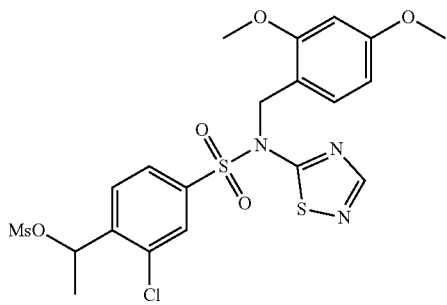 [SMILES: COc1ccc(CN(c2ncns2)S(=O)(=O)c2ccc(C(C)OS(C)(=O)=O)c(Cl)c2)c(OC)c1]

1-(2-chloro-4-(N-(2,4-dimethoxybenzyl)-N-(1,2,4-thiadiazol-5-yl)sulfamoyl)phenyl)ethyl methanesulfonate To a solution of 3-chloro-N-(2,4-dimethoxybenzyl)-4-(1-hydroxyethyl)-N-(1,2,4-thiadiazol-5-yl)benzenesulfonamide (2.3 g, 4.9 mmol) and triethylamine (1.0 mL, 7.3 mmol) in dichloromethane (10 mL) at 0° C. was added methanesulfonyl chloride (0.45 mL, 5.8 mmol). The reaction mixture was stirred at 0° C. for 1 h, then quenched with saturated aqueous of ammonium chloride (10 mL). The reaction mixture was diluted with dichloromethane (100 mL), the phases were separated, and the organic phase was washed with water (20 mL), brine (20 mL), dried over anhydrous sodium sulfate, filtered, and concentrated in vacuo to afford the title compound as an off-white solid (2.5 g, 94% yield). $^1$H NMR (300 MHz, CDCl$_3$) δ 8.23-8.19 (m, 1H), 7.70-7.64 (m, 1H), 7.58-7.50 (m, 2H), 7.07 (d, J=8.4 Hz, 1H), 6.36-6.28 (m, 1H), 6.21-6.16 (m, 1H), 6.03 (q, J=6.4 Hz, 1H), 5.33-5.28 (m, 2H), 3.77-3.74 (m, 3H), 3.61-3.58 (m, 3H), 3.02-2.98 (m, 3H), 1.66-1.57 (m, 3H).

Step 3

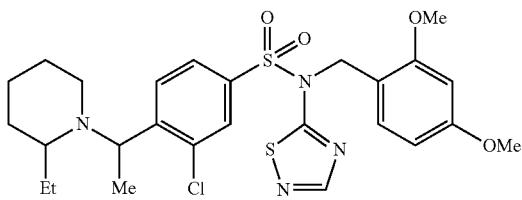 [SMILES: CCC1CCCCN1C(C)c1ccc(S(=O)(=O)N(Cc2ccc(OC)cc2OC)c2ncns2)cc1Cl]

3-chloro-N-(2,4-dimethoxybenzyl)-4-(1-(2-ethylpiperidin-1-yl)ethyl)-N-(1,2,4-thiadiazol-5-yl)benzenesulfonamide To a solution of 1-(2-chloro-4-(N-(2,4-dimethoxybenzyl)-N-(1,2,4-thiadiazol-5-yl)sulfamoyl)phenyl)ethyl methanesulfonate (0.30 g, 0.56 mmol) in acetonitrile (6 mL) was added 2-ethylpiperidine (0.15 mL, 1.1 mmol) and N,N-diisopropylethylamine (0.29 mL, 1.7 mmol). The mixture was stirred at 70° C. for 18 h, cooled to ambient temperature, and concentrated in vacuo.

The crude residue was used in the subsequent step without purification or characterization.

Step 4

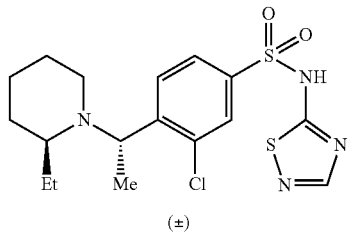 [SMILES: CC[C@H]1CCCCN1[C@@H](C)c1ccc(S(=O)(=O)Nc2ncns2)cc1Cl]

(±)

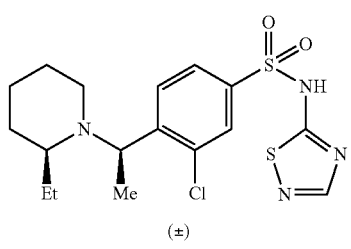 [SMILES: CC[C@H]1CCCCN1[C@H](C)c1ccc(S(=O)(=O)Nc2ncns2)cc1Cl]

(±)

(±)-3-chloro-4-((S)-1-((S)-2-ethylpiperidin-1-yl)ethyl)-N-(1,2,4-thiadiazol-5-yl)benzenesulfonamide
and (±)-3-chloro-4-((R)-1-((S)-2-ethylpiperidin-1-yl)ethyl)-N-(1,2,4-thiadiazol-5-yl)benzenesulfonamide
(Stereochemistry Arbitrarily Assigned)

Following the procedure as described in Example 51, Step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with 3-chloro-N-(2,4-dimethoxybenzyl)-4-(1-(2-ethylpiperidin-1-yl)ethyl)-N-(1,2,4-thiadiazol-5-yl)benzenesulfonamide, the title compounds were obtained.

(±)-3-chloro-4-((S)-1-((S)-2-ethylpiperidin-1-yl)ethyl)-N-(1,2,4-thiadiazol-5-yl)benzenesulfonamide
(Stereochemistry Arbitrarily Assigned)

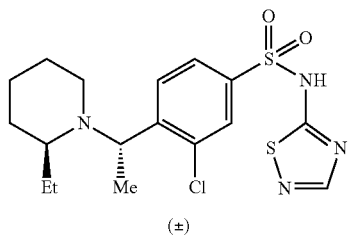

(±)

Colorless solid (0.009 g, 4% yield over 2 steps). MS (ES+) m/z 415.0, 416.9 (M+1). $^1$H NMR (300 MHz, CDCl$_3$) δ 7.98-7.83 (m, 3H), 7.46 (br s, 1H), 4.74 (br s, 1H), 3.41 (d, J=12.3 Hz, 1H), 2.98-2.79 (m, 2H), 2.01-1.41 (m, 8H), 0.93 (t, J=7.2 Hz, 3H), 0.76 (t, J=6.9 Hz, 3H).

Example 58

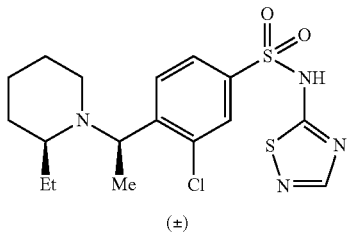

(±)-3-chloro-4-((R)-1-((S)-2-ethylpiperidin-1-yl)ethyl)-N-(1,2,4-thiadiazol-5-yl)benzenesulfonamide (Stereochemistry Arbitrarily Assigned)

This compound was prepared in the same sequence as Example 57. Colorless solid (0.017 g, 7% yield over 2 steps). MS (ES+) m/z 415.0, 416.9 (M+1). $^1$H NMR (300 MHz, CDCl$_3$) δ 7.90-7.83 (m, 2H), 7.79 (d, J=8.4 Hz, 1H), 7.57 (d, J=7.8 Hz, 1H), 4.56-4.44 (m, 1H), 3.51 (d, J=13.5 Hz, 1H), 3.25-3.08 (m, 1H), 3.03-2.85 (m, 2H), 2.69-2.51 (m, 2H), 2.02-1.32 (m, 5H), 0.96-0.88 (m, 6H).

Example 59

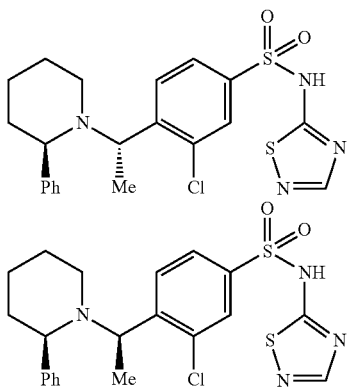

3-chloro-4-((S)-1-((R)-2-phenylpiperidin-1-yl)ethyl)-N-(1,2,4-thiadiazol-5-yl)benzenesulfonamide and 3-chloro-4-((R)-1-((R)-2-phenylpiperidin-1-yl)ethyl)-N-(1,2,4-thiadiazol-5-yl)benzenesulfonamide (Stereochemistry at Benzylic Methyl Arbitrarily Assigned)

Step 1

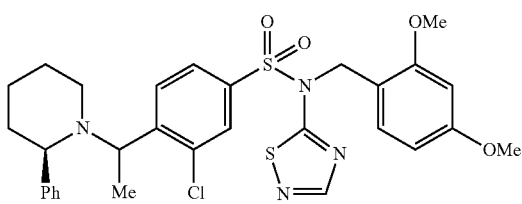 [SMILES: COc1ccc(CN(c2ncns2)S(=O)(=O)c2ccc(C(C)N3CCCC[C@@H]3c3ccccc3)c(Cl)c2)c(OC)c1]

3-chloro-4-(1-((R)-2-phenylpiperidin-1-yl)ethyl)-N-(2,4-dimethoxybenzyl)-N-(1,2,4-thiadiazol-5-yl)benzenesulfonamide Following the procedure as described in Example 55, step 3 and making non-critical variations as required to replace 2-ethylpiperidine with (R)-2-phenylpiperidine, the crude residue was used in the subsequent step without purification or characterization.

Step 2

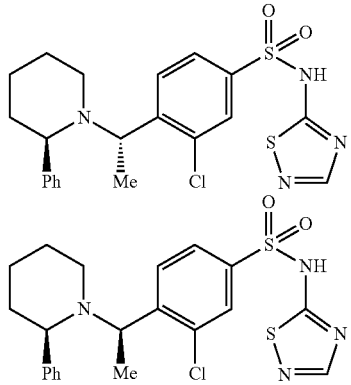

3-chloro-4-((S)-1-((R)-2-phenylpiperidin-1-yl)ethyl)-N-(1,2,4-thiadiazol-5-yl)benzenesulfonamide and 3-chloro-4-((R)-1-((R)-2-phenylpiperidin-1-yl)ethyl)-N-(1,2,4-thiadiazol-5-yl)benzenesulfonamide (Stereochemistry at Benzylic Methyl Arbitrarily Assigned)

Following the procedure as described in Example 51, Step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with 3-chloro-4-(1-((R)-2-phenylpiperidin-1-yl)ethyl)-N-(2,4-dimethoxybenzyl)-N-(1,2,4-thiadiazol-5-yl)benzenesulfonamide, the title compounds were obtained.

3-chloro-4-((S)-1-((R)-2-phenylpiperidin-1-yl)ethyl)-N-(1,2,4-thiadiazol-5-yl)benzenesulfonamide (Stereochemistry at Benzylic Methyl Arbitrarily Assigned)

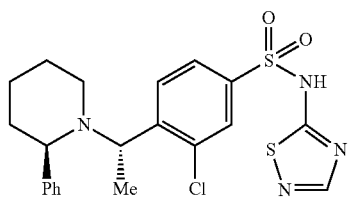 [SMILES: C[C@@H](c1ccc(S(=O)(=O)Nc2ncns2)cc1Cl)N1CCCC[C@@H]1c1ccccc1]

Colorless solid (0.019 g, 5% yield over 2 steps). MS (ES+) m/z 463.0, 465.0 (M+1). $^1$H NMR (300 MHz, CDCl$_3$) δ 8.02 (br s, 1H), 7.86 (br s, 1H), 7.81-7.73 (m, 1H), 7.70-7.61 (m, 1H), 7.51-7.42 (m, 2H), 7.39-7.29 (m, 3H), 4.89-4.74 (m, 1H), 4.11 (d, J=9.0 Hz, 1H), 3.55 (d, J=11.4

Hz, 1H), 2.71-2.52 (m, 1H), 2.30-2.09 (m, 1H), 2.06-1.71 (m, 4H), 1.59-1.46 (m, 1H), 1.39 (d, J=6.3 Hz, 3H).

Example 60

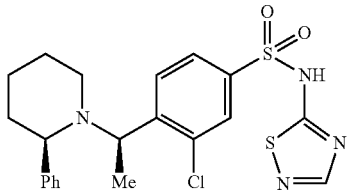 [SMILES: C[C@H](c1ccc(S(=O)(=O)Nc2ncns2)cc1Cl)N1CCCC[C@@H]1c1ccccc1]

3-chloro-4-((R)-1-((R)-2-phenylpiperidin-1-yl)ethyl)-N-(1,2,4-thiadiazol-5-yl)benzenesulfonamide (Stereochemistry at Benzylic Methyl Arbitrarily Assigned)

This compound was prepared in the same sequence as Example 59. Colorless solid (0.020 g, 6% yield over 2 steps). MS (ES+) m/z 463.0, 465.0 (M+1). $^1$H NMR (300 MHz, CDCl$_3$) δ 7.99 (br s, 1H), 7.85-7.76 (m, 1H), 7.72 (br s, 1H), 7.69-7.56 (m, 3H), 7.46-7.36 (m, 3H), 4.71-4.59 (m, 1H), 3.99 (d, J=12.3 Hz, 1H), 3.51 (d, J=7.5 Hz, 1H), 3.08-2.90 (m, 1H), 2.44-2.24 (m, 1H), 2.08-1.82 (m, 4H), 1.65-1.56 (m, 1H), 1.52 (d, J=6.9 Hz, 3H).

Example 61

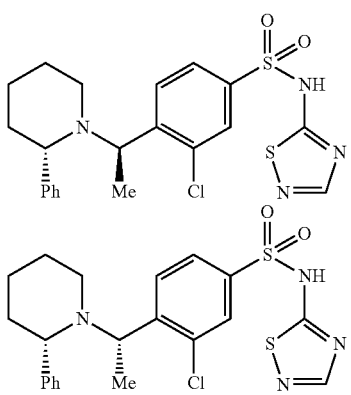

3-chloro-4-((R)-1-((S)-2-phenylpiperidin-1-yl)ethyl)-N-(1,2,4-thiadiazol-5-yl)benzenesulfonamide and 3-chloro-4-((S)-1-((S)-2-phenylpiperidin-1-yl)ethyl)-N-(1,2,4-thiadiazol-5-yl)benzenesulfonamide (Stereochemistry at Benzylic Methyl Arbitrarily Assigned)

Step 1

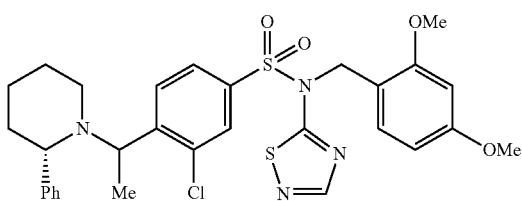

3-chloro-4-(1-((S)-2-phenylpiperidin-1-yl)ethyl)-N-(2,4-dimethoxybenzyl)-N-(1,2,4-thiadiazol-5-yl)benzenesulfonamide Following the procedure as described for Example 57, step 3 and making non-critical variations as required to replace 2-ethylpiperidine with (S)-2-phenylpiperidine, the crude residue was used in the subsequent step without purification or characterization.

Step 2

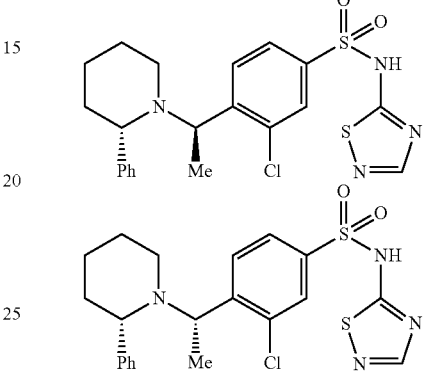

3-chloro-4-((R)-1-((S)-2-phenylpiperidin-1-yl)ethyl)-N-(1,2,4-thiadiazol-5-yl)benzenesulfonamide and 3-chloro-4-((S)-1-((S)-2-phenylpiperidin-1-yl)ethyl)-N-(1,2,4-thiadiazol-5-yl)benzenesulfonamide (Stereochemistry at Benzylic Methyl Arbitrarily Assigned)

Following the procedure as described for Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with 3-chloro-4-(1-((S)-2-phenylpiperidin-1-yl)ethyl)-N-(2,4-dimethoxybenzyl)-N-(1,2,4-thiadiazol-5-yl)benzenesulfonamide, the title compounds were obtained.

3-chloro-4-((R)-1-((S)-2-phenylpiperidin-1-yl)ethyl)-N-(1,2,4-thiadiazol-5-yl)benzenesulfonamide (Stereochemistry at Benzylic Methyl Arbitrarily Assigned)

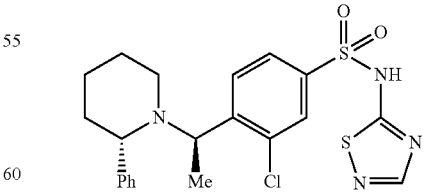

Colorless solid (0.028 g, 8% yield over 2 steps). MS (ES+) m/z 463.0, 465.0 (M+1). $^1$H NMR (300 MHz, CDCl$_3$) δ 8.02 (br s, 1H), 7.86 (br s, 1H), 7.79-7.74 (m, 1H), 7.72-7.63 (m, 1H), 7.47 (br s, 2H), 7.34 (br s, 3H), 4.87-4.75 (m, 1H), 4.10 (d, J=9.3 Hz, 1H), 3.60-3.49 (m, 1H), 2.66-

2.54 (m, 1H), 2.30-2.10 (m, 1H), 2.00-1.88 (m, 4H), 1.53-1.39 (m, 1H), 1.39 (d, J=6.6 Hz, 3H).

Example 62

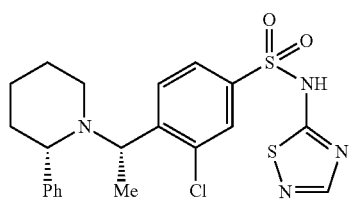 [SMILES: C[C@@H](c1ccc(S(=O)(=O)Nc2ncns2)cc1Cl)N1CCCC[C@H]1c1ccccc1]

3-chloro-4-((S)-1-((S)-2-phenylpiperidin-1-yl)ethyl)-N-(1,2,4-thiadiazol-5-yl)benzenesulfonamide (Stereochemistry at Benzylic Methyl Arbitrarily Assigned)

This compound was prepared in the same sequence as Example 61. Colorless solid (0.032 g, 9% yield over 2 steps). MS (ES+) m/z 463.0, 465.0 (M+1). $^1$H NMR (300 MHz, CDCl$_3$) δ 7.99 (br s, 1H), 7.85-7.78 (m, 1H), 7.72 (br s, 1H), 7.69-7.57 (m, 3H), 7.46-7.38 (m, 3H), 4.71-4.61 (m, 1H), 3.98 (d, J=11.1 Hz, 1H), 3.59-3.44 (m, 1H), 3.08-2.90 (m, 1H), 2.35 (q, J=11.5 Hz, 1H), 2.09-1.83 (m, 4H), 1.52 (d, J=6.6 Hz, 3H), 1.65-1.57 (m, 1H).

Example 63

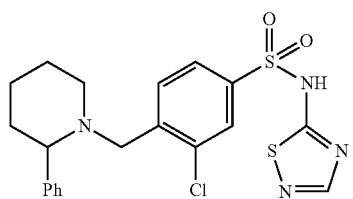

3-chloro-4-((2-phenylpiperidin-1-yl)methyl)-N-(1,2,4-thiadiazol-5-yl)benzenesulfonamide Step 1

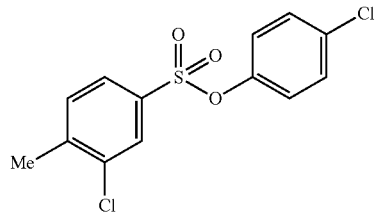 [SMILES: Cc1ccc(S(=O)(=O)Oc2ccc(Cl)cc2)cc1Cl]

4-chlorophenyl 3-chloro-4-methylbenzenesulfonate

To a solution of 3-chloro-4-methylbenzenesulfonyl chloride (15 g, 67 mmol) and triethylamine (18.6 mL, 133 mmol) in THF (200 mL) was added 4-chlorophenol. The reaction mixture was stirred at ambient temperature for 16 h and diluted with ethyl acetate (300 mL) and 1 N hydrochloric acid (50 mL). The phases were separated and the organic phase was washed with water (50 mL), saturated aqueous sodium bicarbonate (50 mL), and brine (50 mL). The mixture was dried over anhydrous sodium sulfate, filtered, and concentrated in vacuo. The residue was purified by column chromatography eluting with a 0-30% gradient of ethyl acetate in hexanes to afford the title compound as an orange solid (13.08 g, 62% yield). $^1$H NMR (300 MHz, CDCl$_3$) δ: 7.84-7.82 (m, 1H), 7.58 (dd, J=1.9, 8.0 Hz, 1H), 7.39 (d, J=8.0 Hz, 1H), 7.31-7.26 (m, 2H), 6.98-6.92 (m, 2H), 2.48 (s, 3H).

Step 2

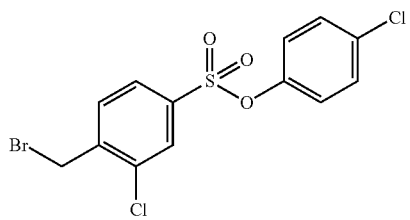 [SMILES: O=S(=O)(Oc1ccc(Cl)cc1)c1ccc(CBr)c(Cl)c1]

4-chlorophenyl 4-(bromomethyl)-3-chlorobenzenesulfonate

To a solution of 4-chlorophenyl 3-chloro-4-methylbenzenesulfonate (3.2 g, 10 mmol) and N-bromosuccinimide (2.0 g, 11 mmol) in carbon tetrachloride (20 mL) was added benzoyl peroxide (0.12 g, 0.5 mmol). The reaction mixture was heated to reflux for 16 h, then the reaction mixture was cooled and diluted with dichloromethane (100 mL). The reaction mixture was washed with water (2×10 mL), brine (10 mL), dried over anhydrous sodium sulfate, filtered, and concentrated in vacuo. The residue was purified by column chromatography eluting with a 0-30% gradient of ethyl acetate in hexanes to afford the title compound as an orange oil (2.4 g, 60% yield). $^1$H NMR (300 MHz, CDCl$_3$) δ 7.89 (d, J=1.7 Hz, 1H), 7.71-7.57 (m, 2H), 7.32-7.27 (m, 2H), 6.98-6.94 (m, 2H), 4.59 (s, 2H).

Step 3

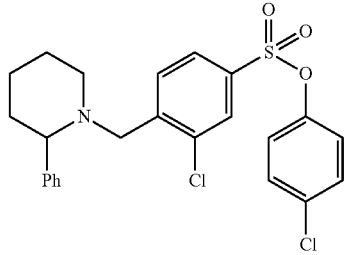 [SMILES: O=S(=O)(Oc1ccc(Cl)cc1)c1ccc(CN2CCCCC2c2ccccc2)c(Cl)c1]

4-chlorophenyl 3-chloro-4-((2-phenylpiperidin-1-yl)methyl)benzenesulfonate

A mixture of 4-chlorophenyl 4-(bromomethyl)-3-chlorobenzenesulfonate (1.12 g, 2.84 mmol), 2-phenylpiperidine (0.48 g, 2.98 mmol) and potassium carbonate (0.41 g, 2.98 mmol) in N,N-dimethylformamide (10 mL) was stirred at ambient temperature for 18 h. The suspension was diluted with ethyl acetate (10 mL) and water (10 mL). The layers were separated and the aqueous phase was extracted with ethyl acetate (3×10 mL). The combined organic phases were washed with brine (10 mL), dried with anhydrous sodium sulfate, filtered, and concentrated in vacuo. The residue was purified by column chromatography eluting with a 6-50% gradient of ethyl acetate in hexanes affording the title compound as a colorless oil (0.77 g, 57% yield). $^1$H NMR (300 MHz, CDCl$_3$): δ 7.89 (d, J=8.2 Hz, 1H), 7.73 (d, J=1.9 Hz, 1H), 7.68 (dd, J=1.9, 8.2 Hz, 1H), 7.40-7.36 (m, 2H), 7.32-7.22 (m, 5H), 6.96-6.93 (m, 2H), 3.61 (d, J=16.2 Hz, 1H), 3.34-3.25 (m, 2H), 2.86-2.81 (m, 1H), 2.15-2.05 (m, 1H), 1.85-1.79 (m, 2H), 1.72-1.57 (m, 2H), 1.50-1.38 (m, 2H).

Step 4

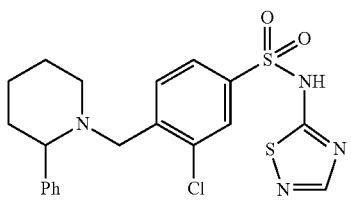 [SMILES: O=S(=O)(Nc1ncns1)c1ccc(CN2CCCCC2c2ccccc2)c(Cl)c1]

3-chloro-4-((2-phenylpiperidin-1-yl)methyl)-N-(1,2,4-thiadiazol-5-yl)benzenesulfonamide A mixture of 4-chlorophenyl 3-chloro-4-((2-phenylpiperidin-1-yl)methyl)benzenesulfonate (0.337 g, 0.706 mmol), 1,2,4-thiadiazol-5-amine (0.143 g, 1.41 mmol) and potassium carbonate (0.411 g, 2.98 mmol) in N,N-dimethylformamide (5 mL) was stirred at 70° C. for 72 h. The suspension was cooled to ambient temperature and diluted with ethyl acetate (10 mL) and water (10 mL). The layers were separated and the aqueous phase was extracted with ethyl acetate (3×10 mL). The combined organic phases were washed with brine (10 mL), dried with anhydrous sodium sulfate, filtered, and concentrated in vacuo. The residue purified by reverse-phase HPLC, eluting with a 20-80% gradient of acetonitrile in water containing 0.1% trifluoroacetic acid to afford the title compound as a trifluoroacetate salt as a colorless solid (0.027 g, 9% yield). MS (ES+) m/z 449.0, 451.0 (M+1). $^1$H NMR (300 MHz, DMSO-d$_6$) δ 8.04 (s, 1H), 7.69 (dd, J=1.8, 8.1 Hz, 1H), 7.65-7.61 (m, 2H), 7.46-7.39 (m, 2H), 7.37-7.29 (m, 3H), 3.72-2.96 (broad m, 5H), 1.79-1.38 (broad m, 6H).

Example 64

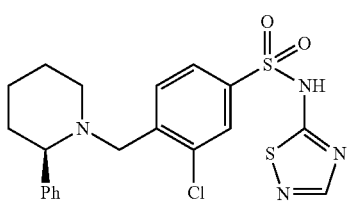

(R)-3-chloro-4-((2-phenylpiperidin-1-yl)methyl)-N-(1,2,4-thiadiazol-5-yl)benzenesulfonamide Step 1

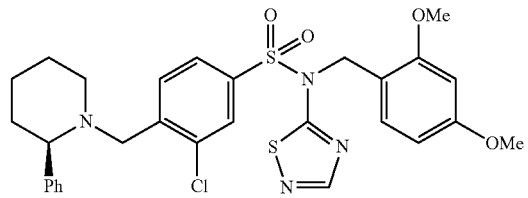 [SMILES: COc1ccc(CN(c2ncns2)S(=O)(=O)c2ccc(CN3CCCC[C@@H]3c3ccccc3)c(Cl)c2)c(OC)c1]

(R)-3-chloro-N-(2,4-dimethoxybenzyl)-4-((2-phenylpiperidin-1-yl)methyl)-N-(1,2,4-thiadiazol-5-yl)benzenesulfonamide A solution of 3-chloro-N-(2,4-dimethoxybenzyl)-4-formyl-N-(1,2,4-thiadiazol-5-yl)benzenesulfonamide (prepared according to Example 45, step 2, 0.250 g, 0.552 mmol) and (R)-2-phenylpiperidine (0.092 g, 0.55 mmol) in tetrahydrofuran (10 mL) was stirred at ambient temperature for thirty minutes. Sodium triacetoxyborohydride (0.234 g, 1.10 mmol) was then added and the mixture stirred for 18 h. The suspension was diluted with ethyl acetate (10 mL), water (10 mL), and saturated aqueous sodium bicarbonate (10 mL). The layers were separated and the aqueous phase was extracted with ethyl acetate (3×10 mL). The combined organic phases were washed with brine (10 mL), dried with anhydrous sodium sulfate, filtered, and concentrated in vacuo. The residue was purified by column chromatography eluting with a 12-100% gradient of ethyl acetate in hexanes affording the title compound as a colorless solid (0.185 g, 56% yield). $^1$H NMR (300 MHz, CDCl$_3$): δ 8.18 (d, J=0.2 Hz, 1H), 7.77 (d, J=8.2 Hz, 1H), 7.65 (dd, J=1.9, 8.2 Hz, 1H), 7.50 (d, J=1.9 Hz, 1H), 7.37-7.34 (m, 2H), 7.30-7.24 (m, 2H), 7.23-7.17 (m, 1H), 7.04 (d, J=8.4 Hz, 1H), 6.28 (dd, J=2.4, 8.4 Hz, 1H), 6.22 (d, J=2.3 Hz, 1H), 5.30-5.18 (m, 2H), 3.53 (d, J=16.5 Hz, 1H), 3.28-3.21 (m, 2H), 2.84-2.79 (m, 1H), 2.11-2.03 (m, 1H), 1.85-1.78 (m, 2H), 1.69-1.56 (m, 3H), 1.49-1.37 (m, 1H).

Step 2

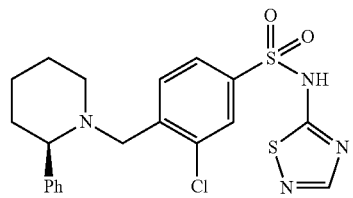 [SMILES: O=S(=O)(Nc1ncns1)c1ccc(CN2CCCC[C@@H]2c2ccccc2)c(Cl)c1]

(R)-3-chloro-4-((2-phenylpiperidin-1-yl)methyl)-N-(1,2,4-thiadiazol-5-yl)benzenesulfonamide Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (R)-3-chloro-N-(2,4-dimethoxybenzyl)-4-((2-phenylpiperidin-1-yl)methyl)-N-(1,2,4-thiadiazol-5-yl)benzenesulfonamide, the title compound

235 was obtained without purification as a trifluoroacetate salt as a colorless solid (0.16 g, 94% yield). MS (ES+) m/z 448.9, 450.9 (M+1). $^1$H NMR (300 MHz, CDCl$_3$) δ 10.70 (br s, 1H), 7.94 (s, 1H), 7.62-7.55 (m, 4H), 7.41-7.28 (m, 3H), 7.18 (d, J=7.5 Hz, 1H), 4.57 (d, J=13.5 Hz, 1H), 4.04 (d, J=13.8 Hz, 1H), 3.89 (d, J=12.8 Hz, 1H), 3.41 (d, J=12.3 Hz, 1H), 2.82 (t, J=12.6 Hz, 1H), 2.40 (q, J=12.6 Hz, 1H), 2.08-1.92 (m, 3H), 1.85 (d, J=13.8 Hz, 1H), 1.72-1.51 (m, 1H).

Example 65

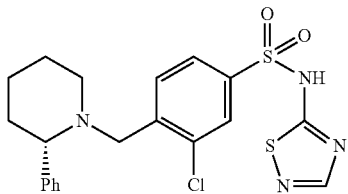 [SMILES: O=S(=O)(Nc1ncns1)c1ccc(CN2CCCC[C@H]2c2ccccc2)c(Cl)c1]

(S)-3-chloro-4-((2-phenylpiperidin-1-yl)methyl)-N-(1,2,4-thiadiazol-5-yl)benzenesulfonamide Step 1

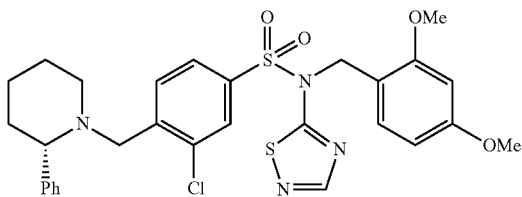 [SMILES: COc1ccc(CN(c2ncns2)S(=O)(=O)c2ccc(CN3CCCC[C@H]3c3ccccc3)c(Cl)c2)c(OC)c1]

(S)-3-chloro-N-(2,4-dimethoxybenzyl)-4-((2-phenylpiperidin-1-yl)methyl)-N-(1,2,4-thiadiazol-5-yl)benzenesulfonamide Following the procedure as described for Example 64, step 1 and making non-critical variations as required to replace (R)-2-phenylpiperidine with (S)-2-phenylpiperidine, the title compound was afforded as a colorless oil (0.21 g, 64% yield). MS (ES+) m/z 599.1, 601.1 (M+1). $^1$H NMR (300 MHz, CDCl$_3$): δ 8.18 (d, J=0.9 Hz, 1H), 7.77 (dd, J=0.4, 7.8 Hz, 1H), 7.66-7.63 (m, 1H), 7.50 (t, J=0.9 Hz, 1H), 7.36-7.32 (m, 2H), 7.29-7.24 (m, 2H), 7.21 (dd, J=0.6, 7.2 Hz, 1H), 7.03 (dd, J=0.5, 8.4 Hz, 1H), 6.30-6.26 (m, 1H), 6.22-6.22 (m, 1H), 5.24-5.23 (m, 2H), 3.67 (s, 6H), 3.56-3.51 (m, 1H), 3.28-3.20 (m, 1H), 2.85-2.79 (m, 1H), 2.23-2.04 (m, 1H), 1.86-1.77 (m, 2H), 1.68-1.59 (m, 3H), 1.49-1.38 (m, 2H).

Step 2

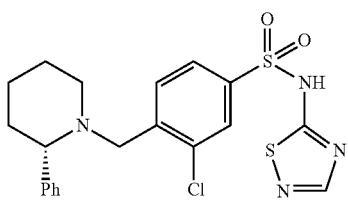

236

(S)-3-chloro-4-((2-phenylpiperidin-1-yl)methyl)-N-(1,2,4-thiadiazol-5-yl)benzenesulfonamide Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (S)-3-chloro-N-(2,4-dimethoxybenzyl)-4-((2-phenylpiperidin-1-yl)methyl)-N-(1,2,4-thiadiazol-5-yl)benzenesulfonamide, the title compound was obtained without purification as a trifluoroacetate salt as a colorless solid (0.060 g, 31% yield). MS (ES+) m/z 449.0, 451.0 (M+1). $^1$H NMR (300 MHz, CDCl$_3$) δ 10.20 (br s, 1H), 7.98 (s, 1H), 7.74 (s, 1H), 7.62-7.58 (m, 2H), 7.51 (d, J=8.1 Hz, 1H), 7.43-7.38 (m, 4H), 4.43 (d, J=13.2 Hz, 1H), 4.03 (d, J=13.5 Hz, 1H), 3.99-3.89 (m, 1H), 3.57 (d, J=11.1 Hz, 1H), 2.95-2.87 (m, 1H), 2.47-2.31 (m, 1H), 2.12-2.01 (m, 3H), 1.95-1.83 (m, 1H), 1.70-1.62 (m, 1H).

Example 66

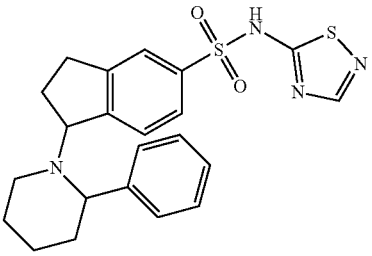 [SMILES: O=S(=O)(Nc1ncns1)c1ccc2c(c1)CCC2N1CCCCC1c1ccccc1]

1-(2-phenylpiperidin-1-yl)-N-(1,2,4-thiadiazol-5-yl)-2,3-dihydro-1H-indene-5-sulfonamide (Two Separated Diastereomers, Mixtures of Enantiomers)

Step 1

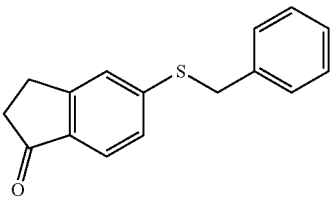 [SMILES: O=C1CCc2cc(SCc3ccccc3)ccc21]

5-(benzylthio)-2,3-dihydro-1H-inden-1-one

To a solution of 5-fluoro-2,3-dihydro-1H-inden-1-one (13.3 g, 88.2 mmol) and phenylmethanethiol (94 mL, 80 mmol) in N,N-dimethylformamide (80 mL) was added potassium carbonate (18.3 g, 132 mmol). The reaction mixture was heated to 70° C. for 3 h then cooled to ambient temperature and diluted with ethyl acetate (300 mL). The mixture was washed with water (3×80 mL) and brine (2×50 mL), dried with anhydrous sodium sulfate, filtered, and concentrated in vacuo. The residue was triturated in diethyl ether (50 mL) and filtered to afford the title compound as pale yellow solid (17.3 g, 85% yield). MS (ES+) m/z 255.2 (M+1). $^1$H NMR (300 MHz, CDCl$_3$) δ 7.62 (d, J=8.2 Hz, 1H), 7.42-7.20 (m, 7H), 4.24 (s, 2H), 3.11-3.02 (m, 2H), 2.71-2.62 (m, 2H).

Step 2

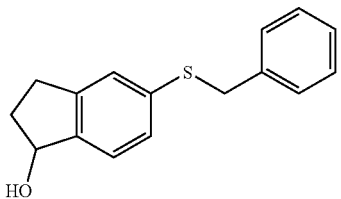 [SMILES: OC1CCc2cc(SCc3ccccc3)ccc21]

5-(benzylthio)-2,3-dihydro-1H-inden-1-ol

Following the procedure as described in Example 51, step 2 and making non-critical variations as required to replace 6-(benzylthio)-3,4-dihydronaphthalen-1(2H)-one with 5-(benzylthio)-2,3-dihydro-1H-inden-1-one, the title compound was obtained as a colorless oil (8.8 g, 91% yield). $^1$H NMR (300 MHz, CDCl$_3$) δ 7.35-7.16 (m, 8H), 5.25-5.16 (m, 1H), 4.12 (s, 2H), 3.08-2.93 (m, 1H), 2.83-2.69 (m, 1H), 2.55-2.40 (m, 1H), 2.01-1.87 (m, 1H), 1.68 (d, J=7.0 Hz, 1H).
Step 3

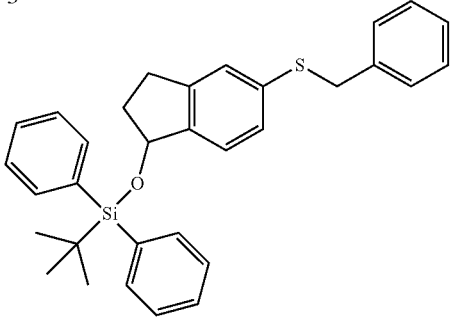 [SMILES: CC(C)(C)[Si](OC1CCc2cc(SCc3ccccc3)ccc21)(c1ccccc1)c1ccccc1]

((5-(benzylthio)-2,3-dihydro-1H-inden-1-yl)oxy)(tert-butyl)diphenylsilane

Following the procedure as described in Example 51, step 3 and making non-critical variations as required to replace 6-(benzylthio)-1,2,3,4-tetrahydronaphthalen-1-ol with 5-(benzylthio)-2,3-dihydro-1H-inden-1-ol, the title compound was obtained as an orange oil (17 g, quant. yield). $^1$H NMR (300 MHz, CDCl$_3$) δ 7.78-7.70 (m, 4H), 7.50-7.21 (m, 11H), 7.19-7.06 (m, 3H), 5.26 (t, J=6.7 Hz, 1H), 4.11 (s, 2H), 2.97-2.83 (m, 1H), 2.67-2.53 (m, 1H), 2.22-2.09 (m, 1H), 2.08-1.92 (m, 1H), 1.12 (s, 9H).
Step 4

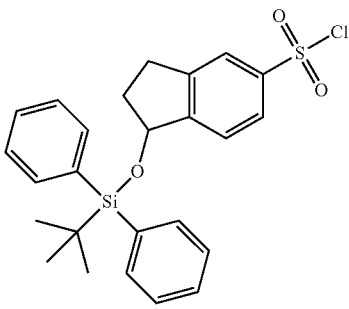 [SMILES: CC(C)(C)[Si](OC1CCc2cc(S(=O)(=O)Cl)ccc21)(c1ccccc1)c1ccccc1]

1-((tert-butyldiphenylsilyl)oxy)-2,3-dihydro-1H-indene-5-sulfonyl chloride

Following the procedure as described in Example 51, step 4 and making non-critical variations as required to replace ((6-(benzylthio)-1,2,3,4-tetrahydronaphthalen-1-yl)oxy)(tert-butyl)diphenylsilane with ((5-(benzylthio)-2,3-dihydro-1H-inden-1-yl)oxy)(tert-butyl)diphenylsilane, the title compound was obtained as a colorless solid (10.7 g, 64% yield). $^1$H NMR (300 MHz, CDCl$_3$) δ 7.85-7.27 (m, 13H), 5.28 (t, J=7.2 Hz, 1H), 3.08-2.93 (m, 1H), 2.79-2.64 (m, 1H), 2.31-2.18 (m, 1H), 2.14-2.03 (m, 1H), 1.10 (s, 9H).
Step 5

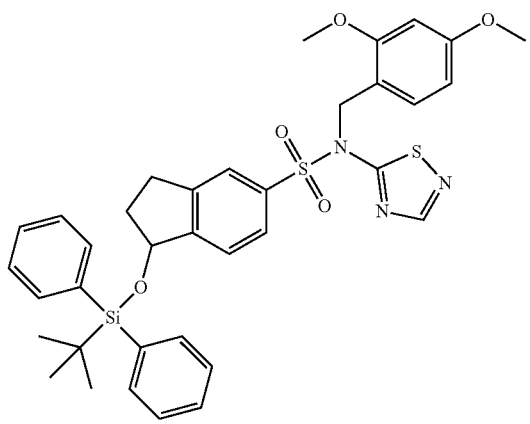 [SMILES: COc1ccc(CN(c2ncns2)S(=O)(=O)c2ccc3c(c2)CCC3O[Si](c2ccccc2)(c2ccccc2)C(C)(C)C)c(OC)c1]

1-((tert-butyldiphenylsilyl)oxy)-N-(2,4-dimethoxybenzyl)-N-(1,2,4-thiadiazol-5-yl)-2,3-dihydro-1H-indene-5-sulfonamide Following the procedure as described in Example 45, step 1 and making non-critical variations as required to replace 4-bromo-3-chlorobenzenesulfonyl chloride with 1-((tert-butyldiphenylsilyl)oxy)-2,3-dihydro-1H-indene-5-sulfonyl chloride, the title compound was obtained as a colorless oil (4.0 g, 50% yield). MS (ES+) m/z 686.3 (M+1). $^1$H NMR (300 MHz, CDCl$_3$) δ 8.14 (s, 1H), 7.74-7.59 (m, 5H), 7.50-7.35 (m, 7H), 7.21 (d, J=8.1 Hz, 1H), 7.06 (d, J=8.1 Hz, 1H), 6.36-6.28 (m, 2H), 5.26-5.14 (m, 3H), 3.74 (s, 3H), 3.69 (s, 3H), 2.94-2.80 (m, 1H), 2.66-2.51 (m, 1H), 2.25-2.12 (m, 1H), 2.04-1.92 (m, 1H), 1.10 (s, 9H).
Step 6

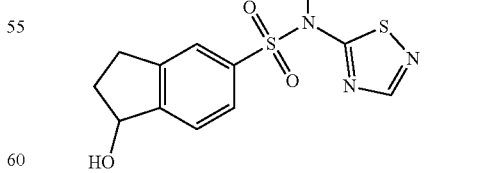

N-(2,4-dimethoxybenzyl)-1-hydroxy-N-(1,2,4-thiadiazol-5-yl)-2,3-dihydro-1H-indene-5-sulfonamide Following the procedure as described in Example 41, step 5 and making non-critical variations as required to replace (R)-4-((tert-butyldimethylsilyl)oxy)-N-(2,4-dimethoxybenzyl)-N-(1,2,4-thiadiazol-5-yl)chromane-7-sulfonamide with 1-((tert-butyldiphenylsilyl)oxy)-N-(2,4-dimethoxybenzyl)-N-(1,2,4-thiadiazol-5-yl)-2,3-dihydro-1H-indene-5-sulfonamide, the title compound was obtained as an off-white solid (2.05 g, 79% yield). MS (ES+) m/z 448.0 (M+1). ¹H NMR (300 MHz, CDCl₃) δ 8.15 (s, 1H), 7.70 (d, J=8.0 Hz, 1H), 7.56 (s, 1H), 7.45 (d, J=8.0 Hz, 1H), 7.05 (d, J=8.2 Hz, 1H), 6.37-6.26 (m, 2H), 5.23 (t, J=6.6 Hz, 1H), 5.21 (s, 2H), 3.76 (s, 3H), 3.71 (s, 3H), 3.05-2.92 (m, 1H), 2.86-2.71 (m, 1H), 2.62-2.48 (m, 1H), 2.06-1.86 (m, 1H) (Note: 1 exchangeable proton not observed).

Step 7

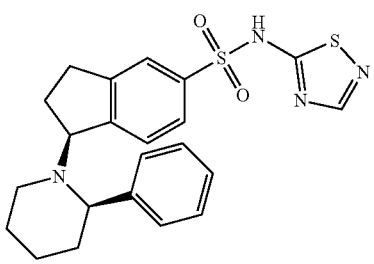 [SMILES: O=S(=O)(Nc1ncns1)c1ccc2c(c1)CC[C@@H]2N1CCCC[C@@H]1c1ccccc1]

1-(2-phenylpiperidin-1-yl)-N-(1,2,4-thiadiazol-5-yl)-2,3-dihydro-1H-indene-5-sulfonamide (Diastereomer 1, Mixtures of Enantiomers, Stereochemistry Assigned Arbitrarily)

Following the procedure as described in Example 51, step 7 and making non-critical variations as required to replace N-(2,4-dimethoxybenzyl)-5-hydroxy-N-(1,2,4-thiadiazol-5-yl)-5,6,7,8-tetrahydronaphthalene-2-sulfonamide with N-(2,4-dimethoxybenzyl)-1-hydroxy-N-(1,2,4-thiadiazol-5-yl)-2,3-dihydro-1H-indene-5-sulfonamide, tetrahydrofuran with dichloromethane, and ethyl acetate with dichloromethane, the title compounds were obtained. Diastereomer 1. Colorless solid (0.037 g, 47% yield). MS (ES+) m/z 441.1 (M+1). ¹H NMR (300 MHz, CD₃OD) δ 7.96 (br s, 1H), 7.79 (s, 2H), 7.65-7.40 (m, 6H), 4.56 (dd, J=3.4, 8.6 Hz, 1H), 4.40 (dd, J=2.0, 11.9 Hz, 1H), 3.15-2.83 (m, 4H), 2.73-2.56 (m, 1H), 2.28-1.67 (m, 7H) (Note: 1 exchangeable proton not observed).

Example 67

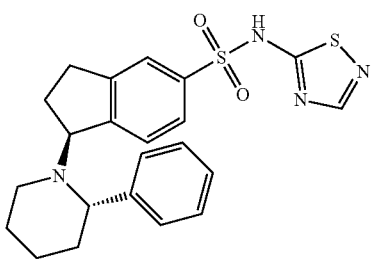 [SMILES: O=S(=O)(Nc1ncns1)c1ccc2c(c1)CC[C@@H]2N1CCCC[C@H]1c1ccccc1]

1-(2-phenylpiperidin-1-yl)-N-(1,2,4-thiadiazol-5-yl)-2,3-dihydro-1H-indene-5-sulfonamide (Diastereomer 2, Mixtures of Enantiomers, Stereochemistry Assigned Arbitrarily)

This compound was prepared in the same sequence as Example 66. Colorless solid (0.029 g, 11% yield). MS (ES+) m/z 441.1 (M+1). ¹H NMR (300 MHz, DMSO-d₆) δ 8.02 (s, 1H), 7.74-7.60 (m, 4H), 7.48 (t, J=7.3 Hz, 2H), 7.38 (t, J=7.2 Hz, 1H), 7.29-6.88 (m, 1H), 4.63-4.47 (m, 1H), 4.47-4.29 (m, 1H), 3.20-3.02 (m, 2H), 2.88-2.70 (m, 1H), 2.42-2.14 (m, 3H), 1.90-1.67 (m, 4H), 1.49 (br s, 1H) (Note: 1 exchangeable proton not observed, 1 aliphatic proton hidden under H₂O peak).

Example 68

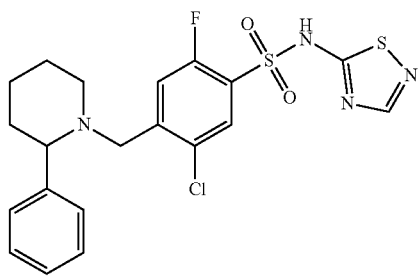 [SMILES: O=S(=O)(Nc1ncns1)c1cc(Cl)c(CN2CCCCC2c2ccccc2)cc1F]

5-chloro-2-fluoro-4-((2-phenylpiperidin-1-yl)methyl)-N-(1,2,4-thiadiazol-5-yl)benzenesulfonamide Step 1

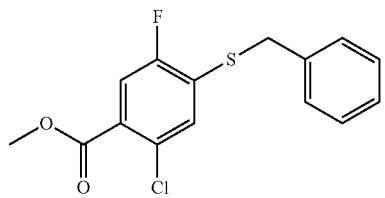 [SMILES: COC(=O)c1cc(F)c(SCc2ccccc2)cc1Cl]

methyl 4-(benzylthio)-2-chloro-5-fluorobenzoate

Following the procedure as described in Example 51, step 1 and making non-critical variations as required to replace 6-bromo-3,4-dihydronaphthalen-1(2H)-one with methyl 4-bromo-2-chloro-5-fluorobenzoate (prepared according to WO2013177224), the title compound was obtained as a colorless solid (2.5 g, 41% yield). ¹H NMR (300 MHz, CDCl₃) δ 7.56 (d, J=9.9 Hz, 1H), 7.38-7.27 (m, 6H), 4.19 (s, 2H), 3.91 (s, 3H).

Step 2

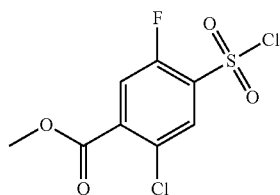 [SMILES: COC(=O)c1cc(F)c(S(=O)(=O)Cl)cc1Cl]

methyl 2-chloro-4-(chlorosulfonyl)-5-fluorobenzoate

To a solution of methyl 4-(benzylthio)-2-chloro-5-fluorobenzoate (1.48 g, 4.76 mmol) in acetonitrile (34 mL), acetic acid (1.6 mL), and water (1.2 mL) at 0° C. was added 1,3-dichloro-5,5-dimethylhydantoin (1.87 g, 9.49 mmol). The reaction mixture was stirred at 0° C. for 5 minutes and was then diluted with water (30 mL) and ethyl acetate (30 mL). The phases were separated and the aqueous phase extracted with ethyl acetate (30 mL). The combined organic phases were then washed with brine (2×30 mL) and concentrated in vacuo. The residue was purified by flash chromatography eluting with a 0-50% gradient of ethyl acetate in hexanes to provide the title compound as a colorless solid (1.3 g, 96% yield). $^1$H NMR (300 MHz, CDCl$_3$) δ 8.06 (d, J=6.0 Hz, 1H), 7.77 (d, J=9.3 Hz, 1H), 4.00 (s, 3H).

Step 3

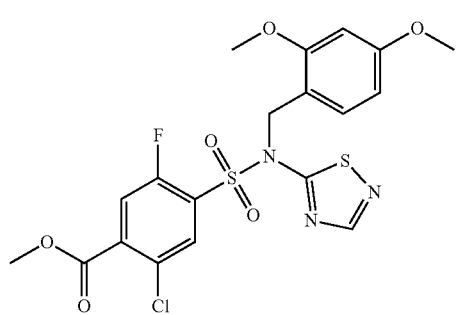

methyl 2-chloro-4-(N-(2,4-dimethoxybenzyl)-N-(1, 2,4-thiadiazol-5-yl)sulfamoyl)-5-fluorobenzoate Following the procedure as described in Example 45, step 1 and making non-critical variations as required to replace 4-bromo-3-chlorobenzenesulfonyl chloride with methyl 2-chloro-4-(chlorosulfonyl)-5-fluorobenzoate, the title compound was obtained following purification by column chromatography eluting with a 10-60% gradient of ethyl acetate in hexanes as a colorless solid (2.15 g, 73% yield). MS (ES+) m/z 501.9, 504.0 (M+1). $^1$H NMR (300 MHz, CDCl$_3$) δ 8.23 (s, 1H), 7.68 (d, J=6.0 Hz, 1H), 7.40 (d, J=9.5 Hz, 1H), 7.20 (d, J=8.5 Hz, 1H), 6.33 (dd, J=2.3, 8.5 Hz, 1H), 6.09 (d, J=2.3 Hz, 1H), 5.37 (s, 2H), 3.94 (s, 3H), 3.73 (s, 3H), 3.64 (s, 3H).

Step 4

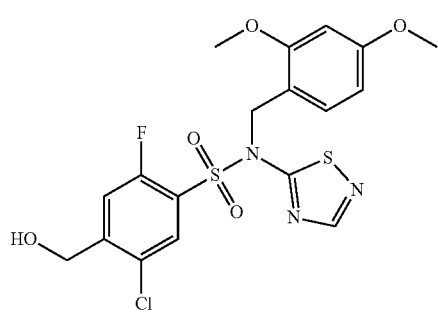 [SMILES: COc1ccc(CN(c2ncns2)S(=O)(=O)c2cc(Cl)c(CO)cc2F)c(OC)c1]

5-chloro-N-(2,4-dimethoxybenzyl)-2-fluoro-4-(hydroxymethyl)-N-(1,2,4-thiadiazol-5-yl)benzenesulfonamide To a solution of methyl 2-chloro-4-(N-(2,4-dimethoxybenzyl)-N-(1,2,4-thiadiazol-5-yl)sulfamoyl)-5-fluorobenzoate (2.15 g, 4.28 mmol) in anhydrous tetrahydrofuran (15 mL) at 0° C. was added a 1.0 M solution of diisobutylaluminum hydride in toluene (8.6 mL, 8.6 mmol). The reaction mixture was warmed to ambient temperature over 1.5 h and then quenched by slow addition of water (50 mL) and diluted with ethyl acetate (50 mL). The phases were separated and the aqueous phase was extracted with ethyl acetate (2×50 mL). The combined organic extracts were washed with brine (2×35 mL), dried over anhydrous magnesium sulfate, filtered, and concentrated in vacuo. The residue was purified by column chromatography eluting with a 0-80% gradient of ethyl acetate in hexanes to provide the title compound as a colorless oil (1.67 g, 82% yield). MS (ES+) m/z 473.9, 476.0 (M+1). $^1$H NMR (300 MHz, DMSO-d$_6$) δ8.47 (s, 1H), 7.54 (d, J=6.1 Hz, 1H), 7.44 (d, J=11.0 Hz, 1H), 7.09 (d, J=8.5 Hz, 1H), 6.40 (dd, J=2.4, 8.5 Hz, 1H), 6.23 (d, J=2.4 Hz, 1H), 5.87-5.78 (m, 1H), 5.25 (s, 2H), 4.53 (d, J=4.4 Hz, 2H), 3.69 (s, 3H), 3.60 (s, 3H).

Step 5

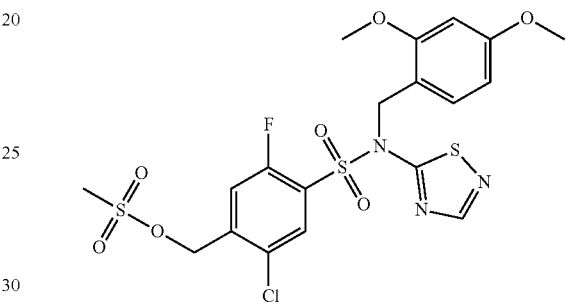

2-chloro-4-(N-(2,4-dimethoxybenzyl)-N-(1,2,4-thiadiazol-5-yl)sulfamoyl)-5-fluorobenzyl methanesulfonate Following the procedure as described in Example 57, step 2 and making non-critical variations as required to replace 3-chloro-N-(2,4-dimethoxybenzyl)-4-(1-hydroxyethyl)-N-(1,2,4-thiadiazol-5-yl)benzenesulfonamide with 5-chloro-N-(2,4-dimethoxybenzyl)-2-fluoro-4-(hydroxymethyl)-N-(1,2,4-thiadiazol-5-yl)benzenesulfonamide, the title compound was obtained as a colorless oil (1.87 g, 96% yield). MS (ES+) m/z 552.0, 553.8 (M+1). $^1$H NMR (300 MHz, CDCl$_3$) δ 8.23 (s, 1H), 7.62 (d, J=6.0 Hz, 1H), 7.25-7.17 (m, 2H), 6.34 (dd, J=2.3, 8.4 Hz, 1H), 6.10 (d, J=2.3 Hz, 1H), 5.37 (s, 2H), 5.24 (s, 2H), 3.75 (s, 3H), 3.63 (s, 3H), 3.15 (s, 3H).

Step 6

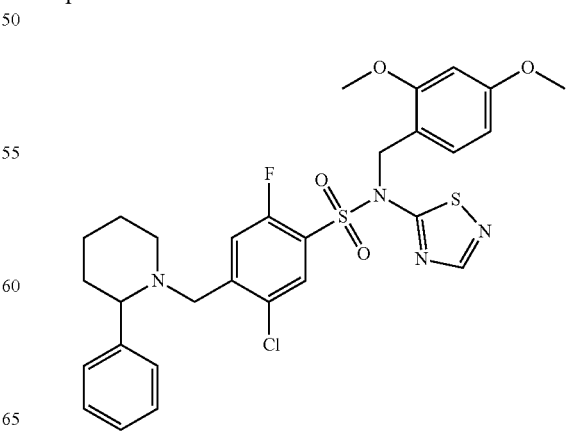

5-chloro-N-(2,4-dimethoxybenzyl)-2-fluoro-4-((2-phenylpiperidin-1-yl)methyl)-N-(1,2,4-thiadiazol-5-yl)benzenesulfonamide To a solution of 2-chloro-4-(N-(2,4-dimethoxybenzyl)-N-(1,2,4-thiadiazol-5-yl)sulfamoyl)-5-fluorobenzyl methanesulfonate (0.20 g, 0.36 mmol) in N,N-dimethylformamide (2.4 mL) was added 2-phenylpiperidine (0.091 g, 0.54 mmol), followed by potassium carbonate (0.075 g, 0.54 mmol). The reaction mixture was stirred at ambient temperature for 16 h and was then diluted with water (2.5 mL) and ethyl acetate (4 mL). The phases were separated and the aqueous phase was extracted with ethyl acetate (2×2 mL). The combined organic extracts were washed with brine (4 mL), dried over anhydrous magnesium sulfate, filtered, and concentrated in vacuo. The residue was purified by column chromatography eluting with a 0-50% gradient of ethyl acetate in hexanes to provide the title compound as a colorless oil (0.070 g, 31% yield). MS (ES+) m/z 617.1, 619.1 (M+1).

Step 7

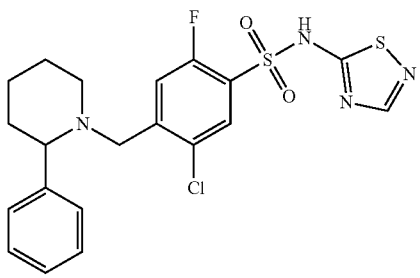 [SMILES: O=S(=O)(Nc1ncns1)c1cc(Cl)c(CN2CCCCC2c2ccccc2)cc1F]

5-chloro-2-fluoro-4-((2-phenylpiperidin-1-yl)methyl)-N-(1,2,4-thiadiazol-5-yl)benzenesulfonamide Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with 5-chloro-N-(2,4-dimethoxybenzyl)-2-fluoro-4-((2-phenylpiperidin-1-yl)methyl)-N-(1,2,4-thiadiazol-5-yl)benzenesulfonamide, the title compound was obtained as a colorless solid (0.023 g, 43% yield). MS (ES+) m/z 467.0, 469.0 (M+1). $^1$H NMR (300 MHz, CDCl$_3$) δ 7.84 (s, 1H), 7.63 (d, J=6.4 Hz, 1H), 7.36 (d, J=10.7 Hz, 1H), 7.22-7.15 (m, 2H), 7.15-6.99 (m, 3H), 3.43 (d, J=16.3 Hz, 1H), 3.13 (d, J=16.3 Hz, 1H), 2.75 (d, J=11.2 Hz, 1H), 2.09-1.94 (m, 1H), 1.77-1.40 (m, 6H), 1.29 (m, 1H) (Note: Exchangeable proton not observed).

Example 69

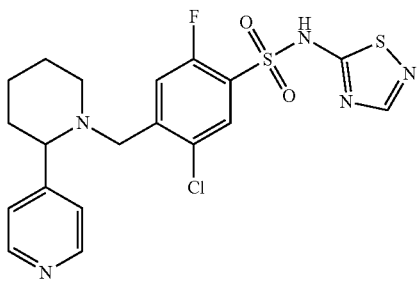 [SMILES: O=S(=O)(Nc1ncns1)c1cc(Cl)c(CN2CCCCC2c2ccncc2)cc1F]

5-chloro-2-fluoro-4-((2-(pyridin-4-yl)piperidin-1-yl)methyl)-N-(1,2,4-thiadiazol-5-yl)benzenesulfonamide To a solution of 2-chloro-4-(N-(2,4-dimethoxybenzyl)-N-(1,2,4-thiadiazol-5-yl)sulfamoyl)-5-fluorobenzyl methanesulfonate (0.20 g, 0.36 mmol) in N,N-dimethylformamide (2.4 mL) was added 4-(piperidin-2-yl)pyridine (0.092 g, 0.54 mmol) then potassium carbonate (0.075 g, 0.54 mmol). The reaction mixture was stirred at ambient temperature for 16 h and was then diluted with water (2.5 mL) and ethyl acetate (4 mL). The phases were separated and the aqueous phase was extracted with ethyl acetate (2×2 mL). The combined organic extracts were washed with brine (4 mL), dried over anhydrous magnesium sulfate, filtered, and concentrated in vacuo. The residue was dissolved in dichloromethane (3.2 mL) and trifluoroacetic acid (0.4 mL) was added. The reaction mixture was stirred at ambient temperature for 1 h, concentrated in vacuo, and triturated in methanol (3 mL). The resulting mixture was filtered and the filtrate concentrated in vacuo. The residue was purified by reverse-phase HPLC eluting with a 20-80% gradient of acetonitrile in water containing 0.1% of trifluoroacetic acid to provide the title compound as a trifluoroacetate salt as a colorless solid (0.017 g, 10% yield). MS (ES+) m/z 468.0, 470.0 (M+1). $^1$H NMR (300 MHz, CD$_3$OD) δ 8.68 (d, J=5.8 Hz, 2H), 8.25 (s, 1H), 8.03 (d, J=5.8 Hz, 2H), 7.81 (d, J=5.8 Hz, 1H), 7.64 (d, J=10.8 Hz, 1H), 3.77 (d, J=10.8 Hz, 1H), 3.61-3.42 (m, 2H), 3.02 (d, J=11.6 Hz, 1H), 2.41-2.24 (m, 1H), 1.90 (d, J=10.3 Hz, 2H), 1.82-1.42 (m, 4H) (Note: Exchangeable protons not observed).

Example 70

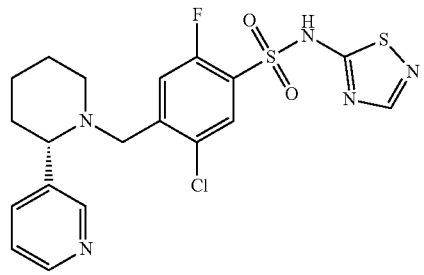 [SMILES: O=S(=O)(Nc1ncns1)c1cc(Cl)c(CN2CCCC[C@H]2c2cccnc2)cc1F]

(S)-5-chloro-2-fluoro-4-((2-(pyridin-3-yl)piperidin-1-yl)methyl)-N-(1,2,4-thiadiazol-5-yl)benzenesulfonamide Following the procedure as described in Example 69 and making non-critical variations as required to replace 4-(piperidin-2-yl)pyridine with (S)-3-(piperidin-2-yl)pyridine, the title compound was obtained as a colorless solid (0.057 g, 23% yield). MS (ES+) m/z 468.1, 470.1 (M+1). $^1$H NMR (300 MHz, CDCl$_3$) δ 8.86 (s, 1H), 8.60 (s, 1H), 8.01 (s, 1H), 7.91 (s, 2H), 7.63-7.32 (m, 2H), 3.68-3.35 (m, 3H), 3.02 (s, 1H), 2.23 (s, 1H), 1.98-1.67 (m, 5H), 1.49 (s, 1H) (Note: Exchangeable proton not observed).

Example 71

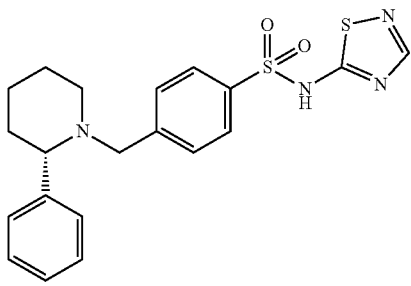 [SMILES: O=S(=O)(Nc1ncns1)c1ccc(CN2CCCC[C@H]2c2ccccc2)cc1]

(S)-4-((2-phenylpiperidin-1-yl)methyl)-N-(1,2,4-thiadiazol-5-yl)benzenesulfonamide Step 1

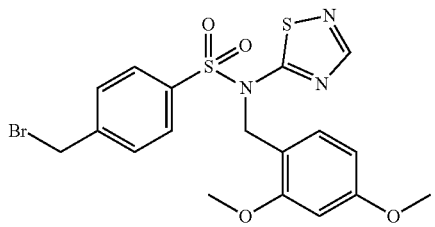 [SMILES: COc1ccc(CN(c2ncns2)S(=O)(=O)c2ccc(CBr)cc2)c(OC)c1]

4-(bromomethyl)-N-(2,4-dimethoxybenzyl)-N-(1,2,4-thiadiazol-5-yl)benzenesulfonamide Following the procedure as described in Example 45, step 1 and making non-critical variations as required to replace 4-bromo-3-chlorobenzenesulfonyl chloride with 4-(bromomethyl)-benzenesulfonyl chloride, the title compound was obtained as an off-white solid (2.2 g, 56% yield). $^1$H NMR (300 MHz, CDCl$_3$) δ 8.16 (s, 1H), 7.76-7.71 (m, 2H), 7.46-7.41 (m, 2H), 7.04 (d, J=8.2 Hz, 1H), 6.38-6.29 (m, 2H), 5.22 (s, 2H), 4.44 (s, 2H), 3.76 (s, 3H), 3.69 (s, 3H).

Step 2

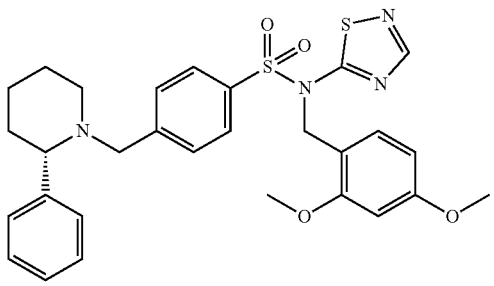 [SMILES: COc1ccc(CN(c2ncns2)S(=O)(=O)c2ccc(CN3CCCC[C@H]3c3ccccc3)cc2)c(OC)c1]

(S)—N-(2,4-dimethoxybenzyl)-4-((2-phenylpiperidin-1-yl)methyl)-N-(1,2,4-thiadiazol-5-yl)benzenesulfonamide Following the procedure as described in Example 68, step 6 and making non-critical variations as required to replace 2-chloro-4-(N-(2,4-dimethoxybenzyl)-N-(1,2,4-thiadiazol-5-yl)sulfamoyl)-5-fluorobenzyl methanesulfonate with 4-(bromomethyl)-N-(2,4-dimethoxybenzyl)-N-(1,2,4-thiadiazol-5-yl)benzenesulfonamide and 2-phenylpiperidine with (S)-2-phenylpiperidine, the title compound was obtained as a colorless oil (0.35 g, quant. yield). MS (ES+) m/z 565.2 (M+1). $^1$H NMR (300 MHz, CDCl$_3$) δ 8.13 (s, 1H), 7.72-7.69 (m, 2H), 7.41-7.22 (m, 7H), 7.05-7.02 (m, 1H), 6.33-6.30 (m, 2H), 5.16 (s, 2H), 3.78-3.68 (m, 6H), 3.16-3.11 (m, 1H), 2.91-2.80 (m, 2H), 2.04-1.93 (m, 1H), 1.84-1.75 (m, 2H), 1.65-1.59 (m, 2H), 1.58-1.54 (m, 2H), 1.46-1.35 (m, 1H).

Step 3

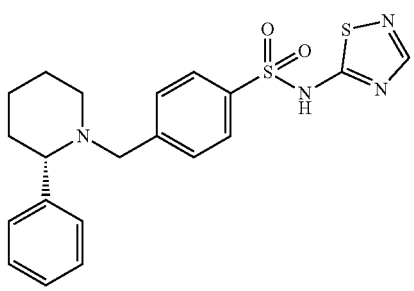 [SMILES: O=S(=O)(Nc1ncns1)c1ccc(CN2CCCC[C@H]2c2ccccc2)cc1]

(S)-4-((2-phenylpiperidin-1-yl)methyl)-N-(1,2,4-thiadiazol-5-yl)benzenesulfonamide Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (S)—N-(2,4-dimethoxybenzyl)-4-((2-phenylpiperidin-1-yl)methyl)-N-(1,2,4-thiadiazol-5-yl)benzenesulfonamide, the title compound was obtained without purification as a trifluoroacetate salt as an off-white solid (0.30 g, 90% yield). MS (ES+) m/z 415.2 (M+1). $^1$H NMR (300 MHz, DMSO-d$_6$) δ 9.75 (br s, 1H), 8.47 (s, 1H), 7.83 (d, J=8.3 Hz, 2H), 7.63-7.57 (m, 2H), 7.56-7.39 (m, 5H), 4.38-4.26 (m, 1H), 4.09-3.91 (m, 2H), 3.35-3.26 (m, 1H), 3.12-2.99 (m, 1H), 2.02-1.91 (m, 2H), 1.88-1.73 (m, 3H), 1.66-1.53 (m, 1H).

Example 72

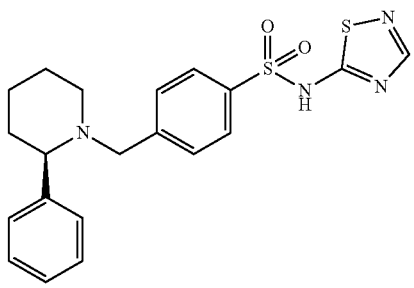 [SMILES: O=S(=O)(Nc1ncns1)c1ccc(CN2CCCC[C@@H]2c2ccccc2)cc1]

(R)-4-((2-phenylpiperidin-1-yl)methyl)-N-(1,2,4-thiadiazol-5-yl)benzenesulfonamide Step 1

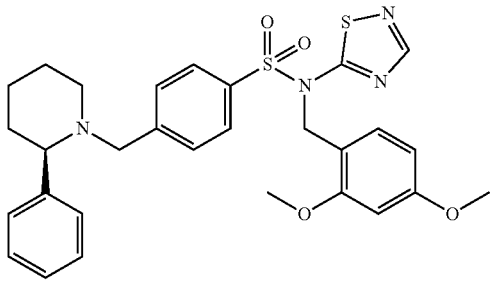 [SMILES: COc1ccc(CN(c2ncns2)S(=O)(=O)c2ccc(CN3CCCC[C@@H]3c3ccccc3)cc2)c(OC)c1]

(R)—N-(2,4-dimethoxybenzyl)-4-((2-phenylpiperidin-1-yl)methyl)-N-(1,2,4-thiadiazol-5-yl)benzenesulfonamide Following the procedure as described in Example 68, step 6 and making non-critical variations as required to replace 2-chloro-4-(N-(2,4-dimethoxybenzyl)-N-(1,2,4-thiadiazol-5-yl)sulfamoyl)-5-fluorobenzyl methanesulfonate with 4-(bromomethyl)-N-(2,4-dimethoxybenzyl)-N-(1,2,4-thiadiazol-5-yl)benzenesulfonamide and 2-phenylpiperidine with (R)-2-phenylpiperidine, the title compound was obtained as a colorless oil (0.35 g, quant. yield). MS (ES+) m/z 565.2 (M+1).

Step 2

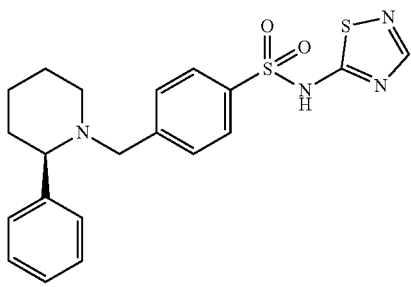 [SMILES: O=S(=O)(Nc1ncns1)c1ccc(CN2CCCC[C@@H]2c2ccccc2)cc1]

(R)-4-((2-phenylpiperidin-1-yl)methyl)-N-(1,2,4-thiadiazol-5-yl)benzenesulfonamide Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (R)—N-(2,4-dimethoxybenzyl)-4-((2-phenylpiperidin-1-yl)methyl)-N-(1,2,4-thiadiazol-5-yl)benzenesulfonamide, the title compound was obtained without purification as a trifluoroacetate salt as an off-white solid (0.30 g, 91% yield). MS (ES+) m/z 415.2 (M+1). ¹H NMR (300 MHz, DMSO-$d_6$) δ 9.75 (br s, 1H), 8.47 (s, 1H), 7.83 (d, J=8.3 Hz, 2H), 7.63-7.57 (m, 2H), 7.56-7.39 (m, 5H), 4.38-4.26 (m, 1H), 4.09-3.91 (m, 2H), 3.35-3.26 (m, 1H), 3.12-2.99 (m, 1H), 2.02-1.91 (m, 2H), 1.88-1.73 (m, 3H), 1.66-1.53 (m, 1H).

Example 73

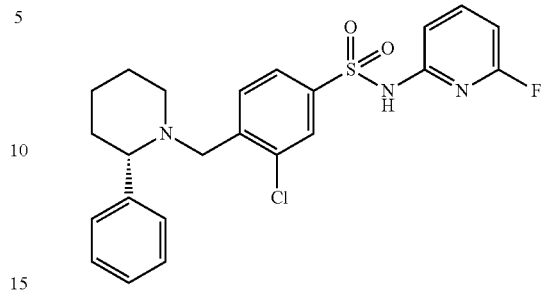

(S)-3-chloro-N-(6-fluoropyridin-2-yl)-4-((2-phenylpiperidin-1-yl)methyl)-benzenesulfonamide Step 1

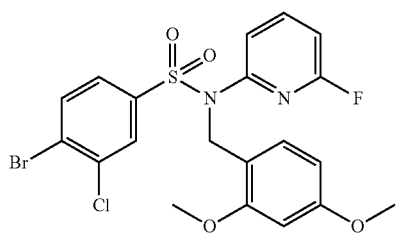 [SMILES: COc1ccc(CN(c2cccc(F)n2)S(=O)(=O)c2ccc(Br)c(Cl)c2)c(OC)c1]

4-bromo-3-chloro-N-(2,4-dimethoxybenzyl)-N-(6-fluoropyridin-2-yl)benzenesulfonamide Following the procedure as described in Example 45, step 1 and making non-critical variations as required to replace N-(2,4-dimethoxybenzyl)-1,2,4-thiadiazol-5-amine with N-(2,4-dimethoxybenzyl)-6-fluoropyridin-2-amine (prepared according to WO2014066490), the title compound was obtained as a yellow oil (6.4 g, 72% yield). ¹H NMR (300 MHz, CDCl$_3$) δ 7.81 (d, J=2.2 Hz, 1H), 7.76-7.68 (m, 2H), 7.50 (dd, J=2.2, 8.4 Hz, 1H), 7.22-7.14 (m, 2H), 6.73 (dd, J=3.0, 8.1 Hz, 1H), 6.38-6.33 (m, 2H), 4.93 (s, 2H), 3.76 (s, 3H), 3.65 (s, 3H).

Step 2

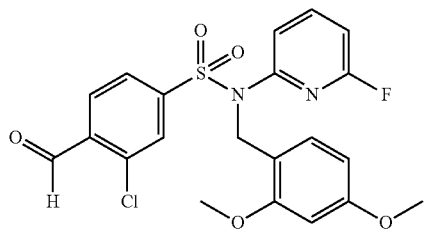 [SMILES: COc1ccc(CN(c2cccc(F)n2)S(=O)(=O)c2ccc(C=O)c(Cl)c2)c(OC)c1]

3-chloro-N-(2,4-dimethoxybenzyl)-N-(6-fluoropyridin-2-yl)-4-formylbenzenesulfonamide Following the procedure as described in Example 45, step 2 and making non-critical variations as required to replace 4-bromo-3-chloro-N-(2,4-dimethoxybenzyl)-N-(1,2,4-thiadiazol-5-yl)benzenesulfonamide with 4-bromo-3-chloro-N-(2,4-dimethoxybenzyl)-N-(6-fluoropyridin-2-yl)benzenesulfonamide, the title compound was obtained as an amorphous solid (5.2 g, 86% yield). $^1$H NMR (300 MHz, CDCl$_3$) δ 10.49 (s, 1H), 7.98 (dd, J=1.4, 8.2 Hz, 1H), 7.84-7.83 (m, 1H), 7.77-7.69 (m, 2H), 7.19-7.15 (m, 2H), 6.77-6.71 (m, 1H), 6.40-6.32 (m, 2H), 4.94 (s, 2H), 3.75 (s, 3H), 3.63 (s, 3H).

Step 3

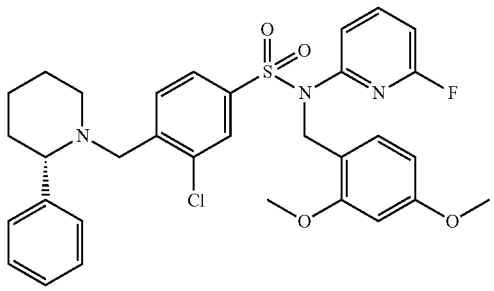 [SMILES: COc1ccc(CN(c2cccc(F)n2)S(=O)(=O)c2ccc(CN3CCCC[C@H]3c3ccccc3)c(Cl)c2)c(OC)c1]

(S)-3-chloro-N-(2,4-dimethoxybenzyl)-N-(6-fluoropyridin-2-yl)-4-((2-phenylpiperidin-1-yl)methyl) benzenesulfonamide To a solution of 3-chloro-N-(2,4-dimethoxybenzyl)-N-(6-fluoropyridin-2-yl)-4-formylbenzenesulfonamide (0.46 g, 1.00 mmol) in THF (5 mL) was added (S)-2-phenylpiperidine (0.24 g, 1.50 mmol). The reaction mixture was stirred at ambient temperature for 1 hour and then sodium triacetoxyborohydride (0.42 g, 2.00 mmol) was added. The reaction mixture was stirred at ambient temperature for 48 hours and was then diluted with CH$_2$Cl$_2$ (150 mL). The reaction mixture was washed with a solution of saturated sodium bicarbonate (15 mL), brine (15 mL), dried over anhydrous sodium sulfate, filtered, and concentrated in vacuo. The residue was purified by flash chromatography (eluting with 0~50% ethyl acetate in hexanes) to afford the desired compound as an amorphous solid (0.37 g, 61% yield). MS (ES+) m/z 610.2, 612.2 (M+1). $^1$H NMR (300 MHz, CDCl$_3$) δ 7.80-7.60 (m, 4H), 7.41-7.34 (m, 2H), 7.31-7.19 (m, 5H), 6.70 (dd, J=3.0, 8.1 Hz, 1H), 6.38-6.33 (m, 2H), 4.95 (s, 2H), 3.74 (s, 3H), 3.67 (s, 3H), 3.63-3.55 (m, 1H), 3.30-3.23 (m, 2H), 2.91-2.86 (m, 1H), 2.12-2.06 (m, 1H), 1.86-1.77 (m, 2H), 1.71-1.59 (m, 3H), 1.50-1.38 (m, 1H).

Step 4

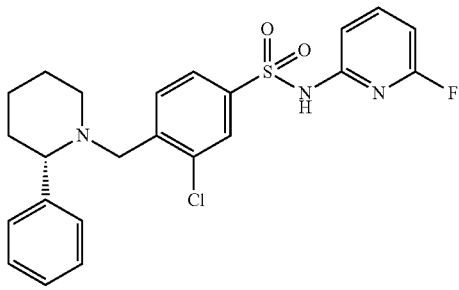 [SMILES: O=S(=O)(Nc1cccc(F)n1)c1ccc(CN2CCCC[C@H]2c2ccccc2)c(Cl)c1]

(S)-3-chloro-N-(6-fluoropyridin-2-yl)-4-((2-phenylpiperidin-1-yl)methyl)-benzenesulfonamide Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (S)-3-chloro-N-(2,4-dimethoxybenzyl)-N-(6-fluoropyridin-2-yl)-4-((2-phenylpiperidin-1-yl)methyl)benzenesulfonamide, the title compound was obtained as a trifluoroacetate salt as an off-white solid (0.24 g, 69% yield). MS (ES+) m/z 460.2, 462.2 (M+1). $^1$H NMR (300 MHz, DMSO-d$_6$) δ 11.67 (br s, 1H), 9.69 (br s, 1H), 7.99 (br s, 1H), 7.93-7.87 (m, 1H), 7.84 (d, J=8.2 Hz, 1H), 7.75-7.52 (m, 3H), 7.52-7.35 (m, 3H), 6.93 (dd, J=2.0, 7.9 Hz, 1H), 6.77 (dd, J=2.4, 8.0 Hz, 1H), 4.61-4.41 (m, 1H), 4.32-4.01 (m, 2H), 3.46-3.17 (m, 2H), 2.05-1.48 (m, 6H).

Example 74

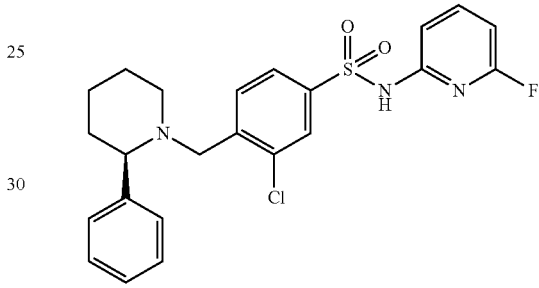

(R)-3-chloro-N-(6-fluoropyridin-2-yl)-4-((2-phenylpiperidin-1-yl)methyl)-benzenesulfonamide Step 1

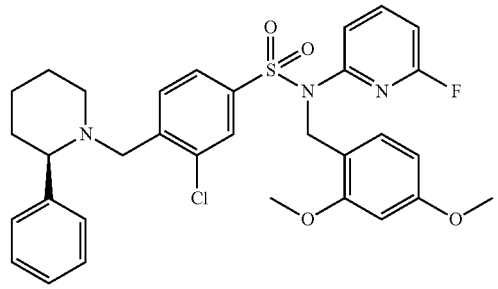 [SMILES: COc1ccc(CN(c2cccc(F)n2)S(=O)(=O)c2ccc(CN3CCCC[C@@H]3c3ccccc3)c(Cl)c2)c(OC)c1]

(R)-3-chloro-N-(2,4-dimethoxybenzyl)-N-(6-fluoropyridin-2-yl)-4-((2-phenylpiperidin-1-yl)methyl) benzenesulfonamide Following the procedure as described in Example 73, step 3 and making non-critical variations as required to replace (S)-2-phenylpiperidine with (R)-2-phenylpiperidine, the title compound was obtained as an off-white amorphous solid (0.34 g, 55% yield). MS (ES+) m/z 610.2, 612.2 (M+1). $^1$H NMR (300 MHz, CDCl$_3$) δ 7.80-7.60 (m, 4H), 7.39-7.37 (m, 2H), 7.31-7.19 (m, 5H), 6.70 (dd, J=2.9, 8.0 Hz, 1H), 6.38-6.33 (m, 2H), 4.95 (s, 2H), 3.74 (s, 3H), 3.67

(s, 3H), 3.62-3.57 (m, 1H), 3.30-3.23 (m, 2H), 2.91-2.86 (m, 1H), 2.12-2.03 (m, 1H), 1.86-1.78 (m, 2H), 1.67-1.61 (m, 3H), 1.51-1.31 (m, 1H).

Step 2

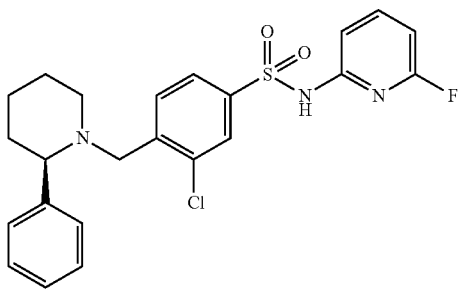 [SMILES: O=S(=O)(Nc1cccc(F)n1)c1ccc(CN2CCCC[C@@H]2c2ccccc2)c(Cl)c1]

(R)-3-chloro-N-(6-fluoropyridin-2-yl)-4-((2-phenylpiperidin-1-yl)methyl)-benzenesulfonamide Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (R)-3-chloro-N-(2,4-dimethoxybenzyl)-N-(6-fluoropyridin-2-yl)-4-((2-phenylpiperidin-1-yl)methyl)benzenesulfonamide, the title compound was obtained as a trifluoroacetate salt as an off-white solid (0.25 g, 80% yield). MS (ES+) m/z 460.0, 462.2 (M+1). $^1$H NMR (300 MHz, DMSO-$d_6$) δ 11.66 (br s, 1H), 9.65 (br s, 1H), 8.04-7.81 (m, 3H), 7.74-7.23 (m, 6H), 6.93 (dd, J=2.0, 7.9 Hz, 1H), 6.77 (dd, J=2.3, 8.0 Hz, 1H), 4.61-4.41 (m, 1H), 4.31-4.02 (m, 2H), 3.49-3.17 (m, 2H), 2.18-1.40 (m, 6H).

Example 75

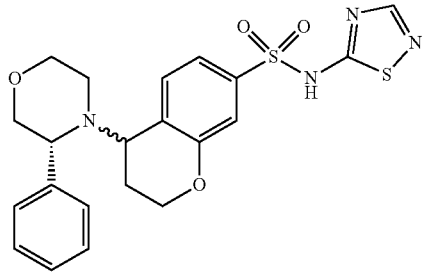 [SMILES: O=S(=O)(Nc1ncns1)c1ccc2c(c1)OCCC2N1CCOC[C@H]1c1ccccc1]

4-((R)-3-phenylmorpholino)-N-(1,2,4-thiadiazol-5-yl)chromane-7-sulfonamide

To a solution of (R)-7-(N-(2,4-dimethoxybenzyl)-N-(1,2,4-thiadiazol-5-yl)sulfamoyl)chroman-4-yl methanesulfonate (prepared according to Example 41, step 6, 1.00 g, 1.84 mmol) in ethyl acetate (10.0 mL) was added (R)-3-phenylmorpholine (0.60 g, 3.7 mmol) and N,N-diisopropylethylamine (0.99 mL, 5.5 mmol). The mixture was heated to 80° C. After 20 h, the reaction was diluted with dichloromethane (20 mL) and water (20 mL). The organic layer was removed and the aqueous layer was extracted with dichloromethane (2×20 mL). The combined organic layers were dried over anhydrous sodium sulfate and filtered. The filtrate was concentrated in vacuo to dryness. The residue was partially purified by column chromatography, eluting with 30% ethyl acetate containing 10% 2-propanol and 10% triethylamine in hexanes to afford an oil. The oil was dissolved in dichloromethane (15 mL) and cooled to 0° C. A solution of trifluoroacetic acid (0.68 mL, 8.9 mmol) in dichloromethane (2 mL) was slowly added to the cooled solution. After 90 minutes the reaction was concentrated in vacuo to dryness. The residue was suspended in methanol (10 mL), filtered, and concentrated in vacuo to dryness. The residue was purified by reverse-phase HPLC, eluting with a 20-80% gradient of acetonitrile in water containing 0.1% formic acid to give the title compound as a yellow solid (0.022 g, 3% yield). MS (ES+) m/z 459.0 (M+1). $^1$H NMR (300 MHz, DMSO-$d_6$+1% $D_2O$) δ 8.33 (s, 1H), 7.85-7.82 (m, 1H), 7.49-7.46 (m, 2H), 7.36-7.24 (m, 4H), 7.01-7.00 (m, 1H), 4.28-4.22 (m, 1H), 3.79-3.54 (m, 6H), 3.38 (t, J=10.6 Hz, 1H), 2.27-2.22 (m, 1H), 2.03-1.97 (m, 1H), 1.88-1.80 (m, 1H), 1.21-1.18 (m, 1H) (Note: acidic proton not observed).

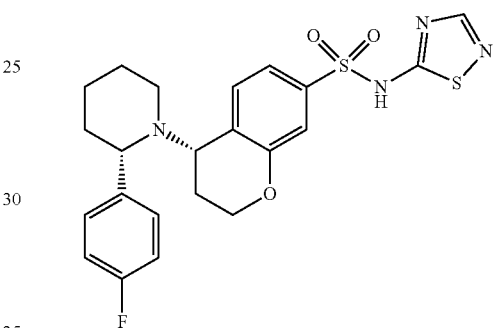

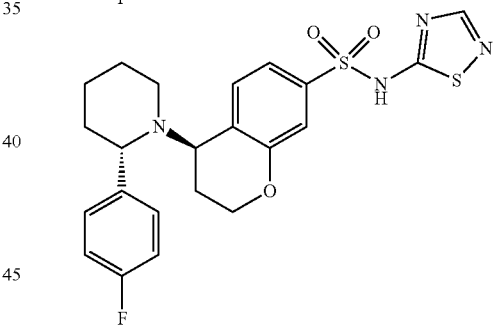

Example 76

(S)-4-((S)-2-(4-fluorophenyl)piperidin-1-yl)-N-(1,2,4-thiadiazol-5-yl)chromane-7-sulfonamide and (R)-4-((S)-2-(4-fluorophenyl)piperidin-1-yl)-N-(1,2,4-thiadiazol-5-yl)chromane-7-sulfonamide
(Stereochemistry Arbitrarily Assigned)

To a solution of (R)-7-(N-(2,4-dimethoxybenzyl)-N-(1,2,4-thiadiazol-5-yl)sulfamoyl)chroman-4-yl methanesulfonate (prepared according to Example 41, step 6, 0.15 g, 0.28 mmol) in ethyl acetate (3.0 mL) was added (S)-2-(4-fluorophenyl)piperidine (0.10 g, 0.56 mmol) and N,N-diisopropylethylamine (0.15 mL, 0.84 mmol). The mixture was heated to 80° C. After 20 h, the reaction was diluted with dichloromethane (10 mL) and water (10 mL). The organic layer was removed and the aqueous layer was extracted with dichloromethane (2×10 mL). The combined organic layers were dried over anhydrous sodium sulfate and filtered. The filtrate was concentrated in vacuo to dryness. The residue was dissolved in dichloromethane (8 mL) and cooled to 0° C. Trifluoroacetic acid (0.13 mL, 1.67 mmol) was slowly added to the cooled solution. After 2 h the reaction was concentrated in vacuo to dryness. The residue was suspended in methanol (5 mL), filtered, and concentrated in vacuo to dryness. The residue was purified by reverse-phase HPLC, eluting with a 20-80% gradient of acetonitrile in water containing 0.1% trifluoroacetic acid to afford two oils. The oils were separately dissolved in dichloromethane (10 mL) and washed with water (2×10 mL) and brine (2×10 mL), dried over anhydrous sodium sulfate and filtered. The filtrates were concentrated in vacuo to give the title compounds as trifluoroacetic acid salts.

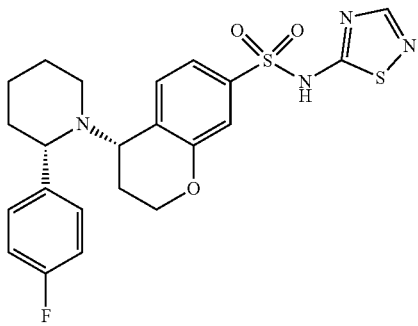 [SMILES: O=S(=O)(Nc1ncns1)c1ccc2c(c1)OCC[C@@H]2N1CCCC[C@H]1c1ccc(F)cc1]

(S)-4-((S)-2-(4-fluorophenyl)piperidin-1-yl)-N-(1,2,4-thiadiazol-5-yl)chromane-7-sulfonamide (Stereochemistry Arbitrarily Assigned)

Colorless solid (0.016 g, 12% yield). MS (ES+) m/z 475.0 (M+1). ¹H NMR (300 MHz, CDCl₃) δ 8.00 (s, 1H), 7.40-7.31 (m, 4H), 7.24-7.20 (m, 1H), 6.96 (t, J=8.7 Hz, 2H), 4.33-4.09 (m, 2H), 3.96-3.81 (m, 2H), 2.73-2.65 (m, 1H), 2.37-2.28 (m, 1H), 1.87-1.43 (m, 9H).

Example 77

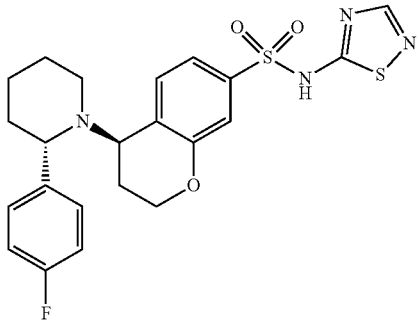 [SMILES: O=S(=O)(Nc1ncns1)c1ccc2c(c1)OCC[C@H]2N1CCCC[C@H]1c1ccc(F)cc1]

(R)-4-((S)-2-(4-fluorophenyl)piperidin-1-yl)-N-(1,2,4-thiadiazol-5-yl)chromane-7-sulfonamide (Stereochemistry Arbitrarily Assigned)

This compound was prepared in the same sequence as Example 76. Colorless solid (0.010 g, 7% yield). MS (ES+) m/z 475.0 (M+1). ¹H NMR (300 MHz, CDCl₃) δ 8.00 (s, 1H), 7.85-7.82 (m, 1H), 7.41-7.32 (m, 3H), 7.20-7.19 (m, 1H), 6.98 (t, J=8.7 Hz, 2H), 4.30-4.25 (m, 1H), 3.87-3.76 (m, 2H), 3.55-3.51 (m, 1H), 2.64-2.54 (m, 1H), 2.29-2.17 (m, 1H), 1.86-1.30 (m, 9H).

Example 78

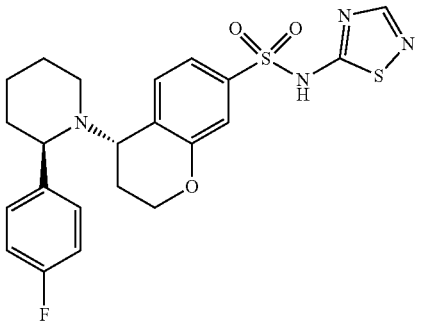 [SMILES: O=S(=O)(Nc1ncns1)c1ccc2c(c1)OCC[C@@H]2N1CCCC[C@@H]1c1ccc(F)cc1]

(S)-4-((R)-2-(4-fluorophenyl)piperidin-1-yl)-N-(1,2,4-thiadiazol-5-yl)chromane-7-sulfonamide (Stereochemistry Arbitrarily Assigned)

Following the procedure as described in Example 76 and making non-critical variations as required to replace (S)-2-(4-fluorophenyl)piperidine with (R)-2-(4-fluorophenyl)piperidine, the title compounds were obtained as trifluoroacetate salts. Colorless solid (0.008 g, 6% yield). MS (ES+) m/z 475.0 (M+1). ¹H NMR (300 MHz, CDCl₃) δ 7.99 (s, 1H), 7.38-7.32 (m, 4H), 7.24-7.20 (m, 1H), 7.02-6.93 (m, 2H), 4.27-4.09 (m, 1H), 3.95-3.81 (m, 3H), 2.74-2.61 (m, 1H), 2.19-1.48 (m, 10H).

Example 79

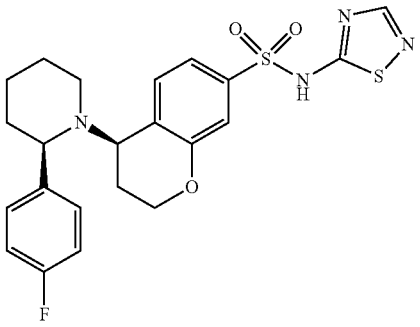 [SMILES: O=S(=O)(Nc1ncns1)c1ccc2c(c1)OCC[C@H]2N1CCCC[C@@H]1c1ccc(F)cc1]

(R)-4-((R)-2-(4-fluorophenyl)piperidin-1-yl)-N-(1,2,4-thiadiazol-5-yl)chromane-7-sulfonamide (Stereochemistry Arbitrarily Assigned)

This compound was prepared in the same sequence as Example 78. Colorless solid (0.010 g, 10% yield). MS (ES+) m/z 475.0 (M+1). ¹H NMR (300 MHz, CDCl₃) δ 7.99 (s, 1H), 7.84-7.81 (m, 1H), 7.42-7.31 (m, 3H), 7.19 (t, J=1.8 Hz, 1H), 7.00-6.95 (m, 2H), 4.30-4.24 (m, 1H), 3.85-3.74 (m, 2H), 3.54-3.50 (m, 1H), 2.62-2.55 (m, 1H), 2.27-2.18 (m, 1H), 1.85-1.31 (m, 9H).

Example 80

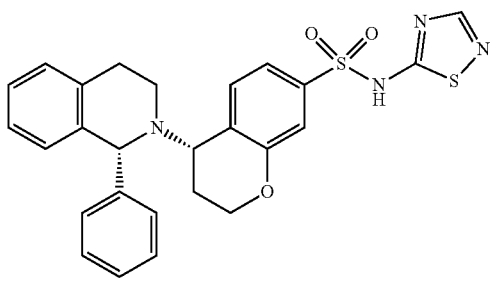 [SMILES: O=S(=O)(Nc1ncns1)c1ccc2c(c1)OCC[C@@H]2N1CCc2ccccc2[C@H]1c1ccccc1]

(S)-4-((R)-1-phenyl-3,4-dihydroisoquinolin-2(1H)-yl)-N-(1,2,4-thiadiazol-5-yl)chromane-7-sulfonamide (Stereochemistry at Chromane Arbitrarily Assigned)

Step 1

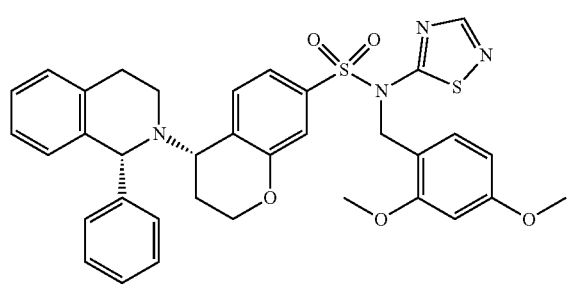 [SMILES: COc1ccc(CN(c2ncns2)S(=O)(=O)c2ccc3c(c2)OCC[C@@H]3N2CCc3ccccc3[C@H]2c2ccccc2)c(OC)c1]

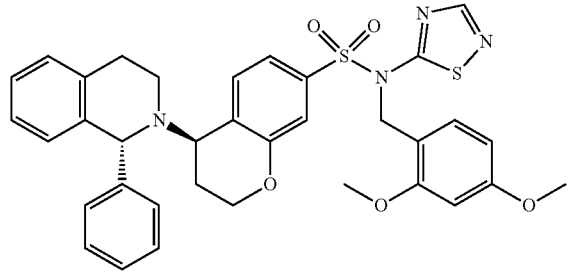 [SMILES: COc1ccc(CN(c2ncns2)S(=O)(=O)c2ccc3c(c2)OCC[C@H]3N2CCc3ccccc3[C@H]2c2ccccc2)c(OC)c1]

(S)—N-(2,4-dimethoxybenzyl)-4-((R)-1-phenyl-3,4-dihydroisoquinolin-2(1H)-yl)-N-(1,2,4-thiadiazol-5-yl)chromane-7-sulfonamide and (R)—N-(2,4-dimethoxybenzyl)-4-((R)-1-phenyl-3,4-dihydroisoquinolin-2(1H)-yl)-N-(1,2,4-thiadiazol-5-yl)chromane-7-sulfonamide To a solution of (R)-7-(N-(2,4-dimethoxybenzyl)-N-(1,2,4-thiadiazol-5-yl)sulfamoyl)chroman-4-yl methanesulfonate (prepared according to Example 41, step 6, 0.32 g, 0.60 mmol) in tetrahydrofuran (6.0 mL) was added (R)-1-phenyl-1,2,3,4-tetrahydroisoquinoline (0.25 g, 1.2 mmol) and N,N-diisopropylethylamine (0.31 mL, 1.8 mmol). The mixture was heated to 80° C. After 16 h, the reaction was diluted with dichloromethane (10 mL) and water (10 mL). The organic layer was removed and the aqueous layer was extracted with dichloromethane (2×10 mL). The combined organic layers were dried over anhydrous sodium sulfate and filtered. The filtrate was concentrated in vacuo to dryness. The residue was purified by column chromatography, eluting with 30% ethyl acetate in hexanes to afford the title compounds.

Diastereomer 1: (S)—N-(2,4-dimethoxybenzyl)-4-((R)-1-phenyl-3,4-dihydroisoquinolin-2(1H)-yl)-N-(1,2,4-thiadiazol-5-yl)chromane-7-sulfonamide (Stereochemistry at Chromane Arbitrarily Assigned)

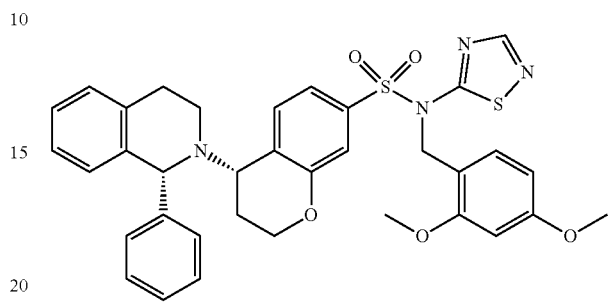

Colorless solid (0.100 g, 26% yield). MS (ES+) m/z 655.1 (M+1).

Diastereomer 2:

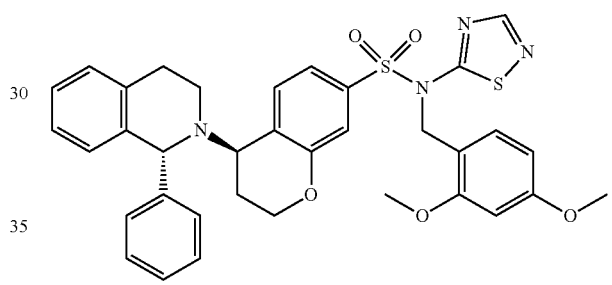

(R)—N-(2,4-dimethoxybenzyl)-4-((R)-1-phenyl-3,4-dihydroisoquinolin-2(1H)-yl)-N-(1,2,4-thiadiazol-5-yl)chromane-7-sulfonamide (Stereochemistry at Chromane Arbitrarily Assigned)

Yellow solid (0.070 g, 18% yield). MS (ES+) m/z 655.1 (M+1).

Step 2

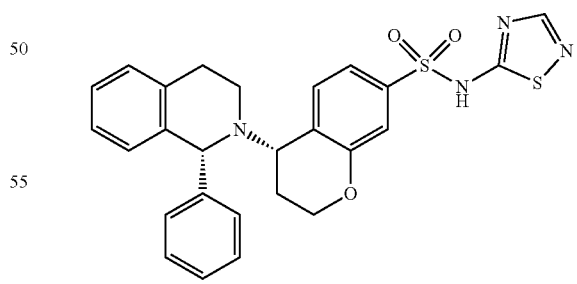

(S)-4-((R)-1-phenyl-3,4-dihydroisoquinolin-2(1H)-yl)-N-(1,2,4-thiadiazol-5-yl)chromane-7-sulfonamide (Stereochemistry at Chromane Arbitrarily Assigned)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (S)—N-(2,4-dimethoxybenzyl)-4-((R)-1-phenyl-3,4-dihydroisoquinolin-2(1H)-yl)-N-(1,2,4-thiadiazol-5-yl)chromane-7-sulfonamide, the title compound was obtained as a trifluoroacetate salt as a colorless solid (0.016 g, 21% yield). MS (ES+) m/z 505.0 (M+1). $^1$H NMR (300 MHz, DMSO-$d_6$) δ 8.49 (s, 1H), 7.73-7.70 (m, 1H), 7.31-7.26 (m, 6H), 7.22-7.15 (m, 2H), 7.10-7.07 (m, 2H), 6.83-6.81 (m, 1H), 5.32 (br s, 1H), 4.32-3.98 (m, 5H), 3.02-2.79 (m, 3H), 1.70-1.55 (m, 1H), 1.06-0.93 (m, 1H).

Example 81

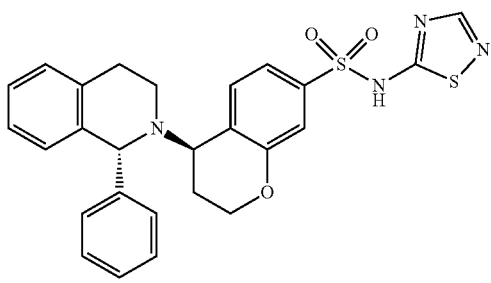 [SMILES: O=S(=O)(Nc1ncns1)c1ccc2c(c1)OCC[C@H]2N1CCc2ccccc2[C@H]1c1ccccc1]

(R)-4-((R)-1-phenyl-3,4-dihydroisoquinolin-2(1H)-yl)-N-(1,2,4-thiadiazol-5-yl)chromane-7-sulfonamide (Stereochemistry at Chromane Arbitrarily Assigned)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (R)—N-(2,4-dimethoxybenzyl)-4-((R)-1-phenyl-3,4-dihydroisoquinolin-2(1H)-yl)-N-(1,2,4-thiadiazol-5-yl)chromane-7-sulfonamide, the title compound was obtained as a trifluoroacetate salt as a colorless solid (0.005 g, 9% yield). MS (ES+) m/z 505.0 (M+1). $^1$H NMR (300 MHz, DMSO-$d_6$) δ 8.47 (s, 1H), 7.76-7.74 (m, 1H), 7.50-7.47 (m, 2H), 7.36-7.22 (m, 4H), 7.13-6.96 (m, 4H), 6.64-6.62 (m, 1H), 5.09 (s, 1H), 4.39-3.76 (m, 4H), 3.11-3.01 (m, 1H), 2.70-2.61 (m, 2H), 2.28-2.18 (m, 1H), 2.06-1.94 (m, 1H), 1.23-1.15 (m, 1H).

Example 82

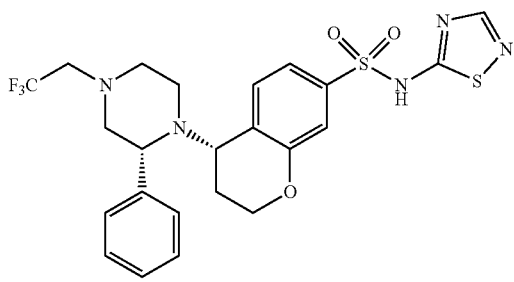

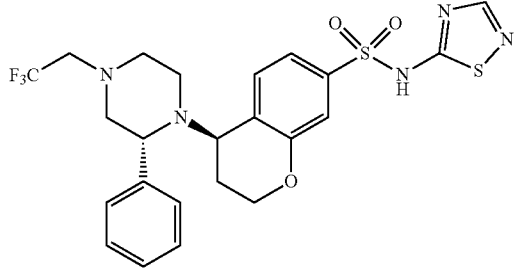

(S)-4-((R)-2-phenyl-4-(2,2,2-trifluoroethyl)piperazin-1-yl)-N-(1,2,4-thiadiazol-5-yl)chromane-7-sulfonamide and (R)-4-((R)-2-phenyl-4-(2,2,2-trifluoroethyl)piperazin-1-yl)-N-(1,2,4-thiadiazol-5-yl)chromane-7-sulfonamide (Stereochemistry at Chromane Arbitrarily Assigned)

Step 1

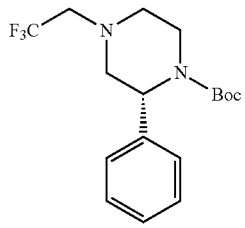

tert-butyl (R)-2-phenyl-4-(2,2,2-trifluoroethyl)piperazine-1-carboxylate

To a solution of tert-butyl (R)-2-phenylpiperazine-1-carboxylate (0.30 g, 1.14 mmol) in acetonitrile (6.0 mL) was added 2,2,2-trifluoroethyl trifluoromethanesulfonate (0.33 mL, 2.29 mmol) and potassium carbonate (0.32 g, 2.29 mmol). After stirring at ambient temperature for 16 h, the reaction was diluted with ethyl acetate (20 mL) and water (20 mL). The aqueous layer was removed and the organic layer was washed with water (10 mL), brine (10 mL), dried over anhydrous sodium sulfate and filtered. The filtrate was concentrated in vacuo to dryness to afford the title compound as a colorless oil (0.389 g, 99% yield). MS (ES+) m/z 345.1 (M+1). $^1$H NMR (300 MHz, CDCl$_3$) δ 7.53-7.50 (m, 2H), 7.36-7.27 (m, 3H), 5.27-5.26 (m, 1H), 3.92-3.87 (m, 1H), 3.48-3.42 (m, 1H), 3.06-2.96 (m, 3H), 2.90-2.81 (m, 2H), 2.58-2.50 (m, 1H), 1.48 (s, 9H); $^{19}$F NMR (282 MHz, CDCl$_3$): δ −68.6 (s, 3F).

Step 2

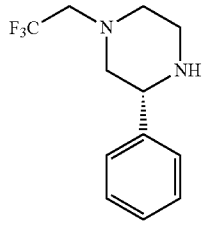

(R)-3-phenyl-1-(2,2,2-trifluoroethyl)piperazine

To a solution of tert-butyl (R)-2-phenyl-4-(2,2,2-trifluoroethyl)piperazine-1-carboxylate (0.39 g, 1.1 mmol) in dichloromethane (1.9 mL) was added trifluoroacetic acid (0.94 mL, 12.3 mmol). After stirring at ambient temperature for 1 h, the reaction was concentrated in vacuo to dryness. The residue was dissolved in dichloromethane (10 mL), washed with saturated aqueous sodium bicarbonate (2×20 mL), dried over anhydrous sodium sulfate and filtered. The filtrate was concentrated in vacuo to give title compound as a yellow oil (0.249 g, 90% yield). MS (ES+) m/z 245.1 (M+1). $^1$H NMR (300 MHz, CDCl$_3$) δ 7.41-7.27 (m, 5H), 3.89 (dd, J=2.7, 10.1 Hz, 1H), 3.10-2.92 (m, 6H), 2.60-2.51 (m, 1H), 2.44-2.36 (m, 1H), 1.86 (br s, 1H); $^{19}$F NMR (282 MHz, CDCl$_3$): δ −68.8 (s, 3F).

Step 3

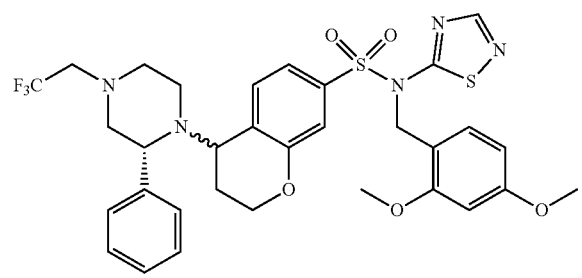 [SMILES: COc1ccc(CN(c2ncns2)S(=O)(=O)c2ccc3c(c2)OCCC3N2CCN(CC(F)(F)F)C[C@H]2c2ccccc2)c(OC)c1]

N-(2,4-dimethoxybenzyl)-4-((R)-2-phenyl-4-(2,2,2-trifluoroethyl)piperazin-1-yl)-N-(1,2,4-thiadiazol-5-yl)chromane-7-sulfonamide Following the procedure as described in Example 80, step 1 and making non-critical variations as required to replace (R)-1-phenyl-1,2,3,4-tetrahydroisoquinoline with (R)-3-phenyl-1-(2,2,2-trifluoroethyl)piperazine, the title compound was obtained as a colorless solid (0.185 g, 35% yield). MS (ES+) m/z 690.1 (M+1). $^1$H NMR (300 MHz, CDCl$_3$) δ 8.14-8.13 (m, 1H), 7.78-7.74 (m, 0.5H), 7.46-7.27 (m, 5H), 7.14-7.02 (m, 2H), 6.97-6.94 (m, 0.5H), 6.41-6.28 (m, 3H), 5.96-5.90 (m, 1H), 5.18-5.17 (m, 2H), 4.90-4.88 (m, 1H), 3.94-3.81 (m, 3H), 3.76-3.74 (m, 6H), 3.03-2.84 (m, 5H), 2.65-2.52 (m, 4H).

Step 4

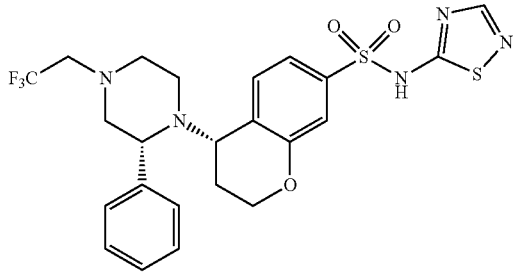 [SMILES: O=S(=O)(Nc1ncns1)c1ccc2c(c1)OCC[C@@H]2N1CCN(CC(F)(F)F)C[C@H]1c1ccccc1]

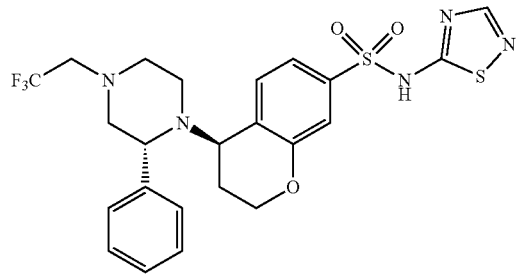 [SMILES: O=S(=O)(Nc1ncns1)c1ccc2c(c1)OCC[C@H]2N1CCN(CC(F)(F)F)C[C@H]1c1ccccc1]

(S)-4-((R)-2-phenyl-4-(2,2,2-trifluoroethyl)piperazin-1-yl)-N-(1,2,4-thiadiazol-5-yl)chromane-7-sulfonamide and (R)-4-((R)-2-phenyl-4-(2,2,2-trifluoroethyl)piperazin-1-yl)-N-(1,2,4-thiadiazol-5-yl)chromane-7-sulfonamide (Stereochemistry at Chromane Arbitrarily Assigned)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with N-(2,4-dimethoxybenzyl)-4-((R)-2-phenyl-4-(2,2,2-trifluoroethyl)piperazin-1-yl)-N-(1,2,4-thiadiazol-5-yl)chromane-7-sulfonamide, the title compounds were obtained as trifluoroacetate salts.

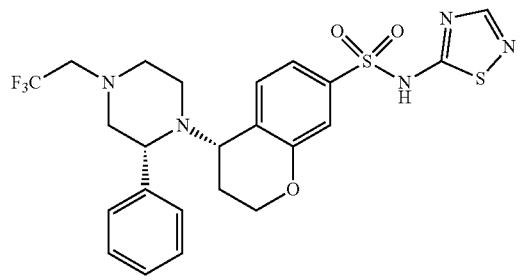

(S)-4-((R)-2-phenyl-4-(2,2,2-trifluoroethyl)piperazin-1-yl)-N-(1,2,4-thiadiazol-5-yl)chromane-7-sulfonamide (Stereochemistry at Chromane Arbitrarily Assigned)

Colorless solid (0.032 g, 22% yield). MS (ES+) m/z 540.0 (M+1). $^1$H NMR (300 MHz, DMSO-d$_6$) δ 8.49 (s, 1H), 7.61-7.56 (m, 3H), 7.36-7.25 (m, 4H), 7.04-7.03 (m, 1H), 4.26-4.18 (m, 3H), 3.27-3.05 (m, 4H), 2.88-2.83 (m, 2H), 2.75-2.60 (m, 2H), 2.04-1.69 (m, 2H), 1.27-1.22 (m, 2H).

Example 83

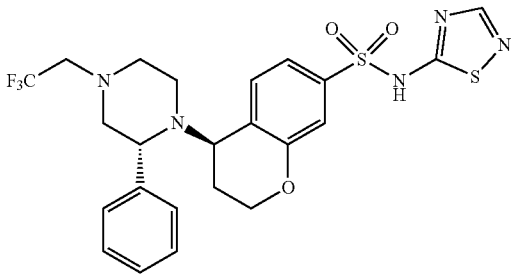

(R)-4-((R)-2-phenyl-4-(2,2,2-trifluoroethyl)piperazin-1-yl)-N-(1,2,4-thiadiazol-5-yl)chromane-7-sulfonamide (Stereochemistry at Chromane Arbitrarily Assigned)

This compound was produced in the same sequence as Example 82. Colorless solid (0.038 g, 26% yield). MS (ES+) m/z 540.0 (M+1). ¹H NMR (300 MHz, DMSO-d₆) δ 8.48 (s, 1H), 7.82-7.79 (m, 1H), 7.52-7.50 (m, 2H), 7.38-7.26 (m, 4H), 7.04-7.03 (m, 1H), 4.29-4.23 (m, 2H), 3.87-3.71 (m, 4H), 3.27-3.15 (m, 2H), 2.89-2.86 (m, 2H), 2.38-2.31 (m, 2H), 2.05-1.81 (m, 3H).

Example 84

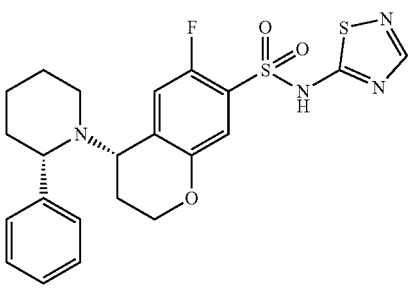

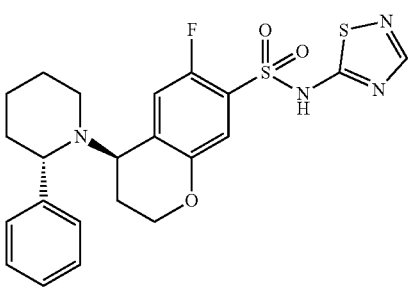

(S)-6-fluoro-4-((S)-2-phenylpiperidin-1-yl)-N-(1,2,4-thiadiazol-5-yl)chromane-7-sulfonamide and (R)-6-fluoro-4-((S)-2-phenylpiperidin-1-yl)-N-(1,2,4-thiadiazol-5-yl)chromane-7-sulfonamide (Stereochemistry at Chromane Arbitrarily Assigned)

Step 1

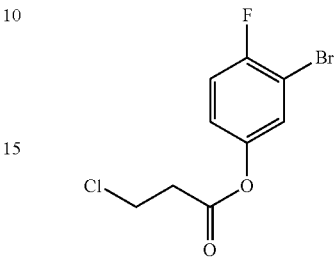

3-bromo-4-fluorophenyl 3-chloropropanoate

To a solution of 3-bromo-4-fluorophenol (4.00 g, 20.9 mmol) in anhydrous dichloromethane (75 mL) at −50° C. was added aluminum chloride (4.20 g, 31.4 mmol). 3-Chloropropanoyl chloride (3.00 mL, 31.4 mmol) was added dropwise and the reaction mixture was stirred overnight while warming to ambient temperature. The reaction was quenched with brine (50 mL) and was extracted with dichloromethane (3×75 mL). The combined organic layers were dried over anhydrous magnesium sulfate, filtered and concentrated in vacuo. The residue was purified by column chromatography, eluting with a 0 to 50% gradient of ethyl acetate in hexanes to afford the title compound as a pale yellow oil (4.3 g, 71% yield). ¹H NMR (300 MHz, CDCl₃) δ 7.37 (dd, J=2.7, 5.7 Hz, 1H), 7.14 (q, J=8.7 Hz, 1H), 7.07 (dq, J=2.1, 6.8 Hz, 1H), 3.88 (t, J=6.5 Hz, 2H), 3.06 (t, J=6.5 Hz, 2H).

Step 2

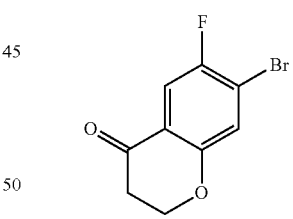

7-bromo-6-fluorochroman-4-one

To a flask containing 3-bromo-4-fluorophenyl 3-chloropropanoate (2.30 g, 8.1 mmol) was added trifluoromethane sulfonic acid (4.50 mL, 50.9 mmol). The reaction was heated to 85° C. for 1 h. The reaction mixture was cooled to 0° C., water (50 mL) was slowly added, and the solution was extracted with dichloromethane (3×50 mL). The combined organic extracts were dried over anhydrous magnesium sulfate, filtered and concentrated in vacuo to afford a tan solid (1.8 g, 90% yield). ¹H NMR (300 MHz, DMSO-d₆) δ 7.59 (d, J=8.4 Hz, 1H), 7.54 (d, J=5.6 Hz, 1H), 4.57 (t, J=6.5 Hz, 2H), 2.82 (t, J=6.5 Hz, 2H).

Step 3

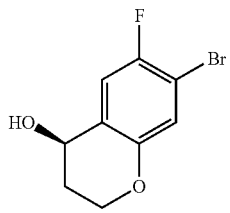 [SMILES: O[C@@H]1CCOc2cc(Br)c(F)cc21]

(R)-7-bromo-6-fluorochroman-4-ol

To a solution of (S)-1-methyl-3,3-diphenyl-tetrahydropyrrolo[1,2c][1,3,2]oxazaborole (1 M in toluene, 0.73 mL, 0.73 mmol) in anhydrous tetrahydrofuran (15 mL) was added borane dimethyl sulfide complex (0.76 mL, 8.04 mmol). The resulting solution was stirred at room temperature for 30 minutes, after which a solution of 7-bromo-6-fluorochroman-4-one (1.79 g, 7.31 mmol) in anhydrous tetrahydrofuran (15 mL) was added dropwise. After 30 minutes, the reaction was quenched with the addition of methanol (20 mL) and concentrated in vacuo to half volume. The resulting solution was diluted with water (50 mL) and extracted with DCM (2×50 mL). The combined organic extracts were washed with 1 M hydrochloric acid (50 mL), brine (50 mL) and water (50 mL), then dried over anhydrous magnesium sulfate. After filtration and concentration in vacuo, the residue was purified by column chromatography, eluting with a 0 to 10% gradient of ethyl acetate in hexanes to provide the title compound as a colorless solid (1.34 g, 74% yield). $^1$H NMR (300 MHz, CDCl$_3$) δ 7.09 (d, J=8.5 Hz, 1H), 7.03 (d, J=5.9 Hz, 1H), 4.78-4.68 (m, 1H), 4.24-4.21 (m, 2H), 2.13-1.97 (m, 2H), 1.87-1.80 (m, 1H).

Step 4

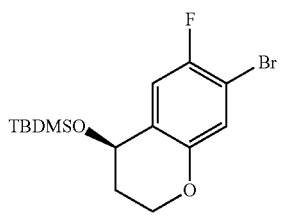 [SMILES: CC(C)(C)[Si](C)(C)O[C@@H]1CCOc2cc(Br)c(F)cc21]

(R)-((7-bromo-6-fluorochroman-4-yl)oxy)(tert-butyl)dimethylsilane

Following the procedure as described in Example 37, step 2 and making non-critical variations as required to replace 7-bromochaoman-4-ol with (R)-7-bromo-6-fluorochroman-4-ol, the title compound was obtained as a colorless oil (1.78 g, 91% yield). $^1$H NMR (300 MHz, CDCl$_3$): δ 7.02-6.97 (m, 2H), 4.73 (t, J=5.0 Hz, 1H), 4.34-4.17 (m, 2H), 2.11-1.92 (m, 2H), 0.93 (s, 9H), 0.18 (s, 6H).

Step 5

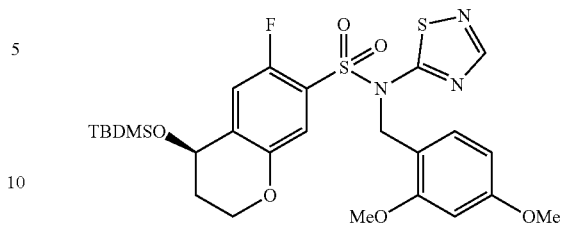

(R)-4-((tert-butyldimethylsilyl)oxy)-N-(2,4-dimethoxybenzyl)-6-fluoro-N-(1,2,4-thiadiazol-5-yl)chromane-7-sulfonamide To a solution of (R)-((7-bromo-6-fluorochroman-4-yl)oxy)(tert-butyl)dimethylsilane (4.40 g, 12.20 mmol) in anhydrous tetrahydrofuran (24 mL) at −78° C. was added a solution of n-butyl lithium (1.6 M in hexanes, 9.20 mL, 14.60 mmol) dropwise over 10 minutes. The reaction mixture was then treated with condensed liquid sulfur dioxide (1.5 mL, 37 mmol) and stirred for 15 minutes, after which it was warmed to ambient temperature for 30 minutes. The mixture was then concentrated in vacuo. The residue was dissolved in heptane (53 mL) and cooled to 0° C. to which sulfuryl chloride (1.20 mL, 14.6 mmol) was added dropwise. After stirring for 1 h at 0° C., and the mixture was concentrated in vacuo to give crude (R)-4-((tert-butyldimethylsilyl)oxy)-6-fluorochromane-7-sulfonyl chloride as a pale yellow solid. A solution of lithium (2,4-dimethoxybenzyl)(1,2,4-thiadiazol-5-yl)amide (synthesized by treating a solution of N-(2,4-dimethoxybenzyl)-1,2,4-thiadiazol-5-amine (3.36 g, 13.40 mmol) in THF (40 mL) with lithium bis(trimethylsilyl)amide (1.0 M in THF, 14.6 mL, 14.6 mmol) at 0° C. for 1 h) was then added dropwise to a solution of (R)-4-((tert-butyldimethylsilyl)oxy)-6-fluorochromane-7-sulfonyl chloride in THF (40 mL) at −78° C. The reaction mixture stirred at ambient temperature for 16 h, then was quenched with saturated aqueous ammonium chloride (50 mL) and extracted with ethyl acetate (3×50 mL). The combined organic extracts were washed with brine (50 mL), dried over anhydrous magnesium sulfate, and concentrated in vacuo. The residue was purified by column chromatography, eluting with a 10 to 65% gradient of ethyl acetate in hexanes to afford the title compound as a colorless solid (3.46 g, 48% yield). MS (ES+) m/z 596.1 (M+1). $^1$H NMR (300 MHz, CDCl$_3$) δ 8.18 (s, 1H), 7.18 (d, J=8.4 Hz, 1H), 7.13 (d, J=5.7 Hz, 1H), 6.95 (d, J=10.1 Hz, 1H), 6.35 (dd, J=2.4, 8.4 Hz, 1H), 6.20 (d, J=2.3 Hz, 1H), 5.30 (q, J=18.6 Hz, 2H), 4.70 (t, J=5.7 Hz, 1H), 4.32-4.19 (m, 2H), 3.75 (s, 3H), 3.69 (s, 3H), 2.07-1.96 (m, 2H), 0.92 (s, 9H), 0.15 (s, 6H).

Step 6

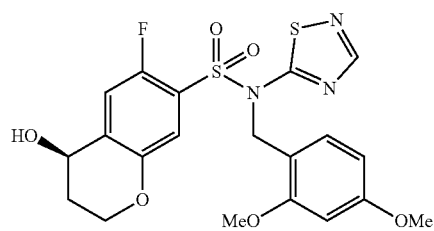 [SMILES: COc1ccc(CN(c2ncns2)S(=O)(=O)c2cc3c(cc2F)[C@H](O)CCO3)c(OC)c1]

(R)—N-(2,4-dimethoxybenzyl)-6-fluoro-4-hydroxy-N-(1,2,4-thiadiazol-5-yl)chromane-7-sulfonamide Following the procedure as described in Example 41, step 5 and making non-critical variations as required to replace (R)-4-((tert-butyldimethylsilyl)oxy)-N-(2,4-dimethoxybenzyl)-N-(1,2,4-thiadiazol-5-yl)chromane-7-sulfonamide with (R)-4-((tert-butyldimethylsilyl)oxy)-N-(2,4-dimethoxybenzyl)-6-fluoro-N-(1,2,4-thiadiazol-5-yl)chromane-7-sulfonamide, the title compound was obtained as a colorless solid (4.71 g, 90% yield). MS (ES+) m/z 482.0 (M+1). $^1$H NMR (300 MHz, CDCl$_3$) δ 8.22 (s, 1H), 7.22 (t, J=7.5 Hz, 2H), 7.00 (d, J=9.8 Hz, 1H), 6.34 (dd, J=2.4, 8.4 Hz, 1H), 6.16 (d, J=2.4 Hz, 1H), 5.36 (q, J=20.3 Hz, 2H), 4.72 (q, J=5.4 Hz, 1H), 4.30-4.26 (m, 2H), 3.78 (s, 3H), 3.71 (s, 3H), 2.21-2.13 (m, 2H), 2.06-2.00 (m, 1H).
Step 7

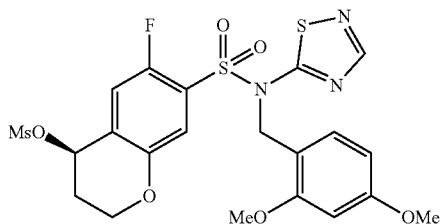 [SMILES: COc1ccc(CN(c2ncns2)S(=O)(=O)c2cc3c(cc2F)[C@H](OS(C)(=O)=O)CCO3)c(OC)c1]

(R)-7-(N-(2,4-dimethoxybenzyl)-N-(1,2,4-thiadiazol-5-yl)sulfamoyl)-6-fluorochroman-4-yl methanesulfonate Following the procedure as described in Example 41, step 6 and making non-critical variations as required to replace (R)—N-(2,4-dimethoxybenzyl)-4-hydroxy-N-(1,2,4-thiadiazol-5-yl)chromane-7-sulfonamide with (R)—N-(2,4-dimethoxybenzyl)-6-fluoro-4-hydroxy-N-(1,2,4-thiadiazol-5-yl)chromane-7-sulfonamide, the title compound was obtained and was used in the subsequent step without any purification or further characterization.
Step 8

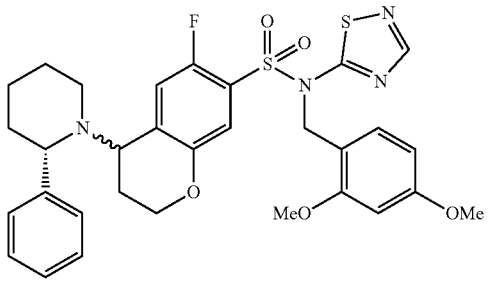 [SMILES: COc1ccc(CN(c2ncns2)S(=O)(=O)c2cc3c(cc2F)C(N2CCCC[C@H]2c2ccccc2)CCO3)c(OC)c1]

N-(2,4-dimethoxybenzyl)-6-fluoro-4-((S)-2-phenylpiperidin-1-yl)-N-(1,2,4-thiadiazol-5-yl)chromane-7-sulfonamide Following the procedure as described in Example 80, Step 1 and making non-critical variations as required to replace (R)-7-(N-(2,4-dimethoxybenzyl)-N-(1,2,4-thiadiazol-5-yl)sulfamoyl)chroman-4-yl methanesulfonate with (R)-7-(N-(2,4-dimethoxybenzyl)-N-(1,2,4-thiadiazol-5-yl)sulfamoyl)-6-fluorochroman-4-yl methanesulfonate and (R)-1-phenyl-1,2,3,4-tetrahydroisoquinoline with (S)-2-phenylpiperidine, the title compound was obtained as a yellow syrup (0.49 g, 36% yield). MS (ES+) m/z 625.2 (M+1). $^1$H NMR (300 MHz, CDCl$_3$) δ 8.20 (s, 1H), 7.38-7.31 (m, 4H), 7.27-7.24 (m, 1H), 7.19-7.01 (m, 3H), 6.44-6.28 (m, 1H), 6.23 (dd, J=2.3, 10.7 Hz, 1H), 5.37-5.24 (m, 2H), 4.25-4.20 (m, 1H), 3.87-3.85 (m, 2H), 3.75 (s, 3H), 3.70 (s, 3H), 2.75-2.54 (m, 1H), 2.16-2.09 (m, 1H), 1.86-1.74 (m, 3H), 1.67-1.65 (m, 2H), 1.52-1.25 (m, 4H).
Step 9

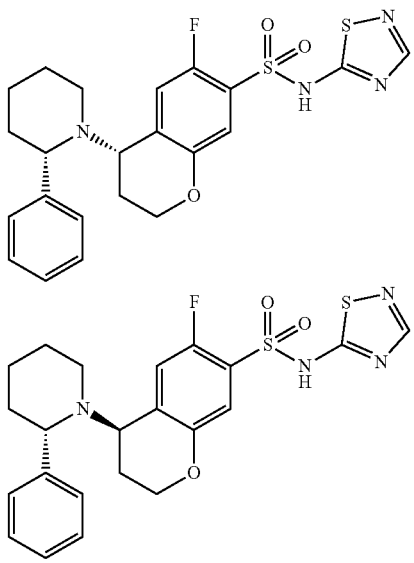

(S)-6-fluoro-4-((S)-2-phenylpiperidin-1-yl)-N-(1,2,4-thiadiazol-5-yl)chromane-7-sulfonamide and (R)-6-fluoro-4-((S)-2-phenylpiperidin-1-yl)-N-(1,2,4-thiadiazol-5-yl)chromane-7-sulfonamide
(Stereochemistry at Chromane Arbitrarily Assigned)

Following the procedure as described in Example 51, Step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with N-(2,4-dimethoxybenzyl)-6-fluoro-4-((S)-2-phenylpiperidin-1-yl)-N-(1,2,4-thiadiazol-5-yl)chromane-7-sulfonamide, the title compounds were obtained.

(S)-6-fluoro-4-((S)-2-phenylpiperidin-1-yl)-N-(1,2,4-thiadiazol-5-yl)chromane-7-sulfonamide (Stereochemistry at Chromane Arbitrarily Assigned)

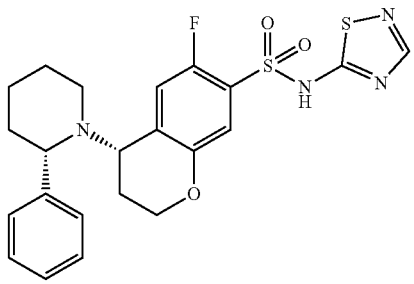 [SMILES: O=S(=O)(Nc1ncns1)c1cc2c(cc1F)[C@@H](N1CCCC[C@H]1c1ccccc1)CCO2]

Colorless solid (0.15 g, 37% yield). MS (ES+) m/z 475.1 (M+1). $^1$H NMR (300 MHz, DMSO-d$_6$) δ 8.29 (s, 1H), 7.48 (d, J=7.3 Hz, 2H), 7.31 (t, J=6.9 Hz, 3H), 7.26-7.18 (m, 1H), 7.03 (d, J=6.1 Hz, 1H), 4.24-4.11 (m, 2H), 4.11-4.00 (m, 1H), 3.95-3.85 (m, 1H), 2.90-2.83 (m, 1H), 2.42-2.29 (m, 1H), 2.09-1.94 (m, 1H), 1.88-1.80 (m, 1H), 1.74-1.57 (m, 5H), 1.50-1.35 (m, 1H) (Note: exchangeable proton not observed); $^{19}$F NMR (282 MHz, DMSO-d$_6$) δ −120.6 (s, 1F).

Example 85

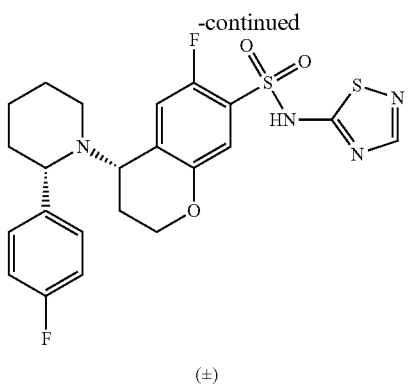

(±)

(±)-(S)-6-fluoro-4-((R)-2-(4-fluorophenyl)piperidin-1-yl)-N-(1,2,4-thiadiazol-5-yl)chromane-7-sulfonamide and (±)-(S)-6-fluoro-4-((S)-2-(4-fluorophenyl)piperidin-1-yl)-N-(1,2,4-thiadiazol-5-yl)chromane-7-sulfonamide (Mixture of Enantiomers; Stereochemistry is Arbitrarily Assigned)

Step 1

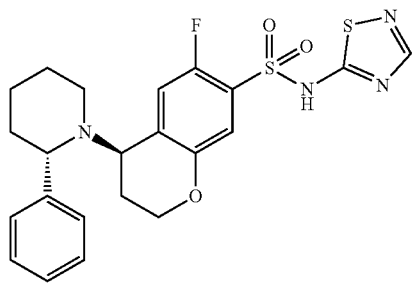 [SMILES: O=S(=O)(Nc1ncns1)c1cc2c(cc1F)[C@H](N1CCCC[C@H]1c1ccccc1)CCO2]

(R)-6-fluoro-4-((S)-2-phenylpiperidin-1-yl)-N-(1,2,4-thiadiazol-5-yl)chromane-7-sulfonamide (Stereochemistry at Chromane Arbitrarily Assigned)

This compound was prepared in the same sequence as Example 84. Colorless solid (0.107 g, 25% yield). MS (ES+) m/z 475.0 (M+1). $^1$H NMR (300 MHz, CDCl$_3$) δ 8.09 (s, 1H), 7.39 (d, J=7.3 Hz, 2H), 7.34-7.21 (m, 4H), 7.06 (d, J=10.6 Hz, 1H), 4.26-4.19 (m, 1H), 3.95-3.77 (m, 4H), 2.75 (d, J=11.7 Hz, 1H), 2.19-2.09 (m, 2H), 1.84-1.75 (m, 3H), 1.70-1.55 (m, 3H) (Note: exchangeable proton not observed); $^{19}$F NMR (282 MHz, CDCl$_3$) δ −120.93 (s, 1F).

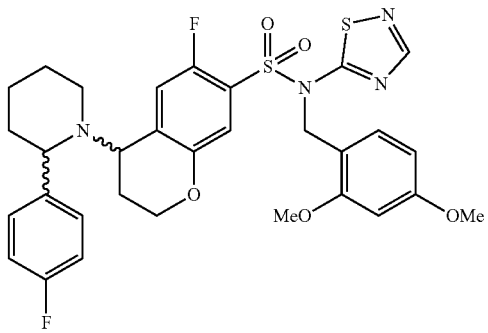 [SMILES: COc1ccc(CN(c2ncns2)S(=O)(=O)c2cc3c(cc2F)C(N2CCCCC2c2ccc(F)cc2)CCO3)c(OC)c1]

N-(2,4-dimethoxybenzyl)-6-fluoro-4-(2-(4-fluorophenyl)piperidin-1-yl)-N-(1,2,4-thiadiazol-5-yl)chromane-7-sulfonamide Following the procedure as described in Example 80, step 1 and making non-critical variations as required to replace (R)-1-phenyl-1,2,3,4-tetrahydroisoquinoline with 2-(4-fluorophenyl)piperidine and (R)-7-(N-(2,4-dimethoxybenzyl)-N-(1,2,4-thiadiazol-5-yl)sulfamoyl)chroman-4-yl methanesulfonate with (R)-7-(N-(2,4-dimethoxybenzyl)-N-(1,2,4-thiadiazol-5-yl)sulfamoyl)-6-fluorochroman-4-yl methanesulfonate, the title compound was obtained as a colorless solid (0.15 g, 27% yield). MS (ES+) m/z 643.1 (M+1). $^1$H NMR (300 MHz, CDCl$_3$) δ 8.19 (s, 1H), 7.40-7.34 (m, 2H), 7.19-7.11 (m, 2H), 7.07-6.97 (m, 3H), 6.38-6.32 (m, 1H), 6.24 (dd, J=2.3, 5.2 Hz, 1H), 5.32-5.30 (m, 2H), 4.29-4.20 (m, 1H), 3.84-3.80 (m, 2H), 3.74 (s, 3H), 3.72 (s, 3H), 2.72-2.54 (m, 1H), 2.14-2.07 (m, 1H), 1.85-1.77 (m, 3H), 1.70-1.48 (m, 5H), 1.44-1.37 (m, 1H).

Example 86

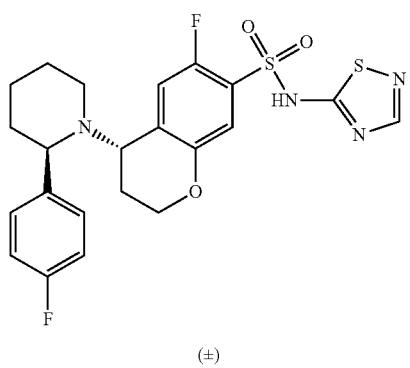 [SMILES: O=S(=O)(Nc1ncns1)c1cc2c(cc1F)[C@@H](N1CCCC[C@@H]1c1ccc(F)cc1)CCO2]

(±)

Step 2

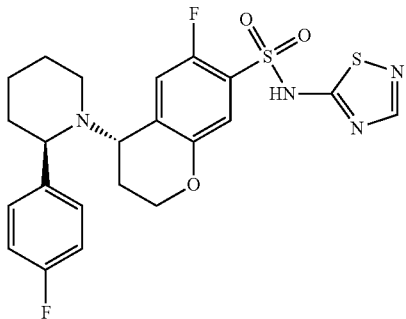
(±)

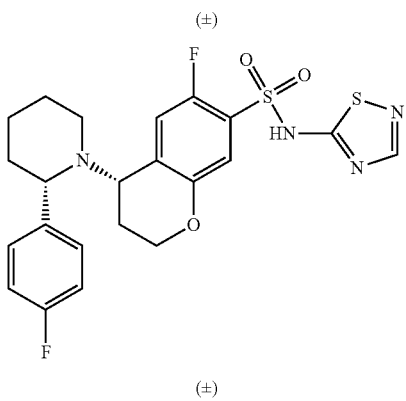
(±)

(±)-(S)-6-fluoro-4-((R)-2-(4-fluorophenyl)piperidin-1-yl)-N-(1,2,4-thiadiazol-5-yl)chromane-7-sulfonamide and (±)-(S)-6-fluoro-4-((S)-2-(4-fluorophenyl)piperidin-1-yl)-N-(1,2,4-thiadiazol-5-yl)chromane-7-sulfonamide (Mixture of Enantiomers; Stereochemistry is Arbitrarily Assigned)

Following the procedure as described in Example 51, Step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with N-(2,4-dimethoxybenzyl)-6-fluoro-4-(2-(4-fluorophenyl)piperidin-1-yl)-N-(1,2,4-thiadiazol-5-yl)chromane-7-sulfonamide, the title compounds were obtained as partial formate salts.

(±)-(S)-6-fluoro-4-((R)-2-(4-fluorophenyl)piperidin-1-yl)-N-(1,2,4-thiadiazol-5-yl)chromane-7-sulfonamide (Stereochemistry Arbitrarily Assigned; Mixture of Enantiomers)

Colorless solid (0.020 g, 24% yield). MS (ES+) m/z 493.0 (M+1). $^1$H NMR (300 MHz, DMSO-$d_6$) δ 8.26 (s, 1H), 8.14 (s, 0.2H), 7.51 (t, J=6.9 Hz, 2H), 7.29-7.26 (m, 1H), 7.13 (t, J=8.8 Hz, 2H), 7.02 (d, J=6.1 Hz, 1H), 6.56 (br s, 1H), 4.14 (m, 2H), 3.97-3.85 (m, 2H), 2.82-2.75 (m, 1H), 2.29-2.24 (m, 1H), 2.02-1.93 (m, 1H), 1.82-1.57 (m, 6H), 1.41-1.35 (m, 1H) (Note: exchangeable proton not observed); $^{19}$F NMR (282 MHz, CDCl$_3$) δ −120.7 (s, 1F).

Example 87

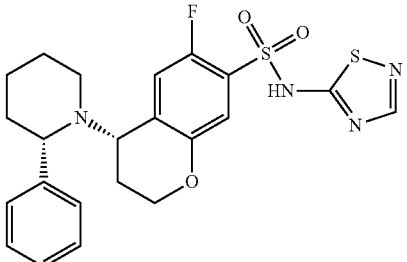
(±)

(±)-(S)-6-fluoro-4-((S)-2-(4-fluorophenyl)piperidin-1-yl)-N-(1,2,4-thiadiazol-5-yl)chromane-7-sulfonamide (Stereochemistry Arbitrarily Assigned; Mixture of Enantiomers)

This compound was prepared in the same sequence as Example 86. Colorless solid (0.022 g, 26% yield). MS (ES+) m/z 493.0 (M+1). $^1$H NMR (300 MHz, CDCl$_3$) δ 8.31 (s, 1H), 8.17 (s, 0.4H), 7.49 (t, J=7.7 Hz, 3H), 7.15 (t, J=8.8 Hz, 2H), 7.03 (d, J=5.9 Hz, 2H), 6.57 (br s, 1H), 4.26-4.20 (m, 1H), 3.78 (t, J=10.7 Hz, 1H), 3.65-3.60 (m, 2H), 2.45-2.40 (m, 1H), 2.35-2.19 (m, 1H), 1.97 (q, J=10.9 Hz, 1H), 1.82-1.23 (m, 6H) (Note: exchangeable proton not observed); $^{19}$F NMR (282 MHz, CDCl$_3$) δ −121.3 (s, 1F).

Example 88

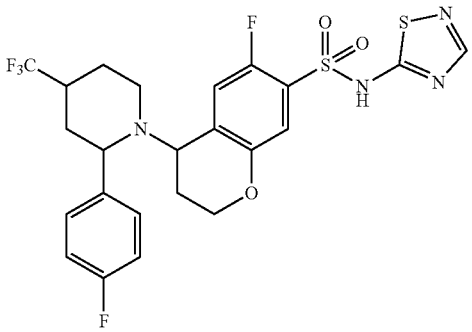 [SMILES: O=S(=O)(Nc1ncns1)c1cc2c(cc1F)C(N1CCC(C(F)(F)F)CC1c1ccc(F)cc1)CCO2]

6-fluoro-4-(cis-2-(4-fluorophenyl)-4-(trifluoromethyl)piperidin-1-yl)-N-(1,2,4-thiadiazol-5-yl)chromane-7-sulfonamide (Mixture of Two Sets of Enantiomers; 4-F-pH and CF₃ are Cis)

Step 1

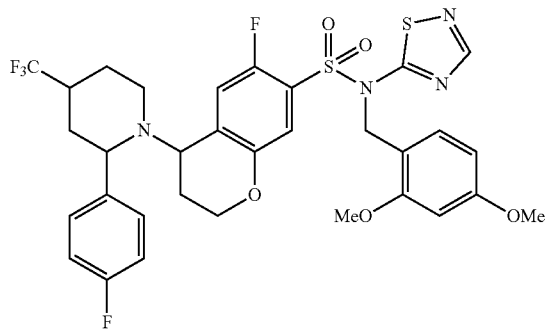 [SMILES: COc1ccc(CN(c2ncns2)S(=O)(=O)c2cc3c(cc2F)C(N2CCC(C(F)(F)F)CC2c2ccc(F)cc2)CCO3)c(OC)c1]

N-(2,4-dimethoxybenzyl)-6-fluoro-4-(cis-2-(4-fluorophenyl)-4-(trifluoromethyl)piperidin-1-yl)-N-(1,2,4-thiadiazol-5-yl)chromane-7-sulfonamide Following the procedure as described in Example 80, step 1 and making non-critical variations as required to replace (R)-1-phenyl-1,2,3,4-tetrahydroisoquinoline with (cis)-2-(4-fluorophenyl)-4-trifluoromethylpiperidine and (R)-7-(N-(2,4-dimethoxybenzyl)-N-(1,2,4-thiadiazol-5-yl)sulfamoyl)chroman-4-yl methanesulfonate with (R)-7-(N-(2,4-dimethoxybenzyl)-N-(1,2,4-thiadiazol-5-yl)sulfamoyl)-6-fluorochroman-4-yl methanesulfonate, the title compound was obtained as a colorless solid contaminated with (cis)-2-(4-fluorophenyl)-4-trifluoromethyl-piperidine (0.80 g crude). MS (ES+) m/z 711.1 (M+1).

Step 2

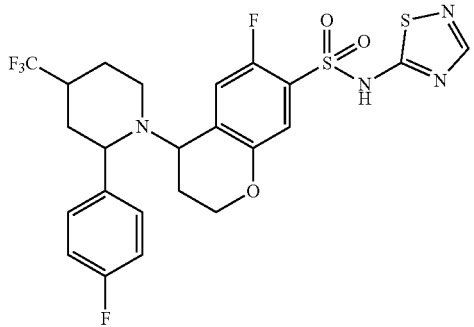 [SMILES: O=S(=O)(Nc1ncns1)c1cc2c(cc1F)C(N1CCC(C(F)(F)F)CC1c1ccc(F)cc1)CCO2]

6-fluoro-4-(cis-2-(4-fluorophenyl)-4-(trifluoromethyl)piperidin-1-yl)-N-(1,2,4-thiadiazol-5-yl)chromane-7-sulfonamide (Mixture of Two Racemic Diastereomers; Ph and CF₃ are Cis)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with N-(2,4-dimethoxybenzyl)-6-fluoro-4-(cis-2-(4-fluorophenyl)-4-(trifluoromethyl)piperidin-1-yl)-N-(1,2,4-thiadiazol-5-yl)chromane-7-sulfonamide, the title compound was obtained as a trifluoroacetate salt (0.35 g, 46% yield). MS (ES+) m/z 561.0 (M+1). ¹H NMR (300 MHz, DMSO-d₆) δ 8.55 (s, 1H), 7.58-7.57 (m, 2H), 7.45-7.40 (m, 1H), 7.13 (t, J=8.4 Hz, 2H), 7.03 (d, J=6.0 Hz, 1H), 4.42-4.39 (m, 1H), 4.26-4.23 (m, 1H), 4.17-4.12 (m, 1H), 3.95 (t, J=9.2 Hz, 1H), 3.11-3.07 (m, 1H), 2.65-2.62 (m, 2H), 2.13-2.10 (m, 1H), 1.94-1.85 (m, 6H) (Note: exchangeable protons not observed); ¹⁹F NMR (282 MHz, DMSO-d₆) δ −72.5 (s, 3F), −74.7 (s, 3F), −120.6 (s, 1F).

Example 89

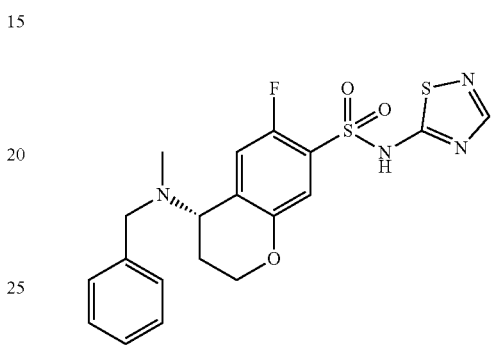

(S)-4-(benzyl(methyl)amino)-6-fluoro-N-(1,2,4-thiadiazol-5-yl)chromane-7-sulfonamide Step 1

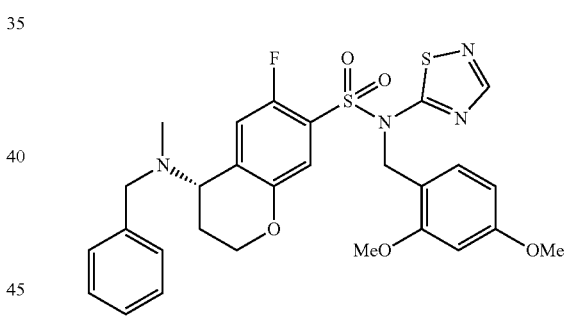

(S)-4-(benzyl(methyl)amino)-N-(2,4-dimethoxybenzyl)-6-fluoro-N-(1,2,4-thiadiazol-5-yl)chromane-7-sulfonamide Following the procedure as described in Example 80, step 1 and making non-critical variations as required to replace (R)-1-phenyl-1,2,3,4-tetrahydroisoquinoline with N-methylbenzylamine and (R)-7-(N-(2,4-dimethoxybenzyl)-N-(1,2,4-thiadiazol-5-yl)sulfamoyl)chroman-4-yl methanesulfonate with (R)-7-(N-(2,4-dimethoxybenzyl)-N-(1,2,4-thiadiazol-5-yl)sulfamoyl)-6-fluorochroman-4-yl methanesulfonate, the title compound was obtained as a colorless solid (0.15 g, 60% yield). MS (ES+) m/z 585.2 (M+1). ¹H NMR (300 MHz, CDCl₃) δ 8.19 (s, 1H), 7.48 (d, J=10.8 Hz, 1H), 7.40-7.28 (m, 5H), 7.20-7.15 (m, 2H), 6.33 (dd, J=2.0, 8.4 Hz, 1H), 6.19 (d, J=2.3 Hz, 1H), 5.33 (q, J=13.4 Hz, 2H), 4.44-4.38 (m, 1H), 4.09-4.04 (m, 1H), 3.96-3.93 (m, 1H), 3.71 (d, J=0.5 Hz, 3H), 3.67 (s, 3H), 3.57 (d, J=13.4 Hz, 1H), 2.20 (s, 3H), 2.07-2.03 (m, 3H).

Step 2

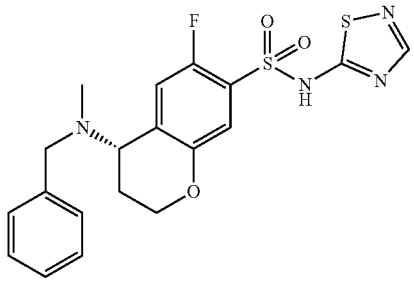 [SMILES: CN(Cc1ccccc1)[C@H]1CCOc2cc(S(=O)(=O)Nc3ncns3)c(F)cc21]

(S)-4-(benzyl(methyl)amino)-6-fluoro-N-(1,2,4-thiadiazol-5-yl)chromane-7-sulfonamide Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (S)-4-(benzyl(methyl)amino)-N-(2,4-dimethoxybenzyl)-6-fluoro-N-(1,2,4-thiadiazol-5-yl)chromane-7-sulfonamide, the title compound was obtained as a trifluoroacetate salt (0.058 g, 41% yield). MS (ES+) m/z 435.0 (M+1). $^1$H NMR (300 MHz, DMSO-$d_6$) δ 8.53 (s, 1H), 7.71 (d, J=10.8 Hz, 1H), 7.47-7.41 (m, 5H), 7.24 (d, J=6.1 Hz, 1H), 4.73-4.69 (m, 1H), 4.44-4.38 (m, 1H), 4.25-4.20 (m, 1H), 4.17-4.12 (m, 2H), 2.46 (s, 3H), 2.43-2.36 (m, 1H), 2.33-2.27 (m, 1H) (Note: exchangeable protons not observed).

Example 90

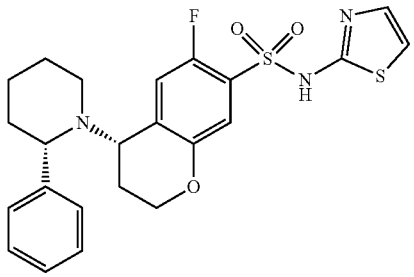

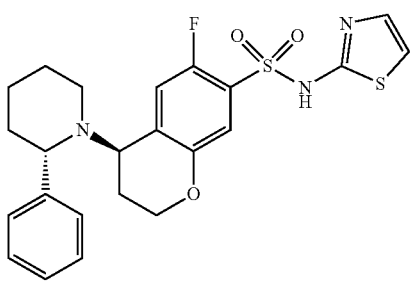

(S)-6-fluoro-4-((S)-2-phenylpiperidin-1-yl)-N-(thiazol-2-yl)chromane-7-sulfonamide and (R)-6-fluoro-4-((S)-2-phenylpiperidin-1-yl)-N-(thiazol-2-yl)chromane-7-sulfonamide (Stereochemistry at Chromane Arbitrarily Assigned)

Step 1

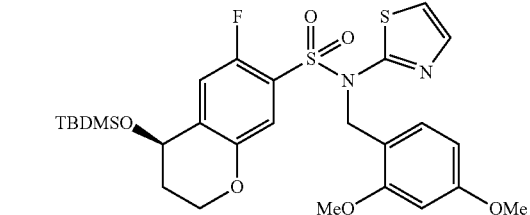 [SMILES: COc1ccc(CN(c2nccs2)S(=O)(=O)c2cc3c(cc2F)[C@H](O[Si](C)(C)C(C)(C)C)CCO3)c(OC)c1]

(R)-4-((tert-butyldimethylsilyl)oxy)-N-(2,4-dimethoxybenzyl)-6-fluoro-N-(thiazol-2-yl)chromane-7-sulfonamide Following the procedure as described in Example 37, Step 4 and making non-critical variations as required to replace N-(2,4-dimethoxybenzyl)-1,2,4-thiadiazol-5-amine with N-(2,4-dimethoxybenzyl)thiazol-2-amine and 4-((tert-butyldimethylsilyl)oxy)chromane-7-sulfonyl chloride with 4-((tert-butyldimethylsilyl)oxy)-6-fluorochromane-7-sulfonyl chloride (prepared as described in Example 75, step 5), the title compound was obtained as a colorless solid (4.60 g, 27% yield). MS (ES+) m/z 595.1 (M+1). $^1$H NMR (300 MHz, CDCl$_3$) δ 7.41 (d, J=3.6 Hz, 1H), 7.31 (d, J=5.8 Hz, 1H), 7.23 (d, J=8.2 Hz, 1H), 7.04 (d, J=10.1 Hz, 1H), 6.99 (d, J=3.6 Hz, 1H), 6.41-6.37 (m, 2H), 5.23 (s, 2H), 4.76 (t, J=5.6 Hz, 1H), 4.37-4.19 (m, 2H), 3.78 (s, 3H), 3.75 (s, 3H), 2.09-1.99 (m, 2H), 0.94 (s, 9H), 0.18 (s, 6H).

Step 2

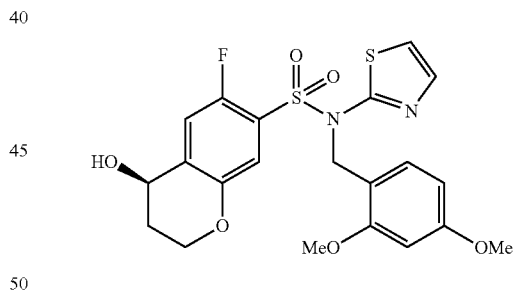

(R)—N-(2,4-dimethoxybenzyl)-6-fluoro-4-hydroxy-N-(thiazol-2-yl)chromane-7-sulfonamide Following the procedure as described in Example 37, Step 5 and making non-critical variations as required to replace (R)-4-((tert-butyldimethylsilyl)oxy)-N-(2,4-dimethoxybenzyl)-N-(1,2,4-thiadiazol-5-yl)chromane-7-sulfonamide with (R)-4-((tert-butyldimethylsilyl)oxy)-N-(2,4-dimethoxybenzyl)-6-fluoro-N-(thiazol-2-yl)chromane-7-sulfonamide, the title compound was obtained as a colorless solid (3.19 g, 93% yield). MS (ES+) m/z 481.0 (M+1). $^1$H NMR (300 MHz, CDCl$_3$) δ 7.41 (d, J=3.6 Hz, 1H), 7.34 (d, J=5.7 Hz, 1H), 7.24 (d, J=8.3 Hz, 1H), 7.14 (d, J=9.8 Hz, 1H), 7.00 (d, J=3.6 Hz, 1H), 6.40-6.34 (m, 2H), 5.23 (s, 2H), 4.77 (q, J=4.6 Hz, 1H), 4.30-4.26 (m, 2H), 3.78 (s, 3H), 3.75 (s, 3H), 2.22-2.00 (m, 3H).

Step 3

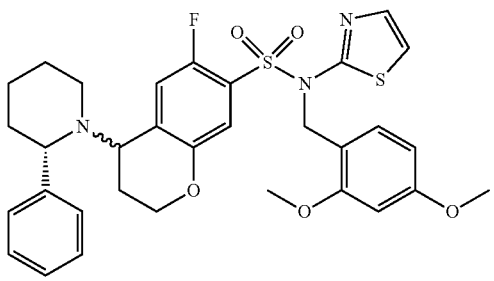 [SMILES: COc1ccc(CN(c2nccs2)S(=O)(=O)c2cc3c(cc2F)C(N2CCCC[C@H]2c2ccccc2)CCO3)c(OC)c1]

N-(2,4-dimethoxybenzyl)-6-fluoro-4-((S)-2-phenylpiperidin-1-yl)-N-(thiazol-2-yl)chromane-7-sulfonamide Following the procedures as described in Example 41, step 6 followed by Example 80, step 1 and making non-critical variations as required to replace (R)—N-(2,4-dimethoxybenzyl)-4-hydroxy-N-(1,2,4-thiadiazol-5-yl)chromane-7-sulfonamide with (R)—N-(2,4-dimethoxybenzyl)-6-fluoro-4-hydroxy-N-(thiazol-2-yl)chromane-7-sulfonamide and (R)-1-phenyl-1,2,3,4-tetrahydroisoquinoline with (S)-2-phenylpiperidine, the title compound was obtained as a colorless solid (0.382 g, 34% yield). MS (ES+) m/z 624.1 (M+1). $^1$H NMR (300 MHz, CDCl$_3$) δ 7.56-7.52 (m, 1H), 7.40-7.28 (m, 7H), 7.23-7.18 (m, 2H), 7.07-7.03 (m, 1H), 6.96-6.94 (m, 1H), 6.38-6.34 (m, 2H), 5.23-5.22 (m, 2H), 4.25-4.16 (m, 1H), 3.91-3.76 (m, 2H), 3.75 (s, 3H), 3.74 (s, 3H), 3.54-3.49 (m, 1H), 2.73-2.53 (m, 1H), 2.29-2.06 (m, 2H), 1.87-1.57 (m, 5H).

Step 4

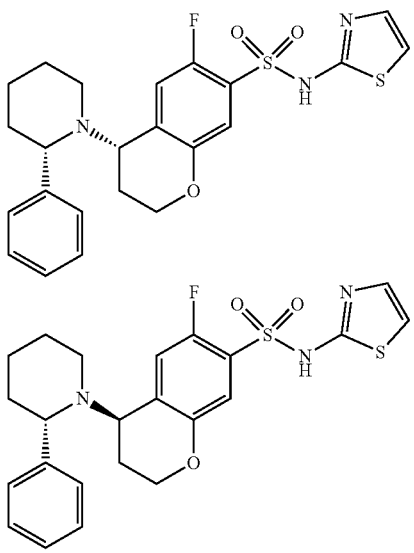

(S)-6-fluoro-4-((S)-2-phenylpiperidin-1-yl)-N-(thiazol-2-yl)chromane-7-sulfonamide and (R)-6-fluoro-4-((S)-2-phenylpiperidin-1-yl)-N-(thiazol-2-yl)chromane-7-sulfonamide (Stereochemistry at Chromane Arbitrarily Assigned)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with 6-fluoro-4-((S)-2-phenylpiperidin-1-yl)-N-(thiazol-2-yl)chromane-7-sulfonamide, the title compounds were obtained as formate salts.

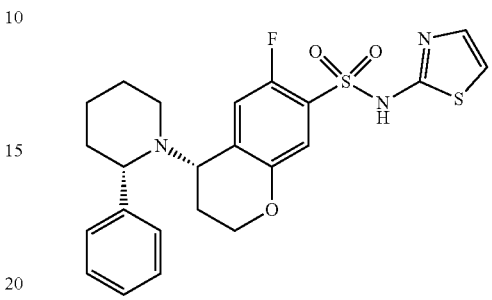

(S)-6-fluoro-4-((S)-2-phenylpiperidin-1-yl)-N-(thiazol-2-yl)chromane-7-sulfonamide (Stereochemistry at Chromane Arbitrarily Assigned)

Colorless solid (0.123 g, 44% yield). MS (ES+) m/z 474.0 (M+1). $^1$H NMR (300 MHz, DMSO-d$_6$) δ 7.82-7.15 (m, 7H), 7.03-6.97 (m, 1H), 6.89-6.88 (m, 1H), 4.19-4.14 (m, 1H), 3.91-3.79 (m, 2H), 3.15-3.04 (m, 1H), 2.73-2.63 (m, 1H), 2.18-1.98 (m, 2H), 1.78-1.45 (m, 6H), 1.35-1.22 (m, 2H).

Example 91

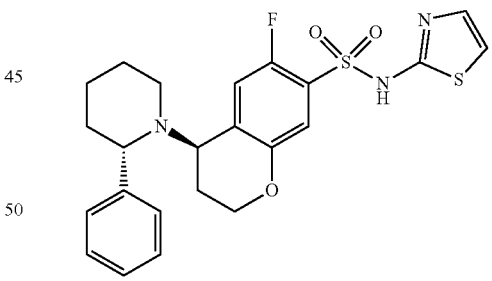

(R)-6-fluoro-4-((S)-2-phenylpiperidin-1-yl)-N-(thiazol-2-yl)chromane-7-sulfonamide (Stereochemistry at Chromane Arbitrarily Assigned)

This compound was prepared in the same sequence as Example 90. Colorless solid (0.080 g, 29% yield). MS (ES+) m/z 474.0 (M+1). $^1$H NMR (300 MHz, DMSO-d$_6$) δ 7.52-7.43 (m, 3H), 7.35-7.21 (m, 4H), 7.05-7.03 (m, 1H), 6.87-6.85 (m, 1H), 4.26-4.20 (m, 1H), 3.78-3.45 (m, 3H), 3.16-3.05 (m, 1H), 2.28-2.21 (m, 1H), 2.05-1.92 (m, 1H), 1.82-1.25 (m, 8H).

Example 92

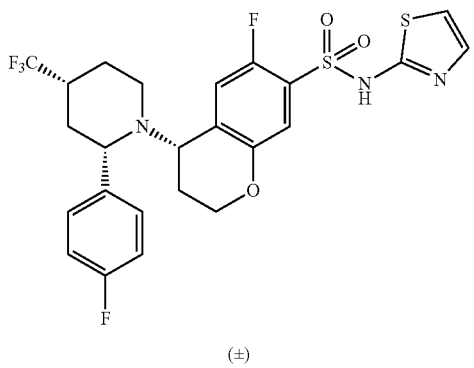 [SMILES: O=S(=O)(Nc1nccs1)c1cc2c(cc1F)[C@@H](N1CC[C@@H](C(F)(F)F)C[C@H]1c1ccc(F)cc1)CCO2]

(±)

(±)-(S)-6-fluoro-4-(cis-2-(4-fluorophenyl)-4-(trifluoromethyl)piperidin-1-yl)-N-(thiazol-2-yl)chromane-7-sulfonamide (Stereochemistry Arbitrarily Assigned)

Step 1

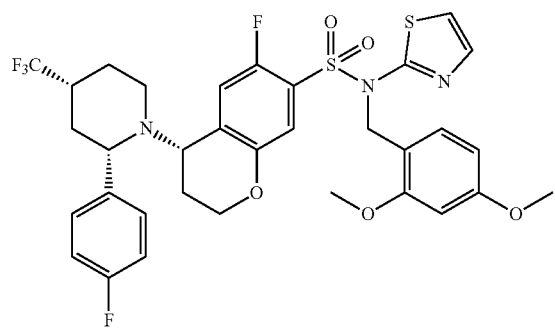

(±)

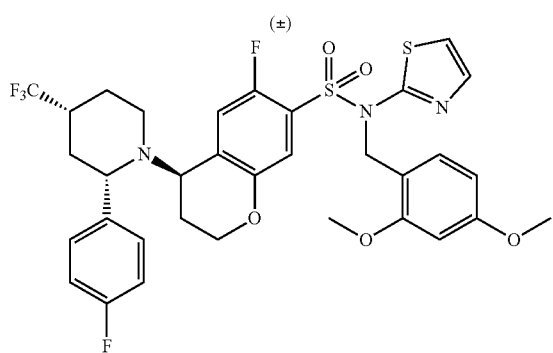

(±)

(±)-(S)—N-(2,4-dimethoxybenzyl)-6-fluoro-4-((cis)-2-(4-fluorophenyl)-4-(trifluoromethyl)piperidin-1-yl)-N-(thiazol-2-yl)chromane-7-sulfonamide and (±)-(R)—N-(2,4-dimethoxybenzyl)-6-fluoro-4-((cis)-2-(4-fluorophenyl)-4-(trifluoromethyl)-piperidin-1-yl)-N-(thiazol-2-yl)chromane-7-sulfonamide (Stereochemistry Arbitrarily Assigned)

Following the procedure as described in Example 41, step 6 followed by Example 80, step 1 and making non-critical variations as required to replace (R)—N-(2,4-dimethoxybenzyl)-4-hydroxy-N-(1,2,4-thiadiazol-5-yl)chromane-7-sulfonamide with (R)—N-(2,4-dimethoxybenzyl)-6-fluoro-4-hydroxy-N-(thiazol-2-yl)chromane-7-sulfonamide and (R)-1-phenyl-1,2,3,4-tetrahydroisoquinoline with (cis)-2-(4-fluorophenyl)-4-trifluoromethylpiperidine, the title compounds were obtained.

Diastereomer 1. (±)-(S)—N-(2,4-dimethoxybenzyl)-6-fluoro-4-((cis)-2-(4-fluorophenyl)-4-(trifluoromethyl)piperidin-1-yl)-N-(thiazol-2-yl)chromane-7-sulfonamide (Stereochemistry Arbitrarily Assigned)

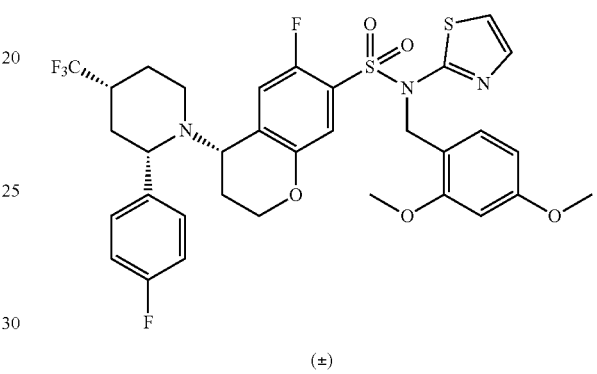

(±)

Colorless foamy solid (0.48 g, 19% yield). MS (ES+) m/z 710.1 (M+1). $^1$H NMR (300 MHz, CDCl$_3$) δ 7.46 (d, J=10.8 Hz, 1H), 7.41-7.32 (m, 3H), 7.26-7.21 (m, 1H), 7.12-7.01 (m, 3H), 6.98 (dd, J=1.0, 3.6 Hz, 1H), 6.40-6.35 (m, 2H), 5.25-5.22 (m, 2H), 4.31-4.25 (m, 1H), 3.86-3.74 (m, 8H), 3.62-3.58 (m, 1H), 3.10-2.93 (m, 1H), 2.78-2.72 (m, 1H), 2.37-2.20 (m, 1H), 2.08-1.84 (m, 3H), 1.80-1.56 (m, 3H).

Diastereomer 2. (±)-(R)—N-(2,4-dimethoxybenzyl)-6-fluoro-4-((cis)-2-(4-fluorophenyl)-4-(trifluoromethyl)-piperidin-1-yl)-N-(thiazol-2-yl)chromane-7-sulfonamide (Stereochemistry Arbitrarily Assigned)

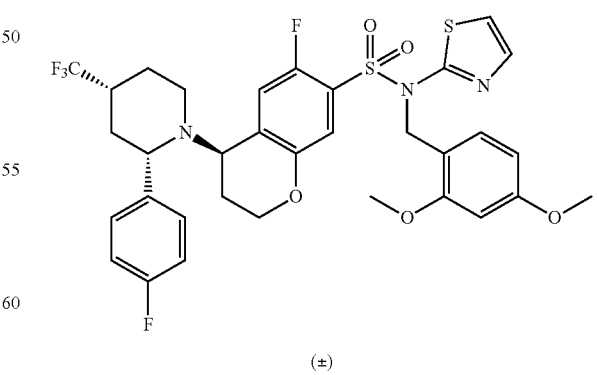

(±)

Yellow syrup, heavily contaminated with (cis)-2-(4-fluorophenyl)-4-(trifluoromethyl)piperidine (1.85 g crude). MS (ES+) m/z 710.1 (M+1).

Step 2

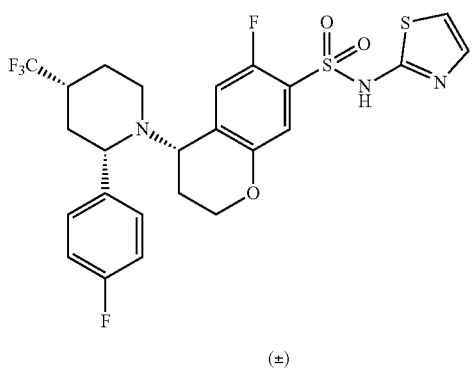 [SMILES: O=S(=O)(Nc1nccs1)c1cc2c(cc1F)[C@@H](N1CC[C@@H](C(F)(F)F)C[C@H]1c1ccc(F)cc1)CCO2]

(±)

(±)-(S)-6-fluoro-4-(cis-2-(4-fluorophenyl)-4-(trifluoromethyl)piperidin-1-yl)-N-(thiazol-2-yl)chromane-7-sulfonamide (Stereochemistry Arbitrarily Assigned)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (±)-(S)—N-(2,4-dimethoxybenzyl)-6-fluoro-4-((cis)-2-(4-fluorophenyl)-4-(trifluoromethyl)piperidin-1-yl)-N-(thiazol-2-yl)chromane-7-sulfonamide, the title compound was obtained as a colorless solid (0.18 g, 47% yield). MS (ES+) m/z 560.0 (M+1). $^1$H NMR (300 MHz, DMSO-$d_6$) δ 12.93 (s, 1H), 7.57-7.53 (m, 3H), 7.30 (dd, J=2.1, 4.6 Hz, 1H), 7.20-7.14 (m, 2H), 7.05 (d, J=6.0 Hz, 1H), 6.87 (d, J=4.5 Hz, 1H), 4.27-4.21 (m, 1H), 3.85-3.62 (m, 4H), 2.59-2.54 (m, 1H), 2.40-2.31 (m, 1H), 2.03-1.47 (m, 6H).

Example 93

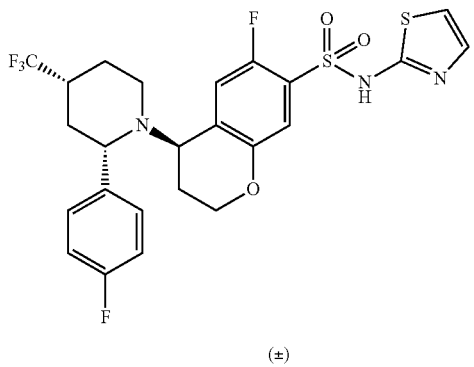 [SMILES: O=S(=O)(Nc1nccs1)c1cc2c(cc1F)[C@H](N1CC[C@@H](C(F)(F)F)C[C@H]1c1ccc(F)cc1)CCO2]

(±)

(±)-(R)-6-fluoro-4-(cis-2-(4-fluorophenyl)-4-(trifluoromethyl)piperidin-1-yl)-N-(thiazol-2-yl)chromane-7-sulfonamide (Stereochemistry Arbitrarily Assigned)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with crude (±)-(R)—N-(2,4-dimethoxybenzyl)-6-fluoro-4-((cis)-2-(4-fluorophenyl)-4-(trifluoromethyl)piperidin-1-yl)-N-(thiazol-2-yl)chromane-7-sulfonamide, the title compound was obtained as a colorless solid (0.25 g, 13% yield over 2 steps). MS (ES+) m/z 560.0 (M+1). $^1$H NMR (300 MHz, DMSO-$d_6$) δ 12.96 (s, 1H), 7.53 (br s, 2H), 7.32 (d, J=4.6 Hz, 1H), 7.20-7.13 (m, 3H), 7.05 (d, J=5.9 Hz, 1H), 6.89 (d, J=4.6 Hz, 1H), 4.25-4.10 (m, 2H), 3.98-3.82 (m, 2H), 2.84-2.72 (m, 1H), 2.64-2.55 (m, 1H), 2.35-2.22 (m, 1H), 2.08-1.45 (m, 6H).

Example 94

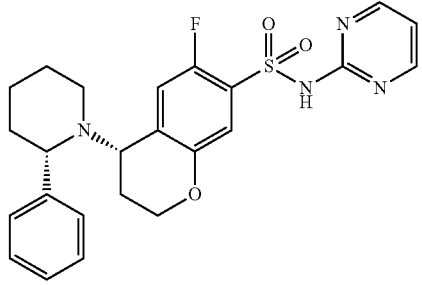

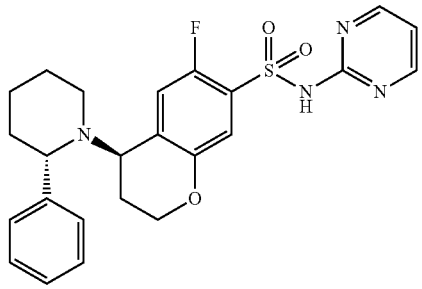

(S)-6-fluoro-4-((S)-2-phenylpiperidin-1-yl)-N-(pyrimidin-2-yl)chromane-7-sulfonamide and (R)-6-fluoro-4-((S)-2-phenylpiperidin-1-yl)-N-(pyrimidin-2-yl)chromane-7-sulfonamide (Stereochemistry at Chromane Arbitrarily Assigned)

Step 1

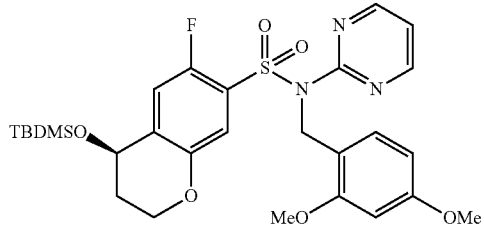 [SMILES: COc1ccc(CN(c2ncccn2)S(=O)(=O)c2cc3c(cc2F)[C@H](O[Si](C)(C)C(C)(C)C)CCO3)c(OC)c1]

(R)-4-((tert-butyldimethylsilyl)oxy)-N-(2,4-dimethoxybenzyl)-6-fluoro-N-(pyrimidin-2-yl)chromane-7-sulfonamide Following the procedure as described in Example 37, step 4 and making non-critical variations as required to replace N-(2,4-dimethoxybenzyl)-1,2,4-thiadiazol-5-amine with N-(2,4-dimethoxybenzyl) pyrimidin-2-amine and 4-((tert-butyldimethylsilyl)oxy)chromane-7-sulfonyl chloride with 4-((tert-butyldimethylsilyl)oxy)-6-fluorochromane-7-sulfonyl chloride (prepared as described in Example 75, step 5), the title compound was obtained as a colorless solid (5.56 g, 32% yield). MS (ES+) m/z 590.1 (M+1). $^1$H NMR (300 MHz, CDCl$_3$) δ 8.57 (d, J=4.8 Hz, 1H), 8.42 (d, J=4.8 Hz, 2H), 7.60 (d, J=5.9 Hz, 1H), 7.01-6.98 (m, 1H), 6.86 (t, J=4.8 Hz, 1H), 6.48-6.45 (m, 2H), 5.44 (s, 2H), 4.79-4.76 (m, 1H), 4.39-4.23 (m, 2H), 3.85 (s, 3H), 3.81 (s, 3H), 2.40-2.31 (m, 1H), 2.06-1.96 (m, 1H), 0.93 (s, 9H), 0.17 (s, 6H).

Step 2

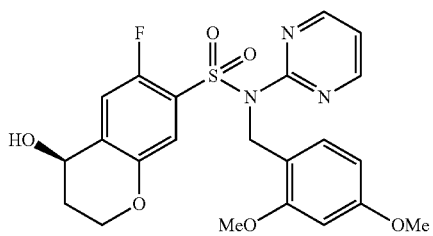 [SMILES: COc1ccc(CN(c2ncccn2)S(=O)(=O)c2cc3c(cc2F)[C@H](O)CCO3)c(OC)c1]

(R)—N-(2,4-dimethoxybenzyl)-6-fluoro-4-hydroxy-N-(pyrimidin-2-yl)chromane-7-sulfonamide Following the procedure as described in Example 37, step 5 and making non-critical variations as required to replace (R)-4-((tert-butyldimethylsilyl)oxy)-N-(2,4-dimethoxybenzyl)-N-(1,2,4-thiadiazol-5-yl)chromane-7-sulfonamide with (R)-4-((tert-butyldimethylsilyl)oxy)-N-(2,4-dimethoxybenzyl)-6-fluoro-N-(pyrimidin-2-yl)chromane-7-sulfonamide, the title compound was obtained as a colorless solid (2.46 g, 55% yield). MS (ES+) m/z 476.0 (M+1). $^1$H NMR (300 MHz, DMSO-d$_6$) δ 8.54 (d, J=4.8 Hz, 2H), 7.40-7.28 (m, 2H), 7.12 (t, J=4.8 Hz, 1H), 7.00 (d, J=8.4 Hz, 1H), 6.58 (d, J=2.3 Hz, 1H), 6.47 (dd, J=2.3, 8.4 Hz, 1H), 5.73 (d, J=5.6 Hz, 1H), 5.26 (s, 2H), 4.67 (q, J=5.4 Hz, 1H), 4.32-4.18 (m, 2H), 3.81 (s, 3H), 3.73 (s, 3H), 2.07-2.01 (m, 1H), 1.95-1.80 (m, 1H); $^{19}$F-NMR (282 MHz, DMSO-d$_6$): δ −123.7 (s, 1F).

Step 3

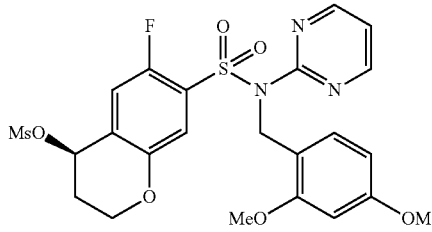

(R)-7-(N-(2,4-dimethoxybenzyl)-N-(pyrimidin-2-yl)sulfamoyl)-6-fluorochroman-4-yl methanesulfonate Following the procedure as described in Example 41, step 6 and making non-critical variations as required to replace (R)—N-(2,4-dimethoxybenzyl)-4-hydroxy-N-(1,2,4-thiadiazol-5-yl)chromane-7-sulfonamide with (R)—N-(2,4-dimethoxybenzyl)-6-fluoro-4-hydroxy-N-(pyrimidin-2-yl)chromane-7-sulfonamide, the title compound was obtained as a yellow syrup. The intermediate was used directly without further purification or characterization.

Step 4

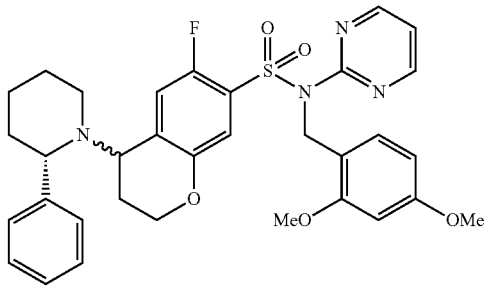 [SMILES: COc1ccc(CN(c2ncccn2)S(=O)(=O)c2cc3c(cc2F)C(N2CCCC[C@H]2c2ccccc2)CCO3)c(OC)c1]

N-(2,4-dimethoxybenzyl)-6-fluoro-4-((S)-2-phenylpiperidin-1-yl)-N-(pyrimidin-2-yl)chromane-7-sulfonamide Following the procedure as described in Example 80, step 1 and making non-critical variations as required to replace (R)-1-phenyl-1,2,3,4-tetrahydroisoquinoline with (S)-2-phenylpiperidine and (R)-7-(N-(2,4-dimethoxybenzyl)-N-(1,2,4-thiadiazol-5-yl)sulfamoyl)chroman-4-yl methanesulfonate with (R)-7-(N-(2,4-dimethoxybenzyl)-N-(pyrimidin-2-yl)sulfamoyl)-6-fluorochroman-4-yl methanesulfonate, the title compound was obtained as a colorless solid (0.17 g, 21% yield). MS (ES+) m/z 619.2 (M+1). $^1$H NMR (300 MHz, CDCl$_3$) δ 8.40 (d, J=4.8 Hz, 2H), 7.54-7.50 (m, 1H), 7.41-7.25 (m, 7H), 6.92-6.80 (m, 1H), 6.51-6.48 (m, 1H), 6.46-6.41 (dd, J=2.3, 8.3 Hz, 1H), 5.46 (s, 2H), 4.30-4.22 (m, 1H), 3.93 (t, J=8.1 Hz, 1H), 3.86 (s, 3H), 3.79 (s, 3H), 2.74-2.58 (m, 1H), 2.31-2.09 (m, 2H), 1.88-1.57 (m, 8H), 1.48-1.32 (m, 1H).

Step 5

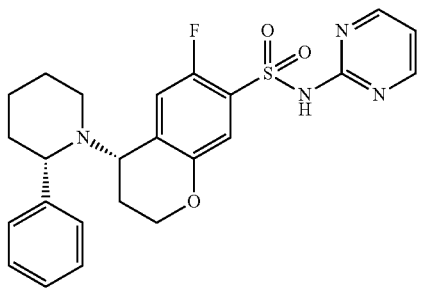 [SMILES: O=S(=O)(Nc1ncccn1)c1cc2c(cc1F)[C@@H](N1CCCC[C@H]1c1ccccc1)CCO2]

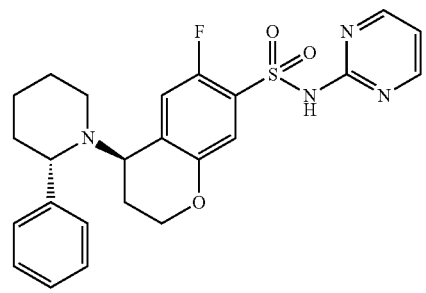 [SMILES: O=S(=O)(Nc1ncccn1)c1cc2c(cc1F)[C@H](N1CCCC[C@H]1c1ccccc1)CCO2]

(S)-6-fluoro-4-((S)-2-phenylpiperidin-1-yl)-N-(pyrimidin-2-yl)chromane-7-sulfonamide and (R)-6-fluoro-4-((S)-2-phenylpiperidin-1-yl)-N-(pyrimidin-2-yl)chromane-7-sulfonamide (Stereochemistry at Chromane Arbitrarily Assigned)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with N-(2,4-dimethoxybenzyl)-6-fluoro-4-((S)-2-phenylpiperidin-1-yl)-N-(pyrimidin-2-yl)chromane-7-sulfonamide, the title compounds were obtained as trifluoroacetate salts.

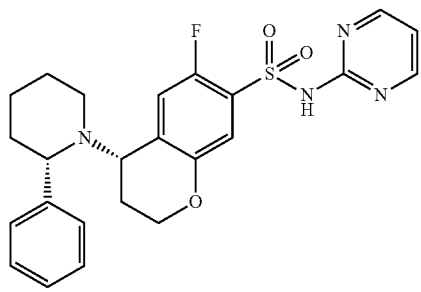

(S)-6-fluoro-4-((S)-2-phenylpiperidin-1-yl)-N-(pyrimidin-2-yl)chromane-7-sulfonamide (Stereochemistry at Chromane Arbitrarily Assigned)

Colorless solid (0.053 g, 33% yield). MS (ES+) m/z 469.1 (M+1). $^1$H NMR (300 MHz, DMSO-$d_6$) δ 9.87-9.56 (br s, 1H), 8.51 (d, J=5.0 Hz, 2H), 7.63 (s, 3H), 7.36 (t, J=7.1 Hz, 2H), 7.28 (d, J=7.3 Hz, 1H), 7.21 (d, J=6.3 Hz, 1H), 7.05 (t, J=5.0 Hz, 1H), 4.80-4.50 (m, 2H), 4.32-4.28 (m, 1H), 4.15-4.10 (m, 1H), 2.20-1.74 (m, 9H), 1.65-1.50 (m, 1H) (Note: exchangeable proton not observed).

Example 95

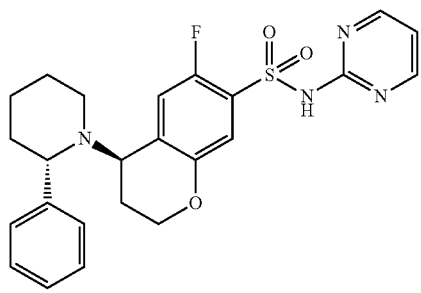

(R)-6-fluoro-4-((S)-2-phenylpiperidin-1-yl)-N-(pyrimidin-2-yl)chromane-7-sulfonamide (Stereochemistry at Chromane Arbitrarily Assigned)

This compound was produced in the same sequence as Example 96. Colorless solid (0.036 g, 22% yield). MS (ES+) m/z 469.1 (M+1). $^1$H NMR (300 MHz, DMSO-$d_6$): δ 8.49 (d, J=4.9 Hz, 2H), 7.80-7.20 (m, 7H), 7.03 (t, J=4.9 Hz, 1H), 4.29-4.23 (m, 1H), 3.85-3.53 (m, 2H), 2.47-2.38 (m, 2H), 2.32-2.20 (m, 1H), 1.86-1.84 (m, 2H), 1.86-1.29 (m, 6H) (Note: exchangeable protons not observed).

Example 96

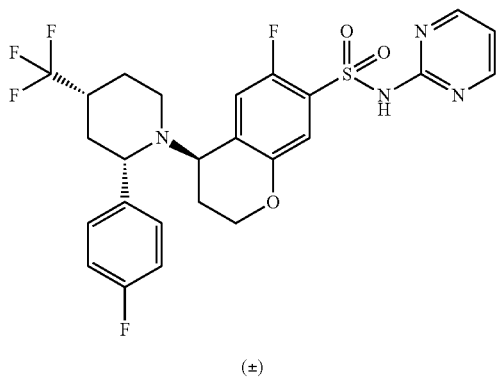 [SMILES: O=S(=O)(Nc1ncccn1)c1cc2c(cc1F)[C@H](N1CC[C@@H](C(F)(F)F)C[C@H]1c1ccc(F)cc1)CCO2]

(±)-(R)-6-fluoro-4-((cis)-2-(4-fluorophenyl)-4-(trifluoromethyl)piperidin-1-yl)-N-(pyrimidin-2-yl)chromane-7-sulfonamide (Stereochemistry Arbitrarily Assigned)

Step 1

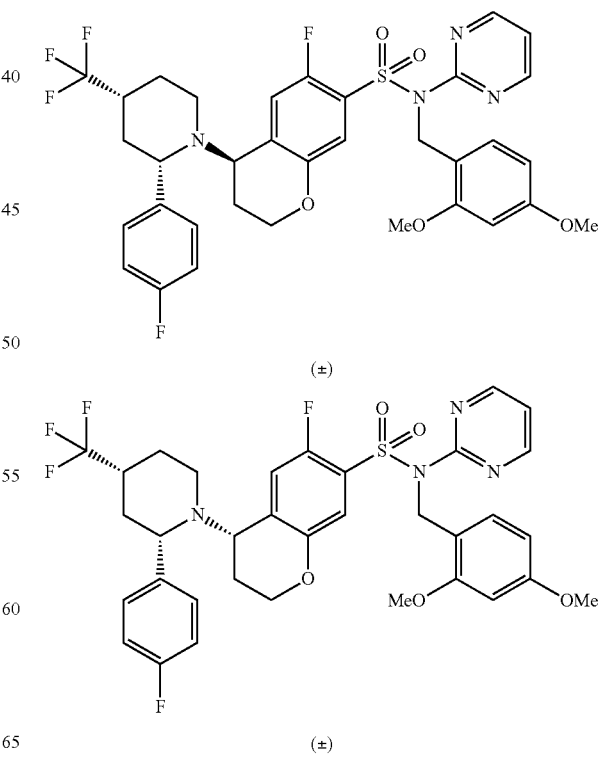

(±)-(R)—N-(2,4-dimethoxybenzyl)-6-fluoro-4-((cis)-2-(4-fluorophenyl)-4-(trifluoromethyl)piperidin-1-yl)-N-(pyrimidin-2-yl)chromane-7-sulfonamide and (±)-(S)—N-(2,4-dimethoxybenzyl)-6-fluoro-4-((cis)-2-(4-fluorophenyl)-4-(trifluoromethyl)-piperidin-1-yl)-N-(pyrimidin-2-yl)chromane-7-sulfonamide (Stereochemistry Arbitrarily Assigned)

Following the procedure as described in Example 80, step 1 and making non-critical variations as required to replace (R)-1-phenyl-1,2,3,4-tetrahydroisoquinoline with (cis)-2-(4-fluorophenyl)-4-trifluoromethylpiperidine and (R)-7-(N-(2,4-dimethoxybenzyl)-N-(1,2,4-thiadiazol-5-yl)sulfamoyl)chroman-4-yl methanesulfonate with (R)-7-(N-(2,4-dimethoxybenzyl)-N-(pyrimidin-2-yl)sulfamoyl)-6-fluorochroman-4-yl methanesulfonate, the title compounds were obtained.

Diastereomer 1. (±)-(R)—N-(2,4-dimethoxybenzyl)-6-fluoro-4-((cis)-2-(4-fluorophenyl)-4-(trifluoromethyl)piperidin-1-yl)-N-(pyrimidin-2-yl)chromane-7-sulfonamide (Stereochemistry Arbitrarily Assigned)

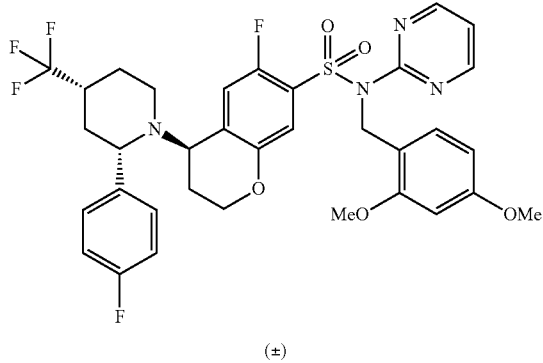 [SMILES: COc1ccc(CN(c2ncccn2)S(=O)(=O)c2cc3c(cc2F)[C@H](N2CC[C@@H](C(F)(F)F)C[C@H]2c2ccc(F)cc2)CCO3)c(OC)c1]

(±)

Yellow syrup, contaminated with N-(2,4-dimethoxybenzyl)-6-fluoro-N-(pyrimidin-2-yl)-2H-chromene-7-sulfonamide (0.55 g crude yield). MS (ES+) m/z 705.2 (M+1).

Diastereomer 2. (±)-(S)—N-(2,4-dimethoxybenzyl)-6-fluoro-4-((cis)-2-(4-fluorophenyl)-4-(trifluoromethyl)piperidin-1-yl)-N-(pyrimidin-2-yl)chromane-7-sulfonamide (Stereochemistry Arbitrarily Assigned)

Yellow syrup, heavily contaminated with (cis)-2-(4-fluorophenyl)-4-(trifluoromethyl)piperidine (0.68 g crude yield). MS (ES+) m/z 705.2 (M+1).

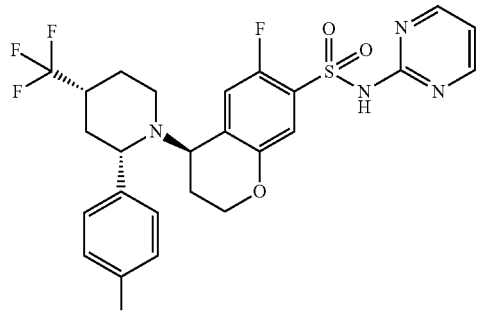

(±)

Step 2

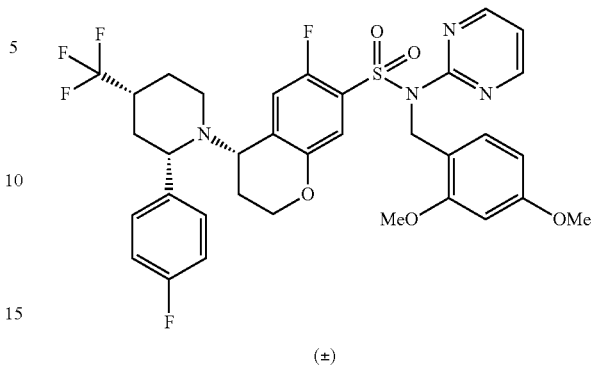

(±)

(±)-(R)-6-fluoro-4-((cis)-2-(4-fluorophenyl)-4-(trifluoromethyl)piperidin-1-yl)-N-(pyrimidin-2-yl)chromane-7-sulfonamide (Stereochemistry Arbitrarily Assigned)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with (±)-(S)—N-(2,4-dimethoxybenzyl)-6-fluoro-4-((cis)-2-(4-fluorophenyl)-4-(trifluoromethyl)piperidin-1-yl)-N-(pyrimidin-2-yl)chromane-7-sulfonamide, the title compound was obtained as a trifluoroacetate salt as a colorless solid (0.17 g, 32% yield). MS (ES+) m/z 555.0 (M+1). $^1$H NMR (300 MHz, DMSO-$d_6$) δ 8.49 (d, J=4.9 Hz, 2H), 7.60-7.53 (m, 3H), 7.22-7.12 (m, 3H), 7.04 (t, J=4.9 Hz, 1H), 4.29-4.23 (m, 1H), 3.88-3.81 (m, 1H), 3.73-3.61 (m, 2H), 2.59-2.56 (m, 1H), 2.42-2.32 (m, 2H), 2.02-1.96 (m, 1H), 1.88-1.78 (m, 3H), 1.69-1.53 (m, 2H) (Note: exchangeable protons not observed).

Example 97

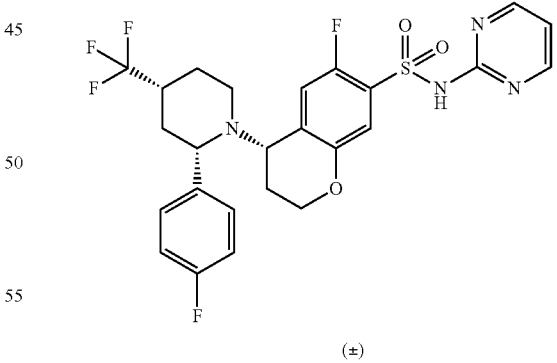

(±)

(±)-(S)-6-fluoro-4-((cis)-2-(4-fluorophenyl)-4-(trifluoromethyl)piperidin-1-yl)-N-(pyrimidin-2-yl)chromane-7-sulfonamide (Stereochemistry Arbitrarily Assigned)

Following the procedure as described in Example 51, step 8 and making non-critical variations as required to replace (±)-N-(2,4-dimethoxybenzyl)-5-((R)-2-phenylpiperidin-1- yl)-N-(1,2,4-thiadiazol-5-yl)-5,6,7,8-tetrahydronaphthalene-2-sulfonamide with (±)-(S)—N-(2,4-dimethoxybenzyl)-6-fluoro-4-((cis)-2-(4-fluorophenyl)-4-(trifluoromethyl)piperidin-1-yl)-N-(pyrimidin-2-yl)chromane-7-sulfonamide, the title compound was obtained as a trifluoroacetate salt as a colorless solid (0.12 g, 19% yield). MS (ES+) m/z 555.1 (M+1). $^1$H NMR (300 MHz, DMSO-$d_6$) δ 8.48 (d, J=4.9 Hz, 2H), 7.57 (dd, J=5.5, 8.1 Hz, 2H), 7.35 (d, J=10.5 Hz, 1H), 7.25-7.11 (m, 3H), 7.04 (t, J=4.9 Hz, 1H), 4.50-4.37 (m, 1H), 4.26-4.13 (m, 2H), 4.01-3.96 (m, 2H), 3.15-2.97 (m, 1H), 2.66-2.56 (m, 2H), 1.93-1.83 (m, 3H), 1.83-1.69 (m, 2H) (Note: exchangeable protons not observed).

Example 98

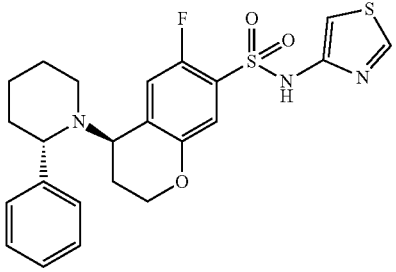

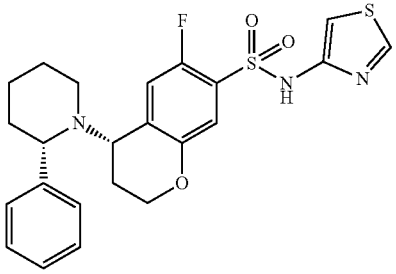

(R)-6-fluoro-4-((S)-2-phenylpiperidin-1-yl)-N-(thiazol-4-yl)chromane-7-sulfonamide and (S)-6-fluoro-4-((S)-2-phenylpiperidin-1-yl)-N-(thiazol-4-yl)chromane-7-sulfonamide (Stereochemistry at Chromane Arbitrarily Assigned)

Step 1

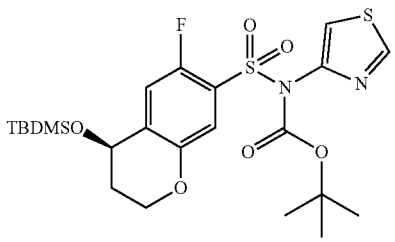 [SMILES: CC(C)(C)OC(=O)N(c1cscn1)S(=O)(=O)c1cc2c(cc1F)[C@H](O[Si](C)(C)C(C)(C)C)CCO2]

tert-butyl (R)-((4-((tert-butyldimethylsilyl)oxy)-6-fluorochroman-7-yl)sulfonyl)(thiazol-4-yl)carbamate Following the procedure as described in Example 37, step 4 and making non-critical variations as required to replace N-(2,4-dimethoxybenzyl)-1,2,4-thiadiazol-5-amine with N-(tert-butoxycarbonyl)(thiazol-4-yl)amine and 4-((tert-butyldimethylsilyl)oxy)chromane-7-sulfonyl chloride with 4-((tert-butyldimethylsilyl)oxy)-6-fluorochromane-7-sulfonyl chloride (prepared as described in Example 75, step 5), the title compound was obtained as a yellow syrup (1.23 g, 43% yield). MS (ES+) m/z 545.1 (M+1). $^1$H NMR (300 MHz, CDCl$_3$) δ 8.82 (d, J=2.3 Hz, 1H), 7.56-7.54 (m, 2H), 7.13-7.09 (m, 1H), 4.81 (t, J=5.4 Hz, 1H), 4.41-4.23 (m, 2H), 2.12-2.01 (m, 2H), 1.36 (s, 9H), 0.93 (s, 9H), 0.20 (s, 3H), 0.19 (s, 3H).

Step 2

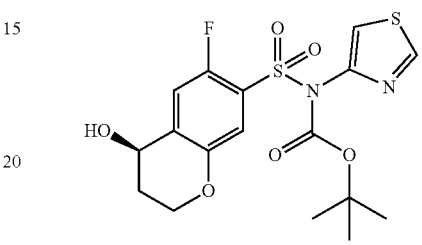

tert-butyl (R)-((6-fluoro-4-hydroxychroman-7-yl)sulfonyl)(thiazol-4-yl)carbamate Following the procedure as described in Example 37, step 5 and making non-critical variations as required to replace (R)-4-((tert-butyldimethylsilyl)oxy)-N-(2,4-dimethoxybenzyl)-N-(1,2,4-thiadiazol-5-yl)chromane-7-sulfonamide with tert-butyl (R)-((4-((tert-butyldimethylsilyl)oxy)-6-fluorochroman-7-yl)sulfonyl)(thiazol-4-yl)carbamate, the title compound was obtained as a colorless solid (0.84 g, 87% yield). MS (ES+) m/z 431.0 (M+1). $^1$H NMR (300 MHz, CDCl$_3$) δ 8.82 (d, J=2.2 Hz, 1H), 7.61-7.55 (m, 2H), 7.27 (d, J=9.0 Hz, 1H), 4.85 (q, J=5.2 Hz, 1H), 4.35-4.30 (m, 2H), 2.25-2.10 (m, 3H), 1.38 (s, 9H).

Step 3

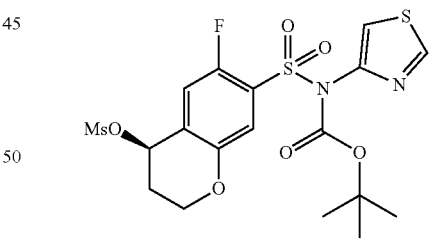

(R)-7-(N-(tert-butoxycarbonyl)-N-(thiazol-4-yl)sulfamoyl)-6-fluorochroman-4-yl methanesulfonate Following the procedure as described in Example 41, step 6 and making non-critical variations as required to replace (R)—N-(2,4-dimethoxybenzyl)-4-hydroxy-N-(1,2,4-thiadiazol-5-yl)chromane-7-sulfonamide with tert-butyl (R)-((6-fluoro-4-hydroxychroman-7-yl)sulfonyl)(thiazol-4-yl)carbamate, the title compound was obtained as a yellow syrup. The intermediate was used directly without further purification or characterization.

Step 4

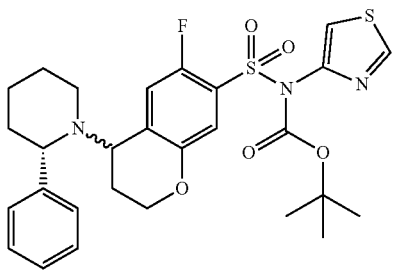 [SMILES: CC(C)(C)OC(=O)N(c1cscn1)S(=O)(=O)c1cc2c(cc1F)C(N1CCCC[C@H]1c1ccccc1)CCO2]

tert-butyl ((6-fluoro-4-((S)-2-phenylpiperidin-1-yl)chroman-7-yl)sulfonyl)(thiazol-4-yl)carbamate Following the procedure as described in Example 80, step 1 and making non-critical variations as required to replace (R)-1-phenyl-1,2,3,4-tetrahydroisoquinoline with (S)-2-phenylpiperidine and (R)-7-(N-(2,4-dimethoxybenzyl)-N-(1,2,4-thiadiazol-5-yl)sulfamoyl)chroman-4-yl methanesulfonate with (R)-7-(N-(tert-butoxycarbonyl)-N-(thiazol-4-yl)sulfamoyl)-6-fluorochroman-4-yl methanesulfonate, the title compound was obtained as a colorless solid (0.30 g, 27% yield). MS (ES+) m/z 574.1 (M+1). $^1$H NMR (300 MHz, CDCl$_3$) δ 8.85-8.80 (m, 1H), 7.64-7.34 (m, 7H), 7.11 (d, J=10.5 Hz, 1H), 4.31-4.21 (m, 1H), 3.88-3.81 (m, 2H), 3.57-3.46 (m, 1H), 2.76-2.55 (m, 1H), 2.13-2.09 (m, 1H), 1.89-1.59 (m, 8H), 1.35 (s, 9H).

Step 5

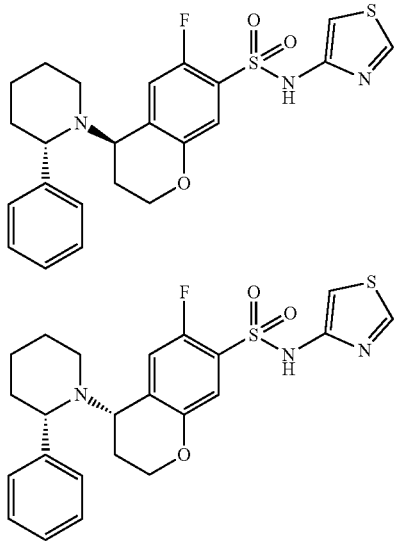

(R)-6-fluoro-4-((S)-2-phenylpiperidin-1-yl)-N-(thiazol-4-yl)chromane-7-sulfonamide and (S)-6-fluoro-4-((S)-2-phenylpiperidin-1-yl)-N-(thiazol-4-yl)chromane-7-sulfonamide (Stereochemistry at Chromane Arbitrarily Assigned)

To a solution of tert-butyl ((6-fluoro-4-((S)-2-phenylpiperidin-1-yl)chroman-7-yl)sulfonyl)(thiazol-4-yl)carbamate (0.30 g, 0.52 mmol) in DCM (5.2 mL) was added TFA (1.20 mL, 15.68 mmol) dropwise. After 3 h, the solution was concentrated in vacuo and purified by reverse-phase HPLC eluting with a 20-80% gradient of acetonitrile in water containing 0.1% trifluoroacetic acid to afford the title compounds.

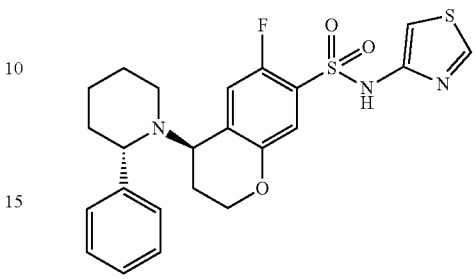

(R)-6-fluoro-4-((S)-2-phenylpiperidin-1-yl)-N-(thiazol-4-yl)chromane-7-sulfonamide (Stereochemistry at Chromane Arbitrarily Assigned)

Colorless solid, obtained as a partial formate salt (0.070 g, 28% yield). MS (ES+) m/z 474.0 (M+1). $^1$H NMR (300 MHz, DMSO-d$_6$) δ 8.87 (d, J=2.2 Hz, 1H), 8.16 (s, 0.2H), 7.54 (d, J=10.9 Hz, 1H), 7.45 (d, J=7.0 Hz, 2H), 7.39 (d, J=4.4 Hz, 1H), 7.32 (t, J=7.4 Hz, 2H), 7.27-7.20 (m, 1H), 7.06 (d, J=6.0 Hz, 1H), 6.95 (d, J=2.1 Hz, 1H), 4.26-4.19 (m, 1H), 3.77-3.56 (m, 3H), 2.45-2.39 (m, 1H), 2.28-2.20 (m, 1H), 2.00-1.91 (m, 1H), 1.83-1.72 (m, 2H), 1.69-1.49 (m, 4H), 1.35-1.31 (m, 1H) (Note: exchangeable proton not observed); $^{19}$F NMR (282 MHz, DMSO-d$_6$) δ −121.4 (s, 1F).

Example 99

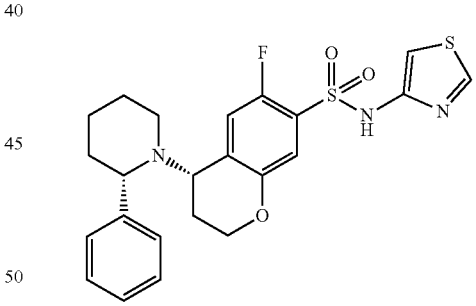

(S)-6-fluoro-4-((S)-2-phenylpiperidin-1-yl)-N-(thiazol-4-yl)chromane-7-sulfonamide (Stereochemistry at Chromane Arbitrarily Assigned)

This compound was prepared in the same sequence as Example 98. This diastereomer was re-purified by column chromatography, eluting with a 0-10% gradient of methanol in ethyl acetate to afford the title compound as a colorless solid (0.043 g, 17% yield). MS (ES+) m/z 474.1 (M+1). $^1$H NMR (300 MHz, CDCl$_3$) δ 11.17 (br s, 1H), 8.80 (d, J=2.3 Hz, 1H), 7.41-7.34 (m, 2H), 7.32-7.27 (m, 3H), 7.25-7.20 (m, 1H), 7.05 (d, J=10.5 Hz, 1H), 6.92 (d, J=2.3 Hz, 1H), 4.23-4.18 (m, 1H), 3.95-3.85 (m, 1H), 3.85-3.76 (m, 2H), 2.70 (d, J=11.6 Hz, 1H), 2.17-2.09 (m, 2H), 1.84-1.74 (m, 3H), 1.63-1.58 (m, 3H), 1.47-1.32 (m, 1H); ¹⁹F NMR (282 MHz, CDCl₃) δ −121.1 (s, 1F).

Example 100

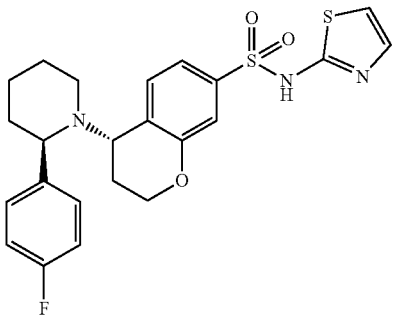

(±)

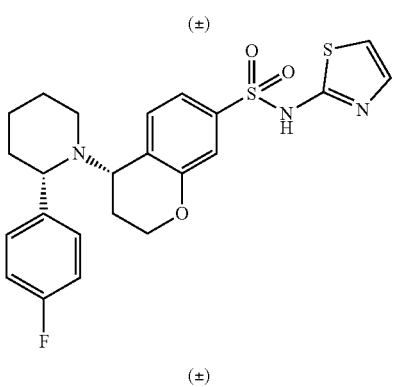

(±)

(±)-(S)-4-((R)-2-(4-fluorophenyl)piperidin-1-yl)-N-(thiazol-2-yl)chromane-7-sulfonamide and (±)-(S)-4-((S)-2-(4-fluorophenyl)piperidin-1-yl)-N-(thiazol-2-yl)chromane-7-sulfonamide (Stereochemistry Arbitrarily Assigned)

Step 1

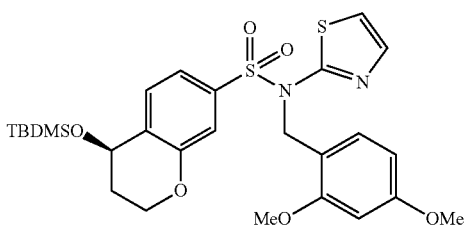 [SMILES: COc1ccc(CN(c2nccs2)S(=O)(=O)c2ccc3c(c2)OCC[C@H]3O[Si](C)(C)C(C)(C)C)c(OC)c1]

(R)-4-((tert-butyldimethylsilyl)oxy)-N-(2,4-dimethoxybenzyl)-N-(thiazol-2-yl)chromane-7-sulfonamide Following the procedure as described in Example 37, Step 4 and making non-critical variations as required to replace N-(2,4-dimethoxybenzyl)-1,2,4-thiadiazol-5-amine with N-(2,4-dimethoxybenzyl)thiazol-2-amine, the title compound was obtained as a colorless solid (3.7 g, 26% yield). MS (ES+) m/z 578.1 (M+1).

Step 2

(R)—N-(2,4-dimethoxybenzyl)-4-hydroxy-N-(thiazol-2-yl)chromane-7-sulfonamide

Following the procedure as described in Example 37, Step 5 and making non-critical variations as required to replace (R)-4-((tert-butyldimethylsilyl)oxy)-N-(2,4-dimethoxybenzyl)-N-(1,2,4-thiadiazol-5-yl)chromane-7-sulfonamide with (R)-4-((tert-butyldimethylsilyl)oxy)-N-(2,4-dimethoxybenzyl)-N-(thiazol-2-yl)chromane-7-sulfonamide, the title compound was obtained as a colorless solid (0.75 g, 25% yield). MS (ES+) m/z 464.0 (M+1).

Step 3

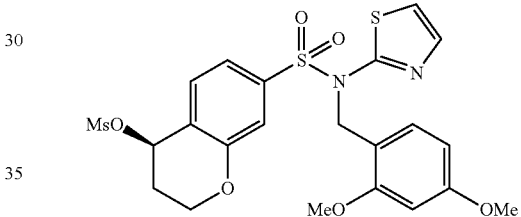

(R)-7-(N-(2,4-dimethoxybenzyl)-N-(thiazol-2-yl)sulfamoyl)chroman-4-yl methanesulfonate Following the procedure as described in Example 41, step 6 and making non-critical variations as required to replace (R)—N-(2,4-dimethoxybenzyl)-4-hydroxy-N-(1,2,4-thiadiazol-5-yl)chromane-7-sulfonamide with (R)—N-(2,4-dimethoxybenzyl)-4-hydroxy-N-(thiazol-2-yl)chromane-7-sulfonamide, the title compound was obtained as a yellow syrup. The intermediate was used directly without further purification or characterization.

Step 4

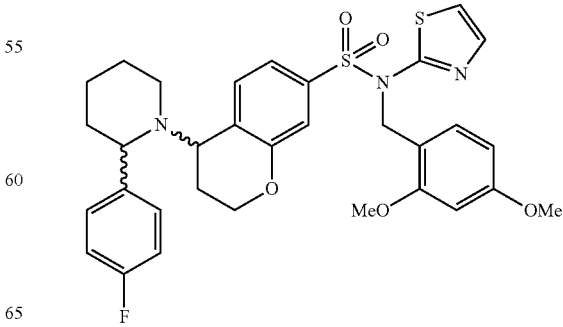

293

N-(2,4-dimethoxybenzyl)-4-(2-(4-fluorophenyl)piperidin-1-yl)-N-(thiazol-2-yl)chromane-7-sulfonamide Following the procedure as described in Example 80, step 1 and making non-critical variations as required to replace (R)-1-phenyl-1,2,3,4-tetrahydroisoquinoline with 2-(4-fluorophenyl)piperidine and (R)-7-(N-(2,4-dimethoxybenzyl)-N-(1,2,4-thiadiazol-5-yl)sulfamoyl)chroman-4-yl methanesulfonate with (R)-7-(N-(2,4-dimethoxybenzyl)-N-(thiazol-2-yl)sulfamoyl)chroman-4-yl methanesulfonate, the title compound was obtained as a colorless solid, contaminated with N-(2,4-dimethoxybenzyl)-N-(thiazol-2-yl)-2H-chromene-7-sulfonamide (0.057 g crude yield). MS (ES+) m/z 624.2 (M+1).

Step 5

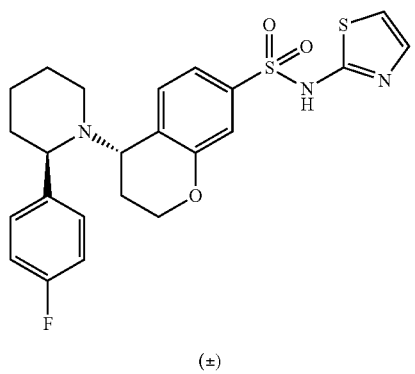 [SMILES: O=S(=O)(Nc1nccs1)c1ccc2c(c1)OCC[C@@H]2N1CCCC[C@@H]1c1ccc(F)cc1]

(±)

(±)-(S)-4-((R)-2-(4-fluorophenyl)piperidin-1-yl)-N-(thiazol-2-yl)chromane-7-sulfonamide and (±)-(S)-4-((S)-2-(4-fluorophenyl)piperidin-1-yl)-N-(thiazol-2-yl)chromane-7-sulfonamide (Stereochemistry Arbitrarily Assigned)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with N-(2,4-dimethoxybenzyl)-4-(2-(4-fluorophenyl)piperidin-1-yl)-N-(thiazol-2-yl)chromane-7-sulfonamide, the title compounds were obtained as trifluoroacetate salts.

294

(S)-4-((R)-2-(4-fluorophenyl)piperidin-1-yl)-N-(thiazol-2-yl)chromane-7-sulfonamide (Stereochemistry Arbitrarily Assigned)

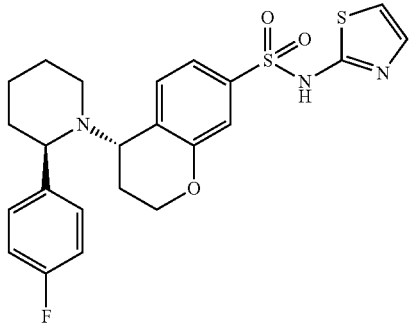

(±)

Colorless solid (0.013 g, 28% yield). MS (ES+) m/z 474.0 (M+1). $^1$H NMR (300 MHz, DMSO-$d_6$) δ 12.85 (s, 1H), 7.71-7.66 (m, 3H), 7.34 (dd, J=1.4, 8.1 Hz, 1H), 7.29-7.22 (m, 3H), 7.11 (d, J=1.1 Hz, 1H), 6.86 (d, J=4.6 Hz, 1H), 4.31-4.24 (m, 1H), 4.13-4.08 (m, 1H), 2.15-1.74 (m, 7H), 1.54-1.47 (m, 1H), 1.23-1.14 (m, 1H) (Note: 2 protons presumably appeared under the water signal, exchangeable protons not observed).

Example 101

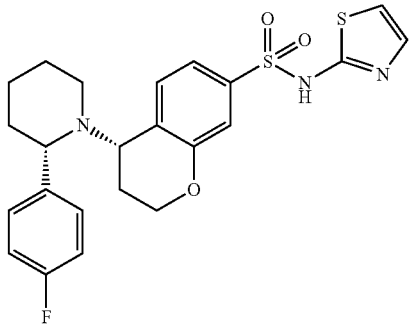

(±)

(S)-4-((S)-2-(4-fluorophenyl)piperidin-1-yl)-N-(thiazol-2-yl)chromane-7-sulfonamide (Stereochemistry Arbitrarily Assigned)

This compound was prepared in the same sequence as Example 100. Colorless solid (0.007 g, 15% yield). MS (ES+) m/z 474.0 (M+1). $^1$H NMR (300 MHz, DMSO-$d_6$) δ 12.75 (s, 1H), 7.80-7.77 (m, 1H), 7.51-7.47 (m, 1H), 7.35-7.33 (m, 2H), 7.26 (d, J=4.8 Hz, 1H), 7.17-7.15 (m, 2H), 7.04-7.01 (m, 1H), 6.83 (d, J=4.2 Hz, 1H), 4.27-4.21 (m, 1H), 2.47-2.38 (m, 1H), 2.28-2.18 (m, 1H), 1.98 (d, J=13.2 Hz, 1H), 1.87-1.23 (m, 7H) (Note: 2 protons presumably appeared under the water signal, exchangeable protons not observed).

Example 10

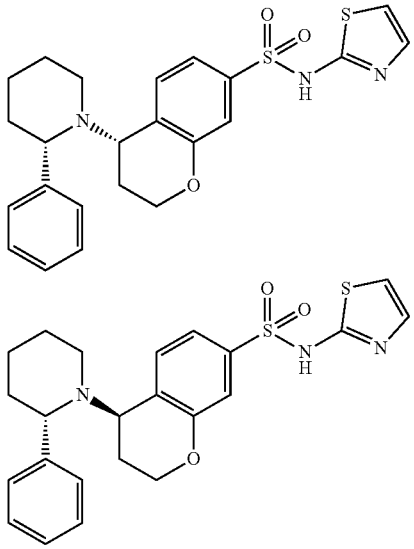

(S)-4-((S)-2-phenylpiperidin-1-yl)-N-(thiazol-2-yl)chromane-7-sulfonamide and (R)-4-((S)-2-phenylpiperidin-1-yl)-N-(thiazol-2-yl)chromane-7-sulfonamide (Stereochemistry at Chromane Arbitrarily Assigned)

Step 1

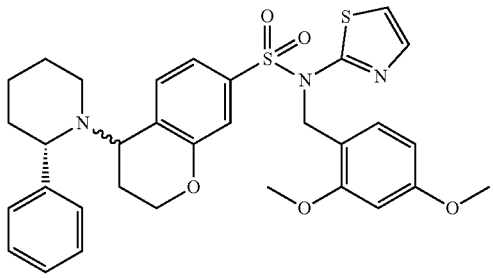 [SMILES: COc1ccc(CN(c2nccs2)S(=O)(=O)c2ccc3c(c2)OCCC3N2CCCC[C@H]2c2ccccc2)c(OC)c1]

N-(2,4-dimethoxybenzyl)-4-((S)-2-phenylpiperidin-1-yl)-N-(thiazol-2-yl)chromane-7-sulfonamide To a solution of (R)-7-(N-(2,4-dimethoxybenzyl)-N-(thiazol-2-yl)sulfamoyl)chroman-4-yl methanesulfonate (0.58 g, 1.08 mmol) in anhydrous tetrahydrofuran (8 mL) was added (S)-2-phenylpiperidine hydrochloride (0.43 g, 2.18 mmol) and N,N-diisopropylethylamine (0.94 mL, 5.4 mmol). The mixture was heated to reflux under a nitrogen atmosphere for 17 h, then cooled to ambient temperature and 1,8-diazabicycloundec-7-ene (0.65 mL, 4.3 mmol) and a further portion of (S)-2-phenylpiperidine hydrochloride (0.43 g, 2.18 mmol) were added. The mixture was heated to reflux for 3 days, then cooled to ambient temperature. The reaction was concentrated in vacuo and the residue purified by column chromatography, eluting with a 0-50% gradient of ethyl acetate in hexanes to afford the title compound as a yellow syrup (0.091 g, 14% yield). MS (ES+) m/z: 606.1 (M+1).

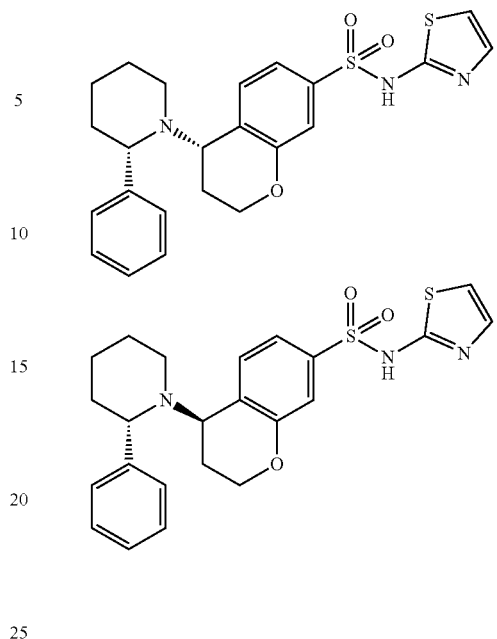

(S)-4-((S)-2-phenylpiperidin-1-yl)-N-(thiazol-2-yl)chromane-7-sulfonamide and (R)-4-((S)-2-phenylpiperidin-1-yl)-N-(thiazol-2-yl)chromane-7-sulfonamide (Stereochemistry at Chromane Arbitrarily Assigned)

Following the procedure as described in Example 51, step 8 and making non-critical variations as required to replace (±)-N-(2,4-dimethoxybenzyl)-5-((R)-2-phenylpiperidin-1-yl)-N-(1,2,4-thiadiazol-5-yl)-5,6,7,8-tetrahydronaphthalene-2-sulfonamide with N-(2,4-dimethoxybenzyl)-4-((S)-2-phenylpiperidin-1-yl)-N-(thiazol-2-yl)chromane-7-sulfonamide, the title compounds were obtained as trifluoroacetate salts.

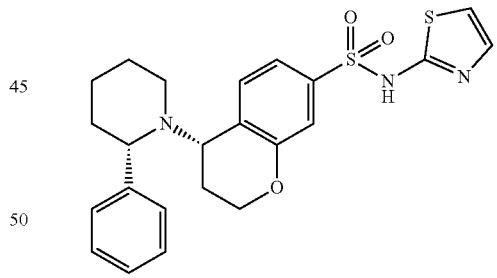

(S)-4-((S)-2-phenylpiperidin-1-yl)-N-(thiazol-2-yl)chromane-7-sulfonamide (Stereochemistry at Chromane Arbitrarily Assigned)

Colorless solid (0.018 g, 21% yield). MS (ES+) m/z 456.0 (M+1). $^1$H NMR (300 MHz, DMSO-$d_6$) δ 12.87 (br s, 1H), 9.45 (br s, 1H), 7.68 (br s, 2H), 7.42-7.29 (m, 6H), 7.10 (s, 1H), 6.88 (d, J=4.6 Hz, 1H), 4.79-4.70 (m, 1H), 4.57-4.49 (m, 1H), 4.34-4.12 (m, 2H), 3.41-3.31 (m, 1H), 2.78-2.69 (m, 1H), 2.28-1.71 (m, 6H), 1.63-1.50 (m, 1H) (Note: one proton presumably under the water peak); $^{19}$F NMR (282 MHz, DMSO-$d_6$) δ −73.8 (s, 3F).

Example 103

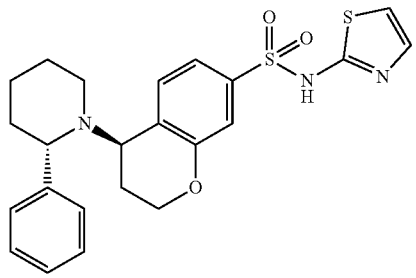 [SMILES: O=S(=O)(Nc1nccs1)c1ccc2c(c1)OCC[C@H]2N1CCCC[C@H]1c1ccccc1]

(R)-4-((S)-2-phenylpiperidin-1-yl)-N-(thiazol-2-yl)chromane-7-sulfonamide (Stereochemistry at Chromane Arbitrarily Assigned)

This compound was produced in the same sequence as Example 102. Colorless solid (0.007 g, 8% yield). MS (ES+) m/z 456.0 (M+1). $^1$H NMR (300 MHz, DMSO-$d_6$) δ 12.75 (br s, 1H), 9.22 (br s, 1H), 7.80-7.77 (m, 2H), 7.50-7.42 (m, 3H), 7.35-7.24 (m, 3H), 7.02 (s, 1H), 6.83 (br s, 1H), 4.79-4.68 (m, 1H), 4.28-4.21 (m, 2H), 3.81-3.67 (m, 2H), 3.63-3.57 (m, 1H), 2.45-2.42 (m, 1H), 2.29-2.18 (m, 1H), 2.06-1.53 (m, 6H); $^{19}$F NMR (282 MHz, DMSO-$d_6$) δ −74.1 (s, 3F).

Example 104

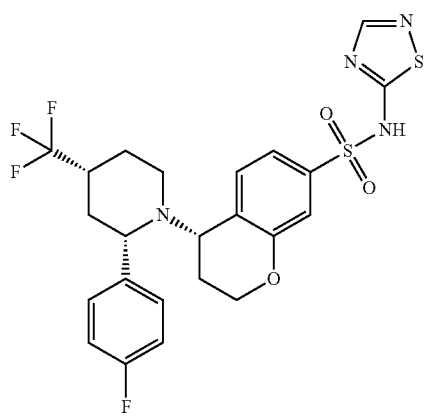 [SMILES: O=S(=O)(Nc1ncns1)c1ccc2c(c1)OCC[C@@H]2N1CC[C@@H](C(F)(F)F)C[C@H]1c1ccc(F)cc1]

(S)-4-((2S,4S)-2-(4-fluorophenyl)-4-(trifluoromethyl)piperidin-1-yl)-N-(1,2,4-thiadiazol-5-yl)chroman-7-sulfonamide

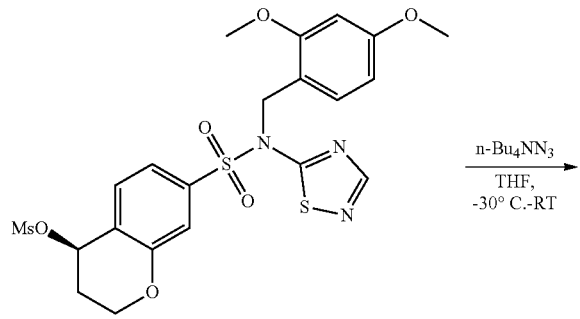

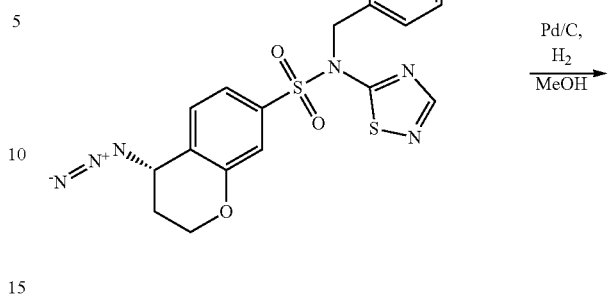

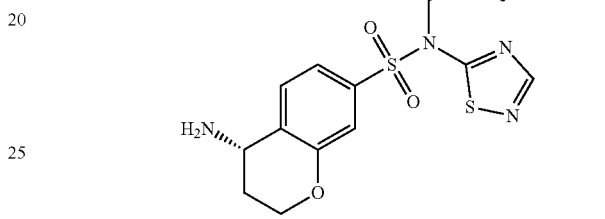

(S)-4-azido-N-(2,4-dimethoxybenzyl)-N-(1,2,4-thiadiazol-5-yl)chromane-7-sulfonamide Step 1

To a solution of (R)-7-(N-(2,4-dimethoxybenzyl)-N-(1,2,4-thiadiazol-5-yl)sulfamoyl)chroman-4-yl methanesulfonate (3 g, 3.36 mmol) in THF (100 mL) was added tetra-N-butylammonium azide (1.91 g, 6.71 mmol) under −30° C. The resulting slurry was allowed to slowly warm to ambient temperature overnight, quenched with water (50 mL), extracted with EtOAc (50 mL×3), washed with brine (50 mL), dried over anhydrous sodium sulfate and concentrated to give an oil. The residue was purified by chromatography (eluting with 10-30% EtOAc in petroleum ether) to give the desired product (1.8 g, 97.3%) as yellow solid. LCMS (ESI) m/z: 511.1 [M+Na]$^+$.

Step 2

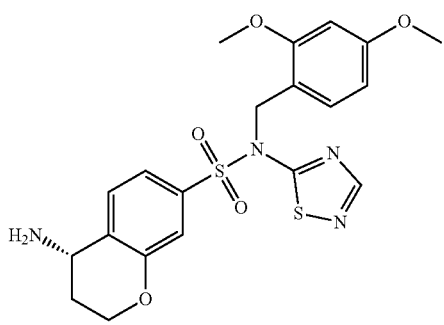 [SMILES: COc1ccc(CN(c2ncns2)S(=O)(=O)c2ccc3c(c2)OCC[C@@H]3N)c(OC)c1]

(S)-4-amino-N-(2,4-dimethoxybenzyl)-N-(1,2,4-thiadiazol-5-yl)chromane-7-sulfonamide A mixture of (S)-4-azido-N-(2,4-dimethoxybenzyl)-N-(1,2,4-thiadiazol-5-yl)chromane-7-sulfonamide (1.8 g, 3.29 mmol) and Pd/C (10%, 180 mg) in MeOH (150 mL) and THF (60 mL) was stirred under hydrogene atmosphere at 25° C. overnight. The reaction mixture was filtered and concentrated to give an oil. The residue was purified by chromatography (eluting with 1-10% MeOH in DCM) to afford the title product (Ig, 65.8%) as pale yellow solid. LCMS (ESI) m/z: 485.0 [M+Na]$^+$.

The enantiomer was purified by chiral SFC from the racemate, Chiral-HPLC (column: AY-H, 4.6×250 mm, 5 μm; mobile Phase: A: n-Hexane (0.1% DEA), B: EtOH (0.1% DEA), A:B=50:50; column temperature: 40° C.; RT=10.44 min).

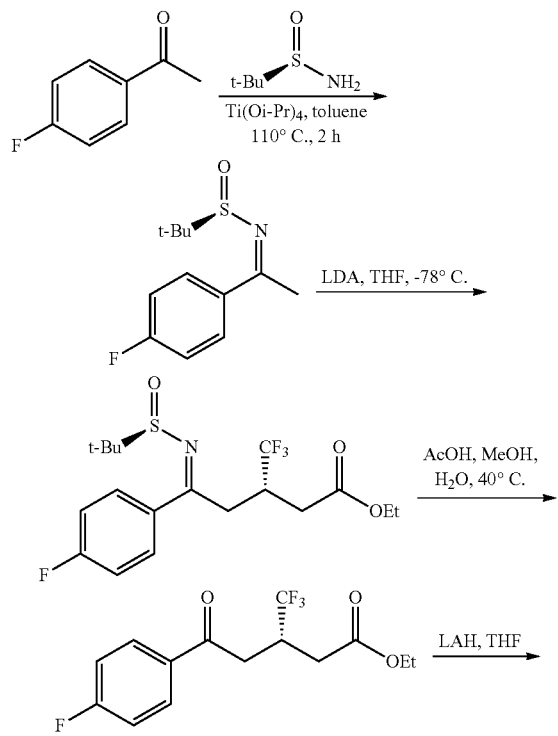

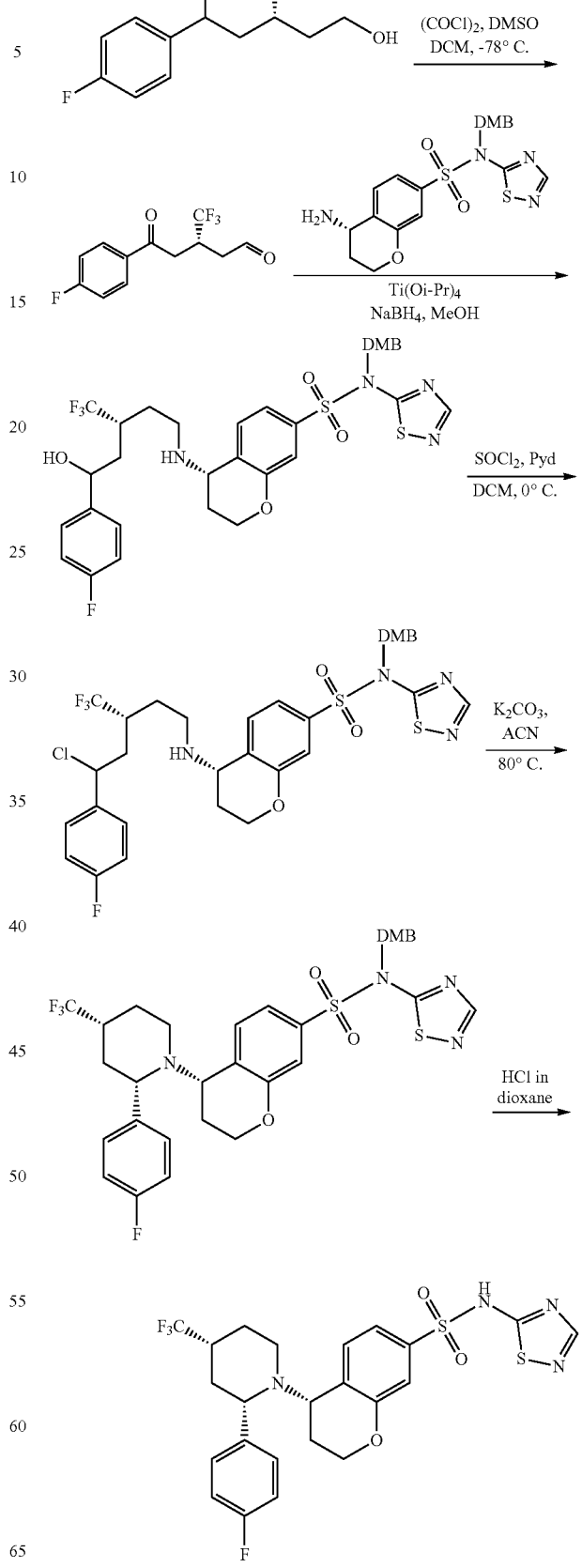

Step 1

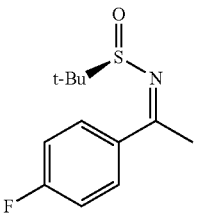 [SMILES: C/C(=N/[S@](=O)C(C)(C)C)c1ccc(F)cc1]

(R)—N-(1-(4-fluorophenyl)ethylidene)-2-methylpropane-2-sulfinamide

A mixture of 1-(4-fluorophenyl)ethanone (1.0 g, 7.24 mmol) and titanium tetraisopropanolate (4.41 g, 14.48 mmol) in toluene (50 mL) was stirred at 110° C. for 16 h. The reaction mixture was cooled to room temperature, quenched with sat. sodium bicarbonate (50 mL) and stirred vigorously for 0.5 h, filtered and diluted with EtOAc (200 mL). The combined organic layer was washed with brine, dried over anhydrous Na$_2$SO$_4$ and concentrated. The residue was purified by silica gel column chromatography (eluting with 20% EtOAc in petroleum ether) to afford the desired compound (1.14 g, 65.3%) as a yellow oil. LCMS (ESI) m/z: 242.1 [M+H]$^+$.

Step 2

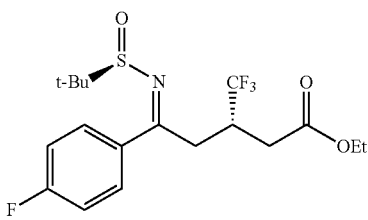 [SMILES: CCOC(=O)C[C@H](C/C(=N/[S@](=O)C(C)(C)C)c1ccc(F)cc1)C(F)(F)F]

ethyl (S)-5-(((R)-tert-butylsulfinyl)imino)-5-(4-fluorophenyl)-3-(trifluoromethyl) pentanoate To a solution of (R)—N-(1-(4-fluorophenyl)ethylidene)-2-methylpropane-2-sulfinamide (1.14 g, 4.73 mmol) and ethyl 4,4,4-trifluorobut-2-enoate (1.19 g, 7.1 mmol) in dry THF (10.0 mL) was added lithium diisopropylamide (2.0 M, 4.73 mL, 9.46 mmol) at −78° C. The reaction mixture was stirred at −78° C. for 1 h, then warmed up to 0° C. over 20 min period and stirred at 0° C. for 0.5 h, quenched with sat. ammonium chloride (10 mL), extracted with EtOAc (25 mL×3), washed with brine, dried over anhydrous sodium sulfate, and filtered. The filtrate was concentrated and the residue was purified by silica gel chromatography (eluting with 20% EtOAc in petroleum ether) to afford the desired compound (0.81 g, 41%) as a yellow oil. LCMS (ESI) m/z: 410.1 [M+H]$^+$.

Step 3

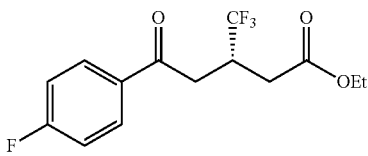 [SMILES: CCOC(=O)C[C@H](CC(=O)c1ccc(F)cc1)C(F)(F)F]

ethyl (S)-5-(4-fluorophenyl)-5-oxo-3-(trifluoromethyl)pentanoate

A solution of ethyl (S)-5-(((R)-tert-butylsulfinyl)imino)-5-(4-fluorophenyl)-3-(trifluoromethyl)-pentanoate (0.81 g, 1.98 mmol) in MeOH (5.0 mL) and acetic acid (1.0 M, 5.0 mL) was stirred at 40° C. for 24 h. The solvent was reduced to half volume under reduced pressure, brine (5 mL) was added, extracted with EtOAc (10 mL×3), dried over anhydrous sodium sulfate, filtered, and concentrated. The residue was purified by silica gel chromatography (eluting with 15% EtOAc in petroleum ether) to afford the desired compound (560 mg, 93%) as a yellow oil. LCMS (ESI) m/z: 307.1 [M+H]$^+$.

Step 4

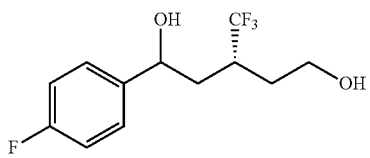 [SMILES: OCC[C@H](CC(O)c1ccc(F)cc1)C(F)(F)F]

(3R)-1-(4-fluorophenyl)-3-(trifluoromethyl)pentane-1,5-diol

A solution of ethyl (S)-5-(4-fluorophenyl)-5-oxo-3-(trifluoromethyl)pentanoate (560 mg, 1.84 mmol) in dry THF (10.0 mL) was added dropwise to a stirred mixture of lithium aluminium hydride (200 mg, 5.50 mmol) in dry THF (10.0 mL) at 0° C. under a nitrogen atmosphere. The reaction mixture was stirred at 0° C. for 30 min, quenched with sat. ammonium chloride (5 mL) and extracted with EtOAc (25 mL×3). The combined organic layers were washed with brine (10 mL), dried over anhydrous sodium sulfate, and filtered. The filtrate was concentrated to give the crude product (510 mg, 91%), which was used in next step without further purification. LCMS (ESI) m/z: 267.1 [M+H]$^+$.

Step 5

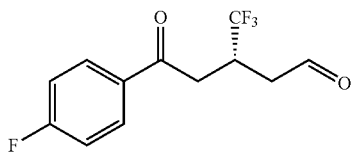

(R)-5-(4-fluorophenyl)-5-oxo-3-(trifluoromethyl) pentanal

To a solution of dimethyl sulfoxide (520 mg, 6.68 mmol) in DCM (5 mL) was added oxalyl chloride (640 mg, 5.00 mmol) at −65° C. Then a solution of (3R)-1-(4-fluorophenyl)-3-(trifluoromethyl)pentane-1,5-diol (510 mg, 1.67 mmol) in DCM (5 mL) was added. The reaction mixture was stirred at −65° C. for 20 min, quenched with triethylamine (1 mL) and water (1 mL), extracted with DCM (10 mL×3), washed with brine, dried over anhydrous sodium sulfate, and concentrated. The residue was purified with column chromatography (eluting with 20% EtOAc in petroleum ether) to afford the desired compound (250 mg, 49%) as a pale yellow oil. LCMS (ESI) m/z: 263.1 [M+H]$^+$.

Step 6

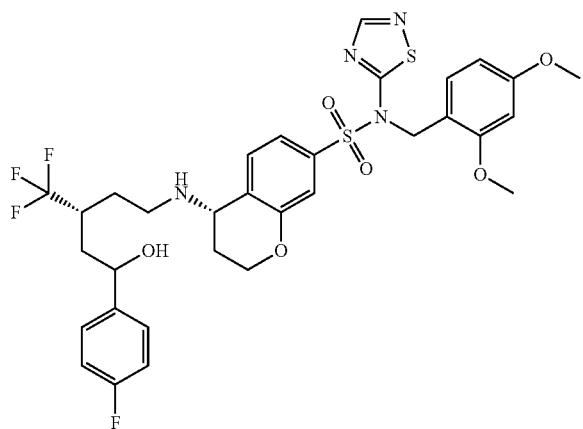 [SMILES: COc1ccc(CN(c2ncns2)S(=O)(=O)c2ccc3c(c2)OCC[C@@H]3NCC[C@H](CC(O)c2ccc(F)cc2)C(F)(F)F)c(OC)c1]

(4S)—N-(2,4-dimethoxybenzyl)-4-(((3R)-5-(4-fluorophenyl)-5-hydroxy-3-(trifluoromethyl)pentyl)amino)-N-(1,2,4-thiadiazol-5-yl)chromane-7-sulfonamide Titanium(IV) isopropoxide (570 mg, 2.0 mmol) was added to a mixture of (R)-5-(4-fluorophenyl)-5-oxo-3-(trifluoromethyl)pentanal (250 mg, 0.95 mmol) and (S)-4-amino-N-(2,4-dimethoxybenzyl)-N-(1,2,4-thiadiazol-5-yl)chromane-7-sulfonamide (482 mg, 1.05 mmol) in dry THF (8 mL). The reaction mixture was stirred at room temperature under nitrogen for 16 h. MeOH (5 mL) was added which was followed by careful addition of sodium borohydride (180 mg, 5.0 mmol). The reaction was monitored by TLC. After 5 min, the reaction was quenched by NaOH (0.1 N, 5 mL). The resulting mixture was filtered through celite, diluted with DCM (50 mL), dried over anhydrous MgSO$_4$ and concentrated. The residue was purified by chromatography (eluting with 50% EtOAc in petroleum ether) to afford the desired compound (310 mg, 46%) as a colorless oil. LCMS (ESI) m/z: 711.2[M+H]$^+$.

Step 7

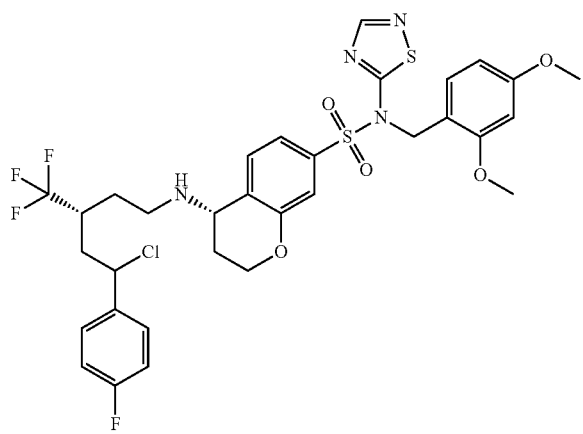 [SMILES: COc1ccc(CN(c2ncns2)S(=O)(=O)c2ccc3c(c2)OCC[C@@H]3NCC[C@H](CC(Cl)c2ccc(F)cc2)C(F)(F)F)c(OC)c1]

(4S)-4-(((3R)-5-chloro-5-(4-fluorophenyl)-3-(trifluoromethyl)pentyl)amino)-N-(2,4-dimethoxybenzyl)-N-(1,2,4-thiadiazol-5-yl)chromane-7-sulfonamide To a solution of (4S)—N-(2,4-dimethoxybenzyl)-4-(((3R)-5-(4-fluorophenyl)-5-hydroxy-3-(trifluoromethyl)pentyl)amino)-N-(1,2,4-thiadiazol-5-yl)chromane-7-sulfonamide (310 mg, 0.44 mmol), pyridine (0.5 mL) in ethyl ether (10 mL) was added thionyl chloride (0.2 mL) at 0° C. After stirred at 0° C. for 30 min, the reaction mixture was quenched with water (10 mL), extracted with ethyl ether (10 mL×3), washed with brine (10 mL), dried over anhydrous MgSO$_4$, and concentrated. The residue (250 mg) was used in next step without further purification. LCMS (ESI) m/z: 729.1 [M+H]$^+$.

Step 8

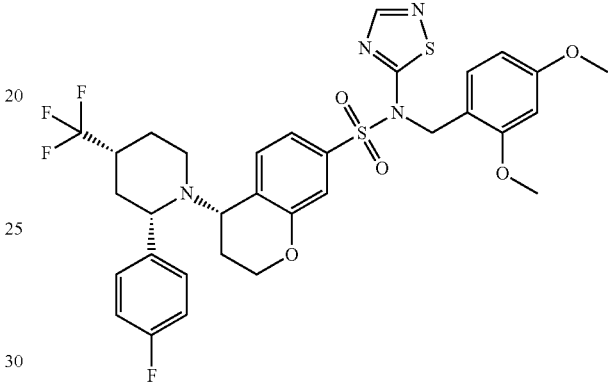

(S)—N-(2,4-dimethoxybenzyl)-4-((2S,4R)-2-(4-fluorophenyl)-4-(trifluoromethyl)piperidin-1-yl)-N-(1,2,4-thiadiazol-5-yl)chroman-7-sulfonamide A mixture of (4S)-4-(((3R)-5-chloro-5-(4-fluorophenyl)-3-(trifluoromethyl)pentyl)-amino)-N-(2,4-dimethoxybenzyl)-N-(1,2,4-thiadiazol-5-yl)chromane-7-sulfonamide (250 mg, 0.34 mmol) and potassium carbonate (140 mg, 1.02 mmol) in CH$_3$CN (10 mL) was stirred at 60° C. for 16 h. The mixture was quenched with water (10 mL) and EtOAc (30 mL), washed with brine, dried over anhydrous MgSO$_4$, and concentrated. The crude was purified by chromatography (eluting with 10~20% EtOAc in petroleum ether) and the second eluting fraction was identified as (S)—N-(2,4-dimethoxybenzyl)-4-((2S,4R)-2-(4-fluorophenyl)-4-(trifluoromethyl)piperidin-1-yl)-N-(1,2,4-thiadiazol-5-yl)chroman-7-sulfonamide (89 mg, 38%), LCMS(ESI) m/z: 693.2[M+H]$^+$.

Step 9

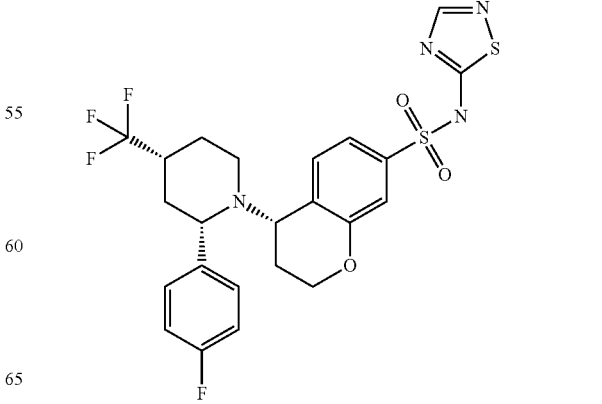

(S)-4-((2S,4R)-2-(4-fluorophenyl)-4-(trifluoromethyl)piperidin-1-yl)-N-(1,2,4-thiadiazol-5-yl)chroman-7-sulfonamide A mixture of (S)—N-(2,4-dimethoxybenzyl)-4-((2S,4R)-2-(4-fluorophenyl)-4-(trifluoromethyl)piperidin-1-yl)-N-(1,2,4-thiadiazol-5-yl)chroman-7-sulfonamide (80 mg, 0.11 mmol) and HCl in dioxane (4 M, 0.5 mL) was stirred at 0° C. for 30 min, the reaction mixture was concentrated and the residue was purified by prep-HPLC (eluting with 0~50% gradient $CH_3CN$ in 0.5% $NH_4HCO_3$) to afford the title compound (41 mg, 66%) as a white solid. LCMS (ESI) Method A: RT=5.84 min, m/z 543.1 $[M+H]^+$. $^1$H NMR (400 MHz, DMSO-$d_6$) δ 8.23 (s, 1H), 7.78 (d, J=8 Hz, 1H), 7.55-7.52 (m, 2H), 7.33-7.16 (m, 3H), 7.03 (s, 1H), 4.22-4.20 (m, 1H), 3.78-3.76 (m, 2H), 3.68-3.65 (m, 2H), 2.54-2.50 (m, 2H), 2.01-1.73 (m, 4H), 1.76-1.744 (m, 2H).

Example 105

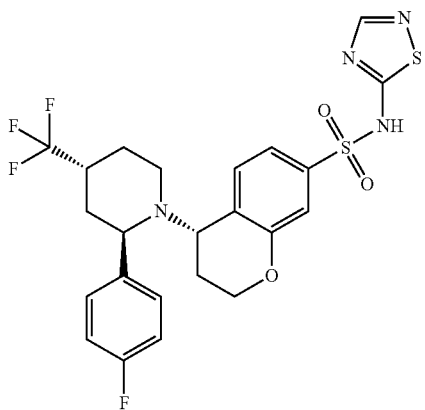 [SMILES: O=S(=O)(Nc1ncns1)c1ccc2c(c1)OCC[C@@H]2N1CC[C@@H](C(F)(F)F)C[C@@H]1c1ccc(F)cc1]

(S)-4-((2R,4S)-2-(4-fluorophenyl)-4-(trifluoromethyl)piperidin-1-yl)-N-(1,2,4-thiadiazol-5-yl)chroman-7-sulfonamide The compound was synthesized as for Example 104. The first eluting fraction in step 8 was identified as (S)—N-(2,4-dimethoxybenzyl)-4-((2R,4R)-2-(4-fluorophenyl)-4-(trifluoromethyl)piperidin-1-yl)-N-(1,2,4-thiadiazol-5-yl)chroman-7-sulfonamide and used to synthesize the target compound. LCMS (ESI) Method A: RT=5.65 min, m/z 543.1 $[M+H]^+$. $^1$H NMR (400 MHz, DMSO-$d_6$) δ 7.83 (s, 1H), 7.54-7.50 (m, 2H), 7.34-7.15 (m, 3H), 7.04 (s, 1H), 6.67 (d, J=16 Hz, 1H), 6.06-6.00 (m, 1H), 4.24-4.10 (m, 2H), 3.67-3.65 (m, 3H), 3.33-3.30 (m, 1H), 2.65-2.58 (m, 2H), 1.88-1.68 (m, 4H).

Example 106

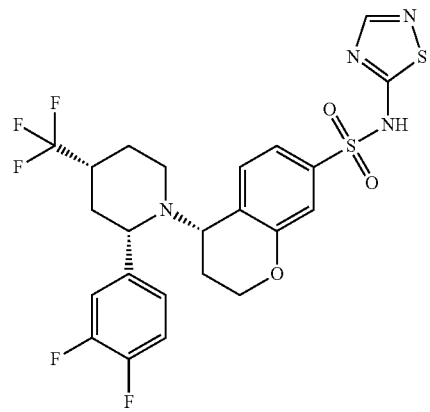 [SMILES: O=S(=O)(Nc1ncns1)c1ccc2c(c1)OCC[C@@H]2N1CC[C@@H](C(F)(F)F)C[C@H]1c1ccc(F)c(F)c1]

(S)-4-((2S,4R)-2-(3,4-difluorophenyl)-4-(trifluoromethyl)piperidin-1-yl)-N-(1,2,4-thiadiazol-5-yl)chroman-7-sulfonamide The compound was synthesized as for Example 104. LCMS (ESI) Method A: RT=5.85 min, m/z: 561.1 $[M+H]^+$. $^1$H NMR (400 MHz, DMSO-$d_6$) δ 8.13 (s, 1H), 7.77 (d, J=7.9 Hz, 1H), 7.64-7.49 (m, 1H), 7.45-7.31 (m, 2H), 7.29 (d, J=7.9 Hz, 1H), 7.01 (d, J=1.6 Hz, 1H), 4.32-4.16 (m, 1H), 3.96-3.61 (m, 4H), 2.55 (s, 1H), 2.39-2.28 (m, 1H), 2.01-1.74 (m, 4H), 1.66-1.40 (m, 2H).

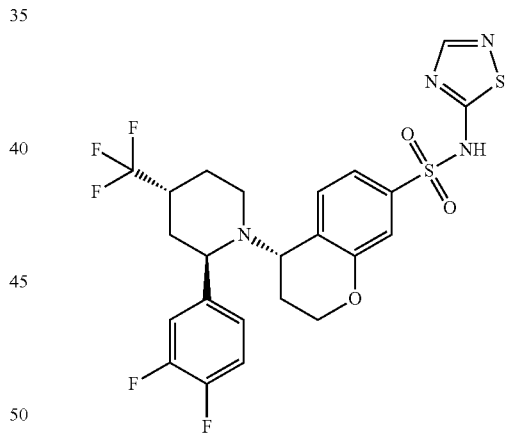

Example 107

(S)-4-((2R,4R)-2-(3,4-difluorophenyl)-4-(trifluoromethyl)piperidin-1-yl)-N-(1,2,4-thiadiazol-5-yl)chroman-7-sulfonamide The compound was synthesized as for Example 104. LCMS (ESI) Method A: RT=5.83 min, m/z: 561.1 $[M+H]^+$. 1H NMR (400 MHz, DMSO-$d_6$) δ 8.28 (s, 1H), 7.84 (s, 1H), 7.68-7.59 (m, 1H), 7.46-7.27 (m, 3H), 7.17 (d, J=7.1 Hz, 1H), 7.04 (s, 1H), 6.67 (d, J=15.8 Hz, 1H), 6.20-6.03 (m, 1H), 4.29-4.18 (m, 1H), 4.16-4.04 (m, 1H), 3.68 (s, 3H), 3.46-3.19 (m, 1H), 2.70-2.58 (m, 2H), 1.96-1.76 (m, 3H), 1.75-1.62 (m, 1H).

Example 108

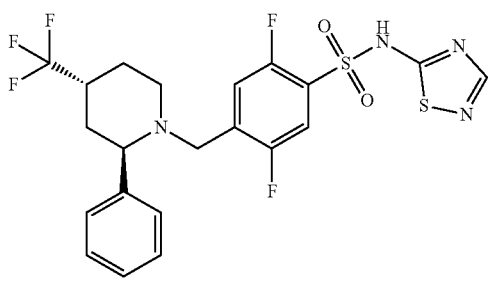

2,5-Difluoro-4-(((2R,4R)-2-phenyl-4-(trifluoromethyl)piperidin-1-yl)methyl)-N-(1,2,4-thiadiazol-5-yl)benzenesulfonamide The compound was synthesized as for Example 34. LCMS (ESI) Method C: RT=5.68 min, m/z 519.0 [M+H]⁺. ¹H NMR (400 MHz, DMSO-d₆) δ 8.07 (s, 1H), 7.44-7.23 (m, 7H), 3.64-3.55 (m, 3H), 2.75-2.72 (m, 1H), 2.66-2.61 (m, 1H), 2.43-2.40 (m, 1H). 1.99-1.81 (m, 4H).

Example 109

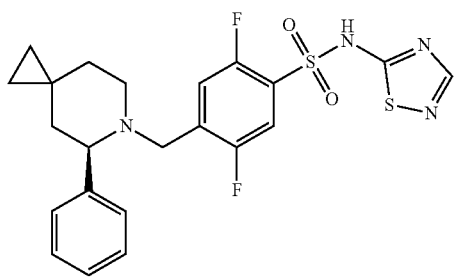

(R)-2,5-difluoro-4-((5-phenyl-6-azaspiro[2.5]octan-6-yl)methyl)-N-(1,2,4-thiadiazol-5-yl)benzenesulfonamide

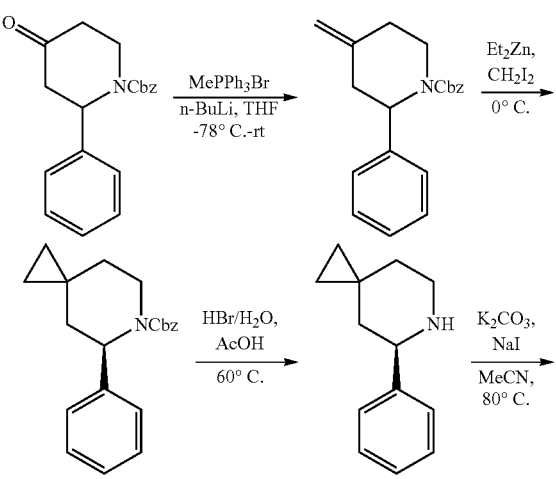

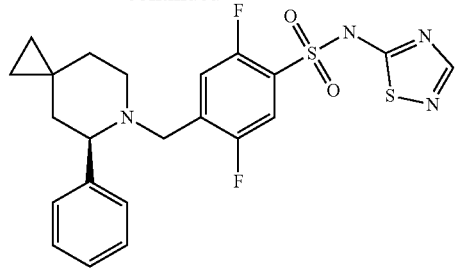 [SMILES: O=S(=O)(Nc1ncns1)c1cc(F)c(CN2CCC3(CC3)C[C@@H]2c2ccccc2)cc1F]

Step 1

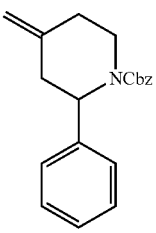 [SMILES: C=C1CCN(C(=O)OCc2ccccc2)C(c2ccccc2)C1]

Benzyl 4-methylene-2-phenylpiperidine-1-carboxylate

To a suspension of methyltriphenylphosphonium bromide (2.31 g, 6.49 mmol) in tetrahydrofuran (50 mL) was added n-butyllithium in hexane (4.0 mL, 2.5 M, 10.0 mmol) at −78° C. and stirred at −78° C. for 30 minutes. Then a solution of benzyl 4-oxo-2-phenyl-piperidine-1-carboxylate (1.0 g, 3.23 mmol) in tetrahydrofuran (10 mL) was added slowly. The reaction mixture was stirred at −78° C. for 2 hours and then at room temperature overnight. The reaction was quenched by water and concentrated to dryness. The residue was taken up in EtOAc (30 mL), washed with water (2×10 mL) and brine (10 mL), dried over anhydrous sodium sulfate and concentrated. The crude was purified by chromatography (eluting with 10% EtOAc in petroleum ether) to afford the desired product (300 mg, 30.2%). LCMS (ESI) m/z: 330.1 [M+Na]⁺.

Step 2

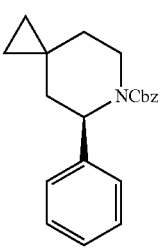 [SMILES: O=C(OCc1ccccc1)N1CCC2(CC2)C[C@@H]1c1ccccc1]

(R)-benzyl 5-phenyl-6-azaspiro[2.5]octane-6-carboxylate

A mixture of Benzyl 4-methylene-2-phenylpiperidine-1-carboxylate (600 mg, 1.95 mmol) and diethylzinc in hexane (60 mL, 1M, 60 mmol) was stirred at 0° C. for 30 min. Then diiodomethane (6.0 mL, 73.9 mmol) was added and stirred at 0° C. for 2 h and room temperature overnight. The reaction mixture was filtered through celite, washed with EtOAc (20 mL), concentrated and purified by chromatography (eluting with 10% EtOAc in petroleum ether) to afford the desired product (380 mg) as colorless oil. The enantiomer was separated by chiral SFC from the racemate. The first eluting fraction was arbitrarily assigned as (R)-benzyl 5-phenyl-6-azaspiro[2.5]octane-6-carboxylate (160 mg, 25.5%). Chiral HPLC (column: OZ-H, 4.6×250 mm, 5 μm; mobile Phase: A: supercritical $CO_2$, B: MeOH (0.2% ammonia), A:B=75:25; flow: 3.0 mL/min; column temperature: 40° C.; RT=2.41 min). LCMS (ESI) m/z: 322.2 $[M+H]^+$.

Step 3

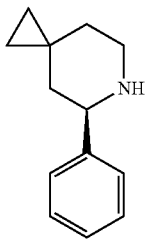 [SMILES: c1ccc([C@H]2CC3(CCN2)CC3)cc1]

(R)-5-phenyl-6-azaspiro[2.5]octane

A mixture of (R)-benzyl 5-phenyl-6-azaspiro[2.5]octane-6-carboxylate (90 mg, 0.28 mmol) and hydrogen bromide (40%, 0.5 mL) in acetic acid (2 mL) was stirred at 60° C. for 2 h. The reaction was concentrated to dryness and the crude was purified by Combiflash (eluting with 0~8% MeCN in 4% FA) to afford the desired product as a colorless oil (30 mg, 57.2%). LCMS (ESI) m/z: 188.1 $[M+H]^+$.

Step 4

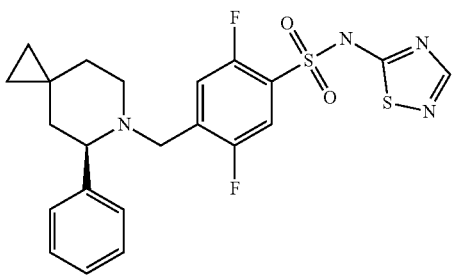 [SMILES: O=S(=O)(Nc1ncns1)c1cc(F)c(CN2CCC3(CC3)C[C@@H]2c2ccccc2)cc1F]

(R)-2,5-difluoro-4-((5-phenyl-6-azaspiro[2.5]octan-6-yl)methyl)-N-(1,2,4-thiadiazol-5-yl)benzenesulfonamide The compound was synthesized as for step 5 of Example 1. LCMS (ESI) Method C: RT=5.72 min, m/z 477.1 $[M+H]^+$. $^1$H NMR (400 MHz, DMSO-$d_6$) δ: 8.17 (s, 1H), 7.50-7.47 (m, 3H), 7.38-7.29 (m, 4H), 3.72-3.70 (m, 3H), 3.23-3.17 (m, 2H), 2.16-2.13 (m, 2H), 1.07-0.94 (m, 2H), 0.44-0.38 (m, 4H).

Example 110

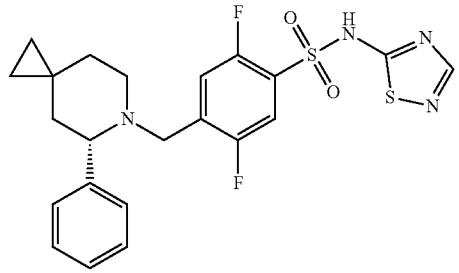 [SMILES: O=S(=O)(Nc1ncns1)c1cc(F)c(CN2CCC3(CC3)C[C@H]2c2ccccc2)cc1F]

(S)-2,5-difluoro-4-((5-phenyl-6-azaspiro[2.5]octan-6-yl)methyl)-N-(1,2,4-thiadiazol-5-yl)benzenesulfonamide The compound was synthesized as for Example 109. LCMS (ESI) Method C: RT=5.72 min, m/z 477.1 $[M+H]^+$. $^1$H NMR (400 MHz, DMSO-$d_6$) δ: 8.16 (s, 1H), 7.50-7.47 (m, 3H), 7.38-7.30 (m, 4H), 3.73-3.71 (m, 3H), 3.32-3.27 (m, 2H), 2.16-2.13 (m, 2H), 1.07-0.94 (m, 2H), 0.44-0.38 (m, 4H).

Example 111

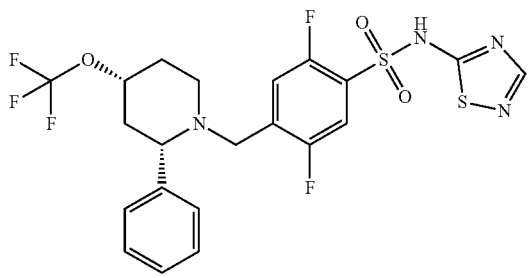 [SMILES: O=S(=O)(Nc1ncns1)c1cc(F)c(CN2CC[C@@H](OC(F)(F)F)C[C@H]2c2ccccc2)cc1F]

2,5-Difluoro-4-(((2S,4R)-2-phenyl-4-(trifluoromethoxy)piperidin-1-yl)methyl)-N-(1,2,4-thiadiazol-5-yl)benzenesulfonamide

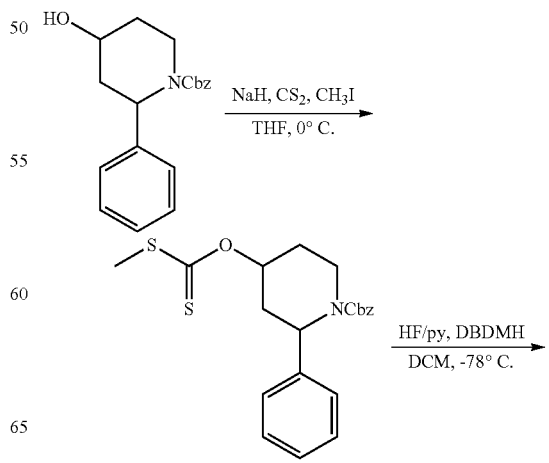

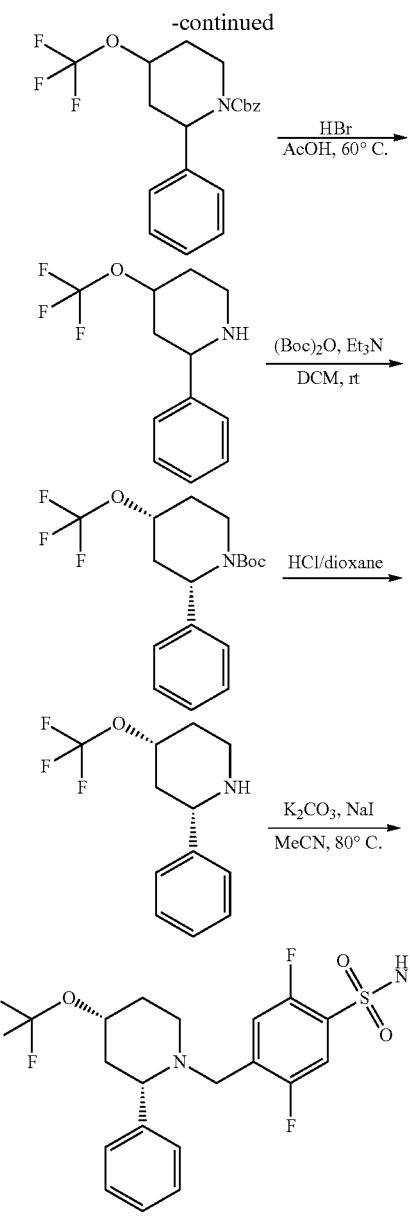

Step 1

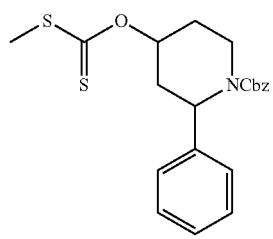 [SMILES: CSC(=S)OC1CCN(C(=O)OCc2ccccc2)C(c2ccccc2)C1]

Benzyl 4-(methylthiocarbonothioyloxy)-2-phenylpiperidine-1-carboxylate

A solution of benzyl 4-hydroxy-2-phenyl-piperidine-1-carboxylate (2.2 g, 7.07 mmol) in THF (10.0 mL) was added dropwise to a suspension of sodium hydride (565 mg, 14.13 mmol) in THF at 0° C. in 5 min. The mixture became dense by complete addition. A solution of carbon disulfide (806 mg, 10.6 mmol) in THE (5.0 mL) was added dropwise in 5 min and then the reaction mixture stirred at 0-5° C. for 15 min. Then a solution of iodomethane (1.3 g, 9.19 mmol) in THF (5.0 mL) was added dropwise in 2 min. The reaction mixture was stirred for 10 min at 0-5° C., quenched with distilled water (5.0 mL), and concentrated. The residue was diluted with EtOAc (100 mL), washed with water (3×50 mL), dried over anhydrous sodium sulfate and concentrated. The crude product was purified by column chromatography (eluting with 10% EtOAc in petroleum ether) to afford the desired product (2.0 g, 70.5%). LCMS (ESI) m/z: 424.1 [M+Na]$^+$.

Step 2

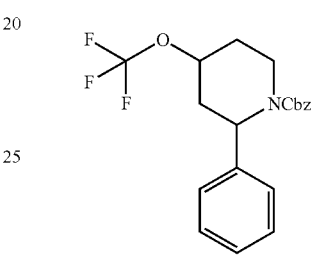

Benzyl 2-phenyl-4-(trifluoromethoxy)piperidine-1-carboxylate

To a solution of 1 1,3-dibromo-5,5-dimethylhydantoin (2.13 g, 7.47 mmol) in DCM (50 mL) was added pyridine hydrofluoride (10 mL, 77.69 mmol) at −78° C. and stirred for 10 min, then benzyl-4-methylsulfanylcarbothioyloxy-2-phenyl-piperidine-1-carboxylate (1.0 g, 2.49 mmol) in DCM (10 mL) was added at −78° C. The reaction was stirred at room temperature overnight, diluted with DCM (50 mL), washed with aqueous sodium carbonate (3×30 mL), dried over anhydrous sodium sulfate, and concentrated in vacuo. The crude product was used in the next step without further purification.

Step 3

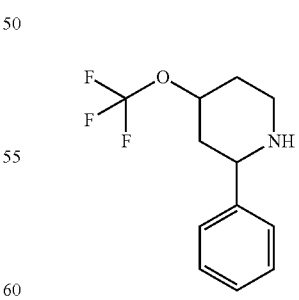

2-Phenyl-4-(trifluoromethoxy)piperidine

The compound was synthesized as for Step 3 of Example 93. LCMS (ESI) m/z: 246.1 [M+H]$^+$.

Step 4

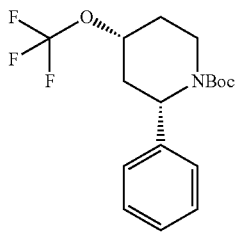 [SMILES: O=C(OCc1ccccc1)N1CCC(OC(F)(F)F)CC1c1ccccc1]

(2S,4R)-tert-butyl 2-phenyl-4-(trifluoromethoxy)piperidine-1-carboxylate

To a solution of 2-phenyl-4-(trifluoromethoxy)piperidine (150 mg, 0.61 mmol) in DCM (20 mL) was added triethylamine (0.5 mL, 0.61 mmol) and di-tert-butyl dicarbonate (300 mg, 1.37 mmol). The reaction mixture was stirred at 25° C. for 16 h and then concentrated to dryness. The residue was purified by chromatography (eluting with 10% EtOAc in petroleum ether). The enantiomer was separated by chiral SFC from the racemate. The second eluting fraction was arbitrarily assigned as (2S,4R)-tert-butyl 2-phenyl-4-(trifluoromethoxy)piperidine-1-carboxylate (50 mg, 23.7%). Chiral HPLC (column: (R,R)-Whelk-O1, 4.6×250 mm, 5 μm; mobile Phase: A: supercritical CO₂, B: MeOH (0.2% ammonia), A:B=90:10; flow: 3.0 mL/min; column temperature: 40.2° C.; RT=2.62 min). LCMS (ESI) m/z: 290.0 [M–55]⁺.

Step 5

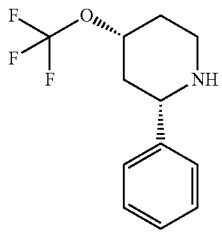 [SMILES: FC(F)(F)O[C@@H]1CCN[C@H](c2ccccc2)C1]

(2S,4R)-2-phenyl-4-(trifluoromethoxy)piperidine

A mixture of (2S,4R)-tert-butyl 2-phenyl-4-(trifluoromethoxy)piperidine-1-carboxylate (40 mg, 0.12 mmol) and hydrogen chloride in dioxane (5 mL, 1M) was stirred at 25° C. for 2 h. The reaction was concentrated to dryness and used in the next step without further purification. LCMS (ESI) m/z: 246.1 [M+H]⁺.

Step 6

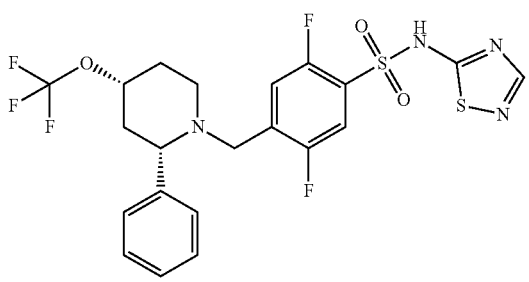 [SMILES: O=S(=O)(Nc1ncns1)c1cc(F)c(CN2CC[C@@H](OC(F)(F)F)C[C@H]2c2ccccc2)cc1F]

2,5-Difluoro-4-(((2S,4R)-2-phenyl-4-(trifluoromethoxy)piperidin-1-yl)methyl)-N-(1,2,4-thiadiazol-5-yl)benzenesulfonamide The compound was synthesized as for step 5 of Example 1. LCMS (ESI) method C: RT=6.05 min, m/z 535.1 [M+H]⁺. ¹H NMR (400 MHz, DMSO-d₆) δ: 8.51 (s, 1H), 7.55-7.28 (m, 7H), 4.59-4.57 (m, 1H), 4.08-3.88 (m, 3H), 3.58-3.50 (m, 1H), 2.42-2.33 (m, 1H), 2.11-2.06 (m, 2H), 1.87-1.82 (m, 2H).

Example 112

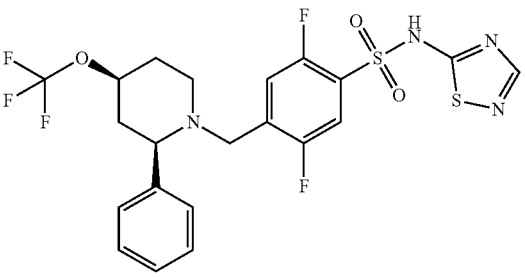 [SMILES: O=S(=O)(Nc1ncns1)c1cc(F)c(CN2CC[C@H](OC(F)(F)F)C[C@@H]2c2ccccc2)cc1F]

2,5-Difluoro-4-(((2R,4S)-2-phenyl-4-(trifluoromethoxy)piperidin-1-yl)methyl)-N-(1,2,4-thiadiazol-5-yl)benzenesulfonamide The compound was synthesized as for Example 111. LCMS (ESI) Method C: RT=6.05 min, m/z 535.0 [M+H]⁺. ¹H NMR (400 MHz, DMSO-d₆) δ: 8.52 (s, 1H), 7.56-7.29 (m, 7H), 4.59-4.54 (m, 1H), 4.08-3.88 (m, 3H), 3.61-3.51 (m, 1H), 2.42-2.33 (m, 1H), 2.11-2.06 (m, 2H), 1.92-1.82 (m, 2H).

Example 113

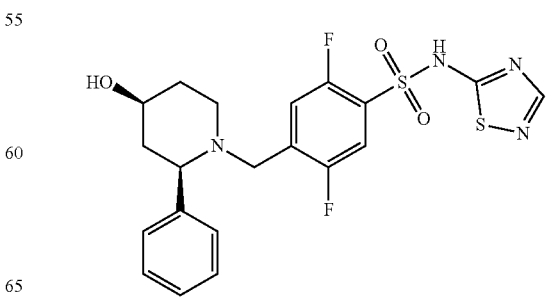

2,5-Difluoro-4-(((2R,4S)-4-hydroxy-2-phenylpiperidin-1-yl)methyl)-N-(1,2,4-thiadiazol-5-yl)benzenesulfonamide

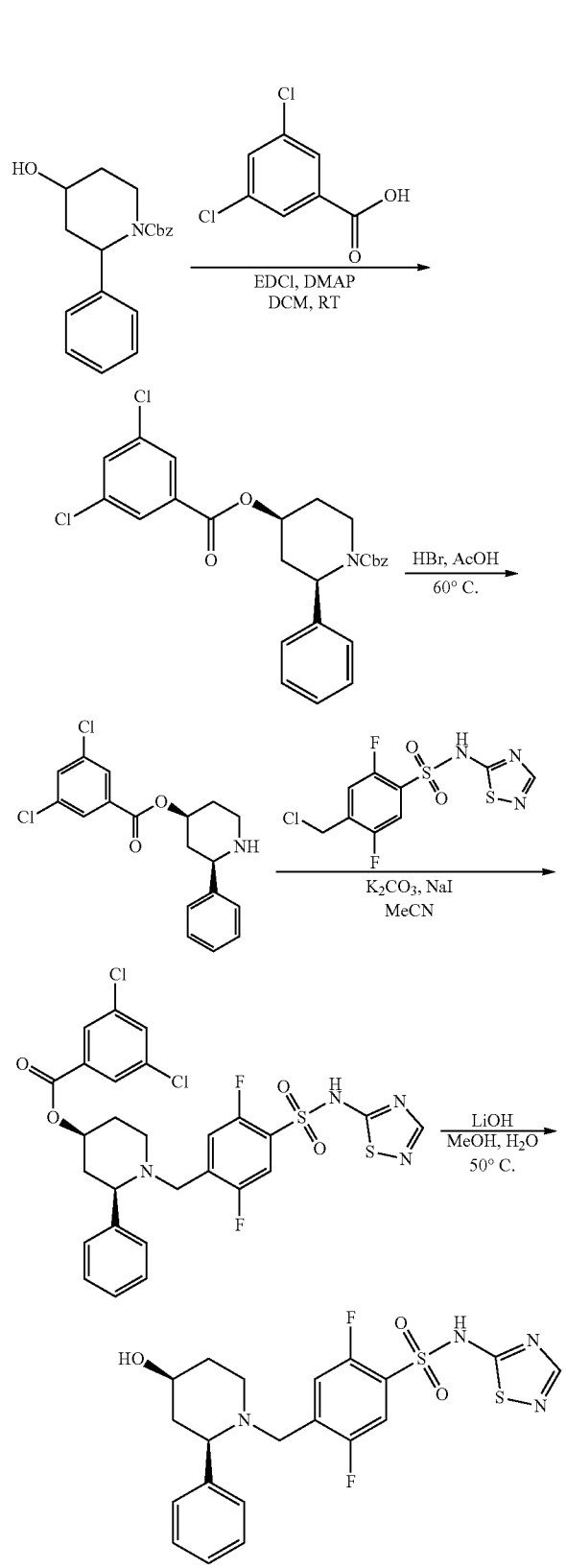

Step 1

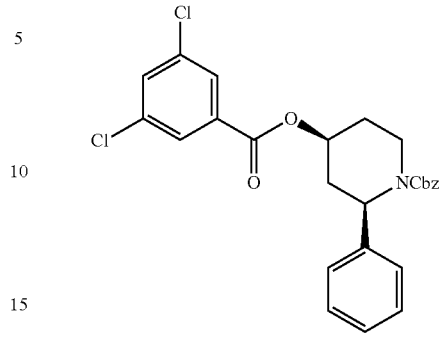

(2R,4S)-benzyl 4-(3,5-dichlorobenzoyloxy)-2-phenylpiperidine-1-carboxylate

A mixture of benzyl 4-hydroxy-2-phenyl-piperidine-1-carboxylate (1.0 g, 3.21 mmol), 3,5-dichlorobenzoic acid (1.23 g, 6.42 mmol), N-(3-dimethylaminopropyl)-N'-ethylcarbodiimide hydrochloride (1.23 g, 6.42 mmol), 4-dimethylaminopyridine (392 mg, 3.21 mmol) in DCM (30 mL) was stirred at 25° C. for 16 h. The reaction was concentrated to dryness and purified by chromatography (eluting with 50% EtOAc in petroleum ether) to afford the desired compound (1.1 g). The enantiomer was separated by chiral SFC from the racemate and the second eluting fraction was arbitrarily assigned as (2R,4S)-benzyl 4-(3,5-dichlorobenzoyloxy)-2-phenylpiperidine-1-carboxylate (500 mg, 32.1%). Chiral HPLC (column: AS-H, 4.6×250 mm, 5 μm; mobile Phase: A: supercritical $CO_2$, B: MeOH (0.2% ammonia), A:B=65:35; flow: 3.0 mL/min; column temperature: 40.2° C.; RT=4.16 min). LCMS (ESI) m/z: 506.1, 508.1 $[M+23]^+$.

Step 2

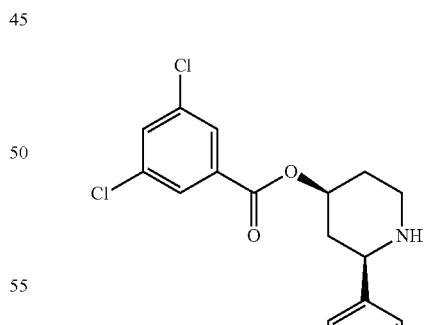

(2R,4S)-2-phenylpiperidin-4-yl 3,5-dichlorobenzoate

The compound was synthesized as for Step 3 of Example 109. LCMS (ESI) m/z: 350.1 $[M+H]^+$.

Step 3

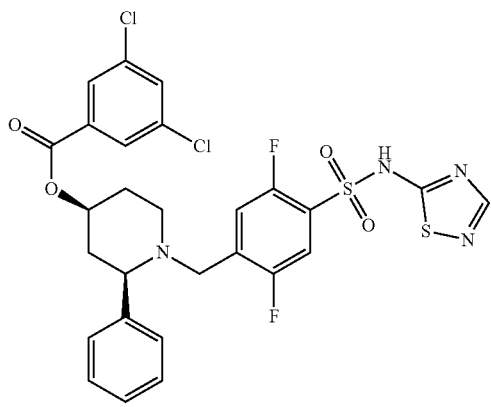 [SMILES: O=C(O[C@H]1CCN(Cc2cc(F)c(S(=O)(=O)Nc3ncns3)cc2F)[C@@H](c2ccccc2)C1)c1cc(Cl)cc(Cl)c1]

(2R,4S)-1-(4-(N-1,2,4-thiadiazol-5-ylsulfamoyl)-2,5-difluorobenzyl)-2-phenylpiperidin-4-yl 3,5-dichlorobenzoate The compound was synthesized as for step 5 of Example 1. LCMS (ESI) m/z: 639.1 [M+H]$^+$.

Step 4

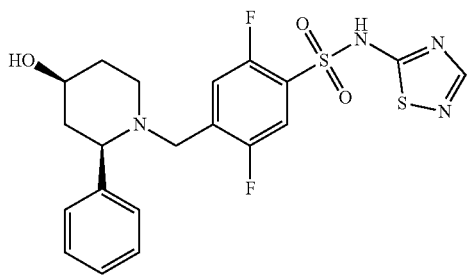 [SMILES: O=S(=O)(Nc1ncns1)c1cc(F)c(CN2CC[C@H](O)C[C@@H]2c2ccccc2)cc1F]

2,5-Difluoro-4-(((2R,4S)-4-hydroxy-2-phenylpiperidin-1-yl)methyl)-N-(1,2,4-thiadiazol-5-yl)benzenesulfonamide A mixture of (2R,4S)-1-[[2,5-difluoro-4-(1,2,4-thiadiazol-5-ylsulfamoyl)phenyl]methyl]-2-phenyl-4-piperidyl] 3,5-dichlorobenzoate (40 mg, 0.06 mmol), lithium hydroxide (10 mg, 0.42 mmol) in MeOH (10 mL) and water (2 mL) was stirred at 50° C. for 1 h. The reaction mixture was purified by prep-HPLC (eluting with 30-50% MeCN in 0.05% FA) to afford the desired product (5 mg, 17.1%) as a white solid. LCMS (ESI) method C: RT=3.58 min, m/z: 467.1 [M+H]$^+$. $^1$H NMR (400 MHz, DMSO-d$_6$) δ: 8.00 (s, 1H), 7.39-7.24 (m, 7H), 7.46-7.43 (m, 1H), 3.54-3.43 (m, 2H), 3.16-3.08 (m, 1H), 2.85-2.80 (m, 1H), 2.14-2.08 (m, 1H), 1.88-1.82 (m, 2H), 1.47-1.46 (m, 2H).

Example 114

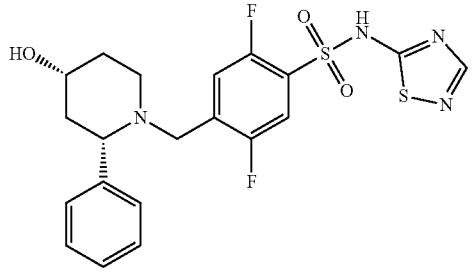 [SMILES: O=S(=O)(Nc1ncns1)c1cc(F)c(CN2CC[C@@H](O)C[C@H]2c2ccccc2)cc1F]

2,5-Difluoro-4-(((2S,4R)-4-hydroxy-2-phenylpiperidin-1-yl)methyl)-N-(1,2,4-thiadiazol-5-yl)benzenesulfonamide The compound was synthesized as for Example 113. LCMS (ESI) Method C: RT=3.63 min, m/z: 467.1 [M+H]$^+$. $^1$H NMR (400 MHz, DMSO-d$_6$) δ: 8.00 (s, 1H), 7.39-7.24 (m, 7H), 4.74-4.76 (m, 1H), 3.54-3.51 (m, 2H), 3.16-3.13 (m, 1H), 2.82-2.85 (m, 1H), 2.14-2.08 (m, 1H), 1.88-1.80 (m, 2H), 1.48-1.45 (m, 2H).

Example 115

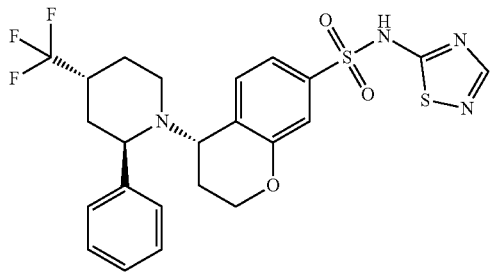 [SMILES: O=S(=O)(Nc1ncns1)c1ccc2c(c1)OCC[C@@H]2N1CC[C@@H](C(F)(F)F)C[C@@H]1c1ccccc1]

(S)-4-((2R,4R)-2-phenyl-4-(trifluoromethyl)piperidin-1-yl)-N-(1,2,4-thiadiazol-5-yl)chroman-7-sulfonamide The compound was synthesized as for Example 104. LCMS (ESI) Method C: RT=4.83 min, m/z: 525.2 [M+H]$^+$. $^1$H NMR (400 MHz, DMSO-d$_6$) δ: 8.85 (s, 1H), 8.36 (s, 1H), 7.63 (d, J=8.4 Hz, 1H), 7.49 (m, 2H), 7.39-7.29 (m, 4H), 7.21 (s, 1H), 6.76 (d, J=16 Hz, 1H), 6.14-6.08 (m, 1H), 4.59 (brs, 1H), 4.30-4.28 (m, 2H), 3.44-3.39 (m, 2H), 3.24-3.20 (m, 1H), 3.06-3.03 (m, 1H), 2.24-2.22 (m, 2H), 2.09-2.05 (m, 1H), 2.00-1.97 (m, 1H).

Example 116

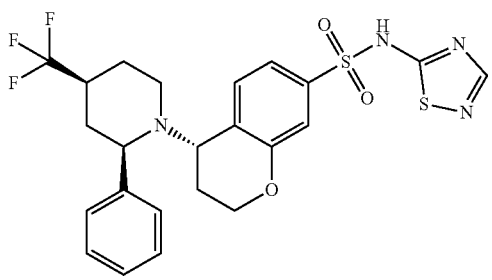 [SMILES: O=S(=O)(Nc1ncns1)c1ccc2c(c1)OCC[C@@H]2N1CC[C@H](C(F)(F)F)C[C@@H]1c1ccccc1]

(S)-4-((2R,4S)-2-phenyl-4-(trifluoromethyl)piperidin-1-yl)-N-(1,2,4-thiadiazol-5-yl)chroman-7-sulfonamide The compound was synthesized as for Example 104. LCMS (ESI) Method C: RT=5.59 min, m/z: 525.2 [M+H]$^+$. $^1$H NMR (400 MHz, DMSO-d$_6$) δ: 8.49 (S, 1H), 7.64-7.62 (m, 1H), 7.52-7.50 (m, 2H), 7.38-7.34 (m, 2H), 7.28-7.27 (m, 2H), 7.05 (s, 1H), 4.36-4.32 (m, 1H), 4.23-4.14 (m, 2H), 4.03-3.96 (m, 2H), 2.97-2.91 (m, 1H), 2.67-2.63 (m, 1H), 2.11-1.79 (m, 4H), 1.60-1.56 (m, 1H), 1.38-1.35 (m, 1H).

Example 117

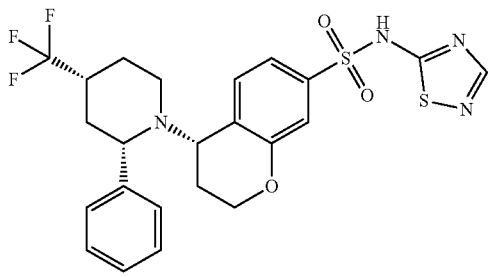

(S)-4-((2S,4R)-2-phenyl-4-(trifluoromethyl)piperidin-1-yl)-N-(1,2,4-thiadiazol-5-yl)chroman-7-sulfonamide The compound was synthesized as for Example 104. LCMS (ESI) Method C: RT=6.50 min, m/z: 525.2 [M+H]$^+$. $^1$H NMR (400 MHz, DMSO-d$_6$) δ: 8.47 (s, 1H), 7.84-7.82 (m, 1H), 7.49-7.47 (m, 2H), 7.38-7.28 (m, 4H), 7.03 (s, 1H), 4.27-4.25 (m, 1H), 3.82-3.73 (m, 4H), 2.58-2.50 (m, 1H), 2.41-2.31 (m, 1H), 2.03-1.80 (m, 4H), 1.67-1.46 (m, 2H).

Example 118

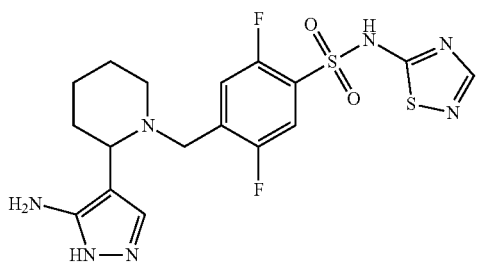 [SMILES: Nc1[nH]ncc1C1CCCCN1Cc1cc(F)c(S(=O)(=O)Nc2ncns2)cc1F]

4-((2-(5-Amino-1H-pyrazol-4-yl)piperidin-1-yl)methyl)-2,5-difluoro-N-(1,2,4-thiadiazol-5-yl)benzenesulfonamide

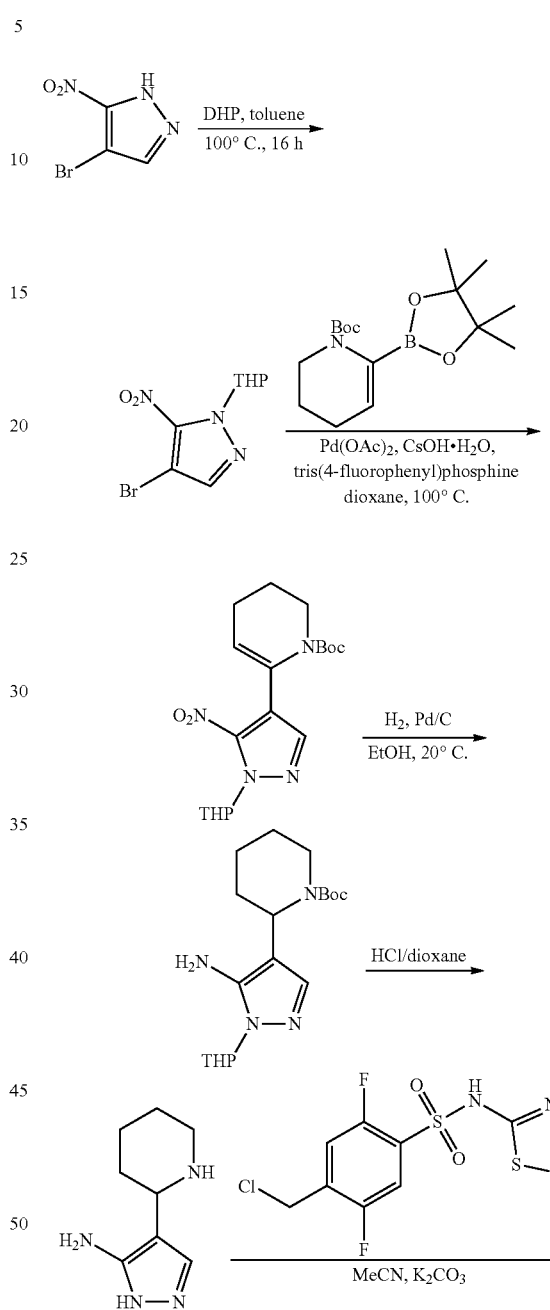

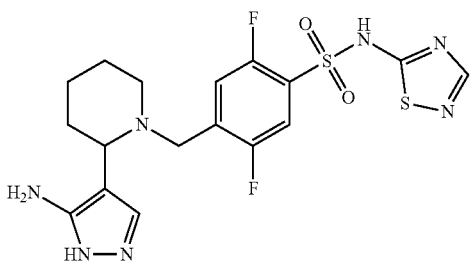

Step 1

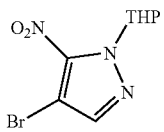

4-Bromo-5-nitro-1-(tetrahydro-2H-pyran-2-yl)-1H-pyrazole

To a mixture of 4-bromo-5-nitro-1H-pyrazole (5 g, 26.0 mmol) and dihydropyran (3.32 g, 39.1 mmol) in toluene (80 mL) was added trifluoroacetic acid (0.5 mL). The reaction mixture was stirred at 100° C. for 16 hours, cooled down and concentrated. The residue was purified by chromatography (eluting with 0-30% EtOAc in petroleum ether) to afford the desired compound as white solid (6.5 g, 81%).

Step 2

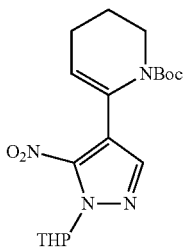

Tert-butyl 6-(5-nitro-1-(tetrahydro-2H-pyran-2-yl)-1H-pyrazol-4-yl)-3,4-dihydropyridine-1(2H)-carboxylate To a mixture of 4-bromo-5-nitro-1-(tetrahydro-2H-pyran-2-yl)-1H-pyrazole (700 mg, 2.54 mmol), tert-butyl 6-(4,4,5,5-tetramethyl-1,3,2-dioxaborolan-2-yl)-3,4-dihydropyridine-1 (2H)-carboxylate (942 mg, 3.05 mmol), cesium hydroxide monohydrate (853 mg, 5.08 mmol) and tris(4-fluorophenyl)phosphine (160 mg, 0.5 mmol) in dioxane (50 mL) was added palladium acetate (55 mg, 0.25 mmol). The reaction mixture was stirred at 100° C. for 16 h, quenched with water (50 mL), extracted with EtOAc (3×100 mL), dried over anhydrous sodium sulfate and concentrated. The crude was purified by chromatography (eluting with 0-35% EtOAc in petroleum ether) to give the desired compound as a pale yellow solid (600 mg, 62%). LCMS (ESI) m/z: 323.1 [M−55]$^+$.

Step 3

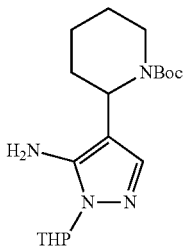

Tert-butyl 2-(5-amino-1-(tetrahydro-2H-pyran-2-yl)-1H-pyrazol-4-yl)piperidine-1-carboxylate A mixture of Pd/C (10%, 65 mg) and tert-butyl 6-(5-nitro-1-(tetrahydro-2H-pyran-2-yl)-1H-pyrazol-4-yl)-3,4-dihydropyridine-1(2H)-carboxylate (650 mg, 1.72 mmol) in MeOH (20 mL) was stirred at 50° C. under hydrogen for 16 h, filtered and concentrated. The residue was used in next step without further purification. LCMS (ESI) m/z: 295.1 [M−55]$^+$.

Step 4

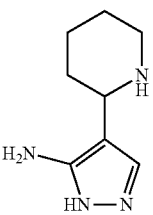

4-(Piperidin-2-yl)-1H-pyrazol-5-amine

A mixture of tert-butyl 2-(5-amino-1-(tetrahydro-2H-pyran-2-yl)-1H-pyrazol-4-yl)piperidine-1-carboxylate (600 mg, 1.58 mmol) and HCl in dioxane (4M, 10 mL) was stirred at 50° C. for 2 h. The solvents was removed under vacuo to afford the desired compound as a gray solid (240 mg, 91%). LCMS (ESI) m/z: 167.1 [M+H]$^+$.

Step 5

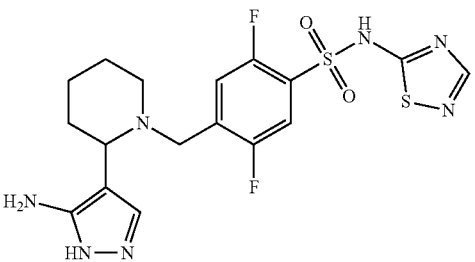

4-((2-(5-Amino-1H-pyrazol-4-yl)piperidin-1-yl)methyl)-2,5-difluoro-N-(1,2,4-thiadiazol-5-yl)benzenesulfonamide The compound was synthesized as for step 5 of Example 1. LCMS (ESI) method C: RT=3.18 min, m/z 456.2 [M+H]$^+$. $^1$H NMR (400 MHz, DMSO-d$_6$) δ: 8.14 (s, 1H), 7.90 (s, 1H), 7.30-7.26 (m, 3H), 3.45 (brs, 2H), 1.76-1.55 (m, 8H).

323

Example 119

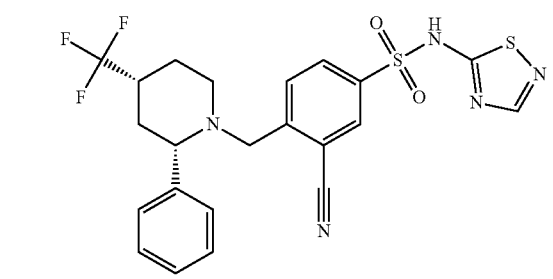 [SMILES: N#Cc1cc(S(=O)(=O)Nc2ncns2)ccc1CN1CC[C@@H](C(F)(F)F)C[C@H]1c1ccccc1]

3-Cyano-4-(((2S,4R)-2-phenyl-4-(trifluoromethyl)piperidin-1-yl)methyl)-N-(1,2,4-thiadiazol-5-yl)benzenesulfonamide

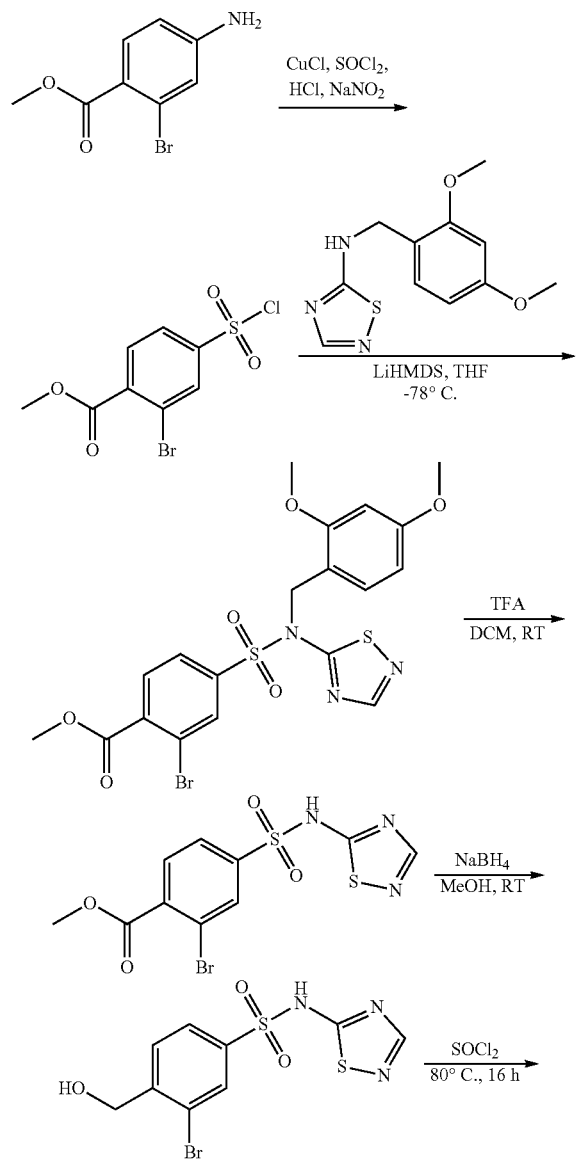

324

-continued

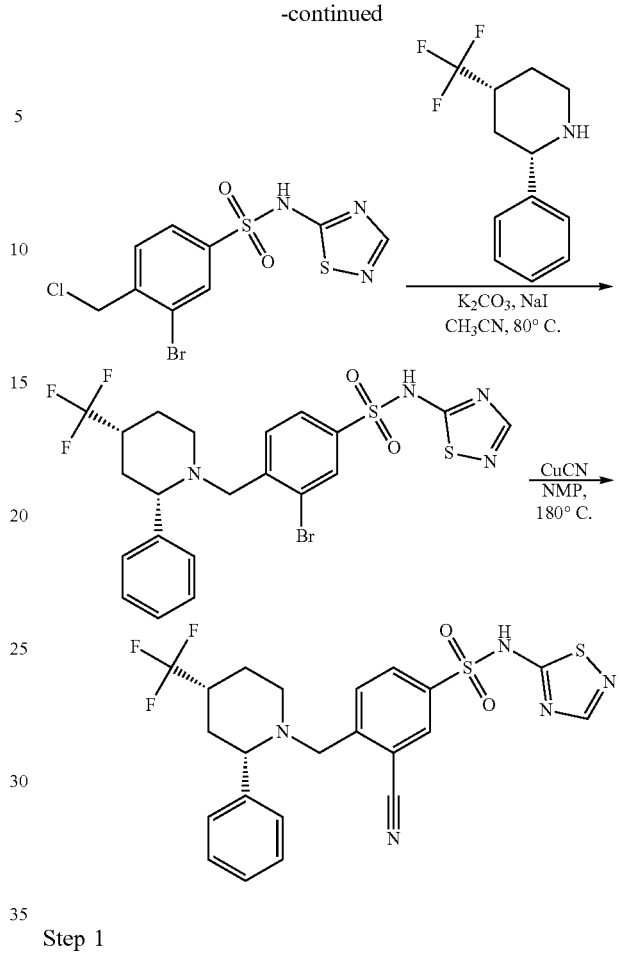

Step 1

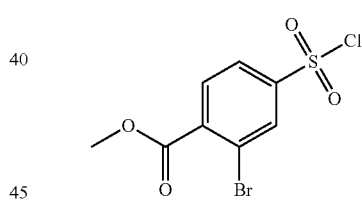

Methyl 2-bromo-4-(chlorosulfonyl)benzoate (A) To a solution of copper(I) chloride (50 mg, 0.51 mmol) in water (15 mL) was added dropwise thionyl chloride (2.5 mL, 34.4 mmol) under ice-cooling. Then the reaction temperature was gradually elevated, and the mixture was stirred at room temperature overnight.

(B) To a solution of methyl 4-amino-2-bromo-benzoate (1.0 g, 4.35 mmol) in concentrated hydrochloric acid (16 mL, 517.4 mmol) and water (60 mL) was added dropwise a solution of sodium nitrite (330 mg, 4.78 mmol) in water (15 mL) at −5° C., and the mixture was stirred at −5° C. for 30 minutes. To the reaction mixture was added dropwise a solution prepared in (A) at −5° C., the reaction temperature was gradually elevated, and the mixture was stirred at room temperature for 2 h. The obtained viscous material was collected by filtration, redissolved in DCM, dried, and concentrated under reduced pressure. The crude was used directly without further purification.

Step 2

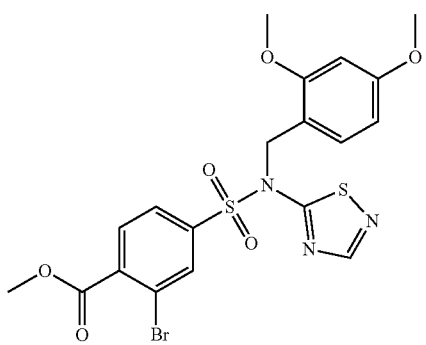

Methyl 2-bromo-4-(N-(2,4-dimethoxybenzyl)-N-(1,2,4-thiadiazol-5-yl)sulfamoyl)benzoate To a cold (−78° C.) solution of N-[(2,4-dimethoxyphenyl)methyl]-1,2,4-thiadiazol-5-amine (400 mg, 1.59 mmol) in THF (25 mL) was added lithium bis(trimethylsilyl)amide in THF (2.5 mL, 1M, 2.5 mmol). The reaction mixture was allowed to warm to ambient temperature and stirred for over 4 h. The reaction solution was cooled again to −78° C., and a solution of methyl 2-bromo-4-chlorosulfonyl-benzoate (500 mg, 1.59 mmol) in THF (5 mL) was added. The reaction mixture was warmed to ambient temperature overnight followed by the addition of saturated ammonium chloride solution (30 mL), extracted with ethyl acetate (3×30 mL), dried over anhydrous sodium sulphate, and concentrated. The crude was purified by chromatography (eluting with 30% EtOAc in petroleum ether) to afford the desired product (445 mg, 45.5%).

LCMS (ESI) m/z: 550.0 [M+Na]$^+$.

Step 3

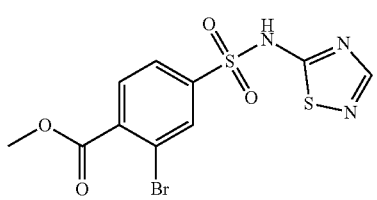 [SMILES: COC(=O)c1ccc(S(=O)(=O)Nc2ncns2)cc1Br]

Methyl 4-(N-1,2,4-thiadiazol-5-ylsulfamoyl)-2-bromobenzoate

To a solution of methyl 2-bromo-4-[(2,4-dimethoxyphenyl)methyl-(1,2,4-thiadiazol-5-yl)sulfamoyl]benzoate (440 mg, 0.83 mmol) in DCM (5 mL) was added trifluoroacetic acid (1 mL) and the reaction was stirred at 25° C. for 3 h. The reaction was concentrated to dryness and the crude was used directly without further purification. LCMS (ESI) m/z: 377.9 [M+H]$^+$.

Step 4

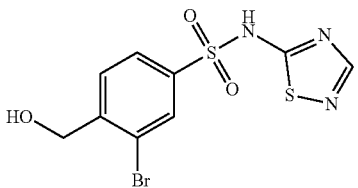 [SMILES: O=S(=O)(Nc1ncns1)c1ccc(CO)c(Br)c1]

3-Bromo-4-(hydroxymethyl)-N-(1,2,4-thiadiazol-5-yl)benzenesulfonamide

Sodium boronhydride (200 mg, 5.26 mmol) was added to a solution of methyl 2-bromo-4-(1,2,4-thiadiazol-5-ylsulfamoyl)benzoate (400 mg, 1.06 mmol) in MeOH (30 mL) at 25° C. After 48 h, the reaction was quenched with water (30 mL), extracted with EtOAc (3×30 mL), washed with saturated brine solution (30 mL), dried over anhydrous sodium sulfate and concentrated. The crude was purified by Chromatography (eluting with 20% MeCN in 0.01% FA) to afford the desired product (190 mg, 49.8%. LCMS (ESI) m/z: 350.0 [M+H]$^+$.

Step 5

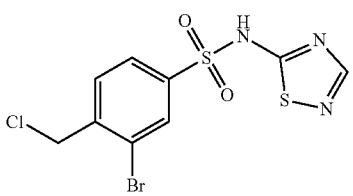 [SMILES: O=S(=O)(Nc1ncns1)c1ccc(CCl)c(Br)c1]

3-Bromo-4-(chloromethyl)-N-(1,2,4-thiadiazol-5-yl)benzenesulfonamide

The compound was synthesized as for step 4 of Example 1. LCMS (ESI) m/z: 367.9 [M+H]$^+$.

Step 6

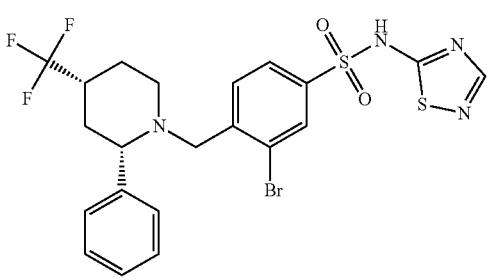 [SMILES: O=S(=O)(Nc1ncns1)c1ccc(CN2CC[C@@H](C(F)(F)F)C[C@H]2c2ccccc2)c(Br)c1]

3-Bromo-4-(((2S,4R)-2-phenyl-4-(trifluoromethyl)piperidin-1-yl)methyl)-N-(1,2,4-thiadiazol-5-yl)benzenesulfonamide The compound was synthesized as for step 5 of Example 1. LCMS (ESI) m/z: 561.0 [M+H]$^+$.

Step 7

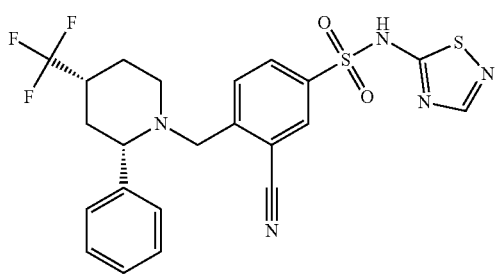 [SMILES: N#Cc1cc(S(=O)(=O)Nc2ncns2)ccc1CN1CC[C@@H](C(F)(F)F)C[C@H]1c1ccccc1]

3-Cyano-4-(((2S,4R)-2-phenyl-4-(trifluoromethyl)
piperidin-1-yl)methyl)-N-(1,2,4-thiadiazol-5-yl)benzenesulfonamide A mixture of copper(I) cyanide (100 mg, 1.12 mmol) and 3-bromo-4-(((2S,4R)-2-phenyl-4-(trifluoromethyl)-1-piperidyl)methyl)-N-(1,2,4-thiadiazol-5-yl)benzenesulfonamide (50 mg, 0.09 mmol) in 1-methyl-2-pyrrolidinone (3 mL) was sealed and stirred under microwave at 180° C. for 3 h. The mixture was directly purified by chromatography (eluting with 40-60% MeCN in 10 mM ammonium hydrogen carbonate in water) to afford the desired product (10 mg, 22.1%) as a white solid. LCMS (ESI) Method C: RT=6.00 min, m/z: 508.1 [M+H]⁺. ¹H NMR (400 MHz, DMSO-d₆) δ: 8.33 (s, 1H), 8.03-8.01 (m, 2H), 7.76-7.73 (m, 1H), 7.43-7.40 (m, 2H), 7.30-7.18 (m, 3H), 3.76-3.72 (m, 2H), 3.51-3.47 (m, 1H), 3.39-3.35 (m, 1H), 2.93-2.89 (m, 1H), 2.36-2.29 (m, 1H), 1.89-1.85 (m, 2H), 1.66-1.56 (m, 2H).

Example 120

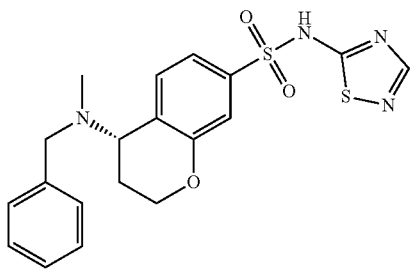 [SMILES: CN(Cc1ccccc1)[C@H]1CCOc2cc(S(=O)(=O)Nc3ncns3)ccc21]

(S)-4-(benzyl(methyl)amino)-N-(1,2,4-thiadiazol-5-yl)chroman-7-sulfonamide

The compound was synthesized as for Example 37. LCMS (ESI) Method C: RT=3.38 min, m/z: 417.1 [M+H]⁺. ¹H NMR (400 MHz, DMSO-d₆) δ: 8.27 (s, 1H), 7.75 (d, J=8 Hz, 1H), 7.41-7.27 (m, 6H), 7.10 (d, J=1.6 Hz, 1H), 4.40-4.37 (m, 1H), 4.18-4.13 (m, 2H), 3.70-3.68 (m, 2H), 2.17 (s, 3H), 2.10-2.07 (m, 2H).

Example 121

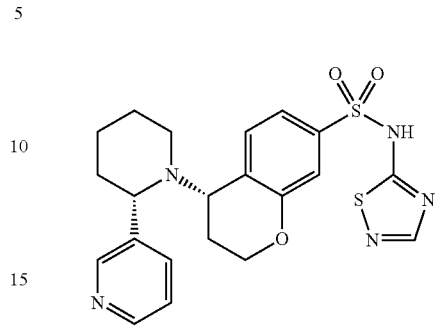

(R)-4-((S)-2-(pyridin-3-yl)piperidin-1-yl)-N-(1,2,4-thiadiazol-5-yl)chromane-7-sulfonamide The compound was synthesized as for Example 37 using commercially available (S)-2-(pyridin-3-yl)piperidine. The stereochemistry was assigned arbitrarily. m/z 458.2 [M+H]⁺. ¹H NMR (400 MHz, DMSO-d₆) δ 8.66 (s, 1H), 8.41 (s, 1H), 8.21 (s, 1H), 7.82 (d, J=7.8 Hz, 1H), 7.47 (d, J=8.1 Hz, 1H), 7.32-7.23 (m, 2H), 6.98 (d, J=1.9 Hz, 1H), 4.26-4.12 (m, 1H), 4.02 (s, 1H), 3.88 (t, J=10.8 Hz, 2H), 2.78-2.61 (m, 1H), 2.13 (s, 1H), 2.06-1.92 (m, 1H), 1.88-1.42 (m, 6H), 1.35 (s, 1H).

Example 122

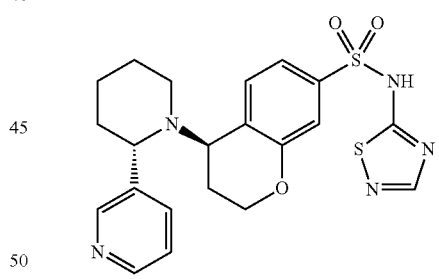

(R)-4-((S)-2-(pyridin-3-yl)piperidin-1-yl)-N-(1,2,4-thiadiazol-5-yl)chromane-7-sulfonamide The compound was synthesized as for Example 37 using commercially available (S)-2-(pyridin-3-yl)piperidine. The stereochemistry was assigned arbitrarily. m/z 458.2 [M+H]⁺. ¹H NMR (400 MHz, DMSO-d₆) δ 8.64 (d, J=2.1 Hz, 1H), 8.46 (dd, J=4.7, 1.7 Hz, 1H), 8.08 (s, 1H), 7.88 (dt, J=7.8, 2.0 Hz, 1H), 7.78-7.69 (m, 1H), 7.37 (dd, J=7.9, 4.7 Hz, 1H), 7.27 (dd, J=8.1, 1.9 Hz, 1H), 6.99 (d, J=1.8 Hz, 1H), 4.22 (dt, J=11.2, 3.6 Hz, 1H), 3.85-3.57 (m, 4H), 2.23 (t, J=11.3 Hz, 1H), 2.06-1.93 (m, 1H), 1.89-1.68 (m, 3H), 1.59 (s, 2H), 1.41 (dd, J=54.0, 11.8 Hz, 2H).

Example 123

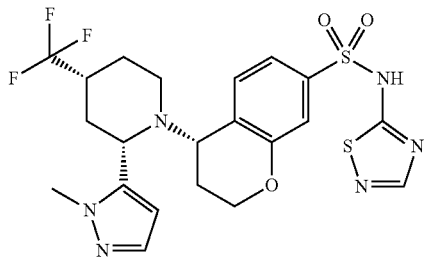 [SMILES: Cn1nccc1[C@@H]1C[C@H](C(F)(F)F)CCN1[C@H]1CCOc2cc(S(=O)(=O)Nc3ncns3)ccc21]

(S)-4-((2S,4R)-2-(1-methyl-1H-pyrazol-5-yl)-4-(trifluoromethyl)piperidin-1-yl)-N-(1,2,4-thiadiazol-5-yl)chroman-7-sulfonamide

2-(1-methyl-1H-pyrazol-5-yl)-4-(trifluoromethyl)pyridine

To a heat dried flask, (2-methylpyrazol-3-yl)boronic acid (2 g, 1.2 equiv., 15.9 mmol), cesium carbonate (8.65 g, 2 equiv., 26.550 mmol) and [1,1'-bis(diphenylphosphino)ferrocene]-dichloropalladium(ii) DCM complex (0.558 g, 0.05 equiv., 0.66375 mmol) were added. The flask was sealed and vacuumed and backfilled with nitrogen 3 times. 1,4-dioxane (66.4 mL, 0.2 M) and water (22.1 mL, 0.6M) were added, followed by 2-bromo-4-(trifluoromethyl)pyridine (3 g, 13.275 mmol), and the reaction was heated to 100° C. The reaction was ran for 48 h and full conversion was seen. The reaction was cooled to room temperature, was filtered through silica gel (isopropyl acetate eluting). The crude reaction was concentrated and purified by column chromatography to give a pale yellow oil (2.59 g, 86% yield). $^1$H NMR (400 MHz, Chloroform-d) δ 8.85 (d, J=5.2 Hz, 1H), 7.81-7.75 (m, 1H), 7.54 (d, J=2.0 Hz, 1H), 7.45 (dd, J=5.2, 1.5 Hz, 1H), 6.68 (d, J=2.0 Hz, 1H), 4.25 (s, 3H).

Step 2

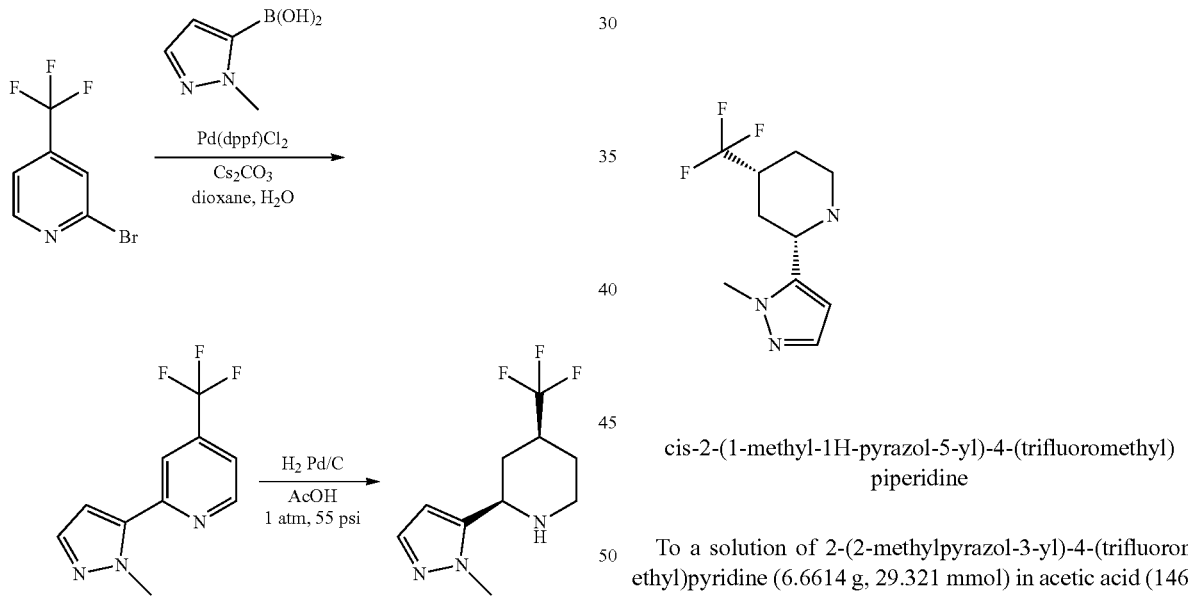

Step 1 cis-2-(1-methyl-1H-pyrazol-5-yl)-4-(trifluoromethyl)piperidine

To a solution of 2-(2-methylpyrazol-3-yl)-4-(trifluoromethyl)pyridine (6.6614 g, 29.321 mmol) in acetic acid (146.6 mL, 0.2 M) in a Parr shaker, platinum(IV) oxide (0.666 g, 0.1 equiv.) was added. The reaction was ran in a Parr shaker at 50 psi overnight. Full conversion was seen and the platinum oxide was filtered through a plug of celite with DCM and isopropyl acetate. The solution which was collected was concentrated, extracted with saturated NaOH solution (2×100 mL), and the organic layer was collected. The solution was concentrated to give a very pale yellow oil (6.7615 g, 98.8% yield). 1H NMR (400 MHz, Chloroform-d) δ 7.40 (q, J=3.1 Hz, 1H), 6.20-6.11 (m, 1H), 3.91 (d, J=4.2 Hz, 3H), 3.76 (tt, J=11.6, 3.8 Hz, 1H), 3.35-3.25 (m, 1H), 2.88-2.72 (m, 1H), 2.31 (dqq, J=16.4, 8.4, 3.9 Hz, 1H), 2.09 (ddd, J=13.5, 6.0, 3.1 Hz, 1H), 2.05-1.79 (m, 1H), 1.66-1.43 (m, 3H).

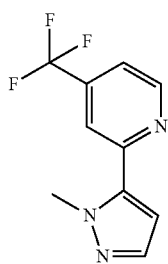 [SMILES: Cn1nccc1-c1cc(C(F)(F)F)ccn1]

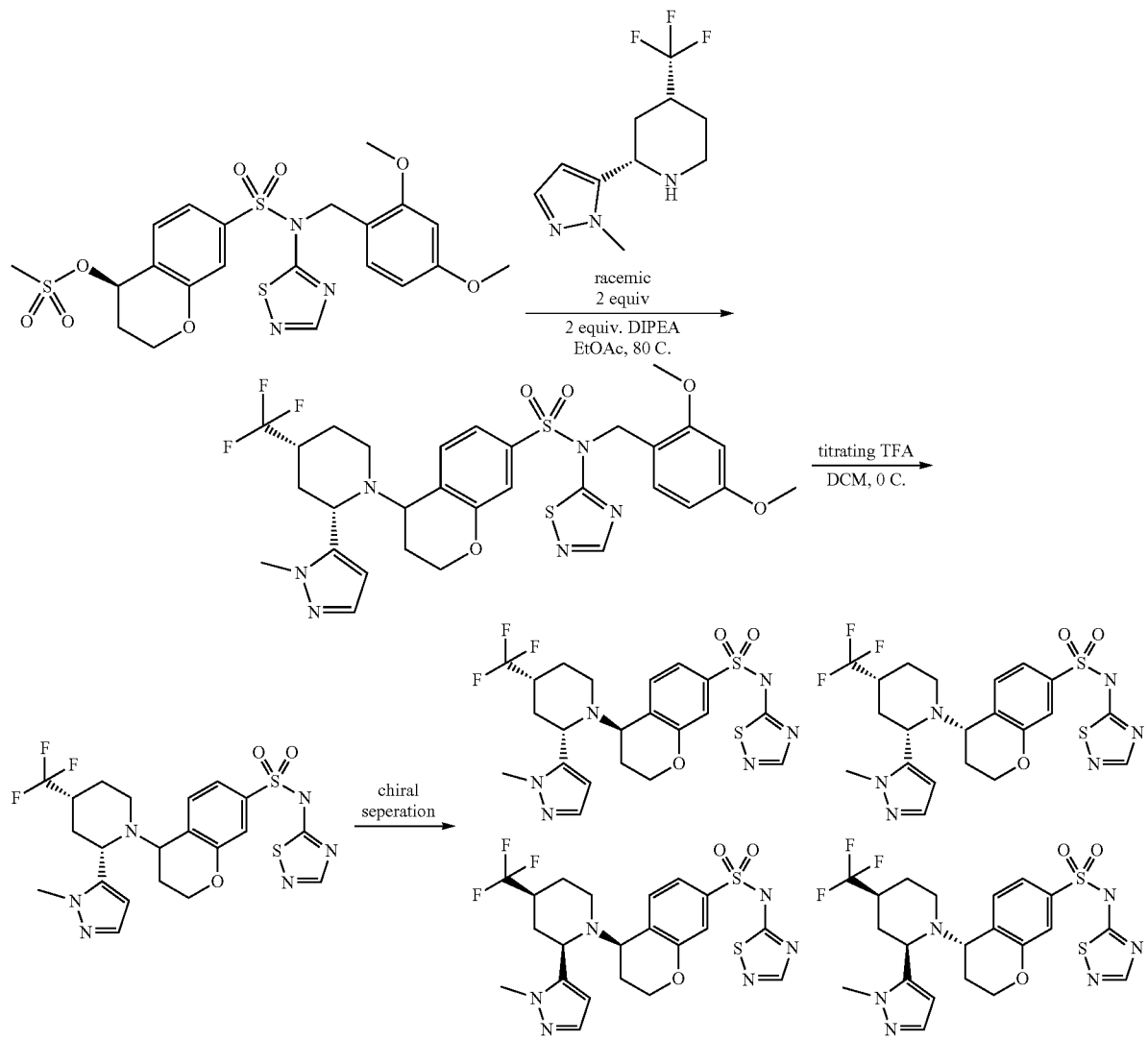

Step 3

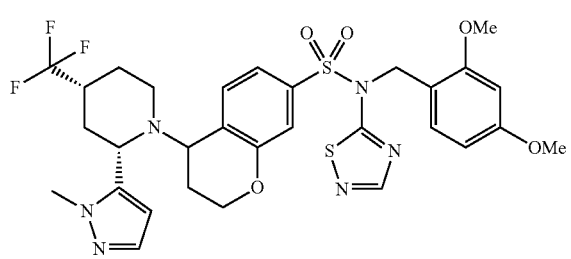 [SMILES: COc1ccc(CN(c2ncns2)S(=O)(=O)c2ccc3c(c2)OCCC3N2CC[C@@H](C(F)(F)F)C[C@H]2c2ccnn2C)c(OC)c1]

N-(2,4-dimethoxybenzyl)-4-(cis)-2-(1-methyl-1H-pyrazol-5-yl)-4-(trifluoromethyl)-piperidin-1-yl)-N-(1,2,4-thiadiazol-5-yl)chroman-7-sulfonamide Crude (R)-7-(N-(2,4-dimethoxybenzyl)-N-(1,2,4-thiadiazol-5-yl)sulfamoyl)chroman-4-yl methanesulfonate (1.052 g, 1.942 mmol) was suspended in ethyl acetate (9.712 mL, 0.2 M) was added to a sealed vial of (+/−) cis-2-(1-methyl-1H-pyrazol-5-yl)-4-(trifluoromethyl)piperidine (0.906 g, 2 equiv., 3.885 mmol) under Nitrogen. N,n-diisopropylethylamine (1.02 mL, 3 equiv., 5.827 mmol) was immediately added to the reaction vial and the reaction was heated to 80° C. and stirred overnight. Full conversion of the mesylate was seen with most of the products being the desired product and 15% being hydrolyzed mesylate. The reaction was cooled to room temperature and concentrated. The crude product was used in the subsequent step without further purification.

Step 4

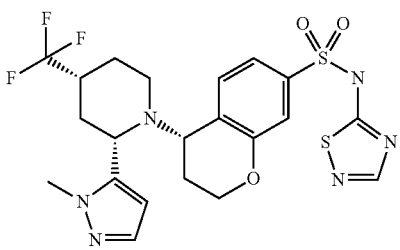 [SMILES: Cn1nccc1[C@@H]1C[C@H](C(F)(F)F)CCN1[C@H]1CCOc2cc(S(=O)(=O)Nc3ncns3)ccc21]

333

(S)-4-((2S,4R)-2-(1-methyl-1H-pyrazol-5-yl)-4-(trifluoromethyl)piperidin-1-yl)-N-(1,2,4-thiadiazol-5-yl)chroman-7-sulfonamide A solution of the crude N-(2,4-dimethoxybenzyl)-4-((2S,4R)-2-(1-methyl-1H-pyrazol-5-yl)-4-(trifluoromethyl)piperidin-1-yl)-N-(1,2,4-thiadiazol-5-yl)chroman-7-sulfonamide (0.25 g, 0.3684 mmol) in dichloromethane (3.684 mL, 0.1 M, 57.46 mmol) at 0° C., was titrated with trifluoroacetic acid (0.028 mL, 1 equiv., 0.3684 mmol, 100 mass %) in series of 1 equivalents, checking results by LCMS every 10 minute intervals, until full conversion to the desired product was seen. The reaction was quenched with trimethylamine (1 mL) and diluted with dichloromethane (1 ml) and water (3 mL). The organic layer was removed and the aqueous layer was extracted with DCM (2×2 mL). The combined organic layers were dried with $Na_2SO_4$, concentrated, and purified with column chromatography in a 0-100% gradient of DCM/10% MeOH in DCM. The desired product was collected, concentrated, and purified by Chiral SFC to obtain the desired product (as one of the four products of the reaction) as a white powder (6.3 mg, 13% yield). The stereochemistry was assigned arbitrarily. m/z 529.1 [M+H]$^+$, 1H NMR (400 MHz, DMSO-d6) δ 8.37 (s, 1H), 7.78-7.70 (m, 1H), 7.36 (d, J=1.8 Hz, 1H), 7.31 (dd, J=8.2, 1.9 Hz, 1H), 7.04 (d, J=1.8 Hz, 4H), 6.31 (d, J=1.9 Hz, 1H), 4.27 (dt, J=11.0, 3.6 Hz, 1H), 4.08 (dd, J=10.9, 2.9 Hz, 1H), 3.93 (s, 3H), 2.57 (d, J=10.6 Hz, 1H), 2.33 (s, 1H), 1.97 (s, 2H), 1.83 (dd, J=17.5, 9.9 Hz, 2H), 1.49 (d, J=12.7 Hz, 1H).

Example 124

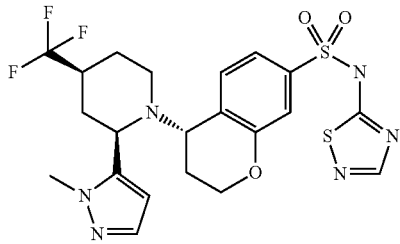 [SMILES: Cn1nccc1[C@H]1C[C@@H](C(F)(F)F)CCN1[C@H]1CCOc2cc(S(=O)(=O)Nc3ncns3)ccc21]

(R)-4-((2S,4R)-2-(1-methyl-1H-pyrazol-5-yl)-4-(trifluoromethyl)piperidin-1-yl)-N-(1,2,4-thiadiazol-5-yl)chroman-7-sulfonamide This compound was prepared in the same sequence as Example 123 and was purified by SFC from the products produced in Example 123 (4.2 mg, 8.6% yield). The stereochemistry was assigned arbitrarily. m/z 529.1 [M+H]$^+$, 1H NMR (400 MHz, DMSO-d6) δ 8.34 (s, 1H), 7.42 (d, J=8.2 Hz, 1H), 7.38 (d, J=1.8 Hz, 1H), 7.28 (dd, J=8.0, 1.9 Hz, 1H), 7.09-7.03 (m, 1H), 6.35 (d, J=1.9 Hz, 1H), 4.40 (d, J=10.8 Hz, 1H), 4.22 (dt, J=11.2, 4.3 Hz, 1H), 3.93 (s, 4H), 3.78-3.69 (m, 1H), 2.71 (d, J=12.5 Hz, 1H), 2.53 (d, J=7.6 Hz, 1H), 2.22 (t, J=12.3 Hz, 1H), 2.05-1.83 (m, 3H), 1.77 (d, J=12.6 Hz, 1H), 1.64 (q, J=12.1 Hz, 1H), 1.46 (td, J=13.5, 9.5 Hz, 1H).

334

Example 125

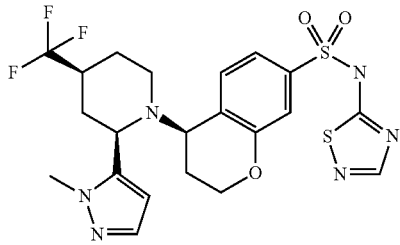 [SMILES: Cn1nccc1[C@H]1C[C@@H](C(F)(F)F)CCN1[C@@H]1CCOc2cc(S(=O)(=O)Nc3ncns3)ccc21]

(S)-4-((2R,4S)-2-(1-methyl-1H-pyrazol-5-yl)-4-(trifluoromethyl)piperidin-1-yl)-N-(1,2,4-thiadiazol-5-yl)chroman-7-sulfonamide This compound was prepared in the same sequence as Example 123 and was purified by SFC from the products produced in Example 123 (8.3 mg, 17% yield). The stereochemistry was assigned arbitrarily. m/z 529.1 [M+H]$^+$, $^1$H NMR (400 MHz, DMSO-d$_6$) δ 8.36 (s, 1H), 7.46-7.33 (m, 2H), 7.32-7.17 (m, 2H), 7.09-7.03 (m, 1H), 6.35 (d, J=1.9 Hz, 1H), 4.40 (d, J=10.8 Hz, 1H), 4.22 (dt, J=11.3, 4.3 Hz, 1H), 3.93 (s, 3H), 3.78-3.69 (m, 1H), 2.72 (d, J=12.4 Hz, 1H), 2.22 (t, J=12.2 Hz, 1H), 2.03-1.92 (m, 1H), 1.95-1.84 (m, 2H), 1.77 (d, J=12.6 Hz, 1H), 1.64 (q, J=12.1 Hz, 1H), 1.53-1.41 (m, 1H), 1.24 (s, 1H).

Example 126

(R)-4-((2R,4S)-2-(1-methyl-1H-pyrazol-5-yl)-4-(trifluoromethyl)piperidin-1-yl)-N-(1,2,4-thiadiazol-5-yl)chroman-7-sulfonamide This compound was prepared in the same sequence as Example 123 and was purified by SFC from the products produced in Example 123 (3.4 mg, 7% yield). The stereochemistry was assigned arbitrarily. m/z 529.1 [M+H]$^+$, 1H NMR (400 MHz, DMSO-d6) δ 8.29 (s, 1H), 7.72 (d, J=8.1 Hz, 1H), 7.36 (d, J=1.8 Hz, 1H), 7.29 (dd, J=8.1, 1.9 Hz, 1H), 7.09-7.01 (m, 1H), 6.31 (s, 1H), 4.26 (dt, J=11.1, 3.7 Hz, 1H), 4.07 (dd, J=11.0, 2.9 Hz, 1H), 3.93 (s, 4H), 3.69 (s, 1H), 2.62-2.51 (m, 2H), 2.33 (s, 1H), 1.97 (s, 2H), 1.82 (t, J=13.0 Hz, 2H), 1.50 (s, 1H).

Example 127

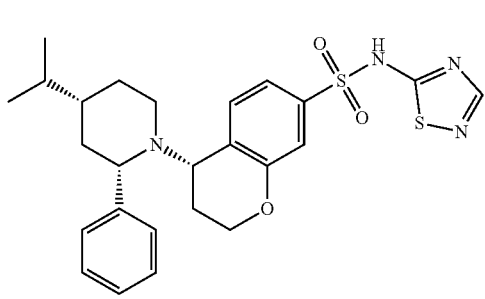 [SMILES: CC(C)[C@@H]1CCN([C@H]2CCOc3cc(S(=O)(=O)Nc4ncns4)ccc32)[C@H](c2ccccc2)C1]

(S)-4-((2S,4R)-4-isopropyl-2-phenylpiperidin-1-yl)-
N-(1,2,4-thiadiazol-5-yl)chroman-7-sulfonamide Step 1

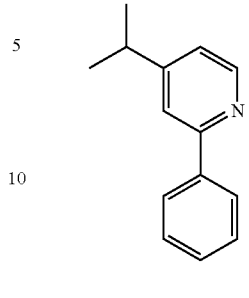

4-isopropyl-2-phenylpyridine

To a heat dried flask, phenylboronic acid (319.9 mg, 1.05 equiv., 2.624 mmol), potassium carbonate (1.036 g, 3 equiv., 7.5 mmol) and palladium(ii) acetate (56 mg, 0.1 equiv., 0.24990 mmol %) were added. The flask was sealed and vacuumed and backfilled with nitrogen 3 times. Degassed ethanol (11.3 mL, 0.221 M) and water (2.8 mL, 0.885 M) were added, followed by 2-bromo-4-isopropyl-pyridine (500 mg, 2.4990 mmol), and the reaction was heated to 80° C. The reaction was ran overnight, then was cooled to room temperature, was filtered through silica gel (isopropyl acetate eluting). The crude reaction was concentrated and purified by column chromatography to give a pale yellow oil (118.4 mg, 24% yield). 1H NMR (400 MHz, Chloroform-d) δ 8.58 (d, J=5.2 Hz, 1H), 8.02-7.90 (m, 2H), 7.59-7.54 (m, 1H), 7.50-7.34 (m, 4H), 7.08 (dd, J=5.2, 1.6 Hz, 1H), 2.94 (hept, J=6.9 Hz, 1H), 1.29 (d, J=7.0 Hz, 6H).

Step 2

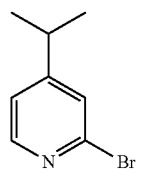

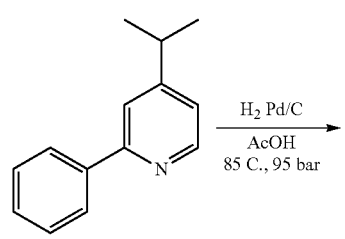

(+/−) cis-4-isopropyl-2-phenylpiperidine

A solution of 4-isopropyl-2-phenyl-pyridine (118.4 mg, 0.6001 mmol) in acetic acid (12 mL, 0.05 M) as passed through a flow hydrogenation reactor using a Pd/C column at 85° C. and 90 psi. After one run of the solution was done, full conversion was seen. The crude reaction was concentrated to dryness. The crude was then dissolved in methanol (6 mL, 0.1M) with MP-Carbonate (1.5 g, 4.802 mmol, 8 equiv.) for 3 hours. The MP-Carbonate was filtered and the remaining solution was concentrated to give a clear oil (80 mg, 66% yield). $^1$H NMR (400 MHz, Chloroform-d) δ 7.47-7.28 (m, 5H), 3.98 (dt, J=12.3, 2.5 Hz, 1H), 3.54-3.43 (m, 1H), 2.95 (dd, J=12.8, 3.2 Hz, 1H), 1.90-1.71 (m, 3H), 1.64-1.49 (m, 1H), 1.46 (tdd, J=11.7, 6.1, 3.0 Hz, 1H), 1.25 (q, J=6.8, 6.1 Hz, 1H), 0.92 (t, J=6.6 Hz, 6H).

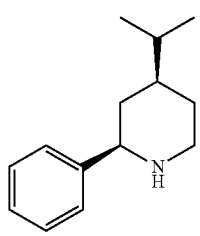

Step 3

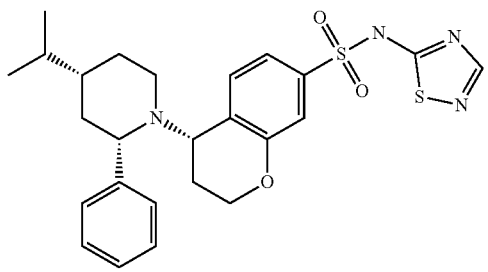 [SMILES: CC(C)[C@@H]1CCN([C@H]2CCOc3cc(S(=O)(=O)Nc4ncns4)ccc32)[C@H](c2ccccc2)C1]

(S)-4-((2S,4R)-4-isopropyl-2-phenylpiperidin-1-yl)-
N-(1,2,4-thiadiazol-5-yl)chroman-7-sulfonamide This compound was prepared using the same reaction sequence as Example 123, using (cis)-4-isopropyl-2-phenylpiperidine, and was purified by SFC (5.8 mg, 21.8% yield over 2 steps). The stereochemistry was assigned arbitrarily. m/z 499.2 [M+H]$^+$, 1H NMR (400 MHz, DMSO-d6) δ 7.93 (s, 1H), 7.68 (dd, J=8.1, 1.2 Hz, 1H), 7.53-7.40 (m, 3H), 7.37-7.17 (m, 4H), 6.97 (d, J=1.8 Hz, 1H), 6.51 (s, 1H), 4.26-4.15 (m, 1H), 3.71 (ddt, J=16.6, 6.9, 4.3 Hz, 2H), 3.58 (d, J=10.3 Hz, 1H), 3.10 (d, J=8.1 Hz, 1H), 2.54 (s, 1H), 2.22 (t, J=10.7 Hz, 1H), 1.98 (q, J=11.8, 10.8 Hz, 1H), 1.80-1.68 (m, 2H), 1.58 (dd, J=22.0, 8.9 Hz, 1H), 1.45-1.13 (m, 4H), 0.83 (t, J=6.4 Hz, 7H)

Example 128

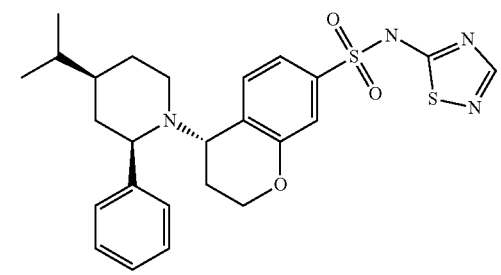 [SMILES: CC(C)[C@H]1CCN([C@H]2CCOc3cc(S(=O)(=O)Nc4ncns4)ccc32)[C@@H](c2ccccc2)C1]

(R)-4-((2S,4R)-4-isopropyl-2-phenylpiperidin-1-yl)-
N-(1,2,4-thiadiazol-5-yl)chroman-7-sulfonamide This compound was prepared using the same reaction sequence as Example 127 and was purified by SFC from the products produced in Example 127 (4.1 mg, 15.2% yield over 2 steps). The stereochemistry was assigned arbitrarily. m/z 499.2 [M+H]$^+$, 1H NMR (400 MHz, DMSO-d6) δ 8.12 (d, J=7.1 Hz, 1H), 7.48 (s, 2H), 7.43-7.23 (m, 5H), 7.02 (d, J=1.9 Hz, 1H), 6.51 (s, 1H), 4.18 (dd, J=11.4, 5.5 Hz, 1H), 3.89 (s, 2H), 2.76-2.70 (m, 1H), 2.01 (s, 2H), 1.83 (s, 1H), 1.66 (s, 2H), 1.38 (p, J=6.7 Hz, 1H), 1.30-1.17 (m, 4H), 0.81 (t, J=6.6 Hz, 6H).

Example 129

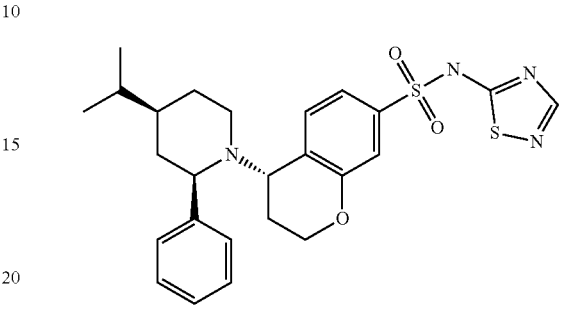

(S)-4-((2R,4S)-4-isopropyl-2-phenylpiperidin-1-yl)-
N-(1,2,4-thiadiazol-5-yl)chroman-7-sulfonamide This compound was prepared using the same reaction sequence as Example 127 and was purified by SFC from the products produced in Example 127 (6.6 mg, 24.4% yield over 2 steps). The stereochemistry was assigned arbitrarily. m/z 499.2 [M+H]$^+$, 1H NMR (400 MHz, DMSO-d6) δ 8.08 (s, 1H), 7.48 (s, 2H), 7.34 (t, J=7.4 Hz, 3H), 7.30-7.17 (m, 2H), 7.10-6.99 (m, 1H), 6.51 (s, 1H), 4.18 (dt, J=10.5, 4.7 Hz, 1H), 3.87 (s, 3H), 2.00 (s, 2H), 1.82 (s, 1H), 1.66 (s, 2H), 1.38 (q, J=6.5 Hz, 1H), 1.26-1.13 (m, 4H), 0.81 (t, J=6.6 Hz, 6H).

Example 130

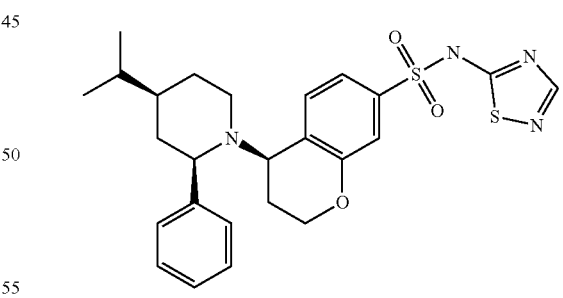

(R)-4-((2R,4S)-4-isopropyl-2-phenylpiperidin-1-yl)-
N-(1,2,4-thiadiazol-5-yl)chroman-7-sulfonamide This compound was prepared using the same reaction sequence as Example 127 and was purified by SFC from the products produced in Example 127 (5.7 mg, 21.1% yield over 2 steps). The stereochemistry was assigned arbitrarily. m/z 499.2 [M+H]$^+$, $^1$H NMR (400 MHz, DMSO-d$_6$) δ 8.10 (s, 1H), 7.72 (dd, J=8.1, 1.1 Hz, 1H), 7.45 (d, J=7.4 Hz, 2H), 7.28 (ddt, J=24.3, 14.6, 7.4 Hz, 4H), 6.99 (d, J=1.8 Hz, 1H), 6.51 (s, 1H), 4.22 (dt, J=11.3, 3.7 Hz, 1H), 3.74 (dq, J=16.0, 8.7 Hz, 2H), 3.59 (d, J=10.1 Hz, 1H), 3.10 (dd, J=7.3, 4.1 Hz, 1H), 2.22 (s, 1H), 1.99 (d, J=12.5 Hz, 1H), 1.75 (dd, J=20.9, 14.4 Hz, 2H), 1.61 (d, J=8.6 Hz, 1H), 1.46-1.13 (m, 4H), 0.83 (t, J=6.4 Hz, 6H).

Example 131

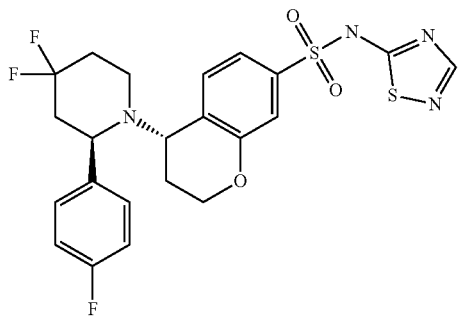 [SMILES: O=S(=O)(Nc1ncns1)c1ccc2c(c1)OCC[C@@H]2N1CCC(F)(F)C[C@@H]1c1ccc(F)cc1]

(S)-4-((R)-4,4-difluoro-2-(4-fluorophenyl)piperidin-1-yl)-N-(1,2,4-thiadiazol-5-yl)chroman-7-sulfonamide

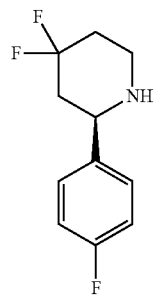 [SMILES: Fc1ccc([C@H]2CC(F)(F)CCN2)cc1]

(R)-4,4-difluoro-2-(4-fluorophenyl)piperidine

The compound was synthesized as for Example 32. The enantiomer was separated by chiral SFC from the crude racemate. The first eluting fraction was arbitrarily assigned as (R)-4,4-difluoro-2-(4-fluorophenyl)piperidine. Chiral HPLC (column: AD-H, 4.6×250 mm, 5 μm; mobile Phase: A: supercritical $CO_2$, B: MeOH (0.2% ammonia), A:B=65:35; flow: 3.0 mL/min; column temperature: 40.1° C.; RT=1.81 min). LCMS (ESI) Method A: RT=3.03 min, m/z: 216.1 [M+H]$^+$. $^1$H NMR (400 MHz, CDCl$_3$) δ 7.68 (d, J=5.2 Hz, 2H), 7.37-7.32 (m, 2H), 4.63-4.60 (m, 1H), 3.55 (m, 1H), 3.25-3.23 (m, 1H), 2.59-2.54 (m, 2H), 2.41-2.37 (m, 2H).

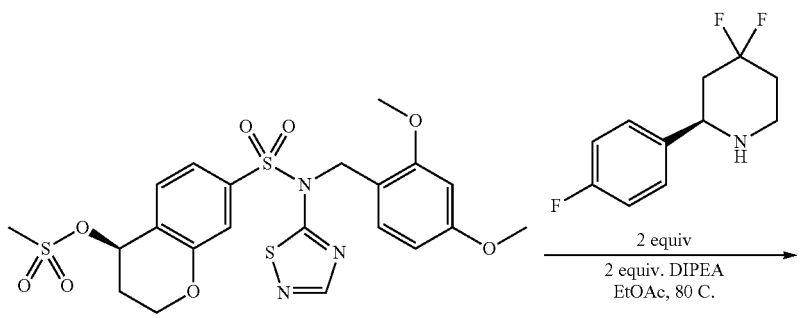

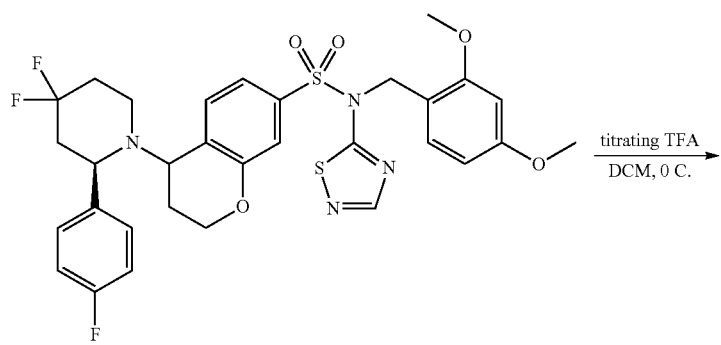

341

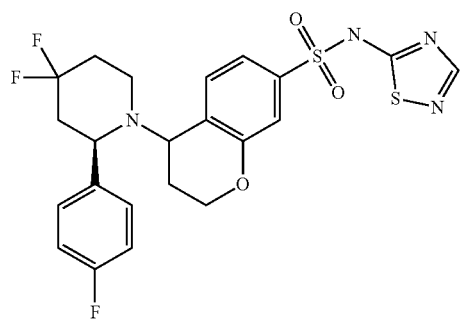

-continued

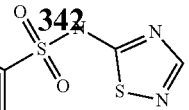

chiral
seperation →

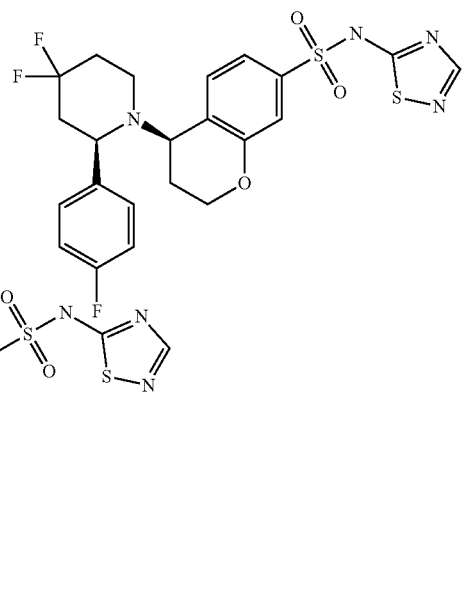

(S)-4-((R)-4,4-difluoro-2-(4-fluorophenyl)piperidin-1-yl)-N-(1,2,4-thiadiazol-5-yl)chroman-7-sulfonamide This compound was prepared using the same sequence as Example 123 with (R)-4,4-difluoro-2-(4-fluorophenyl)piperidine, to give two diastereomers in the reaction sequence. This compound was purified by HPLC to give a white solid (8.5 mg, 48.5% yield over 2 steps). The stereochemistry was assigned arbitrarily. m/z 511.1 [M+H]$^+$, $^1$H NMR (400 MHz, DMSO-d$_6$) δ 8.89 (s, 1H), 8.26 (s, 1H), 7.63-7.51 (m, 2H), 7.41 (d, J=8.1 Hz, 1H), 7.27 (dd, J=8.0, 1.9 Hz, 1H), 7.21-7.12 (m, 2H), 7.02 (d, J=1.9 Hz, 1H), 6.51 (s, 1H), 4.19 (dt, J=11.9, 4.5 Hz, 2H), 3.92-3.78 (m, 2H), 2.76-2.67 (m, 1H), 2.03 (dtdd, J=22.4, 13.1, 8.6, 3.5 Hz, 6H), 1.79 (dddd, J=14.1, 7.0, 4.5, 2.6 Hz, 1H).

Example 132

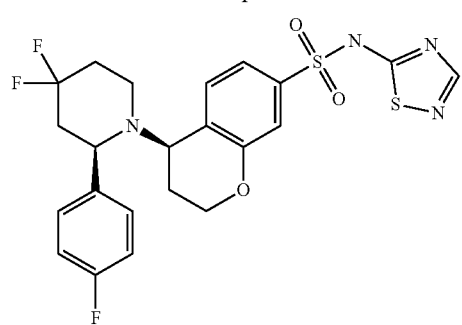

(R)-4-((R)-4,4-difluoro-2-(4-fluorophenyl)piperidin-1-yl)-N-(1,2,4-thiadiazol-5-yl)chroman-7-sulfonamide This compound was prepared in the same sequence as Example 131 and was purified by HPLC to give a white solid (3.7 mg, 21% yield over two steps). The stereochemistry was assigned arbitrarily. m/z 511.1 [M+H]$^+$, $^1$H NMR (400 MHz, DMSO-d$_6$) δ 8.27 (s, 1H), 7.80 (dd, J=8.1, 1.0 Hz, 1H), 7.58 (dd, J=8.4, 5.5 Hz, 2H), 7.29 (dd, J=8.1, 1.9 Hz, 1H), 7.19 (t, J=8.9 Hz, 2H), 7.01 (d, J=1.9 Hz, 1H), 4.23 (dt, J=11.4, 3.6 Hz, 1H), 3.91-3.74 (m, 2H), 3.65 (dd, J=10.5, 5.8 Hz, 1H), 2.43 (dd, J=13.1, 9.1 Hz, 2H), 2.28-2.09 (m, 2H), 2.07-1.88 (m, 3H), 1.88-1.73 (m, 1H).

Example 133

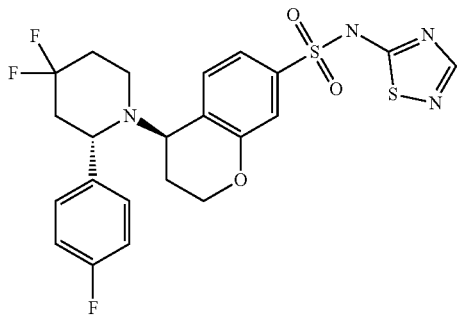 [SMILES: O=S(=O)(Nc1ncns1)c1ccc2c(c1)OCC[C@H]2N1CCC(F)(F)C[C@H]1c1ccc(F)cc1]

343

(R)-4-((S)-4,4-difluoro-2-(4-fluorophenyl)piperidin-1-yl)-N-(1,2,4-thiadiazol-5-yl)chroman-7-sulfonamide

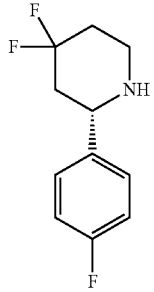

(S)-4,4-difluoro-2-(4-fluorophenyl)piperidine

The compound was synthesized as for Example 32. The enantiomer was separated by chiral SFC from the crude racemate. The second eluting fraction was arbitrarily assigned as (S)-4,4-difluoro-2-(4-fluorophenyl)piperidine. Chiral HPLC (column: AD-H, 4.6×250 mm, 5 μm; mobile Phase: A: supercritical CO$_2$, B: MeOH (0.2% ammonia), A:B=65:35; flow: 3.0 mL/min; column temperature: 40.1° C.; RT=2.62 min). LCMS (ESI) Method A: RT=3.06 min, m/z: 216.1 [M+H]$^+$. $^1$H NMR (400 MHz, CDCl$_3$) δ 7.68 (m, 2H), 7.37-7.32 (m, 2H), 4.63-4.60 (m, 1H), 3.55 (m, 1H), 3.25-3.23 (m, 1H), 2.63-2.59 (m, 2H), 2.42-2.38 (m, 2H).

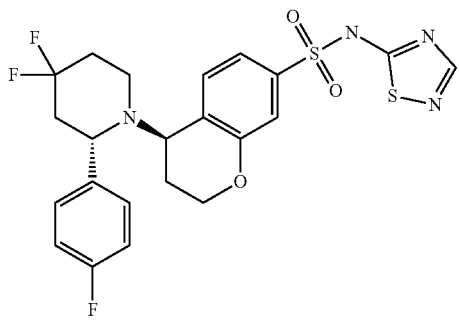 [SMILES: O=S(=O)(Nc1ncns1)c1ccc2c(c1)OCC[C@H]2N1CCC(F)(F)C[C@H]1c1ccc(F)cc1]

(R)-4-((S)-4,4-difluoro-2-(4-fluorophenyl)piperidin-1-yl)-N-(1,2,4-thiadiazol-5-yl)chroman-7-sulfonamide This compound was prepared using the same reaction sequence as Example 131, using (S)-4,4-difluoro-2-(4-fluorophenyl)piperidine as the piperidine, and was purified by HPLC to give a white solid (4.1 mg, 24% yield over two steps). The stereochemistry was assigned arbitrarily. m/z 511.1 [M+H]$^+$, $^1$H NMR (400 MHz, DMSO-d$_6$) δ 8.26 (s, 1H), 7.60-7.51 (m, 2H), 7.41 (d, J=8.1 Hz, 1H), 7.27 (dd, J=8.1, 1.9 Hz, 1H), 7.17 (t, J=8.8 Hz, 2H), 7.02 (d, J=1.9 Hz, 1H), 6.51 (s, 1H), 4.19 (dt, J=12.2, 4.5 Hz, 2H), 3.92-3.78 (m, 2H), 2.76-2.67 (m, 1H), 2.50-2.44 (m, 1H), 2.25-1.91 (m, 6H), 1.85-1.73 (m, 1H).

344

Example 134

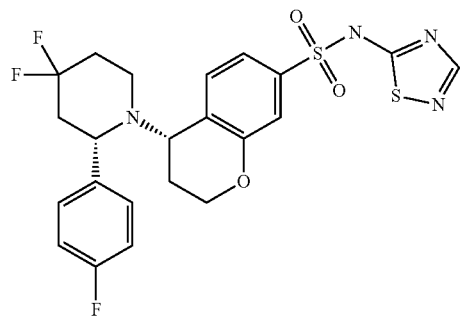 [SMILES: O=S(=O)(Nc1ncns1)c1ccc2c(c1)OCC[C@@H]2N1CCC(F)(F)C[C@H]1c1ccc(F)cc1]

(S)-4-((S)-4,4-difluoro-2-(4-fluorophenyl)piperidin-1-yl)-N-(1,2,4-thiadiazol-5-yl)chroman-7-sulfonamide This compound was prepared in the same sequence as Example 133 and was purified by HPLC to give a white solid (2.5 mg, 14.7%). The stereochemistry was assigned arbitrarily. m/z 511.1 [M+H]$^+$. Not enough material was obtained for an NMR.

Example 135

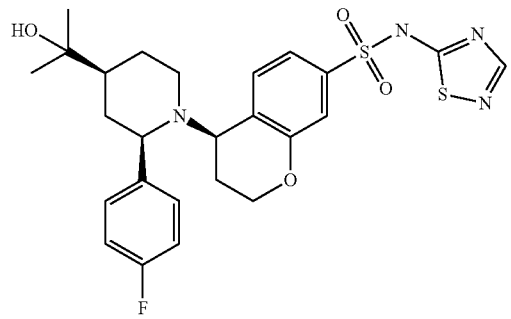 [SMILES: CC(C)(O)[C@H]1CCN([C@@H]2CCOc3cc(S(=O)(=O)Nc4ncns4)ccc32)[C@@H](c2ccc(F)cc2)C1]

(R)-4-((2R,4S)-2-(4-fluorophenyl)-4-(2-hydroxypropan-2-yl)piperidin-1-yl)-N-(1,2,4-thiadiazol-5-yl)chroman-7-sulfonamide

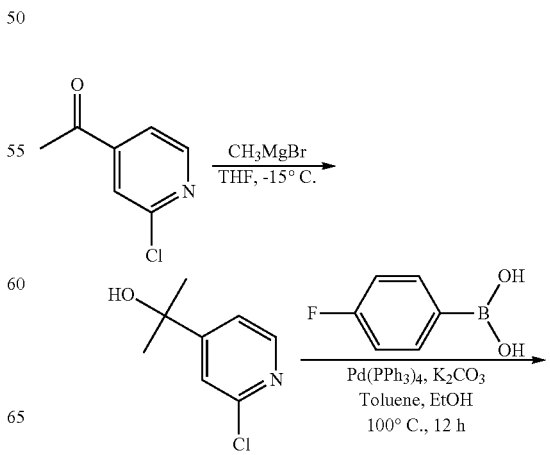

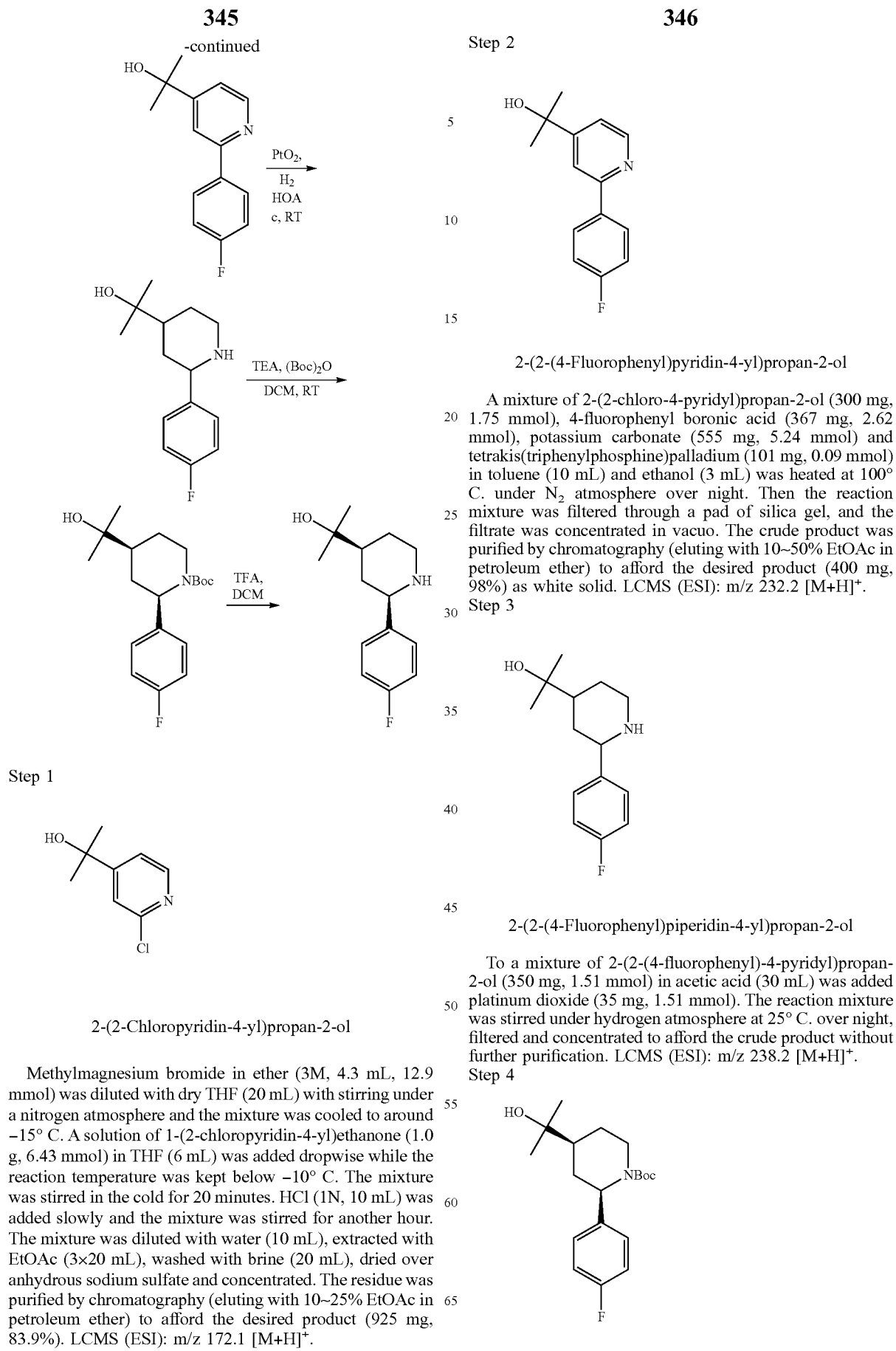

Step 2

2-(2-(4-Fluorophenyl)pyridin-4-yl)propan-2-ol

A mixture of 2-(2-chloro-4-pyridyl)propan-2-ol (300 mg, 1.75 mmol), 4-fluorophenyl boronic acid (367 mg, 2.62 mmol), potassium carbonate (555 mg, 5.24 mmol) and tetrakis(triphenylphosphine)palladium (101 mg, 0.09 mmol) in toluene (10 mL) and ethanol (3 mL) was heated at 100° C. under $N_2$ atmosphere over night. Then the reaction mixture was filtered through a pad of silica gel, and the filtrate was concentrated in vacuo. The crude product was purified by chromatography (eluting with 10~50% EtOAc in petroleum ether) to afford the desired product (400 mg, 98%) as white solid. LCMS (ESI): m/z 232.2 [M+H]$^+$.

Step 3

2-(2-(4-Fluorophenyl)piperidin-4-yl)propan-2-ol

To a mixture of 2-(2-(4-fluorophenyl)-4-pyridyl)propan-2-ol (350 mg, 1.51 mmol) in acetic acid (30 mL) was added platinum dioxide (35 mg, 1.51 mmol). The reaction mixture was stirred under hydrogen atmosphere at 25° C. over night, filtered and concentrated to afford the crude product without further purification. LCMS (ESI): m/z 238.2 [M+H]$^+$.

Step 4

Step 1

2-(2-Chloropyridin-4-yl)propan-2-ol

Methylmagnesium bromide in ether (3M, 4.3 mL, 12.9 mmol) was diluted with dry THF (20 mL) with stirring under a nitrogen atmosphere and the mixture was cooled to around −15° C. A solution of 1-(2-chloropyridin-4-yl)ethanone (1.0 g, 6.43 mmol) in THF (6 mL) was added dropwise while the reaction temperature was kept below −10° C. The mixture was stirred in the cold for 20 minutes. HCl (1N, 10 mL) was added slowly and the mixture was stirred for another hour. The mixture was diluted with water (10 mL), extracted with EtOAc (3×20 mL), washed with brine (20 mL), dried over anhydrous sodium sulfate and concentrated. The residue was purified by chromatography (eluting with 10~25% EtOAc in petroleum ether) to afford the desired product (925 mg, 83.9%). LCMS (ESI): m/z 172.1 [M+H]$^+$.

Tert-butyl 2-(4-fluorophenyl)-4-(2-hydroxypropan-2-yl)piperidine-1-carboxylate A mixture of 2-(2-(4-fluorophenyl)-4-piperidyl)propan-2-ol (350 mg, 1.47 mmol), di-tert-butyl dicarbonate (676 mg, 3.1 mmol), triethylamine (1.01 mL, 7.32 mmol) in DCM (20 mL) was stirred at 25° C. for 4 h. The reaction mixture was concentrated and the residue was purified by CombiFlash (eluting with 0~30% MeCN in 0.01% FA) to afford the desired compound. The enantiomer was separated by chiral SFC from the racemate. The first eluting fraction was arbitrarily assigned as (2R,4S)-tert-butyl 2-(4-fluorophenyl)-4-(2-hydroxypropan-2-yl)piperidine-1-carboxylate. Chiral-HPLC (column: (R,R)-Whelk-O1, 4.6×250 mm, 5 μm; mobile Phase: A: supercritical C02, B: MeOH (0.2% ammonia), A:B=85:15; flow: 3.0 mL/min; column temperature: 40° C.; RT=2.67 min). LCMS (ESI), m/z: 238.1 [M-Boc+H]$^+$.

Step 5

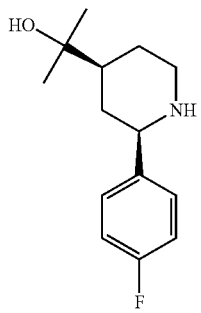 [SMILES: CC(C)(O)[C@H]1CCN[C@@H](c2ccc(F)cc2)C1]

2-((2R,4S)-2-(4-fluorophenyl)piperidin-4-yl)propan-2-ol

A solution of (2R)-tert-butyl 2-(4-fluorophenyl)-4-(2-hydroxypropan-2-yl)piperidine-1-carboxylate (360 mg, 1.07 mmol) in DCM (10 mL) and trifluoroacetic acid (1.5 mL) was stirred at 25° C. for 2 h. The reaction mixture was concentrated to dryness and the crude was purified by CombiFlash (eluting with 5% MeCN in 0.01% FA) to afford the desired compound (220 mg, 85.5%). LCMS (ESI) Method C: RT=2.68 min, m/z 238.3 [M+H]$^+$. $^1$H NMR (400 MHz, DMSO-d$_6$) δ 7.57-7.53 (m, 2H), 7.30-7.25 (m, 2H), 4.19-4.15 (m, 1H), 3.40-3.36 (m, 1H), 3.01-2.95 (m, 1H), 1.95-1.85 (m, 2H), 1.65-1.47 (m, 3H), 1.07 (s, 6H).

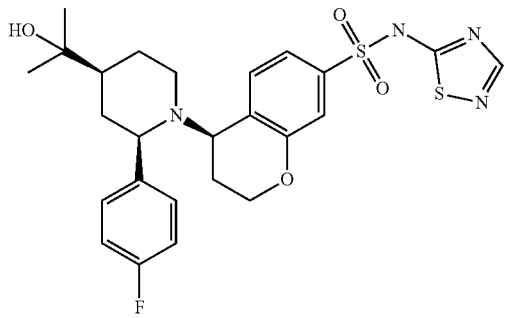 [SMILES: CC(C)(O)[C@H]1CCN([C@@H]2CCOc3cc(S(=O)(=O)Nc4ncns4)ccc32)[C@@H](c2ccc(F)cc2)C1]

(R)-4-((2R,4S)-2-(4-fluorophenyl)-4-(2-hydroxypropan-2-yl)piperidin-1-yl)-N-(1,2,4-thiadiazol-5-yl)chroman-7-sulfonamide This compound was prepared using the same reaction sequence as Example 123, using 2-((2R,4S)-2-(4-fluorophenyl)piperidin-4-yl)propan-2-ol, and was purified by HPLC to give a white solid (0.4 mg, 2.25% yield over two steps). The stereochemistry was assigned arbitrarily. m/z 533.2 [M+H]$^+$. Not enough material was obtained for an NMR.

Example 136

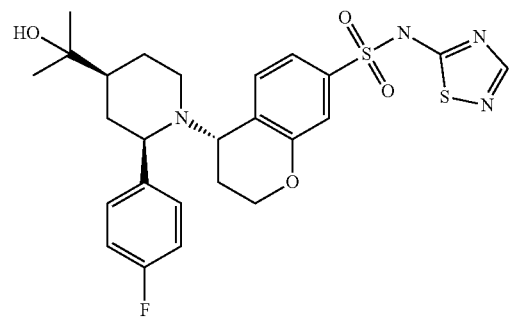 [SMILES: CC(C)(O)[C@H]1CCN([C@H]2CCOc3cc(S(=O)(=O)Nc4ncns4)ccc32)[C@@H](c2ccc(F)cc2)C1]

(S)-4-((2R,4S)-2-(4-fluorophenyl)-4-(2-hydroxypropan-2-yl)piperidin-1-yl)-N-(1,2,4-thiadiazol-5-yl)chroman-7-sulfonamide This compound was prepared in the same reaction sequence as Example 135 and was purified by HPLC to give a white solid (4.4 mg, 24.8% yield over two steps). The stereochemistry was assigned arbitrarily. m/z 533.2 [M+H]$^+$. 1H NMR (400 MHz, DMSO-d6) δ 12.70 (s, 1H), 7.87 (s, 1H), 7.49 (dd, J=8.4, 5.5 Hz, 2H), 7.32 (d, J=8.2 Hz, 1H), 7.22 (dd, J=8.0, 1.9 Hz, 1H), 7.15 (t, J=8.7 Hz, 2H), 7.00 (d, J=1.8 Hz, 1H), 4.15 (dt, J=11.2, 4.3 Hz, 1H), 4.01 (s, 1H), 3.95 (s, 1H), 3.81 (dd, J=21.4, 10.2 Hz, 2H), 2.64 (d, J=10.1 Hz, 1H), 1.95 (dtd, J=13.6, 9.2, 3.9 Hz, 2H), 1.68 (dd, J=19.0, 10.5 Hz, 2H), 0.98 (s, 6H).

Example 137

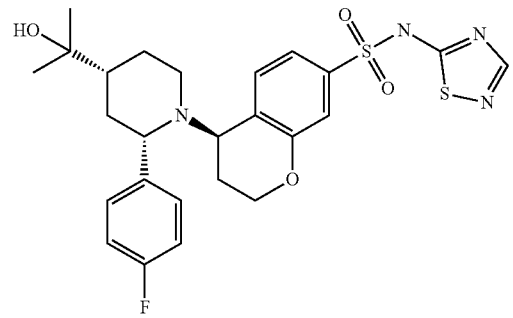 [SMILES: CC(C)(O)[C@@H]1CCN([C@@H]2CCOc3cc(S(=O)(=O)Nc4ncns4)ccc32)[C@H](c2ccc(F)cc2)C1]

(R)-4-((2S,4R)-2-(4-fluorophenyl)-4-(2-hydroxypropan-2-yl)piperidin-1-yl)-N-(1,2,4-thiadiazol-5-yl)chroman-7-sulfonamide

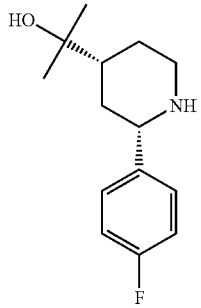 [SMILES: CC(C)(O)[C@@H]1CCN[C@H](c2ccc(F)cc2)C1]

2-((2S,4R)-2-(4-fluorophenyl)piperidin-4-yl)propan-2-ol

The compound was synthesized as for Example 135. The enantiomer was arbitrarily assigned as 2-((2S,4R)-2-(4-fluorophenyl)piperidin-4-yl)propan-2-ol. LCMS (ESI) Method C: RT=2.69 min, m/z 238.3 [M+H]⁺. ¹H NMR (400 MHz, DMSO-d₆) δ 7.57-7.53 (m, 2H), 7.31-7.26 (m, 2H), 4.23-4.18 (m, 1H), 3.41-3.29 (m, 1H), 3.03-2.97 (m, 1H), 1.97-1.86 (m, 2H), 1.66-1.49 (m, 3H), 1.07 (s, 6H).

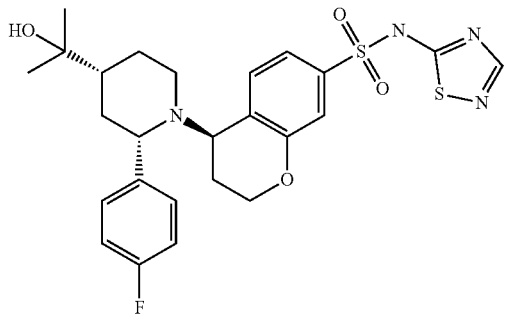 [SMILES: CC(C)(O)[C@@H]1CCN([C@@H]2CCOc3cc(S(=O)(=O)Nc4ncns4)ccc32)[C@H](c2ccc(F)cc2)C1]

(R)-4-((2S,4R)-2-(4-fluorophenyl)-4-(2-hydroxypropan-2-yl)piperidin-1-yl)-N-(1,2,4-thiadiazol-5-yl)chroman-7-sulfonamide This compound was prepared using the same reaction sequence as Example 123, using 2-((2S,4R)-2-(4-fluorophenyl)piperidin-4-yl)propan-2-ol as the piperidine in step 1, and was purified by HPLC to give a white solid (1.6 mg, 8.5% yield over two steps). The stereochemistry was assigned arbitrarily. m/z 533.2 [M+H]⁺. Not enough material was obtained for an NMR.

Example 138

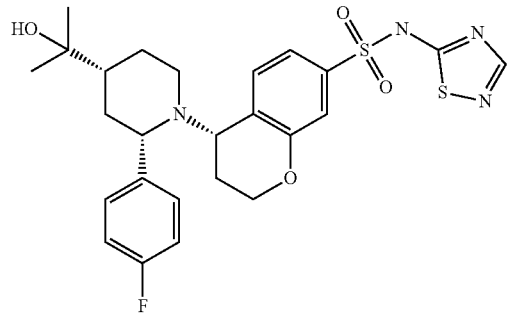 [SMILES: CC(C)(O)[C@@H]1CCN([C@H]2CCOc3cc(S(=O)(=O)Nc4ncns4)ccc32)[C@H](c2ccc(F)cc2)C1]

(S)-4-((2S,4R)-2-(4-fluorophenyl)-4-(2-hydroxypropan-2-yl)piperidin-1-yl)-N-(1,2,4-thiadiazol-5-yl)chroman-7-sulfonamide This compound was prepared in the same reaction sequence as Example 137 and was purified by HPLC to give a white solid (1 mg, 5.3% yield). The stereochemistry was assigned arbitrarily. m/z 533.2 [M+H]⁺. Not enough material was obtained for an NMR.

Example 139

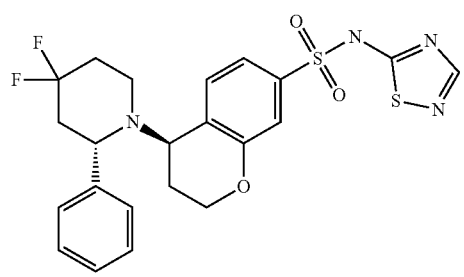 [SMILES: O=S(=O)(Nc1ncns1)c1ccc2c(c1)OCC[C@H]2N1CCC(F)(F)C[C@H]1c1ccccc1]

(R)-4-((S)-4,4-difluoro-2-phenylpiperidin-1-yl)-N-(1,2,4-thiadiazol-5-yl)chroman-7-sulfonamide This compound was prepared using the same reaction sequence as Example 123, using (S)-4,4-difluoro-2-phenylpiperidine (Example 32), and was purified by HPLC to give a white solid (4.6 mg, 7.9% yield over 2 steps). The stereochemistry was assigned arbitrarily. m/z 493.1 [M+H]⁺. ¹H NMR (400 MHz, DMSO-d6) δ 8.31 (s, 1H), 7.51 (d, J=7.5 Hz, 2H), 7.45-7.24 (m, 5H), 7.02 (d, J=1.8 Hz, 1H), 6.51 (s, 1H), 4.24-4.10 (m, 2H), 3.85 (td, J=9.5, 8.6, 3.1 Hz, 2H), 2.76-2.67 (m, 1H), 2.24-1.88 (m, 6H), 1.80 (dtd, J=15.6, 9.2, 7.9, 4.5 Hz, 1H).

Example 140

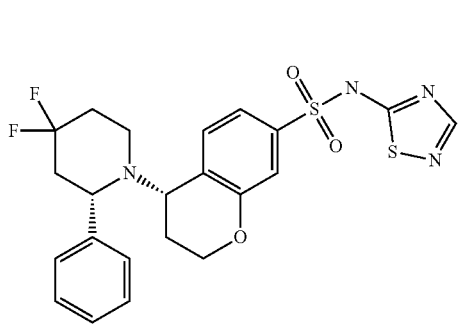 [SMILES: O=S(=O)(Nc1ncns1)c1ccc2c(c1)OCC[C@@H]2N1CCC(F)(F)C[C@H]1c1ccccc1]

(S)-4-((S)-4,4-difluoro-2-phenylpiperidin-1-yl)-N-(1,2,4-thiadiazol-5-yl)chroman-7-sulfonamide This compound was prepared in the same reaction sequence as Example 139 and was purified by HPLC to give a white solid (4.6 mg, 9.3% yield over 2 steps). The stereochemistry was assigned arbitrarily. m/z 493.1 [M+H]$^+$. $^1$H NMR (400 MHz, DMSO-d$_6$) δ 8.31 (s, 1H), 7.82 (d, J=8.1 Hz, 1H), 7.53 (d, J=7.4 Hz, 2H), 7.42-7.26 (m, 4H), 7.02 (d, J=1.8 Hz, 1H), 6.51 (s, 1H), 4.24 (dt, J=11.3, 3.6 Hz, 1H), 3.88-3.64 (m, 3H), 2.55 (d, J=11.1 Hz, 1H), 2.42 (dd, J=12.0, 4.2 Hz, 1H), 2.30-1.88 (m, 6H), 1.87-1.73 (m, 1H).

Example 141

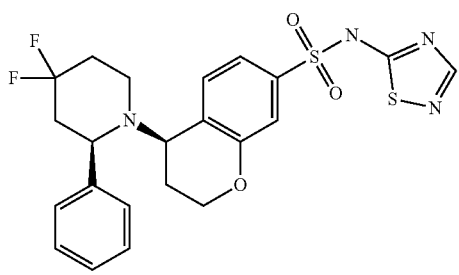 [SMILES: O=S(=O)(Nc1ncns1)c1ccc2c(c1)OCC[C@H]2N1CCC(F)(F)C[C@@H]1c1ccccc1]

(R)-4-((R)-4,4-difluoro-2-phenylpiperidin-1-yl)-N-(1,2,4-thiadiazol-5-yl)chroman-7-sulfonamide This compound was prepared using the same reaction sequence as Example 123, using (R)-4,4-difluoro-2-phenylpiperidine (Example 32), and was purified by HPLC to give a white solid (3 mg, 5.2% yield over 2 steps). The stereochemistry was assigned arbitrarily. m/z 493.1 [M+H]$^+$. 1H NMR (400 MHz, DMSO-d6) δ 8.34 (s, 1H), 7.83 (d, J=8.1 Hz, 1H), 7.53 (d, J=7.4 Hz, 2H), 7.44-7.26 (m, 4H), 7.09-6.99 (m, 1H), 4.24 (dt, J=11.3, 3.6 Hz, 1H), 3.88-3.64 (m, 3H), 2.58-2.50 (m, 1H), 2.44 (td, J=11.9, 11.2, 3.5 Hz, 1H), 2.30-1.91 (m, 8H), 1.88-1.73 (m, 1H).

Example 142

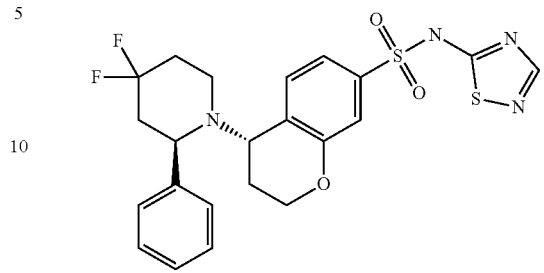

(S)-4-((R)-4,4-difluoro-2-phenylpiperidin-1-yl)-N-(1,2,4-thiadiazol-5-yl)chroman-7-sulfonamide This compound was prepared in the same reaction sequence as Example 141 and was purified by HPLC to give a white solid (4.6 mg, 10.2% yield over 2 steps). The stereochemistry was assigned arbitrarily. m/z 493.1 [M+H]$^+$. 1H NMR (400 MHz, DMSO-d6) δ 8.20 (s, 1H), 7.51 (d, J=7.5 Hz, 2H), 7.42-7.24 (m, 5H), 7.02 (d, J=1.8 Hz, 1H), 6.51 (s, 1H), 4.17 (ddd, J=16.0, 11.5, 4.4 Hz, 2H), 3.84 (td, J=9.5, 8.4, 3.1 Hz, 2H), 2.74-2.66 (m, 1H), 2.23-1.91 (m, 7H), 1.86-1.73 (m, 1H).

Example 143

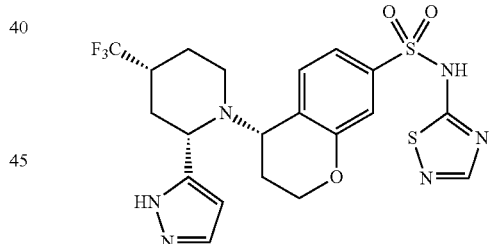

(S)-4-((2S,4R)-2-(1H-pyrazol-5-yl)-4-(trifluoromethyl)piperidin-1-yl)-N-(1,2,4-thiadiazol-5-yl)chromane-7-sulfonamide

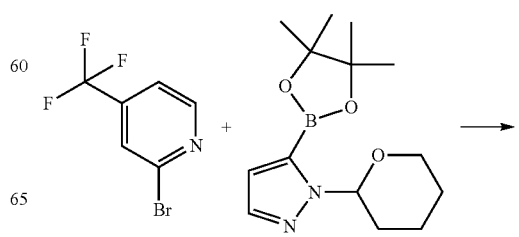

-continued

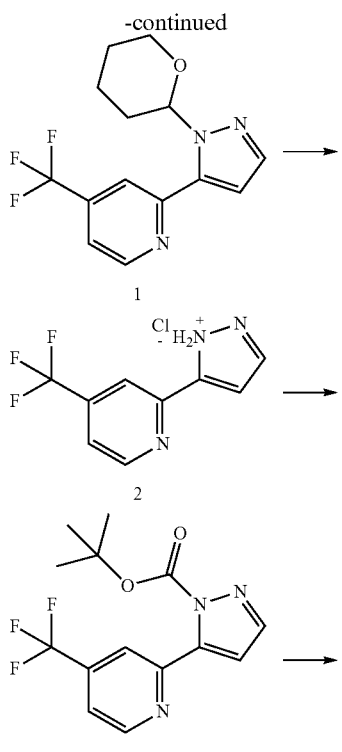

Step 1

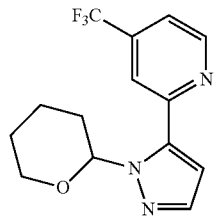 [SMILES: FC(F)(F)c1ccnc(-c2ccnn2C2CCCCO2)c1]

2-(2-tetrahydropyran-2-ylpyrazol-3-yl)-4-(trifluoromethyl)pyridine 2-bromo-4-(trifluoromethyl)pyridine (2.0 g, 8.85 mmol) was added to a mixture of 1-(tetrahydro-2H-pyran-2-yl)-5-(4,4,5,5-tetramethyl-1,3,2-dioxaborolan-2-yl)-1H-pyrazole (2.85 g, 9.73 mmol,), tetrakis(triphenylphosphine)palladium (0) (511 mg, 0.44 mmol,) and potassium carbonate (3.67 g 26.55 mmol,) in ethanol (10 mL) and toluene (10 mL). The mixture was stirred at 100° C. for 2 h. The reaction was cooled down and water was added. The aqueous phase was extracted with 3×50 mL of dichloromethane. The organic phase was dried with MgSO$_4$, filtered and concentrated. Purification by flash chromatography (100% heptane to 100% ethyl acetate gradient, 40 g column) afforded 2.34 g (89%) of 2-(2-tetrahydropyran-2-ylpyrazol-3-yl)-4-(trifluoromethyl)pyridine as a yellow oil. LCMS (Method Shimadzu): RT=1.45 min, m+H=298.1. $^1$H NMR (400 MHz, Chloroform-d) δ 8.87 (d, J=5.0 Hz, 1H), 7.86 (d, J=1.5 Hz, 1H), 7.63 (dd, J=14.6, 2.2 Hz, 1H), 7.48 (dd, J=5.2, 1.6 Hz, 1H), 6.70 (d, J=1.9 Hz, 1H), 6.14 (dd, J=10.0, 2.5 Hz, 1H), 4.04 (ddt, J=11.5, 4.3, 2.1 Hz, 1H), 3.61 (td, J=11.4, 2.6 Hz, 1H), 2.63-2.48 (m, 1H), 2.17-1.99 (m, 2H), 1.83-1.62 (m, 2H), 1.58 (s, 1H).

Step 2

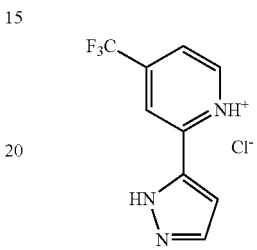

2-(1H-pyrazol-5-yl)-4-(trifluoromethyl)pyridine hydrochloride

Hydrochloric acid (4 mol/L) in 1,4-dioxane (9.7 mL, 39 mmol) was added to a solution of 2-(2-tetrahydropyran-2-ylpyrazol-3-yl)-4-(trifluoromethyl)pyridine (2.3 g, 7.7 mmol) in dichloromethane (10 mL) and the mixture was stirred at room temperature for 5 h. The resulting solid was collected by filtration and washed with dichloromethane to afford 1.62 g (84%) of 2-(1H-pyrazol-5-yl)-4-(trifluoromethyl)pyridine hydrochloride as a yellow solid. The compound was used for next step without purification. LCMS (Method Shimadzu): RT=1.45 min, m+H=214.1. $^1$H NMR (400 MHz, DMSO-d6) δ 8.87 (d, J=5.1 Hz, 1H), 8.21 (d, J=1.7 Hz, 1H), 7.85 (d, J=2.3 Hz, 1H), 7.69 (dd, J=5.2, 1.7 Hz, 1H), 6.97 (d, J=2.2 Hz, 1H).

Step 3

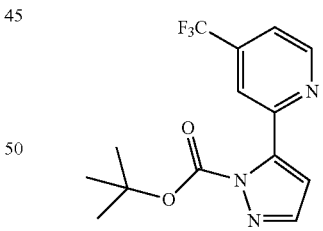

Tert-butyl 5-[4-(trifluoromethyl)-2-pyridyl]pyrazole-1-carboxylate

Di-tert-butyl dicarbonate (4.4 g, 19.4 mmol) was added to a solution of 2-(1H-pyrazol-5-yl)-4-(trifluoromethyl)pyridine hydrochloride (1.62 g, 6.49 mmol) and triethylamine (3.6 mL, 26.0 mmol) in dichloromethane (30 mL) and the mixture was stirred at 45° C. for 48 h. The reaction was then cooled down and water was added. The phases were separated and the aqueous phase was extracted with 2×25 mL of dichloromethane. The organic phase was dried with MgSO$_4$, filtered and concentrated. Purification by flash chromatography (100% heptane to 100% ethyl acetate gradient, 40 g column) afforded 1.14 g (56%) of tert-butyl 5-[4-(trifluoromethyl)-2-pyridyl]pyrazole-1-carboxylate as a white solid. LCMS (Method Shimadzu): RT=1.48 min, m+H=314.1. ¹H NMR (400 MHz, Chloroform-d) δ 8.81 (d, J=5.2 Hz, 1H), 8.44 (s, 1H), 8.15 (d, J=2.8 Hz, 1H), 7.48 (dd, J=5.1, 1.7 Hz, 1H), 7.11 (d, J=2.8 Hz, 1H), 1.69 (s, 9H).
Step 4

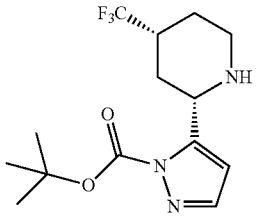 [SMILES: CC(C)(C)OC(=O)n1nccc1[C@@H]1C[C@H](C(F)(F)F)CCN1]

(±)-Tert-butyl 5-[cis-4-(trifluoromethyl)-2-piperidyl]pyrazole-1-carboxylate

A mixture of tert-butyl 5-[4-(trifluoromethyl)-2-pyridyl]pyrazole-1-carboxylate (1.1 g, 3.5 mmol) and platinum(IV) oxide (80 mg, 0.35 mmol) in acetic acid (18 mL) was placed under vacuum for 2 min and then the atmosphere was replaced with hydrogen. The process was repeated 2 times. The mixture was then stirred under hydrogen at room temperature for 16 h. The mixture was diluted in dichloromethane and filtered over celite. The filtrate was concentrated under vacuum to give 1.1 g (98%) of (±)-tert-butyl 5-[cis-4-(trifluoromethyl)-2-piperidyl]pyrazole-1-carboxylate as a white solid. LCMS (Method Shimadzu): RT=1.0 min, m+H=320.1. ¹H NMR (400 MHz, Chloroform-d) δ 8.01 (dd, J=6.8, 2.8 Hz, 1H), 6.36 (dd, J=21.7, 2.8 Hz, 1H), 3.86 (dd, J=11.5, 2.7 Hz, 1H), 3.28 (d, J=12.0 Hz, 1H), 2.79 (td, J=12.2, 2.8 Hz, 1H), 2.20-2.11 (m, 1H), 1.94-1.84 (m, 1H), 1.64 (s, 1H), 1.64 (s, 9H), 1.62-1.41 (m, 2H).

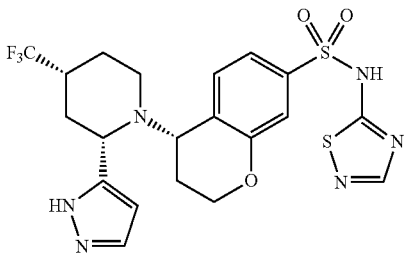 [SMILES: O=S(=O)(Nc1ncns1)c1ccc2c(c1)OCC[C@@H]2N1CC[C@@H](C(F)(F)F)C[C@H]1c1ccn[nH]1]

(S)-4-((2S,4R)-2-(1H-pyrazol-5-yl)-4-(trifluoromethyl)piperidin-1-yl)-N-(1,2,4-thiadiazol-5-yl)chromane-7-sulfonamide The compound was synthesized with the sequence from Example 123 using tert-butyl 5-[cis-4-(trifluoromethyl)-2-piperidyl]pyrazole-1-carboxylate and purified by SFC. The stereochemistry was assigned arbitrarily. m/z 515.1 [M+H]⁺, ¹H NMR (400 MHz, DMSO-d6) δ 12.66 (s, 1H), 8.08 (s, 1H), 7.65 (d, J=8.1 Hz, 1H), 7.29-7.18 (m, 1H), 7.00 (d, J=1.8 Hz, 1H), 6.51 (s, 1H), 6.32 (d, J=2.2 Hz, 1H), 4.26 (dt, J=11.2, 3.7 Hz, 1H), 3.91-3.76 (m, 2H), 3.65 (s, 1H), 2.29 (d, J=11.4 Hz, 1H), 2.03-1.73 (m, 4H), 1.52-1.37 (m, 1H).

Example 144

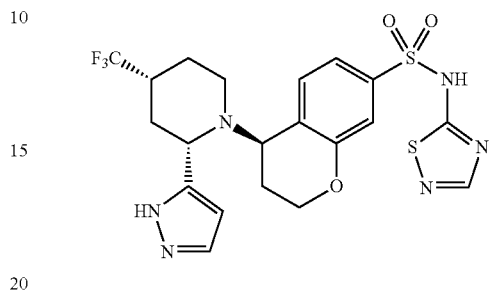

(R)-4-((2S,4R)-2-(1H-pyrazol-5-yl)-4-(trifluoromethyl)piperidin-1-yl)-N-(1,2,4-thiadiazol-5-yl)chromane-7-sulfonamide The compound was synthesized in the same sequence as Example 143 and was purified by SFC from the products produced in Example 143. The stereochemistry was assigned arbitrarily. m/z 515.1 [M+H]⁺, ¹H NMR (400 MHz, DMSO-d6) δ 12.62 (s, 1H), 8.07 (s, 1H), 7.59 (s, 1H), 7.42 (s, 1H), 7.27-7.17 (m, 1H), 7.07 (s, 1H), 7.01 (d, J=1.8 Hz, 1H), 6.94 (s, 1H), 6.25 (s, 1H), 4.18 (dt, J=11.2, 4.5 Hz, 1H), 3.92-3.82 (m, 2H), 3.44 (q, J=7.0 Hz, 1H), 2.13 (s, 1H), 1.96 (s, 1H), 1.78 (d, J=10.7 Hz, 3H), 1.49 (s, 1H), 1.06 (t, J=7.0 Hz, 1H).

Example 145

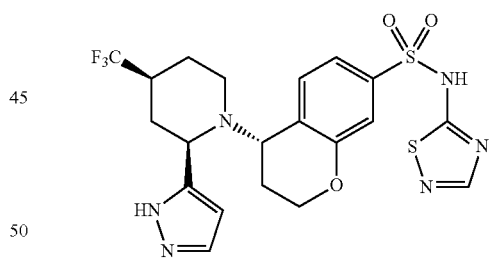

(S)-4-((2R,4S)-2-(1H-pyrazol-5-yl)-4-(trifluoromethyl)piperidin-1-yl)-N-(1,2,4-thiadiazol-5-yl)chromane-7-sulfonamide The compound was synthesized in the same sequence as Example 143 and was purified by SFC from the products produced in Example 143. The stereochemistry was assigned arbitrarily. m/z 515.1 [M+H]⁺, 1H NMR (400 MHz, DMSO-d6) δ 12.68 (s, 1H), 8.28 (d, J=10.4 Hz, 1H), 7.60-7.55 (m, 1H), 7.48 (d, J=8.1 Hz, 1H), 7.31-7.17 (m, 1H), 7.05 (d, J=19.1 Hz, 1H), 6.25 (s, 1H), 4.20 (dt, J=10.0, 4.6 Hz, 1H), 4.14 (s, 1H), 3.92 (d, J=12.2 Hz, 2H), 2.73 (s, 1H), 2.17 (s, 1H), 2.00 (s, 1H), 1.80 (s, 3H), 1.53 (s, 1H).

Example 146

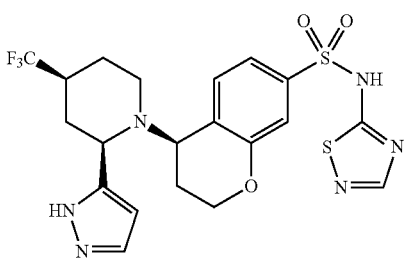 [SMILES: O=S(=O)(Nc1ncns1)c1ccc2c(c1)OCC[C@H]2N1CC[C@H](C(F)(F)F)C[C@@H]1c1ccn[nH]1]

(R)-4-((2R,4S)-2-(1H-pyrazol-5-yl)-4-(trifluoromethyl)piperidin-1-yl)-N-(1,2,4-thiadiazol-5-yl)chromane-7-sulfonamide The compound was synthesized in the same sequence as Example 143 and was purified by SFC from the products produced in Example 143. The stereochemistry was assigned arbitrarily. m/z 515.1 [M+H]+, 1H NMR (400 MHz, DMSO-d6) δ 12.63 (s, 1H), 8.26 (s, 1H), 7.69 (d, J=8.2 Hz, 1H), 7.62 (s, 1H), 7.28 (dd, J=8.2, 1.8 Hz, 1H), 7.01 (d, J=1.8 Hz, 1H), 6.32 (d, J=2.2 Hz, 1H), 4.27 (dt, J=11.3, 3.7 Hz, 1H), 3.91-3.77 (m, 2H), 3.66 (s, 1H), 2.31 (t, J=11.5 Hz, 1H), 2.04-1.85 (m, 3H), 1.79 (t, J=10.8 Hz, 2H), 1.52-1.38 (m, 1H).

Example 147

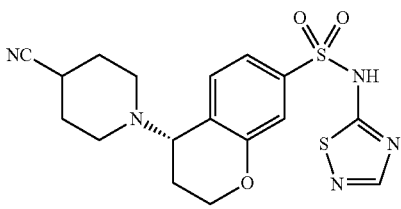 [SMILES: N#CC1CCN([C@H]2CCOc3cc(S(=O)(=O)Nc4ncns4)ccc32)CC1]

(S)-4-(4-cyanopiperidine-1-yl)-N-(1,2,4-thiadiazol-5-yl)chromane-7-sulfonamide

The compound was synthesized as for Example 37. m/z 406.1 [M+H]+. 1H NMR (400 MHz, DMSO-d6) δ 8.20 (s, 1H), 7.56 (d, J=8.1 Hz, 1H), 7.26 (dd, J=8.1, 1.9 Hz, 1H), 7.07 (d, J=1.9 Hz, 1H), 4.33 (dt, J=11.0, 4.4 Hz, 1H), 4.14 (dt, J=11.7, 6.2 Hz, 1H), 3.99 (t, J=7.4 Hz, 1H), 2.90 (dd, J=9.0, 4.7 Hz, 1H), 2.62 (s, 2H), 2.40 (s, 1H), 1.97 (s, 1H), 2.01-1.92 (m, 1H), 1.89 (s, 1H), 1.81-1.66 (m, 2H).

Example 148

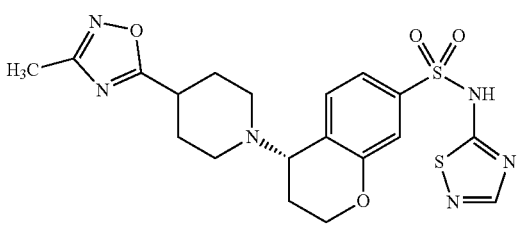 [SMILES: Cc1noc(C2CCN([C@H]3CCOc4cc(S(=O)(=O)Nc5ncns5)ccc43)CC2)n1]

(S)-4-(4-(3-methyl-1,2,4-oxadiazol-5-yl)piperidin-1-yl)-N-(1,2,4-thiadiazol-5-yl)chromane-7-sulfonamide The compound was synthesized as for Example 37. m/z 463.1 [M+H]+.

Example 149

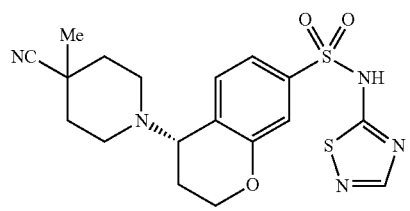 [SMILES: CC1(C#N)CCN([C@H]2CCOc3cc(S(=O)(=O)Nc4ncns4)ccc32)CC1]

(S)-4-(4-cyano-4-methylpiperidin-1-yl)-N-(1,2,4-thiadiazol-5-yl)chromane-7-sulfonamide The compound was synthesized as for Example 37. m/z 420.1 [M+H]+, 1H NMR (400 MHz, DMSO-d6) δ 8.29 (s, 1H), 7.57 (d, J=8.1 Hz, 1H), 7.27 (dd, J=8.1, 1.9 Hz, 1H), 7.08 (d, J=1.8 Hz, 1H), 4.40-4.31 (m, 1H), 4.16 (dt, J=11.6, 6.3 Hz, 1H), 4.02 (t, J=7.1 Hz, 1H), 3.62-3.53 (m, 1H), 2.95-2.79 (m, 2H), 2.71 (t, J=11.2 Hz, 1H), 2.29 (s, 1H), 2.10-1.88 (m, 3H), 1.86-1.73 (m, 1H), 1.69-1.32 (m, 6H).

Example 150

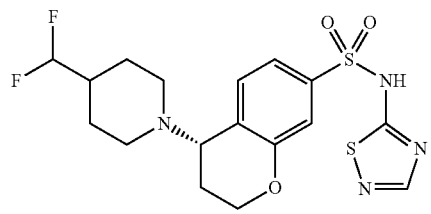 [SMILES: O=S(=O)(Nc1ncns1)c1ccc2c(c1)OCC[C@@H]2N1CCC(C(F)F)CC1]

(S)-4-(4-(difluoromethyl)piperidin-1-yl)-N-(1,2,4-thiadiazol-5-yl)chromane-7-sulfonamide The compound was synthesized as for Example 37. m/z 431.1 [M+H]+, 1H NMR (400 MHz, DMSO-d6) δ 8.07 (s, 1H), 7.54 (d, J=8.2 Hz, 1H), 7.27 (dd, J=8.1, 1.9 Hz, 1H), 7.12-7.03 (m, 1H), 6.51 (s, 1H), 6.03-5.90 (m, 1H), 4.37-4.25 (m, 1H), 4.16 (ddd, J=11.6, 8.7, 3.3 Hz, 1H), 3.01 (s, 1H), 2.76-2.69 (m, 1H), 2.07 (s, 1H), 2.02 (s, 2H), 1.89-1.73 (m, 2H), 1.67 (d, J=12.9 Hz, 1H), 1.51 (tt, J=13.2, 6.6 Hz, 1H), 1.35 (d, J=12.9 Hz, 1H), 1.25 (q, J=7.3, 6.6 Hz, 1H).

Example 151

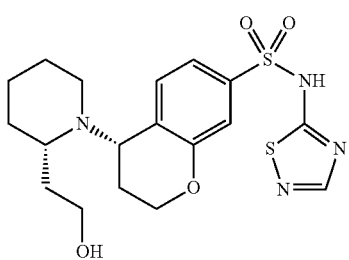 [SMILES: O=S(=O)(Nc1ncns1)c1ccc2c(c1)OCC[C@@H]2N1CCCC[C@H]1CCO]

(S)-4-((S)-2-(2-hydroxyethyl)piperidin-1-yl)-N-(1,2,4-thiadiazol-5-yl)chromane-7-sulfonamide The compound was synthesized as for Example 37. The stereochemistry was assigned arbitrarily. m/z 425.1 [M+H]+.

Example 152

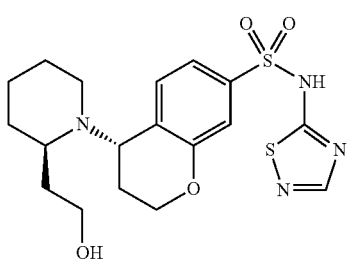 [SMILES: O=S(=O)(Nc1ncns1)c1ccc2c(c1)OCC[C@@H]2N1CCCC[C@@H]1CCO]

(S)-4-((R)-2-(2-hydroxyethyl)piperidin-1-yl)-N-(1,2,4-thiadiazol-5-yl)chromane-7-sulfonamide The compound was synthesized as for Example 37. The stereochemistry was assigned arbitrarily. m/z 425.1 [M+H]+, 1H NMR (400 MHz, DMSO-d6) δ 8.13 (s, 1H), 7.83 (s, 1H), 7.49 (t, J=8.3 Hz, 1H), 7.25-7.14 (m, 1H), 7.02 (d, J=10.4 Hz, 1H), 6.51 (s, 1H), 4.30 (d, J=7.8 Hz, 1H), 4.12 (s, 1H), 3.52 (t, J=7.5 Hz, 2H), 2.88 (d, J=6.6 Hz, 1H), 1.98 (s, 3H), 1.79-1.69 (m, 1H), 1.67 (s, 5H), 1.41 (s, 5H), 1.24 (dd, J=9.4, 6.9 Hz, 1H).

Example 153

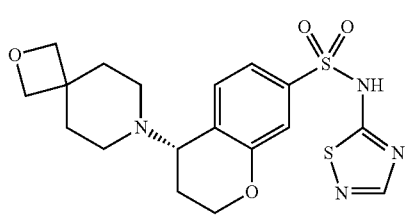 [SMILES: O=S(=O)(Nc1ncns1)c1ccc2c(c1)OCC[C@@H]2N1CCC2(CC1)COC2]

(S)-4-(2-oxa-7-azaspiro[3.5]nonan-7-yl)-N-(1,2,4-thiadiazol-5-yl)chromane-7-sulfonamide The compound was synthesized as for Example 37. m/z 423.1 [M+H]+, 1H NMR (400 MHz, DMSO-d6) δ 8.23 (s, 1H), 7.43 (d, J=8.0 Hz, 1H), 7.27 (dd, J=8.0, 1.9 Hz, 1H), 7.08 (d, J=1.9 Hz, 1H), 6.51 (s, 1H), 5.50 (s, 1H), 4.62 (t, J=5.1 Hz, 1H), 4.21 (dd, J=6.7, 4.2 Hz, 2H), 3.23-3.01 (m, 2H), 2.94-2.79 (m, 1H), 2.10-1.94 (m, 1H), 1.92-1.80 (m, 1H), 1.53 (s, 1H).

Example 154

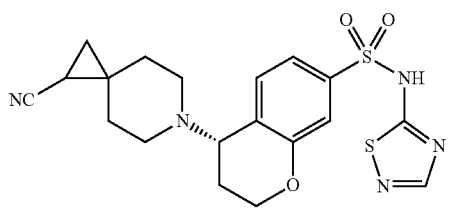 [SMILES: N#CC1CC12CCN([C@H]1CCOc3cc(S(=O)(=O)Nc4ncns4)ccc31)CC2]

(S)-4-(2-oxa-7-azaspiro[3.5]nonan-7-yl)-N-(1,2,4-thiadiazol-5-yl)chromane-7-sulfonamide (Mixture of Diastereomers)

The compound was synthesized as for Example 37. m/z 432.1

Example 155

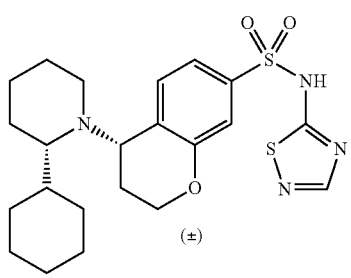 [SMILES: O=S(=O)(Nc1ncns1)c1ccc2c(c1)OCC[C@@H]2N1CCCC[C@H]1C1CCCCC1]

(S)-4-((S)-2-cyclohexylpiperidin-1-yl)-N-(1,2,4-thiadiazol-5-yl)chromane-7-sulfonamide The compound was synthesized as for Example 37 and purified by HPLC. The stereochemistry was arbitrarily assigned. m/z 463.2 [M+H]+.

Example 156

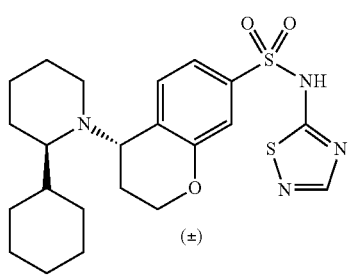 [SMILES: O=S(=O)(Nc1ncns1)c1ccc2c(c1)OCC[C@@H]2N1CCCC[C@@H]1C1CCCCC1]

361

(S)-4-((R)-2-cyclohexylpiperidin-1-yl)-N-(1,2,4-thiadiazol-5-yl)chromane-7-sulfonamide The compound was synthesized as for Example 37 and purified by HPLC. The stereochemistry was arbitrarily assigned. m/z 463.2 [M+H]⁺

Example 157

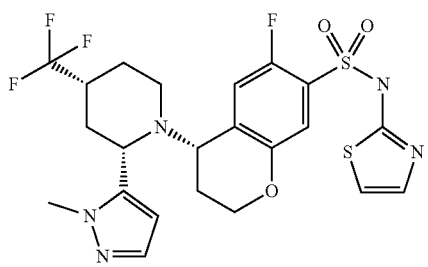 [SMILES: Cn1nccc1[C@@H]1C[C@H](C(F)(F)F)CCN1[C@H]1CCOc2cc(S(=O)(=O)Nc3nccs3)c(F)cc21]

This compound was synthesized using the same procedure as Example 92, using cis-2-(1-methyl-1H-pyrazol-5-yl)-4-(trifluoromethyl)piperidine (Example 123), and was purified by SFC. m/z 546.1[M+H]⁺, 1H NMR (400 MHz, DMSO-d6) δ 12.94 (s, 1H), 7.47 (d, J=10.6 Hz, 1H), 7.36 (d, J=1.8 Hz, 1H), 7.29 (d, J=4.6 Hz, 1H), 7.07 (d, J=5.8 Hz, 1H), 6.86 (d, J=4.6 Hz, 1H), 6.36 (s, 1H), 4.26 (dt, J=11.5, 3.6 Hz, 1H), 4.06 (dd, J=10.9, 3.0 Hz, 1H), 3.90 (s, 5H), 3.67 (s, 1H), 2.56 (s, 1H), 1.97 (s, 2H), 1.82 (dd, J=15.2, 8.6 Hz, 2H), 1.54 (s, 2H).

Example 158

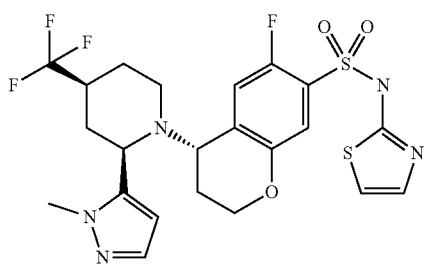 [SMILES: Cn1nccc1[C@H]1C[C@@H](C(F)(F)F)CCN1[C@H]1CCOc2cc(S(=O)(=O)Nc3nccs3)c(F)cc21]

This compound was synthesized in the same sequence as Example 157 and was purified by SFC from the products produced in Example 157. m/z 546.1 [M+H]⁺, 1H NMR (400 MHz, DMSO-d6) δ 12.95 (s, 1H), 7.36 (s, 1H), 7.29 (d, J=4.5 Hz, 1H), 7.18 (d, J=10.4 Hz, 1H), 7.07 (d, J=6.0 Hz, 1H), 6.86 (d, J=4.5 Hz, 1H), 6.33 (d, J=2.0 Hz, 1H), 4.48-4.34 (m, 1H), 4.20 (dt, J=11.5, 3.8 Hz, 1H), 3.92 (s, 3H), 3.71 (t, J=7.9 Hz, 1H), 3.61 (s, 1H), 3.50-3.38 (m, 2H), 2.74 (d, J=12.4 Hz, 1H), 2.35 (t, J=11.7 Hz, 1H), 2.08 (s, 2H), 1.78 (d, J=12.1 Hz, 1H), 1.65 (t, J=12.0 Hz, 1H), 1.52-1.38 (m, 1H).

362

Example 159

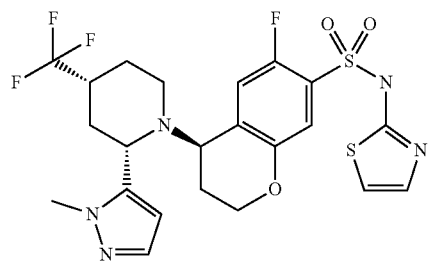 [SMILES: Cn1nccc1[C@@H]1C[C@H](C(F)(F)F)CCN1[C@@H]1CCOc2cc(S(=O)(=O)Nc3nccs3)c(F)cc21]

This compound was synthesized in the same sequence as Example 157 and was purified by SFC from the products produced in Example 157. m/z 546.1 [M+H]-, 1H NMR (400 MHz, DMSO-d6) δ 12.94 (s, 1H), 7.36 (d, J=1.8 Hz, 1H), 7.29 (d, J=4.6 Hz, 1H), 7.18 (d, J=10.4 Hz, 1H), 7.07 (d, J=6.0 Hz, 1H), 6.86 (d, J=4.5 Hz, 1H), 6.33 (d, J=1.9 Hz, 1H), 4.44 (dd, J=11.2, 2.7 Hz, 1H), 4.20 (dt, J=11.2, 4.0 Hz, 1H), 3.92 (s, 4H), 3.71 (dd, J=9.2, 6.6 Hz, 1H), 2.78-2.69 (m, 1H), 2.59 (td, J=9.1, 4.8 Hz, 1H), 2.41-2.29 (m, 1H), 2.04-1.73 (m, 4H), 1.63 (q, J=12.1 Hz, 1H), 1.45 (qd, J=12.5, 4.0 Hz, 1H).

Example 160

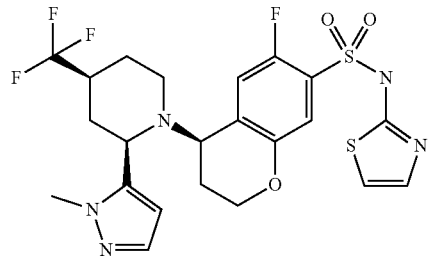 [SMILES: Cn1nccc1[C@H]1C[C@@H](C(F)(F)F)CCN1[C@@H]1CCOc2cc(S(=O)(=O)Nc3nccs3)c(F)cc21]

This compound was synthesized in the same sequence as Example 157 and was purified by SFC from the products produced in Example 157. m/z 546.1 [M+H]⁺, 1H NMR (400 MHz, DMSO-d6) δ 12.94 (s, 1H), 7.46 (d, J=10.6 Hz, 1H), 7.41-7.33 (m, 1H), 7.28 (d, J=4.5 Hz, 1H), 7.12-7.03 (m, 1H), 6.84 (d, J=4.5 Hz, 1H), 6.36 (s, 1H), 4.26 (dd, J=11.2, 4.1 Hz, 1H), 4.06 (d, J=12.0 Hz, 1H), 3.91 (d, J=7.4 Hz, 4H), 3.71 (d, J=37.9 Hz, 1H), 2.67 (p, J=1.9 Hz, 1H), 2.59-2.53 (m, 1H), 1.96 (s, 2H), 1.81 (d, J=12.9 Hz, 3H), 1.55 (s, 3H).

Example 161

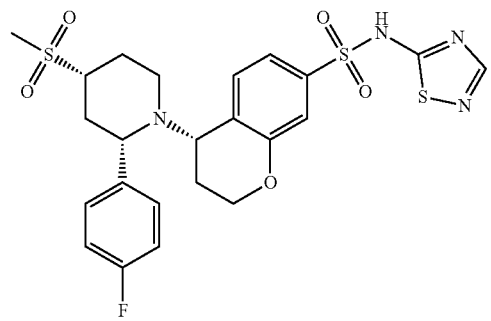 [SMILES: CS(=O)(=O)[C@@H]1CCN([C@H]2CCOc3cc(S(=O)(=O)Nc4ncns4)ccc32)[C@H](c2ccc(F)cc2)C1]

363
(S)-4-((2S,4R)-2-(4-fluorophenyl)-4-(methylsulfonyl)piperidin-1-yl)-N-(1,2,4-thiadiazol-5-yl)chroman-7-sulfonamide
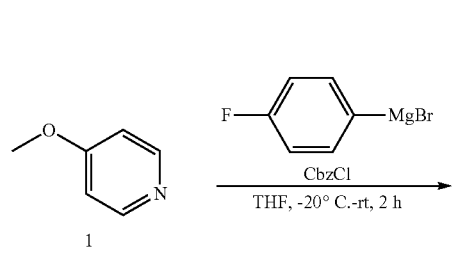
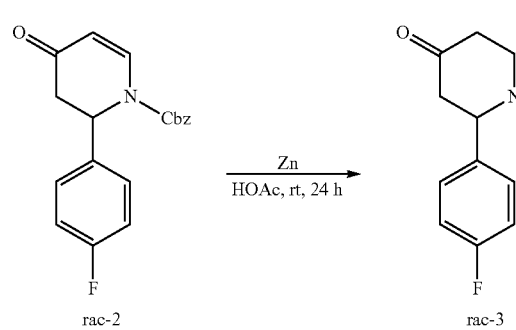
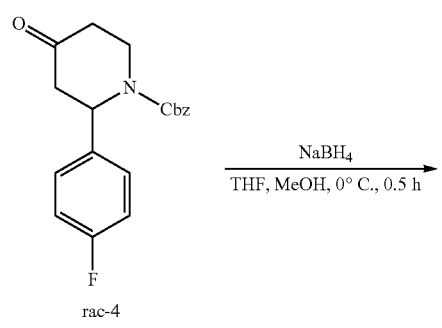
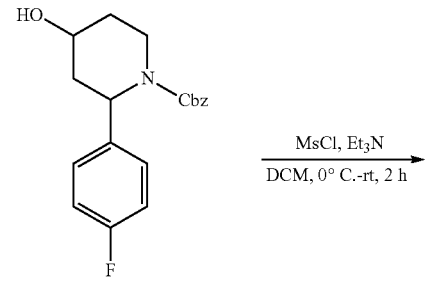
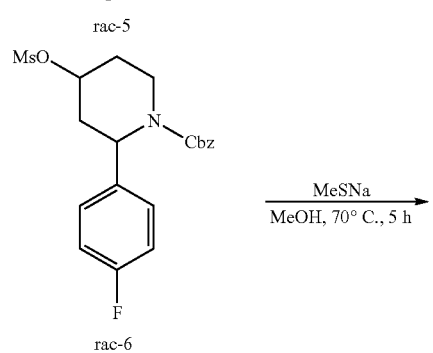
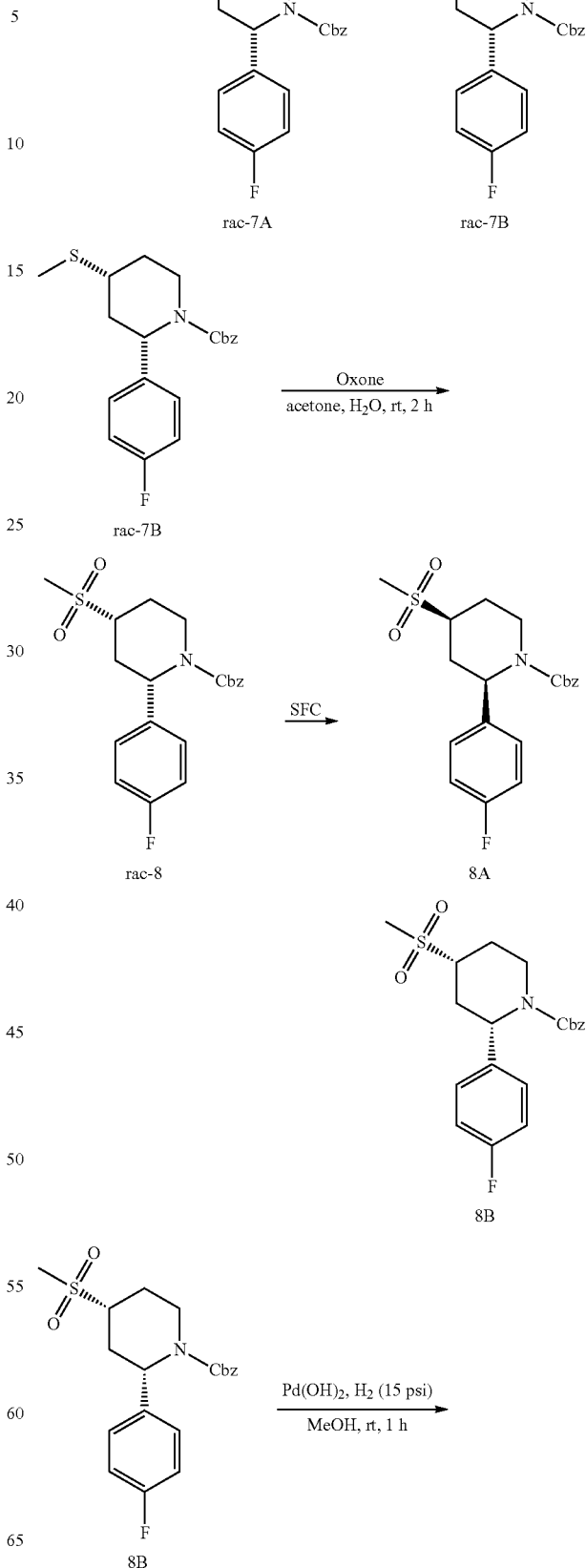

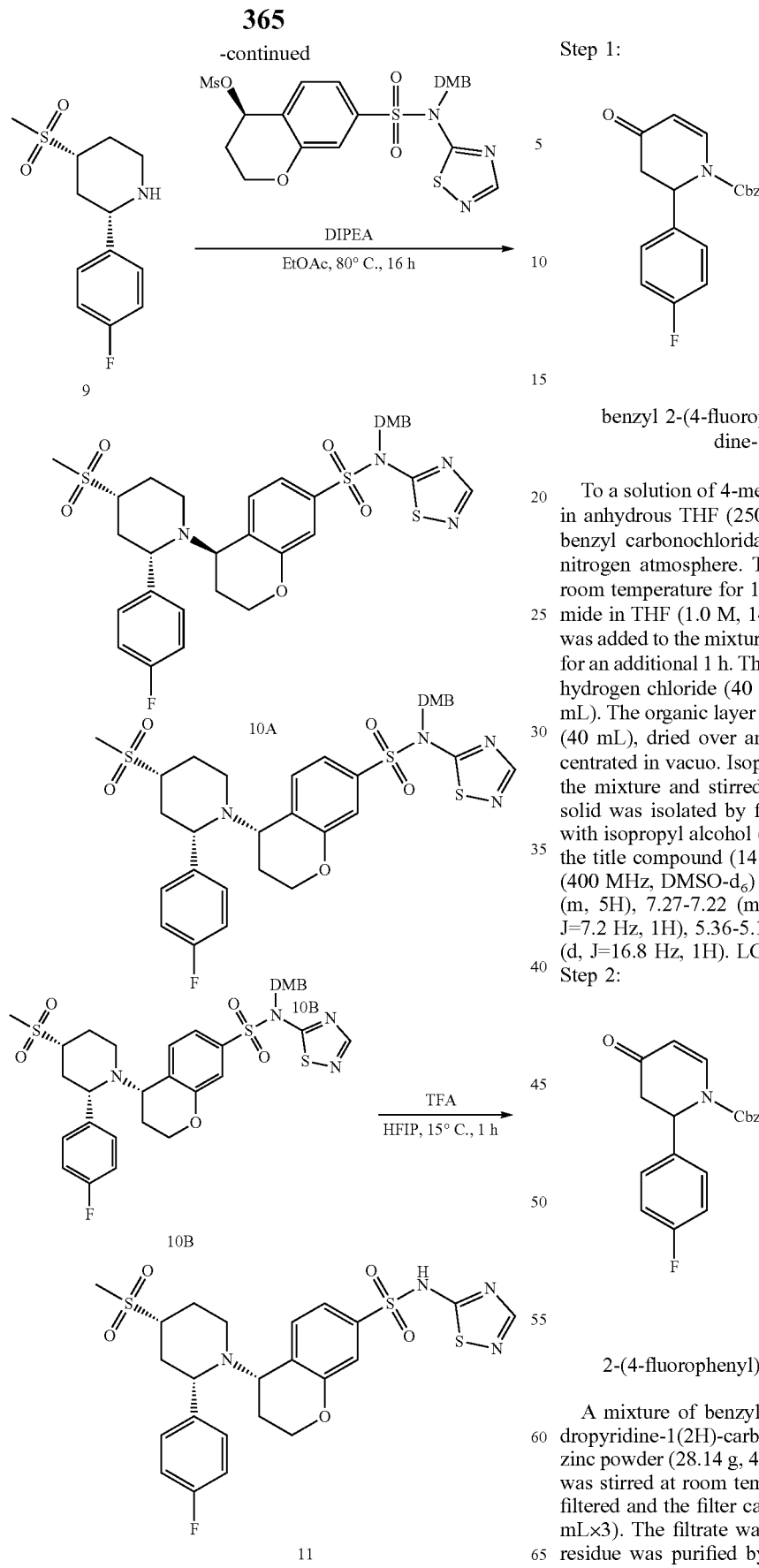

Step 1:

benzyl 2-(4-fluorophenyl)-4-oxo-3,4-dihydropyridine-1(2H)-carboxylate

To a solution of 4-methoxypyridine (10.0 g, 91.63 mmol) in anhydrous THF (250 mL) at −20° C. was slowly added benzyl carbonochloridate (17.01 mL, 119 mmol) under a nitrogen atmosphere. The reaction mixture was stirred at room temperature for 1 h. (4-fluorophenyl)magnesium bromide in THF (1.0 M, 146.61 mL, 146.61 mmol) at −20° C. was added to the mixture and stirred at the same temperature for an additional 1 h. The mixture was quenched with 3% aq. hydrogen chloride (40 mL) and extracted with toluene (40 mL). The organic layer was washed with 4.5% aq. NaHCO₃ (40 mL), dried over anhydrous Na₂SO₄, filtered and concentrated in vacuo. Isopropyl alcohol (15 mL) was added to the mixture and stirred at room temperature for 1 h. The solid was isolated by filtered. The filter cake was washed with isopropyl alcohol (5 mL×3) and dried in vacuo to give the title compound (14 g, 47%) as a white solid. $^1$H NMR (400 MHz, DMSO-$d_6$) δ 8.06 (d, J=8.4 Hz, 1H), 7.42-7.30 (m, 5H), 7.27-7.22 (m, 2H), 7.20-7.12 (m, 2H), 5.74 (d, J=7.2 Hz, 1H), 5.36-5.17 (m, 3H), 3.32-3.20 (m, 1H), 2.62 (d, J=16.8 Hz, 1H). LCMS M/Z (M+H) 326.

Step 2:

benzyl 2-(4-fluorophenyl)-4-oxopiperidine-1-carboxylate

A mixture of benzyl 2-(4-fluorophenyl)-4-oxo-3,4-dihydropyridine-1(2H)-carboxylate (14.0 g, 43.03 mmol) and zinc powder (28.14 g, 430.33 mmol) in acetic acid (100 mL) was stirred at room temperature for 24 h. The mixture was filtered and the filter cake was washed with acetic acid (30 mL×3). The filtrate was concentrated in vacuo. The crude residue was purified by silica gel chromatography (petroleum ether/EtOAc=3:1) to give the title compound (14 g, 99%) as colorless oil. LCMS M/Z (M+H) 328.

Step 3:

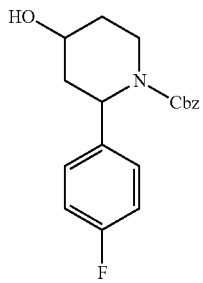 [SMILES: O=C(OCc1ccccc1)N1CCC(O)CC1c1ccc(F)cc1]

benzyl 2-(4-fluorophenyl)-4-hydroxypiperidine-1-carboxylate

To a solution of benzyl 2-(4-fluorophenyl)-4-oxopiperidine-1-carboxylate (2.6 g, 7.94 mmol) in THF (25 mL) and MeOH (5 mL) at 0° C. was added sodium borohydride (331 mg, 8.74 mmol). The reaction mixture was stirred at 0° C. for 0.5 h. The reaction was quenched with aq. hydrogen chloride (1.0 M, 15 mL), diluted with water (50 mL) and extracted with EtOAc (200 mL). The organic layer was washed with brine (100 mL), dried over Na$_2$SO$_4$, filtered, and concentrated in vacuo. The crude residue was purified by silica gel chromatography (petroleum ether/EtOAc=1:1) to give the title compound (2.3 g, 88%) as colorless oil. LCMS M/Z (M+H) 330.

Step 4:

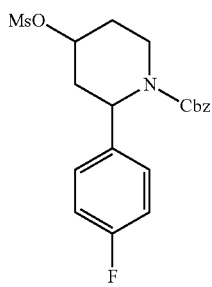 [SMILES: CS(=O)(=O)OC1CCN(C(=O)OCc2ccccc2)C(c2ccc(F)cc2)C1]

benzyl 2-(4-fluorophenyl)-4-((methylsulfonyl)oxy) piperidine-1-carboxylate

To a solution of benzyl 2-(4-fluorophenyl)-4-hydroxypiperidine-1-carboxylate (2.3 g, 6.98 mmol) and triethylamine (1.95 mL, 13.97 mmol) in DCM (25 mL) at 0° C. was added methanesulfonyl chloride (8.92 mL, 115.23 mmol) dropwise. The reaction mixture was stirred at room temperature for 2 h. DCM (200 mL) was added, washed with 10% aq. citric acid (100 mL), sat. aq. NaHCO$_3$ (100 mL), brine (100 mL), dried over anhydrous Na$_2$SO$_4$, filtered and concentrated in vacuo to give the title compound (2.81 g, crude) as colorless oil that required no further purification.

Step 5:

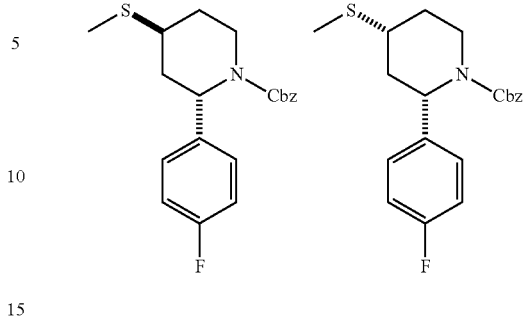

(trans)-benzyl 2-(4-fluorophenyl)-4-(methylthio) piperidine-1-carboxylate & (cis)-benzyl 2-(4-fluorophenyl)-4-(methylthio)piperidine-1-carboxylate To a solution of benzyl 2-(4-fluorophenyl)-4-((methyl sulfonyl)oxy)piperidine-1-carboxylate (2.81 g, 6.9 mmol) in MeOH (50 mL) was added sodium thiomethoxide (0.9 g, 12.84 mmol). The reaction mixture was heated to 70° C. for 5 h. After cooling to room temperature, the mixture was concentrated in vacuo. EtOAc (200 mL) was added, washed with water (100 mL), brine (100 mL), dried over anhydrous Na$_2$SO$_4$, filtered and concentrated in vacuo. The crude residue was purified by silica gel chromatography (petroleum ether/EtOAc=10:1) to give (trans)-benzyl 2-(4-fluorophenyl)-4-(methylthio)piperidine-1-carboxylate (750 mg, less polar on TLC) as colorless oil and (cis)-benzyl 2-(4-fluorophenyl)-4-(methylthio)piperidine-1-carboxylate (810 mg, more polar on TLC) as colorless oil. Trans-isomer: $^1$H NMR (400 MHz, CDCl$_3$) δ 7.42-7.29 (m, 5H), 7.20-7.12 (m, 2H), 7.08-7.00 (m, 2H), 5.60 (s, 1H), 5.20 (s, 2H), 4.30-4.17 (m, 1H), 2.90-2.80 (m, 1H), 2.73-2.56 (m, 2H), 2.10 (s, 3H), 1.97-1.87 (m, 2H), 1.57-1.48 (m, 1H). LCMS M/Z (M+H) 360. Cis-isomer: $^1$H NMR (400 MHz, CDCl$_3$) δ 7.35-7.26 (m, 3H), 7.23-7.13 (m, 4H), 7.04-6.96 (m, 2H), 5.14-5.04 (m, 3H), 4.22-4.09 (m, 1H), 3.53-3.39 (m, 1H), 3.00-2.89 (m, 1H), 2.39-2.29 (m, 1H), 2.23-2.06 (m, 2H), 2.03 (s, 3H), 1.71-1.62 (m, 1H). LCMS M/Z (M+H) 360.

Step 6:

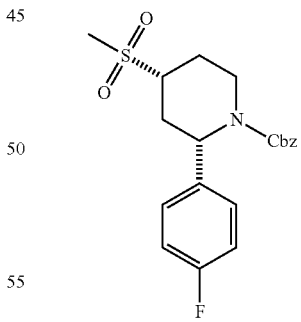

(cis)-benzyl 2-(4-fluorophenyl)-4-(methylsulfonyl) piperidine-1-carboxylate

To a solution of (cis)-benzyl 2-(4-fluorophenyl)-4-(methylthio)piperidine-1-carboxylate (810 mg, 2.25 mmol) in acetone (12 mL) was added potassium peroxymonosulfate (2.91 g, 4.73 mmol) in water (12 mL). The reaction mixture was stirred at room temperature for 2 h. EtOAc (150 mL) was added, washed with sat. aq. NaHCO$_3$ (100 mL) and brine (100 mL), dried over anhydrous Na₂SO₄, filtered and concentrated in vacuo. The crude residue was purified by silica gel chromatography (DCM/EtOAc=1:2) to give the title compound (0.8 g, 91%) as a white solid. LCMS M/Z (M+H) 392.

Step 7:

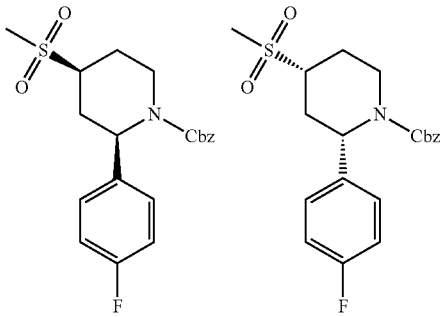 [SMILES: CS(=O)(=O)[C@H]1CCN(C(=O)OCc2ccccc2)[C@@H](c2ccc(F)cc2)C1 ; CS(=O)(=O)[C@@H]1CCN(C(=O)OCc2ccccc2)[C@H](c2ccc(F)cc2)C1]

(2R,4S)-benzyl 2-(4-fluorophenyl)-4-(methylsulfonyl)piperidine-1-carboxylate & (2S,4R)-benzyl 2-(4-fluorophenyl)-4-(methylsulfonyl)piperidine-1-carboxylate (cis)-benzyl 2-(4-fluorophenyl)-4-(methylsulfonyl)piperidine-1-carboxylate (1.0 g) was separated by using chiral SFC (Chiralpak OD (250 mm*30 mm, 5 um), Supercritical CO2/EtOH+0.05% DEA=70/30; 60 mL/min) to give (2R, 4S)-benzyl 2-(4-fluorophenyl)-4-(methylsulfonyl)piperidine-1-carboxylate (0.45 g, first peak) as a white solid and (2S,4R)-benzyl 2-(4-fluorophenyl)-4-(methylsulfonyl)piperidine-1-carboxylate (0.46 g, second peak) as a white solid. First peak: ¹H NMR (400 MHz, CDCl₃) δ 7.32-7.27 (m, 3H), 7.26-7.16 (m, 2H), 7.15-7.08 (m, 2H), 7.05-6.97 (m, 2H), 5.12-4.98 (m, 2H), 4.97-4.89 (m, 1H), 4.36-4.26 (m, 1H), 3.48-3.36 (m, 1H), 3.29-3.16 (m, 1H), 2.87 (s, 3H), 2.56-2.46 (m, 1H), 2.38-2.24 (m, 1H), 2.18-2.01 (m, 2H). LCMS M/Z (M+H) 392. Second peak: ¹H NMR (400 MHz, CDCl₃) δ 7.32-7.27 (m, 3H), 7.26-7.16 (m, 2H), 7.15-7.08 (m, 2H), 7.04-6.97 (m, 2H), 5.12-4.98 (m, 2H), 4.97-4.89 (m, 1H), 4.36-4.26 (m, 1H), 3.48-3.36 (m, 1H), 3.29-3.16 (m, 1H), 2.87 (s, 3H), 2.56-2.46 (m, 1H), 2.38-2.24 (m, 1H), 2.18-2.01 (m, 2H). LCMS M/Z (M+H) 392.

Step 8:

(2S,4R)-2-(4-fluorophenyl)-4-(methylsulfonyl)piperidine

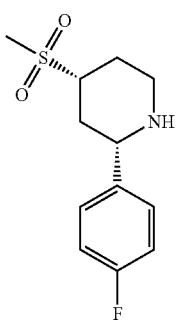 [SMILES: CS(=O)(=O)[C@@H]1CCN[C@H](c2ccc(F)cc2)C1]

To a solution of (2S,4R)-benzyl 2-(4-fluorophenyl)-4-(methyl sulfonyl)piperidine-1-carboxylate (350 mg, 0.89 mmol) in MeOH (10 mL) was added 20% palladium hydroxide (350 mg). The mixture was stirred at room temperature for 1 h under a hydrogen atmosphere (15 psi). The mixture was filtered and the filtrate was concentrated in vacuo to give the title compound (220 mg, crude) as a white solid that required no further purification. LCMS M/Z (M+H) 258.

Step 9:

(R)—N-(2,4-dimethoxybenzyl)-4-((2S,4R)-2-(4-fluorophenyl)-4-(methylsulfonyl)piperidin-1-yl)-N-(1,2,4-thiadiazol-5-yl)chroman-7-sulfonamide and (S)—N-(2,4-dimethoxybenzyl)-4-((2S,4R)-2-(4-fluorophenyl)-4-(methylsulfonyl)piperidin-1-yl)-N-(1,2,4-thiadiazol-5-yl)chroman-7-sulfonamide

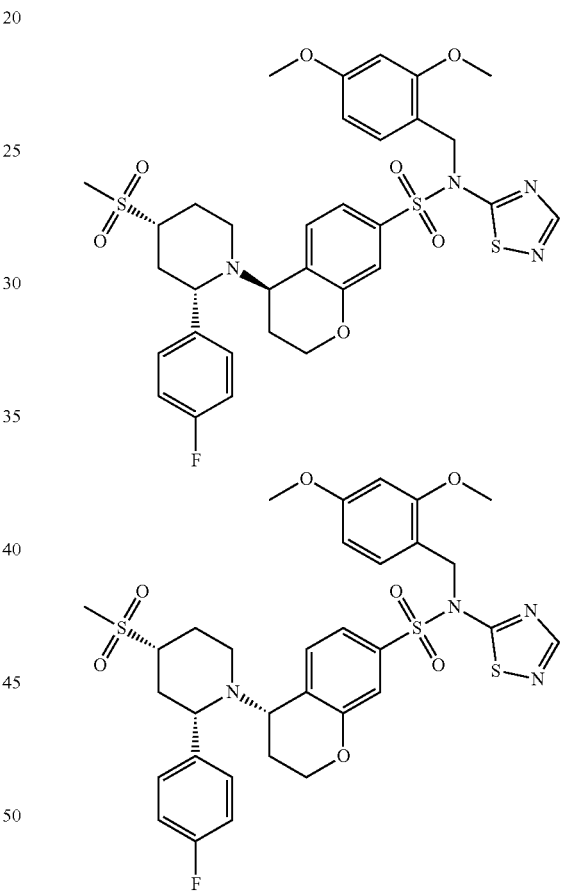

To a solution of (2S,4R)-2-(4-fluorophenyl)-4-(methylsulfonyl)piperidine (220 mg, 0.85 mmol) and N,N-diisopropylethylamine (0.71 mL, 4.27 mmol) in EtOAc (12 mL) was added (R)-7-(N-(2,4-dimethoxybenzyl)-N-(1,2,4-thiadiazol-5-yl)sulfamoyl)chroman-4-yl methanesulfonate (926 mg, 1.71 mmol). The reaction mixture was heated to 80° C. for 16 h under a nitrogen atmosphere. After cooling to room temperature, the mixture was concentrated in vacuo. The crude residue was purified by Prep-TLC (petroleum ether/EtOAc=1:2) to give (R)—N-(2,4-dimethoxybenzyl)-4-((2S,4R)-2-(4-fluorophenyl)-4-(methylsulfonyl)piperidin-1-yl)-N-(1,2,4-thiadiazol-5-yl)chroman-7-sulfonamide (150 mg, less polar on TLC) as colorless oil and (S)—N-(2,4-dimethoxybenzyl)-4-((2S,4R)-2-(4-fluorophenyl)-4-(methyl sulfonyl)piperidin-1-yl)-N-(1,2,4-thiadiazol-5-yl)chroman-7-sulfonamide (150 mg, more polar on TLC) as colorless oil. LCMS M/Z (M+H) 703.

Step 10:

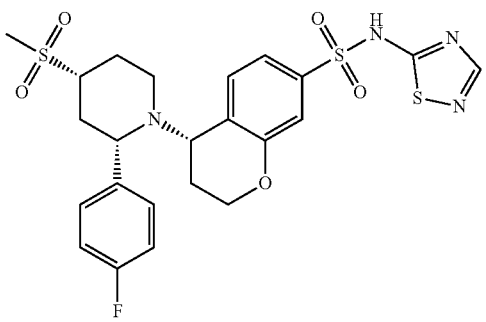 [SMILES: CS(=O)(=O)[C@@H]1CCN([C@H]2CCOc3cc(S(=O)(=O)Nc4ncns4)ccc32)[C@H](c2ccc(F)cc2)C1]

(S)-4-((2S,4R)-2-(4-fluorophenyl)-4-(methylsulfonyl)piperidin-1-yl)-N-(1,2,4-thiadiazol-5-yl)chroman-7-sulfonamide A mixture of (S)—N-(2,4-dimethoxybenzyl)-4-((2S,4R)-2-(4-fluorophenyl)-4-(methylsulfonyl)piperidin-1-yl)-N-(1,2,4-thiadiazol-5-yl)chroman-7-sulfonamide (180 mg, 0.26 mmol) and trifluoroacetic acid in 1,1,1,3,3,3-hexafluoropropan-2-ol (1.0 M, 6 mL) was stirred at 15° C. for 1 h. The mixture was concentrated in vacuo. The crude residue was purified by reverse phase chromatography (acetonitrile 28-58%/0.225% formic acid in water) to give the title compound (59 mg, 42%) as a white solid. $^1$H NMR (400 MHz, CD$_3$OD) δ 8.17 (s, 1H), 7.85 (d, J=8.4 Hz, 1H), 7.59-7.49 (m, 2H), 7.41-7.38 (m, 1H), 7.17-7.07 (m, 3H), 4.32-4.24 (m, 1H), 3.90-3.74 (m, 3H), 3.28-3.18 (m, 1H), 2.91 (s, 3H), 2.81-2.72 (m, 1H), 2.48-2.37 (m, 1H), 2.24-2.16 (m, 1H), 2.15-2.03 (m, 2H), 1.97-1.74 (m, 3H). LCMS M/Z (M+H) 553.

Example 162

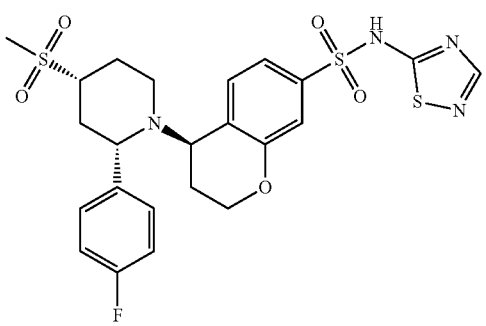 [SMILES: CS(=O)(=O)[C@@H]1CCN([C@@H]2CCOc3cc(S(=O)(=O)Nc4ncns4)ccc32)[C@H](c2ccc(F)cc2)C1]

(R)-4-((2S,4R)-2-(4-fluorophenyl)-4-(methylsulfonyl)piperidin-1-yl)-N-(1,2,4-thiadiazol-5-yl)chroman-7-sulfonamide Following the procedure as described in Example 161, step 10 and making non-critical variations as required to replace (S)—N-(2,4-dimethoxybenzyl)-4-((2S,4R)-2-(4-fluorophenyl)-4-(methyl sulfonyl)piperidin-1-yl)-N-(1,2,4-thiadiazol-5-yl)chroman-7-sulfonamide with (R)—N-(2,4-dimethoxybenzyl)-4-((2S,4R)-2-(4-fluorophenyl)-4-(methyl sulfonyl)piperidin-1-yl)-N-(1,2,4-thiadiazol-5-yl)chroman-7-sulfonamide, the title compound was obtained as a white solid (37 mg, 26%). $^1$H NMR (400 MHz, CD$_3$OD) δ 8.17 (s, 1H), 7.51-7.48 (m, 2H), 7.44-7.34 (m, 2H), 7.14 (d, J=1.6 Hz, 1H), 7.09-7.01 (m, 2H), 4.29-4.21 (m, 1H), 4.10-4.03 (m, 1H), 4.02-3.95 (m, 1H), 3.92-3.83 (m, 1H), 3.24-3.14 (m, 1H), 2.94-2.89 (m, 1H), 2.88 (s, 3H), 2.33-2.21 (m, 1H), 2.20-2.04 (m, 3H), 1.97-1.75 (m, 3H). LCMS M/Z (M+H) 553.

Example 163 & Example 164

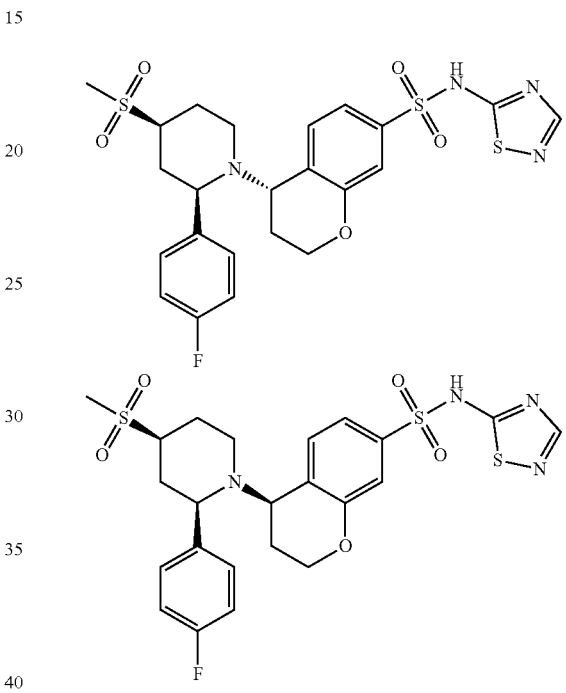

(S)-4-((2R,4S)-2-(4-fluorophenyl)-4-(methylsulfonyl)piperidin-1-yl)-N-(1,2,4-thiadiazol-5-yl)chroman-7-sulfonamide and (R)-4-((2R,4S)-2-(4-fluorophenyl)-4-(methylsulfonyl)piperidin-1-yl)-N-(1,2,4-thiadiazol-5-yl)chroman-7-sulfonamide Following the procedure as described in Example 161 and making non-critical variations as required to replace (2S,4R)-benzyl 2-(4-fluorophenyl)-4-(methyl sulfonyl)piperidine-1-carboxylate with (2R,4S)-benzyl 2-(4-fluorophenyl)-4-(methylsulfonyl)piperidine-1-carboxylate, (S)-4-((2R,4S)-2-(4-fluorophenyl)-4-(methylsulfonyl)piperidin-1-yl)-N-(1,2,4-thiadiazol-5-yl)chroman-7-sulfonamide (53 mg, less polar on TLC) and (R)-4-((2R,4S)-2-(4-fluorophenyl)-4-(methylsulfonyl)piperidin-1-yl)-N-(1,2,4-thiadiazol-5-yl)chroman-7-sulfonamide (46 mg, more polar on TLC) were obtained as white solid. Example 163: $^1$H NMR (400 MHz, CD$_3$OD) δ 8.18 (s, 1H), 7.51-7.49 (m, 2H), 7.45-7.34 (m, 2H), 7.14 (d, J=2.0 Hz, 1H), 7.09-7.01 (m, 2H), 4.29-4.21 (m, 1H), 4.11-4.04 (m, 1H), 4.03-3.95 (m, 1H), 3.93-3.84 (m, 1H), 3.25-3.15 (m, 1H), 2.96-2.90 (m, 1H), 2.88 (s, 3H), 2.33-2.22 (m, 1H), 2.19-2.06 (m, 3H), 1.97-1.78 (m, 3H). LCMS M/Z (M+H) 553. Example 164: $^1$H NMR (400 MHz, CD$_3$OD) δ 8.16 (s, 1H), 7.84 (d, J=8.4 Hz, 1H), 7.59-7.48 (m, 2H), 7.41-7.38 (m, 1H), 7.17-7.05 (m, 3H), 4.31-4.22

(m, 1H), 3.89-3.74 (m, 3H), 3.27-3.18 (m, 1H), 2.90 (s, 3H), 2.81-2.72 (m, 1H), 2.47-2.37 (m, 1H), 2.25-2.16 (m, 1H), 2.14-2.01 (m, 2H), 1.98-1.73 (m, 3H). LCMS M/Z (M+H) 553.

Example 165 & Example 166

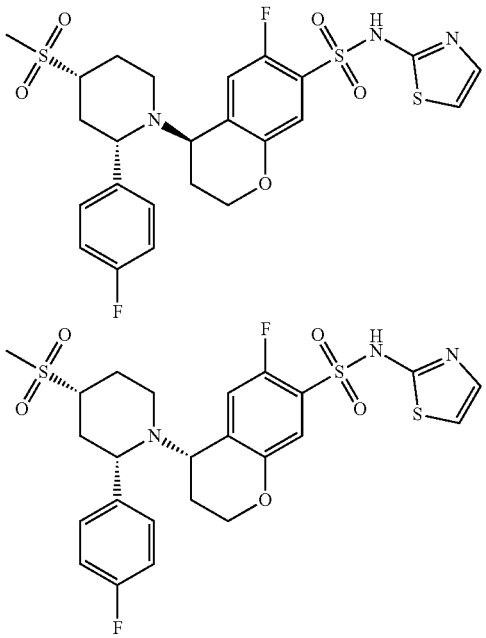

(R)-6-fluoro-4-((2S,4R)-2-(4-fluorophenyl)-4-(methylsulfonyl)piperidin-1-yl)-N-(thiazol-2-yl)chroman-7-sulfonamide and (S)-6-fluoro-4-((2S,4R)-2-(4-fluorophenyl)-4-(methylsulfonyl)piperidin-1-yl)-N-(thiazol-2-yl)chroman-7-sulfonamide Following the procedure as described in Example 161 and making non-critical variations as required to replace (R)-7-(N-(2,4-dimethoxybenzyl)-N-(1,2,4-thiadiazol-5-yl)sulfamoyl)chroman-4-yl methanesulfonate with (R)-7-(N-(2,4-dimethoxybenzyl)-N-(thiazol-2-yl)sulfamoyl)-6-fluorochroman-4-yl methanesulfonate, (R)-6-fluoro-4-((2S,4R)-2-(4-fluorophenyl)-4-(methylsulfonyl)piperidin-1-yl)-N-(thiazol-2-yl)chroman-7-sulfonamide (72 mg, less polar on TLC) and (S)-6-fluoro-4-((2S,4R)-2-(4-fluorophenyl)-4-(methylsulfonyl)piperidin-1-yl)-N-(thiazol-2-yl)chroman-7-sulfonamide (145 mg, more polar on TLC) were obtained as white solid. Example 165: $^1$H NMR (400 MHz, CDCl$_3$) δ 12.91 (s, 1H), 7.45-7.30 (m, 3H), 7.20 (d, J=4.4 Hz, 1H), 7.06-7.01 (m, 1H), 6.87 (d, J=10.0 Hz, 1H), 6.55 (d, J=4.4 Hz, 1H), 4.27-4.19 (m, 1H), 3.97-3.79 (m, 3H), 3.05-2.87 (m, 2H), 2.82 (s, 3H), 2.30-2.03 (m, 4H), 1.98-1.81 (m, 3H). LCMS M/Z (M+H) 570. Example 166: $^1$H NMR (400 MHz, CDCl$_3$) δ 7.45-7.30 (m, 4H), 7.21 (d, J=4.8 Hz, 1H), 7.06-7.01 (m, 2H), 6.54 (d, J=4.4 Hz, 1H), 4.32-4.27 (m, 1H), 3.87-3.76 (m, 2H), 3.65-3.62 (m, 1H), 3.03-2.83 (m, 1H), 2.87-2.85 (m, 1H), 2.84 (s, 3H), 2.41-2.22 (m, 2H), 2.18-2.12 (m, 1H), 2.08-1.83 (m, 3H), 1.78-1.65 (m, 1H). LCMS M/Z (M+H) 570.

Example 167 & Example 168

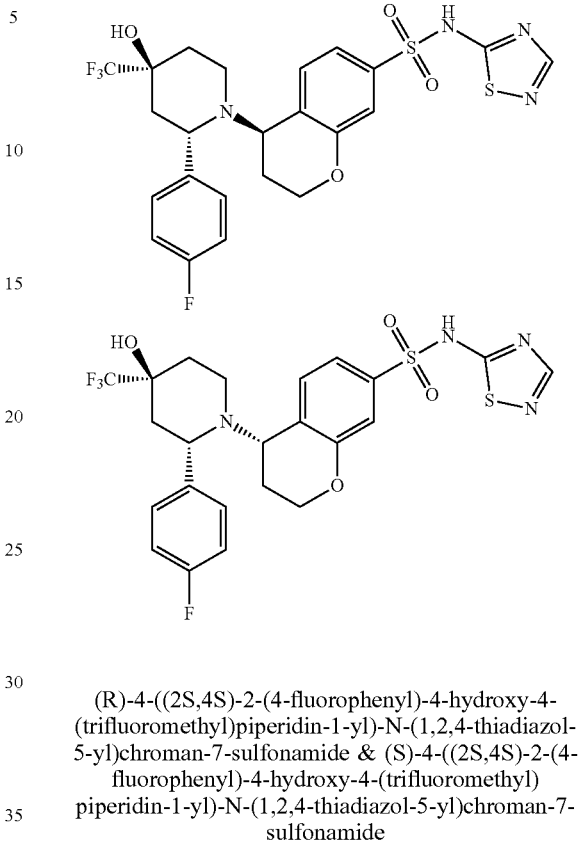

(R)-4-((2S,4S)-2-(4-fluorophenyl)-4-hydroxy-4-(trifluoromethyl)piperidin-1-yl)-N-(1,2,4-thiadiazol-5-yl)chroman-7-sulfonamide & (S)-4-((2S,4S)-2-(4-fluorophenyl)-4-hydroxy-4-(trifluoromethyl) piperidin-1-yl)-N-(1,2,4-thiadiazol-5-yl)chroman-7-sulfonamide Step 1:

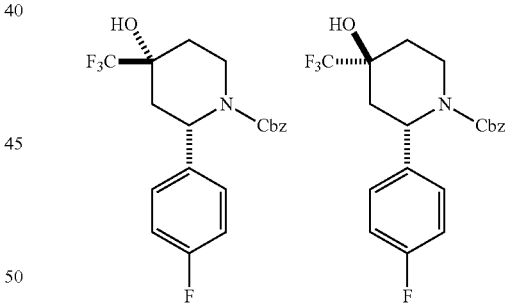

(trans)-benzyl 2-(4-fluorophenyl)-4-hydroxy-4-(trifluoromethyl)piperidine-1-carboxylate & (cis)-benzyl 2-(4-fluorophenyl)-4-hydroxy-4-(trifluoromethyl) piperidine-1-carboxylate To a solution of benzyl 2-(4-fluorophenyl)-4-oxopiperidine-1-carboxylate (12.0 g, 36.66 mmol) in anhydrous THF (200 mL) at 0° C. was added (trifluoromethyl)trimethylsilane (19.06 mL, 47.66 mmol) and tetrabutylammonium fluoride in THF (1.0 M, 3.67 mL, 3.67 mmol). The reaction mixture was stirred at room temperature for 16 h. Water (50 mL) was added and extracted with EtOAc (50 mL). The organic layer was dried over anhydrous Na$_2$SO$_4$, filtered and concentrated in vacuo. The crude residue was purified by silica gel chromatography (petroleum ether/EtOAc=10:1) to give (trans)-benzyl 2-(4-fluorophenyl)-4-hydroxy-4-(trifluoromethyl)piperidine-1-carboxylate (3.4 g, less polar on TLC) as a white solid and (cis)-benzyl 2-(4-fluorophenyl)-4-hydroxy-4-(trifluoromethyl)piperidine-1-carboxylate (0.88 g, more polar on TLC) as a white solid. Trans-isomer: ¹H NMR (400 MHz, CDCl₃) δ 7.31-7.25 (m, 3H), 7.22-7.16 (m, 2H), 7.11-7.05 (m, 2H), 7.03-6.96 (m, 2H), 5.15-4.97 (m, 3H), 4.33-4.25 (m, 1H), 3.42-3.28 (m, 1H), 2.55 (s, 1H), 2.27-2.12 (m, 2H), 2.06-1.99 (m, 1H), 1.97-1.86 (m, 1H). LCMS M/Z (M+H) 398. Cis-isomer: ¹H NMR (400 MHz, CDCl₃) δ 7.30-7.24 (m, 3H), 7.22-7.15 (m, 2H), 7.11-7.05 (m, 2H), 7.03-6.95 (m, 2H), 5.15-4.97 (m, 3H), 4.35-4.22 (m, 1H), 3.41-3.29 (m, 1H), 2.57 (s, 1H), 2.28-2.12 (m, 2H), 2.08-1.98 (m, 1H), 1.97-1.84 (m, 1H). LCMS M/Z (M+H) 398.

Step 2:

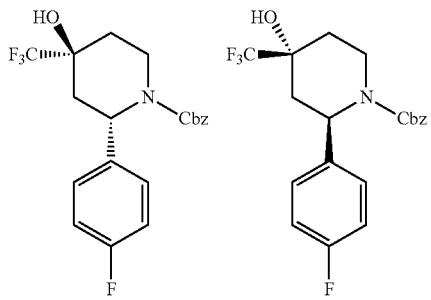 [SMILES: O=C(OCc1ccccc1)N1CC[C@@](O)(C(F)(F)F)C[C@H]1c1ccc(F)cc1 ; O=C(OCc1ccccc1)N1CC[C@](O)(C(F)(F)F)C[C@@H]1c1ccc(F)cc1]

(2S,4S)-benzyl 2-(4-fluorophenyl)-4-hydroxy-4-(trifluoromethyl)piperidine-1-carboxylate & (2R,4R)-benzyl 2-(4-fluorophenyl)-4-hydroxy-4-(trifluoromethyl)piperidine-1-carboxylate (cis)-benzyl 2-(4-fluorophenyl)-4-hydroxy-4-(trifluoromethyl)piperidine-1-carboxylate (0.88 g) was separated by using chiral SFC (Whelk-01 250 mm*30 mm, 10 UM, Supercritical CO2/MeOH+DEA=70/30; 70 ml/min) to give (2S,4S)-benzyl 2-(4-fluorophenyl)-4-hydroxy-4-(trifluoromethyl)piperidine-1-carboxylate (0.37 g, first peak) as a white solid and (2R,4R)-benzyl 2-(4-fluorophenyl)-4-hydroxy-4-(trifluoromethyl)piperidine-1-carboxylate (0.38 g, second peak) as a white solid.

Step 3:

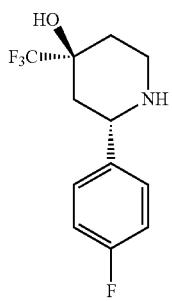

(2S,4S)-2-(4-fluorophenyl)-4-(trifluoromethyl)piperidin-4-ol

Following the procedure as described in Example 161, step 8 and making non-critical variations as required to replace (2S,4R)-benzyl 2-(4-fluorophenyl)-4-(methylsulfonyl)piperidine-1-carboxylate with (2S,4S)-benzyl 2-(4-fluorophenyl)-4-hydroxy-4-(trifluoromethyl)piperidine-1-carboxylate, the title compound was obtained as a white solid (210 mg, 86%). ¹H NMR (400 MHz, CDCl₃) δ 7.37-7.35 (m, 2H), 7.04-7.00 (m, 2H), 4.02-3.98 (m, 1H), 3.19-3.12 (m, 2H), 1.90-1.65 (m, 4H).

Step 4:

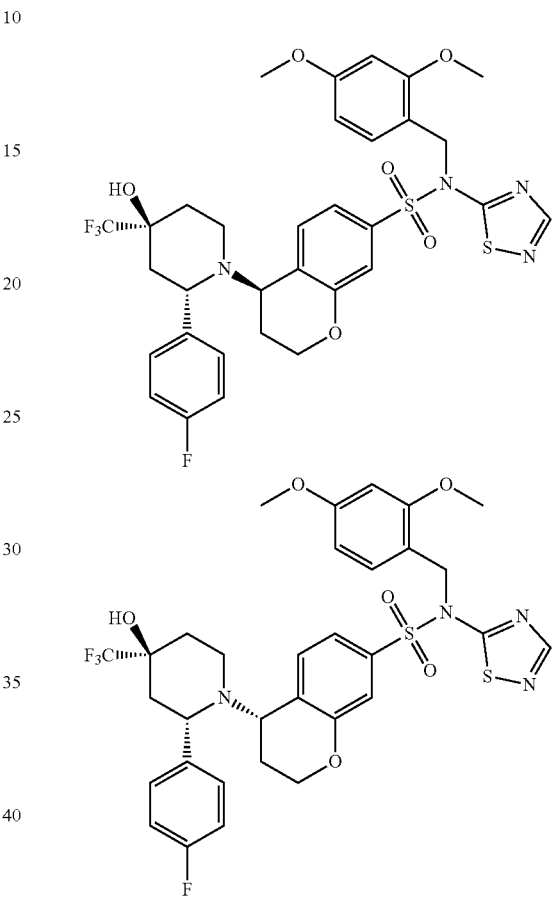

(R)—N-(2,4-dimethoxybenzyl)-4-((2S,4S)-2-(4-fluorophenyl)-4-hydroxy-4-(trifluoromethyl)piperidin-1-yl)-N-(1,2,4-thiadiazol-5-yl)chroman-7-sulfonamide & (S)—N-(2,4-dimethoxybenzyl)-4-((2S,4S)-2-(4-fluorophenyl)-4-hydroxy-4-(trifluoromethyl)piperidin-1-yl)-N-(1,2,4-thiadiazol-5-yl)chroman-7-sulfonamide Following the procedure as described in Example 161, step 9 and making non-critical variations as required to replace (2S,4R)-2-(4-fluorophenyl)-4-(methylsulfonyl)piperidine with (2S,4S)-2-(4-fluorophenyl)-4-(trifluoromethyl)piperidin-4-ol, (R)—N-(2,4-dimethoxybenzyl)-4-((2S,4S)-2-(4-fluorophenyl)-4-hydroxy-4-(trifluoromethyl)piperidin-1-yl)-N-(1,2,4-thiadiazol-5-yl)chroman-7-sulfonamide (130 mg, less polar on TLC) and (S)—N-(2,4-dimethoxybenzyl)-4-((2S,4S)-2-(4-fluorophenyl)-4-hydroxy-4-(trifluoromethyl)piperidin-1-yl)-N-(1,2,4-thiadiazol-5-yl)chroman-7-sulfonamide (170 mg, more polar on TLC) were obtained as white solid. LCMS M/Z (M+H) 709.

Step 5:

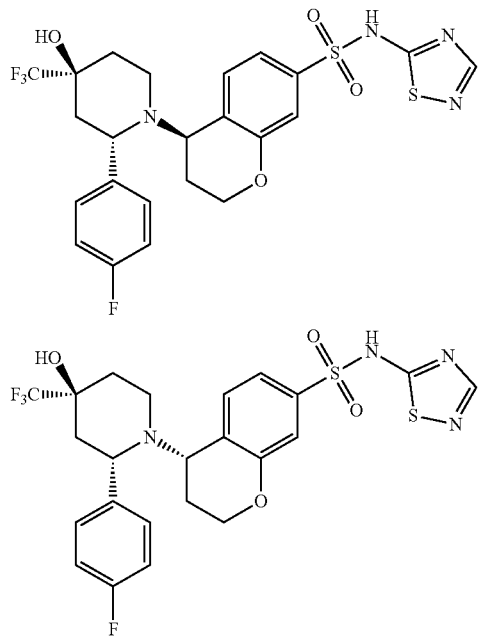

(R)-4-((2S,4S)-2-(4-fluorophenyl)-4-hydroxy-4-(trifluoromethyl)piperidin-1-yl)-N-(1,2,4-thiadiazol-5-yl)chroman-7-sulfonamide & (S)-4-((2S,4S)-2-(4-fluorophenyl)-4-hydroxy-4-(trifluoromethyl)piperidin-1-yl)-N-(1,2,4-thiadiazol-5-yl)chroman-7-sulfonamide Following the procedure as described in Example 161, step 10 and making non-critical variations as required to replace (S)—N-(2,4-dimethoxybenzyl)-4-((2S,4R)-2-(4-fluorophenyl)-4-(methyl sulfonyl)piperidin-1-yl)-N-(1,2,4-thiadiazol-5-yl)chroman-7-sulfonamide with (R)—N-(2,4-dimethoxybenzyl)-4-((2S,4S)-2-(4-fluorophenyl)-4-hydroxy-4-(trifluoromethyl)piperidin-1-yl)-N-(1,2,4-thiadiazol-5-yl)chroman-7-sulfonamide and (S)—N-(2,4-dimethoxybenzyl)-4-((2S,4S)-2-(4-fluorophenyl)-4-hydroxy-4-(trifluoromethyl)piperidin-1-yl)-N-(1,2,4-thiadiazol-5-yl)chroman-7-sulfonamide, (R)-4-((2S,4S)-2-(4-fluorophenyl)-4-hydroxy-4-(trifluoromethyl)piperidin-1-yl)-N-(1,2,4-thiadiazol-5-yl)chroman-7-sulfonamide (30 mg, less polar on TLC) and (S)-4-((2S,4S)-2-(4-fluorophenyl)-4-hydroxy-4-(trifluoromethyl)piperidin-1-yl)-N-(1,2,4-thiadiazol-5-yl)chroman-7-sulfonamide (42 mg, more polar on TLC) were obtained as a white solid. Example 167: $^1$H NMR (400 MHz, CD$_3$OD) δ 7.90 (s, 1H), 7.50-7.47 (m, 2H), 7.38-7.35 (m, 2H), 7.20 (s, 1H), 7.10-7.07 (m, 2H), 4.32-4.29 (m, 1H), 4.23-4.20 (m, 1H), 3.95-3.90 (m, 1H), 3.86-3.85 (m, 1H), 2.57-2.49 (m, 2H), 2.14-2.02 (m, 1H), 1.95-1.84 (m, 2H), 1.81-1.68 (m, 3H). LCMS M/Z (M+H) 559. Example 168: $^1$H NMR (400 MHz, CD$_3$OD) δ 7.90 (s, 1H), 7.76 (d, J=8.4 Hz, 1H), 7.57-7.46 (m, 2H), 7.42-7.39 (m, 1H), 7.18 (d, J=1.2 Hz, 1H), 7.11-7.06 (m, 2H), 4.29-4.21 (m, 1H), 4.01-3.98 (m, 1H), 3.87-3.74 (m, 2H), 2.76-2.67 (m, 1H), 2.49-2.46 (m, 1H), 2.18-2.06 (m, 1H), 1.92-1.79 (m, 4H), 1.73-1.69 (m, 1H). LCMS M/Z (M+H) 559.

Example 169 & Example 170

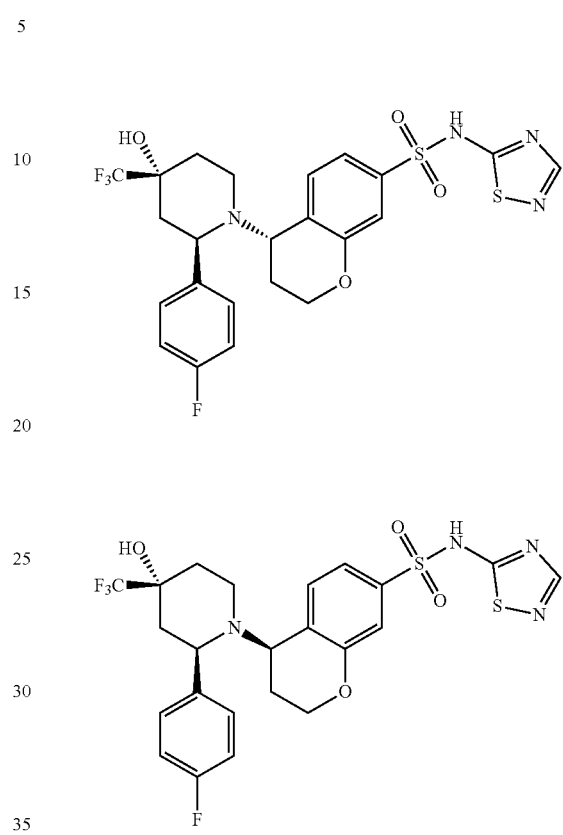

(S)-4-((2R,4R)-2-(4-fluorophenyl)-4-hydroxy-4-(trifluoromethyl)piperidin-1-yl)-N-(1,2,4-thiadiazol-5-yl)chroman-7-sulfonamide & (R)-4-((2R,4R)-2-(4-fluorophenyl)-4-hydroxy-4-(trifluoromethyl)piperidin-1-yl)-N-(1,2,4-thiadiazol-5-yl)chroman-7-sulfonamide Following the procedure as described in Example 167 and making non-critical variations as required to replace (2S,4S)-benzyl 2-(4-fluorophenyl)-4-hydroxy-4-(trifluoromethyl)piperidine-1-carboxylate with (2R,4R)-benzyl 2-(4-fluorophenyl)-4-hydroxy-4-(trifluoromethyl)piperidine-1-carboxylate, (S)-4-((2R,4R)-2-(4-fluorophenyl)-4-hydroxy-4-(trifluoromethyl)piperidin-1-yl)-N-(1,2,4-thiadiazol-5-yl)chroman-7-sulfonamide (46 mg, less polar on TLC) and (R)-4-((2R,4R)-2-(4-fluorophenyl)-4-hydroxy-4-(trifluoromethyl)piperidin-1-yl)-N-(1,2,4-thiadiazol-5-yl)chroman-7-sulfonamide (25 mg, more polar on TLC) were obtained as a white solid. Example 169: $^1$H NMR (400 MHz, CD$_3$OD) δ 7.80 (s, 1H), 7.41-7.34 (m, 2H), 7.31-7.20 (m, 3H), 7.10 (s, 1H), 7.01-6.94 (m, 1H), 4.25-4.05 (m, 2H), 3.87-3.69 (m, 2H), 2.48-2.34 (m, 2H), 2.05-1.92 (m, 1H), 1.78-1.59 (m, 5H). LCMS M/Z (M+H) 559. Example 170: $^1$H NMR (400 MHz, CD$_3$OD) δ 7.90 (s, H), 7.76 (d, J=8.4 Hz, 1H), 7.55-7.46 (m, 2H), 7.40 (d, J=8.0, 1H), 7.18 (s, 1H), 7.11-7.06 (m, 2H), 4.30-4.20 (m, 1H), 4.00-3.98 (m, 1H), 3.88-3.71 (m, 2H), 2.72-2.68 (m, 1H), 2.49-2.45 (m, 1H), 2.18-2.05 (m, 1H), 1.93-1.79 (m, 4H), 1.75-1.66 (m, 1H). LCMS M/Z (M+H) 559.

Example 171 & Example 172

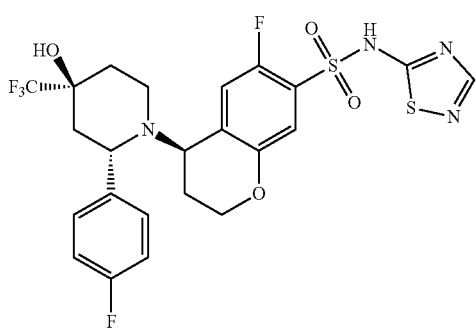

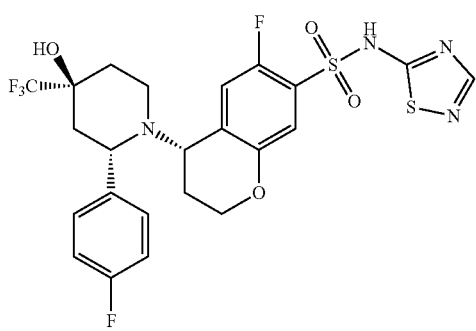

(R)-6-fluoro-4-((2S,4S)-2-(4-fluorophenyl)-4-hydroxy-4-(trifluoromethyl)piperidin-1-yl)-N-(1,2,4-thiadiazol-5-yl)chroman-7-sulfonamide & (S)-6-fluoro-4-((2S,4S)-2-(4-fluorophenyl)-4-hydroxy-4-(trifluoromethyl)piperidin-1-yl)-N-(1,2,4-thiadiazol-5-yl)chroman-7-sulfonamide Following the procedure as described in Example 167 and making non-critical variations as required to replace (R)-7-(N-(2,4-dimethoxybenzyl)-N-(1,2,4-thiadiazol-5-yl)sulfamoyl)chroman-4-yl methanesulfonate with (R)-7-(N-(2,4-dimethoxybenzyl)-N-(1,2,4-thiadiazol-5-yl)sulfamoyl)-6-fluorochroman-4-yl methanesulfonate, (R)-6-fluoro-4-((2S,4S)-2-(4-fluorophenyl)-4-hydroxy-4-(trifluoromethyl)piperidin-1-yl)-N-(1,2,4-thiadiazol-5-yl)chroman-7-sulfonamide (37 mg, less polar on TLC) and (S)-6-fluoro-4-((2S,4S)-2-(4-fluorophenyl)-4-hydroxy-4-(trifluoromethyl)piperidin-1-yl)-N-(1,2,4-thiadiazol-5-yl)chroman-7-sulfonamide (113 mg, more polar on TLC) were obtained as white solid. Example 171: $^1$H NMR (400 MHz, CD$_3$OD) δ 8.20 (s, 1H), 7.46-7.37 (m, 2H), 7.20-7.07 (m, 2H), 7.06-6.96 (m, 2H), 4.28-4.20 (m, 2H), 4.02-3.94 (m, 1H), 3.90-3.81 (m, 1H), 2.75-2.64 (m, 2H), 2.22-2.12 (m, 1H), 1.99-1.89 (m, 2H), 1.87-1.71 (m, 3H). LCMS M/Z (M+H) 577. Example 172: $^1$H NMR (400 MHz, CD$_3$OD) δ 8.20 (s, 1H), 7.59-7.45 (m, 3H), 7.17 (d, J=5.6 Hz, 1H), 7.13-7.06 (m, 2H), 4.32-4.24 (m, 1H), 4.03-3.97 (m, 1H), 3.85-3.75 (m, 2H), 2.81-2.72 (m, 1H), 2.51-2.43 (m, 1H), 2.18-2.07 (m, 1H), 1.98-1.82 (m, 4H), 1.79-1.71 (m, 1H). LCMS M/Z (M+H) 577.

Example 173 & Example 174

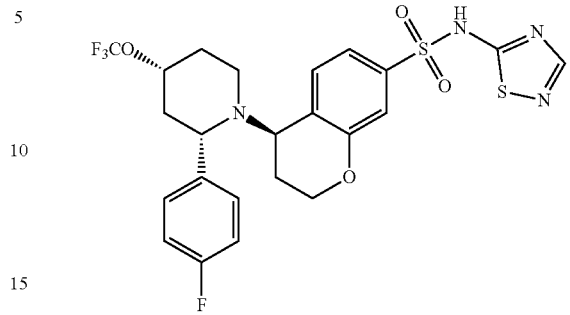

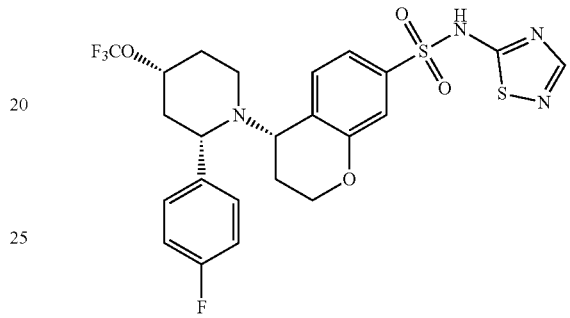

(R)-4-((2S,4R)-2-(4-fluorophenyl)-4-(trifluoromethoxy)piperidin-1-yl)-N-(1,2,4-thiadiazol-5-yl)chroman-7-sulfonamide & (S)-4-((2S,4R)-2-(4-fluorophenyl)-4-(trifluoromethoxy)piperidin-1-yl)-N-(1,2,4-thiadiazol-5-yl)chroman-7-sulfonamide Step 1:

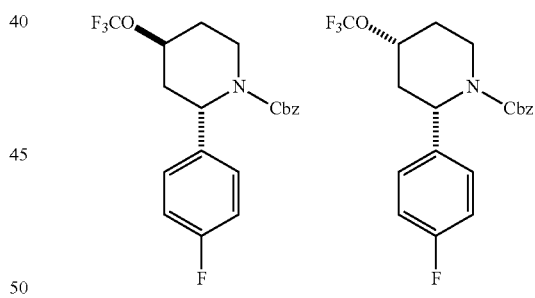

(trans)-benzyl 2-(4-fluorophenyl)-4-(trifluoromethoxy)piperidine-1-carboxylate & (cis)-benzyl 2-(4-fluorophenyl)-4-(trifluoromethoxy)piperidine-1-carboxylate To a solution of silver trifluoromethanesulfonate (9.36 g, 36.43 mmol), 1-chloromethyl-4-fluoro-1,4-diazoniabicyclo[2.2.2]octane bis(tetrafluoroborate) (6.45 g, 18.22 mmol), potassium fluoride (2.82 g, 48.58 mmol) and benzyl 2-(4-fluorophenyl)-4-hydroxypiperidine-1-carboxylate (4.0 g, 12.14 mmol) in EtOAc (40 mL) was added 2-fluoropyridine (3.54 g, 36.43 mmol) and (trifluoromethyl)trimethylsilane (5.18 g, 36.43 mmol) under a nitrogen atmosphere. The reaction mixture was stirred at room temperature for 16 h. The reaction mixture was filtered through a plug of silica (eluted with EtOAc). The filtrate was concentrated in vacuo. The crude residue was purified by silica gel chromatography (petroleum ether/EtOAc=3:1) to give (trans)-benzyl 2-(4-fluorophenyl)-4-(trifluoromethoxy)piperidine-1-carboxylate (0.87 g, less polar on TLC) as colorless oil and (cis)-benzyl 2-(4-fluorophenyl)-4-(trifluoromethoxy)piperidine-1-carboxylate (1.15 g, more polar on TLC) as colorless oil. Trans-isomer: $^1$H NMR (400 MHz, CDCl$_3$) δ 7.41-7.32 (m, 5H), 7.21-7.15 (m, 2H), 7.09-7.03 (m, 2H), 5.75-5.65 (m, 1H), 5.22 (s, 2H), 4.38-4.25 (m, 2H), 2.88-2.71 (m, 2H), 2.08-1.98 (m, 2H), 1.79-1.69 (m, 1H). LCMS M/Z (M+H) 398. Cis-isomer: $^1$H NMR (400 MHz, CDCl$_3$) δ 7.38-7.23 (m, 5H), 7.18-7.15 (m, 2H), 7.03-6.98 (m, 2H), 5.43 (s, 1H), 5.17 (s, 2H), 4.68-4.60 (m, 1H), 4.27-4.11 (m, 1H), 3.35-3.29 (m, 1H), 2.61-2.57 (m, 1H), 2.29-2.13 (m, 1H), 2.00-1.86 (m, 2H). LCMS M/Z (M+H) 398.

Step 2:

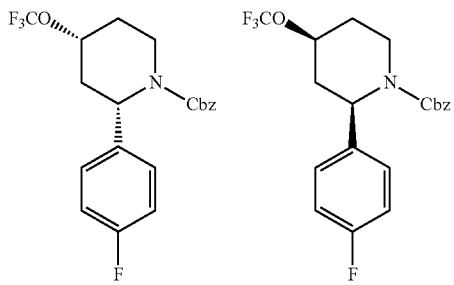 [SMILES: O=C(OCc1ccccc1)N1CC[C@@H](OC(F)(F)F)C[C@H]1c1ccc(F)cc1 ; O=C(OCc1ccccc1)N1CC[C@H](OC(F)(F)F)C[C@@H]1c1ccc(F)cc1]

(2S,4R)-benzyl 2-(4-fluorophenyl)-4-(trifluoromethoxy)piperidine-1-carboxylate & (2R,4S)-benzyl 2-(4-fluorophenyl)-4-(trifluoromethoxy)piperidine-1-carboxylate (cis)-benzyl 2-(4-fluorophenyl)-4-(trifluoromethoxy)piperidine-1-carboxylate (0.95 g) was separated by using chiral SFC (Chiralpak OD (250 mm*30 mm, 5 um), Supercritical CO2/MeOH+DEA=85/15; 60 ml/min) to give (2S,4R)-benzyl 2-(4-fluorophenyl)-4-(trifluoromethoxy)piperidine-1-carboxylate (0.46 g, first peak) as colorless oil and (2R,4S)-benzyl 2-(4-fluorophenyl)-4-(trifluoromethoxy)piperidine-1-carboxylate (0.45 g, second peak) as colorless oil. LCMS M/Z (M+H) 398.

Step 3:

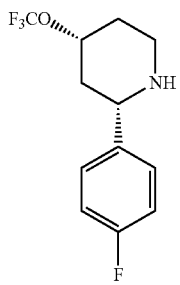

(2S,4R)-2-(4-fluorophenyl)-4-(trifluoromethoxy)piperidine

Following the procedure as described in Example 161, step 8 and making non-critical variations as required to replace (2S,4R)-benzyl 2-(4-fluorophenyl)-4-(methylsulfonyl)piperidine-1-carboxylate with (2S,4R)-benzyl 2-(4-fluorophenyl)-4-(trifluoromethoxy)piperidine-1-carboxylate, the title compound was obtained as colorless oil (110 mg, 83%).

Step 4:

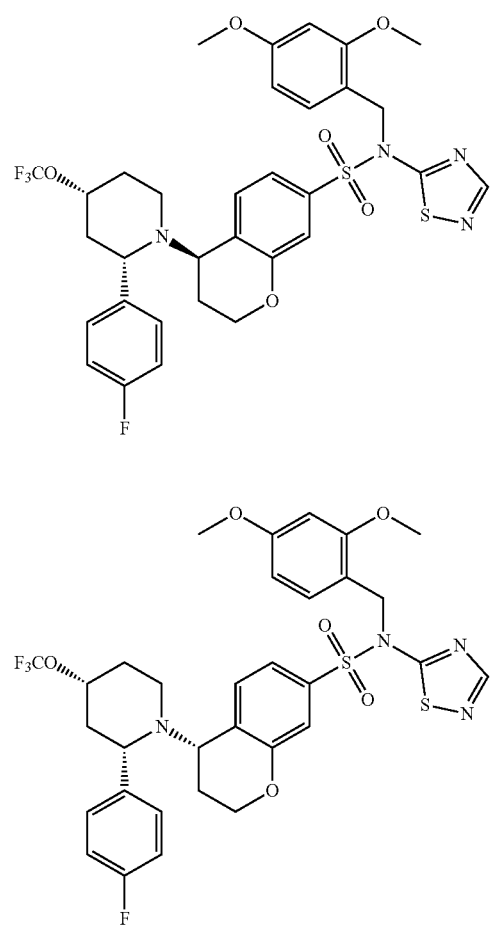

(R)—N-(2,4-dimethoxybenzyl)-4-((2S,4R)-2-(4-fluorophenyl)-4-(trifluoromethoxy)piperidin-1-yl)-N-(1,2,4-thiadiazol-5-yl)chroman-7-sulfonamide & (S)—N-(2,4-dimethoxybenzyl)-4-((2S,4R)-2-(4-fluorophenyl)-4-(trifluoromethoxy)piperidin-1-yl)-N-(1,2,4-thiadiazol-5-yl)chroman-7-sulfonamide Following the procedure as described in Example 161, step 9 and making non-critical variations as required to replace (2S,4R)-2-(4-fluorophenyl)-4-(methylsulfonyl)piperidine with (2S,4R)-2-(4-fluorophenyl)-4-(trifluoromethoxy)piperidine, (R)—N-(2,4-dimethoxybenzyl)-4-((2S,4R)-2-(4-fluorophenyl)-4-(trifluoromethoxy)piperidin-1-yl)-N-(1,2,4-thiadiazol-5-yl)chroman-7-sulfonamide (45 mg, less polar on TLC) and (S)—N-(2,4-dimethoxybenzyl)-4-((2S,4R)-2-(4-fluorophenyl)-4-(trifluoromethoxy)piperidin-1-yl)-N-(1,2,4-thiadiazol-5-yl)chroman-7-sulfonamide (45 mg, more polar on TLC) were obtained as colorless oil. LCMS M/Z (M+H) 709.

Step 5:

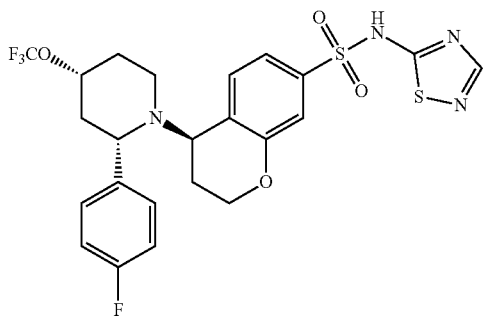

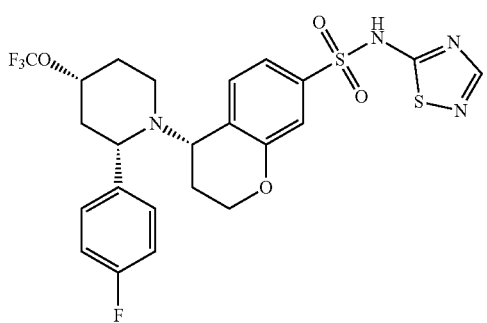

(R)-4-((2S,4R)-2-(4-fluorophenyl)-4-(trifluoromethoxy)piperidin-1-yl)-N-(1,2,4-thiadiazol-5-yl)chroman-7-sulfonamide & (S)-4-((2S,4R)-2-(4-fluorophenyl)-4-(trifluoromethoxy)piperidin-1-yl)-N-(1,2,4-thiadiazol-5-yl)chroman-7-sulfonamide Following the procedure as described in Example 161, step 10 and making non-critical variations as required to replace (S)—N-(2,4-dimethoxybenzyl)-4-((2S,4R)-2-(4-fluorophenyl)-4-(methyl sulfonyl)piperidin-1-yl)-N-(1,2,4-thiadiazol-5-yl)chroman-7-sulfonamide with (R)—N-(2,4-dimethoxybenzyl)-4-((2S,4R)-2-(4-fluorophenyl)-4-(trifluoromethoxy)piperidin-1-yl)-N-(1,2,4-thiadiazol-5-yl)chroman-7-sulfonamide and (S)—N-(2,4-dimethoxybenzyl)-4-((2S,4R)-2-(4-fluorophenyl)-4-(trifluoromethoxy)piperidin-1-yl)-N-(1,2,4-thiadiazol-5-yl)chroman-7-sulfonamide, (R)-4-((2S,4R)-2-(4-fluorophenyl)-4-(trifluoromethoxy)piperidin-1-yl)-N-(1,2,4-thiadiazol-5-yl)chroman-7-sulfonamide (14 mg, less polar on TLC) and (S)-4-((2S,4R)-2-(4-fluorophenyl)-4-(trifluoromethoxy)piperidin-1-yl)-N-(1,2,4-thiadiazol-5-yl)chroman-7-sulfonamide (12 mg, more polar on TLC) were obtained as white solid. Example 173: $^1$H NMR (400 MHz, CDCl$_3$) δ 8.02 (s, 1H), 7.78 (d, J=8.0 Hz, 1H), 7.44-7.34 (m, 3H), 7.23 (d, J=1.6 Hz, 1H), 7.05-7.01 (m, 2H), 4.31-4.21 (m, 2H), 3.87-3.78 (m, 2H), 3.68-3.64 (m, 1H), 2.74-2.66 (m, 1H), 2.35-2.26 (m, 1H), 2.25-2.15 (m, 1H), 2.12-1.97 (m, 3H), 1.95-1.87 (m, 1H), 1.81-1.73 (m, 2H). LCMS M/Z (M+H) 559. Example 174: $^1$H NMR (400 MHz, CDCl$_3$) δ 8.03 (s, 1H), 7.41-7.33 (m, 3H), 7.26-7.24 (m, 2H), 7.03-6.99 (m, 2H), 4.27-4.15 (m, 2H), 3.97-3.84 (m, 3H), 2.75-2.71 (m, 1H), 2.32-1.95 (m, 5H), 1.89-1.76 (m, 3H). LCMS M/Z (M+H) 559.

Example 175 & Example 176

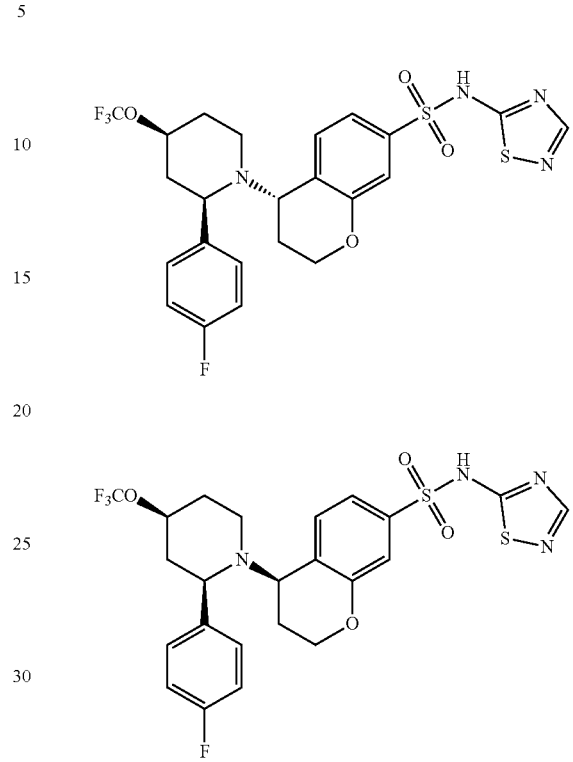

(S)-4-((2R,4S)-2-(4-fluorophenyl)-4-(trifluoromethoxy)piperidin-1-yl)-N-(1,2,4-thiadiazol-5-yl)chroman-7-sulfonamide & (R)-4-((2R,4S)-2-(4-fluorophenyl)-4-(trifluoromethoxy)piperidin-1-yl)-N-(1,2,4-thiadiazol-5-yl)chroman-7-sulfonamide Following the procedure as described in Example 173 and making non-critical variations as required to replace (2S,4R)-benzyl 2-(4-fluorophenyl)-4-(trifluoromethoxy)piperidine-1-carboxylate with (2R,4S)-benzyl 2-(4-fluorophenyl)-4-(trifluoromethoxy)piperidine-1-carboxylate, (S)-4-((2R,4S)-2-(4-fluorophenyl)-4-(trifluoromethoxy)piperidin-1-yl)-N-(1,2,4-thiadiazol-5-yl)chroman-7-sulfonamide (12 mg, less polar on TLC) and (R)-4-((2R,4S)-2-(4-fluorophenyl)-4-(trifluoromethoxy)piperidin-1-yl)-N-(1,2,4-thiadiazol-5-yl)chroman-7-sulfonamide (3 mg, more polar on TLC) were obtained as white solid. Example 175: $^1$H NMR (400 MHz, CDCl$_3$) δ 8.02 (s, 1H), 7.78 (d, J=8.0 Hz, 1H), 7.45-7.34 (m, 3H), 7.23 (d, J=2.0 Hz, 1H), 7.06-7.01 (m, 2H), 4.33-4.19 (m, 2H), 3.90-3.78 (m, 2H), 3.73-3.63 (m, 1H), 2.72-2.66 (m, 1H), 2.35-2.27 (m, 1H), 2.25-2.18 (m, 1H), 2.11-2.04 (m, 2H), 2.04-1.98 (m, 1H), 1.96-1.88 (m, 1H), 1.82-1.72 (m, 2H). LCMS M/Z (M+H) 559. Example 176: $^1$H NMR (400 MHz, CDCl$_3$) δ 8.02 (s, 1H), 7.43-7.30 (m, 3H), 7.28-7.21 (m, 2H), 7.06-6.97 (m, 2H), 3.97-3.87 (m, 5H), 2.75-2.71 (m, 1H), 2.19-2.12 (m, 3H), 2.11-2.00 (m, 3H), 1.88-1.76 (m, 2H). LCMS M/Z (M+H) 559.

Example 177
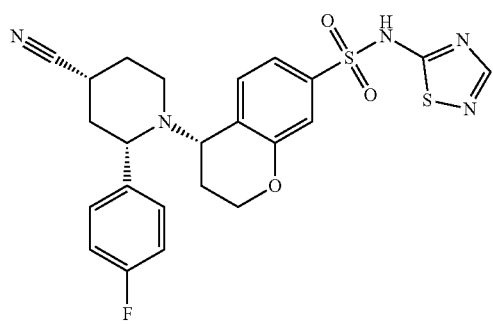 [SMILES: N#C[C@@H]1CCN([C@H]2CCOc3cc(S(=O)(=O)Nc4ncns4)ccc32)[C@H](c2ccc(F)cc2)C1]
(S)-4-((2S,4R)-4-cyano-2-(4-fluorophenyl)piperidin-1-yl)-N-(1,2,4-thiadiazol-5-yl)chroman-7-sulfonamide
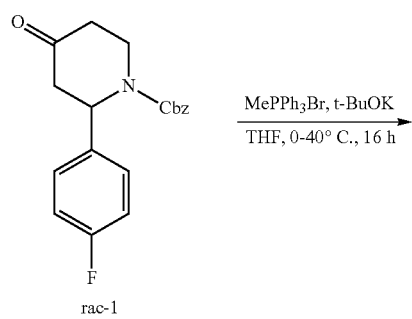
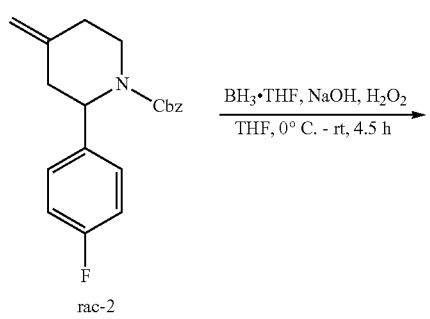
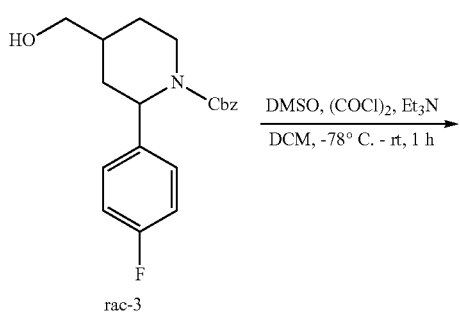
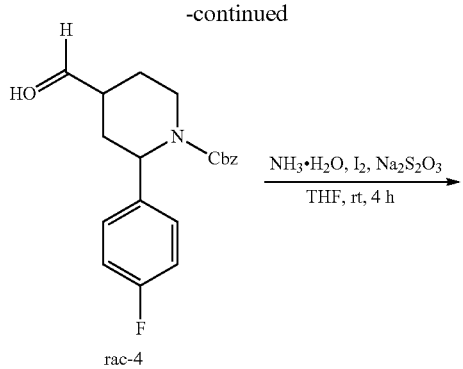
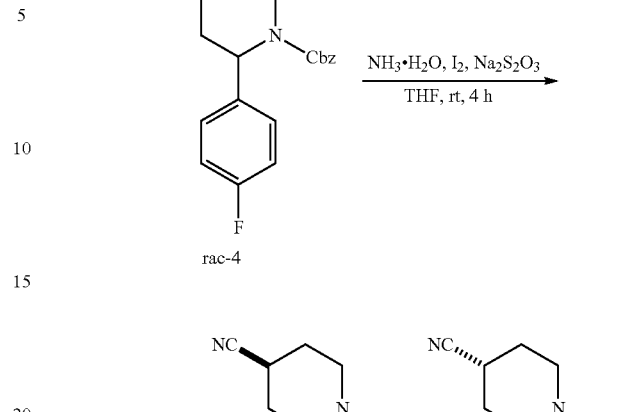
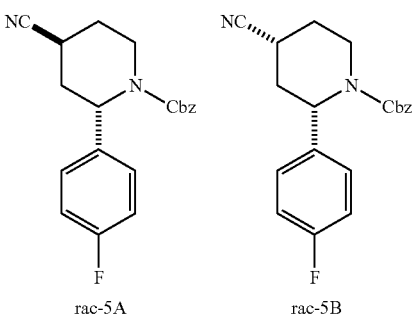

387
-continued

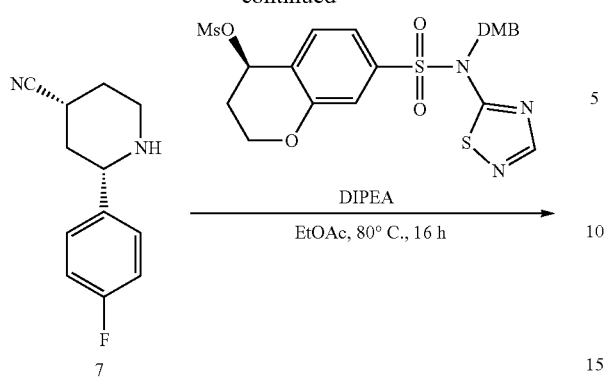

388
-continued

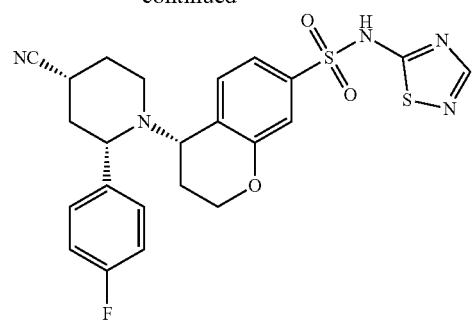

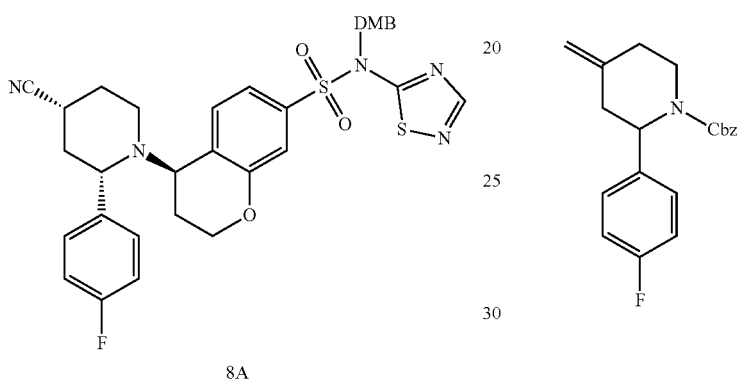

Step 1:

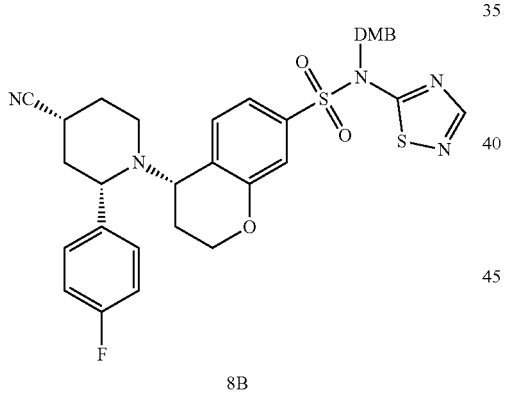

benzyl 2-(4-fluorophenyl)-4-methylenepiperidine-1-carboxylate

To a solution of methyltriphenylphosphonium bromide (9.93 g, 27.8 mmol) in anhydrous THF (80 mL) at 0° C. was slowly added potassium tert-butoxide in THF (1.0 M, 27.8 mL, 27.8 mmol). The reaction mixture was heated to 40° C. for 0.5 h under a nitrogen atmosphere. After cooling to room temperature, benzyl 2-(4-fluorophenyl)-4-oxo-piperidine-1-carboxylate (7.0 g, 21.38 mmol) in anhydrous THF (20 mL) was added to the mixture and heated to 40° C. for an additional 16 h. The mixture was quenched with water (200 mL) and extracted with EtOAc (80 mL×3). The combined organic layers were dried over anhydrous Na₂SO₄, filtered and concentrated in vacuo. The crude residue was purified by silica gel chromatography (petroleum ether/EtOAc=30:1) to give the title compound (6.8 g, 98%) as colorless oil. LCMS M/Z (M+H) 326.

Step 2:

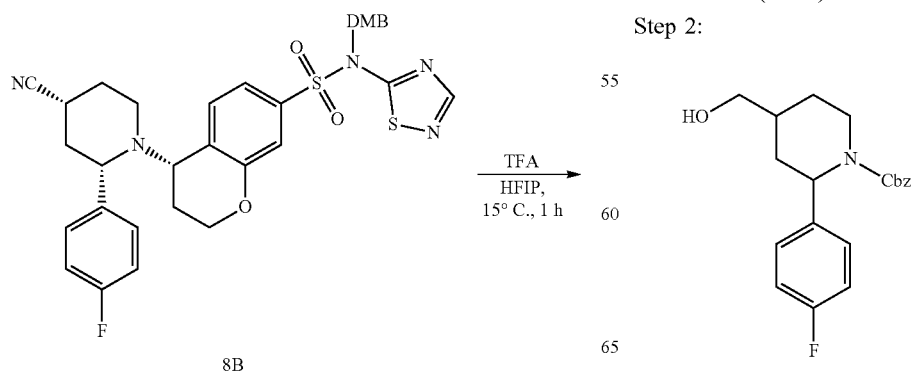

benzyl 2-(4-fluorophenyl)-4-(hydroxymethyl)piperidine-1-carboxylate

To a solution of benzyl 2-(4-fluorophenyl)-4-methylenepiperidine-1-carboxylate (6.8 g, 20.9 mmol) in anhydrous THF (100 mL) at 0° C. was added borane-tetrahydrofuran complex (1.0 M, 31.35 mL, 31.35 mmol). The reaction mixture was stirred at 0° C. for 1 h and warmed to room temperature for an additional 2 h. After cooling to 0° C., aq. NaOH (2.0 M, 20.9 mL, 41.8 mmol) and 30% aq. hydrogen peroxide (12.92 mL, 125.39 mmol) were added to the mixture dropwise and stirred at room temperature for an additional 1.5 h. Water (70 mL) was added and extracted with EtOAc (80 mL). The organic layer was washed with aq. sodium thiosulfate (2.0 M, 60 mL), brine (60 mL), dried over anhydrous $Na_2SO_4$, filtered and concentrated in vacuo. The crude residue was purified by silica gel chromatography (petroleum ether/EtOAc=2:1) to give the title compound (6.3 g, 88%) as colorless oil. LCMS M/Z (M+H) 344.

Step 3:

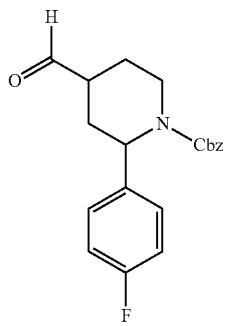 [SMILES: O=CC1CCN(C(=O)OCc2ccccc2)C(c2ccc(F)cc2)C1]

benzyl 2-(4-fluorophenyl)-4-formylpiperidine-1-carboxylate

To a solution of dimethyl sulfoxide (1.71 g, 21.84 mmol) in anhydrous DCM (20 mL) at −78° C. was added ethanedioyl dichloride (2.31 g, 18.2 mmol). After the mixture was stirred at −78° C. for 10 min, a solution of benzyl 2-(4-fluorophenyl)-4-(hydroxymethyl)piperidine-1-carboxylate (2.50 g, 7.28 mmol) in anhydrous DCM (20 mL) was added slowly. After the mixture was stirred at −78° C. for 40 min, triethylamine (5.07 mL, 36.4 mmol) was added slowly. The reaction mixture was stirred at −78° C. for 5 min and warmed to room temperature for an additional 20 min. Water (30 mL) was added and extracted with DCM (30 mL×2). The organic layer was washed with sat. aq. $NaHCO_3$ (60 mL), brine (60 mL), dried over anhydrous $MgSO_4$, filtered and concentrated in vacuo to give the title compound (2.7 g, 97%) as brown oil that required no further purification.

Step 4:

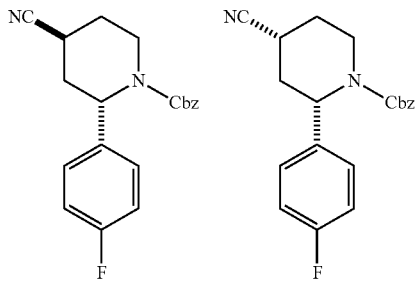 [SMILES: N#C[C@H]1CCN(C(=O)OCc2ccccc2)[C@H](c2ccc(F)cc2)C1 ; N#C[C@@H]1CCN(C(=O)OCc2ccccc2)[C@H](c2ccc(F)cc2)C1]

(trans)-benzyl 4-cyano-2-(4-fluorophenyl)piperidine-1-carboxylate & (cis)-benzyl 4-cyano-2-(4-fluorophenyl)piperidine-1-carboxylate To a solution of benzyl 2-(4-fluorophenyl)-4-formylpiperidine-1-carboxylate (2.7 g, 7.91 mmol) in anhydrous THF (20 mL) was added ammonium hydroxide (28.73 mL, 791 mmol). After the mixture was stirred at room temperature for 10 min, iodine (2.21 g, 8.7 mmol) was added slowly. After the mixture was stirred at room temperature for 2 h, 5% aq. $Na_2S_2O_3$ (30 mL) was added. The mixture was stirred at room temperature for an additional 2 h. Water (50 mL) was added and the mixture was acidified with conc. HCl to pH 3 and then extracted with EtOAc (100 mL×2). The combined organic layers were washed with brine, dried over anhydrous $Na_2SO_4$, filtered and concentrated in vacuo. The crude residue was purified by silica gel chromatography (petroleum ether/EtOAc=3:1) to give (trans)-benzyl 4-cyano-2-(4-fluorophenyl)piperidine-1-carboxylate (2 g, less polar on TLC) as colorless oil and (cis)-benzyl 4-cyano-2-(4-fluorophenyl)piperidine-1-carboxylate (0.4 g, more polar on TLC) as colorless oil. Trans-isomer: $^1$H NMR (400 MHz, $CDCl_3$) δ 7.42-7.30 (m, 5H), 7.17-7.02 (m, 4H), 5.64-5.62 (m, 1H), 5.21 (s, 2H), 4.27-4.22 (m, 1H), 2.88-2.76 (m, 1H), 2.74-2.58 (m, 2H), 2.25-2.10 (m, 1H), 2.05-1.93 (m, 1H), 1.90-1.75 (m, 1H). LCMS M/Z (M+H) 339.
Cis-isomer: $^1$H NMR (400 MHz, $CDCl_3$) δ 7.39-7.30 (m, 3H), 7.27-7.23 (m, 2H), 7.22-7.15 (m, 2H), 7.09-7.00 (m, 2H), 5.46-5.39 (m, 1H), 5.16 (s, 2H), 4.34-4.23 (m, 1H), 3.41-3.29 (m, 1H), 3.00-2.91 (m, 1H), 2.58-2.44 (m, 1H), 2.28-2.17 (m, 1H), 2.02-1.89 (m, 2H). LCMS M/Z (M+H) 339.

Step 5:

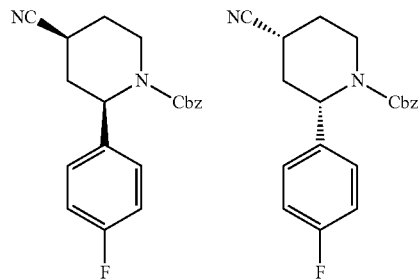 [SMILES: N#C[C@H]1CCN(C(=O)OCc2ccccc2)[C@@H](c2ccc(F)cc2)C1 ; N#C[C@@H]1CCN(C(=O)OCc2ccccc2)[C@H](c2ccc(F)cc2)C1]

(2R,4S)-benzyl 4-cyano-2-(4-fluorophenyl)piperidine-1-carboxylate & (2S,4R)-benzyl 4-cyano-2-(4-fluorophenyl)piperidine-1-carboxylate (cis)-benzyl 4-cyano-2-(4-fluorophenyl)piperidine-1-carboxylate (0.4 g) was separated by using chiral SFC (Chiralpak OD (250 mm*30 mm, 5 um), Supercritical $CO_2$/MeOH+0.05% DEA=55/45; 65 mL/min) to give (2R,4S)-benzyl 4-cyano-2-(4-fluorophenyl)piperidine-1-carboxylate (0.15 g, first peak) as colorless oil and (2S,4R)-benzyl 4-cyano-2-(4-fluorophenyl)piperidine-1-carboxylate (0.15 g, second peak) as colorless oil.

Step 6:

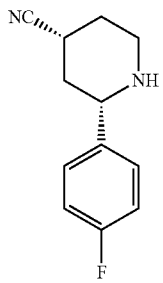 [SMILES: N#C[C@@H]1CCN[C@H](c2ccc(F)cc2)C1]

(2S,4R)-2-(4-fluorophenyl)piperidine-4-carbonitrile

Following the procedure as described in Example 161, step 8 and making non-critical variations as required to replace (2S,4R)-benzyl 2-(4-fluorophenyl)-4-(methylsulfonyl)piperidine-1-carboxylate with (2S,4R)-benzyl 4-cyano-2-(4-fluorophenyl)piperidine-1-carboxylate, the title compound was obtained as a white solid (90 mg, 99%).

Step 7:

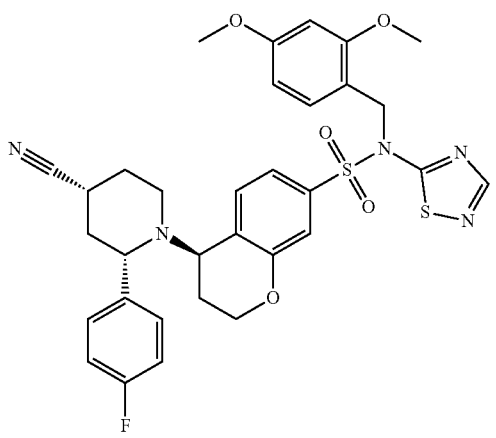

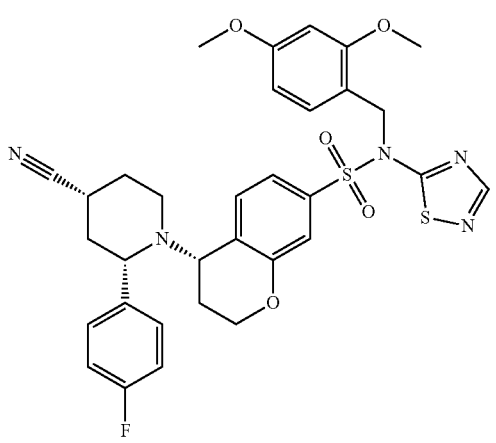

(R)-4-((2S,4R)-4-cyano-2-(4-fluorophenyl)piperidin-1-yl)-N-(2,4-dimethoxybenzyl)-N-(1,2,4-thiadiazol-5-yl)chroman-7-sulfonamide & (S)-4-((2S,4R)-4-cyano-2-(4-fluorophenyl)piperidin-1-yl)-N-(2,4-dimethoxybenzyl)-N-(1,2,4-thiadiazol-5-yl)chroman-7-sulfonamide Following the procedure as described in Example 161, step 9 and making non-critical variations as required to replace (2S,4R)-2-(4-fluorophenyl)-4-(methylsulfonyl)piperidine with (2S,4R)-2-(4-fluorophenyl)piperidine-4-carbonitrile, (R)-4-((2S,4R)-4-cyano-2-(4-fluorophenyl)piperidin-1-yl)-N-(2,4-dimethoxybenzyl)-N-(1,2,4-thiadiazol-5-yl)chroman-7-sulfonamide (50 mg, less polar on TLC) and (S)-4-((2S,4R)-4-cyano-2-(4-fluorophenyl)piperidin-1-yl)-N-(2,4-dimethoxybenzyl)-N-(1,2,4-thiadiazol-5-yl)chroman-7-sulfonamide (75 mg, more polar on TLC) were obtained as light yellow solid.

Step 8:

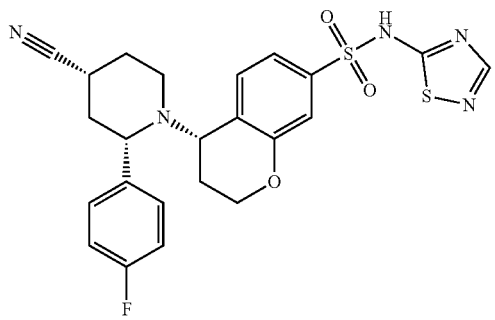 [SMILES: N#C[C@@H]1CCN([C@H]2CCOc3cc(S(=O)(=O)Nc4ncns4)ccc32)[C@H](c2ccc(F)cc2)C1]

(S)-4-((2S,4R)-4-cyano-2-(4-fluorophenyl)piperidin-1-yl)-N-(1,2,4-thiadiazol-5-yl)chroman-7-sulfonamide Following the procedure as described in Example 161, step 10 and making non-critical variations as required to replace (S)—N-(2,4-dimethoxybenzyl)-4-((2S,4R)-2-(4-fluorophenyl)-4-(methylsulfonyl)piperidin-1-yl)-N-(1,2,4-thiadiazol-5-yl)chroman-7-sulfonamide with (S)-4-((2S,4R)-4-cyano-2-(4-fluorophenyl)piperidin-1-yl)-N-(2,4-dimethoxybenzyl)-N-(1,2,4-thiadiazol-5-yl)chroman-7-sulfonamide, the title compound was obtained as a white solid (12 mg, 21%). $^1$H NMR (400 MHz, CD$_3$OD) δ 8.08 (s, 1H), 7.80 (d, J=8.4 Hz, 1H), 7.56-7.45 (m, 2H), 7.46-7.32 (m, 1H), 7.15 (d, J=2.0 Hz, 1H), 7.13-7.05 (m, 2H), 4.30-4.20 (m, 1H), 3.85-3.66 (m, 3H), 2.85-2.73 (m, 1H), 2.67-2.57 (m, 1H), 2.40-2.28 (m, 1H), 2.15-1.74 (m, 6H). LCMS M/Z (M+H) 500.

Example 178

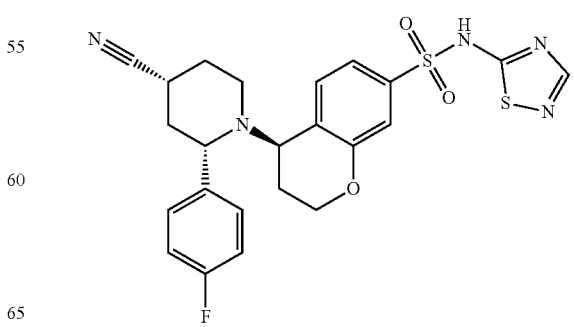

(R)-4-((2S,4R)-4-cyano-2-(4-fluorophenyl)piperidin-1-yl)-N-(1,2,4-thiadiazol-5-yl)chroman-7-sulfonamide Following the procedure as described in Example 177, step 8 and making non-critical variations as required to replace (S)-4-((2S,4R)-4-cyano-2-(4-fluorophenyl)piperidin-1-yl)-N-(2,4-dimethoxybenzyl)-N-(1,2,4-thiadiazol-5-yl)chroman-7-sulfonamide with (R)-4-((2S,4R)-4-cyano-2-(4-fluorophenyl)piperidin-1-yl)-N-(2,4-dimethoxybenzyl)-N-(1,2,4-thiadiazol-5-yl)chroman-7-sulfonamide, the title compound was obtained as a white solid (10 mg, 26%). $^1$H NMR (400 MHz, CD$_3$OD) δ 8.13 (s, 1H), 7.51-7.43 (m, 2H), 7.42-7.32 (m, 2H), 7.14 (s, 1H), 7.12-6.97 (m, 2H), 4.27-4.18 (m, 1H), 4.03-3.79 (m, 3H), 2.82-2.68 (m, 2H), 2.24-1.96 (m, 4H), 1.95-1.76 (m, 3H). LCMS M/Z (M+H) 500.

Example 179 & Example 180

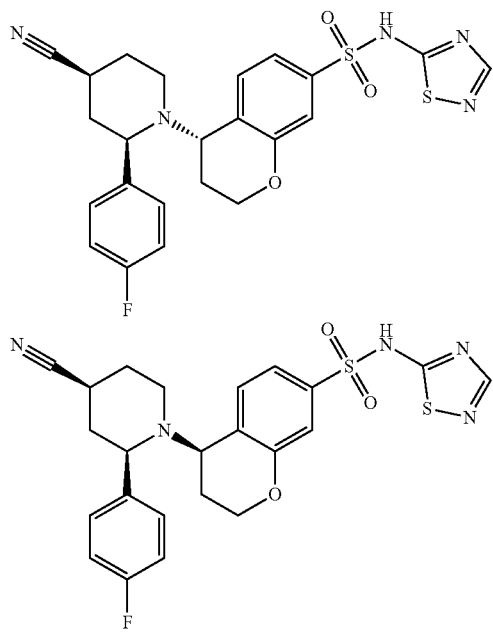

(S)-4-((2R,4S)-4-cyano-2-(4-fluorophenyl)piperidin-1-yl)-N-(1,2,4-thiadiazol-5-yl)chroman-7-sulfonamide & (R)-4-((2R,4S)-4-cyano-2-(4-fluorophenyl)piperidin-1-yl)-N-(1,2,4-thiadiazol-5-yl)chroman-7-sulfonamide Following the procedure as described in Example 177 and making non-critical variations as required to replace (2S,4R)-benzyl 4-cyano-2-(4-fluorophenyl)piperidine-1-carboxylate with (2R,4S)-benzyl 4-cyano-2-(4-fluorophenyl)piperidine-1-carboxylate, (S)-4-((2R,4S)-4-cyano-2-(4-fluorophenyl)piperidin-1-yl)-N-(1,2,4-thiadiazol-5-yl)chroman-7-sulfonamide (15 mg, less polar on TLC) and (R)-4-((2R,4S)-4-cyano-2-(4-fluorophenyl)piperidin-1-yl)-N-(1,2,4-thiadiazol-5-yl)chroman-7-sulfonamide (11 mg, more polar on TLC) were obtained as white solid. Example 179: $^1$H NMR (400 MHz, CD$_3$OD) δ 8.02 (s, 1H), 7.52-7.42 (m, 2H), 7.41-7.29 (m, 2H), 7.16 (s, 1H), 7.12-6.98 (m, 2H), 4.24-4.16 (m, 1H), 3.98 (d, J=10.0 Hz, 1H), 3.93-3.77 (m, 2H), 2.80-2.67 (m, 2H), 2.20-1.95 (m, 4H), 1.91-1.75 (m, 3H). LCMS M/Z (M+H) 500. Example 180: $^1$H NMR (400 MHz, CD$_3$OD) δ 8.05 (s, 1H), 7.79 (d, J=8.0 Hz, 1H), 7.56-7.46 (m, 2H), 7.45-7.33 (m, 1H), 7.15 (d, J=1.6 Hz, 1H), 7.15-7.02 (m, 2H), 4.28-4.18 (m, 1H), 3.84-3.65 (m, 3H), 2.84-2.73 (m, 1H), 2.67-2.57 (m, 1H), 2.38-2.27 (m, 1H), 2.14-1.89 (m, 4H), 1.86-1.74 (m, 2H). LCMS M/Z (M+H) 500.

Example 181 & Example 182

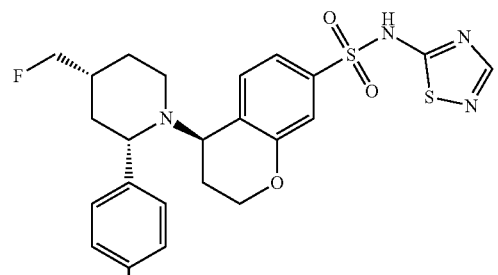

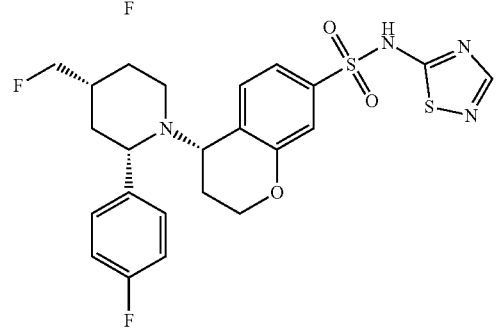

(R)-4-((2S,4R)-4-(fluoromethyl)-2-(4-fluorophenyl)piperidin-1-yl)-N-(1,2,4-thiadiazol-5-yl)chroman-7-sulfonamide & (S)-4-((2S,4R)-4-(fluoromethyl)-2-(4-fluorophenyl)piperidin-1-yl)-N-(1,2,4-thiadiazol-5-yl)chroman-7-sulfonamide Step 1:

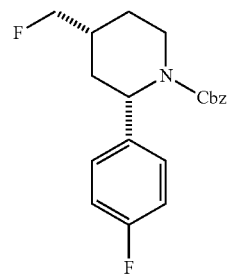 [SMILES: O=C(OCc1ccccc1)N1CC[C@@H](CF)C[C@H]1c1ccc(F)cc1]

(cis)-benzyl 4-(fluoromethyl)-2-(4-fluorophenyl)piperidine-1-carboxylate

To a solution of benzyl 2-(4-fluorophenyl)-4-(hydroxymethyl)piperidine-1-carboxylate (2.0 g, 5.82 mmol) in anhydrous DCM (20 mL) at 0° C. was added diethylaminosulfur trifluoride (2.82 g, 17.47 mmol). The reaction mixture was stirred at room temperature for 16 h. The reaction was quenched with 5% aq. NaHCO₃ (20 mL). The organic layer was washed with brine (20 mL), dried over anhydrous Na₂SO₄, filtered and concentrated in vacuo. The crude residue was purified by silica gel chromatography (petroleum ether/EtOAc=3:1) to give the title compound (0.84 g, 42%) as colorless oil.
Step 2:

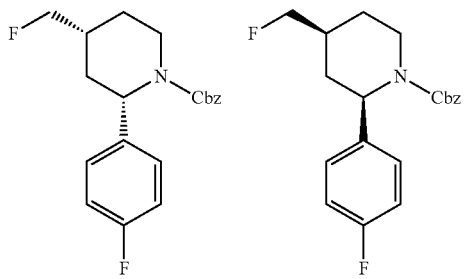 [SMILES: O=C(OCc1ccccc1)N1CC[C@@H](CF)C[C@H]1c1ccc(F)cc1 ; O=C(OCc1ccccc1)N1CC[C@H](CF)C[C@@H]1c1ccc(F)cc1]

(2S,4R)-benzyl 4-(fluoromethyl)-2-(4-fluorophenyl) piperidine-1-carboxylate & (2R,4S)-benzyl 4-(fluoromethyl)-2-(4-fluorophenyl)piperidine-1-carboxylate (cis)-benzyl 4-(fluoromethyl)-2-(4-fluorophenyl)piperidine-1-carboxylate (0.90 g) was separated by using chiral SFC (Whelk-01 250 mm*30 mm, 10 UM; Mobile phase: 45% of ethanol (0.05% DEA) in CO₂; Flow rate: 60 mL/min) to give (2S,4R)-benzyl 4-(fluoromethyl)-2-(4-fluorophenyl)piperidine-1-carboxylate (0.3 g, first peak) as colorless oil and (2R,4S)-benzyl 4-(fluoromethyl)-2-(4-fluorophenyl)piperidine-1-carboxylate (0.29 g, second peak) as colorless oil. First peak: ¹H NMR (400 MHz, CDCl₃) δ 7.29-7.27 (m, 3H), 7.20-7.16 (m, 4H), 7.06-6.98 (m, 2H), 5.21-4.98 (m, 3H), 4.33-4.13 (m, 3H), 3.33-3.25 (m, 1H), 2.15-2.11 (m, 2H), 2.01-1.99 (m, 1H), 1.79-1.76 (m, 1H), 1.48-1.44 (m, 1H). Second peak: ¹H NMR (400 MHz, CDCl₃) δ 7.29-7.27 (m, 3H), 7.20-7.16 (m, 4H), 7.06-6.98 (m, 2H), 5.21-4.98 (m, 3H), 4.33-4.13 (m, 3H), 3.33-3.25 (m, 1H), 2.15-2.11 (m, 2H), 2.01-1.99 (m, 1H), 1.79-1.76 (m, 1H), 1.48-1.44 (m, 1H).
Step 3:

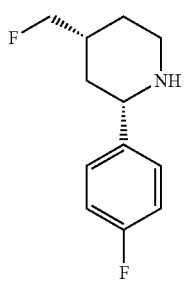 [SMILES: FC[C@@H]1CCN[C@H](c2ccc(F)cc2)C1]

(2S,4R)-4-(fluoromethyl)-2-(4-fluorophenyl)piperidine

Following the procedure as described in Example 161, step 8 and making non-critical variations as required to replace (2S,4R)-benzyl 2-(4-fluorophenyl)-4-(methylsulfonyl)piperidine-1-carboxylate with (2S,4R)-benzyl 4-(fluoromethyl)-2-(4-fluorophenyl)piperidine-1-carboxylate, the title compound was obtained as colorless oil (122 mg, 99%).
Step 4:

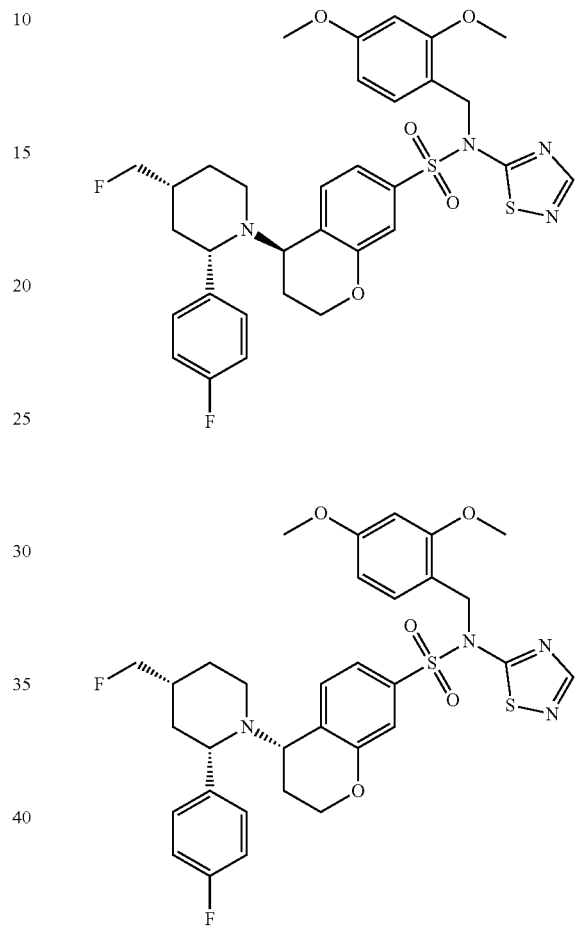

(R)—N-(2,4-dimethoxybenzyl)-4-((2S,4R)-4-(fluoromethyl)-2-(4-fluorophenyl)piperidin-1-yl)-N-(1,2,4-thiadiazol-5-yl)chroman-7-sulfonamide & (S)—N-(2,4-dimethoxybenzyl)-4-((2S,4R)-4-(fluoromethyl)-2-(4-fluorophenyl)piperidin-1-yl)-N-(1,2,4-thiadiazol-5-yl)chroman-7-sulfonamide Following the procedure as described in Example 161, step 9 and making non-critical variations as required to replace (2S,4R)-2-(4-fluorophenyl)-4-(methylsulfonyl)piperidine with (2S,4R)-4-(fluoromethyl)-2-(4-fluorophenyl) piperidine, (R)—N-(2,4-dimethoxybenzyl)-4-((2S,4R)-4-(fluoromethyl)-2-(4-fluorophenyl)piperidin-1-yl)-N-(1,2,4-thiadiazol-5-yl)chroman-7-sulfonamide (40 mg, less polar on TLC) and (S)—N-(2,4-dimethoxybenzyl)-4-((2S,4R)-4-(fluoromethyl)-2-(4-fluorophenyl)piperidin-1-yl)-N-(1,2,4-thiadiazol-5-yl)chroman-7-sulfonamide (40 mg, more polar on TLC) were obtained as white solid. LCMS M/Z (M+H) 657.

Step 5:

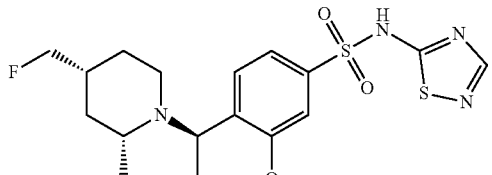

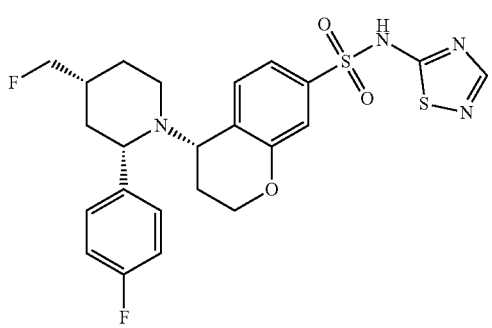

(R)-4-((2S,4R)-4-(fluoromethyl)-2-(4-fluorophenyl)piperidin-1-yl)-N-(1,2,4-thiadiazol-5-yl)chroman-7-sulfonamide & (S)-4-((2S,4R)-4-(fluoromethyl)-2-(4-fluorophenyl)piperidin-1-yl)-N-(1,2,4-thiadiazol-5-yl)chroman-7-sulfonamide Following the procedure as described in Example 161, step 10 and making non-critical variations as required to replace (S)—N-(2,4-dimethoxybenzyl)-4-((2S,4R)-2-(4-fluorophenyl)-4-(methyl sulfonyl)piperidin-1-yl)-N-(1,2,4-thiadiazol-5-yl)chroman-7-sulfonamide with (R)—N-(2,4-dimethoxybenzyl)-4-((2S,4R)-4-(fluoromethyl)-2-(4-fluorophenyl)piperidin-1-yl)-N-(1,2,4-thiadiazol-5-yl)chroman-7-sulfonamide and (S)—N-(2,4-dimethoxybenzyl)-4-((2S,4R)-4-(fluoromethyl)-2-(4-fluorophenyl)piperidin-1-yl)-N-(1,2,4-thiadiazol-5-yl)chroman-7-sulfonamide, (R)-4-((2S,4R)-4-(fluoromethyl)-2-(4-fluorophenyl)piperidin-1-yl)-N-(1,2,4-thiadiazol-5-yl)chroman-7-sulfonamide (12 mg, less polar on TLC) and (S)-4-((2S,4R)-4-(fluoromethyl)-2-(4-fluorophenyl)piperidin-1-yl)-N-(1,2,4-thiadiazol-5-yl)chroman-7-sulfonamide (15 mg, more polar on TLC) were obtained as white solid. Example 181: $^1$H NMR (400 MHz, CDCl$_3$) δ 7.97 (s, 1H), 7.39-7.35 (m, 3H), 7.27-7.24 (m, 2H), 7.01-6.97 (m, 2H), 4.30-4.19 (m, 3H), 3.91-3.85 (m, 3H), 2.72-2.69 (m, 1H), 2.14-2.04 (m, 2H), 1.90-1.75 (m, 3H), 1.73-1.64 (m, 3H), 1.42-1.36 (m, 2H). LCMS M/Z (M+H) 507. Example 182: $^1$H NMR (400 MHz, CDCl$_3$) δ 7.95 (s, 1H), 7.76 (d, J=8.0 Hz, 1H), 7.40-7.36 (m, 3H), 7.20 (s, 1H), 7.02-6.97 (m, 2H), 4.37-4.30 (m, 1H), 4.29-4.22 (m, 2H), 3.82-3.78 (m, 2H), 3.61-3.57 (m, 1H), 2.67-2.63 (m, 1H), 2.28-2.27 (m, 1H), 2.05-2.23 (m, 1H), 1.89-1.66 (m, 4H), 1.47-1.32 (m, 2H). LCMS M/Z (M+H) 507.

Example 183 & Example 184

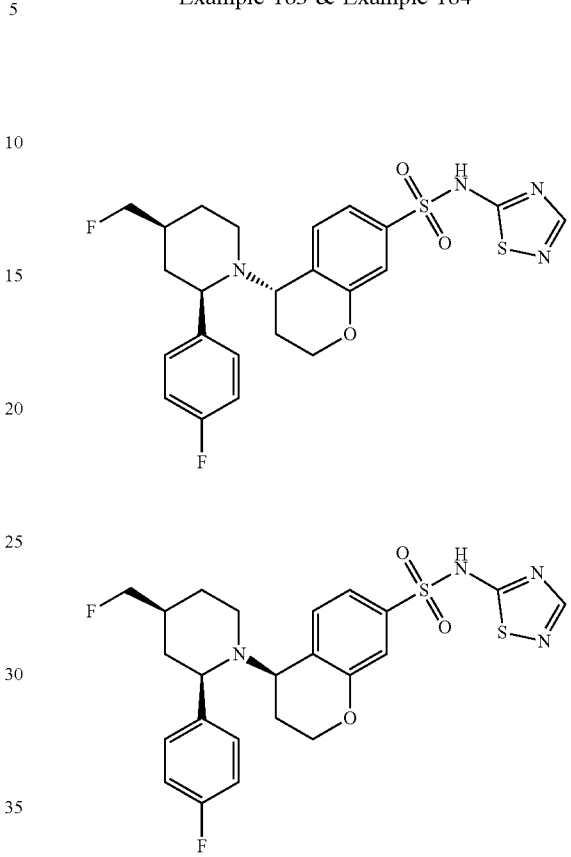

(S)-4-((2R,4S)-4-(fluoromethyl)-2-(4-fluorophenyl)piperidin-1-yl)-N-(1,2,4-thiadiazol-5-yl)chroman-7-sulfonamide & (R)-4-((2R,4S)-4-(fluoromethyl)-2-(4-fluorophenyl)piperidin-1-yl)-N-(1,2,4-thiadiazol-5-yl)chroman-7-sulfonamide Following the procedure as described in Example 181 and making non-critical variations as required to replace (2S,4R)-benzyl 4-(fluoromethyl)-2-(4-fluorophenyl)piperidine-1-carboxylate with (2R,4S)-benzyl 4-(fluoromethyl)-2-(4-fluorophenyl)piperidine-1-carboxylate, (S)-4-((2R,4S)-4-(fluoromethyl)-2-(4-fluorophenyl)piperidin-1-yl)-N-(1,2,4-thiadiazol-5-yl)chroman-7-sulfonamide (33 mg, less polar on TLC) and (R)-4-((2R,4S)-4-(fluoromethyl)-2-(4-fluorophenyl)piperidin-1-yl)-N-(1,2,4-thiadiazol-5-yl)chroman-7-sulfonamide (20 mg, more polar on TLC) were obtained as white solid. Example 183: $^1$H NMR (400 MHz, CDCl$_3$) δ 8.01 (s, 1H), 7.40-7.25 (m, 5H), 7.02-6.98 (m, 2H), 4.31-4.19 (m, 3H), 3.92-3.86 (m, 3H), 2.76-2.72 (m, 1H), 2.17-2.04 (m, 2H), 1.83-1.70 (m, 4H), 1.41-1.38 (m, 2H). LCMS M/Z (M+H) 507. Example 184: $^1$H NMR (400 MHz, CDCl$_3$) δ 7.99 (s, 1H), 7.82 (d, J=8.0 Hz, 1H), 7.44-7.37 (m, 3H), 7.25-7.23 (m, 1H), 7.03-6.99 (m, 2H), 4.34-4.22 (m, 3H), 3.85-3.82 (m, 2H), 3.63-3.60 (m, 1H), 2.71-2.68 (m, 3H), 2.35-2.29 (m, 1H), 2.10-2.07 (m, 1H), 1.91-1.70 (m, 3H), 1.49-1.26 (m, 1H). LCMS M/Z (M+H) 507.

Example 185 & Example 186

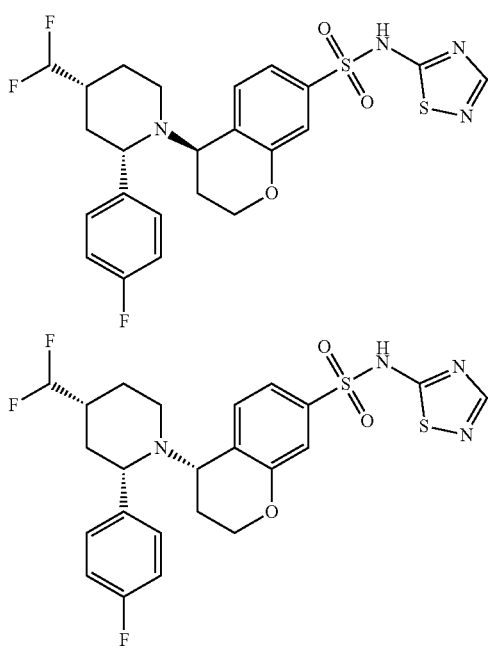

(R)-4-((2S,4R)-4-(difluoromethyl)-2-(4-fluorophenyl)piperidin-1-yl)-N-(1,2,4-thiadiazol-5-yl)chroman-7-sulfonamide & (S)-4-((2S,4R)-4-(difluoromethyl)-2-(4-fluorophenyl)piperidin-1-yl)-N-(1,2,4-thiadiazol-5-yl)chroman-7-sulfonamide Step 1:

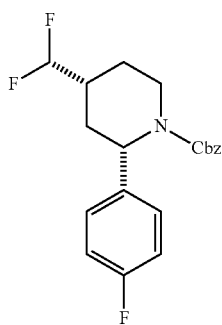 [SMILES: O=C(OCc1ccccc1)N1CC[C@@H](C(F)F)C[C@H]1c1ccc(F)cc1]

(cis)-benzyl 4-(difluoromethyl)-2-(4-fluorophenyl)piperidine-1-carboxylate

To a solution of benzyl 2-(4-fluorophenyl)-4-formylpiperidine-1-carboxylate (1.6 g, 4.69 mmol) in anhydrous DCM (25 mL) at 0° C. was added diethylaminosulfur trifluoride (2.27 g, 14.06 mmol). The reaction mixture was stirred at room temperature for 16 h. The reaction was quenched with 5% aq. NaHCO₃ (40 mL). The organic layer was washed with brine (40 mL), dried over anhydrous Na₂SO₄, filtered and concentrated in vacuo to give the title compound (1.7 g, crude) as brown oil that required no further purification. LCMS M/Z (M+H) 364.

Step 2:

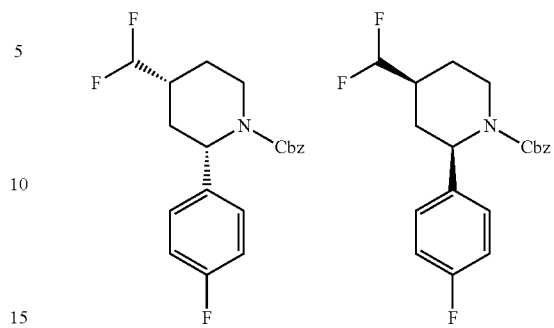

(2S,4R)-benzyl 4-(difluoromethyl)-2-(4-fluorophenyl)piperidine-1-carboxylate & (2R,4S)-benzyl 4-(difluoromethyl)-2-(4-fluorophenyl)piperidine-1-carboxylate (cis)-benzyl 4-(difluoromethyl)-2-(4-fluorophenyl)piperidine-1-carboxylate (1.0 g) was separated by using chiral SFC (Chiralpak AD (250 mm*30 mm, 5 um), 45% of methanol (0.05% DEA) in CO₂; Flow rate: 60 mL/min) to give (2S,4R)-benzyl 4-(difluoromethyl)-2-(4-fluorophenyl)piperidine-1-carboxylate (0.47 g, first peak) as colorless oil and (2R,4S)-benzyl 4-(difluoromethyl)-2-(4-fluorophenyl)piperidine-1-carboxylate (0.42 g, second peak) as colorless oil. First peak: $^1$H NMR (400 MHz, CDCl₃) δ 7.29-7.27 (m, 3H), 7.20-7.15 (m, 4H), 7.03-6.98 (m, 2H), 5.76-5.47 (m, 1H), 5.12-4.96 (m, 3H), 4.21-4.16 (m, 1H), 3.36-3.28 (m, 1H), 2.19-2.12 (m, 2H), 2.10-1.96 (m, 1H), 1.85-1.81 (m, 1H), 1.69-1.66 (m, 1H). Second peak: $^1$H NMR (400 MHz, CDCl₃) δ 7.29-7.27 (m, 3H), 7.20-7.15 (m, 4H), 7.03-6.98 (m, 2H), 5.76-5.47 (m, 1H), 5.12-4.96 (m, 3H), 4.21-4.16 (m, 1H), 3.36-3.28 (m, 1H), 2.19-2.12 (m, 2H), 2.10-1.96 (m, 1H), 1.85-1.81 (m, 1H), 1.69-1.66 (m, 1H).

Step 3:

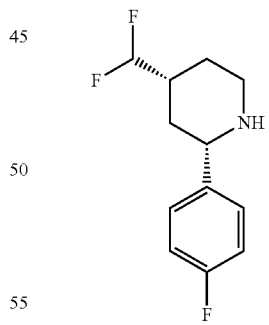

(2S,4R)-4-(difluoromethyl)-2-(4-fluorophenyl)piperidine

Following the procedure as described in Example 161, step 8 and making non-critical variations as required to replace (2S,4R)-benzyl 2-(4-fluorophenyl)-4-(methylsulfonyl)piperidine-1-carboxylate with (2S,4R)-benzyl 4-(difluoromethyl)-2-(4-fluorophenyl)piperidine-1-carboxylate, the title compound was obtained as colorless oil (200 mg, 86%).

Step 4:

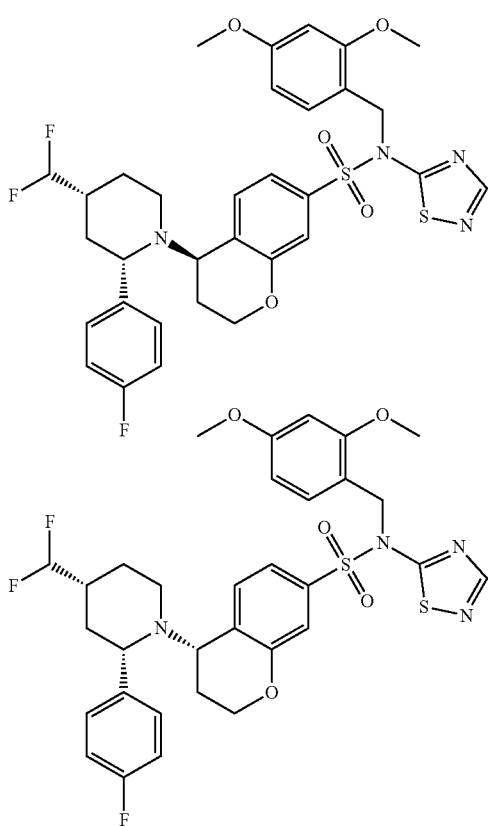

(R)-4-((2S,4R)-4-(difluoromethyl)-2-(4-fluorophenyl)piperidin-1-yl)-N-(2,4-dimethoxybenzyl)-N-(1,2,4-thiadiazol-5-yl)chroman-7-sulfonamide & (S)-4-((2S,4R)-4-(difluoromethyl)-2-(4-fluorophenyl)piperidin-1-yl)-N-(2,4-dimethoxybenzyl)-N-(1,2,4-thiadiazol-5-yl)chroman-7-sulfonamide Following the procedure as described in Example 161, step 9 and making non-critical variations as required to replace (2S,4R)-2-(4-fluorophenyl)-4-(methylsulfonyl)piperidine with (2S,4R)-4-(difluoromethyl)-2-(4-fluorophenyl)piperidine, (R)-4-((2S,4R)-4-(difluoromethyl)-2-(4-fluorophenyl)piperidin-1-yl)-N-(2,4-dimethoxybenzyl)-N-(1,2,4-thiadiazol-5-yl)chroman-7-sulfonamide (40 mg, less polar on TLC) and (S)-4-((2S,4R)-4-(difluoromethyl)-2-(4-fluorophenyl)piperidin-1-yl)-N-(2,4-dimethoxybenzyl)-N-(1,2,4-thiadiazol-5-yl)chroman-7-sulfonamide (40 mg, more polar on TLC) were obtained as white solid. LCMS M/Z (M+H) 675.

Step 5:

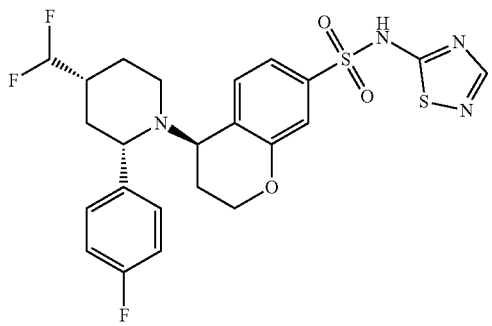

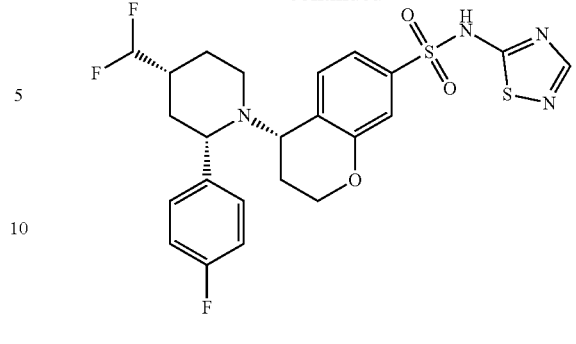

(R)-4-((2S,4R)-4-(difluoromethyl)-2-(4-fluorophenyl)piperidin-1-yl)-N-(1,2,4-thiadiazol-5-yl)chroman-7-sulfonamide & (S)-4-((2S,4R)-4-(difluoromethyl)-2-(4-fluorophenyl)piperidin-1-yl)-N-(1,2,4-thiadiazol-5-yl)chroman-7-sulfonamide Following the procedure as described in Example 161, step 10 and making non-critical variations as required to replace (S)—N-(2,4-dimethoxybenzyl)-4-((2S,4R)-2-(4-fluorophenyl)-4-(methyl sulfonyl)piperidin-1-yl)-N-(1,2,4-thiadiazol-5-yl)chroman-7-sulfonamide with (R)-4-((2S,4R)-4-(difluoromethyl)-2-(4-fluorophenyl)piperidin-1-yl)-N-(2,4-dimethoxybenzyl)-N-(1,2,4-thiadiazol-5-yl)chroman-7-sulfonamide & (S)-4-((2S,4R)-4-(difluoromethyl)-2-(4-fluorophenyl)piperidin-1-yl)-N-(2,4-dimethoxybenzyl)-N-(1,2,4-thiadiazol-5-yl)chroman-7-sulfonamide, (R)-4-((2S,4R)-4-(difluoromethyl)-2-(4-fluorophenyl)piperidin-1-yl)-N-(1,2,4-thiadiazol-5-yl)chroman-7-sulfonamide (7 mg, less polar on TLC) and (S)-4-((2S,4R)-4-(difluoromethyl)-2-(4-fluorophenyl)piperidin-1-yl)-N-(1,2,4-thiadiazol-5-yl)chroman-7-sulfonamide (13 mg, more polar on TLC) were obtained as white solid. Example 185: $^1$H NMR (400 MHz, CDCl$_3$) δ 8.02 (s, 1H), 7.40-7.30 (m, 4H), 7.27-7.24 (m, 1H), 7.02-7.00 (m, 2H), 5.71-5.41 (m, 1H), 4.26-4.23 (m, 1H), 3.95-3.85 (m, 3H), 2.77-2.74 (m, 1H), 2.17-2.10 (m, 2H), 1.88-1.75 (m, 4H), 1.54-1.49 (m, 2H). LCMS M/Z (M+H) 525. Example 186: $^1$H NMR (400 MHz, CDCl$_3$) δ 7.90 (s, 1H), 7.69 (d, J=7.2 Hz, 1H), 7.36-7.34 (m, 3H), 7.18-7.16 (m, 1H), 7.01-6.97 (m, 2H), 5.57 (t, J=57.6 Hz, 1H), 4.20-4.17 (m, 1H), 3.77-3.74 (m, 2H), 3.57-3.54 (m, 1H), 2.64-2.62 (m, 1H), 2.21-2.15 (m, 1H), 1.99-1.88 (m, 3H), 1.76-1.62 (m, 2H), 1.61-1.51 (m, 1H), 1.50-1.35 (m, 1H). LCMS M/Z (M+H) 525.

Example 187 & Example 188

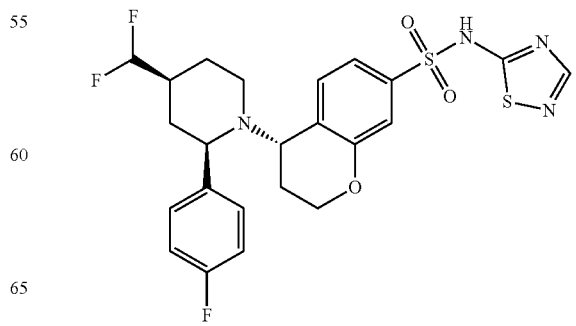

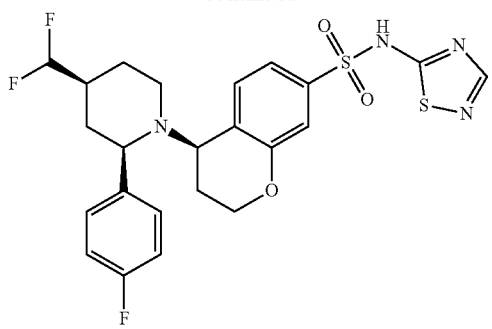

(S)-4-((2R,4S)-4-(difluoromethyl)-2-(4-fluorophenyl)piperidin-1-yl)-N-(1,2,4-thiadiazol-5-yl)chroman-7-sulfonamide & (R)-4-((2R,4S)-4-(difluoromethyl)-2-(4-fluorophenyl)piperidin-1-yl)-N-(1,2,4-thiadiazol-5-yl)chroman-7-sulfonamide Following the procedure as described in Example 185 and making non-critical variations as required to replace (2S, 4R)-benzyl 4-(difluoromethyl)-2-(4-fluorophenyl)piperidine-1-carboxylate with (2R,4S)-benzyl 4-(difluoromethyl)-2-(4-fluorophenyl)piperidine-1-carboxylate, (S)-4-((2R,4S)-4-(difluoromethyl)-2-(4-fluorophenyl)piperidin-1-yl)-N-(1,2,4-thiadiazol-5-yl)chroman-7-sulfonamide (26 mg, less polar on TLC) and (R)-4-((2R,4S)-4-(difluoromethyl)-2-(4-fluorophenyl)piperidin-1-yl)-N-(1,2,4-thiadiazol-5-yl)chroman-7-sulfonamide (4 mg, more polar on TLC) were obtained as white solid. Example 187: $^1$H NMR (400 MHz, CDCl$_3$) δ 8.01 (s, 1H), 7.40-7.30 (m, 4H), 7.27-7.25 (m, 1H), 7.02-7.00 (m, 2H), 5.71-5.42 (m, 1H), 4.26-4.22 (m, 1H), 3.96-3.86 (m, 3H), 2.78-2.75 (m, 1H), 2.18-2.11 (m, 2H), 1.90-1.83 (m, 4H), 1.53-1.49 (m, 2H). LCMS M/Z (M+H) 525. Example 188: $^1$H NMR (400 MHz, CDCl$_3$) δ 8.00 (s, 1H), 7.80 (d, J=7.2 Hz, 1H), 7.43-7.37 (m, 3H), 7.25-7.23 (m, 1H), 7.04-7.00 (m, 2H), 5.60 (t, J=55.2 Hz, 1H), 4.31-4.27 (m, 1H), 3.86-3.83 (m, 2H), 3.62-3.59 (m, 1H), 2.74-2.71 (m, 1H), 2.33-2.27 (m, 1H), 2.15-1.87 (m, 3H), 1.85-1.62 (m, 2H), 1.66-1.42 (m, 2H). LCMS M/Z (M+H) 525.

Example 189

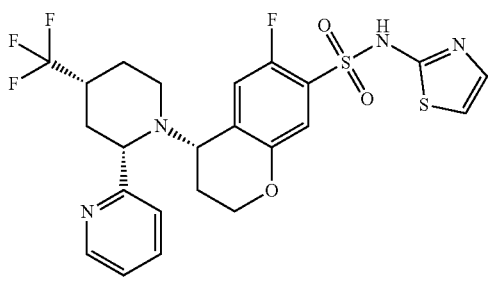 [SMILES: O=S(=O)(Nc1nccs1)c1cc2c(cc1F)[C@@H](N1CC[C@@H](C(F)(F)F)C[C@H]1c1ccccn1)CCO2]

(S)-6-fluoro-4-((2S,4R)-2-(pyridin-2-yl)-4-(trifluoromethyl)piperidin-1-yl)-N-(thiazol-2-yl)chroman-7-sulfonamide

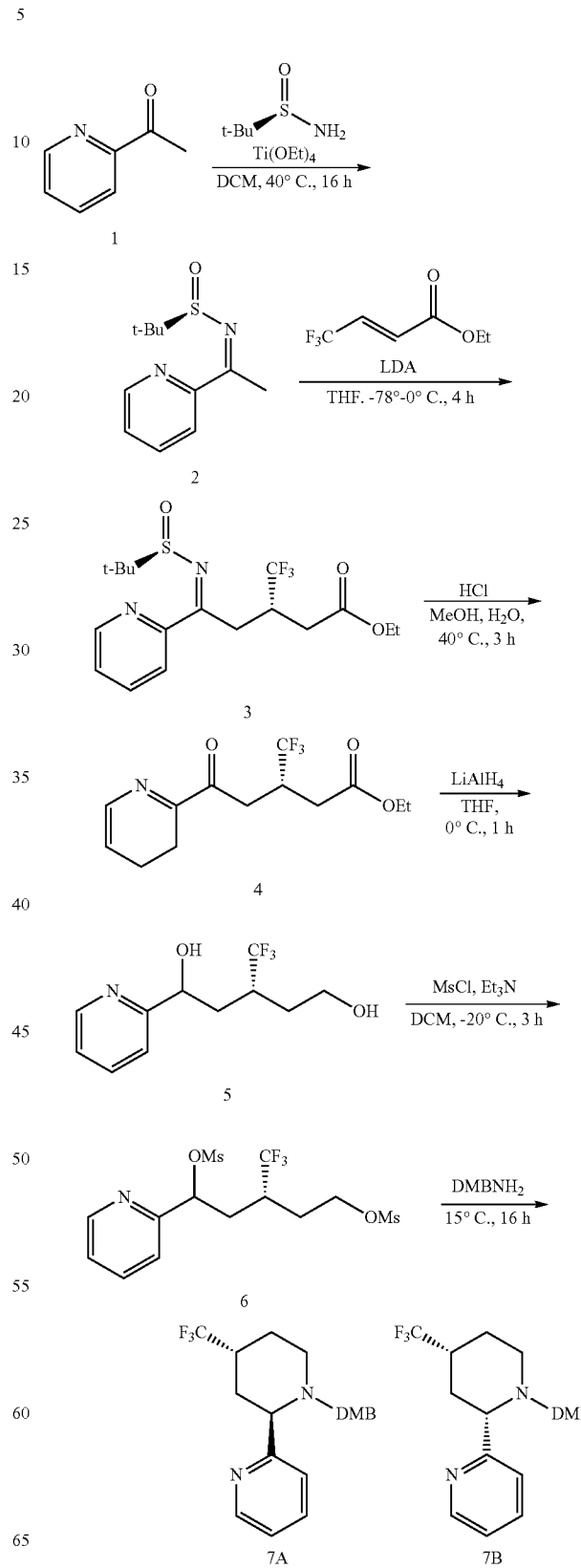

405
-continued

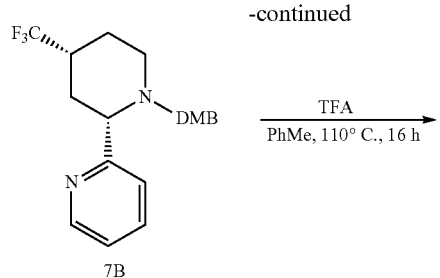
7B

→ TFA, PhMe, 110° C., 16 h

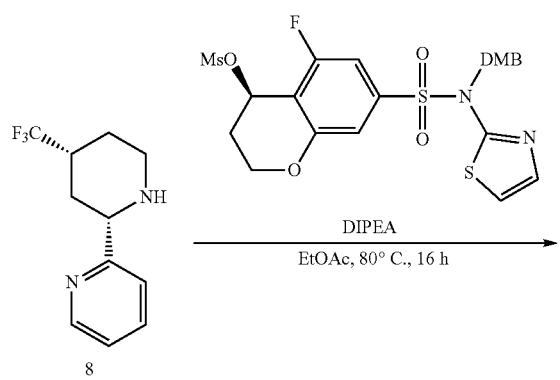
8

→ DIPEA, EtOAc, 80° C., 16 h

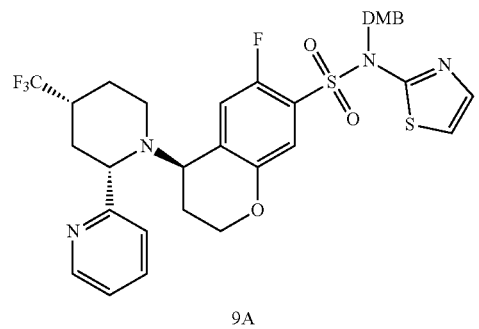
9A

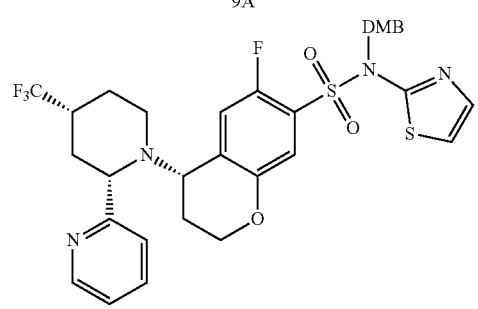
9B

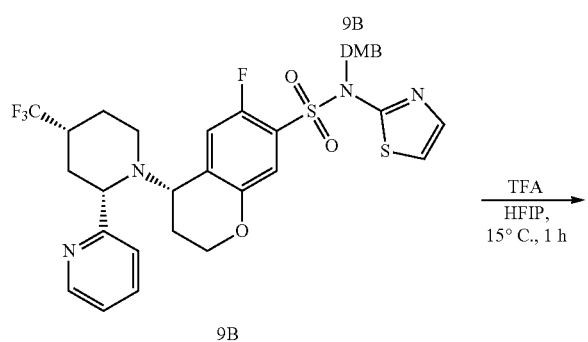
9B

→ TFA, HFIP, 15° C., 1 h

406
-continued

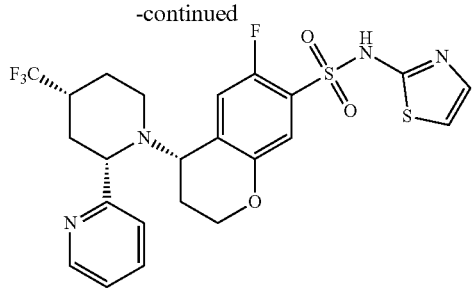
10

Step 1:

(R,Z)-2-methyl-N-(1-(pyridin-2-yl)ethylidene)propane-2-sulfinamide

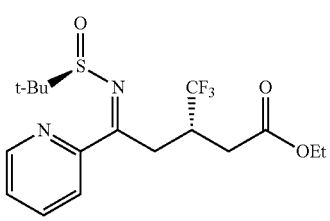 [SMILES: CCOC(=O)C[C@H](C/C(=N/[S@](=O)C(C)(C)C)c1ccccn1)C(F)(F)F]

To a mixture of (R)-2-methylpropane-2-sulfinamide (11.01 g, 90.8 mmol) and 1-(pyridin-2-yl)ethanone (10.0 g, 82.55 mmol) in DCM (300 mL) was slowly added titanium (IV) ethoxide (33.93 mL, 165.1 mmol) under a nitrogen atmosphere. The reaction mixture was heated to 40° C. for 16 h. Sat. aq. NaHCO$_3$ (40 mL) was added and filtered through a short pad of anhydrous Na$_2$SO$_4$, washed with DCM (500 mL). The organic layer was concentrated in vacuo. The crude residue was purified by silica gel chromatography (petroleum ether/EtOAc=5:1) to give the title compound (8.2 g, 44%) as a yellow solid. $^1$H NMR (400 MHz, CDCl$_3$) δ 8.66 (d, J=4.4 Hz, 1H), 8.14 (d, J=8.0 Hz, 1H), 7.81-7.73 (m, 1H), 7.43-7.33 (m, 1H), 2.88 (s, 3H), 1.34 (s, 9H).

Step 2:

(S,Z)-ethyl 5-(((R)-tert-butylsulfinyl)imino)-5-(pyridin-2-yl)-3-(trifluoromethyl)pentanoate To a solution of (R,Z)-2-methyl-N-(1-(pyridin-2-yl)ethylidene)propane-2-sulfinamide (5.7 g, 25.41 mmol) in anhydrous THF (60 mL) at −78° C. was added lithium diisopropylamide (2.0 M, 31.76 mL, 63.53 mmol). The reaction mixture was stirred at −78° C. for 1 h, ethyl 4,4,4-trifluorobut-2-enoate (8.54 g, 50.82 mmol) in anhydrous THF (10.0 mL) was added. The reaction mixture was warmed up to 0° C. over 20 min period and stirred at 0° C. for 3 h. The reaction was quenched with sat. aq. ammonium chloride (150 mL), extracted with EtOAc (150 mL×2), washed with brine (150 mL), dried over anhydrous Na$_2$SO$_4$, filtered and concentrated in vacuo. The crude residue was purified by silica gel chromatography (petroleum ether/EtOAc=5:1) to give the title compound (2.9 g, 29%) as yellow oil. $^1$H NMR (400 MHz, CDCl$_3$) δ 8.67 (d, J=4.8 Hz, 1H), 8.00 (s, 1H), 7.81-7.74 (m, 1H), 7.43-7.35 (m, 1H), 4.09-3.92 (m, 3H), 3.64-3.46 (m, 2H), 2.68 (d, J=6.0 Hz, 2H), 1.36 (s, 9H), 1.17 (t, J=7.2 Hz, 3H).

Step 3:

(S)-ethyl 5-oxo-5-(pyridin-2-yl)-3-(trifluoromethyl) pentanoate

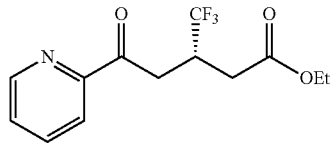 [SMILES: CCOC(=O)C[C@H](CC(=O)c1ccccn1)C(F)(F)F]

To a solution of (S,Z)-ethyl 5-(((R)-tert-butylsulfinyl) imino)-5-(pyridin-2-yl)-3-(trifluoromethyl)pentanoate (2.2 g, 5.61 mmol) in MeOH (22.0 mL) was added aq. HCl (4.0 M, 7.0 mL, 28.03 mmol). The reaction mixture was stirred at 40° C. for 3 h. EtOAc (200 mL) was added, washed with sat. aq. Na$_2$CO$_3$ (150 mL), brine (150 mL), dried over anhydrous Na$_2$SO$_4$, filtered and concentrated in vacuo. The crude residue was purified by silica gel chromatography (petroleum ether/EtOAc=10:1) to give the title compound (1.25 g, 77%) as yellow oil. LCMS M/Z (M+H) 290.

Step 4:

(3R)-1-(pyridin-2-yl)-3-(trifluoromethyl)pentane-1, 5-diol

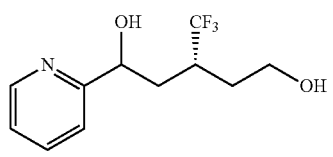 [SMILES: OCC[C@H](CC(O)c1ccccn1)C(F)(F)F]

To a solution of lithium aluminium hydride (0.49 g, 12.96 mmol) in anhydrous THF (20.0 mL) at 0° C. was added (S)-ethyl 5-oxo-5-(pyridin-2-yl)-3-(trifluoromethyl)pentanoate (1.25 g, 4.32 mmol) in anhydrous THF (10.0 mL) dropwise under a nitrogen atmosphere. The reaction mixture was stirred at 0° C. for 1 h. The reaction was quenched with water (0.5 mL) and 15% aq. NaOH (0.5 mL), dried over anhydrous MgSO$_4$, filtered. The filtrate was concentrated in vacuo to give the title compound (0.95 g, crude) as light yellow oil that required no further purification. LCMS M/Z (M+H) 250.

Step 5:

(3R)-1-(pyridin-2-yl)-3-(trifluoromethyl)pentane-1, 5-diyl dimethanesulfonate

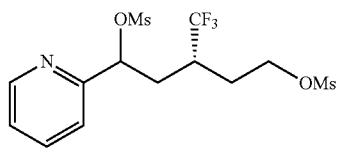 [SMILES: CS(=O)(=O)OCC[C@H](CC(OS(C)(=O)=O)c1ccccn1)C(F)(F)F]

To a solution of methanesulfonyl chloride (1.03 mL, 13.34 mmol) in DCM (15 mL) at −20° C. was added triethylamine (2.66 mL, 19.06 mmol) and (3R)-1-(pyridin-2-yl)-3-(trifluoromethyl)pentane-1,5-diol (0.95 g, 3.81 mmol) in DCM (5 mL) dropwise. The reaction mixture was stirred at −20° C. for 3 h. DCM (100 mL) was added, washed with sat. aq. NaHCO$_3$ (50 mL), water (50 mL), brine (50 mL), dried over anhydrous Na$_2$SO$_4$, filtered and concentrated in vacuo to give the title compound (1.5 g, crude) as colorless oil that required no further purification. $^1$H NMR (400 MHz, CDCl$_3$) δ 8.65 (d, J=4.4 Hz, 1H), 7.82-7.78 (m, 1H), 7.53-7.46 (m, 1H), 7.38-7.30 (m, 1H), 5.81-5.73 (m, 1H), 4.44-4.33 (m, 2H), 3.08 (s, 3H), 2.91 (s, 3H), 2.55-2.44 (m, 1H), 2.34-2.18 (m, 4H).

Step 6:

2-((2R,4R)-1-(2,4-dimethoxybenzyl)-4-(trifluoromethyl)piperidin-2-yl)pyridine & 2-((2S,4R)-1-(2,4-dimethoxybenzyl)-4-(trifluoromethyl)piperidin-2-yl) pyridine

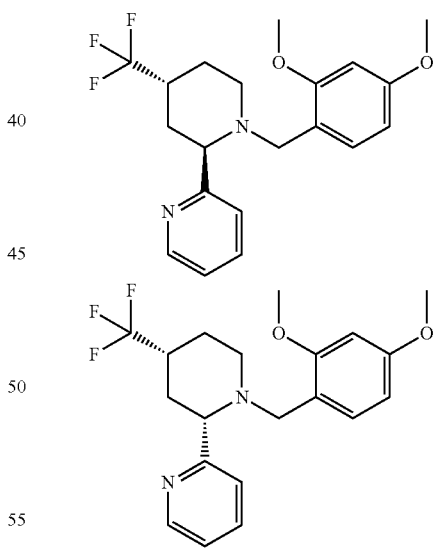

A mixture of (3R)-1-(pyridin-2-yl)-3-(trifluoromethyl) pentane-1,5-diyl dimethanesulfonate (1.5 g, 3.7 mmol) and 2,4-dimethoxybenzylamine (15 mL, 99.58 mmol) was stirred at 15° C. for 16 h. The mixture was purified by silica gel chromatography (petroleum ether/EtOAc=5:1) to give 2-((2R,4R)-1-(2,4-dimethoxybenzyl)-4-(trifluoromethyl)piperidin-2-yl)pyridine (260 mg, less polar on TLC) as colorless oil and 2-((2S,4R)-1-(2,4-dimethoxybenzyl)-4-(trifluoromethyl)piperidin-2-yl)pyridine (550 mg, more polar on TLC) as colorless oil. Trans-isomer: $^1$H NMR (400 MHz, CDCl$_3$) δ 8.57 (d, J=4.0 Hz, 1H), 7.68-7.61 (m, 1H), 7.52 (d, J=8.0 Hz, 1H), 7.31 (d, J=8.4 Hz, 1H), 7.18-7.11 (m, 1H), 6.48 (d, J=8.4 Hz, 1H), 6.44 (s, 2H), 4.00-3.94 (m, 1H), 3.81 (s, 3H), 3.76 (s, 3H), 3.69-3.52 (m, 2H), 3.03-2.92 (m, 1H), 2.72-2.58 (m, 2H), 2.31-2.22 (m, 1H), 2.13-2.04 (m, 1H), 1.91-1.81 (m, 1H), 1.80-1.71 (m, 1H). LCMS M/Z (M+H) 381. Cis-isomer: $^1$H NMR (400 MHz, CDCl$_3$) δ 8.56 (d, J=4.4 Hz, 1H), 7.72-7.65 (m, 1H), 7.65-7.59 (m, 1H), 7.25 (d, J=8.4 Hz, 1H), 7.21-7.15 (m, 1H), 6.52-6.42 (m, 1H), 6.40 (d, J=2.0 Hz, 1H), 3.80 (s, 3H), 3.72 (s, 3H), 3.55-3.48 (m, 1H), 3.47-3.41 (m, 1H), 3.21-3.11 (m, 2H), 2.31-2.15 (m, 1H), 2.13-2.02 (m, 2H), 1.91-1.80 (m, 1H), 1.76-1.64 (m, 2H). LCMS M/Z (M+H) 381.

Step 7:

2-((2S,4R)-4-(trifluoromethyl)piperidin-2-yl)pyridine

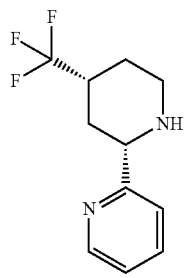 [SMILES: FC(F)(F)[C@@H]1CCN[C@H](c2ccccn2)C1]

To a solution of 2-((2S,4R)-1-(2,4-dimethoxybenzyl)-4-(trifluoromethyl)piperidin-2-yl)pyridine (550 mg, 1.45 mmol) in toluene (10 mL) was added trifluoroacetic acid (3.22 mL, 43.38 mmol). The mixture was heated to 110° C. for 16 h. After cooling to room temperature, the mixture was concentrated in vacuo. EtOAc (150 mL) was added, washed with aq. NaOH (1.0 M, 100 mL), brine (100 mL), dried over anhydrous Na$_2$SO$_4$, filtered and concentrated in vacuo. The crude residue was purified by silica gel chromatography (DCM/MeOH=20:1) to give the title compound (320 mg, 96%) as brown oil. $^1$H NMR (400 MHz, CDCl$_3$) δ 8.57 (d, J=3.6 Hz, 1H), 7.73-7.64 (m, 1H), 7.36 (d, J=8.0 Hz, 1H), 7.23-7.16 (m, 1H), 3.83-3.76 (m, 2H), 3.42-3.33 (m, 1H), 2.91-2.80 (m, 1H), 2.45-2.29 (m, 1H), 2.23-2.15 (m, 1H), 1.97-1.88 (m, 1H), 1.65-1.52 (m, 2H).

Step 8:

(R)—N-(2,4-dimethoxybenzyl)-6-fluoro-4-((2S,4R)-2-(pyridin-2-yl)-4-(trifluoromethyl)piperidin-1-yl)-N-(thiazol-2-yl)chroman-7-sulfonamide & (S)—N-(2,4-dimethoxybenzyl)-6-fluoro-4-((2S,4R)-2-(pyridin-2-yl)-4-(trifluoromethyl)piperidin-1-yl)-N-(thiazol-2-yl)chroman-7-sulfonamide

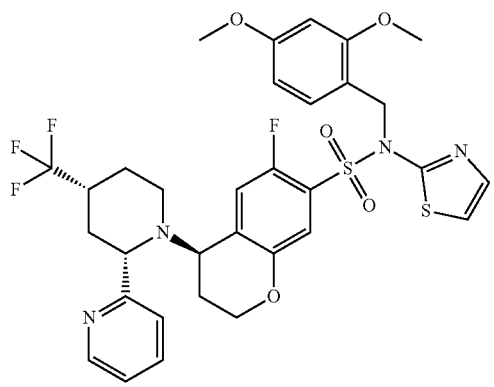

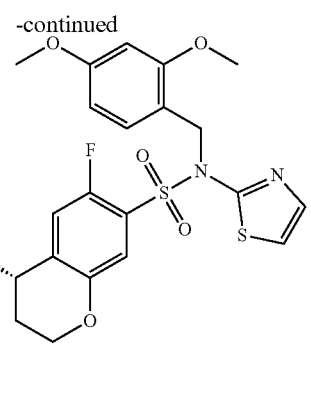

To a solution of 2-((2S,4R)-4-(trifluoromethyl)piperidin-2-yl)pyridine (130 mg, 0.56 mmol) and N,N-diisopropylethylamine (0.49 mL, 2.82 mmol) in EtOAc (10 mL) was added (R)-7-(N-(2,4-dimethoxybenzyl)-N-(thiazol-2-yl)sulfamoyl)-6-fluorochroman-4-yl methanesulfonate (473 mg, 0.85 mmol). The reaction mixture was heated to 80° C. for 16 h under a nitrogen atmosphere. After cooling to room temperature, the mixture was concentrated in vacuo. The crude residue was purified by Prep-TLC (petroleum ether/EtOAc=1:1) to give (R)—N-(2,4-dimethoxybenzyl)-6-fluoro-4-((2S,4R)-2-(pyridin-2-yl)-4-(trifluoromethyl)piperidin-1-yl)-N-(thiazol-2-yl)chroman-7-sulfonamide (120 mg, less polar on TLC) as colorless oil and (S)—N-(2,4-dimethoxybenzyl)-6-fluoro-4-((2S,4R)-2-(pyridin-2-yl)-4-(trifluoromethyl)piperidin-1-yl)-N-(thiazol-2-yl)chroman-7-sulfonamide (150 mg, more polar on TLC) as colorless oil. LCMS M/Z (M+H) 693.

Step 9:

(S)-6-fluoro-4-((2S,4R)-2-(pyridin-2-yl)-4-(trifluoromethyl)piperidin-1-yl)-N-(thiazol-2-yl)chroman-7-sulfonamide

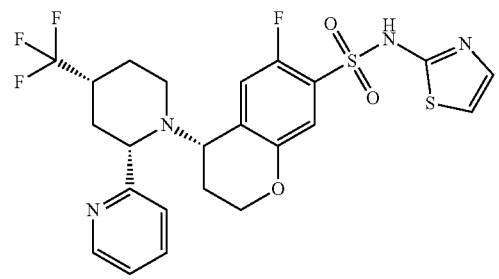 [SMILES: O=S(=O)(Nc1nccs1)c1cc2c(cc1F)[C@@H](N1CC[C@@H](C(F)(F)F)C[C@H]1c1ccccn1)CCO2]

A mixture of (S)—N-(2,4-dimethoxybenzyl)-6-fluoro-4-((2S,4R)-2-(pyridin-2-yl)-4-(trifluoromethyl)piperidin-1-yl)-N-(thiazol-2-yl)chroman-7-sulfonamide (150 mg, 0.22 mmol) and trifluoroacetic acid in 1,1,1,3,3,3-hexafluoropropan-2-ol (1.0 M, 5 mL) was stirred at 15° C. for 1 h. The mixture was concentrated in vacuo. The crude residue was purified by reverse phase chromatography (acetonitrile 35-65%/0.225% formic acid in water) to give the title compound (53 mg, 45%) as a white solid. $^1$H NMR (400 MHz, CD$_3$OD) δ 8.51 (d, J=4.4 Hz, 1H), 7.91-7.83 (m, 1H), 7.70 (d, J=8.0 Hz, 1H), 7.60 (d, J=10.4 Hz, 1H), 7.42-7.30 (m, 1H), 7.18 (d, J=5.6 Hz, 1H), 7.12 (d, J=4.4 Hz, 1H), 6.74 (d, J=4.8 Hz, 1H), 4.31-4.22 (m, 1H), 3.94-3.85 (m, 1H), 3.84-3.74 (m, 1H), 3.69-3.59 (m, 1H), 2.76-2.68 (m, 1H), 2.49-2.33 (m, 2H), 2.18-2.06 (m, 1H), 2.03-1.96 (m, 1H), 1.94-1.78 (m, 3H), 1.72-1.58 (m, 1H). LCMS M/Z (M+H) 543.

Example 190

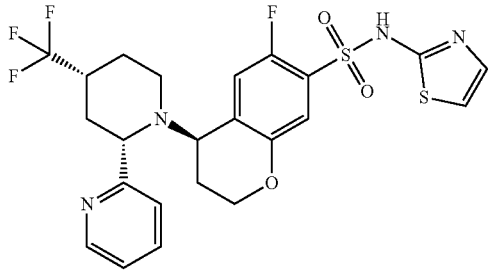 [SMILES: O=S(=O)(Nc1nccs1)c1cc2c(cc1F)[C@H](N1CC[C@@H](C(F)(F)F)C[C@H]1c1ccccn1)CCO2]

(R)-6-fluoro-4-((2S,4R)-2-(pyridin-2-yl)-4-(trifluoromethyl)piperidin-1-yl)-N-(thiazol-2-yl)chroman-7-sulfonamide Following the procedure as described in Example 189, step 9 and making non-critical variations as required to replace (S)—N-(2,4-dimethoxybenzyl)-6-fluoro-4-((2S, 4R)-2-(pyridin-2-yl)-4-(trifluoromethyl)piperidin-1-yl)-N-(thiazol-2-yl)chroman-7-sulfonamide with (R)—N-(2,4-dimethoxybenzyl)-6-fluoro-4-((2S,4R)-2-(pyridin-2-yl)-4-(trifluoromethyl)piperidin-1-yl)-N-(thiazol-2-yl)chroman-7-sulfonamide, the title compound was obtained as a white solid (37 mg, 39%). $^1$H NMR (400 MHz, CD$_3$OD) δ 8.38 (d, J=4.4 Hz, 1H), 7.66-7.56 (m, 1H), 7.43 (d, J=8.0 Hz, 1H), 7.26 (d, J=10.4 Hz, 1H), 7.15 (d, J=4.8 Hz, 1H), 7.14-7.08 (m, 1H), 7.02 (d, J=5.6 Hz, 1H), 6.78 (d, J=4.4 Hz, 1H), 4.30-4.21 (m, 1H), 4.05-3.97 (m, 1H), 3.93-3.80 (m, 2H), 3.07-2.97 (m, 1H), 2.55-2.43 (m, 1H), 2.42-2.25 (m, 2H), 2.04-1.72 (m, 5H). LCMS M/Z (M+H) 543.

Example 191 & Example 192

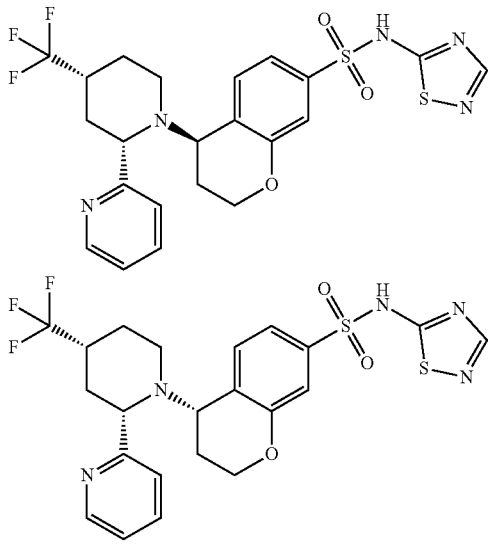

(R)-4-((2S,4R)-2-(pyridin-2-yl)-4-(trifluoromethyl)piperidin-1-yl)-N-(1,2,4-thiadiazol-5-yl)chroman-7-sulfonamide & (S)-4-((2S,4R)-2-(pyridin-2-yl)-4-(trifluoromethyl)piperidin-1-yl)-N-(1,2,4-thiadiazol-5-yl)chroman-7-sulfonamide Following the procedure as described in Example 189 and making non-critical variations as required to replace (R)-7-(N-(2,4-dimethoxybenzyl)-N-(thiazol-2-yl)sulfamoyl)-6-fluorochroman-4-yl methanesulfonate with (R)-7-(N-(2,4-dimethoxybenzyl)-N-(1,2,4-thiadiazol-5-yl)sulfamoyl)chroman-4-yl methanesulfonate, (R)-4-((2S,4R)-2-(pyridin-2-yl)-4-(trifluoromethyl)piperidin-1-yl)-N-(1,2,4-thiadiazol-5-yl)chroman-7-sulfonamide (33 mg, less polar on TLC) and (S)-4-((2S,4R)-2-(pyridin-2-yl)-4-(trifluoromethyl)piperidin-1-yl)-N-(1,2,4-thiadiazol-5-yl)chroman-7-sulfonamide (52 mg, more polar on TLC) were obtained as white solid. Example 191: $^1$H NMR (400 MHz, CD$_3$OD) δ 8.44 (d, J=4.4 Hz, 1H), 8.16 (s, 1H), 7.75-7.64 (m, 1H), 7.53-7.47 (m, 2H), 7.40-7.30 (m, 1H), 7.26-7.19 (m, 1H), 7.08 (s, 1H), 4.32-4.24 (m, 1H), 4.23-4.15 (m, 1H), 4.01-3.87 (m, 2H), 3.06-2.98 (m, 1H), 2.47-2.25 (m, 3H), 2.03-1.90 (m, 3H), 1.86-1.72 (m, 2H). LCMS M/Z (M+H) 526. Example 192: $^1$H NMR (400 MHz, CD$_3$OD) δ 8.52 (d, J=4.8 Hz, 1H), 8.16 (s, 1H), 7.91-7.85 (m, 2H), 7.73 (d, J=7.6 Hz, 1H), 7.43-7.33 (m, 2H), 7.14 (d, J=1.6 Hz, 1H), 4.33-4.25 (m, 1H), 3.98-3.90 (m, 1H), 3.87-3.78 (m, 1H), 3.76-3.68 (m, 1H), 2.79-2.69 (m, 1H), 2.50-2.35 (m, 2H), 2.21-2.09 (m, 1H), 2.05-1.98 (m, 1H), 1.97-1.77 (m, 3H), 1.71-1.60 (m, 1H). LCMS M/Z (M+H) 526.

Example 193 & Example 194

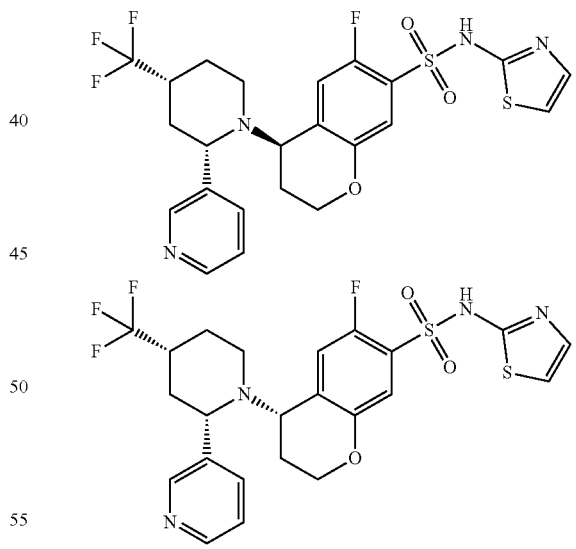

(R)-6-fluoro-4-((2S,4R)-2-(pyridin-3-yl)-4-(trifluoromethyl)piperidin-1-yl)-N-(thiazol-2-yl)chroman-7-sulfonamide & (S)-6-fluoro-4-((2S,4R)-2-(pyridin-3-yl)-4-(trifluoromethyl)piperidin-1-yl)-N-(thiazol-2-yl)chroman-7-sulfonamide Following the procedure as described in Example 189 and making non-critical variations as required to replace 1-(pyridin-2-yl)ethanone with 1-(pyridin-3-yl)ethanone, (R)-6- fluoro-4-((2S,4R)-2-(pyridin-3-yl)-4-(trifluoromethyl)piperidin-1-yl)-N-(thiazol-2-yl)chroman-7-sulfonamide (13 mg, less polar on TLC) and (S)-6-fluoro-4-((2S,4R)-2-(pyridin-3-yl)-4-(trifluoromethyl)piperidin-1-yl)-N-(thiazol-2-yl)chroman-7-sulfonamide (22 mg, more polar on TLC) were obtained as white solid. Example 193: $^1$H NMR (400 MHz, CD$_3$OD) δ 8.55 (s, 1H), 8.25 (s, 1H), 7.79 (d, J=6.8 Hz, 1H), 7.30-7.10 (m, 3H), 7.20 (d, J=5.6 Hz, 1H), 6.78 (d, J=4.8 Hz, 1H), 4.30-4.20 (m, 1H), 4.05-3.90 (m, 2H), 3.90-3.80 (m, 1H), 3.02-2.97 (m, 1H), 2.60-2.15 (m, 3H), 2.05-1.60 (m, 5H). LCMS M/Z (M+H) 543. Example 194: $^1$H NMR (400 MHz, CD$_3$OD) δ 8.64 (s, 1H), 8.48 (d, J=3.2 Hz, 1H), 8.04 (d, J=7.2 Hz, 1H), 7.58-7.40 (m, 2H), 7.25-7.10 (m, 2H), 6.74 (d, J=4.4 Hz, 1H), 4.35-4.20 (m, 1H), 3.90-3.65 (m, 3H), 2.73-2.70 (m, 1H), 2.50-2.30 (m, 2H), 2.20-1.55 (m, 6H). LCMS M/Z (M+H) 543.

Example 195 & Example 196

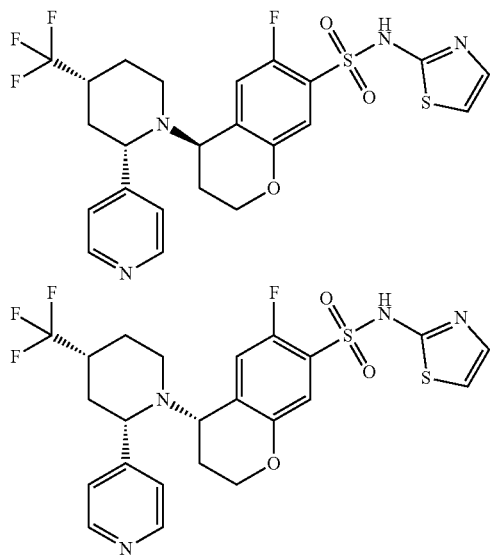

(R)-6-fluoro-4-((2S,4R)-2-(pyridin-4-yl)-4-(trifluoromethyl)piperidin-1-yl)-N-(thiazol-2-yl)chroman-7-sulfonamide & (S)-6-fluoro-4-((2S,4R)-2-(pyridin-4-yl)-4-(trifluoromethyl)piperidin-1-yl)-N-(thiazol-2-yl)chroman-7-sulfonamide Following the procedure as described in Example 189 and making non-critical variations as required to replace 1-(pyridin-2-yl)ethanone with 1-(pyridin-4-yl)ethanone, (R)-6-fluoro-4-((2S,4R)-2-(pyridin-4-yl)-4-(trifluoromethyl)piperidin-1-yl)-N-(thiazol-2-yl)chroman-7-sulfonamide (4 mg, less polar on TLC) and (S)-6-fluoro-4-((2S,4R)-2-(pyridin-4-yl)-4-(trifluoromethyl)piperidin-1-yl)-N-(thiazol-2-yl)chroman-7-sulfonamide (6 mg, more polar on TLC) were obtained as white solid. Example 195: $^1$H NMR (400 MHz, CD$_3$OD) δ 8.44 (d, J=5.2 Hz, 2H), 7.50 (d, J=5.6 Hz, 2H), 7.25-7.10 (m, 3H), 6.75 (d, J=4.4 Hz, 1H), 4.30-4.15 (m, 1H), 4.05 (d, J=9.2 Hz, 1H), 3.95-3.60 (m, 2H), 2.94-2.89 (m, 1H), 2.45-2.30 (m, 2H), 2.25-2.10 (m, 1H), 2.05-1.80 (m, 3H), 1.75-1.50 (m, 2H). LCMS M/Z (M+H) 543. Example 196: $^1$H NMR (400 MHz, CD$_3$OD) δ 8.52 (d, J=5.6 Hz, 2H), 7.59 (d, J=5.6 Hz, 2H), 7.54 (d, J=10.8 Hz, 1H), 7.18 (d, J=5.6 Hz, 1H), 7.12 (d, J=4.8 Hz, 1H), 6.74 (d, J=4.4 Hz, 1H), 4.35-4.20 (m, 1H), 3.90-3.70 (m, 3H), 2.73-2.68 (m, 1H), 2.50-2.35 (m, 2H), 2.20-1.80 (m, 4H), 1.75-1.55 (m, 2H). LCMS M/Z (M+H) 543.

Example 197 & Example 198

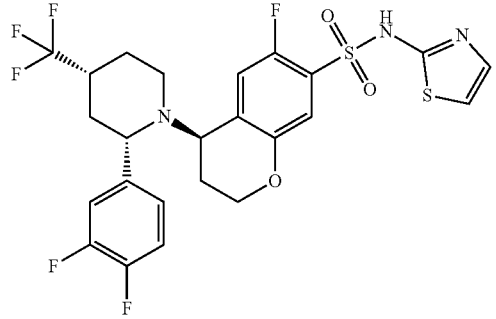

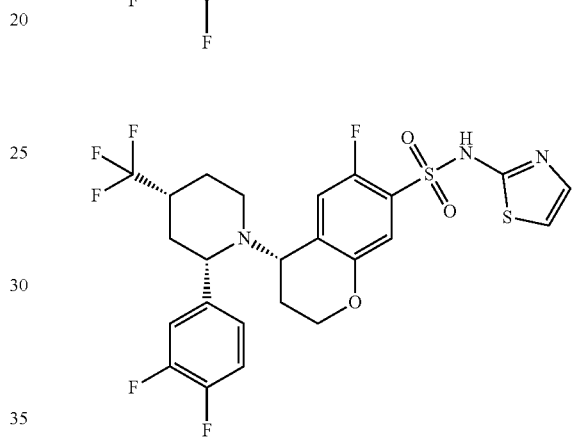

(R)-4-((2S,4R)-2-(3,4-difluorophenyl)-4-(trifluoromethyl)piperidin-1-yl)-6-fluoro-N-(thiazol-2-yl)chroman-7-sulfonamide & (S)-4-((2S,4R)-2-(3,4-difluorophenyl)-4-(trifluoromethyl)piperidin-1-yl)-6-fluoro-N-(thiazol-2-yl)chroman-7-sulfonamide Following the procedure as described in Example 189 and making non-critical variations as required to replace 1-(pyridin-2-yl)ethanone with 1-(3,4-difluorophenyl)ethanone, (R)-4-((2S,4R)-2-(3,4-difluorophenyl)-4-(trifluoromethyl)piperidin-1-yl)-6-fluoro-N-(thiazol-2-yl)chroman-7-sulfonamide (50 mg, less polar on TLC) and (S)-4-((2S,4R)-2-(3,4-difluorophenyl)-4-(trifluoromethyl)piperidin-1-yl)-6-fluoro-N-(thiazol-2-yl)chroman-7-sulfonamide (53 mg, more polar on TLC) were obtained as white solid. Example 197: $^1$H NMR (400 MHz, DMSO-d$_6$) δ 12.90 (s, 1H), 7.53-7.51 (m, 1H), 7.35-7.29 (m, 3H), 7.23 (d, J=10.4 Hz, 1H), 7.04 (d, J=6.0 Hz, 1H), 6.87 (d, J=4.8 Hz, 1H), 4.20-4.16 (m, 2H), 3.90-3.83 (m, 2H), 2.77-2.74 (m, 1H), 2.25-2.24 (m, 1H), 1.99-1.98 (m, 1H), 1.84-1.77 (m, 3H), 1.53-1.48 (m, 2H). LCMS M/Z (M+H) 578. Example 198: $^1$H NMR (400 MHz, DMSO-d$_6$) δ 12.90 (s, 1H), 7.63-7.58 (m, 2H), 7.39-7.36 (m, 2H), 7.29 (d, J=4.4 Hz, 1H), 7.05 (d, J=6.0 Hz, 1H), 6.86 (d, J=4.8 Hz, 1H), 4.25-4.22 (m, 1H), 3.89-3.81 (m, 1H), 3.76-3.65 (m, 2H), 2.34-2.33 (m, 1H), 1.84-1.79 (m, 4H), 1.66-1.63 (m, 2H). LCMS M/Z (M+H) 578.

Example 199 & Example 200

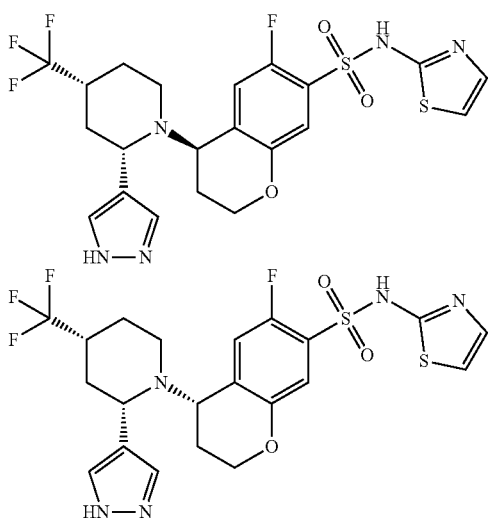

(R)-4-((2S,4R)-2-(1H-pyrazol-4-yl)-4-(trifluoromethyl)piperidin-1-yl)-6-fluoro-N-(thiazol-2-yl)chroman-7-sulfonamide & (S)-4-((2S,4R)-2-(1H-pyrazol-4-yl)-4-(trifluoromethyl)piperidin-1-yl)-6-fluoro-N-(thiazol-2-yl)chroman-7-sulfonamide Following the procedure as described in Example 189 and making non-critical variations as required to replace 1-(pyridin-2-yl)ethanone with 1-(1-((2-(trimethylsilyl)ethoxy)methyl)-1H-pyrazol-4-yl)ethanone, (R)-4-((2S,4R)-2-(1H-pyrazol-4-yl)-4-(trifluoromethyl)piperidin-1-yl)-6-fluoro-N-(thiazol-2-yl)chroman-7-sulfonamide (6 mg, less polar on TLC) and (S)-4-((2S,4R)-2-(1H-pyrazol-4-yl)-4-(trifluoromethyl)piperidin-1-yl)-6-fluoro-N-(thiazol-2-yl)chroman-7-sulfonamide (16 mg, more polar on TLC) were obtained as white solid. Example 199: $^1$H NMR (400 MHz, CD$_3$OD) δ 7.80-7.60 (m, 2H), 7.28-7.16 (m, 2H), 7.13 (d, J=4.8 Hz, 1H), 6.76 (d, J=4.4 Hz, 1H), 4.41-4.08 (m, 3H), 4.05-3.92 (m, 1H), 3.10-2.94 (m, 1H), 2.61-2.33 (m, 2H), 2.21-1.67 (m, 6H). LCMS M/Z (M+H) 532. Example 200: $^1$H NMR (400 MHz, CD$_3$OD) δ 7.80-7.65 (m, 2H), 7.45 (d, J=10.4 Hz, 1H), 7.19 (d, J=6.0 Hz, 1H), 7.12 (d, J=4.4 Hz, 1H), 6.75 (d, J=4.4 Hz, 1H), 4.36-4.20 (m, 1H), 4.10-3.69 (m, 3H), 2.78-2.60 (m, 1H), 2.50-2.25 (m, 2H), 2.15-1.73 (m, 5H), 1.66-1.50 (m, 1H). LCMS M/Z (M+H) 532.

Example 201

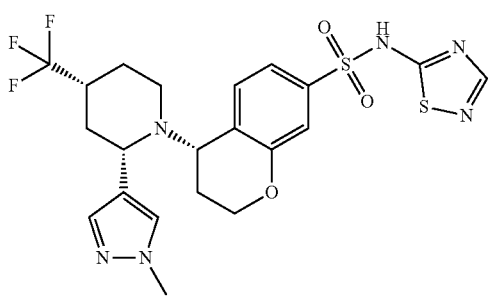 [SMILES: Cn1cc([C@@H]2C[C@H](C(F)(F)F)CCN2[C@H]2CCOc3cc(S(=O)(=O)Nc4ncns4)ccc32)cn1]

(S)-4-((2S,4R)-2-(1-methyl-1H-pyrazol-4-yl)-4-(trifluoromethyl)piperidin-1-yl)-N-(1,2,4-thiadiazol-5-yl)chroman-7-sulfonamide

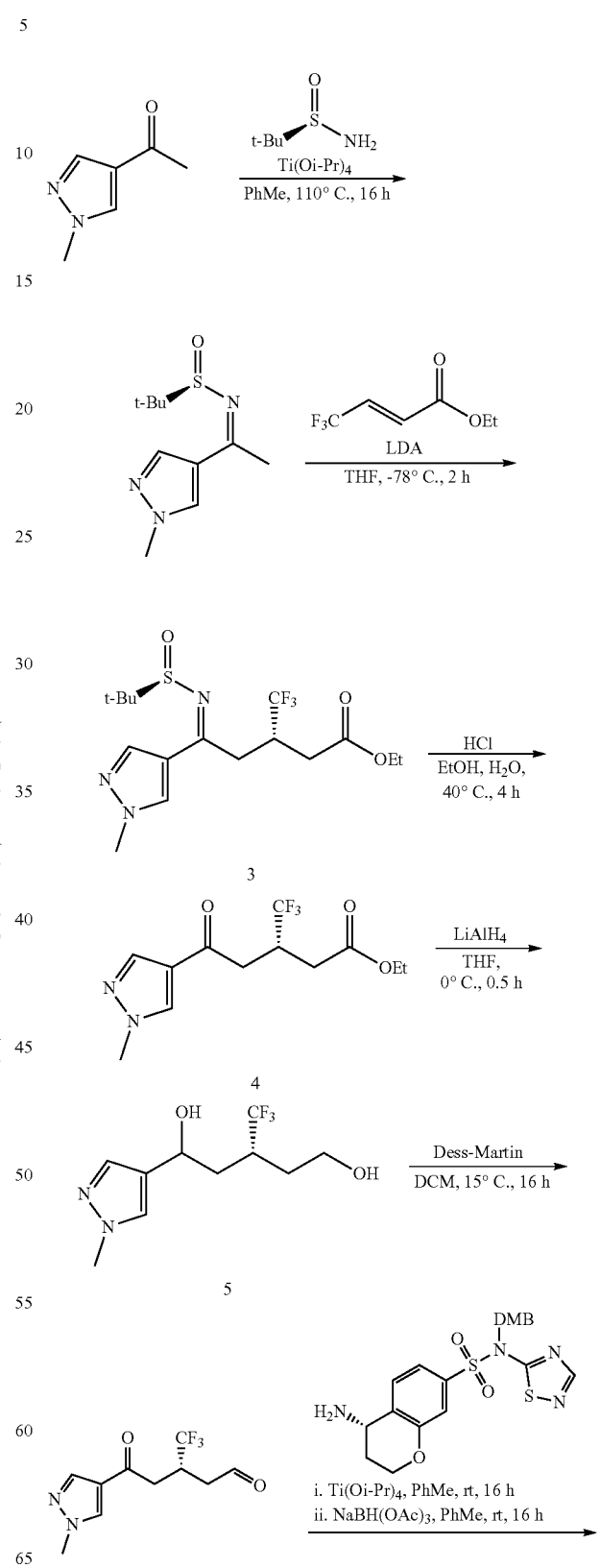

-continued

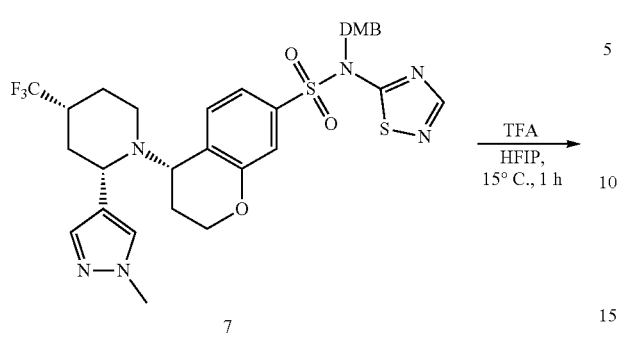

7

↓ TFA HFIP, 15° C., 1 h

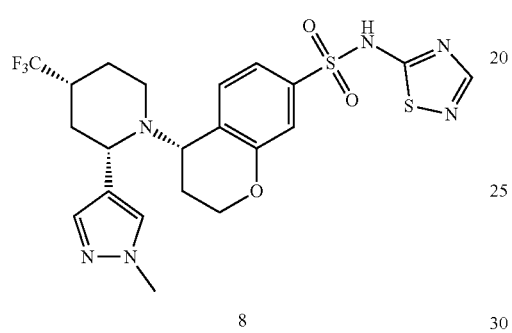

8

Step 1:

(R,Z)-2-methyl-N-(1-(1-methyl-1H-pyrazol-4-yl)ethylidene)propane-2-sulfinamide

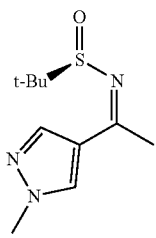

To a mixture of (R)-2-methylpropane-2-sulfinamide (2.58 g, 21.27 mmol) and 1-(1-methyl-1H-pyrazol-4-yl)ethanone (2.2 g, 17.72 mmol) in toluene (35 mL) was added titanium (IV) isopropoxide (10.49 mL, 35.44 mmol) under a nitrogen atmosphere. The reaction mixture was heated to 110° C. for 16 h. Sat. aq. NaHCO₃ (10 mL) was added and filtered through a short pad of anhydrous Na₂SO₄, washed with EtOAc (20 mL×3). The combined organic layers were concentrated in vacuo. The crude residue was purified by silica gel chromatography (petroleum ether/EtOAc=2:3) to give the title compound (2.5 g, 62%) as a yellow solid. $^1$H NMR (400 MHz, CDCl₃) δ 7.85 (s, 1H), 7.81 (s, 1H), 3.93 (s, 3H), 2.61 (s, 3H), 1.27 (s, 9H).

Step 2:

(S,Z)-ethyl 5-(((R)-tert-butylsulfinyl)imino)-5-(1-methyl-1H-pyrazol-4-yl)-3-(trifluoromethyl)pentanoate

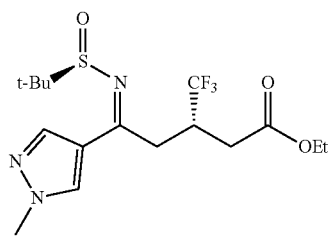 [SMILES: CCOC(=O)C[C@H](C/C(=N/[S@](=O)C(C)(C)C)c1cnn(C)c1)C(F)(F)F]

To a solution of (R,Z)-2-methyl-N-(1-(1-methyl-1H-pyrazol-4-yl)ethylidene)propane-2-sulfinamide (2.4 g, 10.56 mmol) and ethyl 4,4,4-trifluorobut-2-enoate (2.66 g, 15.84 mmol) in anhydrous THF (50 mL) at −78° C. was added lithium diisopropylamide (2.0 M, 10.56 mL, 21.12 mmol). The reaction mixture was stirred at −78° C. for 2 h. The reaction was quenched with sat. aq. ammonium chloride (10 mL), extracted with EtOAc (30 mL×3). The combined organic layers were concentrated in vacuo. The crude residue was purified by silica gel chromatography (petroleum ether/EtOAc=1:1) to give the title compound (2.85 g, 68%) as red oil. $^1$H NMR (400 MHz, CDCl₃) δ 8.50-7.88 (m, 2H), 4.19-4.09 (m, 2H), 3.96 (s, 3H), 3.71-3.51 (m, 1H), 3.39-2.88 (m, 2H), 2.79-2.55 (m, 2H), 1.34-1.20 (m, 12H).

Step 3:

(S)-ethyl 5-(1-methyl-1H-pyrazol-4-yl)-5-oxo-3-(trifluoromethyl)pentanoate

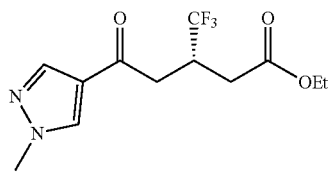 [SMILES: CCOC(=O)C[C@H](CC(=O)c1cnn(C)c1)C(F)(F)F]

To a solution of (S,Z)-ethyl 5-(((R)-tert-butylsulfinyl)imino)-5-(1-methyl-1H-pyrazol-4-yl)-3-(trifluoromethyl)pentanoate (2.85 g, 7.21 mmol) in EtOH (8.0 mL) was added aq. HCl (4.0 M, 9.01 mL, 36.04 mmol). The reaction mixture was stirred at 40° C. for 4 h. The mixture was basified with sat. aq. Na₂CO₃ to pH 8 and then extracted with EtOAc (30 mL×2). The combined organic layers were concentrated in vacuo. The crude residue was purified by silica gel chromatography (petroleum ether/EtOAc=1:1) to give the title compound (1.4 g, 67%) as yellow oil. $^1$H NMR (400 MHz, CDCl₃) δ 7.93 (s, 1H), 7.92 (s, 1H), 4.15 (q, J=7.2 Hz, 2H), 3.96 (s, 3H), 3.61-3.42 (m, 1H), 3.12-2.95 (m, 2H), 2.71-2.48 (m, 2H), 1.25 (t, J=7.2 Hz, 3H).

Step 4:

(3R)-1-(1-methyl-1H-pyrazol-4-yl)-3-(trifluoromethyl)pentane-1,5-diol

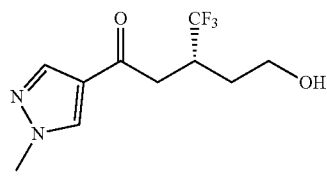 [SMILES: Cn1cc(C(=O)C[C@@H](CCO)C(F)(F)F)cn1]

To a solution of lithium aluminium hydride (0.83 g, 21.76 mmol) in anhydrous THF (20.0 mL) at 0° C. was added (S)-ethyl 5-(1-methyl-1H-pyrazol-4-yl)-5-oxo-3-(trifluoromethyl)pentanoate (2.12 g, 7.25 mmol) in anhydrous THF (5.0 mL) dropwise under a nitrogen atmosphere. The reaction mixture was stirred at 0° C. for 0.5 h. The reaction was quenched with water (0.9 mL) and 15% aq. NaOH (0.9 mL), dried over anhydrous MgSO$_4$, filtered. The filtrate was concentrated in vacuo. The crude residue was purified by silica gel chromatography (DCM/MeOH=10:1) to give the title compound (1.0 g, 55%) as yellow oil. $^1$H NMR (400 MHz, CDCl$_3$) δ 7.44 (s, 1H), 7.35 (s, 1H), 4.93-4.77 (m, 1H), 3.87 (s, 3H), 3.85-3.67 (m, 2H), 2.75-2.45 (m, 2H), 2.18-2.06 (m, 1H), 2.04-1.85 (m, 2H), 1.85-1.58 (m, 2H).

Step 5:

(R)-5-(1-methyl-1H-pyrazol-4-yl)-5-oxo-3-(trifluoromethyl)pentanal

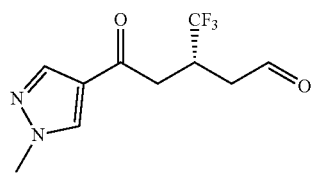

To a solution of (3R)-1-(1-methyl-1H-pyrazol-4-yl)-3-(trifluoromethyl)pentane-1,5-diol (500 mg, 1.98 mmol) in DCM (10 mL) was added Dess-Martin periodinane (5.04 g, 11.89 mmol). The reaction mixture was stirred at 15° C. for 16 h. The reaction mixture was washed with sat. aq. Na$_2$CO$_3$ (50 mL×2), brine (50 mL). The organic layer was dried over anhydrous MgSO$_4$, filtered and concentrated in vacuo. The crude residue was purified by silica gel chromatography (petroleum ether/EtOAc=1:1) to give the title compound (400 mg, 81%) as a yellow solid. LCMS M/Z (M+H) 249.

Step 6:

(S)—N-(2,4-dimethoxybenzyl)-4-((2S,4R)-2-(1-methyl-1H-pyrazol-4-yl)-4-(trifluoromethyl)piperidin-1-yl)-N-(1,2,4-thiadiazol-5-yl)chroman-7-sulfonamide

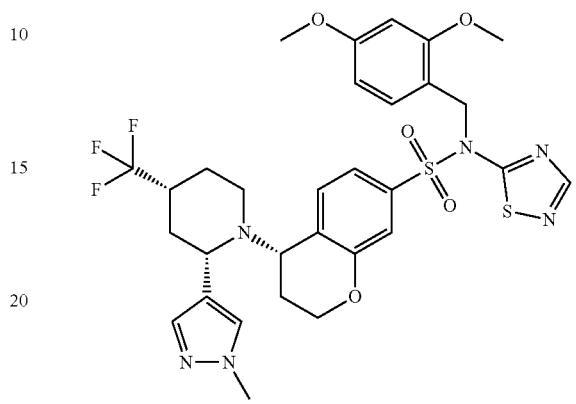

To a solution of (R)-5-(1-methyl-1H-pyrazol-4-yl)-5-oxo-3-(trifluoromethyl)pentanal (161 mg, 0.65 mmol) and (S)-4-amino-N-(2,4-dimethoxybenzyl)-N-(1,2,4-thiadiazol-5-yl)chroman-7-sulfonamide (200 mg, 0.43 mmol) in toluene (10 mL) was added titanium(IV) isopropoxide (0.32 mL, 1.08 mmol) under a nitrogen atmosphere. The reaction mixture was stirred at room temperature for 16 h. Sodium triacetoxyborohydride (916 mg, 4.32 mmol) was added to the mixture and stirred at room temperature for an additional 16 h. EtOAc (30 mL) was added and washed with water (20 mL×2), brine (20 mL). The organic layer was dried over anhydrous MgSO$_4$, filtered and concentrated in vacuo. The crude residue was purified by silica gel chromatography (petroleum ether/EtOAc=1:1) to give the title compound (150 mg, 51%) as colorless oil. LCMS M/Z (M+H) 679.

Step 7:

(S)-4-((2S,4R)-2-(1-methyl-1H-pyrazol-4-yl)-4-(trifluoromethyl)piperidin-1-yl)-N-(1,2,4-thiadiazol-5-yl)chroman-7-sulfonamide

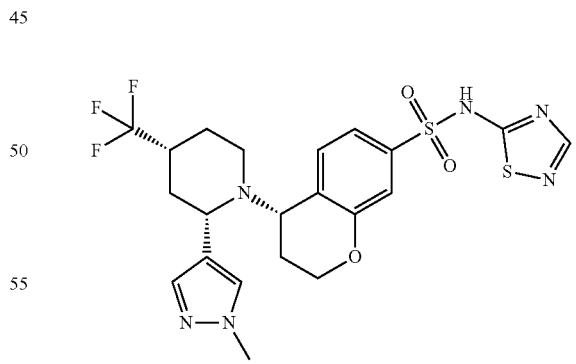

A mixture of (S)—N-(2,4-dimethoxybenzyl)-4-((2S,4R)-2-(1-methyl-1H-pyrazol-4-yl)-4-(trifluoromethyl)piperidin-1-yl)-N-(1,2,4-thiadiazol-5-yl)chroman-7-sulfonamide (150 mg, 0.22 mmol) and trifluoroacetic acid in 1,1,1,3,3,3-hexafluoropropan-2-ol (1.0 M, 10 mL) was stirred at 15° C. for 1 h. The mixture was concentrated in vacuo. The crude residue was purified by reverse phase chromatography (acetonitrile 40-70%/0.225% formic acid in water) to give the title compound (83 mg, 69%) as a white solid. ¹H NMR (400 MHz, CDCl₃) δ 8.16 (s, 1H), 7.76 (d, J=8.0 Hz, 1H), 7.69 (s, 1H), 7.54 (s, 1H), 7.36 (d, J=8.4 Hz, 1H), 7.15 (s, 1H), 4.29 (d, J=10.8 Hz, 1H), 4.15-4.05 (m, 1H), 3.95-3.85 (m, 1H), 3.86 (s, 3H), 3.76 (d, J=10.8 Hz, 1H), 2.66 (d, J=11.2 Hz, 1H), 2.45-2.25 (m, 2H), 2.15-1.96 (m, 2H), 1.95-1.73 (m, 3H), 1.65-1.50 (m, 1H). LCMS M/Z (M+H) 529.

Example 202

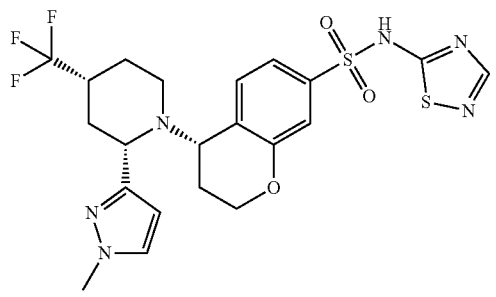 [SMILES: Cn1ccc([C@@H]2C[C@H](C(F)(F)F)CCN2[C@H]2CCOc3cc(S(=O)(=O)Nc4ncns4)ccc32)n1]

(S)-4-((2S,4R)-2-(1-methyl-1H-pyrazol-3-yl)-4-(trifluoromethyl)piperidin-1-yl)-N-(1,2,4-thiadiazol-5-yl)chroman-7-sulfonamide Following the procedure as described in Example 201 and making non-critical variations as required to replace 1-(1-methyl-1H-pyrazol-4-yl)ethanone with 1-(1-methyl-1H-pyrazol-3-yl)ethanone, the title compound was obtained as a white solid (21 mg). ¹H NMR (400 MHz, CDCl₃) δ 7.98 (s, 1H), 7.77 (d, J=8.4 Hz, 1H), 7.37 (d, J=8.4 Hz, 1H), 7.29 (d, J=6.0 Hz, 1H), 7.22 (d, J=6.0 Hz, 1H), 6.25 (d, J=2.0 Hz, 1H), 4.40-4.25 (m, 1H), 3.95-3.86 (m, 2H), 3.84 (s, 3H), 3.82-3.78 (m, 1H), 2.69 (d, J=11.6 Hz, 1H), 2.32-2.25 (m, 1H), 2.24-2.14 (m, 1H), 2.12-1.95 (m, 3H), 1.93-1.75 (m, 2H), 1.70-1.50 (m, 1H). LCMS M/Z (M+H) 529.

Example 203

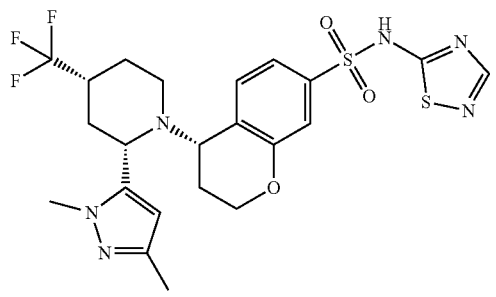 [SMILES: Cc1cc([C@@H]2C[C@H](C(F)(F)F)CCN2[C@H]2CCOc3cc(S(=O)(=O)Nc4ncns4)ccc32)n(C)n1]

(S)-4-((2S,4R)-2-(1,3-dimethyl-1H-pyrazol-5-yl)-4-(trifluoromethyl)piperidin-1-yl)-N-(1,2,4-thiadiazol-5-yl)chroman-7-sulfonamide Following the procedure as described in Example 201 and making non-critical variations as required to replace 1-(1-methyl-1H-pyrazol-4-yl)ethanone with 1-(1,3-dimethyl-1H-pyrazol-5-yl)ethanone, the title compound was obtained as a white solid (8 mg). ¹H NMR (400 MHz, acetone-d₆) δ 7.98 (s, 1H), 7.77 (d, J=8.4 Hz, 1H), 7.37 (d, J=8.4 Hz, 1H), 7.16 (s, 1H), 6.25 (s, 1H), 4.40-4.25 (m, 1H), 3.95-3.75 (m, 6H), 2.69 (d, J=11.6 Hz, 1H), 2.55-2.35 (m, 2H), 2.18-2.00 (m, 6H), 1.99-1.91 (m, 1H), 1.90-1.80 (m, 1H), 1.70-1.55 (m, 1H). LCMS M/Z (M+H) 543.

Example 204

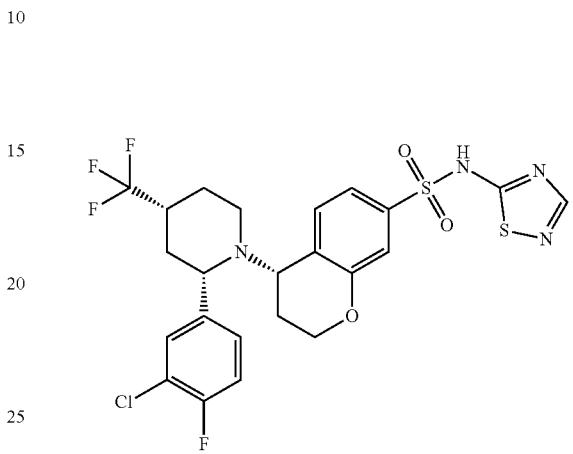

(S)-4-((2S,4R)-2-(3-chloro-4-fluorophenyl)-4-(trifluoromethyl)piperidin-1-yl)-N-(1,2,4-thiadiazol-5-yl)chroman-7-sulfonamide Following the procedure as described in Example 201 and making non-critical variations as required to replace 1-(1-methyl-1H-pyrazol-4-yl)ethanone with 1-(3-chloro-4-fluorophenyl)ethanone, the title compound was obtained as a white solid (126 mg). ¹H NMR (400 MHz, CD₃OD) δ 8.16 (s, 1H), 7.82 (d, J=8.0, 1H), 7.60 (d, J=6.4, 1H), 7.50 (s, 1H), 7.38 (d, J=6.4, 1H), 7.24-7.14 (m, 1H), 7.13 (s, 1H), 4.27-4.24 (m, 1H), 3.83-3.72 (m, 3H), 2.68-2.65 (m, 1H), 2.40-2.15 (m, 2H), 2.08-2.01 (m, 1H), 2.00-1.93 (m, 1H), 1.85-1.81 (m, 2H), 1.67-1.61 (m, 2H). LCMS M/Z (M+H) 577.

Example 205

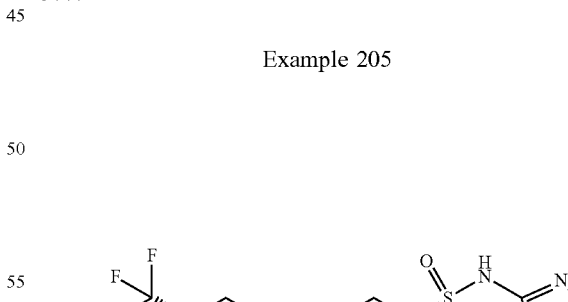
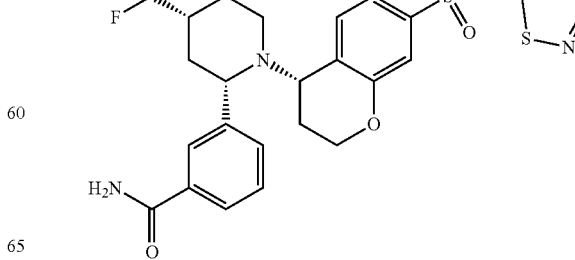

3-((2S,4R)-1-((S)-7-(N-(1,2,4-thiadiazol-5-yl)sulfamoyl)chroman-4-yl)-4-(trifluoromethyl)piperidin-2-yl)benzamide Step 1:

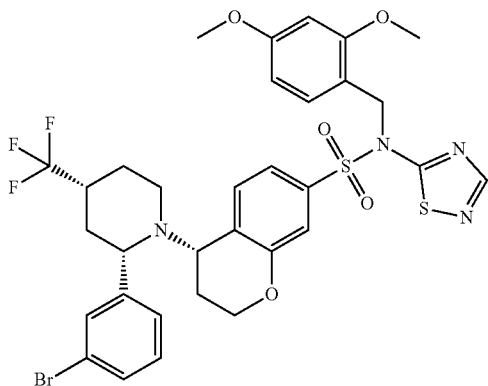 [SMILES: COc1ccc(CN(c2ncns2)S(=O)(=O)c2ccc3c(c2)OCC[C@@H]3N2CC[C@@H](C(F)(F)F)C[C@H]2c2cccc(Br)c2)c(OC)c1]

(S)-4-((2S,4R)-2-(3-bromophenyl)-4-(trifluoromethyl)piperidin-1-yl)-N-(2,4-dimethoxybenzyl)-N-(1,2,4-thiadiazol-5-yl)chroman-7-sulfonamide Following the procedure as described in Example 201 and making non-critical variations as required to replace 1-(1-methyl-1H-pyrazol-4-yl)ethanone with 1-(3-bromophenyl)ethanone, the title compound was obtained as a white solid (600 mg). $^1$H NMR (400 MHz, CDCl$_3$) δ 8.15 (s, 1H), 7.73 (d, J=8.4 Hz, 1H), 7.59-7.51 (m, 1H), 7.44 (d, J=8.0 Hz, 1H), 7.43-7.30 (m, 2H), 7.26-7.21 (m, 1H), 7.13 (d, J=1.6 Hz, 1H), 7.08-7.03 (m, 1H), 6.34-6.28 (m, 2H), 5.21 (s, 2H), 4.32-4.25 (m, 1H), 3.88-3.80 (m, 2H), 3.76 (s, 3H), 3.72 (s, 3H), 3.61-3.54 (m, 1H), 2.74-2.67 (m, 1H), 2.34-2.25 (m, 1H), 2.08-1.98 (m, 2H), 1.93-1.85 (m, 1H), 1.82-1.59 (m, 3H).

Step 2:

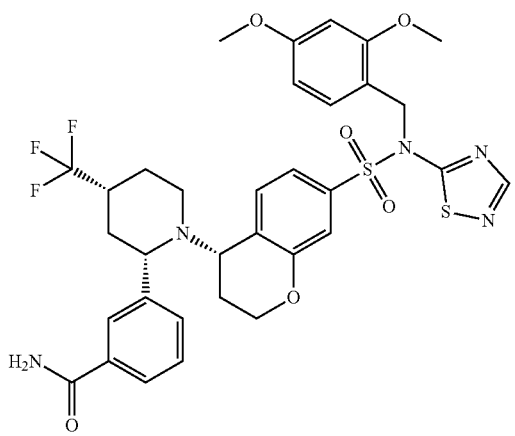 [SMILES: COc1ccc(CN(c2ncns2)S(=O)(=O)c2ccc3c(c2)OCC[C@@H]3N2CC[C@@H](C(F)(F)F)C[C@H]2c2cccc(C(N)=O)c2)c(OC)c1]

3-((2S,4R)-1-((S)-7-(N-(2,4-dimethoxybenzyl)-N-(1,2,4-thiadiazol-5-yl)sulfamoyl)chroman-4-yl)-4-(trifluoromethyl)piperidin-2-yl)benzamide To a solution of (S)-4-((2S,4R)-2-(3-bromophenyl)-4-(trifluoromethyl)piperidin-1-yl)-N-(2,4-dimethoxybenzyl)-N-(1,2,4-thiadiazol-5-yl)chroman-7-sulfonamide (100 mg, 0.13 mmol), bis(trimethylsilyl)amine (0.42 mL, 1.99 mmol) and N,N-diisopropylethylamine (0.043 mL, 0.26 mmol) in DMF (2 mL) was added tris(dibenzylideneacetone)dipalladium (12 mg, 0.01 mmol) and 1,1'-bis(diphenylphosphino)ferrocene (15 mg, 0.03 mmol). The mixture was heated to 100° C. for 2 h under a carbon monoxide atmosphere (15 psi). After cooling the reaction to room temperature, EtOAc (20 mL) was added and washed with aq. NaOH (1.0 M, 15 mL×2), water (15 mL×2). The organic layer was dried over anhydrous Na$_2$SO$_4$, filtered and concentrated in vacuo. The crude residue was purified by Prep-TLC (DCM/MeOH=20:1) to give the title compound (7 mg, 7%) as a yellow solid. $^1$H NMR (400 MHz, CD$_3$OD) δ 8.25 (s, 1H), 8.02 (s, 1H), 7.86-7.77 (m, 2H), 7.76-7.67 (m, 1H), 7.53-7.42 (m, 1H), 7.30-7.23 (m, 1H), 7.22-7.15 (m, 1H), 7.01 (d, J=1.6 Hz, 1H), 6.44 (d, J=1.2 Hz, 1H), 6.35-6.27 (m, 1H), 5.02 (s, 2H), 4.30-4.21 (m, 1H), 3.85-3.76 (m, 3H), 3.73 (s, 3H), 3.67 (s, 3H), 2.71-2.62 (m, 1H), 2.46-2.32 (m, 2H), 2.14-1.95 (m, 3H), 1.91-1.82 (m, 2H), 1.70-1.58 (m, 1H). LCMS M/Z (M+H) 718.

Step 3:

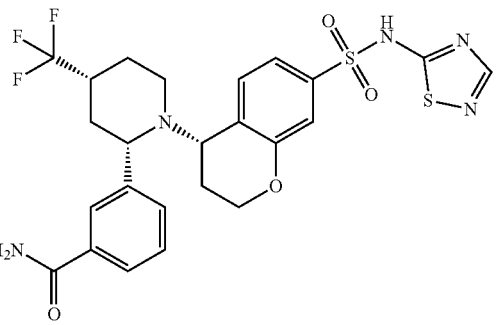

3-((2S,4R)-1-((S)-7-(N-(1,2,4-thiadiazol-5-yl)sulfamoyl)chroman-4-yl)-4-(trifluoromethyl)piperidin-2-yl)benzamide A mixture of 3-((2S,4R)-1-((S)-7-(N-(2,4-dimethoxybenzyl)-N-(1,2,4-thiadiazol-5-yl)sulfamoyl)chroman-4-yl)-4-(trifluoromethyl)piperidin-2-yl)benzamide (7 mg, 0.01 mmol) and trifluoroacetic acid in 1,1,1,3,3,3-hexafluoropropan-2-ol (1.0 M, 2 mL) was stirred at 15° C. for 1 h. The mixture was concentrated in vacuo. The crude residue was purified by reverse phase chromatography (acetonitrile 45-75%/0.225% formic acid in water) to give the title compound (2.4 mg, 43%) as a white solid. $^1$H NMR (400 MHz, CD$_3$OD) δ 8.16 (s, 1H), 8.02 (s, 1H), 7.88 (d, J=8.4 Hz, 1H), 7.82 (d, J=8.0 Hz, 1H), 7.73 (s, 1H), 7.55-7.45 (m, 1H), 7.44-7.37 (m, 1H), 7.16 (s, 1H), 4.33-4.24 (m, 1H), 3.88-3.76 (m, 3H), 2.78-2.69 (m, 1H), 2.49-2.33 (m, 2H), 2.19-2.06 (m, 1H), 2.04-1.95 (m, 1H), 1.93-1.74 (m, 3H), 1.72-1.59 (m, 1H). LCMS M/Z (M+H) 568.

Example 206

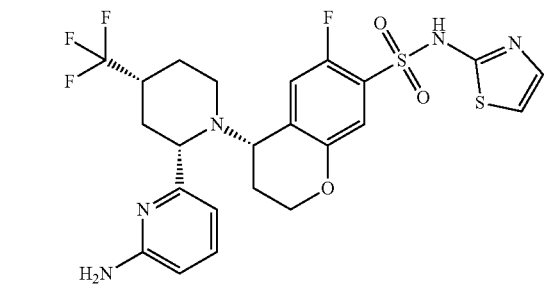 [SMILES: Nc1cccc([C@@H]2C[C@H](C(F)(F)F)CCN2[C@H]2CCOc3cc(S(=O)(=O)Nc4nccs4)c(F)cc32)n1]

(S)-4-((2S,4R)-2-(6-aminopyridin-2-yl)-4-(trifluoromethyl)piperidin-1-yl)-6-fluoro-N-(thiazol-2-yl)chroman-7-sulfonamide

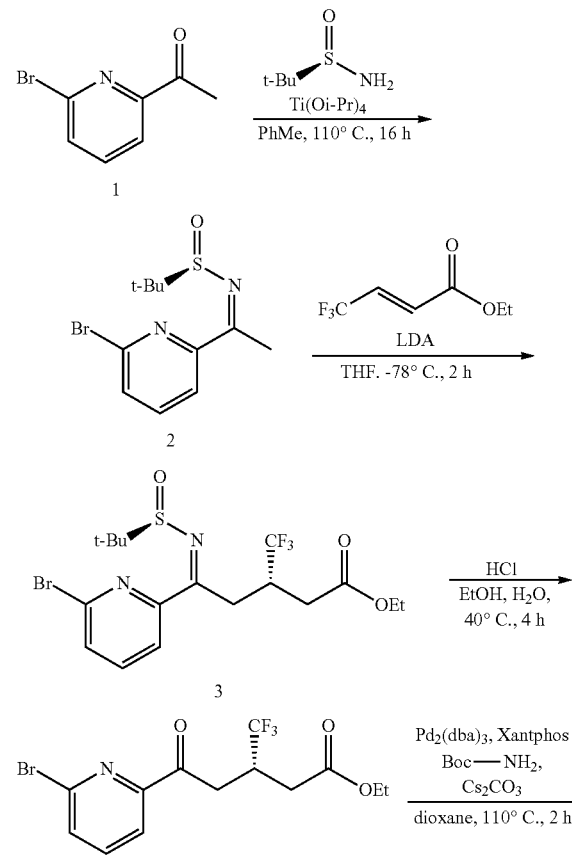

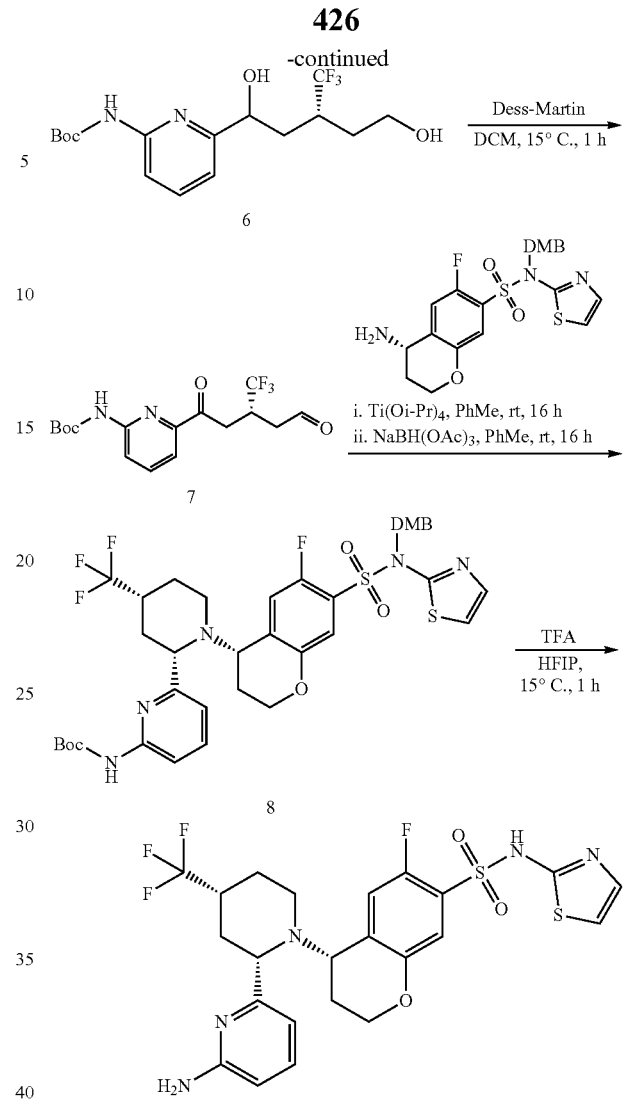

Step 1:

(R,Z)—N-(1-(6-bromopyridin-2-yl)ethylidene)-2-methylpropane-2-sulfinamide

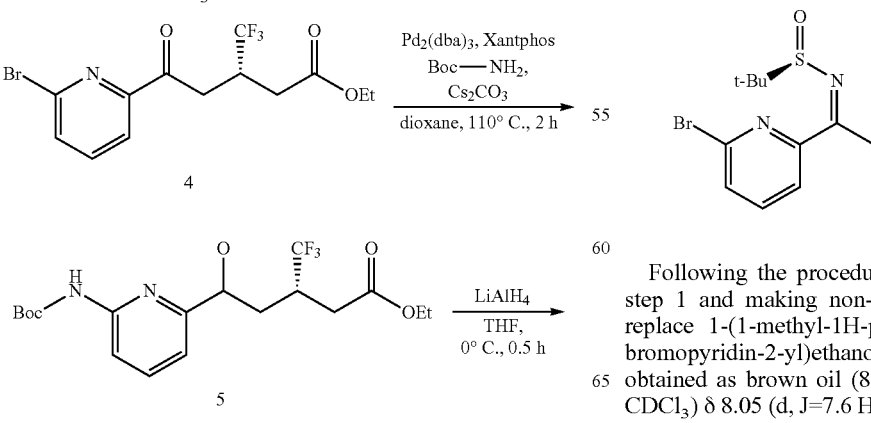

Following the procedure as described in Example 201, step 1 and making non-critical variations as required to replace 1-(1-methyl-1H-pyrazol-4-yl)ethanone with 1-(6-bromopyridin-2-yl)ethanone, the title compound was obtained as brown oil (8.7 g, 64%). $^1$H NMR (400 MHz, CDCl$_3$) δ 8.05 (d, J=7.6 Hz, 1H), 7.65-7.57 (m, 2H), 2.84 (s, 3H), 1.32 (s, 9H).

Step 2:

(S,Z)-ethyl 5-(6-bromopyridin-2-yl)-5-(((R)-tert-butylsulfinyl)imino)-3-(trifluoromethyl)pentanoate

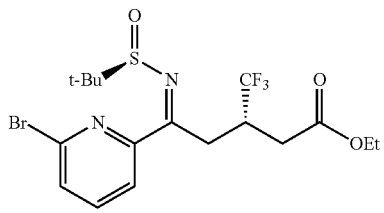 [SMILES: CCOC(=O)C[C@H](C/C(=N/[S@](=O)C(C)(C)C)c1cccc(Br)n1)C(F)(F)F]

Following the procedure as described in Example 201, step 2 and making non-critical variations as required to replace (R,Z)-2-methyl-N-(1-(1-methyl-1H-pyrazol-4-yl)ethylidene)propane-2-sulfinamide with (R,Z)—N-(1-(6-bromopyridin-2-yl)ethylidene)-2-methylpropane-2-sulfinamide, the title compound was obtained as brown oil (6.0 g, 45%).

Step 3:

(S)-ethyl 5-(6-bromopyridin-2-yl)-5-oxo-3-(trifluoromethyl)pentanoate

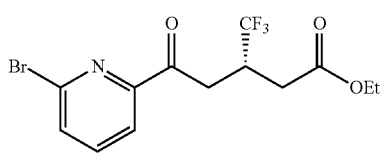 [SMILES: CCOC(=O)C[C@H](CC(=O)c1cccc(Br)n1)C(F)(F)F]

Following the procedure as described in Example 201, step 3 and making non-critical variations as required to replace (S,Z)-ethyl 5-(((R)-tert-butylsulfinyl)imino)-5-(1-methyl-1H-pyrazol-4-yl)-3-(trifluoromethyl)pentanoate with (S,Z)-ethyl 5-(6-bromopyridin-2-yl)-5-(((R)-tert-butylsulfinyl)imino)-3-(trifluoromethyl)pentanoate, the title compound was obtained as yellow oil (4.4 g, 94%).

Step 4:

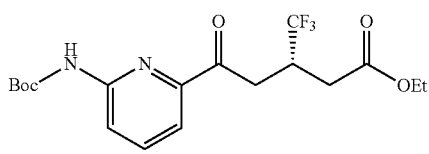 [SMILES: CCOC(=O)C[C@H](CC(=O)c1cccc(NC(=O)OC(C)(C)C)n1)C(F)(F)F]

(S)-ethyl 5-(6-((tert-butoxycarbonyl)amino)pyridin-2-yl)-5-oxo-3-(trifluoromethyl)pentanoate To a solution of (S)-ethyl 5-(6-bromopyridin-2-yl)-5-oxo-3-(trifluoromethyl)pentanoate (3.4 g, 9.24 mmol), tert-butyl carbamate (1.62 g, 13.85 mmol) and Cs$_2$CO$_3$ (9.08 g, 27.71 mmol) in 1,4-dioxane (50 mL) was added tris(dibenzylideneacetone)dipalladium (846 mg, 0.92 mmol) and 4,5-bis(diphenylphosphino)-9,9-dimethylxanthene (1.07 g, 1.85 mmol). The mixture was heated to 110° C. for 2 h under a nitrogen atmosphere. After cooling the reaction to room temperature, the mixture was filtered and concentrated in vacuo. The crude residue was purified by silica gel chromatography (petroleum ether/EtOAc=10:1) to give the title compound (1.6 g, 43%) as yellow oil.

Step 5:

tert-butyl (6-((3R)-1,5-dihydroxy-3-(trifluoromethyl)pentyl)pyridin-2-yl)carbamate

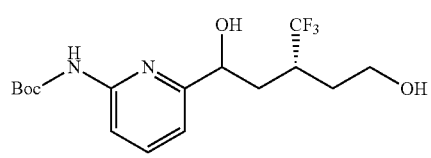 [SMILES: CC(C)(C)OC(=O)Nc1cccc(C(O)C[C@@H](CCO)C(F)(F)F)n1]

Following the procedure as described in Example 201, step 4 and making non-critical variations as required to replace (S)-ethyl 5-(1-methyl-1H-pyrazol-4-yl)-5-oxo-3-(trifluoromethyl)pentanoate with (S)-ethyl 5-(6-((tert-butoxycarbonyl)amino)pyridin-2-yl)-5-oxo-3-(trifluoromethyl)pentanoate, the title compound was obtained as colorless oil (0.6 g, 51%).

Step 6:

(R)-tert-butyl (6-(5-oxo-3-(trifluoromethyl)pentanoyl)pyridin-2-yl)carbamate

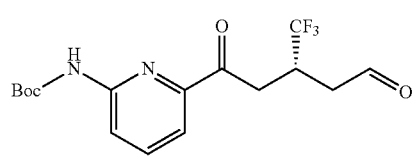 [SMILES: CC(C)(C)OC(=O)Nc1cccc(C(=O)C[C@@H](CC=O)C(F)(F)F)n1]

To a solution of tert-butyl (6-((3R)-1,5-dihydroxy-3-(trifluoromethyl)pentyl)pyridin-2-yl)carbamate (300 mg, 0.82 mmol) in DMF (10 mL) was added Dess-Martin periodinane (698 mg, 1.65 mmol). The reaction mixture was stirred at 15° C. for 1 h. The reaction was quenched with sat. aq. ammonium chloride (10 mL), extracted with EtOAc (30 mL×2). The combined organic layers were washed with water (15 mL), brine (20 mL), dried over anhydrous Na$_2$SO$_4$, filtered and concentrated in vacuo. The crude residue was purified by silica gel chromatography (petroleum ether/EtOAc=2:1) to give the title compound (70 mg, 24%) as yellow oil. $^1$H NMR (400 MHz, CDCl$_3$) δ 9.78 (s, 1H), 8.18 (d, J=8.4 Hz, 1H), 7.87-7.78 (m, 1H), 7.72-7.68 (m, 1H), 3.64-3.51 (m, 2H), 3.38-3.25 (m, 1H), 2.84-2.59 (m, 2H), 1.55 (s, 9H).

Step 7:

tert-butyl (6-((2S,4R)-1-((S)-7-(N-(2,4-dimethoxybenzyl)-N-(thiazol-2-yl)sulfamoyl)-6-fluorochroman-4-yl)-4-(trifluoromethyl)piperidin-2-yl)pyridin-2-yl)carbamate

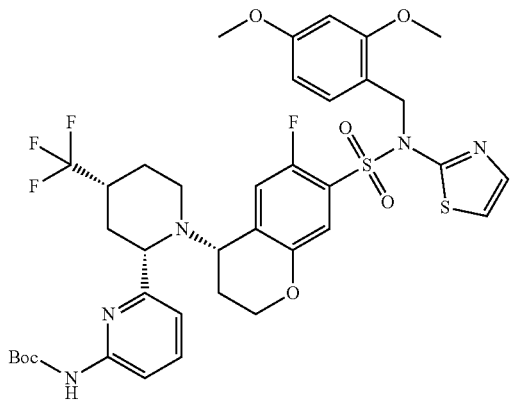 [SMILES: COc1ccc(CN(c2nccs2)S(=O)(=O)c2cc3c(cc2F)[C@@H](N2CC[C@@H](C(F)(F)F)C[C@H]2c2cccc(NC(=O)OC(C)(C)C)n2)CCO3)c(OC)c1]

Following the procedure as described in Example 201, step 6 and making non-critical variations as required to replace (R)-5-(1-methyl-1H-pyrazol-4-yl)-5-oxo-3-(trifluoromethyl)pentanal with (R)-tert-butyl (6-(5-oxo-3-(trifluoromethyl)pentanoyl)pyridin-2-yl)carbamate, the title compound was obtained as a white solid (90 mg, 58%). $^1$H NMR (400 MHz, CDCl$_3$) δ 7.86 (d, J=8.4 Hz, 1H), 7.72-7.63 (m, 1H), 7.51 (d, J=10.4 Hz, 1H), 7.39 (d, J=3.6 Hz, 1H), 7.26-7.09 (m, 4H), 6.97 (d, J=3.6 Hz, 1H), 6.41-6.35 (m, 2H), 5.30-5.16 (m, 2H), 4.27 (d, J=10.4 Hz, 1H), 3.86-3.72 (m, 2H), 3.75 (s, 6H), 3.67-3.57 (m, 1H), 2.73 (d, J=10.8 Hz, 1H), 2.37-2.14 (m, 2H), 2.11-1.72 (m, 6H), 1.54 (s, 9H).

Step 8:

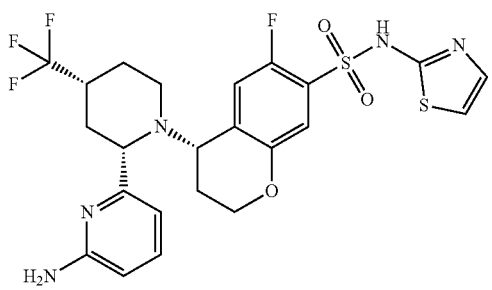 [SMILES: Nc1cccc([C@@H]2C[C@H](C(F)(F)F)CCN2[C@H]2CCOc3cc(S(=O)(=O)Nc4nccs4)c(F)cc32)n1]

(S)-4-((2S,4R)-2-(6-aminopyridin-2-yl)-4-(trifluoromethyl)piperidin-1-yl)-6-fluoro-N-(thiazol-2-yl)chroman-7-sulfonamide Following the procedure as described in Example 201, step 7 and making non-critical variations as required to replace (S)—N-(2,4-dimethoxybenzyl)-4-((2S,4R)-2-(1-methyl-1H-pyrazol-4-yl)-4-(trifluoromethyl)piperidin-1-yl)-N-(1,2,4-thiadiazol-5-yl)chroman-7-sulfonamide with tert-butyl (6-((2S,4R)-1-((S)-7-(N-(2,4-dimethoxybenzyl)-N-(thiazol-2-yl)sulfamoyl)-6-fluorochroman-4-yl)-4-(trifluoromethyl)piperidin-2-yl)pyridin-2-yl)carbamate, the title compound was obtained as a white solid. (6 mg, 10%). $^1$H NMR (400 MHz, CDCl$_3$) δ 7.52 (d, J=10.4 Hz, 1H), 7.46-7.41 (m, 1H), 7.36 (d, J=6.0 Hz, 1H), 7.19 (d, J=4.8 Hz, 1H), 6.82 (d, J=7.2 Hz, 1H), 6.53 (d, J=4.4 Hz, 1H), 6.42 (d, J=7.6 Hz, 1H), 4.68 (s, 2H), 4.31 (d, J=11.2 Hz, 1H), 4.02-3.84 (m, 2H), 3.63 (d, J=10.4 Hz, 1H), 2.76 (d, J=10.8 Hz, 1H), 2.39-2.27 (m, 1H), 2.26-2.16 (m, 1H), 2.15-2.01 (m, 2H), 2.00-1.85 (m, 2H), 1.83-1.62 (m, 2H). LCMS M/Z (M+H) 558.

Example 207

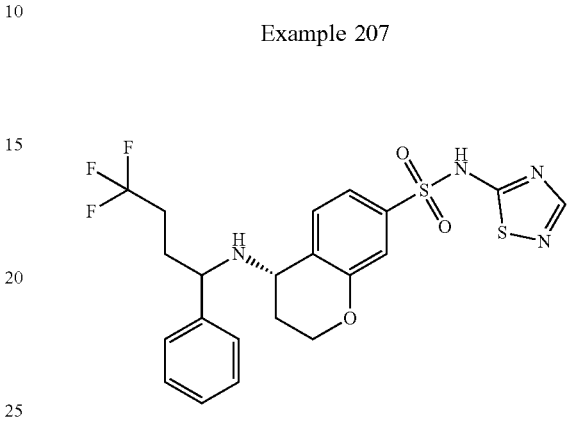

(4S)—N-(1,2,4-thiadiazol-5-yl)-4-((4,4,4-trifluoro-1-phenylbutyl)amino)chroman-7-sulfonamide

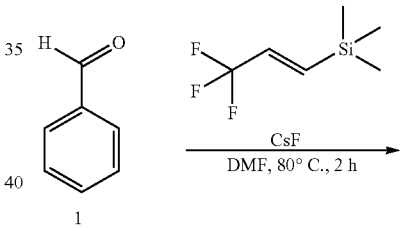

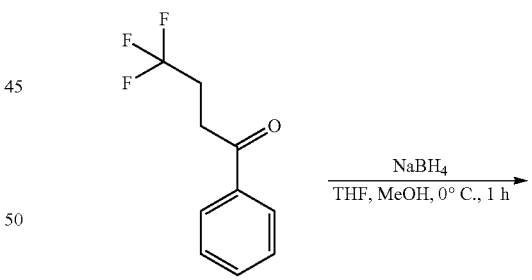

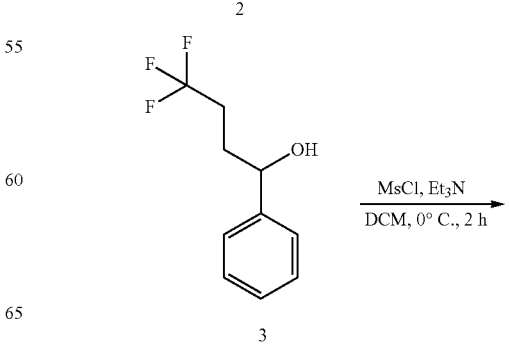

-continued

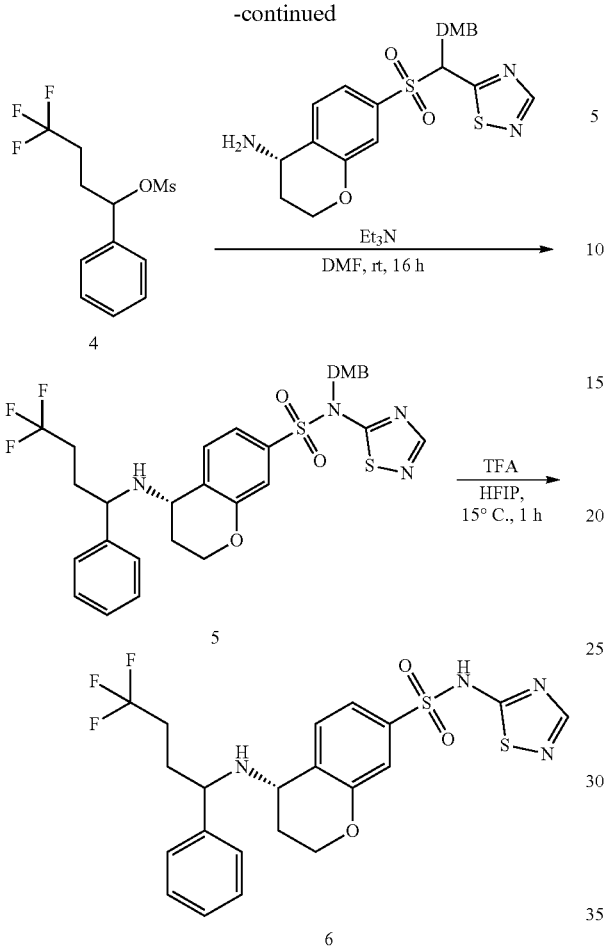

Step 2:

4,4,4-trifluoro-1-phenylbutan-1-ol

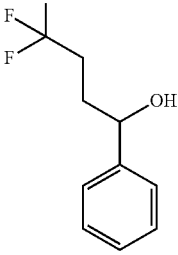

To a solution of 4,4,4-trifluoro-1-phenylbutan-1-one (1.2 g, 5.94 mmol) in THF (10.0 mL) and MeOH (1.0 mL) at 0° C. was added sodium borohydride (561 mg, 14.84 mmol). The reaction mixture was stirred at 0° C. for 1 h. The reaction was quenched with sat. aq. ammonium chloride (5 mL), diluted with EtOAc (20 mL), washed with brine (10 mL). The organic layer was dried over anhydrous $Na_2SO_4$, filtered and concentrated in vacuo. The crude residue was purified by silica gel chromatography (DCM/MeOH=50:1) to give the title compound (0.58 g, 48%) as yellow oil. $^1$H NMR (400 MHz, $CDCl_3$) δ 7.42-7.29 (m, 5H), 4.77 (t, J=6.4 Hz, 1H), 2.37-2.10 (m, 2H), 2.10-1.94 (m, 2H), 1.93-1.88 (m, 1H).

Step 3:

4,4,4-trifluoro-1-phenylbutyl methanesulfonate

Step 1:

4,4,4-trifluoro-1-phenylbutan-1-one

To a solution of benzaldehyde (10.0 g, 9.42 mmol) in DMF (95 mL) was added (E)-trimethyl(3,3,3-trifluoroprop-1-en-1-yl)silane (3.17 g, 18.85 mmol) and cesium fluoride (5.73 g, 37.69 mmol). The mixture was heated to 80° C. for 2 h under a nitrogen atmosphere. After cooling the reaction to room temperature, DCM (50 mL) was added and washed with water (30 mL×3). The organic layer was concentrated in vacuo. The crude residue was purified by silica gel chromatography (petroleum ether/EtOAc=60:1) to give the title compound (1.41 g, 68%) as a yellow solid. $^1$H NMR (400 MHz, $CDCl_3$) δ 7.99 (d, J=7.6 Hz, 2H), 7.64-7.58 (m, 1H), 7.53-7.46 (m, 2H), 3.32-3.23 (m, 2H), 2.68-2.54 (m, 2H).

To a solution of 4,4,4-trifluoro-1-phenylbutan-1-ol (460 mg, 2.25 mmol) and triethylamine (0.94 mL, 6.76 mmol) in DCM (9 mL) at 0° C. was added methanesulfonyl chloride (1.55 mL, 20.08 mmol) dropwise. The reaction mixture was stirred at 0° C. for 2 h. DCM (15 mL) was added and washed with 10% aq. citric acid (10 mL), sat. aq. $NaHCO_3$ (10 mL×2). The organic layer was dried over anhydrous $Na_2SO_4$, filtered and concentrated in vacuo to give the title compound (535 mg, crude) as a yellow solid that required no further purification. $^1$H NMR (400 MHz, $CDCl_3$) δ 7.48-7.33 (m, 5H), 5.59-5.51 (m, 1H), 2.68 (s, 3H), 2.41-2.26 (m, 2H), 2.24-2.08 (m, 2H).

Step 4:

(4S)—N-(2,4-dimethoxybenzyl)-N-(1,2,4-thiadiazol-5-yl)-4-((4,4,4-trifluoro-1-phenylbutyl)amino)chroman-7-sulfonamide

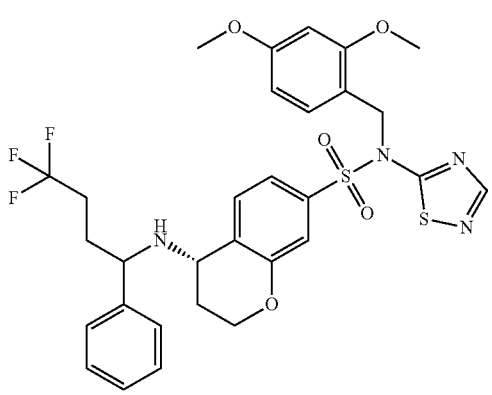 [SMILES: COc1ccc(CN(c2ncns2)S(=O)(=O)c2ccc3c(c2)OCC[C@@H]3NC(CCC(F)(F)F)c2ccccc2)c(OC)c1]

To a solution of (S)-4-amino-N-(2,4-dimethoxybenzyl)-N-(1,2,4-thiadiazol-5-yl)chroman-7-sulfonamide (877 mg, 1.9 mmol) and triethylamine (0.53 mL, 3.79 mmol) in DMF (16 mL) was added 4,4,4-trifluoro-1-phenylbutyl methanesulfonate (535 mg, 1.9 mmol). The reaction mixture was stirred at room temperature for 16 h under a nitrogen atmosphere. EtOAc (20 mL) was added and washed with water (10 mL×3). The organic layer was dried over anhydrous Na$_2$SO$_4$, filtered and concentrated in vacuo. The crude residue was purified by Prep-TLC (petroleum ether/EtOAc=4:1) to give the title compound (40 mg, 3%) as a white solid.

Step 5:

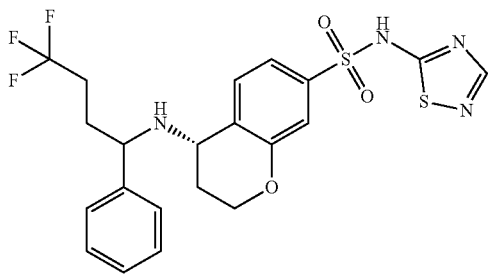 [SMILES: O=S(=O)(Nc1ncns1)c1ccc2c(c1)OCC[C@@H]2NC(CCC(F)(F)F)c1ccccc1]

(4S)—N-(1,2,4-thiadiazol-5-yl)-4-((4,4,4-trifluoro-1-phenylbutyl)amino)chroman-7-sulfonamide A mixture of (4S)—N-(2,4-dimethoxybenzyl)-N-(1,2,4-thiadiazol-5-yl)-4-((4,4,4-trifluoro-1-phenylbutyl)amino)chroman-7-sulfonamide (40 mg, 0.06 mmol) and trifluoroacetic acid in 1,1,1,3,3,3-hexafluoropropan-2-ol (1.0 M, 2 mL) was stirred at 15° C. for 1 h. The mixture was concentrated in vacuo. The crude residue was purified by reverse phase chromatography (acetonitrile 20-50%/0.75% hydrogen chloride in water) to give the title compound (2 mg, 6%) as a white solid. $^1$H NMR (400 MHz, CD$_3$OD) δ 8.22-8.18 (m, 1H), 7.70-7.51 (m, 6H), 7.42-7.27 (m, 2H), 4.73-4.57 (m, 1H), 4.51-4.20 (m, 3H), 2.49-2.19 (m, 5H), 1.87-1.69 (m, 1H). LCMS M/Z (M+H) 499.

Example 208

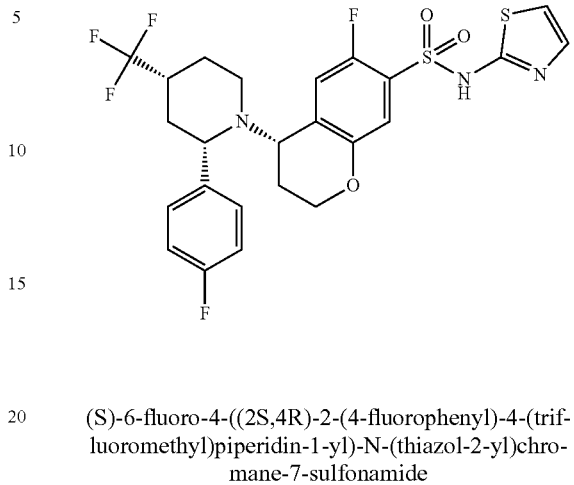

(S)-6-fluoro-4-((2S,4R)-2-(4-fluorophenyl)-4-(trifluoromethyl)piperidin-1-yl)-N-(thiazol-2-yl)chromane-7-sulfonamide Prepared according to procedure in Example 76. MS (ES+) m/z 560.1 (M+1). $^1$H NMR (400 MHz, DMSO-d6) δ 12.93 (s, 1H), 7.58-7.50 (m, 3H), 7.30 (d, J=4.6 Hz, 1H), 7.22-7.13 (m, 2H), 7.05 (d, J=6.0 Hz, 1H), 6.86 (d, J=4.6 Hz, 1H), 4.29-4.19 (m, 1H), 3.86-3.75 (m, 1H), 3.74 (dd, J=11.0, 2.7 Hz, 1H), 3.65 (dd, J=10.7, 5.9 Hz, 1H), 2.56 (d, J=11.6 Hz, 1H), 2.35 (dd, J=13.4, 11.2 Hz, 1H), 2.03-1.84 (m, 1H), 1.81 (d, J=13.3 Hz, 3H), 1.71-1.47 (m, 2H).

Example 209

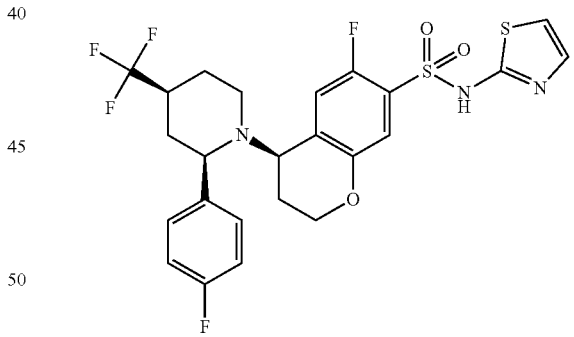

(R)-6-fluoro-4-((2R,4S)-2-(4-fluorophenyl)-4-(trifluoromethyl)piperidin-1-yl)-N-(thiazol-2-yl)chromane-7-sulfonamide Prepared according to procedure in Example 76. MS (ES+) m/z 560.1 (M+1). $^1$H NMR (400 MHz, DMSO-d6) δ 12.93 (s, 1H), 7.58-7.50 (m, 3H), 7.30 (d, J=4.6 Hz, 1H), 7.22-7.13 (m, 2H), 7.05 (d, J=6.0 Hz, 1H), 6.86 (d, J=4.6 Hz, 1H), 4.29-4.19 (m, 1H), 3.86-3.75 (m, 1H), 3.74 (dd, J=11.0, 2.7 Hz, 1H), 3.65 (dd, J=10.7, 5.9 Hz, 1H), 2.56 (d, J=11.6 Hz, 1H), 2.35 (dd, J=13.4, 11.2 Hz, 1H), 2.03-1.84 (m, 1H), 1.81 (d, J=13.3 Hz, 3H), 1.71-1.47 (m, 2H).

Example 210

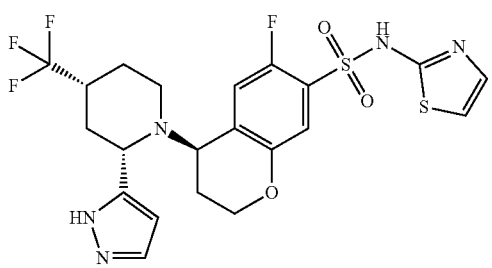 [SMILES: O=S(=O)(Nc1nccs1)c1cc2c(cc1F)[C@H](N1CC[C@@H](C(F)(F)F)C[C@H]1c1ccn[nH]1)CCO2]

(R)-4-((2S,4R)-2-(1H-pyrazol-5-yl)-4-(trifluoromethyl)piperidin-1-yl)-6-fluoro-N-(thiazol-2-yl)chromane-7-sulfonamide Prepared according to procedure in Example 76. MS (ES+) m/z 532.1 (M+1). $^1$H NMR (400 MHz, DMSO-d6) δ 12.88 (s, 1H), 12.55 (s, 1H), 7.47 (s, 1H), 7.28 (d, J=4.5 Hz, 2H), 7.01 (d, J=6.0 Hz, 1H), 6.85 (d, J=4.6 Hz, 1H), 6.16 (s, 1H), 4.20 (dt, J=11.1, 4.1 Hz, 1H), 4.02 (s, 1H), 3.87 (d, J=10.8 Hz, 2H), 3.32-3.25 (m, 1H), 2.79 (s, 1H), 2.25 (s, 1H), 2.14 (s, 1H), 1.79 (s, 3H), 1.79-1.66 (m, 1H), 1.59-1.45 (m, 1H).

Example 211

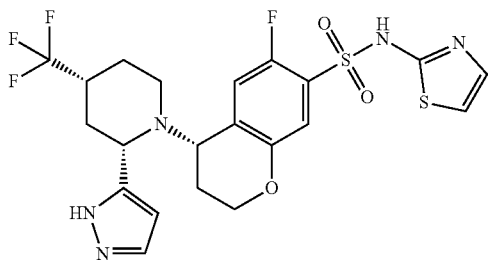 [SMILES: O=S(=O)(Nc1nccs1)c1cc2c(cc1F)[C@@H](N1CC[C@@H](C(F)(F)F)C[C@H]1c1ccn[nH]1)CCO2]

(S)-4-((2S,4R)-2-(1H-pyrazol-5-yl)-4-(trifluoromethyl)piperidin-1-yl)-6-fluoro-N-(thiazol-2-yl)chromane-7-sulfonamide Prepared according to procedure in Example 76. MS (ES+) m/z 532.1 (M+1). $^1$H NMR (400 MHz, DMSO-d6) δ 12.92 (s, 2H), 12.62 (s, 1H), 7.67 (s, 1H), 7.44 (s, 2H), 7.26 (d, J=4.6 Hz, 1H), 7.05 (d, J=5.9 Hz, 1H), 6.83 (d, J=4.5 Hz, 1H), 6.35 (s, 1H), 4.25 (dd, J=9.3, 5.7 Hz, 1H), 3.86 (s, 2H), 3.63 (s, 2H), 2.54 (s, 5H), 2.34 (t, J=11.7 Hz, 1H), 2.03-1.91 (m, 1H), 1.91-1.73 (m, 5H), 1.54-1.40 (m, 1H).

Example 212

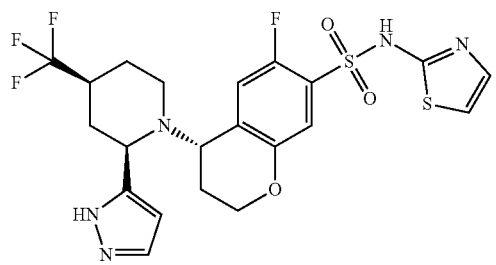 [SMILES: O=S(=O)(Nc1nccs1)c1cc2c(cc1F)[C@@H](N1CC[C@H](C(F)(F)F)C[C@@H]1c1ccn[nH]1)CCO2]

(S)-4-((2R,4S)-2-(1H-pyrazol-5-yl)-4-(trifluoromethyl)piperidin-1-yl)-6-fluoro-N-(thiazol-2-yl)chromane-7-sulfonamide Prepared according to procedure in Example 76. MS (ES+) m/z 532.1 (M+1). $^1$H NMR (400 MHz, DMSO-d6) δ 12.88 (s, 1H), 12.55 (s, 1H), 7.47 (s, 1H), 7.29 (d, J=4.6 Hz, 2H), 7.01 (d, J=6.0 Hz, 1H), 6.85 (d, J=4.6 Hz, 1H), 6.16 (s, 1H), 4.20 (dt, J=11.2, 4.1 Hz, 1H), 4.02 (d, J=10.4 Hz, 1H), 3.87 (d, J=10.6 Hz, 2H), 3.38-3.24 (m, OH), 2.79 (s, 1H), 2.25 (s, 1H), 2.14 (s, 1H), 1.79 (t, J=11.4 Hz, 3H), 1.70 (d, J=11.7 Hz, 0H), 1.52 (q, J=12.2 Hz, 1H).

Example 213

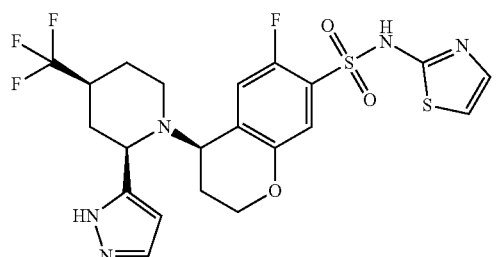

(R)-4-((2R,4S)-2-(1H-pyrazol-5-yl)-4-(trifluoromethyl)piperidin-1-yl)-6-fluoro-N-(thiazol-2-yl)chromane-7-sulfonamide Prepared according to procedure in Example 76. MS (ES+) m/z 532.1 (M+1). $^1$H NMR (400 MHz, DMSO-d6) δ 12.89 (s, 2H), 12.60 (s, 1H), 7.67 (s, 1H), 7.57 (s, 1H), 7.41 (d, J=11.1 Hz, 1H), 7.27 (d, J=4.6 Hz, 1H), 7.05 (d, J=6.0 Hz, 1H), 6.84 (d, J=4.6 Hz, 1H), 6.36 (s, 1H), 4.26 (dt, J=11.3, 3.7 Hz, 1H), 3.85 (s, 3H), 3.80 (d, J=10.7 Hz, 0H), 3.65 (s, 1H), 3.42-3.32 (m, 1H), 3.30 (s, 2H), 3.31-3.21 (m, 1H), 2.53 (d, J=6.5 Hz, 0H), 2.34 (t, J=11.6 Hz, 1H), 2.03-1.91 (m, 1H), 1.90-1.76 (m, 2H), 1.54-1.40 (m, 1H).

Example 214

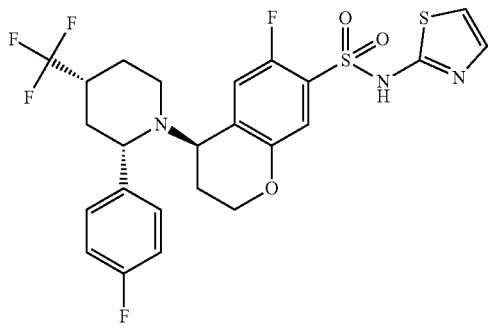 [SMILES: O=S(=O)(Nc1nccs1)c1cc2c(cc1F)[C@H](N1CC[C@@H](C(F)(F)F)C[C@H]1c1ccc(F)cc1)CCO2]

(R)-6-fluoro-4-((2S,4R)-2-(4-fluorophenyl)-4-(trifluoromethyl)piperidin-1-yl)-N-(thiazol-2-yl)chromane-7-sulfonamide Prepared according to procedure in Example 76. MS (ES+) m/z 560.1 (M+1). $^1$H NMR (400 MHz, DMSO-d6) δ 12.68 (s, 1H), 7.48 (dd, J=8.6, 5.7 Hz, 2H), 7.28 (d, J=4.6 Hz, 1H), 7.21-7.08 (m, 3H), 7.03 (d, J=6.1 Hz, 1H), 6.85 (d, J=4.5 Hz, 1H), 4.17 (dt, J=11.3, 4.2 Hz, 1H), 4.09 (d, J=10.5 Hz, 1H), 3.90-3.77 (m, 2H), 2.75 (d, J=11.8 Hz, 1H), 2.24 (t, J=11.9 Hz, 1H), 2.13-1.92 (m, 1H), 1.84-1.73 (m, 3H), 1.59-1.42 (m, 2H).

Example 215

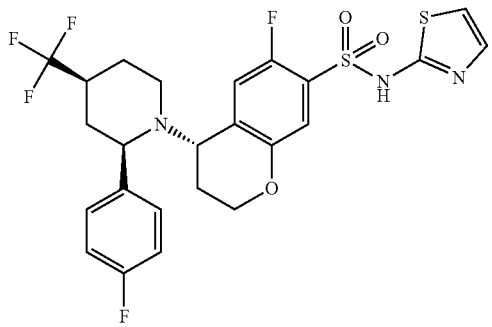 [SMILES: O=S(=O)(Nc1nccs1)c1cc2c(cc1F)[C@@H](N1CC[C@H](C(F)(F)F)C[C@@H]1c1ccc(F)cc1)CCO2]

(S)-6-fluoro-4-((2R,4S)-2-(4-fluorophenyl)-4-(trifluoromethyl)piperidin-1-yl)-N-(thiazol-2-yl)chromane-7-sulfonamide Prepared according to procedure in Example 76. MS (ES+) m/z 560.1 (M+1). $^1$H NMR (400 MHz, DMSO-d6) δ 12.87 (s, 1H), 7.52-7.44 (m, 2H), 7.29 (d, J=4.6 Hz, 1H), 7.22-7.08 (m, 3H), 7.03 (d, J=6.0 Hz, 1H), 6.85 (d, J=4.6 Hz, 1H), 4.17 (dt, J=11.3, 4.2 Hz, 1H), 4.09 (d, J=10.5 Hz, 1H), 3.90-3.78 (m, 2H), 3.30 (s, 1H), 2.76 (d, J=12.0 Hz, 1H), 2.24 (t, J=11.8 Hz, 1H), 2.06-1.92 (m, 1H), 1.84-1.73 (m, 3H), 1.59-1.42 (m, 2H).

Example 216

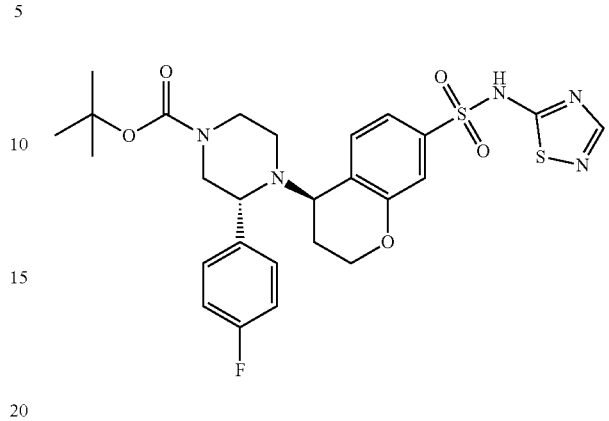

Tert-butyl (R)-4-((R)-7-(N-(1,2,4-thiadiazol-5-yl)sulfamoyl)chroman-4-yl)-3-(4-fluorophenyl)piperazine-1-carboxylate Prepared according to procedure in step 3 and 4 of Example 82. MS (ES+) m/z 576.1 (M+1). $^1$H NMR (400 MHz, DMSO-d6) δ 8.26 (s, 1H), 7.77 (d, J=8.3 Hz, 1H), 7.62-7.53 (m, 2H), 7.30 (dd, J=8.1, 1.8 Hz, 1H), 7.25-7.15 (m, 2H), 7.09-6.99 (m, 1H), 4.27-4.19 (m, 1H), 3.89-3.78 (m, 3H), 3.70 (dq, J=10.5, 6.0, 4.8 Hz, 2H), 2.42 (d, J=11.5 Hz, 1H), 2.32-2.24 (m, 1H), 2.04-1.88 (m, 1H), 1.83 (s, 1H), 1.38 (s, 9H).

Example 217

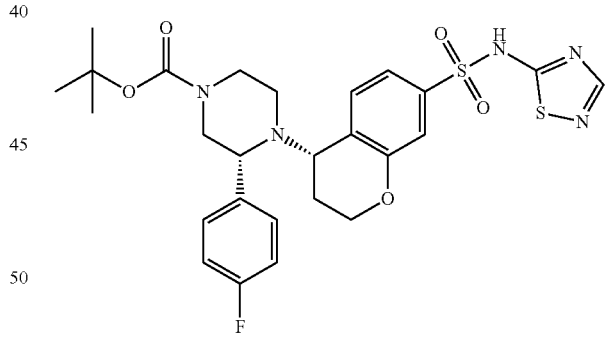

tert-butyl (R)-4-((S)-7-(N-(1,2,4-thiadiazol-5-yl)sulfamoyl)chroman-4-yl)-3-(4-fluorophenyl)piperazine-1-carboxylate Prepared according to procedure in step 3 and 4 of Example 82. MS (ES+) m/z 576.1 (M+1). $^1$H NMR (400 MHz, DMSO-d6) δ 8.35 (s, 1H), 7.56-7.46 (m, 3H), 7.26 (dd, J=8.1, 1.9 Hz, 1H), 7.22-7.11 (m, 2H), 7.02 (d, J=1.9 Hz, 1H), 4.18 (dt, J=11.2, 4.4 Hz, 1H), 4.04-3.97 (m, 1H), 3.97-3.86 (m, 2H), 3.69 (d, J=12.6 Hz, 2H), 3.07 (t, J=11.3 Hz, 1H), 2.07 (s, 2H), 2.00-1.87 (m, 1H), 1.71 (s, 1H), 1.36 (s, 9H).

Example 218

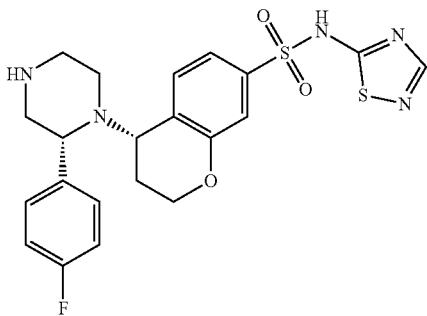 [SMILES: O=S(=O)(Nc1ncns1)c1ccc2c(c1)OCC[C@@H]2N1CCNC[C@H]1c1ccc(F)cc1]

(S)-4-((R)-2-(4-fluorophenyl)piperazin-1-yl)-N-(1,2,4-thiadiazol-5-yl)chromane-7-sulfonamide To a solution of tert-butyl (3R)-4-[(4S)-7-[(2,4-dimethoxyphenyl)methyl-(1,2,4-thiadiazol-5-yl)sulfamoyl]chroman-4-yl]-3-(4-fluorophenyl)piperazine-1-carboxylate (500 mg, 0.69 mmol) in dichloromethane (2 mL) was added trifluoroacetic acid (0.26 mL, 3.4 mmol) and the solution was stirred at room temperature for 1 h. The mixture was then concentrated to give a white solid. 20 mg of crude material was purified by Prep-HPLC (30-50% MeCN in 0.2% ammonia) to give 10.2 mg of (S)-4-((R)-2-(4-fluorophenyl)piperazin-1-yl)-N-(1,2,4-thiadiazol-5-yl)chromane-7-sulfonamide as a white solid. The remainder of the material was used as unpurified TFA salt for the next step. MS (ES+) m/z 476.1 (M+1). $^1$H NMR (400 MHz, DMSO-d6) δ 7.95 (s, 1H), 7.60 (dt, J=8.7, 4.9 Hz, 2H), 7.35-7.14 (m, 4H), 7.15-6.98 (m, 2H), 4.31-4.13 (m, 2H), 3.94-3.77 (m, 2H), 3.27-3.14 (m, 2H), 3.03 (s, 2H), 2.73 (d, J=13.3 Hz, 1H), 2.54 (s, 1H), 1.95 (dtd, J=13.6, 9.0, 8.6, 4.1 Hz, 1H), 1.82 (s, 1H).

Example 219

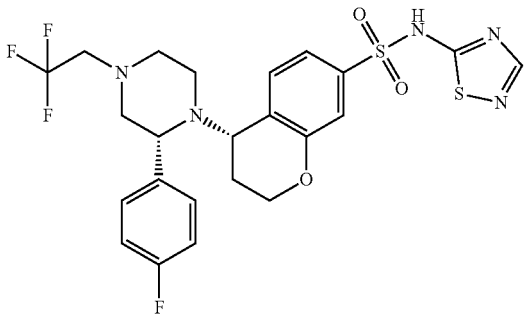 [SMILES: O=S(=O)(Nc1ncns1)c1ccc2c(c1)OCC[C@@H]2N1CCN(CC(F)(F)F)C[C@H]1c1ccc(F)cc1]

(S)-4-((R)-2-(4-fluorophenyl)-4-(2,2,2-trifluoroethyl)piperazin-1-yl)-N-(1,2,4-thiadiazol-5-yl)chromane-7-sulfonamide 2,2,2-Trifluoroethyl trifluoromethanesulfonate (29 mg, 0.12 mmol) was added to a solution of (4S)-4-[(2R)-2-(4-fluorophenyl)piperazin-1-yl]-N-(1,2,4-thiadiazol-5-yl)chromane-7-sulfonamide; 2,2,2-trifluoroacetic acid (65 mg, 0.11 mmol) and N,N-diisopropylethylamine (5 equiv., 0.5512 mmol, 71.24 mg) in dichloromethane (2 mL, 31 mmol,). The mixture was stirred at room temperature for 12 h. The reaction was then concentrated and the diastereomers were separated by Prep-HPLC (30-50% MeCN in 0.2% ammonia) to give 5.9 mg of (S)-4-((R)-2-(4-fluorophenyl)-4-(2,2,2-trifluoroethyl)piperazin-1-yl)-N-(1,2,4-thiadiazol-5-yl)chromane-7-sulfonamide as a white solid. MS (ES+) m/z 558.1 (M+1). $^1$H NMR (400 MHz, DMSO-d6) δ 7.98 (s, 1H), 7.59 (dd, J=8.4, 5.6 Hz, 2H), 7.44 (d, J=8.0 Hz, 1H), 7.25 (dd, J=8.0, 1.8 Hz, 1H), 7.15 (t, J=8.7 Hz, 2H), 7.00 (d, J=1.8 Hz, 1H), 6.51 (s, 2H), 4.19-4.09 (m, 2H), 3.87 (ddd, J=14.7, 9.7, 4.6 Hz, 2H), 3.15 (qd, J=10.1, 3.2 Hz, 2H), 2.79 (t, J=13.4 Hz, 2H), 2.64-2.51 (m, 2H), 2.22-2.11 (m, 1H), 1.85 (dtd, J=13.3, 9.4, 3.9 Hz, 1H), 1.60 (dd, J=12.8, 6.7 Hz, 1H).

Example 220

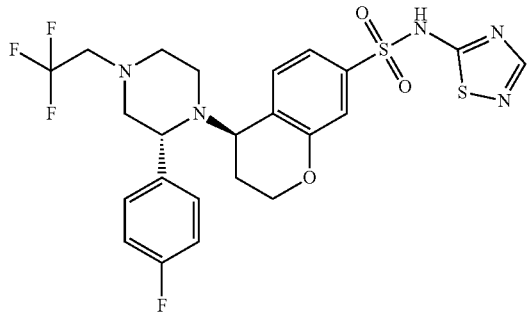 [SMILES: O=S(=O)(Nc1ncns1)c1ccc2c(c1)OCC[C@H]2N1CCN(CC(F)(F)F)C[C@H]1c1ccc(F)cc1]

(R)-4-((R)-2-(4-fluorophenyl)-4-(2,2,2-trifluoroethyl)piperazin-1-yl)-N-(1,2,4-thiadiazol-5-yl)chromane-7-sulfonamide MS (ES+) m/z 558.1 (M+1). $^1$H NMR (400 MHz, DMSO-d6) δ 8.27 (s, 1H), 7.74 (d, J=8.1 Hz, 1H), 7.59-7.44 (m, 2H), 7.30 (dd, J=8.1, 1.9 Hz, 1H), 7.30-7.04 (m, 2H), 7.02 (d, J=1.8 Hz, 1H), 6.51 (s, 1H), 4.29-4.12 (m, 1H), 3.85 (ddd, J=13.4, 10.6, 2.4 Hz, 2H), 3.69 (dd, J=10.5, 5.8 Hz, 1H), 3.19 (qd, J=10.3, 4.9 Hz, 2H), 2.92-2.80 (m, 2H), 2.46 (d, J=9.3 Hz, 1H), 2.37 (d, J=7.5 Hz, 1H), 2.05-1.90 (m, 1H), 1.89-1.79 (m, 1H), 1.35 (s, 1H).

Example 221

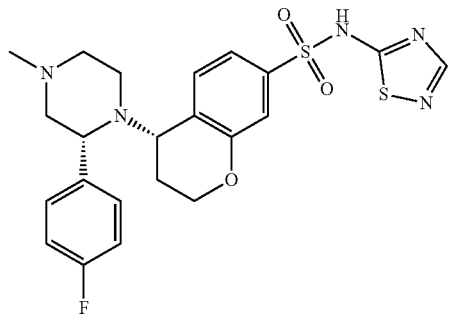 [SMILES: CN1CCN([C@H]2CCOc3cc(S(=O)(=O)Nc4ncns4)ccc32)[C@H](c2ccc(F)cc2)C1]

(S)-4-((R)-2-(4-fluorophenyl)-4-methylpiperazin-1-yl)-N-(1,2,4-thiadiazol-5-yl)chromane-7-sulfonamide Prepared according to Example 219 using iodomethane. MS (ES+) m/z 490.1 (M+1). $^1$H NMR (400 MHz, DMSO-d6) δ 9.54 (s, 1H), 7.84 (d, J=4.7 Hz, 1H), 7.67-7.55 (m, 2H), 7.34-7.20 (m, 3H), 7.02 (dd, J=12.9, 1.6 Hz, 1H), 6.51 (s, 1H), 4.25 (s, 1H), 4.17 (dt, J=11.2, 4.6 Hz, 1H), 3.94-3.78 (m, 2H), 3.30 (s, 2H), 2.93 (s, 3H), 2.75 (d, J=12.7 Hz, 1H), 2.64 (s, 2H), 2.54 (s, 2H), 2.28 (s, 1H), 1.96-1.87 (m, 1H).

Example 222

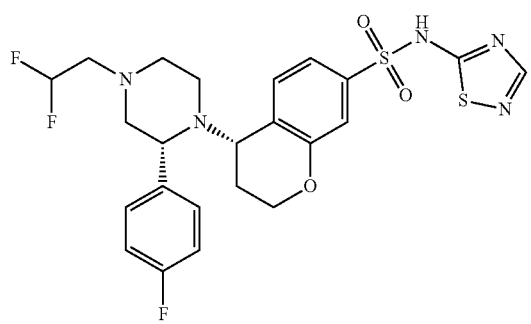 [SMILES: O=S(=O)(Nc1ncns1)c1ccc2c(c1)OCC[C@@H]2N1CCN(CC(F)F)C[C@H]1c1ccc(F)cc1]

(S)-4-((R)-4-(2,2-difluoroethyl)-2-(4-fluorophenyl)piperazin-1-yl)-N-(1,2,4-thiadiazol-5-yl)chromane-7-sulfonamide Prepared according to Example 219 using 1,1-difluoro-2-iodoethane. MS (ES+) m/z 540.1 (M+1).

Example 223

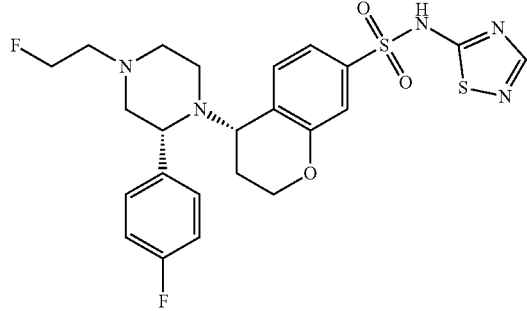 [SMILES: O=S(=O)(Nc1ncns1)c1ccc2c(c1)OCC[C@@H]2N1CCN(CCF)C[C@H]1c1ccc(F)cc1]

(S)-4-((R)-4-(2-fluoroethyl)-2-(4-fluorophenyl)piperazin-1-yl)-N-(1,2,4-thiadiazol-5-yl)chromane-7-sulfonamide Prepared according to Example 219 using 1-fluoro-2-iodoethane. MS (ES+) m/z 522.1 (M+1).

Example 224

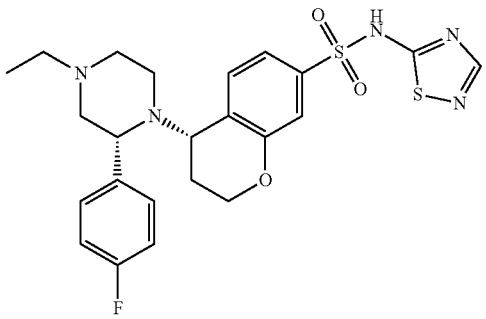 [SMILES: CCN1CCN([C@H]2CCOc3cc(S(=O)(=O)Nc4ncns4)ccc32)[C@H](c2ccc(F)cc2)C1]

(S)-4-((R)-4-ethyl-2-(4-fluorophenyl)piperazin-1-yl)-N-(1,2,4-thiadiazol-5-yl)chromane-7-sulfonamide Prepared according to Example 219 using iodoethane. MS (ES+) m/z 504.1 (M+1). $^1$H NMR (400 MHz, DMSO-d6) δ 9.25 (s, 1H), 7.84 (d, J=4.9 Hz, 1H), 7.68-7.55 (m, 2H), 7.31-7.22 (m, 4H), 7.04 (s, 1H), 4.18 (dt, J=11.3, 4.7 Hz, 1H), 3.94-3.78 (m, 2H), 3.28 (s, 1H), 2.78 (s, 1H), 2.59 (s, 1H), 2.27 (d, J=12.8 Hz, 1H), 1.94 (s, 1H), 1.81 (s, 1H), 1.25 (q, J=7.4, 6.6 Hz, 1H), 1.13 (s, 3H).

Example 225

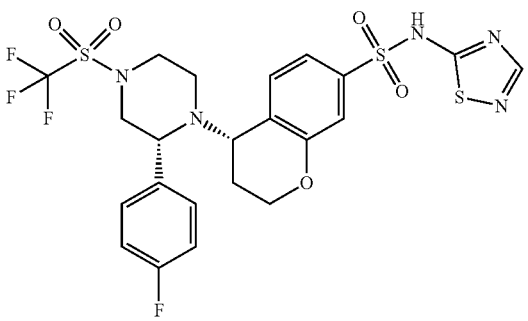 [SMILES: O=S(=O)(Nc1ncns1)c1ccc2c(c1)OCC[C@@H]2N1CCN(S(=O)(=O)C(F)(F)F)C[C@H]1c1ccc(F)cc1]

(S)-4-((R)-2-(4-fluorophenyl)-4-((trifluoromethyl)sulfonyl)piperazin-1-yl)-N-(1,2,4-thiadiazol-5-yl)chromane-7-sulfonamide Prepared according to Example 219 using trifluoromethanesulfonyl chloride. MS (ES+) m/z 607.6 (M+1). $^1$H NMR (400 MHz, DMSO-d6) δ 7.84 (s, 1H), 7.65-7.55 (m, 2H), 7.39 (d, J=8.1 Hz, 1H), 7.28-7.17 (m, 3H), 7.03-6.92 (m, 1H), 6.51 (s, 2H), 4.23 (dd, J=8.8, 3.2 Hz, 1H), 4.14 (dd, J=10.5, 5.3 Hz, 1H), 3.88 (td, J=11.5, 10.8, 3.6 Hz, 2H), 3.67 (d, J=12.7 Hz, 1H), 3.57 (d, J=12.3 Hz, 1H), 2.79 (d, J=12.7 Hz, 1H), 2.21 (t, J=11.4 Hz, 1H), 1.89 (s, 1H), 1.67 (s, 1H).

Example 226

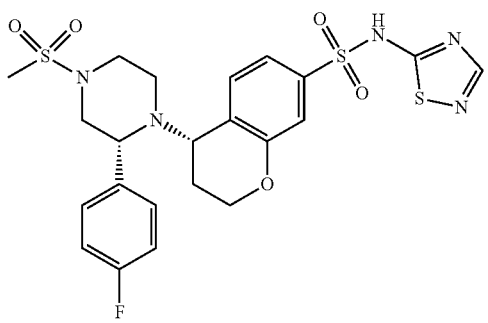 [SMILES: CS(=O)(=O)N1CCN([C@H]2CCOc3cc(S(=O)(=O)Nc4ncns4)ccc32)[C@H](c2ccc(F)cc2)C1]

(S)-4-((R)-2-(4-fluorophenyl)-4-(methylsulfonyl)piperazin-1-yl)-N-(1,2,4-thiadiazol-5-yl)chromane-7-sulfonamide Prepared according to Example 219 using methanesulfonyl chloride. MS (ES+) m/z 554.1 (M+1). $^1$H NMR (400 MHz, DMSO-d6) δ 8.19 (s, 1H), 7.86 (s, 1H), 7.71-7.56 (m, 2H), 7.43 (d, J=8.1 Hz, 1H), 7.29-7.15 (m, 3H), 7.00 (t, J=2.3 Hz, 1H), 4.27-4.10 (m, 2H), 3.97-3.76 (m, 2H), 3.76-3.56 (m, 2H), 3.50-3.33 (m, 1H), 3.14 (qd, J=7.3, 4.1 Hz, 2H), 3.03-2.81 (m, 3H), 2.72 (d, J=8.4 Hz, 1H), 2.54 (s, 1H), 2.22 (t, J=10.6 Hz, 1H), 1.61 (d, J=12.6 Hz, 1H).

Example 227 and Example 228

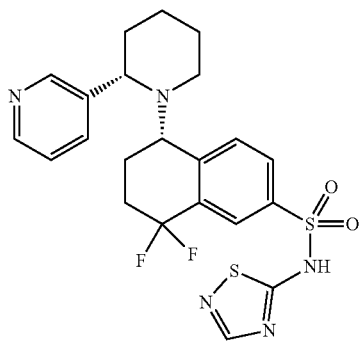

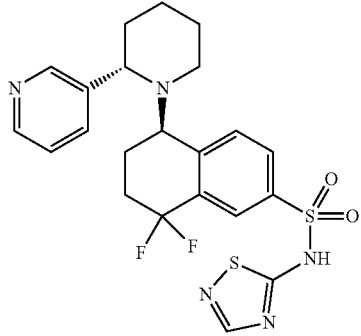

(S)-8,8-difluoro-5-((S)-2-(pyridin-3-yl)piperidin-1-yl)-N-(1,2,4-thiadiazol-5-yl)-5,6,7,8-tetrahydronaphthalene-2-sulfonamide and (R)-8,8-difluoro-5-((S)-2-(pyridin-3-yl)piperidin-1-yl)-N-(1,2,4-thiadiazol-5-yl)-5,6,7,8-tetrahydronaphthalene-2-sulfonamide

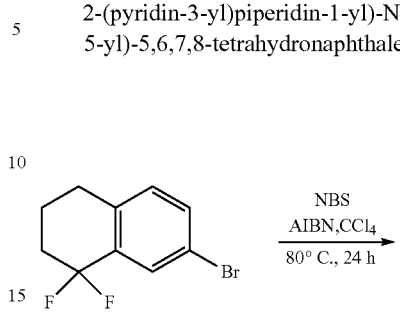

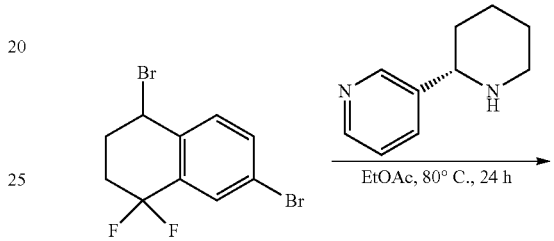

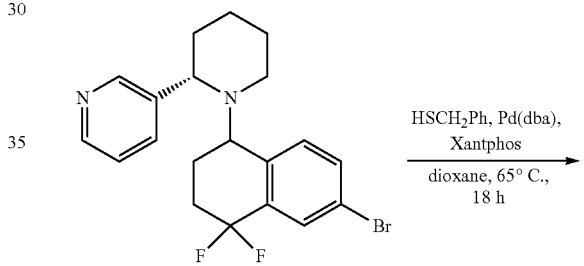

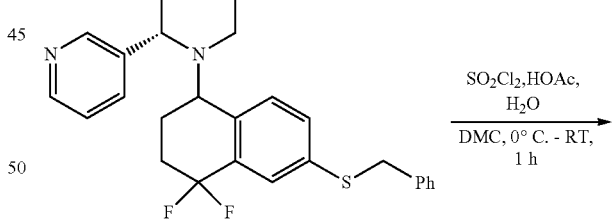

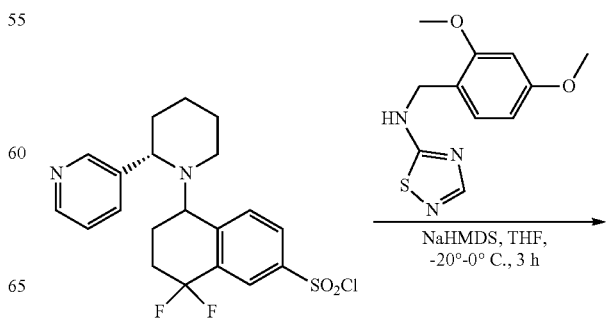

445

-continued

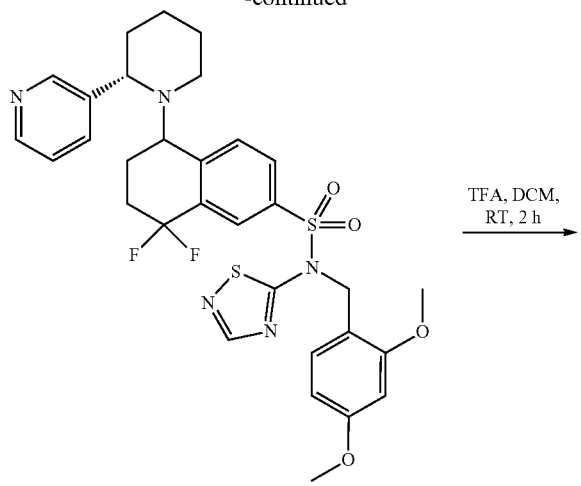

Step 1

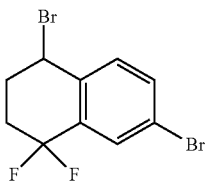 [SMILES: FC1(F)CCC(Br)c2ccc(Br)cc21]

4,7-dibromo-1,1-difluoro-1,2,3,4-tetrahydronaphthalene

NaBH₄ (166 mg, 4.40 mmol) was added to a solution of 7-bromochroman-4-one (2.00 g, 8.80 mmol) in MeOH (45 mL) at r.t. After 30 minutes, the reaction was quenched by the addition of 1% aqueous HCl (100 mL) and DCM (100 mL). The organic layer was removed and the aqueous layer was extracted with DCM (2×100 mL). The combined organic fractions were dried with Na₂SO₄ and concentrated. The crude product was used in the subsequent step without further purification. A mixture of 7-bromo-1,1-difluoro-tetralin (1200 mg, 4.85 mmol), N-bromosuccinimide (864 mg, 4.85 mmol) and 2,2'-azobis(2-methylpropionitrile) (40 mg, 0.24 mmol) in carbon tetrachloride (18 mL) was heated in a sealed vial at 80° C. for 24 hours. The mixture was filtered, concentrated and the residue dry loaded into a 12 g silica gel column. The product was eluted with heptane to afford 4,7-dibromo-1,1-difluoro-1,2,3,4-tetrahydronaphthalene (1414 mg, 89%) as a yellowish foam. ¹H NMR (400 MHz, Chloroform-d) δ 7.81 (t, J=1.9 Hz, 1H), 7.55 (dt, J=8.4, 1.8 Hz, 1H), 7.29 (dd, J=8.5, 1.3 Hz, 1H), 5.53-5.37 (m, 1H), 2.84-2.58 (m, 1H), 2.55-2.33 (m, 3H).

Step 2

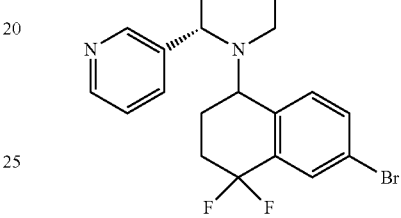

3-((2S)-1-(6-bromo-4,4-difluoro-1,2,3,4-tetrahydronaphthalen-1-yl)piperidin-2-yl)pyridin A mixture of 4,7-dibromo-1,1-difluoro-tetralin (1249 mg, 3.83 mmol) and 3-[(2S)-2-piperidyl]pyridine (1865 mg, 11.5 mmol) in 20 ml of ethyl acetate was heated in a sealed tube at 65° C. for 24 hours. The mixture was partitioned between ethyl acetate and 1M aq. Na₂CO₃. The organic extracts were dried over Na₂SO₄ and concentrated. The residue was purified on a 24 g silica gel column eluting with methanol gradient (0-10%) in DCM to afford 3-((2S)-1-(6-bromo-4,4-difluoro-1,2,3,4-tetrahydronaphthalen-1-yl)piperidin-2-yl)pyridin (770 mg, 49%) as a mixture of diastereomers. m/z 407 [M+H]⁺.

Step 3

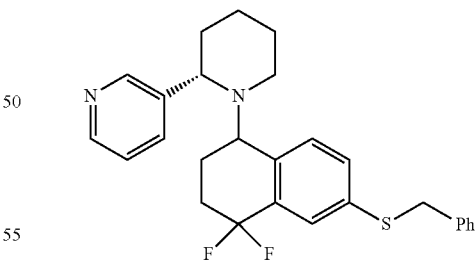

3-((2S)-1-(6-(benzylthio)-4,4-difluoro-1,2,3,4-tetrahydronaphthalen-1-yl)piperidin-2-yl)pyridine A mixture of 3-[(2S)-1-(6-bromo-4,4-difluoro-tetralin-1-yl)-2-piperidyl]pyridine (770 mg, 1.89 mmol), bis(dibenzylideneacetone)palladium (55 mg, 0.095 mmol), 4,5-bis(diphenylphosphino)-9,9-dimethylxanthene (109 mg, 0.1890 mmol) and N,N-diisopropylethylamine (1.32 ml, 7.56 mmol) was degassed and phenylmethanethiol (567 mg,

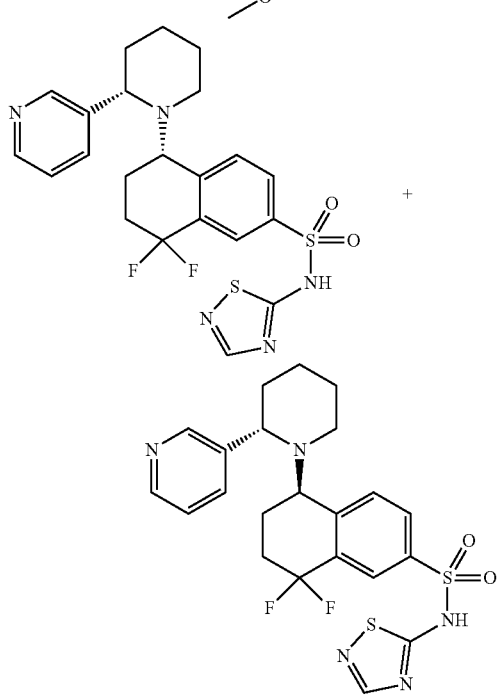

4.537 mmol) was added. The mixture was heated in a sealed vial at 130° C. for 24 hours and after cooling partitioned between water and 1 M aq. Na₂CO₃. The organic extracts were washed with additional 1 M Na₂CO₃, water, brine, dried over MgSO₄ and concentrated. The residue was purified on a 24 g silica gel column eluting with methanol gradient (0-10%) in DCM to afford 3-((2 S)-1-(6-(benzylthio)-4,4-difluoro-1,2,3,4-tetrahydronaphthalen-1-yl)piperidin-2-yl)pyridine (772 mg, 91%) as a mixture of diastereomers. m/z 451.1 [M+H]⁺.

Step 4

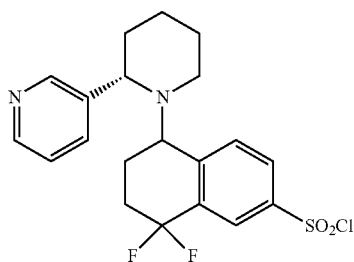 [SMILES: O=S(=O)(Cl)c1ccc2c(c1)C(F)(F)CCC2N1CCCC[C@H]1c1cccnc1]

8,8-difluoro-5-((S)-2-(pyridin-3-yl)piperidin-1-yl)-5,6,7,8-tetrahydronaphthalene-2-sulfonyl chloride 3-[(2S)-1-(6-benzylsulfanyl-4,4-difluoro-tetralin-1-yl)-2-piperidyl]pyridine (160 mg, 0.355 mmol) was dissolved in dichloromethane (4 ml), containing water (26 mg, 1.42 mmol) and acetic acid (85 mg, 1.42 mmol). Sulfuryl chloride (192 mg, 0.115 ml, 1.42 mmol) in 2 ml of DCM was added dropwise at 0° C. After being stirred 1 hour at room temperature, the mixture was concentrated in vacuum and partitioned between ethyl acetate and brine, adjusting pH to neutral by careful addition of 5% aq. NaHCO₃. The ethyl organic extracts were dried with MgSO₄ and concentrated in vacuum. The crude 8,8-difluoro-5-((S)-2-(pyridin-3-yl)piperidin-1-yl)-5,6,7,8-tetrahydronaphthalene-2-sulfonyl chloride (141 mg, 93%) was used in the next step without further purification. m/z 427 [M+H]⁺.

Step 5

N-(2,4-dimethoxybenzyl)-8,8-difluoro-5-((S)-2-(pyridin-3-yl)piperidin-1-yl)-N-(1,2,4-thiadiazol-5-yl)-5,6,7,8-tetrahydronaphthalene-2-sulfonamide sodium bis(trimethylsilyl)amide in tetrahydrofuran (1.1 ml, 1 mol/L) was added to a solution of N-[(2,4-dimethoxyphenyl)methyl]-1,2,4-thiadiazol-5-amine (250 mg, 1.0 mmol) in THF at −20° C. After stirring for 20 min the solution of 8,8-difluoro-5-((S)-2-(pyridin-3-yl)piperidin-1-yl)-5,6,7,8-tetrahydronaphthalene-2-sulfonyl chloride (140 mg, 0.33 mmol) in THF was added dropwise to the above mixture at −20° C. The resulting mixture was stirred for 1 hour at −20° C. and then – at 0° C. for 2 hours. The mixture was quenched with sat aq. NH₄Cl and extracted with ethyl acetate. The organic extracts were washed with water, brine, dried over Na₂SO₄ and concentrated. The residue was purified on a 12 g silica gel column eluting with 0-6% MeOH gradient in DCM to afford N-(2,4-dimethoxybenzyl)-8,8-difluoro-5-((S)-2-(pyridin-3-yl)piperidin-1-yl)-N-(1,2,4-thiadiazol-5-yl)-5,6,7,8-tetrahydronaphthalene-2-sulfonamide (88 mg, 41%) as a mixture of diastereomers. m/z 642 [M+H]⁺.

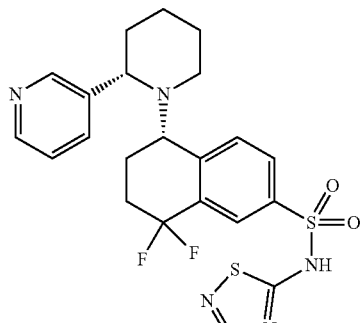

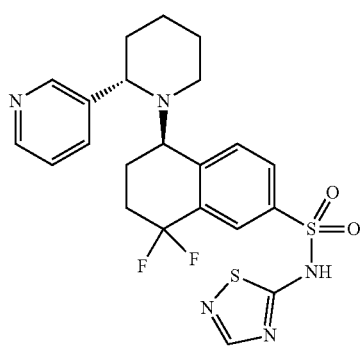

Step 6.

(S)-8,8-difluoro-5-((S)-2-(pyridin-3-yl)piperidin-1-yl)-N-(1,2,4-thiadiazol-5-yl)-5,6,7,8-tetrahydronaphthalene-2-sulfonamide and (R)-8,8-difluoro-5-((S)-2-(pyridin-3-yl)piperidin-1-yl)-N-(1,2,4-thiadiazol-5-yl)-5,6,7,8-tetrahydronaphthalene-2-sulfonamide A mixture of N-[(2,4-dimethoxyphenyl)methyl]-4,4-difluoro-1-[(2S)-2-(3-pyridyl)-1-piperidyl]-N-(1,2,4-thiadiazol-5-yl)tetralin-6-sulfonamide (88 mg, 0.137 mmol) in 6 ml DCM was treated with 2 ml of TFA. The mixture was stirred for 1 hour, concentrated in vacuum and the residue triturated with ethyl ether. The precipitate was collected, washed with ether, and dried in vacuum. The above residue was dissolved in a mixture of water and acetonitrile and lyophilized to afford 32 mg of a mixture of diastereomers which were separated by chiral HPLC.

Diastereomer 1 (7.3 mg, 29%) m/z 642 [M+H]⁺. 1H NMR (400 MHz, DMSO-d6) δ 8.69 (d, J=2.2 Hz, 1H), 8.53-8.46 (m, 1H), 8.30 (s, 1H), 8.15-8.06 (m, 1H), 7.99-7.90 (m, 2H), 7.87 (t, J=1.7 Hz, 1H), 7.41 (dd, J=7.9, 4.8 Hz, 1H), 6.51 (s, 1H), 3.73 (dd, J=10.9, 2.8 Hz, 1H), 3.66-3.58 (m, 1H), 2.42-2.24 (m, 3H), 1.92 (dt, J=12.8, 7.2 Hz, 3H), 1.76 (dd, J=15.9, 11.5 Hz, 2H), 1.70-1.45 (m, 2H), 1.42-1.28 (m, 1H).

Diastereomer 2 (10.6 mg, 42%) m/z 642 [M+H]⁺. 1H NMR (400 MHz, DMSO-d6) δ 8.62 (s, 1H), 8.34-8.30 (m, 2H), 7.89-7.73 (m, 4H), 7.20 (dd, J=8.1, 4.7 Hz, 1H), 6.51 (br.s, 1H), 4.03-3.99 (m, 1H), 3.94-3.85 (m, 1H), 2.72-2.62 (m, 1H), 2.48-2.39 (m, 1H), 2.26-2.22 (m, 1H), 2.06-1.88 (m, 2H), 1.82-1.49 (m, 5H), 1.36 (s, 1H).

Example 229

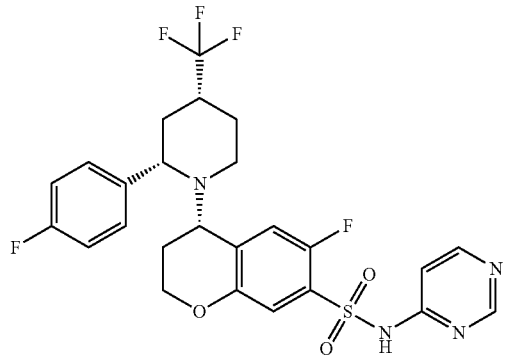

(S)-6-fluoro-4-((2S,4R)-2-(4-fluorophenyl)-4-(trifluoromethyl)piperidin-1-yl)-N-(pyrimidin-4-yl)chroman-7-sulfonamide

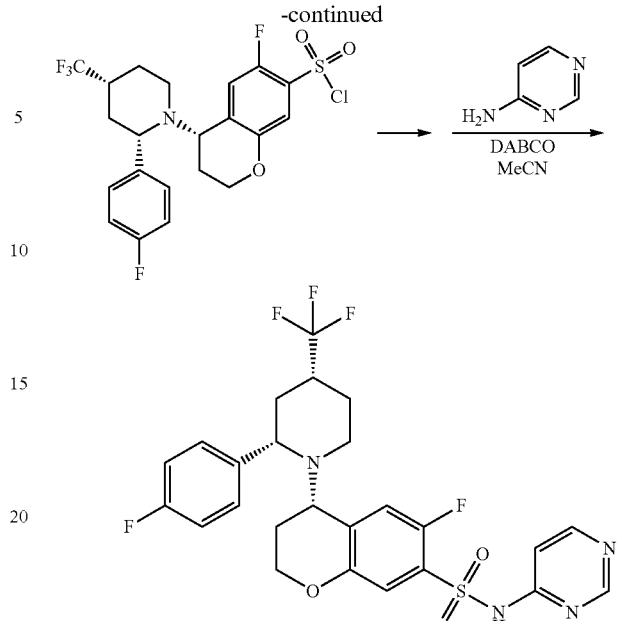

Step 1.

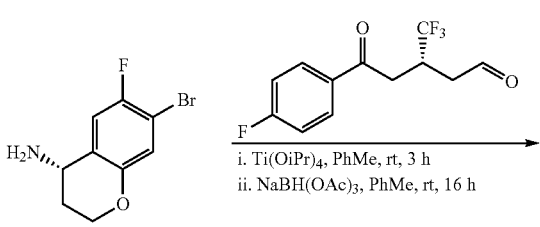

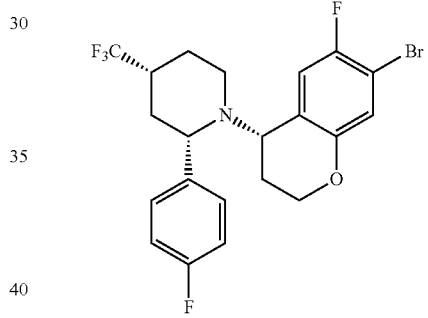

(2S,4R)-1-((S)-7-bromo-6-fluorochroman-4-yl)-2-(4-fluorophenyl)-4-(trifluoromethyl)piperidine To a solution of (4S)-7-bromo-6-fluoro-chroman-4-amine (3.3737 g, 15.19 mmol) and (3R)-5-(4-fluorophenyl)-5-oxo-3-(trifluoromethyl)pentanal (3.982 g, 15.19 mmol, 1 equiv.) in degassed toluene (326.6 mL, 0.0465 M) under Nitrogen at 0° C. was added titanium(iv) isopropoxide (11.3 mL, 2.5 equiv., 37.97 mmol). The reaction was stirred in the ice bath for 20 min, then warmed to room temperature. The reaction was ran for 2 hours at room temperature, was lowered to 0° C., and sodium triacetoxyborohydride (25.75 g, 8 equiv., 121.5 mmol) was added. The reaction was raised back to room temperature and stirred overnight under Nitrogen. The reaction was then diluted with isopropyl acetate (200 mL) washed with sodium bicarbonate (400 mL, 2×) and brine (400 mL). The organic layers were collected, combined, dried with $Na_2SO_4$, and concentrated. The crude mixture was then purified by column chromatography in a 0-50% gradient of Heptane/iPrOAc to give the desired as a clear oil (3.096 g, 43% yield.) 1H NMR (400 MHz, Chloroform-d) δ 7.39 (ddd, J=10.5, 7.6, 3.8 Hz, 3H), 7.03 (t, J=8.7 Hz, 2H), 6.90 (d, J=5.9 Hz, 1H), 4.20 (dt, J=11.2, 3.7 Hz, 1H), 3.82-3.70 (m, 2H), 3.58 (dd, J=11.1, 2.8 Hz, 1H), 2.79 (dt,

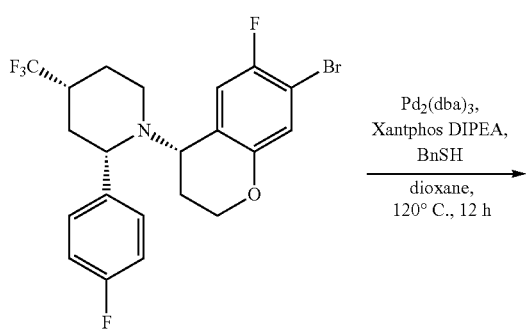

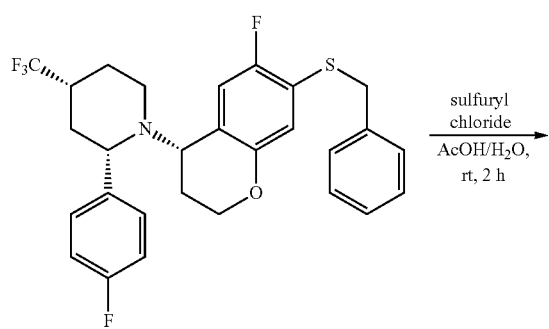

J=11.7, 3.4 Hz, 1H), 2.34-2.10 (m, 2H), 2.09-1.94 (m, 2H), 1.86 (dp, J=11.9, 2.8 Hz, 1H), 1.79-1.58 (m, 3H), 1.36-1.17 (m, 2H), 0.99-0.75 (m, 1H). M+1: 477.95
Step 2.

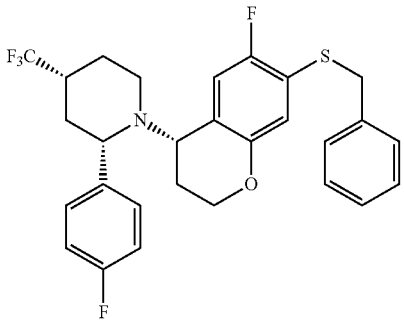 [SMILES: Fc1ccc([C@@H]2C[C@H](C(F)(F)F)CCN2[C@H]2CCOc3cc(SCc4ccccc4)c(F)cc32)cc1]

(2S,4R)-1-((S)-7-(benzylthio)-6-fluorochroman-4-yl)-2-(4-fluorophenyl)-4-(trifluoromethyl)piperidine A mixture of (2s,4r)-1-[(4s)-7-bromo-6-fluoro-chroman-4-yl]-2-(4-fluorophenyl)-4-(trifluoromethyl)piperidine (334.8 mg, 0.7029 mmol), bis(dibenzylideneacetone)palladium (20.1 mg, 0.05 equiv., 0.03515 mmol), 4,5-bis(diphenylphosphino)-9,9-dimethylxanthene (40.7 mg, 0.100 equiv., 0.07029 mmol) in a sealed vial were degassed with nitrogen and placed under nitrogen. Degassed 1,4-dioxane (4.68 mL, 0.15 M) was added to the vial, followed by N,N-Diisopropylethylamine (0.49 mL, 4.00 equiv., 2.812 mmol) and phenylmethanethiol (209.5 mg, 2.40 equiv., 1.687 mmol). The mixture was heated to reflux and ran overnight under $N_2$. The reaction was then cooled to room temperature, diluted with iPrOAc (5 mL), and extracted with water (10 mL, 3×). The organic layer was collected, dried with $Na_2SO_4$, filtered, and concentrated. The crude was purified by column chromatography on a 0-50% heptane/iPrOAc gradient to give the desired as a yellow foam (310.3 mg, 85% yield). 1H NMR (400 MHz, Chloroform-d) δ 7.50-7.15 (m, 7h), 7.03 (t,j=8.8 hz, 2h), 6.66 (d,j=6.3 hz, 1h), 4.15 (dt, j=11.1, 3.7 hz, 1h), 4.06 (s, 2h), 3.82-3.67 (m, 2h), 3.55 (dd, j=11.1, 2.7 hz, 1h), 2.77 (dt, j=11.7, 3.4 hz, 1h), 2.31-2.09 (m, 2h), 2.06-1.92 (m, 2h), 1.86 (dt,j=12.7, 3.2 hz, 1h), 1.73-1.54 (m, 2h). M−1: 519
Step 3.

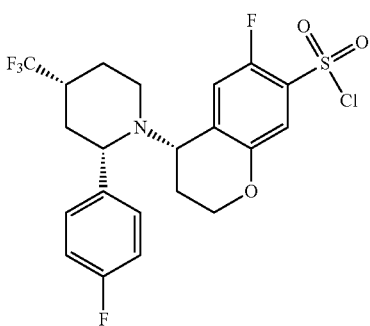 [SMILES: O=S(=O)(Cl)c1cc2c(cc1F)[C@@H](N1CC[C@@H](C(F)(F)F)C[C@H]1c1ccc(F)cc1)CCO2]

(S)-6-fluoro-4-((2S,4R)-2-(4-fluorophenyl)-4-(trifluoromethyl)piperidin-1-yl)chroman-7-sulfonyl chloride (2S,4R)-1-[(4S)-7-benzylsulfanyl-6-fluoro-chroman-4-yl]-2-(4-fluorophenyl)-4-(trifluoromethyl)piperidine (310.3 mg, 0.5972 mmol) was dissolved in dichloromethane (5.97 mL, 0.1 M), containing water (0.43 mL, 4.0 equiv., 2.389 mmol) and acetic acid (0.137 mL, 4.0 equiv., 2.389 mmol). Sulfuryl chloride (0.193 mL, 4.0 equiv., 2.389 mmol) in 2 mL of dichloromethane was added dropwise at 0° C. and the reaction was warmed to room temperature. After 2 hours at room temperature, full conversion was seen. The mixture was then concentrated in vacuum, partitioned between iPrOAc (5 mL) and brine (5 mL), while adjusting pH to neutral. The organic extracts were collected, dried with $Na_2SO_4$ and concentrated to give the desired product as a yellow foam (296 mg, 99% yield). The product was carried on to the next steps as a crude. NMR: 1H NMR (400 MHz, DMSO-d6) δ 14.51 (s, 1H), 7.90 (s, 1H), 7.55 (s, 1H), 7.51-7.14 (m, 4H), 7.09 (d, J=6.2 Hz, 1H), 4.86 (t, J=8.4 Hz, 1H), 4.44 (t, J=7.2 Hz, 1H), 4.20 (dt, J=11.6, 4.8 Hz, 1H), 3.95 (t, J=9.9 Hz, 1H), 3.47-3.36 (m, 1H), 3.18-3.10 (m, 1H), 2.91 (s, 1H), 2.59 (s, 1H), 2.46 (t, J=9.8 Hz, 1H), 2.37-2.29 (m, 1H), 2.13-1.92 (m, 3H). M+1=496
Step 4.

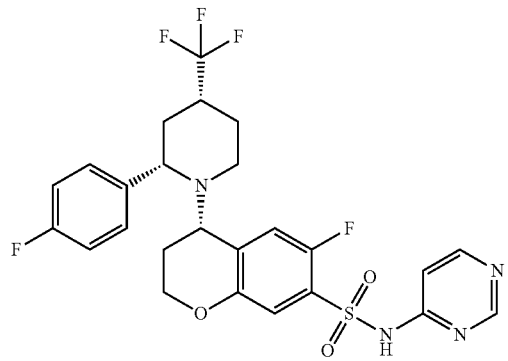

(S)-6-fluoro-4-((2S,4R)-2-(4-fluorophenyl)-4-(trifluoromethyl)piperidin-1-yl)-N-(pyrimidin-4-yl)chroman-7-sulfonamide To a solution of 6-fluoro-4-[(1S,2S,4R)-2-(4-fluorophenyl)-4-(trifluoromethyl)-1-piperidyl]chromane-7-sulfonyl chloride (165 mg, 0.3327 mmol) in acetonitrile (0.2 M, 31.7 mmol) was added pyrimidin-4-amine (34.81 mg, 1.1 equiv., 0.3660 mmol), followed by 1,4-diazabicyclo[2.2.2]octane (74.65 mg, 2 equiv., 0.6655 mmol) at room temperature. The reaction was heated to 50° C. and full conversion was seen after 1 hour. The reaction was cooled to room temperature, concentrated, and submitted to purification to give the desired compound as a white solid (31.6 mg, 17% yield). H NMR (400 MHz, DMSO-d6) δ 8.56 (s, 1H), 8.25 (s, 1H), 7.55 (dd, J=8.9, 5.2 Hz, 3H), 7.21-7.10 (m, 3H), 7.00 (d, J=4.5 Hz, 1H), 4.25 (dt, J=11.3, 3.6 Hz, 1H), 3.82 (td, J=11.2, 2.1 Hz, 1H), 3.74 (dd, J=10.9, 2.8 Hz, 1H), 3.66 (dd, J=10.6, 5.9 Hz, 1H), 2.61-2.50 (m, 1H), 2.42-2.33 (m, 2H), 2.05-1.88 (m, 1H), 1.82 (tdd, J=13.7, 6.7, 4.4 Hz, 3H), 1.71-1.46 (m, 2H). M+1=555.1

Example 230

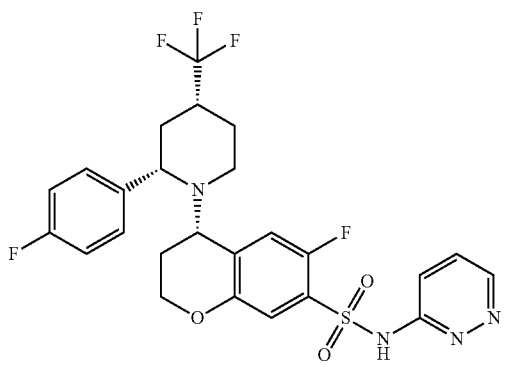

(S)-6-fluoro-4-((2S,4R)-2-(4-fluorophenyl)-4-(trifluoromethyl)piperidin-1-yl)-N-(pyridazin-3-yl)chroman-7-sulfonamide The compound was made the as for Example 229, using pyridazin-3-amine as the amine, to give the desired compound as a white solid (25.1 mg, 14% yield). 1H NMR (400 MHz, DMSO-d6) δ 14.59 (s, 1H), 8.34 (s, 1H), 7.89 (s, 1H), 7.69 (dd, J=9.6, 4.2 Hz, 1H), 7.53 (td, J=7.9, 6.9, 3.4 Hz, 3H), 7.21-7.14 (m, 2H), 7.12 (d, J=6.0 Hz, 1H), 4.24 (dt, J=11.3, 3.6 Hz, 1H), 3.86-3.78 (m, 1H), 3.74 (dd, J=10.9, 2.7 Hz, 1H), 3.65 (dd, J=10.5, 5.9 Hz, 1H), 2.62-2.52 (m, 1H), 2.41-2.33 (m, 1H), 2.04-1.91 (m, 1H), 1.88-1.76 (m, 4H), 1.70-1.46 (m, 2H). M+1=555.1

Example 231

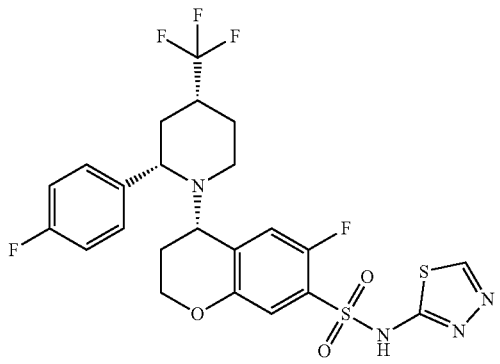 [SMILES: O=S(=O)(Nc1nncs1)c1cc2c(cc1F)[C@@H](N1CC[C@@H](C(F)(F)F)C[C@H]1c1ccc(F)cc1)CCO2]

(S)-6-fluoro-4-((2S,4R)-2-(4-fluorophenyl)-4-(trifluoromethyl)piperidin-1-yl)-N-(1,3,4-thiadiazol-2-yl)chroman-7-sulfonamide 6-fluoro-4-[(1S,2S,4R)-2-(4-fluorophenyl)-4-(trifluoromethyl)-1-piperidyl]chromane-7-sulfonyl chloride (107.4 mg, 0.2166 mmol) in pyridine (3.3 mL, 0.8 M) was added to a solution of 1,3,4-thiadiazol-2-amine (27.38 mg, 1.25 equiv., 0.2707 mmol) in pyridine (3.3 mL, 0.8 M). The reaction was heated to 60° C. After 1 h, full conversion was seen. The reaction was cooled to room temperature, concentrated, and submitted to purification to give the desired compound as a white solid (18.6 mg, 15% yield). 1H NMR (400 MHz, DMSO-d6) δ 14.48 (s, 1H), 8.75 (s, 1H), 7.59-7.50 (m, 3H), 7.22-7.12 (m, 2H), 7.04 (d, J=5.9 Hz, 1H), 4.24 (dt, J=11.3, 3.6 Hz, 1H), 3.82 (dd, J=11.5, 2.2 Hz, 1H), 3.79-3.71 (m, 1H), 3.66 (dd, J=10.6, 5.9 Hz, 1H), 2.62-2.42 (m, 2H), 2.41-2.33 (m, 1H), 2.04-1.73 (m, 4H), 1.71-1.46 (m, 2H). M+1=561

Example 232

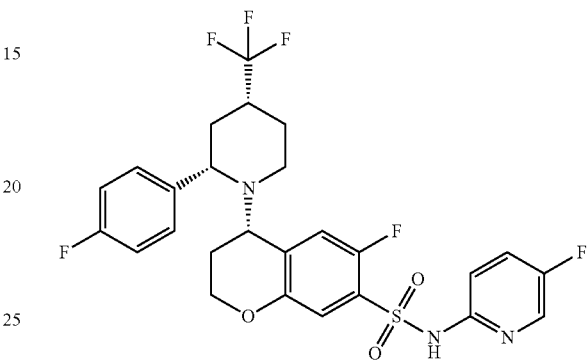

(S)-6-fluoro-4-((2S,4R)-2-(4-fluorophenyl)-4-(trifluoromethyl)piperidin-1-yl)-N-(5-fluoropyridin-2-yl)chroman-7-sulfonamide The compound was made the as for Example 229, using 5-fluoropyridin-2-amine as the amine, dichloromethane as the solvent instead of pyridine, and 2.6 equivalents of pyridine, and the reaction was heated to 30° C., to give the desired compound as a white solid (50.8 mg, 30% yield).

1H NMR (400 MHz, DMSO-d6) δ 11.42 (s, 1H), 8.14 (d, J=3.0 Hz, 1H), 7.65 (td, J=8.6, 3.1 Hz, 1H), 7.59-7.50 (m, 3H), 7.21-7.11 (m, 3H), 7.07 (dd, J=9.0, 3.8 Hz, 1H), 4.25 (dt, J=11.3, 3.6 Hz, 1H), 3.82 (td, J=11.3, 2.1 Hz, 1H), 3.74 (dd, J=11.1, 2.7 Hz, 1H), 3.65 (dd, J=10.6, 5.9 Hz, 1H), 3.42-3.16 (m, 2H), 2.41-2.33 (m, 1H), 1.96 (qd, J=10.9, 5.6 Hz, 1H), 1.88-1.75 (m, 3H), 1.71-1.46 (m, 2H). M+1=572.1

Example 233

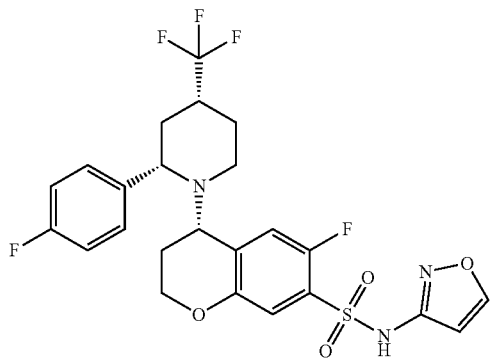 [SMILES: O=S(=O)(Nc1ccon1)c1cc2c(cc1F)[C@@H](N1CC[C@@H](C(F)(F)F)C[C@H]1c1ccc(F)cc1)CCO2]

(S)-6-fluoro-4-((2S,4R)-2-(4-fluorophenyl)-4-(trifluoromethyl)piperidin-1-yl)-N-(isoxazol-3-yl)chroman-7-sulfonamide The compound was made the as for Example 229, using isoxazol-3-amine as the amine, to give the desired compound as a white solid (55.8 mg, 45% yield). 1H NMR (400 MHz, DMSO-d6) δ 11.92 (s, 1H), 8.68 (s, 1H), 7.62 (d, J=10.8 Hz, 1H), 7.55 (dd, J=8.2, 5.5 Hz, 2H), 7.21-7.12 (m, 2H), 7.09 (d, J=5.9 Hz, 1H), 6.35 (d, J=2.0 Hz, 1H), 4.25 (dt, J=11.3, 3.5 Hz, 1H), 3.83 (td, J=11.4, 2.1 Hz, 1H), 3.74 (dd, J=11.0, 2.7 Hz, 1H), 3.67 (dd, J=10.6, 5.8 Hz, 1H), 2.37 (dd, J=11.6, 2.0 Hz, 3H), 2.03-1.90 (m, 2H), 1.83 (dd, J=16.7, 12.8 Hz, 4H), 1.72-1.48 (m, 2H). M+1=544.

Example 234

Using procedures similar to those described herein the following compounds may also be prepared.

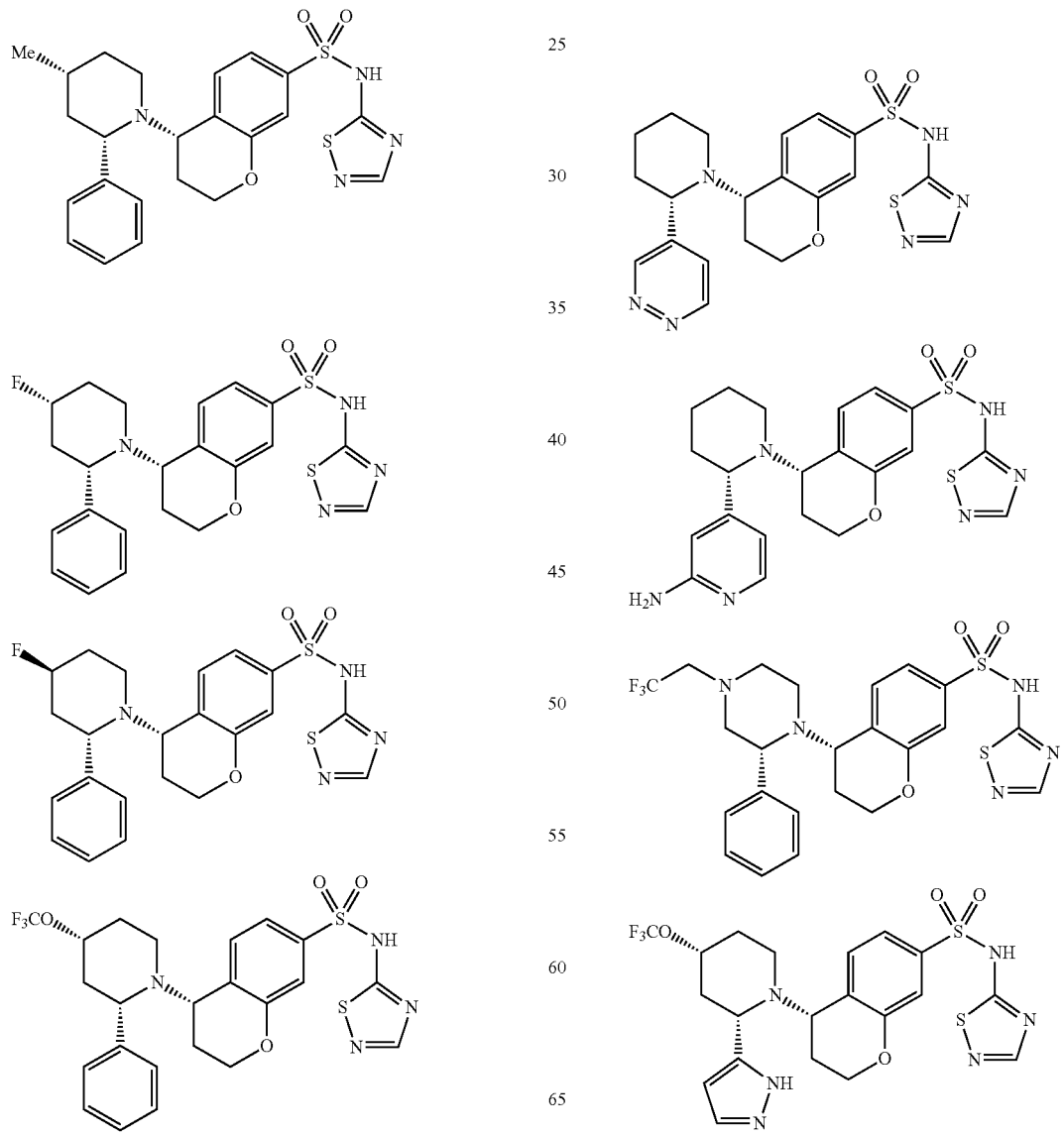

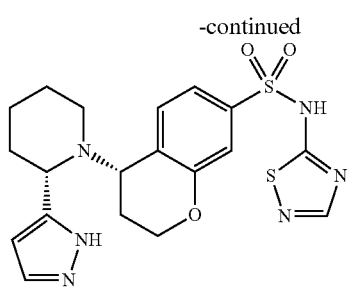

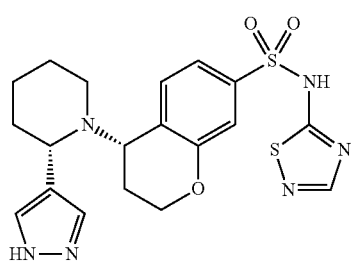

-continued

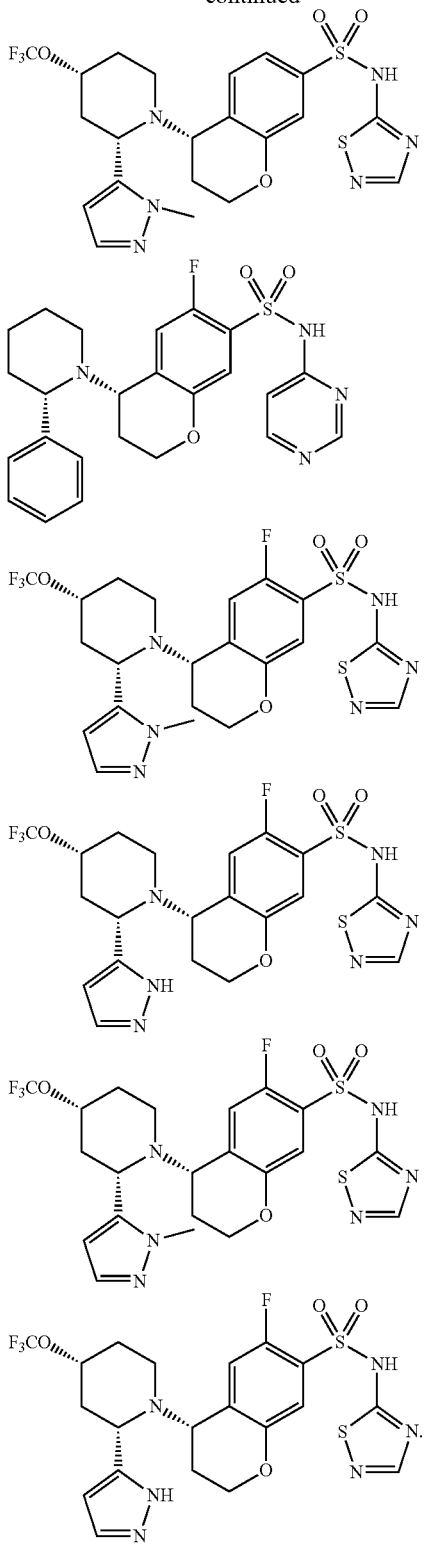

and

Example 235 Tritiated Compound Binding to Membranes Isolated from Cells that Heterologously Express hNav1.7 and the β1 Subunit Preparation of membranes containing recombinantly expressed sodium channels: Frozen recombinant cell pellets were thawed on ice and diluted to 4 times the cell pellet weight with ice cold 50 mM Tris HCl, pH 7.4 buffer. The cell suspensions were homogenized on ice using a motorized glass dounce homogeniser. Homogenates were further diluted 8.4 times with ice cold 50 mM Tris HCl, pH 7.4 buffer and then centrifuged at 200×g at 4° C. for 15 min. The supernatants were collected and centrifuged at 10000×g at 4° C. for 50 min. The pellets were then re-suspended in 100 mM NaCl, 20 mM Tris HCl, pH 7.4 buffer containing 1% v/v protease inhibitors (Calbiochem) and re-homogenized on ice. The homogenized membranes were then processed through a syringe equipped with a 26 gauge needle. Protein concentrations were determined by Bradford Assay and the membranes were stored at −80° C.

Radioligand Binding Studies:

Saturation experiments. A competitive NaV1.7 inhibitor having a methyl group was tritiated. Three tritiums were incorporated in place of methyl hydrogens to generate [³H]compound. Binding of this radioligand was performed in 5 mL borosilicate glass test tubes at room temperature. Binding was initiated by adding membranes to increasing concentrations of [³H]compound in 100 mM NaCl, 20 mM Tris HCl, pH 7.4 buffer containing 0.01% w/v bovine serum albumin (BSA) for 18 h. Non-specific binding was determined in the presence of 1 LM unlabeled compound. After 18 h, the reactants were filtered through GF/C glass fiber filters presoaked in 0.5% w/v polyethylene imine. Filters were washed with 15 mL ice cold 100 mM NaCl, 20 mM Tris HCl, pH7.4 buffer containing 0.25% BSA to separate bound from free ligand. [³H]compound bound to filters was quantified by liquid scintillation counting.

Competitive Binding Experiments:

Binding reactions were performed in 96-well polypropylene plates at room temperature for 18 h. In 360 μL, membranes were incubated with 100 pM [³H]compound and increasing concentrations of Test Compound. Non-specific binding was defined in the presence of 1 LM unlabeled compound. Reactions were transferred and filtered through 96-well glass fiber/C filter plates presoaked with 0.5% polyethylene imine. The filtered reactions were washed 5 times with 200 μL ice cold buffer containing 0.25% BSA. Bound radioactivity was determined by liquid scintillation counting.

Data Analysis: For saturation experiments, non-specific binding was subtracted from total binding to provide specific binding and these values were recalculated in terms of pmol ligand bound per mg protein. Saturation curves were constructed and dissociation constants were calculated using the single site ligand binding model: Beq=(Bmax*X)/(X+Kd), where Beq is the amount of ligand bound at equilibrium, Bmax is the maximum receptor density, Kd is the dissociation constant for the ligand, and X is the free ligand concentration. For competition studies percent inhibition was determined and IC$_{50}$ values were calculated using a 4 parameter logistic model (% inhibition=(A+((B−A)/(1+((x/C)^D)))) using XLfit, where A and B are the maximal and minimum inhibition respectively, C is the IC$_{50}$ concentration and D is the (Hill) slope.

Representative compounds, when tested in this model, demonstrated affinities as set forth in Table 1.

TABLE 1
| Example | Structure | Nav1.7 (LBA) (μM) |
|---|---|---|
| 1 | 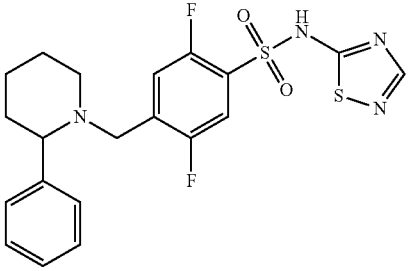 [SMILES: O=S(=O)(Nc1ncns1)c1cc(F)c(CN2CCCCC2c2ccccc2)cc1F] | 0.474 |
| 2 | 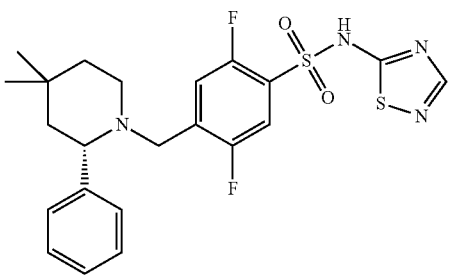 [SMILES: CC1(C)CCN(Cc2cc(F)c(S(=O)(=O)Nc3ncns3)cc2F)[C@H](c2ccccc2)C1] | 0.288 |
| 3 | 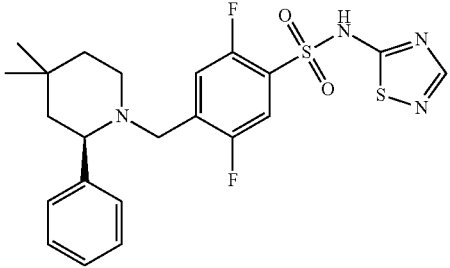 [SMILES: CC1(C)CCN(Cc2cc(F)c(S(=O)(=O)Nc3ncns3)cc2F)[C@@H](c2ccccc2)C1] | 9.28 |
| 4 | 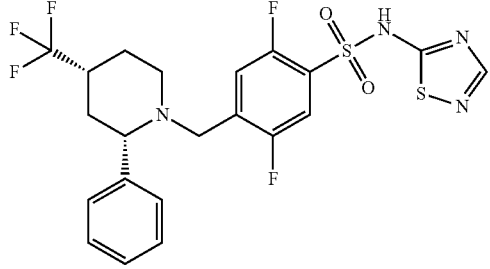 [SMILES: O=S(=O)(Nc1ncns1)c1cc(F)c(CN2CC[C@@H](C(F)(F)F)C[C@H]2c2ccccc2)cc1F] | 0.0226 |
| 5 | 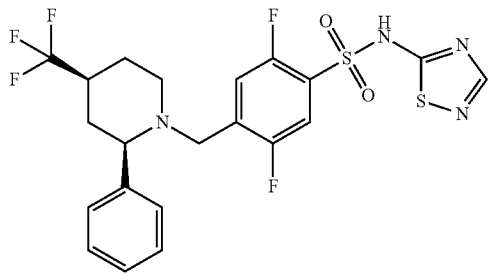 [SMILES: O=S(=O)(Nc1ncns1)c1cc(F)c(CN2CC[C@H](C(F)(F)F)C[C@@H]2c2ccccc2)cc1F] | 1.73 |

TABLE 1-continued

| Example | Structure | Nav1.7 (LBA) (μM) |
|---|---|---|
| 6 | 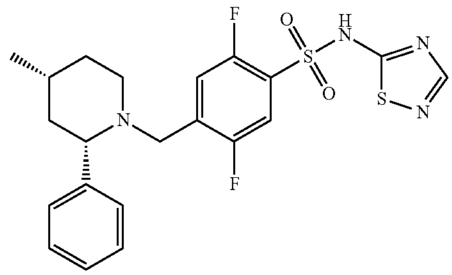 [SMILES: C[C@@H]1CCN(Cc2cc(F)c(S(=O)(=O)Nc3ncns3)cc2F)[C@H](c2ccccc2)C1] | 0.17 |
| 7 | 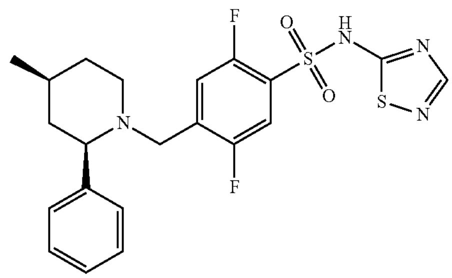 [SMILES: C[C@H]1CCN(Cc2cc(F)c(S(=O)(=O)Nc3ncns3)cc2F)[C@@H](c2ccccc2)C1] | 4.23 |
| 8 | 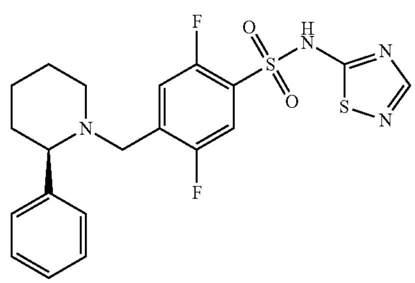 [SMILES: O=S(=O)(Nc1ncns1)c1cc(F)c(CN2CCCC[C@@H]2c2ccccc2)cc1F] | 2.13 |
| 9 | 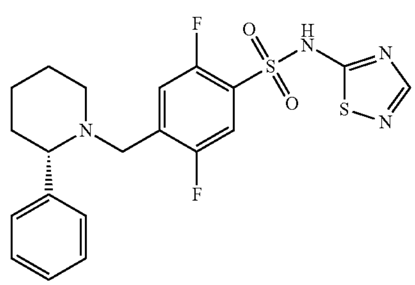 [SMILES: O=S(=O)(Nc1ncns1)c1cc(F)c(CN2CCCC[C@H]2c2ccccc2)cc1F] | 0.452 |
| 10 | 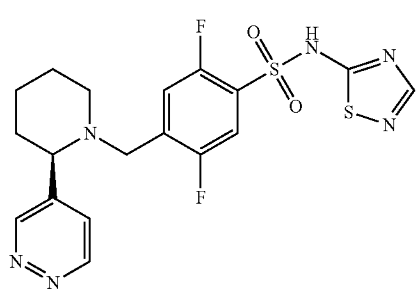 [SMILES: O=S(=O)(Nc1ncns1)c1cc(F)c(CN2CCCC[C@@H]2c2ccnnc2)cc1F] | 10 |

TABLE 1-continued
| Example | Structure | Nav1.7 (LBA) (μM) |
|---|---|---|
| 11 | 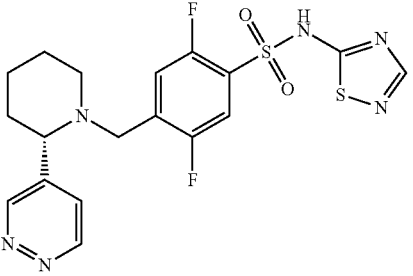 [SMILES: O=S(=O)(Nc1ncns1)c1cc(F)c(CN2CCCC[C@H]2c2ccnnc2)cc1F] | 1.26 |
| 12 | 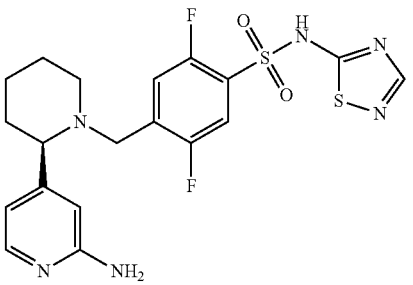 [SMILES: Nc1cc([C@H]2CCCCN2Cc2cc(F)c(S(=O)(=O)Nc3ncns3)cc2F)ccn1] | 10 |
| 13 | 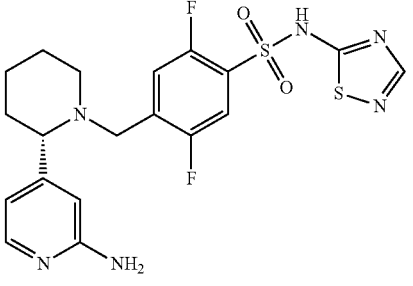 [SMILES: Nc1cc([C@@H]2CCCCN2Cc2cc(F)c(S(=O)(=O)Nc3ncns3)cc2F)ccn1] | 0.158 |
| 14 | 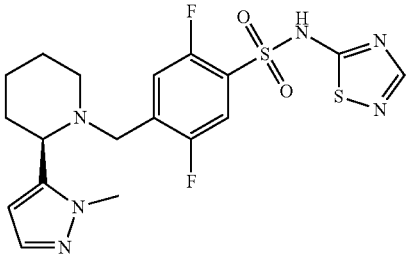 [SMILES: Cn1nccc1[C@H]1CCCCN1Cc1cc(F)c(S(=O)(=O)Nc2ncns2)cc1F] | 0.22 |
| 15 | 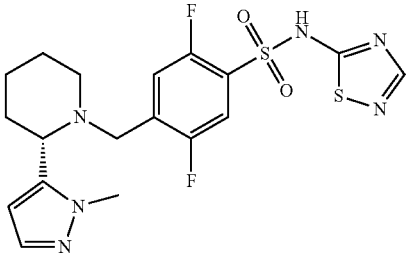 [SMILES: Cn1nccc1[C@@H]1CCCCN1Cc1cc(F)c(S(=O)(=O)Nc2ncns2)cc1F] | 9.36 |

TABLE 1-continued

| Example | Structure | Nav1.7 (LBA) (μM) |
|---|---|---|
| 16 | 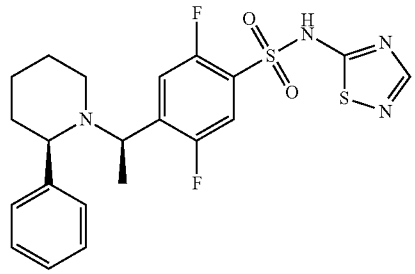 [SMILES: C[C@H](c1cc(F)c(S(=O)(=O)Nc2ncns2)cc1F)N1CCCC[C@@H]1c1ccccc1] | 3.65 |
| 17 | 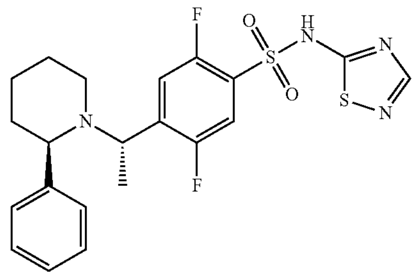 [SMILES: C[C@@H](c1cc(F)c(S(=O)(=O)Nc2ncns2)cc1F)N1CCCC[C@@H]1c1ccccc1] | 10 |
| 18 | 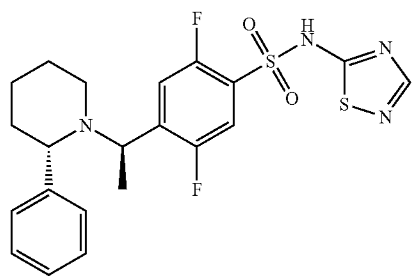 [SMILES: C[C@H](c1cc(F)c(S(=O)(=O)Nc2ncns2)cc1F)N1CCCC[C@H]1c1ccccc1] | 1.38 |
| 19 | 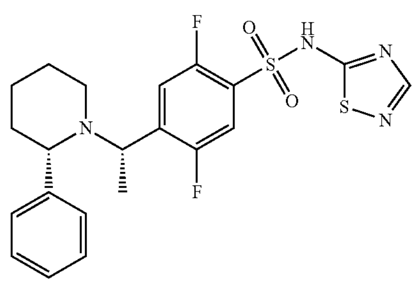 [SMILES: C[C@@H](c1cc(F)c(S(=O)(=O)Nc2ncns2)cc1F)N1CCCC[C@H]1c1ccccc1] | 10 |
| 20 | 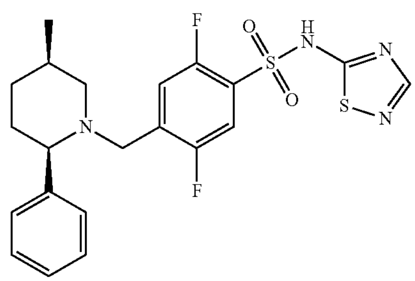 [SMILES: C[C@@H]1CC[C@H](c2ccccc2)N(Cc2cc(F)c(S(=O)(=O)Nc3ncns3)cc2F)C1] | 1.56 |

TABLE 1-continued

| Example | Structure | Nav1.7 (LBA) (µM) |
|---------|-----------|-------------------|
| 21 | 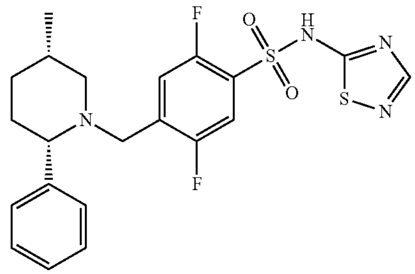 [SMILES: C[C@H]1CC[C@@H](c2ccccc2)N(Cc2cc(F)c(S(=O)(=O)Nc3ncns3)cc2F)C1] | 0.672 |
| 22 | 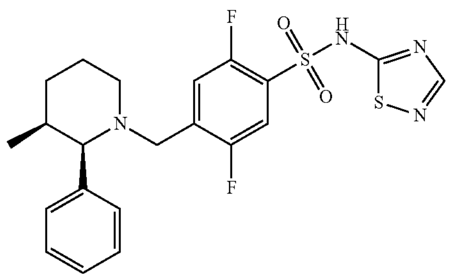 [SMILES: C[C@H]1CCCN(Cc2cc(F)c(S(=O)(=O)Nc3ncns3)cc2F)[C@H]1c1ccccc1] | 1.55 |
| 23 | 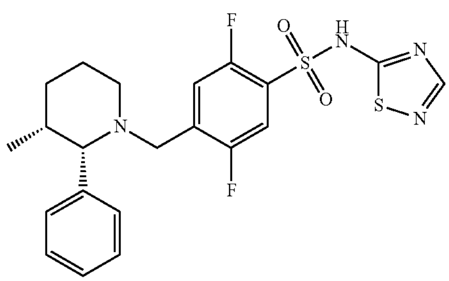 [SMILES: C[C@@H]1CCCN(Cc2cc(F)c(S(=O)(=O)Nc3ncns3)cc2F)[C@@H]1c1ccccc1] | 0.366 |
| 24 | 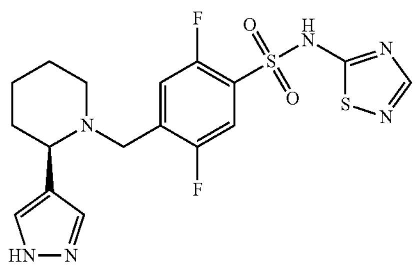 [SMILES: O=S(=O)(Nc1ncns1)c1cc(F)c(CN2CCCC[C@@H]2c2cn[nH]c2)cc1F] | 10 |
| 25 | 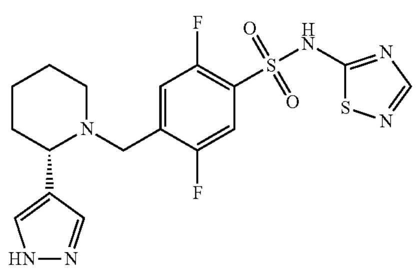 [SMILES: O=S(=O)(Nc1ncns1)c1cc(F)c(CN2CCCC[C@H]2c2cn[nH]c2)cc1F] | 2.24 |

TABLE 1-continued

| Example | Structure | Nav1.7 (LBA) (μM) |
|---------|-----------|-------------------|
| 26 | 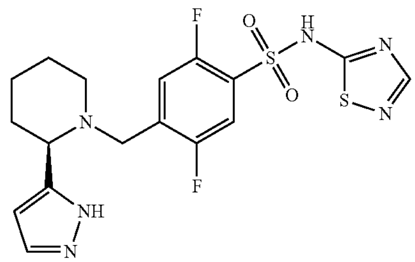 [SMILES: O=S(=O)(Nc1ncns1)c1cc(F)c(CN2CCCC[C@@H]2c2ccn[nH]2)cc1F] | 10 |
| 27 | 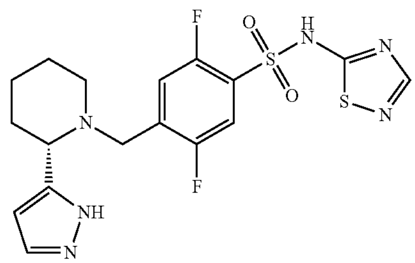 [SMILES: O=S(=O)(Nc1ncns1)c1cc(F)c(CN2CCCC[C@H]2c2ccn[nH]2)cc1F] | 0.118 |
| 28 | 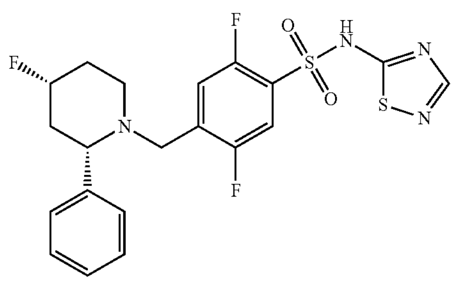 [SMILES: O=S(=O)(Nc1ncns1)c1cc(F)c(CN2CC[C@@H](F)C[C@H]2c2ccccc2)cc1F] | 5.98 |
| 29 | 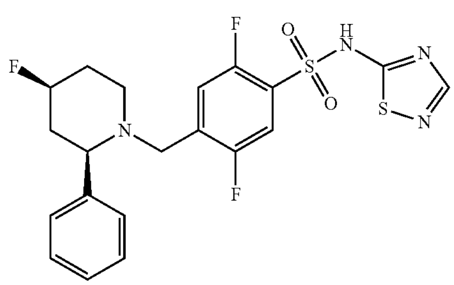 [SMILES: O=S(=O)(Nc1ncns1)c1cc(F)c(CN2CC[C@H](F)C[C@@H]2c2ccccc2)cc1F] | 0.157 |
| 30 | 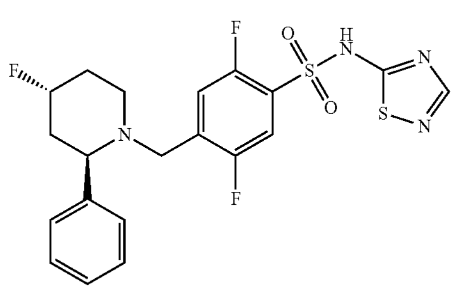 [SMILES: O=S(=O)(Nc1ncns1)c1cc(F)c(CN2CC[C@@H](F)C[C@@H]2c2ccccc2)cc1F] | 1.71 |

TABLE 1-continued
| Example | Structure | Nav1.7 (LBA) (μM) |
|---|---|---|
| 31 | 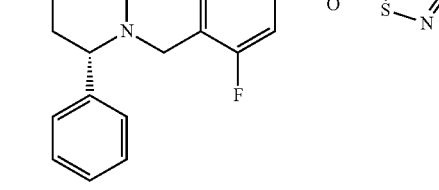 | 0.374 |
| 32 | 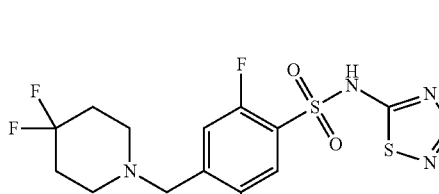 | 0.18 |
| 33 | 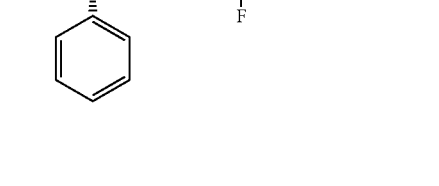 | 4.16 |
| 34 | 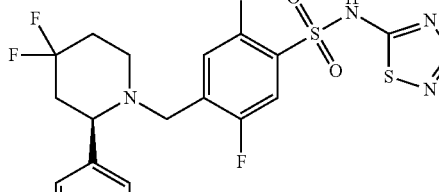 | 1.39 |
| 35 | 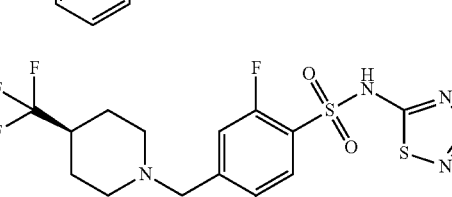 | 0.0786 |

TABLE 1-continued

| Example | Structure | Nav1.7 (LBA) (μM) |
|---|---|---|
| 36 | 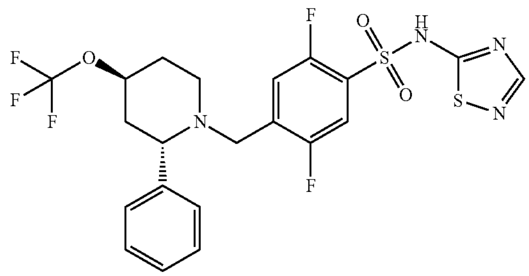 [SMILES: O=S(=O)(Nc1ncns1)c1cc(F)c(CN2CC[C@H](OC(F)(F)F)C[C@H]2c2ccccc2)cc1F] | 0.538 |
| 37 | 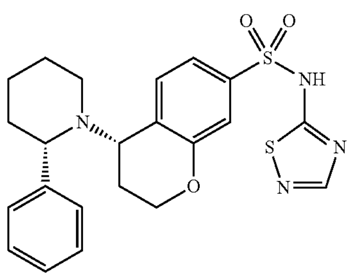 [SMILES: O=S(=O)(Nc1ncns1)c1ccc2c(c1)OCC[C@@H]2N1CCCC[C@H]1c1ccccc1] | 0.0254 |
| 38 | 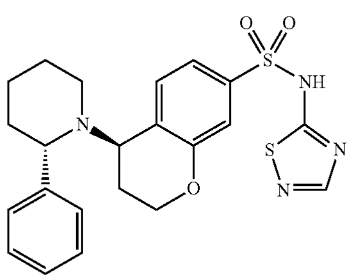 [SMILES: O=S(=O)(Nc1ncns1)c1ccc2c(c1)OCC[C@H]2N1CCCC[C@H]1c1ccccc1] | 0.203 |
| 39 | 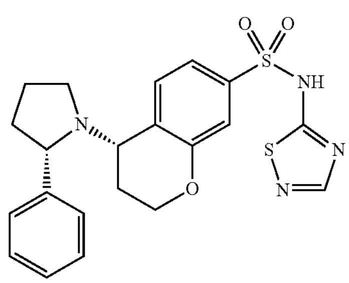 [SMILES: O=S(=O)(Nc1ncns1)c1ccc2c(c1)OCC[C@@H]2N1CCC[C@H]1c1ccccc1] | 0.274 |
| 40 | 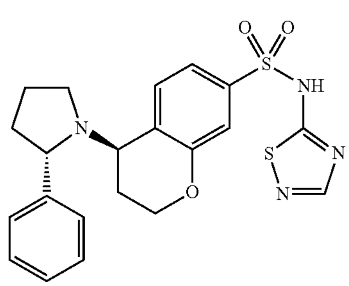 [SMILES: O=S(=O)(Nc1ncns1)c1ccc2c(c1)OCC[C@H]2N1CCC[C@H]1c1ccccc1] | 0.798 |

TABLE 1-continued

| Example | Structure | Nav1.7 (LBA) (μM) |
|---|---|---|
| 41 | 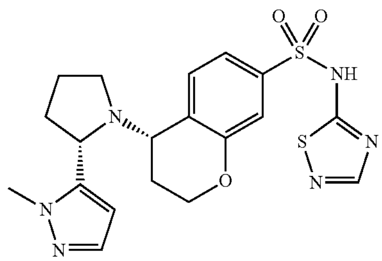 [SMILES: Cn1nccc1[C@@H]1CCCN1[C@H]1CCOc2cc(S(=O)(=O)Nc3ncns3)ccc21] | 0.00609 |
| 42 | 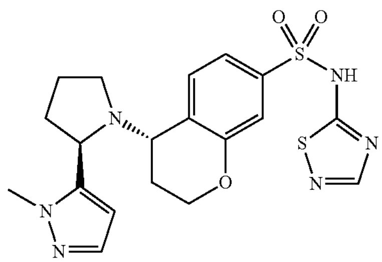 [SMILES: Cn1nccc1[C@H]1CCCN1[C@H]1CCOc2cc(S(=O)(=O)Nc3ncns3)ccc21] | 0.142 |
| 43 | 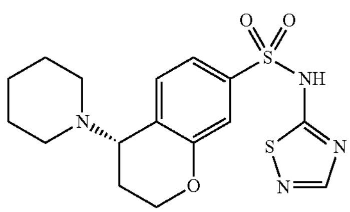 [SMILES: O=S(=O)(Nc1ncns1)c1ccc2c(c1)OCC[C@@H]2N1CCCCC1] | 10 |
| 44 | 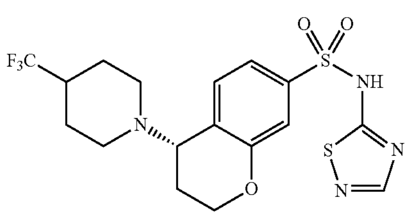 [SMILES: O=S(=O)(Nc1ncns1)c1ccc2c(c1)OCC[C@@H]2N1CCC(C(F)(F)F)CC1] | 0.551 |
| 45 | 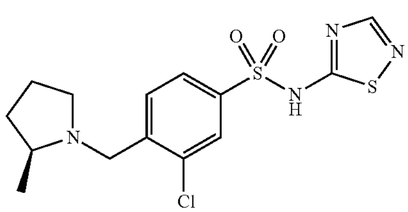 [SMILES: C[C@H]1CCCN1Cc1ccc(S(=O)(=O)Nc2ncns2)cc1Cl] | 10 |
| 46 | 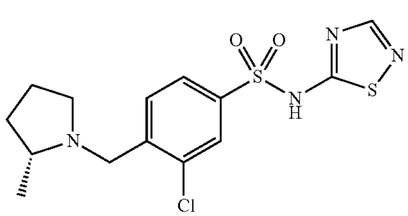 [SMILES: C[C@@H]1CCCN1Cc1ccc(S(=O)(=O)Nc2ncns2)cc1Cl] | 10 |

477
478

TABLE 1-continued

| Example | Structure | Nav1.7 (LBA) (µM) |
|---|---|---|
| 47 | 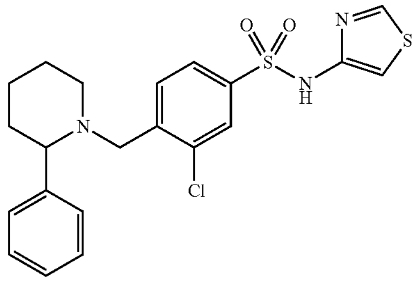 [SMILES: O=S(=O)(Nc1cscn1)c1ccc(CN2CCCCC2c2ccccc2)c(Cl)c1] | 10. |
| 48 | 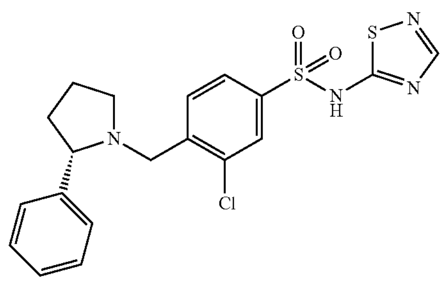 [SMILES: O=S(=O)(Nc1ncns1)c1ccc(CN2CCC[C@H]2c2ccccc2)c(Cl)c1] | 1.48 |
| 49 | 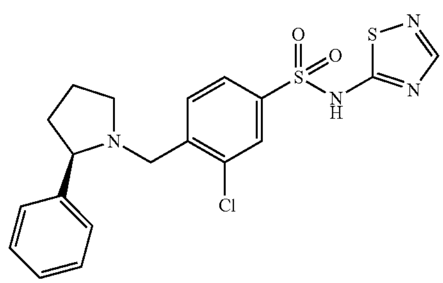 [SMILES: O=S(=O)(Nc1ncns1)c1ccc(CN2CCC[C@@H]2c2ccccc2)c(Cl)c1] | 6.81 |
| 50 | 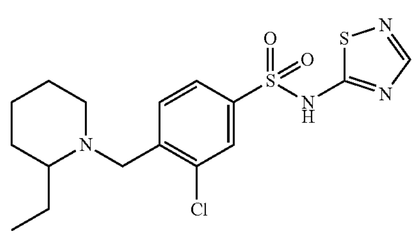 [SMILES: CCC1CCCCN1Cc1ccc(S(=O)(=O)Nc2ncns2)cc1Cl] | 10 |
| 51 | (+/−) | 0.482 |

TABLE 1-continued

| Example | Structure | Nav1.7 (LBA) (μM) |
|---|---|---|
| 52 | (+/−) | 0.269 |
| 53 | 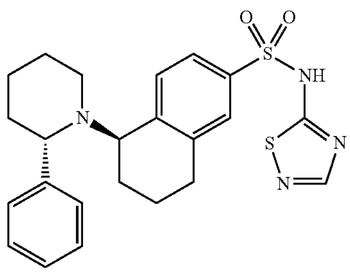 [SMILES: O=S(=O)(Nc1ncns1)c1ccc2c(c1)CCC[C@H]2N1CCCC[C@H]1c1ccccc1] | 0.271 |
| 54 | (S) | 0.411 |
| 55 | (R) | 0.286 |
| 56 | 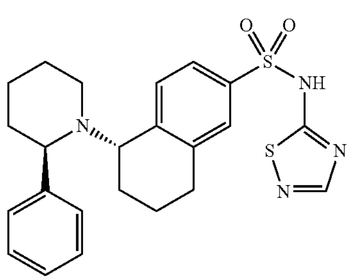 [SMILES: O=S(=O)(Nc1ncns1)c1ccc2c(c1)CCC[C@@H]2N1CCCC[C@@H]1c1ccccc1] | 1.25 |

TABLE 1-continued

| Example | Structure | Nav1.7 (LBA) (μM) |
|---|---|---|
| 57 | (+/−) | 10 |
| 58 | (+/−) | 5.3 |
| 59 | 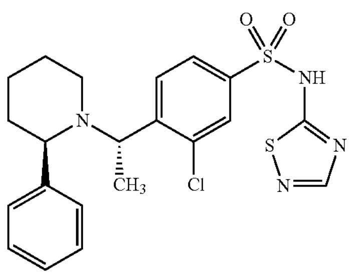 [SMILES: C[C@@H](c1ccc(S(=O)(=O)Nc2ncns2)cc1Cl)N1CCCC[C@@H]1c1ccccc1] | 5.04 |
| 60 | 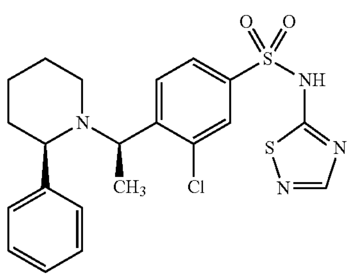 [SMILES: C[C@H](c1ccc(S(=O)(=O)Nc2ncns2)cc1Cl)N1CCCC[C@@H]1c1ccccc1] | 0.33 |
| 61 | 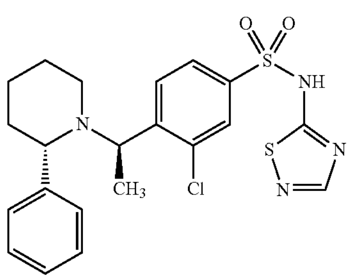 [SMILES: C[C@H](c1ccc(S(=O)(=O)Nc2ncns2)cc1Cl)N1CCCC[C@H]1c1ccccc1] | 3.98 |
| 62 | 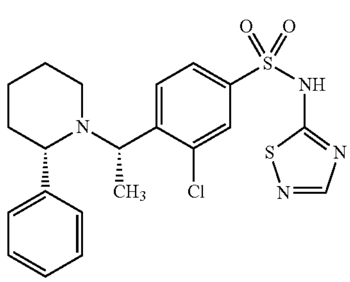 [SMILES: C[C@@H](c1ccc(S(=O)(=O)Nc2ncns2)cc1Cl)N1CCCC[C@H]1c1ccccc1] | 10 |

TABLE 1-continued

| Example | Structure | Nav1.7 (LBA) (μM) |
|---|---|---|
| 63 | 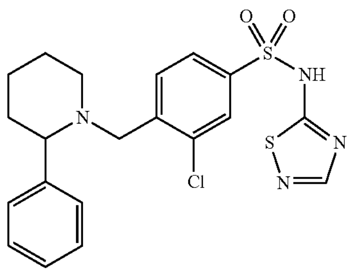 [SMILES: O=S(=O)(Nc1ncns1)c1ccc(CN2CCCCC2c2ccccc2)c(Cl)c1] | 0.609 |
| 64 | 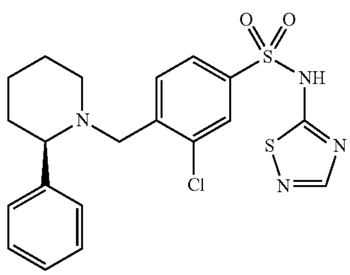 [SMILES: O=S(=O)(Nc1ncns1)c1ccc(CN2CCCC[C@@H]2c2ccccc2)c(Cl)c1] | 0.965 |
| 65 | 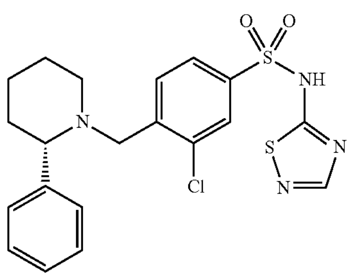 [SMILES: O=S(=O)(Nc1ncns1)c1ccc(CN2CCCC[C@H]2c2ccccc2)c(Cl)c1] | 5.51 |
| 66 | 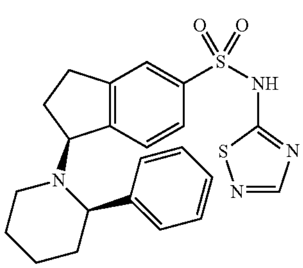 [SMILES: O=S(=O)(Nc1ncns1)c1ccc2c(c1)CC[C@@H]2N1CCCC[C@@H]1c1ccccc1] | 0.597 |
| 67 | 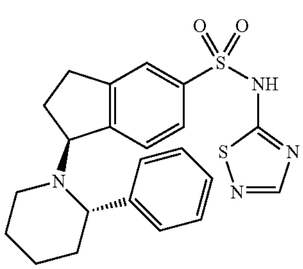 [SMILES: O=S(=O)(Nc1ncns1)c1ccc2c(c1)CC[C@@H]2N1CCCC[C@H]1c1ccccc1] | 0.157 |

TABLE 1-continued

| Example | Structure | Nav1.7 (LBA) (μM) |
|---------|-----------|-------------------|
| 68 | 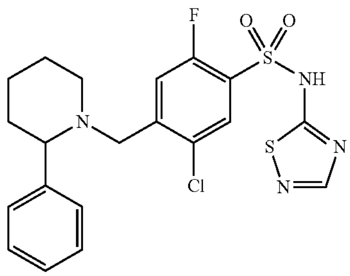 [SMILES: O=S(=O)(Nc1ncns1)c1cc(Cl)c(CN2CCCCC2c2ccccc2)cc1F] | 0.334 |
| 69 | 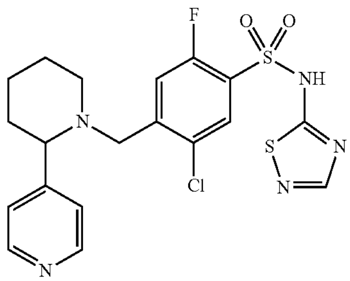 [SMILES: O=S(=O)(Nc1ncns1)c1cc(Cl)c(CN2CCCCC2c2ccncc2)cc1F] | 0.21 |
| 70 | 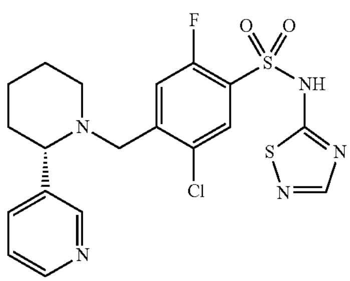 [SMILES: O=S(=O)(Nc1ncns1)c1cc(Cl)c(CN2CCCC[C@H]2c2cccnc2)cc1F] | 0.175 |
| 71 | 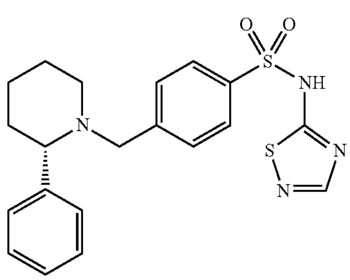 [SMILES: O=S(=O)(Nc1ncns1)c1ccc(CN2CCCC[C@H]2c2ccccc2)cc1] | 10 |
| 72 | 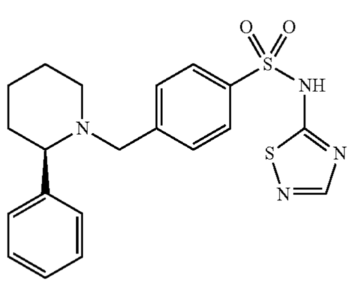 [SMILES: O=S(=O)(Nc1ncns1)c1ccc(CN2CCCC[C@@H]2c2ccccc2)cc1] | 10 |

TABLE 1-continued
| Example | Structure | Nav1.7 (LBA) (μM) |
|---|---|---|
| 73 | 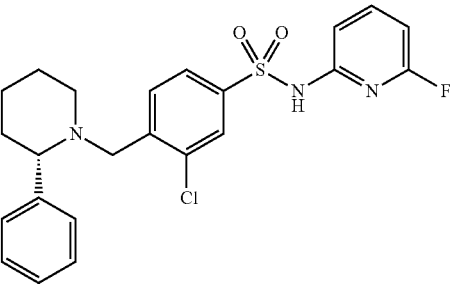 [SMILES: O=S(=O)(Nc1cccc(F)n1)c1ccc(CN2CCCC[C@H]2c2ccccc2)c(Cl)c1] | 6.8 |
| 74 | 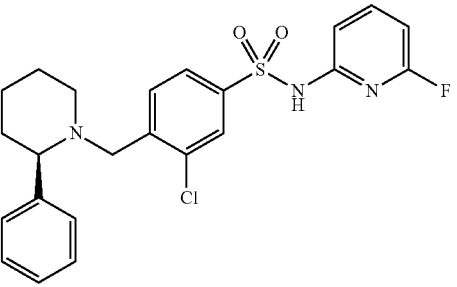 [SMILES: O=S(=O)(Nc1cccc(F)n1)c1ccc(CN2CCCC[C@@H]2c2ccccc2)c(Cl)c1] | 2.67 |
| 75 | 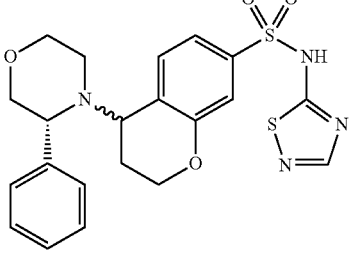 | 0.0859 |
| 76 | 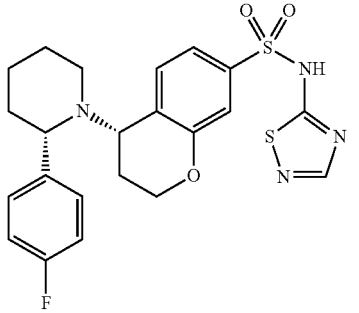 [SMILES: O=S(=O)(Nc1ncns1)c1ccc2c(c1)OCC[C@@H]2N1CCCC[C@H]1c1ccc(F)cc1] | 0.0179 |
| 77 | 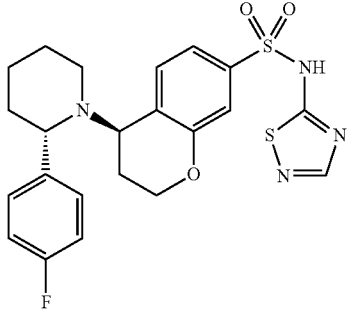 [SMILES: O=S(=O)(Nc1ncns1)c1ccc2c(c1)OCC[C@H]2N1CCCC[C@H]1c1ccc(F)cc1] | 0.198 |

TABLE 1-continued

| Example | Structure | Nav1.7 (LBA) (μM) |
|---|---|---|
| 78 | 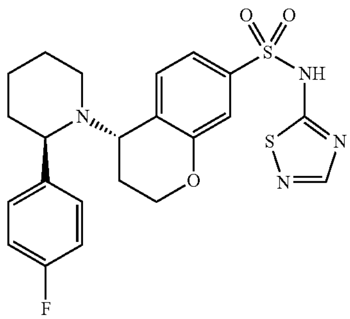 [SMILES: O=S(=O)(Nc1ncns1)c1ccc2c(c1)OCC[C@@H]2N1CCCC[C@@H]1c1ccc(F)cc1] | 0.679 |
| 79 | 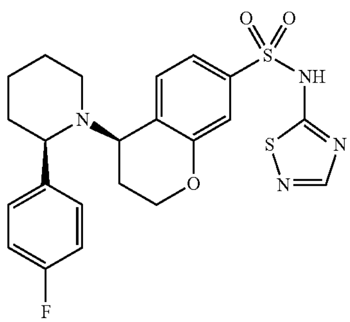 [SMILES: O=S(=O)(Nc1ncns1)c1ccc2c(c1)OCC[C@H]2N1CCCC[C@@H]1c1ccc(F)cc1] | 0.0186 |
| 80 | 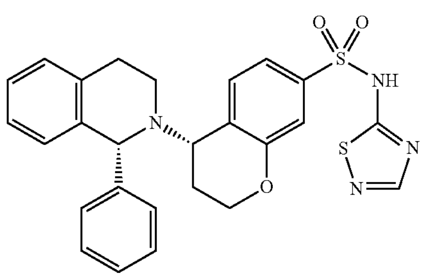 [SMILES: O=S(=O)(Nc1ncns1)c1ccc2c(c1)OCC[C@@H]2N1CCc2ccccc2[C@H]1c1ccccc1] | 0.142 |
| 81 | 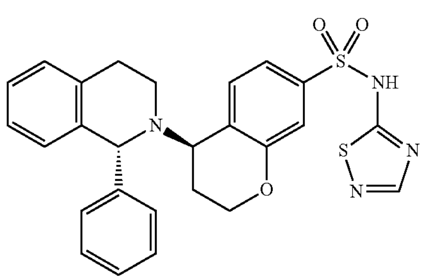 [SMILES: O=S(=O)(Nc1ncns1)c1ccc2c(c1)OCC[C@H]2N1CCc2ccccc2[C@H]1c1ccccc1] | 0.435 |
| 82 | 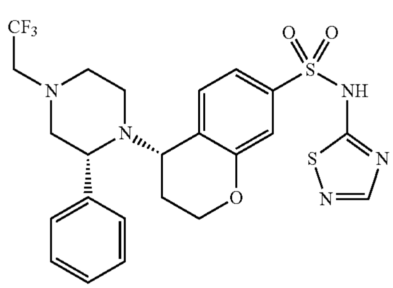 [SMILES: O=S(=O)(Nc1ncns1)c1ccc2c(c1)OCC[C@@H]2N1CCN(CC(F)(F)F)C[C@H]1c1ccccc1] | 0.0156 |

TABLE 1-continued
| Example | Structure | Nav1.7 (LBA) (μM) |
|---|---|---|
| 83 | 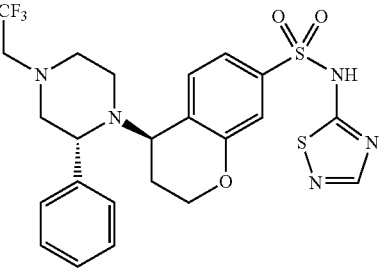 | 0.0128 |
| 84 | 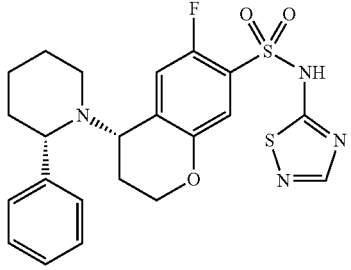 [SMILES: O=S(=O)(Nc1ncns1)c1cc2c(cc1F)[C@@H](N1CCCC[C@H]1c1ccccc1)CCO2] | 0.00991 |
| 85 | 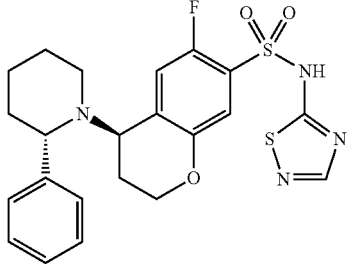 [SMILES: O=S(=O)(Nc1ncns1)c1cc2c(cc1F)[C@H](N1CCCC[C@H]1c1ccccc1)CCO2] | 0.218 |
| 86 | 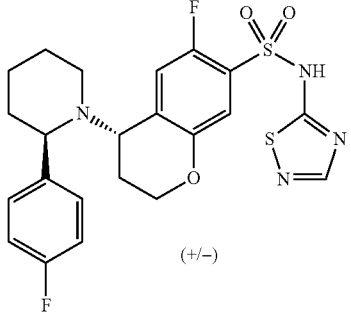 [SMILES: O=S(=O)(Nc1ncns1)c1cc2c(cc1F)[C@@H](N1CCCC[C@@H]1c1ccc(F)cc1)CCO2] (+/−) | 0.00496 |
| 87 | 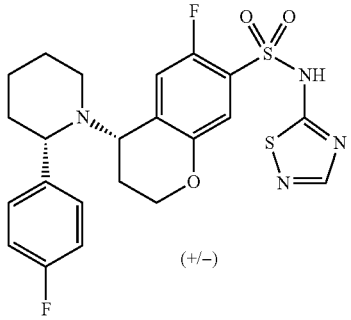 [SMILES: O=S(=O)(Nc1ncns1)c1cc2c(cc1F)[C@@H](N1CCCC[C@H]1c1ccc(F)cc1)CCO2] (+/−) | 0.00726 |

TABLE 1-continued

| Example | Structure | Nav1.7 (LBA) (μM) |
|---------|-----------|-------------------|
| 88 | 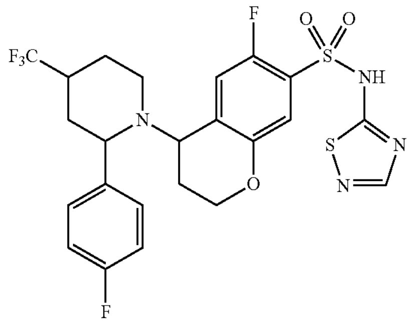 [SMILES: O=S(=O)(Nc1ncns1)c1cc2c(cc1F)C(N1CCC(C(F)(F)F)CC1c1ccc(F)cc1)CCO2] | 0.00168 |
| 89 | 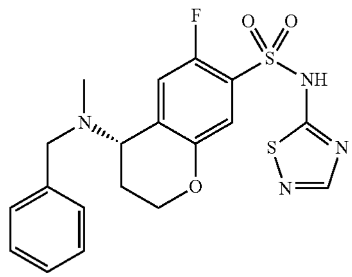 [SMILES: CN(Cc1ccccc1)[C@H]1CCOc2cc(S(=O)(=O)Nc3ncns3)c(F)cc21] | 0.096 |
| 90 | 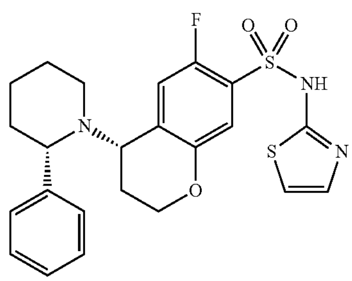 [SMILES: O=S(=O)(Nc1nccs1)c1cc2c(cc1F)[C@@H](N1CCCC[C@H]1c1ccccc1)CCO2] | 0.00862 |
| 91 | 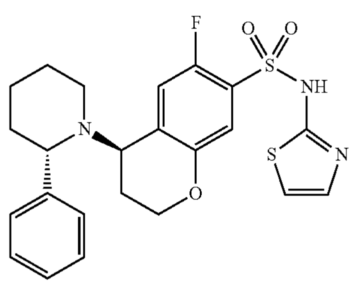 [SMILES: O=S(=O)(Nc1nccs1)c1cc2c(cc1F)[C@H](N1CCCC[C@H]1c1ccccc1)CCO2] | 0.109 |
| 92 | 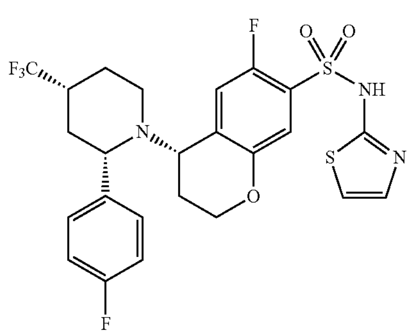 [SMILES: O=S(=O)(Nc1nccs1)c1cc2c(cc1F)[C@@H](N1CC[C@@H](C(F)(F)F)C[C@H]1c1ccc(F)cc1)CCO2] | 0.000828 |

TABLE 1-continued
| Example | Structure | Nav1.7 (LBA) (μM) |
|---|---|---|
| 93 | 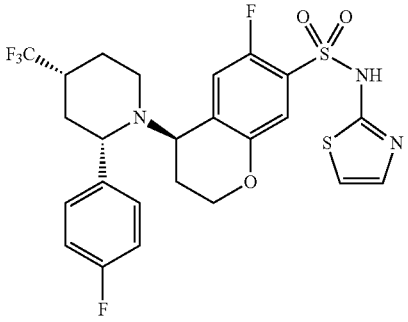 [SMILES: O=S(=O)(Nc1nccs1)c1cc2c(cc1F)[C@H](N1CC[C@@H](C(F)(F)F)C[C@H]1c1ccc(F)cc1)CCO2] | 0.00333 |
| 94 | 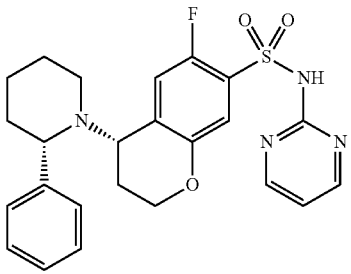 [SMILES: O=S(=O)(Nc1ncccn1)c1cc2c(cc1F)[C@@H](N1CCCC[C@H]1c1ccccc1)CCO2] | 0.423 |
| 95 | 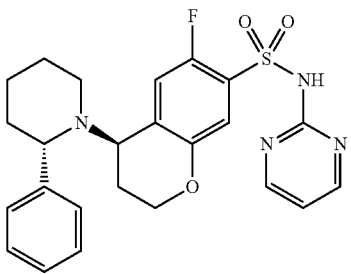 [SMILES: O=S(=O)(Nc1ncccn1)c1cc2c(cc1F)[C@H](N1CCCC[C@H]1c1ccccc1)CCO2] | 1.54 |
| 96 | 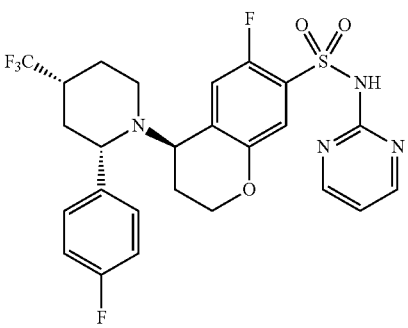 [SMILES: O=S(=O)(Nc1ncccn1)c1cc2c(cc1F)[C@H](N1CC[C@@H](C(F)(F)F)C[C@H]1c1ccc(F)cc1)CCO2] | 0.00994 |
| 97 | 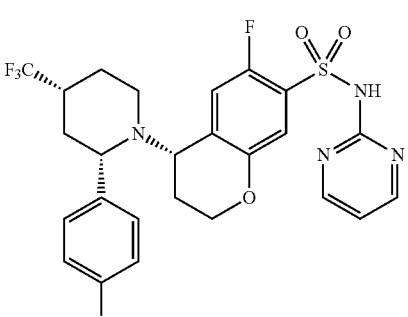 | 0.0217 |

TABLE 1-continued
| Example | Structure | Nav1.7 (LBA) (μM) |
|---------|-----------|-------------------|
| 98 | 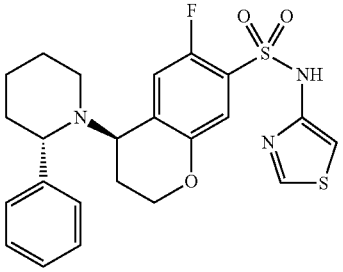 [SMILES: O=S(=O)(Nc1cscn1)c1cc2c(cc1F)[C@H](N1CCCC[C@H]1c1ccccc1)CCO2] | 1.79 |
| 99 | 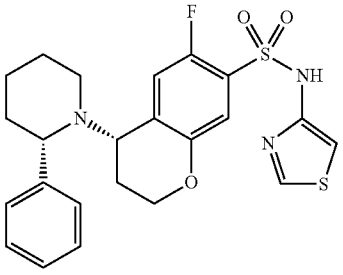 [SMILES: O=S(=O)(Nc1cscn1)c1cc2c(cc1F)[C@@H](N1CCCC[C@H]1c1ccccc1)CCO2] | 0.091 |
| 100 | 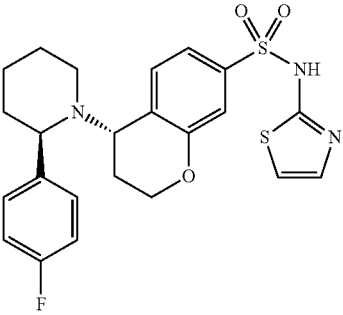 [SMILES: O=S(=O)(Nc1nccs1)c1ccc2c(c1)OCC[C@@H]2N1CCCC[C@@H]1c1ccc(F)cc1] | 0.0221 |
| 101 | 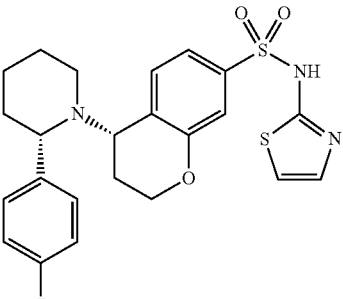 | 0.022 |
| 102 | 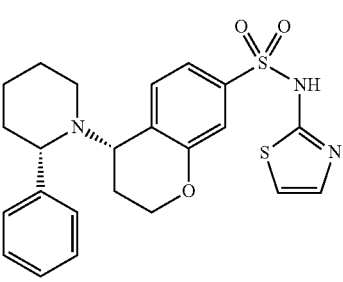 [SMILES: O=S(=O)(Nc1nccs1)c1ccc2c(c1)OCC[C@@H]2N1CCCC[C@H]1c1ccccc1] | 0.072 |

TABLE 1-continued

| Example | Structure | Nav1.7 (LBA) (μM) |
|---|---|---|
| 103 | 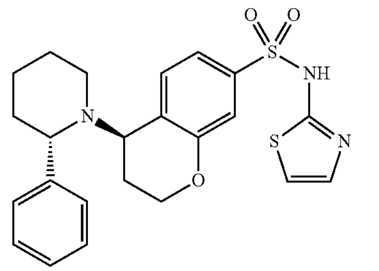 | 0.90 |
| 104 | 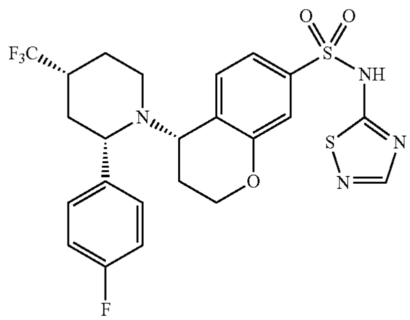 [SMILES: O=S(=O)(Nc1ncns1)c1ccc2c(c1)OCC[C@@H]2N1CC[C@@H](C(F)(F)F)C[C@H]1c1ccc(F)cc1] | 0.000797 |
| 105 | 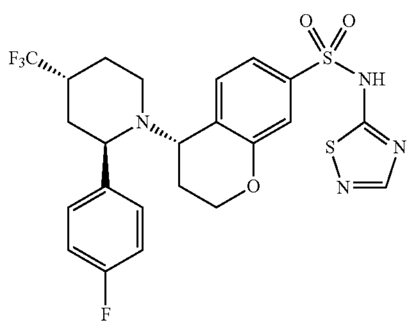 [SMILES: O=S(=O)(Nc1ncns1)c1ccc2c(c1)OCC[C@@H]2N1CC[C@@H](C(F)(F)F)C[C@@H]1c1ccc(F)cc1] | 2.48 |
| 106 | 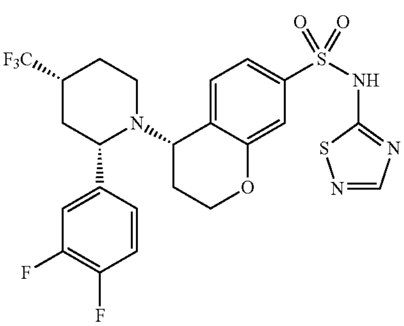 [SMILES: O=S(=O)(Nc1ncns1)c1ccc2c(c1)OCC[C@@H]2N1CC[C@@H](C(F)(F)F)C[C@H]1c1ccc(F)c(F)c1] | 0.0016 |
| 107 | 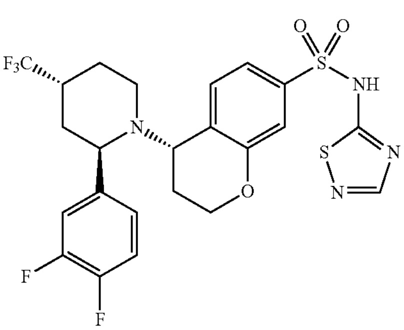 [SMILES: O=S(=O)(Nc1ncns1)c1ccc2c(c1)OCC[C@@H]2N1CC[C@@H](C(F)(F)F)C[C@@H]1c1ccc(F)c(F)c1] | 2.0 |

TABLE 1-continued

| Example | Structure | Nav1.7 (LBA) (μM) |
|---------|-----------|-------------------|
| 108 | 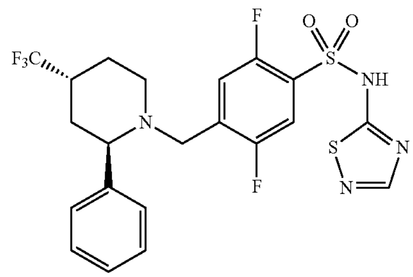 [SMILES: O=S(=O)(Nc1ncns1)c1cc(F)c(CN2CC[C@@H](C(F)(F)F)C[C@@H]2c2ccccc2)cc1F] | 1.41 |
| 109 | 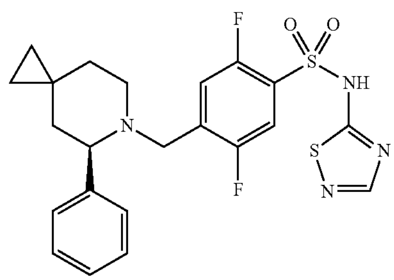 [SMILES: O=S(=O)(Nc1ncns1)c1cc(F)c(CN2CCC3(CC3)C[C@@H]2c2ccccc2)cc1F] | 1.57 |
| 110 | 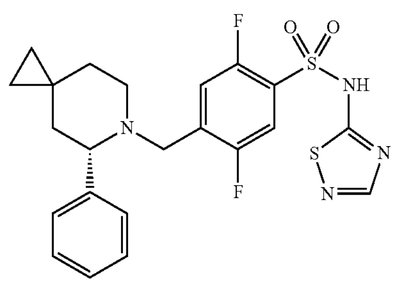 [SMILES: O=S(=O)(Nc1ncns1)c1cc(F)c(CN2CCC3(CC3)C[C@H]2c2ccccc2)cc1F] | 0.337 |
| 111 | 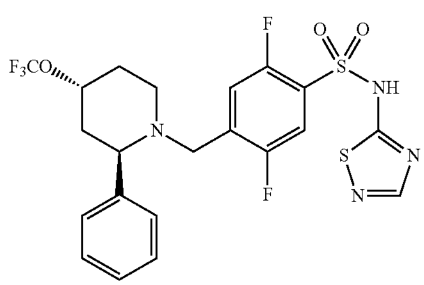 [SMILES: O=S(=O)(Nc1ncns1)c1cc(F)c(CN2CC[C@@H](OC(F)(F)F)C[C@@H]2c2ccccc2)cc1F] | 0.0923 |
| 112 | 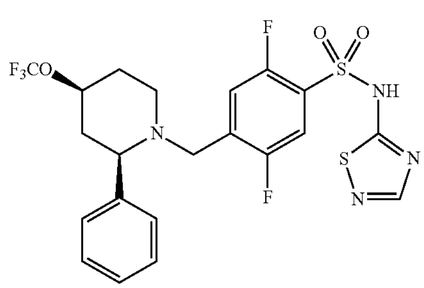 [SMILES: O=S(=O)(Nc1ncns1)c1cc(F)c(CN2CC[C@H](OC(F)(F)F)C[C@@H]2c2ccccc2)cc1F] | 4.21 |

TABLE 1-continued

| Example | Structure | Nav1.7 (LBA) (μM) |
|---|---|---|
| 113 | 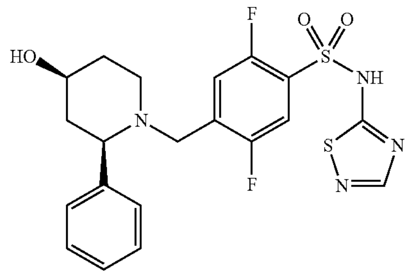 [SMILES: O=S(=O)(Nc1ncns1)c1cc(F)c(CN2CC[C@H](O)C[C@@H]2c2ccccc2)cc1F] | 8.59 |
| 114 | 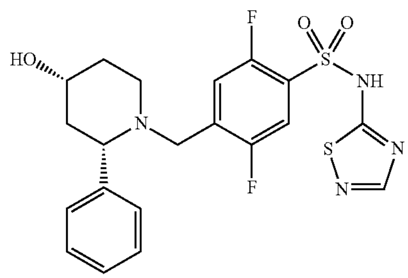 [SMILES: O=S(=O)(Nc1ncns1)c1cc(F)c(CN2CC[C@@H](O)C[C@H]2c2ccccc2)cc1F] | 9.65 |
| 115 | 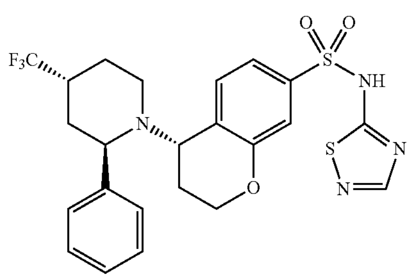 [SMILES: O=S(=O)(Nc1ncns1)c1ccc2c(c1)OCC[C@@H]2N1CC[C@@H](C(F)(F)F)C[C@@H]1c1ccccc1] | 3.0 |
| 116 | 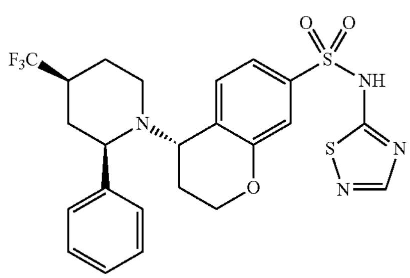 [SMILES: O=S(=O)(Nc1ncns1)c1ccc2c(c1)OCC[C@@H]2N1CC[C@H](C(F)(F)F)C[C@@H]1c1ccccc1] | 0.433 |
| 117 | 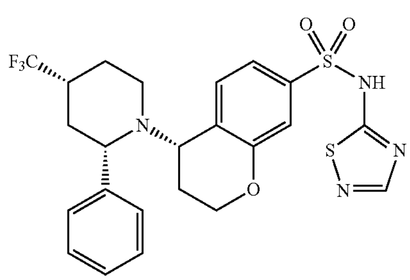 [SMILES: O=S(=O)(Nc1ncns1)c1ccc2c(c1)OCC[C@@H]2N1CC[C@@H](C(F)(F)F)C[C@H]1c1ccccc1] | 0.00142 |

TABLE 1-continued

| Example | Structure | Nav1.7 (LBA) (μM) |
|---|---|---|
| 118 | 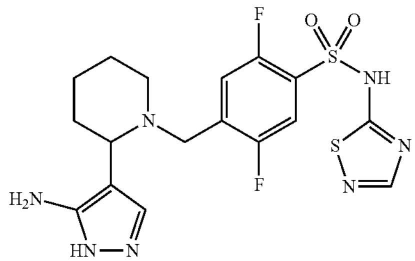 [SMILES: Nc1[nH]ncc1C1CCCCN1Cc1cc(F)c(S(=O)(=O)Nc2ncns2)cc1F] | 2.26 |
| 119 | 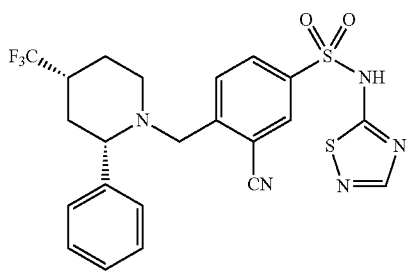 [SMILES: N#Cc1cc(S(=O)(=O)Nc2ncns2)ccc1CN1CC[C@@H](C(F)(F)F)C[C@H]1c1ccccc1] | 0.0181 |
| 120 | 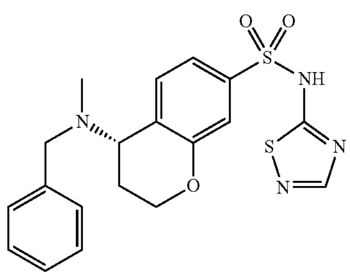 [SMILES: CN(Cc1ccccc1)[C@H]1CCOc2cc(S(=O)(=O)Nc3ncns3)ccc21] | 0.376 |
| 121 | 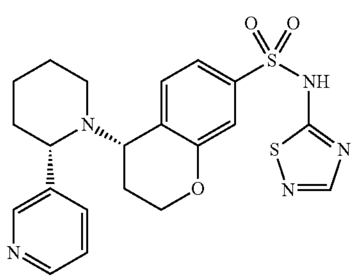 [SMILES: O=S(=O)(Nc1ncns1)c1ccc2c(c1)OCC[C@@H]2N1CCCC[C@H]1c1cccnc1] | 0.0237 |
| 122 | 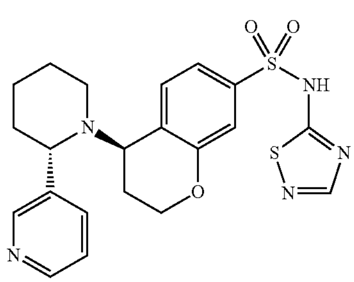 [SMILES: O=S(=O)(Nc1ncns1)c1ccc2c(c1)OCC[C@H]2N1CCCC[C@H]1c1cccnc1] | 0.0125 |

TABLE 1-continued

| Example | Structure | Nav1.7 (LBA) (μM) |
|---|---|---|
| 123 | 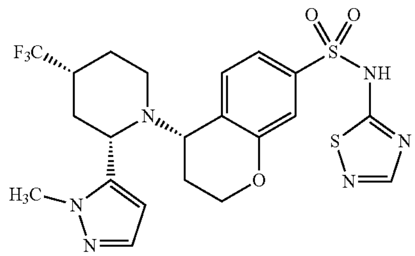 [SMILES: Cn1nccc1[C@@H]1C[C@H](C(F)(F)F)CCN1[C@H]1CCOc2cc(S(=O)(=O)Nc3ncns3)ccc21] | 0.000616 |
| 124 | 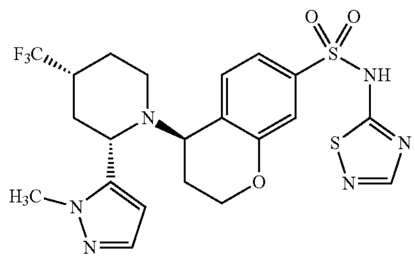 [SMILES: Cn1nccc1[C@@H]1C[C@H](C(F)(F)F)CCN1[C@@H]1CCOc2cc(S(=O)(=O)Nc3ncns3)ccc21] | 0.601 |
| 125 | 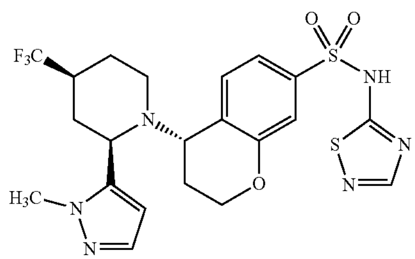 [SMILES: Cn1nccc1[C@H]1C[C@@H](C(F)(F)F)CCN1[C@H]1CCOc2cc(S(=O)(=O)Nc3ncns3)ccc21] | 0.00448 |
| 126 | 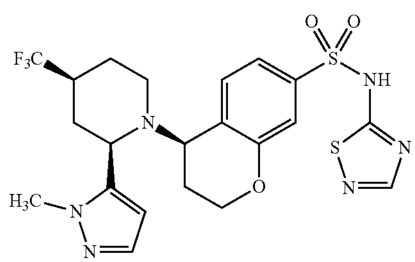 [SMILES: Cn1nccc1[C@H]1C[C@@H](C(F)(F)F)CCN1[C@@H]1CCOc2cc(S(=O)(=O)Nc3ncns3)ccc21] | 0.313 |
| 127 | 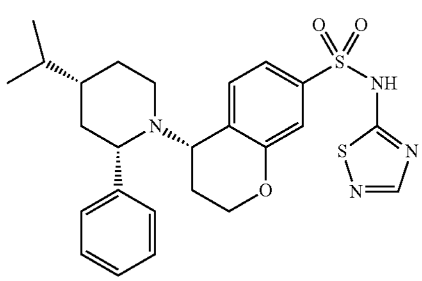 [SMILES: CC(C)[C@@H]1CCN([C@H]2CCOc3cc(S(=O)(=O)Nc4ncns4)ccc32)[C@H](c2ccccc2)C1] | 0.00883 |
| 128 | 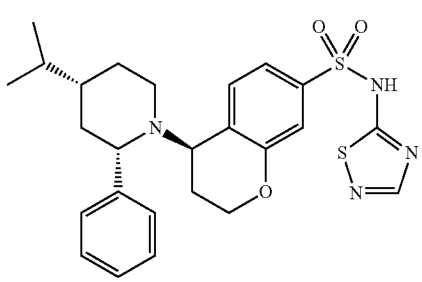 [SMILES: CC(C)[C@@H]1CCN([C@@H]2CCOc3cc(S(=O)(=O)Nc4ncns4)ccc32)[C@H](c2ccccc2)C1] | 0.469 |

TABLE 1-continued
| Example | Structure | Nav1.7 (LBA) (μM) |
|---|---|---|
| 129 | 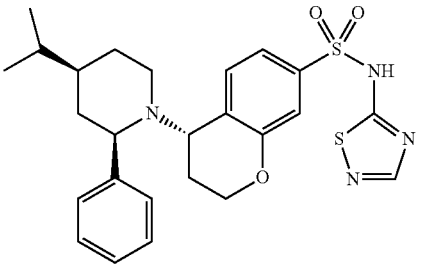 [SMILES: CC(C)[C@H]1CCN([C@H]2CCOc3cc(S(=O)(=O)Nc4ncns4)ccc32)[C@@H](c2ccccc2)C1] | 0.0168 |
| 130 | 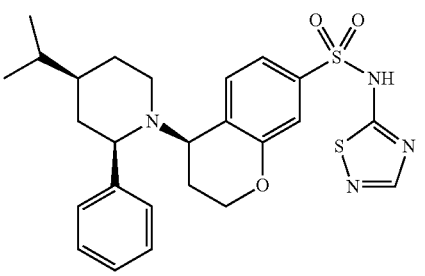 [SMILES: CC(C)[C@H]1CCN([C@@H]2CCOc3cc(S(=O)(=O)Nc4ncns4)ccc32)[C@@H](c2ccccc2)C1] | 0.109 |
| 131 | 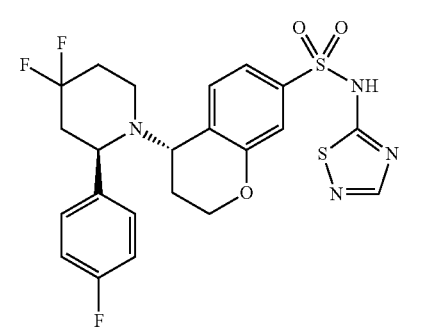 [SMILES: O=S(=O)(Nc1ncns1)c1ccc2c(c1)OCC[C@@H]2N1CCC(F)(F)C[C@@H]1c1ccc(F)cc1] | 0.00851 |
| 132 | 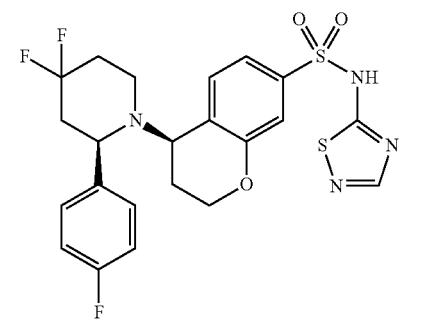 | 0.0757 |
| 133 | 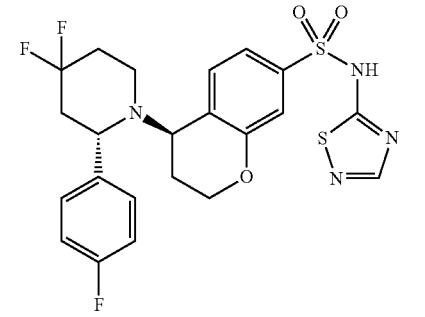 [SMILES: O=S(=O)(Nc1ncns1)c1ccc2c(c1)OCC[C@H]2N1CCC(F)(F)C[C@H]1c1ccc(F)cc1] | 0.0467 |

TABLE 1-continued

| Example | Structure | Nav1.7 (LBA) (μM) |
|---------|-----------|-------------------|
| 134 | 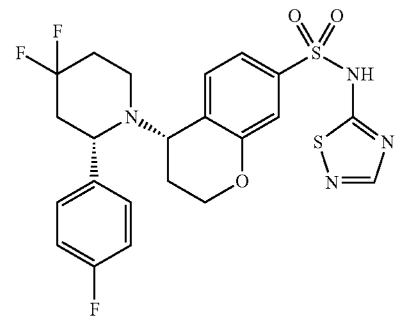 [SMILES: O=S(=O)(Nc1ncns1)c1ccc2c(c1)OCC[C@@H]2N1CCC(F)(F)C[C@H]1c1ccc(F)cc1] | 0.00295 |
| 135 | 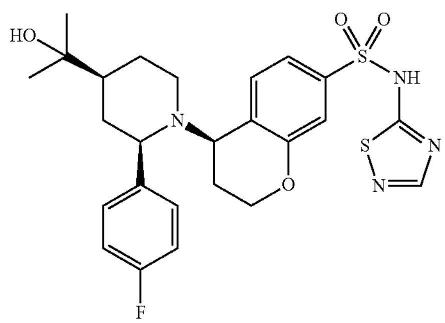 [SMILES: CC(C)(O)[C@H]1CCN([C@@H]2CCOc3cc(S(=O)(=O)Nc4ncns4)ccc32)[C@@H](c2ccc(F)cc2)C1] | 0.0271 |
| 136 | 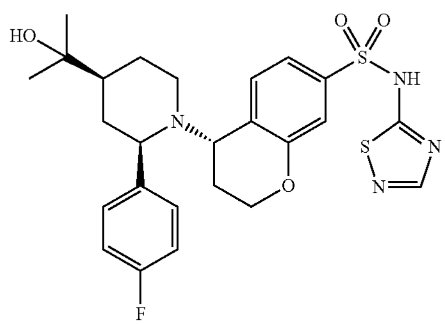 [SMILES: CC(C)(O)[C@H]1CCN([C@H]2CCOc3cc(S(=O)(=O)Nc4ncns4)ccc32)[C@@H](c2ccc(F)cc2)C1] | 0.0194 |
| 137 | 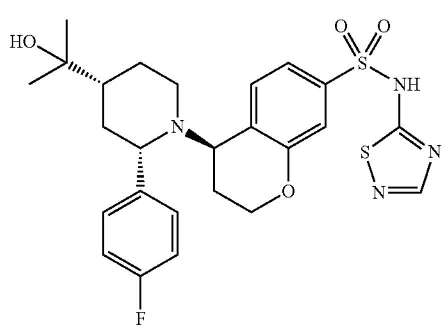 [SMILES: CC(C)(O)[C@@H]1CCN([C@@H]2CCOc3cc(S(=O)(=O)Nc4ncns4)ccc32)[C@H](c2ccc(F)cc2)C1] | 0.736 |

TABLE 1-continued

| Example | Structure | Nav1.7 (LBA) (μM) |
|---|---|---|
| 138 | 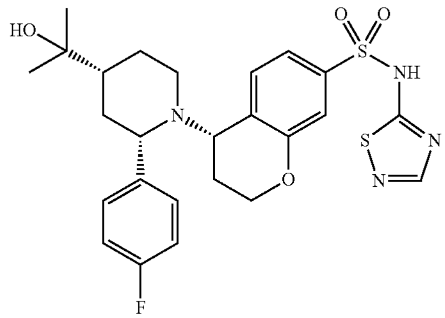 [SMILES: CC(C)(O)[C@@H]1CCN([C@H]2CCOc3cc(S(=O)(=O)Nc4ncns4)ccc32)[C@H](c2ccc(F)cc2)C1] | 0.0035 |
| 139 | 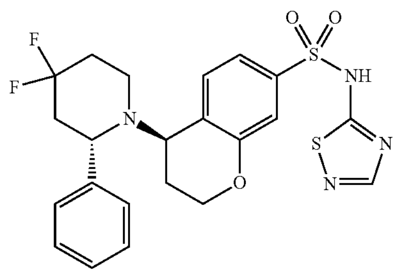 [SMILES: O=S(=O)(Nc1ncns1)c1ccc2c(c1)OCC[C@H]2N1CCC(F)(F)C[C@H]1c1ccccc1] | 2.29 |
| 140 | 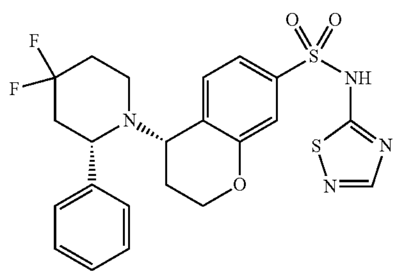 [SMILES: O=S(=O)(Nc1ncns1)c1ccc2c(c1)OCC[C@@H]2N1CCC(F)(F)C[C@H]1c1ccccc1] | 0.0144 |
| 141 | 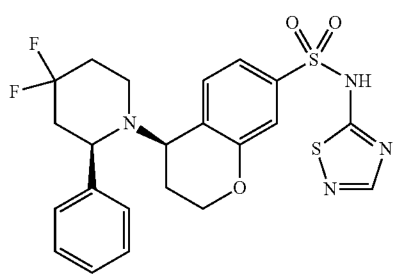 [SMILES: O=S(=O)(Nc1ncns1)c1ccc2c(c1)OCC[C@H]2N1CCC(F)(F)C[C@@H]1c1ccccc1] | 0.486 |
| 142 | 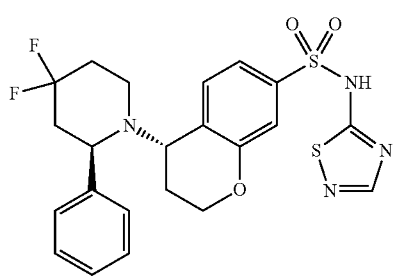 [SMILES: O=S(=O)(Nc1ncns1)c1ccc2c(c1)OCC[C@@H]2N1CCC(F)(F)C[C@@H]1c1ccccc1] | 0.0173 |

TABLE 1-continued

| Example | Structure | Nav1.7 (LBA) (μM) |
|---|---|---|
| 143 | 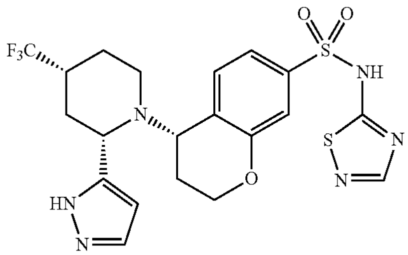 [SMILES: O=S(=O)(Nc1ncns1)c1ccc2c(c1)OCC[C@@H]2N1CC[C@@H](C(F)(F)F)C[C@H]1c1ccn[nH]1] | 8.9 |
| 144 | 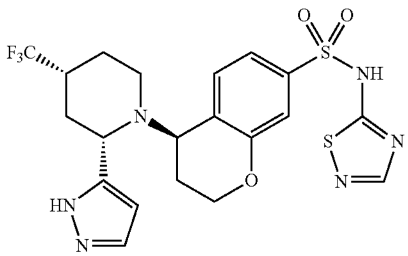 [SMILES: O=S(=O)(Nc1ncns1)c1ccc2c(c1)OCC[C@H]2N1CC[C@@H](C(F)(F)F)C[C@H]1c1ccn[nH]1] | 0.282 |
| 145 | 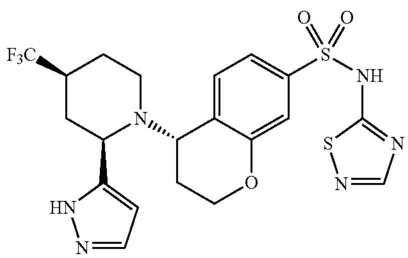 [SMILES: O=S(=O)(Nc1ncns1)c1ccc2c(c1)OCC[C@@H]2N1CC[C@H](C(F)(F)F)C[C@@H]1c1ccn[nH]1] | 0.0117 |
| 146 | 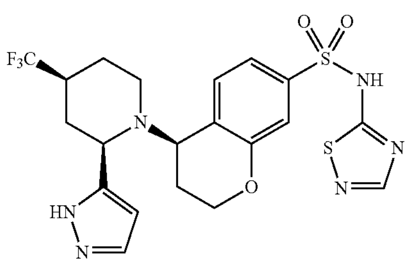 [SMILES: O=S(=O)(Nc1ncns1)c1ccc2c(c1)OCC[C@H]2N1CC[C@H](C(F)(F)F)C[C@@H]1c1ccn[nH]1] | 0.308 |
| 147 | 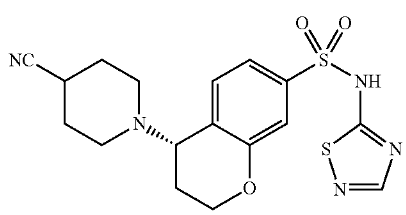 [SMILES: N#CC1CCN([C@H]2CCOc3cc(S(=O)(=O)Nc4ncns4)ccc32)CC1] | 5.36 |
| 148 | 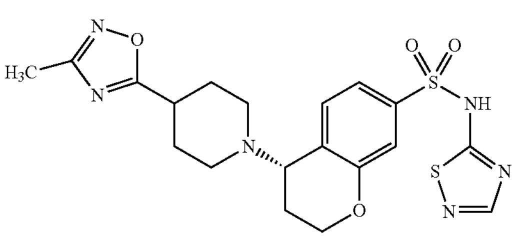 [SMILES: Cc1noc(C2CCN([C@H]3CCOc4cc(S(=O)(=O)Nc5ncns5)ccc43)CC2)n1] | 10 |

TABLE 1-continued

| Example | Structure | Nav1.7 (LBA) (μM) |
|---------|-----------|-------------------|
| 149 | 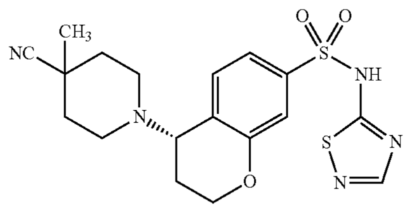 [SMILES: CC1(C#N)CCN([C@H]2CCOc3cc(S(=O)(=O)Nc4ncns4)ccc32)CC1] | 8.6 |
| 150 | 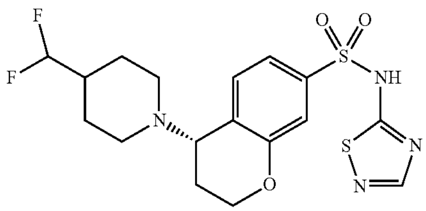 [SMILES: O=S(=O)(Nc1ncns1)c1ccc2c(c1)OCC[C@@H]2N1CCC(C(F)F)CC1] | 1.44 |
| 151 | 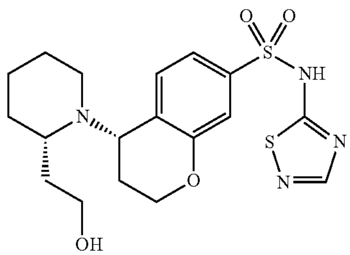 [SMILES: O=S(=O)(Nc1ncns1)c1ccc2c(c1)OCC[C@@H]2N1CCCC[C@H]1CCO] | 3.51 |
| 152 | 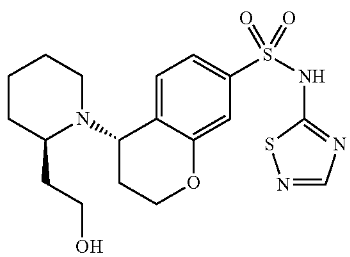 [SMILES: O=S(=O)(Nc1ncns1)c1ccc2c(c1)OCC[C@@H]2N1CCCC[C@@H]1CCO] | 3.31 |
| 153 | 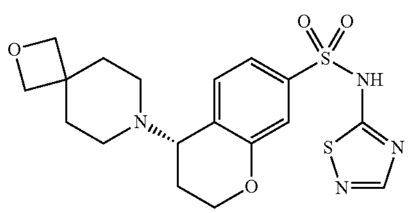 [SMILES: O=S(=O)(Nc1ncns1)c1ccc2c(c1)OCC[C@@H]2N1CCC2(CC1)COC2] | 5.5 |
| 154 | 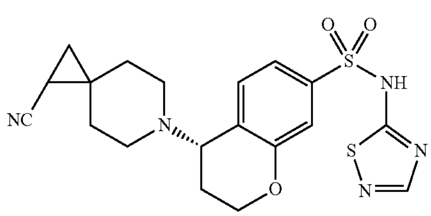 [SMILES: N#CC1CC12CCN([C@H]1CCOc3cc(S(=O)(=O)Nc4ncns4)ccc31)CC2] | 4.52 |

TABLE 1-continued

| Example | Structure | Nav1.7 (LBA) (µM) |
|---|---|---|
| 155 | 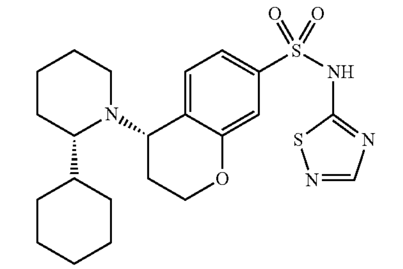 [SMILES: O=S(=O)(Nc1ncns1)c1ccc2c(c1)OCC[C@@H]2N1CCCC[C@H]1C1CCCCC1] | 4.35 |
| 156 | 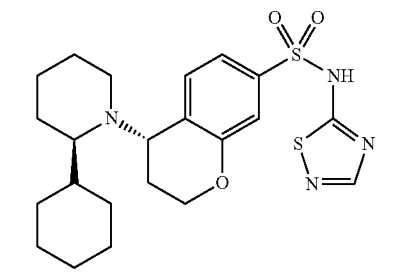 [SMILES: O=S(=O)(Nc1ncns1)c1ccc2c(c1)OCC[C@@H]2N1CCCC[C@@H]1C1CCCCC1] | 0.907 |
| 157 | 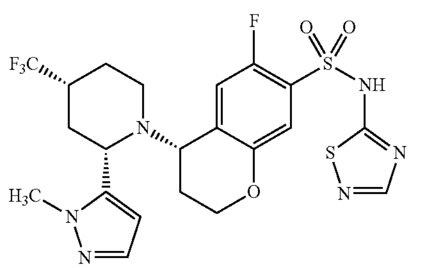 [SMILES: Cn1nccc1[C@@H]1C[C@H](C(F)(F)F)CCN1[C@H]1CCOc2cc(S(=O)(=O)Nc3ncns3)c(F)cc21] | 0.0005 |
| 158 | 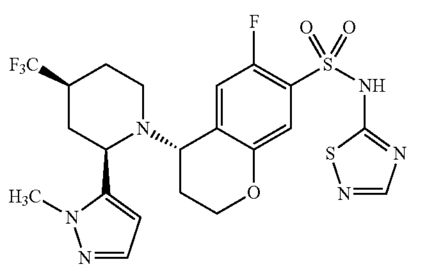 [SMILES: Cn1nccc1[C@H]1C[C@@H](C(F)(F)F)CCN1[C@H]1CCOc2cc(S(=O)(=O)Nc3ncns3)c(F)cc21] | 0.00155 |
| 159 | 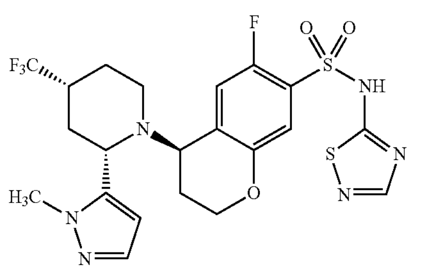 [SMILES: Cn1nccc1[C@@H]1C[C@H](C(F)(F)F)CCN1[C@@H]1CCOc2cc(S(=O)(=O)Nc3ncns3)c(F)cc21] | 0.18 |

TABLE 1-continued

| Example | Structure | Nav1.7 (LBA) (μM) |
|---|---|---|
| 160 | 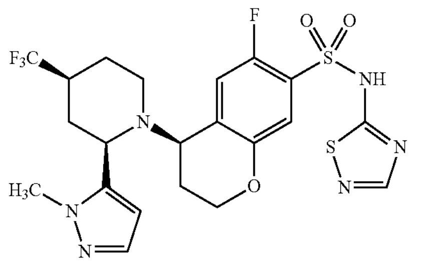 [SMILES: Cn1nccc1[C@H]1C[C@@H](C(F)(F)F)CCN1[C@@H]1CCOc2cc(S(=O)(=O)Nc3ncns3)c(F)cc21] | 0.442 |
| 161 | 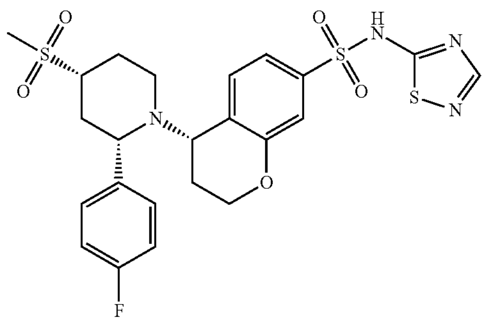 [SMILES: CS(=O)(=O)[C@@H]1CCN([C@H]2CCOc3cc(S(=O)(=O)Nc4ncns4)ccc32)[C@H](c2ccc(F)cc2)C1] | 0.00853 |
| 162 | 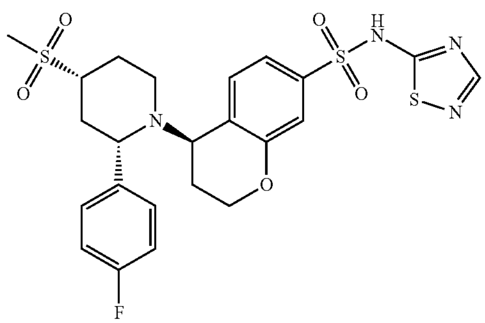 [SMILES: CS(=O)(=O)[C@@H]1CCN([C@@H]2CCOc3cc(S(=O)(=O)Nc4ncns4)ccc32)[C@H](c2ccc(F)cc2)C1] | 3 |
| 163 | 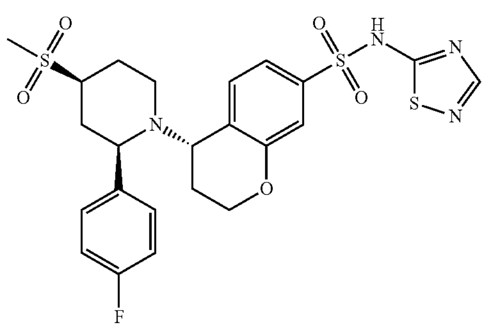 [SMILES: CS(=O)(=O)[C@H]1CCN([C@H]2CCOc3cc(S(=O)(=O)Nc4ncns4)ccc32)[C@@H](c2ccc(F)cc2)C1] | 0.0223 |
| 164 | 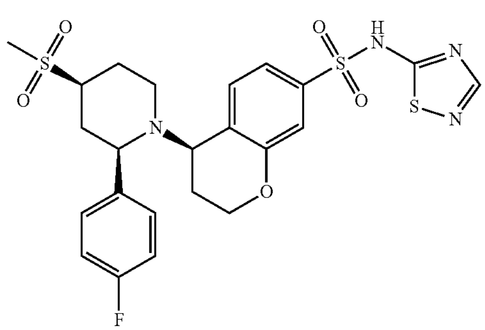 [SMILES: CS(=O)(=O)[C@H]1CCN([C@@H]2CCOc3cc(S(=O)(=O)Nc4ncns4)ccc32)[C@@H](c2ccc(F)cc2)C1] | 0.208 |

TABLE 1-continued
| Example | Structure | Nav1.7 (LBA) (μM) |
|---|---|---|
| 165 | 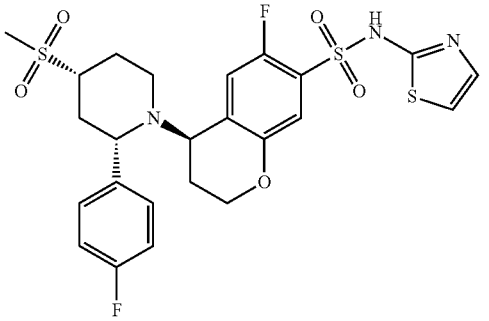 [SMILES: CS(=O)(=O)[C@@H]1CCN([C@@H]2CCOc3cc(S(=O)(=O)Nc4nccs4)c(F)cc32)[C@H](c2ccc(F)cc2)C1] | 1.01 |
| 166 | 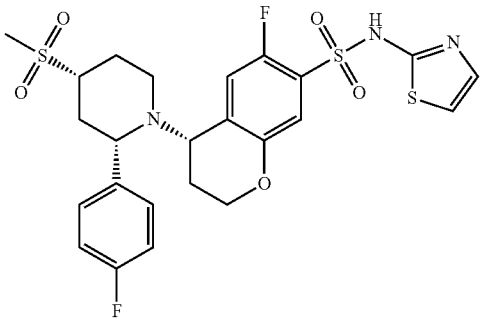 [SMILES: CS(=O)(=O)[C@@H]1CCN([C@H]2CCOc3cc(S(=O)(=O)Nc4nccs4)c(F)cc32)[C@H](c2ccc(F)cc2)C1] | 0.00212 |
| 167 | 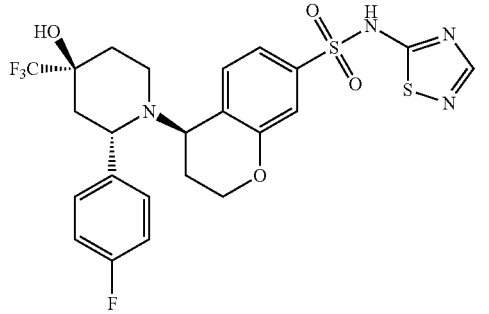 [SMILES: O=S(=O)(Nc1ncns1)c1ccc2c(c1)OCC[C@H]2N1CC[C@@](O)(C(F)(F)F)C[C@H]1c1ccc(F)cc1] | 3 |
| 168 | 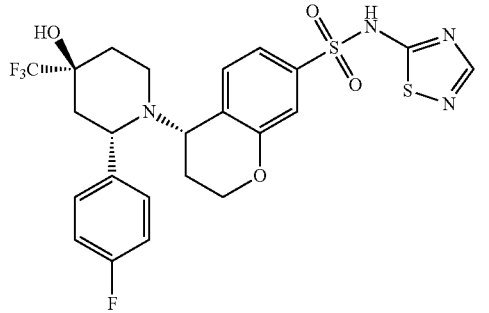 [SMILES: O=S(=O)(Nc1ncns1)c1ccc2c(c1)OCC[C@@H]2N1CC[C@@](O)(C(F)(F)F)C[C@H]1c1ccc(F)cc1] | 0.000878 |

TABLE 1-continued
| Example | Structure | Nav1.7 (LBA) (μM) |
|---|---|---|
| 169 | 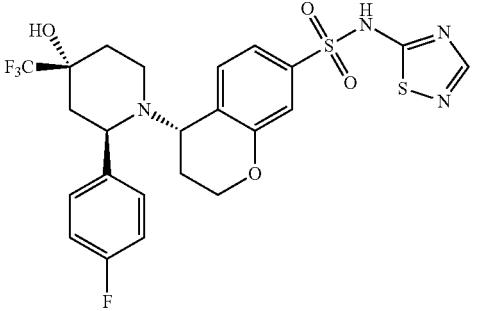 [SMILES: O=S(=O)(Nc1ncns1)c1ccc2c(c1)OCC[C@@H]2N1CC[C@](O)(C(F)(F)F)C[C@@H]1c1ccc(F)cc1] | 0.0682 |
| 170 | 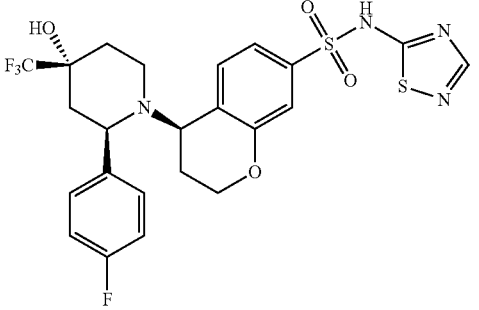 [SMILES: O=S(=O)(Nc1ncns1)c1ccc2c(c1)OCC[C@H]2N1CC[C@](O)(C(F)(F)F)C[C@@H]1c1ccc(F)cc1] | 0.175 |
| 171 | 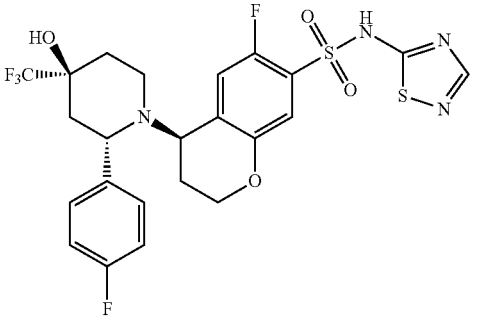 [SMILES: O=S(=O)(Nc1ncns1)c1cc2c(cc1F)[C@H](N1CC[C@@](O)(C(F)(F)F)C[C@H]1c1ccc(F)cc1)CCO2] | 2.028 |
| 172 | 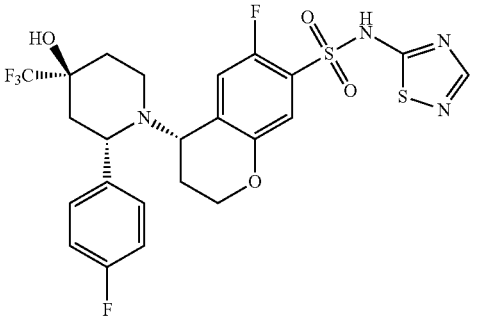 [SMILES: O=S(=O)(Nc1ncns1)c1cc2c(cc1F)[C@@H](N1CC[C@@](O)(C(F)(F)F)C[C@H]1c1ccc(F)cc1)CCO2] | 0.0005 |

TABLE 1-continued

| Example | Structure | Nav1.7 (LBA) (μM) |
|---|---|---|
| 173 | 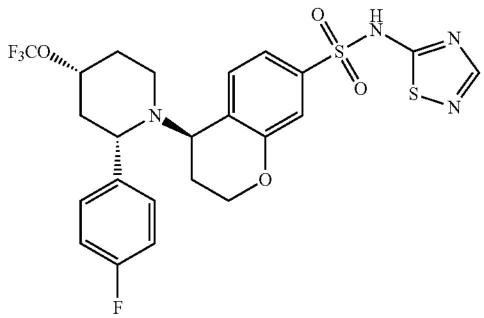 [SMILES: O=S(=O)(Nc1ncns1)c1ccc2c(c1)OCC[C@H]2N1CC[C@@H](OC(F)(F)F)C[C@H]1c1ccc(F)cc1] | 0.000895 |
| 174 | 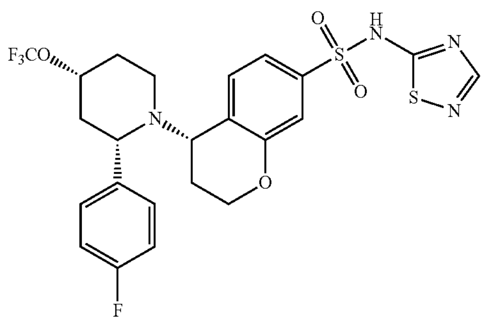 [SMILES: O=S(=O)(Nc1ncns1)c1ccc2c(c1)OCC[C@@H]2N1CC[C@@H](OC(F)(F)F)C[C@H]1c1ccc(F)cc1] | 0.235 |
| 175 | 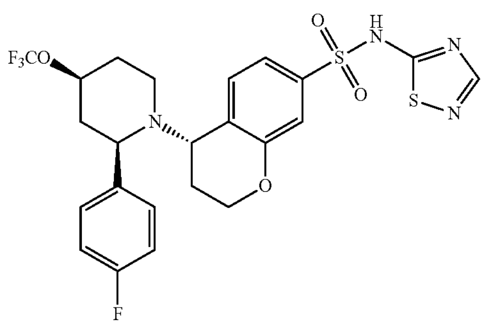 [SMILES: O=S(=O)(Nc1ncns1)c1ccc2c(c1)OCC[C@@H]2N1CC[C@H](OC(F)(F)F)C[C@@H]1c1ccc(F)cc1] | 0.00305 |
| 176 | 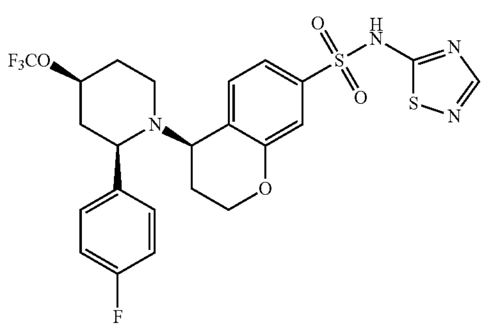 [SMILES: O=S(=O)(Nc1ncns1)c1ccc2c(c1)OCC[C@H]2N1CC[C@H](OC(F)(F)F)C[C@@H]1c1ccc(F)cc1] | 0.0248 |

TABLE 1-continued

| Example | Structure | Nav1.7 (LBA) (µM) |
|---|---|---|
| 177 | 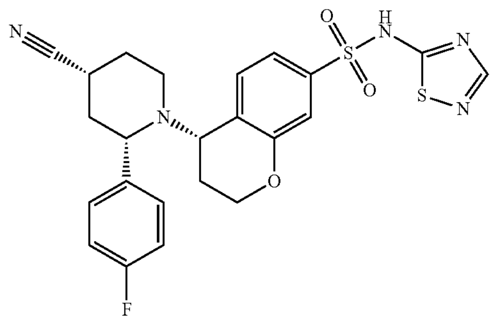 [SMILES: N#C[C@@H]1CCN([C@H]2CCOc3cc(S(=O)(=O)Nc4ncns4)ccc32)[C@H](c2ccc(F)cc2)C1] | 0.00584 |
| 178 | 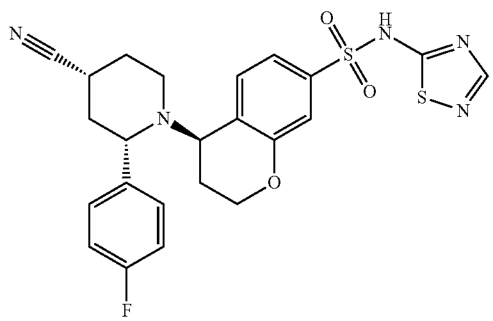 [SMILES: N#C[C@@H]1CCN([C@@H]2CCOc3cc(S(=O)(=O)Nc4ncns4)ccc32)[C@H](c2ccc(F)cc2)C1] | 1.02 |
| 179 | 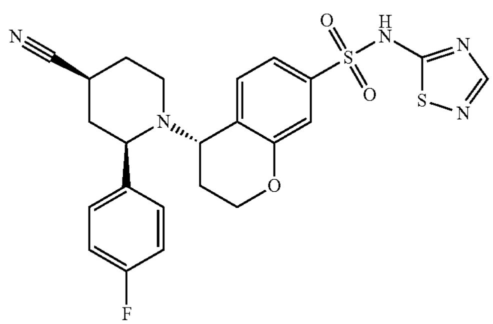 [SMILES: N#C[C@H]1CCN([C@H]2CCOc3cc(S(=O)(=O)Nc4ncns4)ccc32)[C@@H](c2ccc(F)cc2)C1] | 0.0109 |
| 180 | 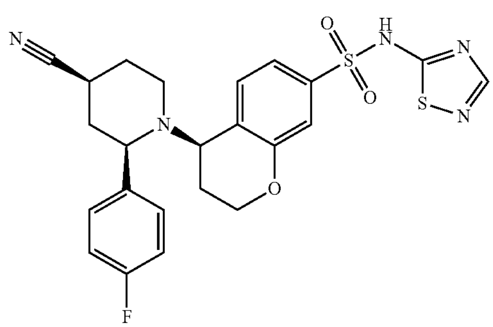 [SMILES: N#C[C@H]1CCN([C@@H]2CCOc3cc(S(=O)(=O)Nc4ncns4)ccc32)[C@@H](c2ccc(F)cc2)C1] | 0.158 |

TABLE 1-continued
| Example | Structure | Nav1.7 (LBA) (μM) |
|---|---|---|
| 181 | 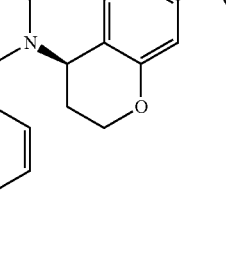 | 0.735 |
| 182 | 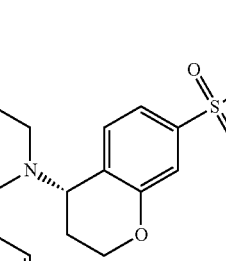 | 0.00399 |
| 183 | 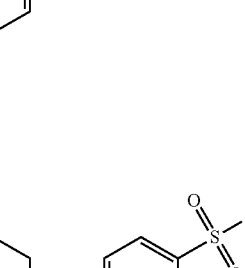 | 0.00652 |
| 184 | 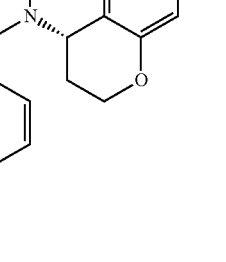 | 0.132 |

TABLE 1-continued

| Example | Structure | Nav1.7 (LBA) (μM) |
|---|---|---|
| 185 | 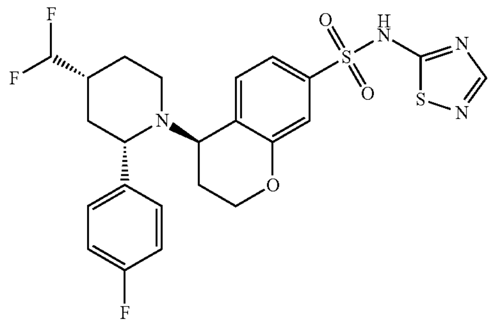 [SMILES: O=S(=O)(Nc1ncns1)c1ccc2c(c1)OCC[C@H]2N1CC[C@@H](C(F)F)C[C@H]1c1ccc(F)cc1] | 2.18 |
| 186 | 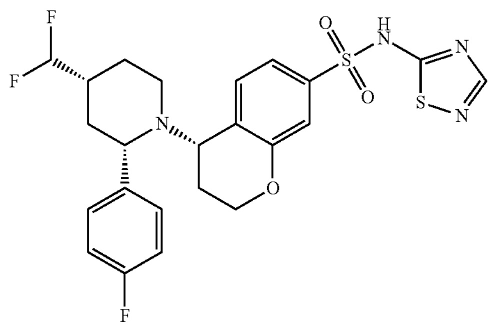 [SMILES: O=S(=O)(Nc1ncns1)c1ccc2c(c1)OCC[C@@H]2N1CC[C@@H](C(F)F)C[C@H]1c1ccc(F)cc1] | 0.00214 |
| 187 | 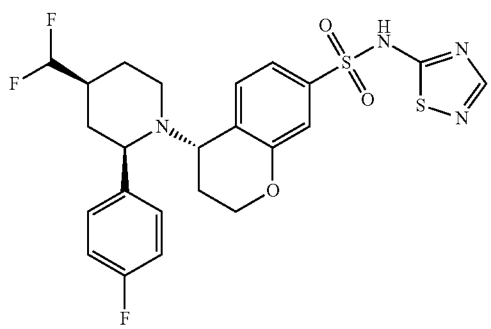 [SMILES: O=S(=O)(Nc1ncns1)c1ccc2c(c1)OCC[C@@H]2N1CC[C@H](C(F)F)C[C@@H]1c1ccc(F)cc1] | 0.00255 |
| 188 | 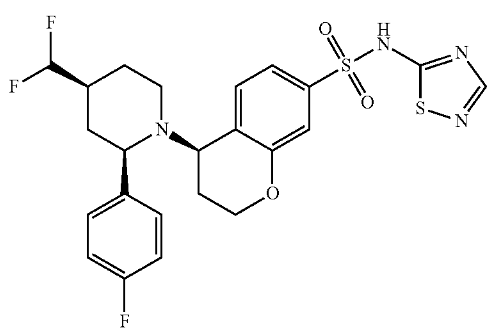 [SMILES: O=S(=O)(Nc1ncns1)c1ccc2c(c1)OCC[C@H]2N1CC[C@H](C(F)F)C[C@@H]1c1ccc(F)cc1] | 0.131 |
| 189 | 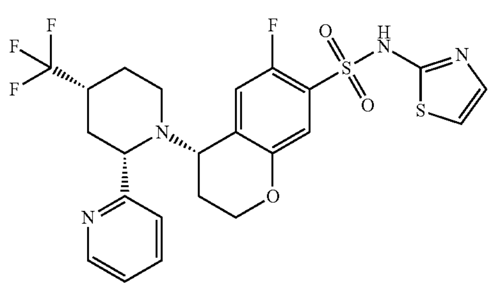 [SMILES: O=S(=O)(Nc1nccs1)c1cc2c(cc1F)[C@@H](N1CC[C@@H](C(F)(F)F)C[C@H]1c1ccccn1)CCO2] | 0.0005 |

TABLE 1-continued

| Example | Structure | Nav1.7 (LBA) (μM) |
|---|---|---|
| 190 | 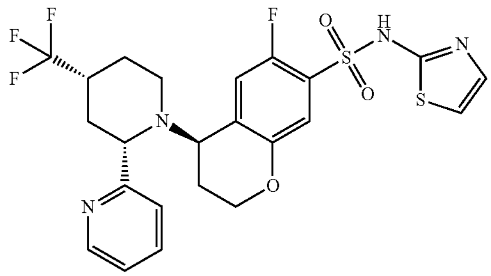 [SMILES: O=S(=O)(Nc1nccs1)c1cc2c(cc1F)[C@H](N1CC[C@@H](C(F)(F)F)C[C@H]1c1ccccn1)CCO2] | 0.0448 |
| 191 | 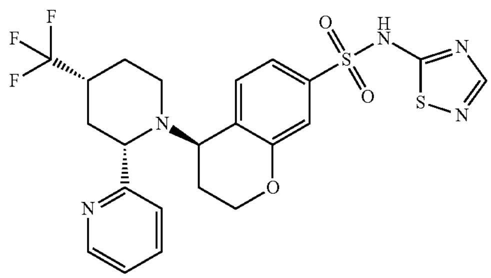 [SMILES: O=S(=O)(Nc1ncns1)c1ccc2c(c1)OCC[C@H]2N1CC[C@@H](C(F)(F)F)C[C@H]1c1ccccn1] | 0.176 |
| 192 | 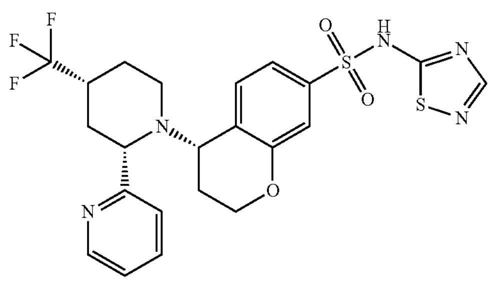 [SMILES: O=S(=O)(Nc1ncns1)c1ccc2c(c1)OCC[C@@H]2N1CC[C@@H](C(F)(F)F)C[C@H]1c1ccccn1] | 0.0005 |
| 193 | 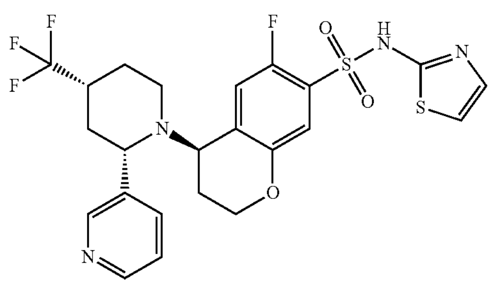 [SMILES: O=S(=O)(Nc1nccs1)c1cc2c(cc1F)[C@H](N1CC[C@@H](C(F)(F)F)C[C@H]1c1cccnc1)CCO2] | 0.0103 |
| 194 | 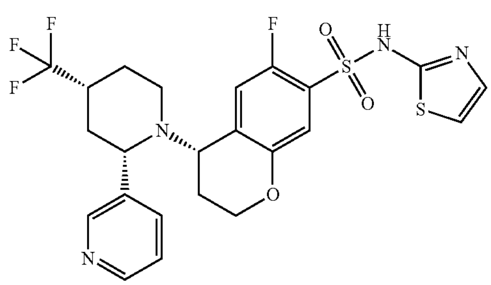 [SMILES: O=S(=O)(Nc1nccs1)c1cc2c(cc1F)[C@@H](N1CC[C@@H](C(F)(F)F)C[C@H]1c1cccnc1)CCO2] | 0.0005 |

TABLE 1-continued

| Example | Structure | Nav1.7 (LBA) (μM) |
|---|---|---|
| 195 | 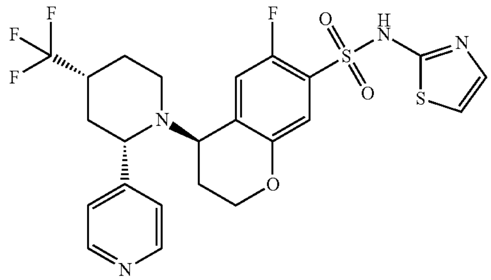 [SMILES: O=S(=O)(Nc1nccs1)c1cc2c(cc1F)[C@H](N1CC[C@@H](C(F)(F)F)C[C@H]1c1ccncc1)CCO2] | 0.0901 |
| 196 | 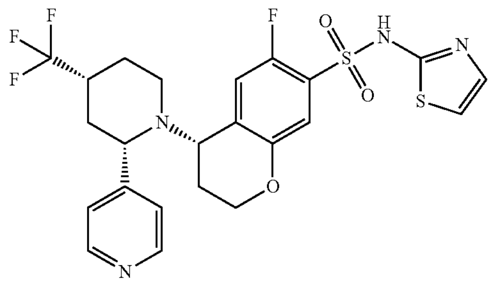 [SMILES: O=S(=O)(Nc1nccs1)c1cc2c(cc1F)[C@@H](N1CC[C@@H](C(F)(F)F)C[C@H]1c1ccncc1)CCO2] | 0.0005 |
| 197 | 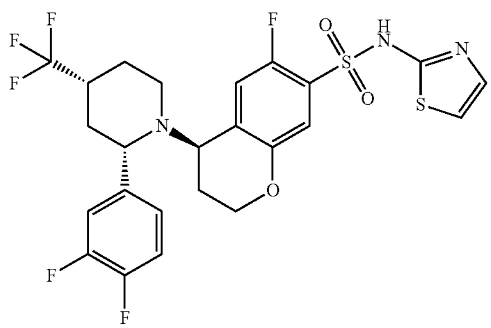 [SMILES: O=S(=O)(Nc1nccs1)c1cc2c(cc1F)[C@H](N1CC[C@@H](C(F)(F)F)C[C@H]1c1ccc(F)c(F)c1)CCO2] | 0.351 |
| 198 | 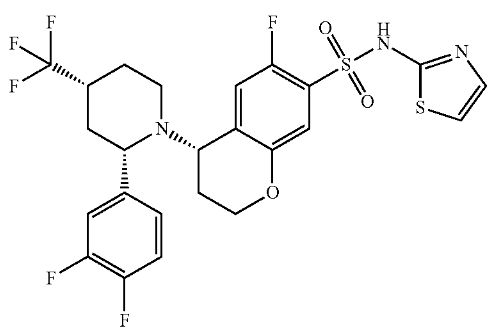 [SMILES: O=S(=O)(Nc1nccs1)c1cc2c(cc1F)[C@@H](N1CC[C@@H](C(F)(F)F)C[C@H]1c1ccc(F)c(F)c1)CCO2] | 0.000649 |
| 199 | 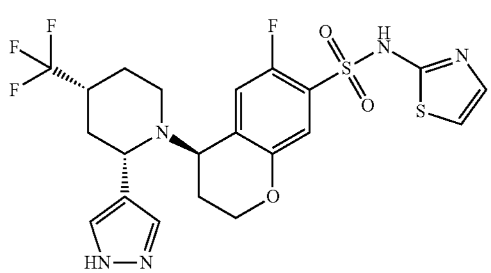 [SMILES: O=S(=O)(Nc1nccs1)c1cc2c(cc1F)[C@H](N1CC[C@@H](C(F)(F)F)C[C@H]1c1cn[nH]c1)CCO2] | 0.11 |

TABLE 1-continued
| Example | Structure | Nav1.7 (LBA) (μM) |
|---|---|---|
| 200 | 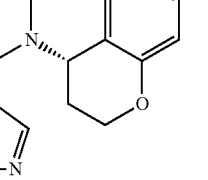 | 0.0005 |
| 201 | 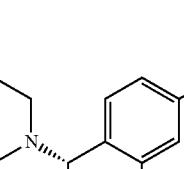 | 0.0037 |
| 202 | 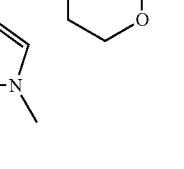 | 0.0005 |
| 203 | 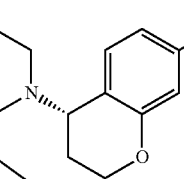 | 0.00824 |
| 204 | 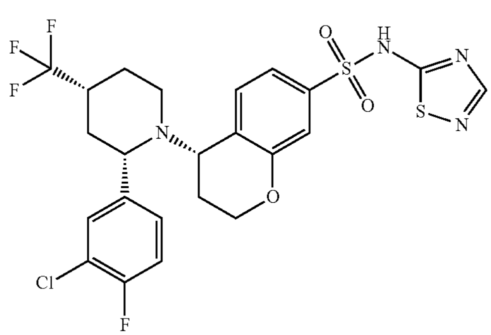 [SMILES: O=S(=O)(Nc1ncns1)c1ccc2c(c1)OCC[C@@H]2N1CC[C@@H](C(F)(F)F)C[C@H]1c1ccc(F)c(Cl)c1] | 0.00398 |

TABLE 1-continued

| Example | Structure | Nav1.7 (LBA) (µM) |
|---|---|---|
| 205 | 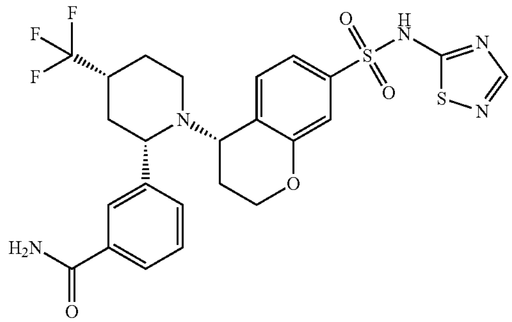 [SMILES: NC(=O)c1cccc([C@@H]2C[C@H](C(F)(F)F)CCN2[C@H]2CCOc3cc(S(=O)(=O)Nc4ncns4)ccc32)c1] | 0.000907 |
| 206 | 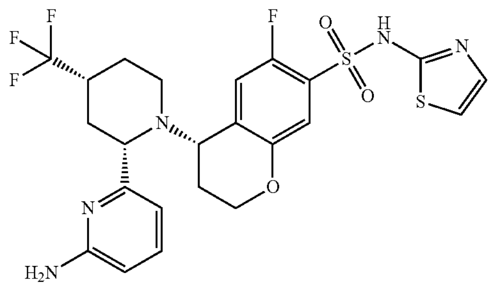 | 0.000515 |
| 207 | 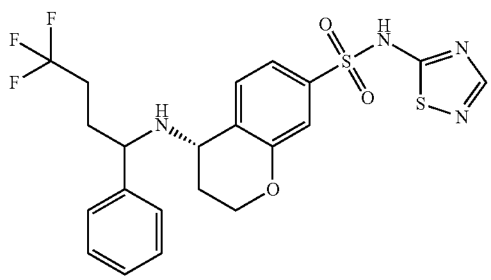 [SMILES: O=S(=O)(Nc1ncns1)c1ccc2c(c1)OCC[C@@H]2NC(CCC(F)(F)F)c1ccccc1] | 0.039 |
| 208 | 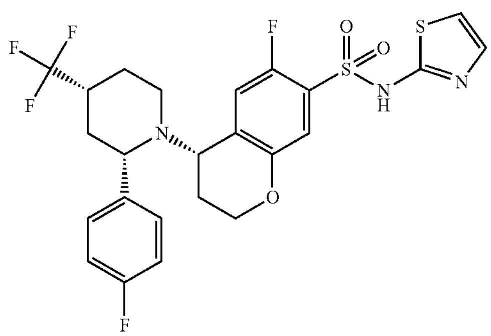 [SMILES: O=S(=O)(Nc1nccs1)c1cc2c(cc1F)[C@@H](N1CC[C@@H](C(F)(F)F)C[C@H]1c1ccc(F)cc1)CCO2] | 0.0005 |
| 209 | 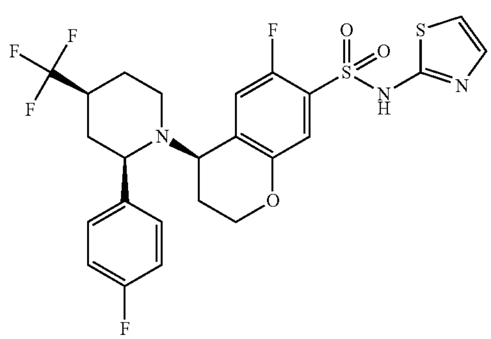 [SMILES: O=S(=O)(Nc1nccs1)c1cc2c(cc1F)[C@H](N1CC[C@H](C(F)(F)F)C[C@@H]1c1ccc(F)cc1)CCO2] | 0.0683 |

TABLE 1-continued

| Example | Structure | Nav1.7 (LBA) (µM) |
|---|---|---|
| 210 | 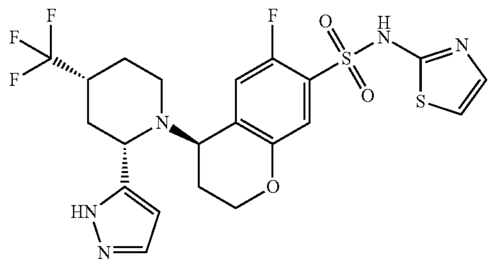 [SMILES: O=S(=O)(Nc1nccs1)c1cc2c(cc1F)[C@H](N1CC[C@@H](C(F)(F)F)C[C@H]1c1ccn[nH]1)CCO2] | 0.0375 |
| 211 | 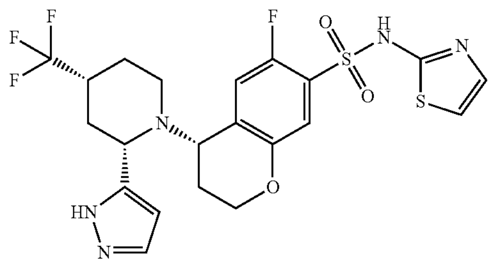 [SMILES: O=S(=O)(Nc1nccs1)c1cc2c(cc1F)[C@@H](N1CC[C@@H](C(F)(F)F)C[C@H]1c1ccn[nH]1)CCO2] | 0.0005 |
| 212 | 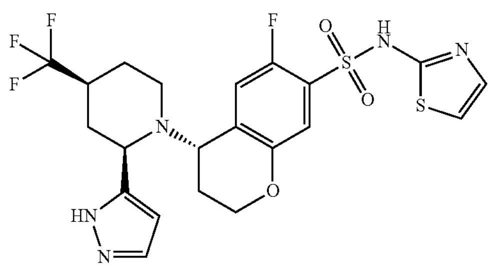 [SMILES: O=S(=O)(Nc1nccs1)c1cc2c(cc1F)[C@@H](N1CC[C@H](C(F)(F)F)C[C@@H]1c1ccn[nH]1)CCO2] | 0.0033 |
| 213 | 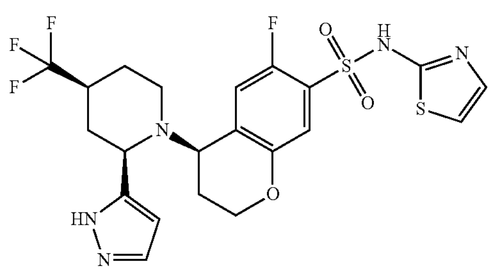 [SMILES: O=S(=O)(Nc1nccs1)c1cc2c(cc1F)[C@H](N1CC[C@H](C(F)(F)F)C[C@@H]1c1ccn[nH]1)CCO2] | 0.0274 |
| 214 | 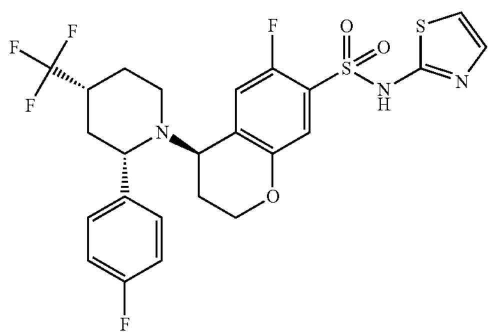 [SMILES: O=S(=O)(Nc1nccs1)c1cc2c(cc1F)[C@H](N1CC[C@@H](C(F)(F)F)C[C@H]1c1ccc(F)cc1)CCO2] | 0.00144 |

TABLE 1-continued

| Example | Structure | Nav1.7 (LBA) (μM) |
|---|---|---|
| 215 | 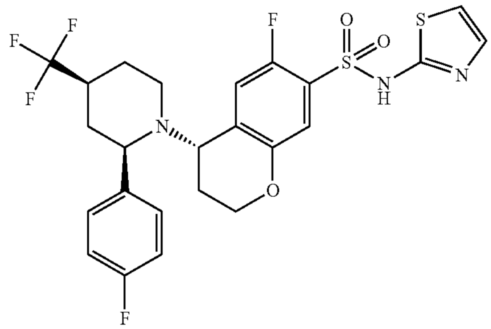 [SMILES: O=S(=O)(Nc1nccs1)c1cc2c(cc1F)[C@@H](N1CC[C@H](C(F)(F)F)C[C@@H]1c1ccc(F)cc1)CCO2] | 0.633 |
| 216 | 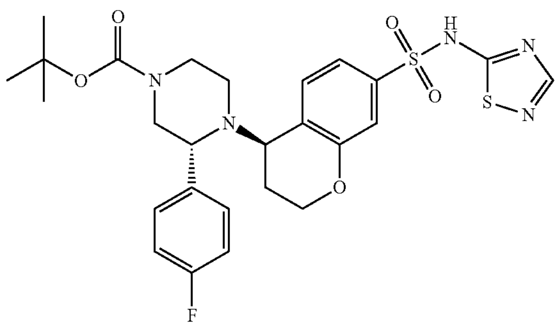 [SMILES: CC(C)(C)OC(=O)N1CCN([C@@H]2CCOc3cc(S(=O)(=O)Nc4ncns4)ccc32)[C@H](c2ccc(F)cc2)C1] | 0.213 |
| 217 | 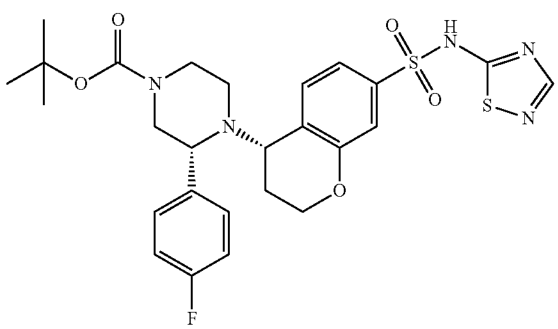 [SMILES: CC(C)(C)OC(=O)N1CCN([C@H]2CCOc3cc(S(=O)(=O)Nc4ncns4)ccc32)[C@H](c2ccc(F)cc2)C1] | 0.0183 |
| 218 | 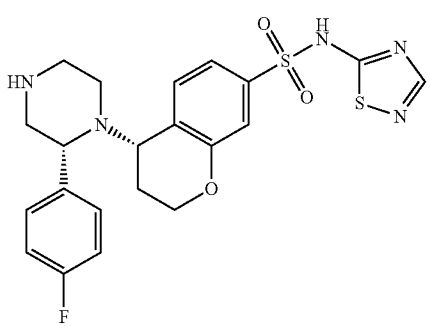 [SMILES: O=S(=O)(Nc1ncns1)c1ccc2c(c1)OCC[C@@H]2N1CCNC[C@H]1c1ccc(F)cc1] | 0.0941 |

TABLE 1-continued

| Example | Structure | Nav1.7 (LBA) (μM) |
|---|---|---|
| 219 | 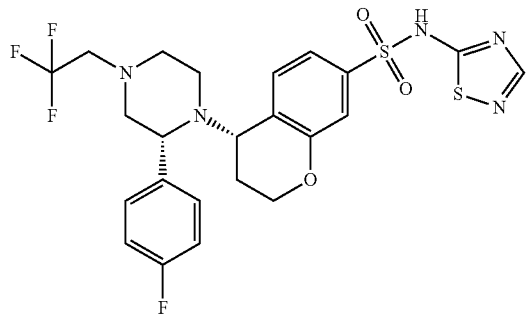 [SMILES: O=S(=O)(Nc1ncns1)c1ccc2c(c1)OCC[C@@H]2N1CCN(CC(F)(F)F)C[C@H]1c1ccc(F)cc1] | 0.00778 |
| 220 | 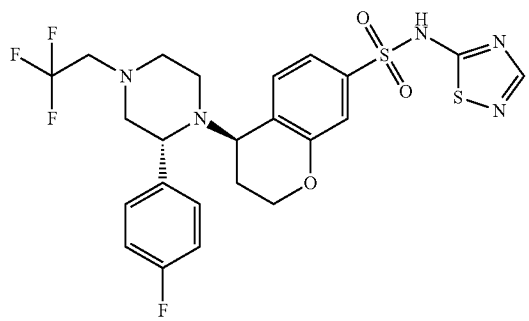 [SMILES: O=S(=O)(Nc1ncns1)c1ccc2c(c1)OCC[C@H]2N1CCN(CC(F)(F)F)C[C@H]1c1ccc(F)cc1] | 0.0494 |
| 221 | 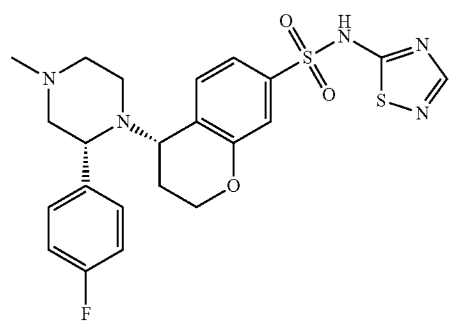 [SMILES: CN1CCN([C@H]2CCOc3cc(S(=O)(=O)Nc4ncns4)ccc32)[C@H](c2ccc(F)cc2)C1] | 0.223 |
| 222 | 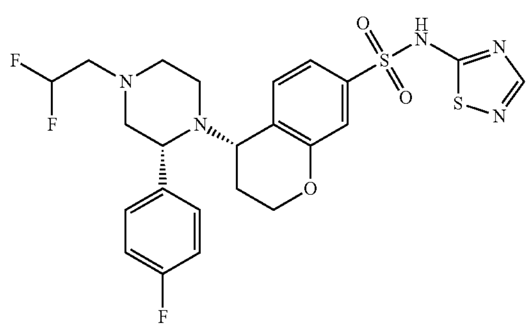 [SMILES: O=S(=O)(Nc1ncns1)c1ccc2c(c1)OCC[C@@H]2N1CCN(CC(F)F)C[C@H]1c1ccc(F)cc1] | 0.0262 |

TABLE 1-continued
| Example | Structure | Nav1.7 (LBA) (μM) |
|---|---|---|
| 223 | 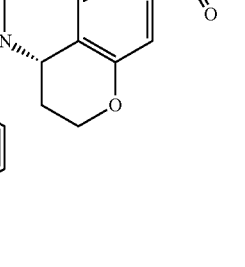 | 0.125 |
| 224 | 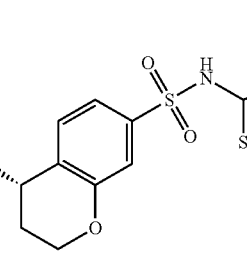 | 0.174 |
| 225 | 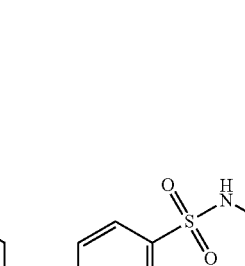 | 0.0057 |
| 226 | 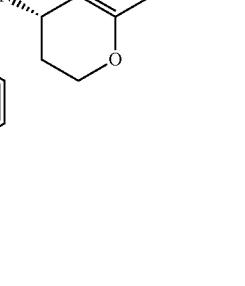 | 0.0305 |

TABLE 1-continued

| Example | Structure | Nav1.7 (LBA) (μM) |
|---|---|---|
| 227 | 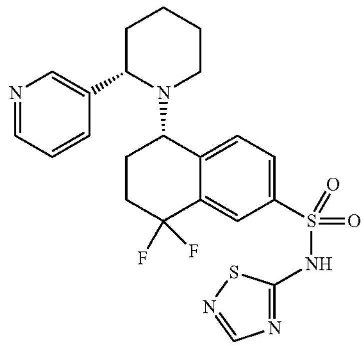 [SMILES: O=S(=O)(Nc1ncns1)c1ccc2c(c1)C(F)(F)CC[C@@H]2N1CCCC[C@H]1c1cccnc1] | 0.249 |
| 228 | 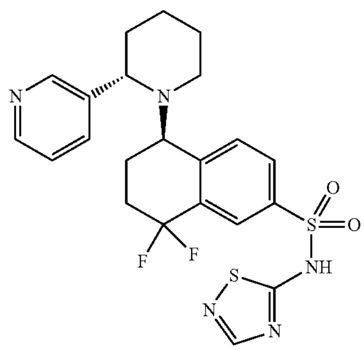 [SMILES: O=S(=O)(Nc1ncns1)c1ccc2c(c1)C(F)(F)CC[C@H]2N1CCCC[C@H]1c1cccnc1] | 0.504 |
| 229 | 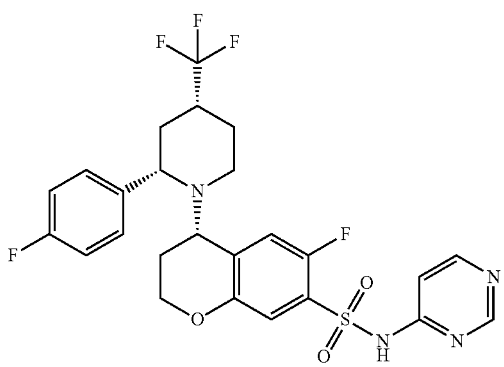 [SMILES: O=S(=O)(Nc1ccncn1)c1cc2c(cc1F)[C@@H](N1CC[C@@H](C(F)(F)F)C[C@H]1c1ccc(F)cc1)CCO2] | 0.0005 |
| 230 | 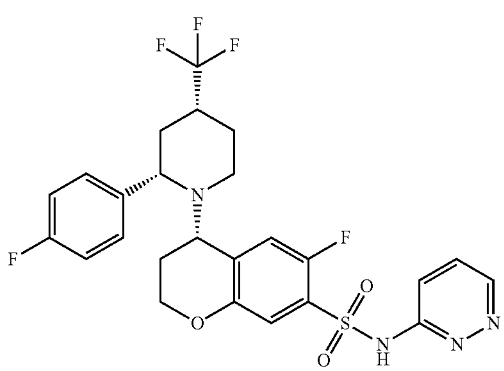 [SMILES: O=S(=O)(Nc1cccnn1)c1cc2c(cc1F)[C@@H](N1CC[C@@H](C(F)(F)F)C[C@H]1c1ccc(F)cc1)CCO2] | 0.00795 |

TABLE 1-continued

| Example | Structure | Nav1.7 (LBA) (µM) |
|---------|-----------|---------------------|
| 231 | 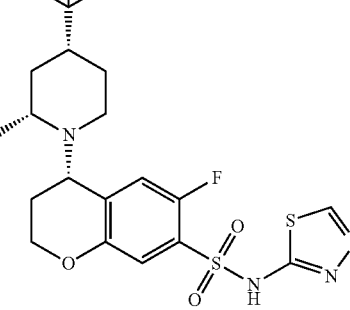 | 0.00495 |
| 232 | 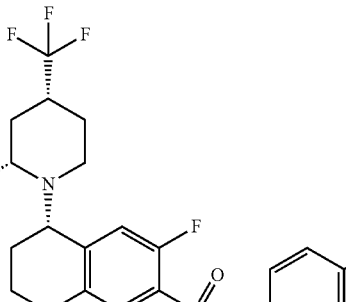 | 0.00455 |
| 233 | 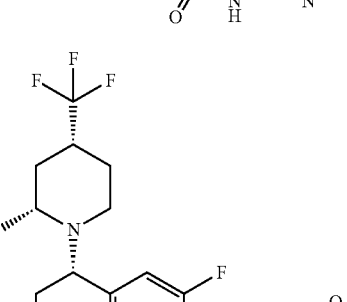 | 0.00404 |

Example 236

Analgesia Induced by Sodium Channel Blockers

Heat Induced Tail Flick Latency Test

In this test, the analgesia effect produced by administering a compound of the invention can be observed through heat-induced tail-flick in mice. The test includes a heat source consisting of a projector lamp with a light beam focused and directed to a point on the tail of a mouse being tested. The tail-flick latencies, which are assessed prior to drug treatment, and in response to a noxious heat stimulus, i.e., the response time from applying radiant heat on the dorsal surface of the tail to the occurrence of tail flick, are measured and recorded at 40, 80, 120, and 160 minutes.

For the first part of this study, 65 animals undergo assessment of baseline tail flick latency once a day over two consecutive days. These animals are then randomly assigned to one of the 11 different treatment groups including a vehicle control, a morphine control, and 9 compounds at 30 mg/Kg are administered intramuscularly. Following dose administration, the animals are closely monitored for signs of toxicity including tremor or seizure, hyperactivity, shallow, rapid or depressed breathing and failure to groom. The optimal incubation time for each compound is determined via regression analysis. The analgesic activity of the test compounds is expressed as a percentage of the maximum possible effect (% MPE) and is calculated using the following formula:

$$\% \; MPE \; \frac{\text{Postdrug latency} - \text{Predrug latency}}{\text{Cut-off time (10 s)} - \text{Predrug latency}} \times 100\%$$

where:
  Postdrug latency=the latency time for each individual animal taken before the tail is removed (flicked) from the heat source after receiving drug.
  Predrug latency=the latency time for each individual animal taken before the tail is flicked from the heat source prior to receiving drug.
  Cut-off time (10 s)=is the maximum exposure to the heat source.

Acute Pain (Formalin Test)

The formalin test is used as an animal model of acute pain. In the formalin test, animals are briefly habituated to the plexiglass test chamber on the day prior to experimental day for 20 minutes. On the test day, animals are randomly injected with the test articles. At 30 minutes after drug administration, 50 μL of 10% formalin is injected subcutaneously into the plantar surface of the left hind paw of the rats. Video data acquisition begins immediately after formalin administration, for duration of 90 minutes.

The images are captured using the Actimetrix Limelight software which stores files under the *.llii extension, and then converts it into the MPEG-4 coding. The videos are then analyzed using behaviour analysis software "The Observer 5.1", (Version 5.0, Noldus Information Technology, Wageningen, The Netherlands). The video analysis is conducted by watching the animal behaviour and scoring each according to type, and defining the length of the behaviour (Dubuisson and Dennis, 1977). Scored behaviours include: (1) normal behaviour, (2) putting no weight on the paw, (3) raising the paw, (4) licking/biting or scratching the paw. Elevation, favoring, or excessive licking, biting and scratching of the injected paw indicate a pain response. Analgesic response or protection from compounds is indicated if both paws are resting on the floor with no obvious favoring, excessive licking, biting or scratching of the injected paw.

Analysis of the formalin test data is done according to two factors: (1) Percent Maximal Potential Inhibitory Effect (% MPIE) and (2) pain score. The % MPIEs is calculated by a series of steps, where the first is to sum the length of non-normal behaviours (behaviours 1, 2, 3) of each animal. A single value for the vehicle group is obtained by averaging all scores within the vehicle treatment group. The following calculation yields the MPIE value for each animal:

MPIE (%)=100−[(treatment sum/average vehicle value)×100%]

The pain score is calculated from a weighted scale as described above. The duration of the behaviour is multiplied by the weight (rating of the severity of the response), and divided by the total length of observation to determine a pain rating for each animal. The calculation is represented by the following formula:

Pain rating=$[0(T_o)+1(T_1)+2(T_2)+3(T_3)]/(T_o+T_1+T_2+T_3)$

CFA Induced Chronic Inflammatory Pain

In this test, tactile allodynia is assessed with calibrated von Frey filaments. Following a full week of acclimatization to the vivarium facility, 150 μL of the "Complete Freund's Adjuvant" (CFA) emulsion (CFA suspended in an oil/saline (1:1) emulsion at a concentration of 0.5 mg/mL) is injected subcutaneously into the plantar surface of the left hind paw of rats under light isoflurane anaesthesia. Animals are allowed to recover from the anaesthesia and the baseline thermal and mechanical nociceptive thresholds of all animals are assessed one week after the administration of CFA.

All animals are habituated to the experimental equipment for 20 minutes on the day prior to the start of the experiment. The test and control articles are administrated to the animals, and the nociceptive thresholds measured at defined time points after drug administration to determine the analgesic responses to each of the six available treatments. The time points used are previously determined to show the highest analgesic effect for each test compound.

Thermal nociceptive thresholds of the animals are assessed using the Hargreaves test. Animals are placed in a Plexiglas enclosure set on top of an elevated glass platform with heating units. The glass platform is thermostatically controlled at a temperature of approximately 30° C. for all test trials. Animals are allowed to accommodate for 20 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 45 respectively, and a cut off time of 20 seconds is employed to prevent tissue damage.

The response thresholds of animals to tactile stimuli are measured using the Model 2290 Electrovonfrey anesthesiometer (IITC Life Science, Woodland Hills, Calif.) following the Hargreaves test. Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Postoperative Models of Nociception

In this model, the hypealgesia caused by an intra-planar incision in the paw is measured by applying increased tactile stimuli to the paw until the animal withdraws its paw from the applied stimuli. While animals are anaesthetized under 3.5% isofluorane, which is delivered via a nose cone, a 1 cm longitudinal incision is made using a number 10 scalpel blade in the plantar aspect of the left hind paw through the skin and fascia, starting 0.5 cm from the proximal edge of the heel and extending towards the toes. Following the incision, the skin is apposed using 2, 3-0 sterilized silk sutures. The injured site is covered with Polysporin and Betadine. Animals are returned to their home cage for overnight recovery.

The withdrawal thresholds of animals to tactile stimuli for both operated (ipsilateral) and unoperated (contralateral) paws can be measured using the Model 2290 Electrovonfrey anesthesiometer (IITC Life Science, Woodland Hills, Calif.). Animals are placed in an elevated Plexiglas enclosure set on a mire mesh surface. After at least 10 minutes of acclimatization, pre-calibrated Von Frey hairs are applied perpendicularly to the plantar surface of both paws of the animals in an ascending order starting from the 10 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Neuropathic pain model; Chronic Constriction Injury

Briefly, an approximately 3 cm incision is made through the skin and the fascia at the mid thigh level of the animals' left hind leg using a no. 10 scalpel blade. The left sciatic nerve is exposed via blunt dissection through the biceps femoris with care to minimize haemorrhagia. Four loose ligatures are tied along the sciatic nerve using 4-0 non-degradable sterilized silk sutures at intervals of 1 to 2 mm apart. The tension of the loose ligatures is tight enough to induce slight constriction of the sciatic nerve when viewed under a dissection microscope at a magnification of 4 fold. In the sham-operated animal, the left sciatic nerve is exposed without further manipulation. Antibacterial ointment is applied directly into the wound, and the muscle is closed using sterilized sutures. Betadine is applied onto the muscle and its surroundings, followed by skin closure with surgical clips.

The response thresholds of animals to tactile stimuli are measured using the Model 2290 Electrovonfrey anesthesiometer (IITC Life Science, Woodland Hills, Calif.). Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represents approximately 10% of the animals' body weight and it serves to prevent raising of the entire limb due to the use of stiffer hairs, which would change the nature of the stimulus.

Thermal nociceptive thresholds of the animals are assessed using the Hargreaves test. Following the measurement of tactile thresholds, animals are placed in a Plexiglass enclosure set on top of an elevated glass platform with heating units. The glass platform is thermostatically controlled at a temperature of approximately 24 to 26° C. for all test trials. Animals are allowed to accommodate for 10 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 55 respectively, and a cut off time of 20 seconds is used to prevent tissue damage.

Neuropathic pain model: Spinal Nerve Ligation

The spinal nerve ligation (SNL) neuropathic pain model is used as an animal (i.e. rat) model of neuropathic pain. In the SNL test, the lumbar roots of spinal nerves L5 and L6 are tightly ligated to cause nerve injury, which results in the development of mechanical hyperalgesia, mechanical allodynia and thermal hypersensitivity. The surgery is performed two weeks before the test day in order for the pain state to fully develop in the animals. Several spinal nerve ligation variations are used to characterize the analgesic properties of a compound of the invention.

Ligation of the L5 spinal nerve;
    Ligation of the L5 and L6 spinal nerves;
    Ligation and transection of the L5 spinal nerve;
    Ligation and transection of the L5 and L6 spinal nerves; or Mild irritation of the L4 spinal nerve in combination with any one of the above (1)-(4).

While the animals are anaesthetized under 3.5% isofluorane delivered via a nose cone, an approximately 2.5 cm longitudinal incision is made using a number 10 scalpel blade in the skin just lateral to the dorsal midline, using the level of the posterior iliac crests as the midpoint of the incision. Following the incision, the isoflourane is readjusted to maintenance levels (1.5%-2.5%). At mid-sacral region, an incision is made with the scalpel blade, sliding the blade along the side of the vertebral column (in the saggital plane) until the blade hits the sacrum. Scissors tips are introduced through the incision and the muscle and ligaments are removed from the spine to expose 2-3 cm of the vertebral column. The muscle and fascia are cleared from the spinal vertebra in order to locate the point where the nerve exits from the vertebra. A small glass hook is placed medial to the spinal nerves and the spinal nerves are gently elevated from the surrounding tissues. Once the spinal nerves have been isolated, a small length of non-degradable 6-0 sterilized silk thread is wound twice around the ball at the tip of the glass hook and passed back under the nerve. The spinal nerves are then firmly ligated by tying a knot, ensuring that the nerve bulges on both sides of the ligature. The procedure may be repeated as needed. In some animals, the L4 spinal nerve may be lightly rubbed (up to 20 times) with the small glass hook to maximize the development of neuropathic pain. Antibacterial ointment is applied directly into the incision, and the muscle is closed using sterilized sutures. Betadine is applied onto the muscle and its surroundings, followed by skin closure with surgical staples or sterile non-absorable monofilament 5-0 nylon sutures.

The analgesic effect produced by topical administration of a compound of the invention to the animals can then be observed by measuring the paw withdrawal threshold of animals to mechanical tactile stimuli. These may be measured using either the mechanical allodynia procedure or the mechanical hyperalgesia procedure as described below. After establishment of the appropriate baseline measurements by either method, topical formulation of a compound of the invention is applied on the ipsilateral ankle and foot. The animals are then placed in plastic tunnels for 15 minutes to prevent them from licking the treated area and removing the compound. Animals are placed in the acrylic enclosure for 15 minutes before testing the ipsilateral paw by either of the methods described below, and the responses are recorded at 0.5, 1.0 and 2.0 hour post treatment.

Mechanical Allodynia Method

The pain threshold of animals to mechanical alloydnia for both operated and control animals can be measured approximately 14 days post-surgery using manual calibrated von Frey filaments as follows. Animals are placed in an elevated plexiglass enclosure set on a mire mesh surface. Animals are allowed to acclimate for 20-30 minutes. Pre-calibrated Von Frey hairs are applied perpendicularly to the plantar surface of the ipsilateral paw of the animals starting from the 2.0 g hair, with sufficient force to cause slight buckling of the hair against the paw to establish the baseline measurements. Stimuli are presented in a consecutive manner, either in an ascending or descending order until the first change in response is noted, after which four additional responses are recorded for a total of six responses. The six responses measured in grams are entered into a formula as described by Chaplan, S. R. et al., J. Neurosci. Methods, 1994 July; 53(1):55-63, and a 50% withdrawal threshold is calculated. This constitutes the mechanical allodynia value.

Mechanical Hyperalgesia Method

The response thresholds of animals to tactile stimuli are measured using the Model 2290 Electrovonfrey anesthesiometer (IITC Life Science, Woodland Hills, Calif.). Animals are placed in an elevated Plexiglas enclosure set on a wire mesh surface. After 15 minutes of accommodation in this enclosure, a von Frey hair is applied perpendicularly to the plantar surface of the ipsilateral hind paws of the animals, with sufficient force, measured in grams, to elicit a crisp response of the paw. A response indicates a withdrawal from the painful stimulus and constitutes the efficacy endpoint. The data are expressed as percent change from baseline threshold measured in grams.

Example 237 In Vivo Assay for Treatment of Pruritus

The compounds of the invention can be evaluated for their activity as antipruritic agents by in vivo test using rodent models. One established model for peripherally elicited pruritus is through the injection of serotonin into the rostral back area (neck) in hairless rats. Prior to serotonin injections (e.g., 2 mg/mL, 50 μL), a dose of a compound of the present invention can be applied systemically through oral, intravenous or intraperitoneal routes or topically to a circular area fixed diameter (e.g. 18 mm). Following dosing, the serotonin injections are given in the area of the topical dosing. After serotonin injection the animal behaviour is monitored by video recording for 20 min-1.5 h, and the number of scratches in this time compared to vehicle treated animals. Thus, application of a compound of the current invention could suppress serotonin-induced scratching in rats.

All of the U.S. patents, U.S. patent application publications, U.S. patent applications, foreign patents, foreign patent applications and non patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

We claim:

1. A compound of formula (I):

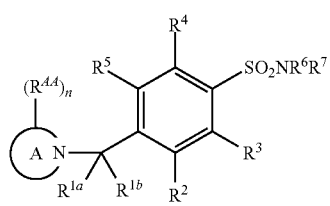

(I)

or a pharmaceutically acceptable salt thereof; wherein each $R^{AA}$ is independently selected from the group consisting of F, Cl, Br, I, —CN, —C(=O)OR$^{A1}$, —SO$_2$R$^{A1}$, —OR$^{A1}$, —(X$^{RA}$)-(3-15 membered carbocyclyl), —(X$^{RA}$)-(6-12 membered aryl), —(X$^{RA}$)-(5-12 membered heteroaryl), and —R$^{A2}$, wherein said 3-15 membered carbocyclyl, 6-12 membered aryl, and 5-12 membered heteroaryl of R$^{AA}$ is optionally substituted with from 1 to 5 substituents R$^b$ that are independently selected from the group consisting of F, Cl, Br, I, C$_{1-4}$ alkyl, C$_{1-4}$ haloalkyl, amino, C$_{1-4}$ alkylamino, di(C$_{1-4}$alkyl)amino, and C$_{1-4}$(halo)alkoxy; R$^{A1}$ is selected from the group consisting of hydrogen, C$_{1-8}$ alkyl, C$_{2-8}$ alkenyl, C$_{1-8}$ haloalkyl, C$_{3-8}$ cycloalkyl, phenyl and benzyl; R$^{A2}$ is selected from the group consisting of C$_{1-8}$ alkyl that is optionally substituted with one or more substituents selected from oxo, fluoro, hydroxy, amino, C$_{1-4}$ alkylamino and di(C$_{1-4}$alkyl)amino; X$^{RA}$ is selected from the group consisting of absent, —C(=O)—, and C$_{1-4}$ alkylene; wherein any C$_{1-4}$ alkylene, of X$^{RA}$ is optionally substituted with 1 to 3 substituents selected from the group consisting of C$_{1-4}$ alkyl, C$_{1-4}$ haloalkyl, and phenyl that is optionally substituted with 1 to 5 substituents selected from, F, Cl, Br, I, —NH$_2$, —OH, —CN, —NO$_2$, C$_{1-4}$ alkyl, C$_{1-4}$ haloalkyl, C$_{1-4}$ alkoxy, C$_{1-4}$(halo)alkoxy, C$_{1-4}$ alkylamino and C$_{1-4}$ dialkylamino;

ring "A" is a 5-6 membered heterocycle;

$R^{1a}$ is H or C$_{1-4}$ alkyl;

$R^{1b}$ is H or C$_{1-4}$ alkyl;

$R^2$ is selected from the group consisting of H, F, Cl, Br, I, —CN, C$_{1-8}$ alkyl, C$_{3-8}$ cycloalkyl, C$_{1-8}$ haloalkyl and C$_{1-8}$ alkoxy;

$R^3$, $R^4$, and $R^5$ are each independently selected from the group consisting of H, F, Cl, Br, I, —CN, C$_{1-8}$ alkyl, C$_{3-8}$ cycloalkyl, C$_{1-8}$ haloalkyl and C$_{1-8}$ alkoxy;

$R^6$ is selected from the group consisting of H, C$_{1-8}$ alkyl, C$_{3-8}$ cycloalkyl, aryl, and aryl(C$_{1-4}$ alkyl); and $R^7$ is selected from the group consisting of 3-15 membered heterocyclyl, 5-12 membered heteroaryl, —C(O)N(R$^c$)$_2$ and —C(=NCN)N(R$^c$)$_2$; or $R^6$ and $R^7$, together with the nitrogen to which they are attached, form a 3-15 membered heterocyclyl or 5-12 membered heteroaryl: wherein any C$_{1-8}$ alkyl, C$_{3-8}$ cycloalkyl, aryl, aryl(C$_{1-4}$ alkyl), 3-15 membered heterocyclyl, and 5-12 membered heteroaryl is optionally substituted with one or more groups R$^d$ that are independently selected from the group consisting of F, Cl, Br, I, —NH$_2$, —OH, —CN, —NO$_2$, C$_{1-4}$ alkyl, C$_{1-4}$ haloalkyl, C$_{1-4}$ alkoxy, C$_{1-4}$(halo)alkoxy, C$_{1-4}$ alkylamino and C$_{1-4}$ dialkylamino;

each R$^c$ is independently selected from the group consisting of hydrogen, C$_{1-8}$ alkyl, C$_{3-8}$ cycloalkyl, phenyl and benzyl; and n is 0, 1, 2, 3, 4, 5, or 6;

provided at least one of R$^2$, R$^3$, R$^4$, and R$^5$ is not H.

2. A compound of formula (Ix):

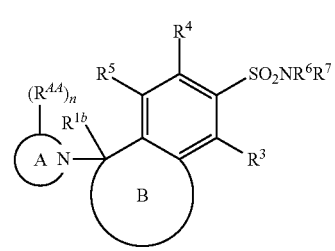

(Ix)

or a pharmaceutically acceptable salt thereof; wherein, each R$^{AA}$ is independently selected from the group consisting of F, Cl, Br, I, —CN, —C(=O)OR$^{A1}$, —SO$_2$R$^{A1}$, —OR$^{A1}$, —(X$^{RA}$)-(3-15 membered carbocyclyl), —(X$^{RA}$)-(6-12 membered aryl), —(X$^{RA}$)-(5-12 membered heteroaryl), and —R$^{A2}$, wherein said 3-15 membered carbocyclyl, 6-12 membered aryl, and 5-12 membered heteroaryl of $R^{AA}$ is optionally substituted with from 1 to 5 substituents $R^b$ that are independently selected from the group consisting of F, Cl, Br, I, $C_{1-4}$ alkyl, $C_{1-4}$ haloalkyl, amino, $C_{1-4}$ alkylamino, di($C_{1-4}$alkyl)amino, $C_{1-4}$(halo)alkoxy, and —C(O)N($R^c$)$_2$; $R^{41}$ is selected from the group consisting of hydrogen, $C_{1-8}$ alkyl, $C_{2-8}$ alkenyl, $C_{1-8}$ haloalkyl, $C_{3-8}$ cycloalkyl, phenyl and benzyl; $R^{42}$ is selected from the group consisting of $C_{1-8}$ alkyl that is optionally substituted with one or more substituents selected from oxo, fluoro, hydroxy, amino, $C_{1-4}$ alkylamino and di($C_{1-4}$alkyl)amino; $X^{RA}$ is selected from the group consisting of absent, —C(=O)—, and $C_{1-4}$ alkylene; wherein any $C_{1-4}$ alkylene, of $X^{RA}$ is optionally substituted with 1 to 3 substituents selected from the group consisting of $C_{1-4}$ alkyl, $C_{1-4}$ haloalkyl, and phenyl that is optionally substituted with 1 to 5 substituents selected from, F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino;

ring "A" is a 5-12 membered heteroaryl, or a 3-15 membered heterocyclyl;

Ring B is a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from $C_{1-4}$ alkyl, halo, and halo$C_{1-4}$ alkyl;

$R^{1b}$ is H or $C_{1-4}$ alkyl;

$R^3$, $R^4$, and $R^5$ are each independently selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy;

$R^6$ is selected from the group consisting of H, $C_{1-8}$ alkyl, $C_{3-8}$ cycloalkyl, aryl, and aryl($C_{1-4}$ alkyl); and $R^7$ is selected from the group consisting of $C_{1-8}$ alkyl, 3-15 membered heterocyclyl, 5-12 membered heteroaryl, —C(O)N($R^c$)$_2$ and —C(=NCN)N($R^c$)$_2$; or $R^6$ and $R^7$, together with the nitrogen to which they are attached, form a 3-15 membered heterocyclyl or 5-12 membered heteroaryl; wherein any $C_{1-8}$ alkyl, $C_{3-8}$ cycloalkyl, aryl, aralkyl, 3-15 membered heterocyclyl, and 5-12 membered heteroaryl is optionally substituted with one or more groups $R^d$ that are independently selected from the group consisting of F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino; each $R^c$ is independently selected from the group consisting of hydrogen, $C_{1-8}$ alkyl, $C_{3-8}$ cycloalkyl, phenyl and benzyl; and n is 0, 1, 2, 3, 4, 5, or 6.

3. The compound of formula (Ix) of claim 2:

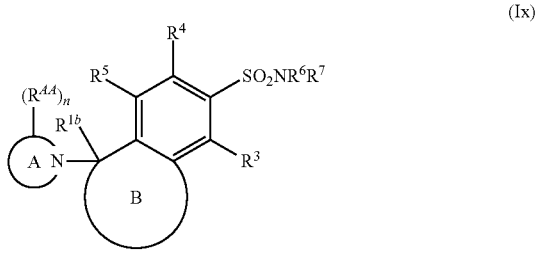

(Ix)

or a pharmaceutically acceptable salt thereof; wherein, each $R^{AA}$ is independently selected from the group consisting of F, Cl, Br, I, —CN, —OR$^{41}$, —(X$^{RA}$)-(3-15 membered carbocyclyl), —(X$^{RA}$)-(6-12 membered aryl), —(X$^{RA}$)-(5-12 membered heteroaryl), and —R$^{42}$, wherein said (3-15 membered carbocyclyl), 6-12 membered aryl, and 5-12 membered heteroaryl of $R^{AA}$ is optionally substituted with from 1 to 5 substituents $R^b$ that are independently selected from the group consisting of F, Cl, Br, I, $C_{1-4}$ alkyl, $C_{1-4}$ haloalkyl, amino, $C_{1-4}$ alkylamino and di($C_{1-4}$alkyl)amino, and $C_{1-4}$(halo)alkoxy; $R^{41}$ is selected from the group consisting of hydrogen, $C_{1-8}$ alkyl, $C_{2-8}$ alkenyl, $C_{1-8}$ haloalkyl, $C_{3-8}$ cycloalkyl, phenyl and benzyl;

$R^{42}$ is selected from the group consisting of $C_{1-8}$ alkyl that is optionally substituted with one or more substituents selected from oxo, fluoro, hydroxy, amino, $C_{1-4}$ alkylamino and di($C_{1-4}$alkyl)amino; $X^{RA}$ is selected from the group consisting of absent, —C(=O)—, and $C_{1-4}$ alkylene; wherein any $C_{1-4}$ alkylene, of $X^{RA}$ is optionally substituted with 1 to 3 substituents selected from the group consisting of $C_{1-4}$ alkyl, $C_{1-4}$ haloalkyl, and phenyl that is optionally substituted with 1 to 5 substituents selected from, F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-8}$ alkylamino and $C_{1-4}$ dialkylamino;

ring "A" is a 5-12 membered heteroaryl, or a 3-15 membered heterocyclyl;

Ring B is a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from $C_{1-4}$ alkyl, halo, and halo$C_{1-4}$ alkyl;

$R^{1b}$ is H or $C_{1-4}$ alkyl;

$R^3$, $R^4$, and $R^5$ are each independently selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy;

$R^6$ is selected from the group consisting of H, $C_{1-8}$ alkyl, $C_{3-8}$ cycloalkyl, aryl, and aryl($C_{1-4}$ alkyl); and $R^7$ is selected from the group consisting of $C_{1-8}$ alkyl, 3-15 membered heterocyclyl, 5-12 membered heteroaryl, —C(O)N($R^c$)$_2$ and —C(=NCN)N($R^c$)$_2$; or $R^6$ and $R^7$, together with the nitrogen to which they are attached, form a 3-15 membered heterocyclyl or 5-12 membered heteroaryl; wherein any $C_{1-8}$ alkyl, $C_{3-8}$ cycloalkyl, aryl, aralkyl, 3-15 membered heterocyclyl, and 5-12 membered heteroaryl is optionally substituted with one of more groups $R^d$ that are independently selected from the group consisting of F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino;

each $R^c$ is independently selected from the group consisting of hydrogen, $C_{1-8}$ alkyl, $C_{3-8}$ cycloalkyl, phenyl and benzyl; and n is 0, 1, 2, 3, 4, 5, or 6.

4. The compound of claim 2 which is a compound of formula Ic:

(Ic)

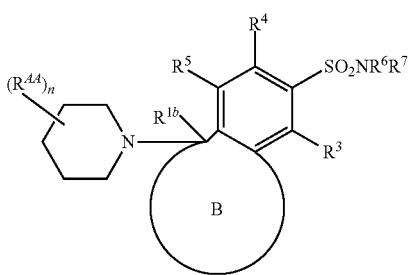

wherein the ring B is a 5, 6, or 7 membered carbocyclyl or a 5, 6, or 7 membered heterocyclyl; or a pharmaceutically acceptable salt thereof.

5. The compound of claim 2 which is a compound of formula Id:

(Id)

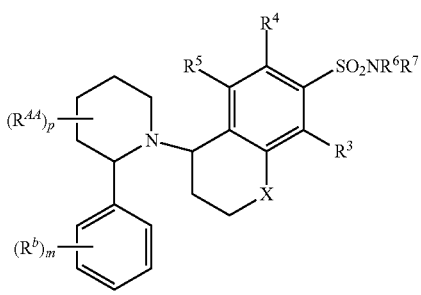

wherein X is O, S, SO, or $SO_2$; m is 0, 1, 2, 3, 4 or 5; and p is 0, 1, 2, 3, 4, or 5: or a pharmaceutically acceptable salt thereof.

6. The compound of claim 2, which is a compound of formula Ih:

(Ih)

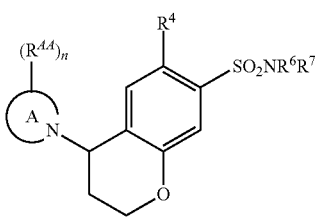

or a pharmaceutically acceptable salt thereof.

7. The compound of claim 2, which is a compound of formula Ij:

(Ij)

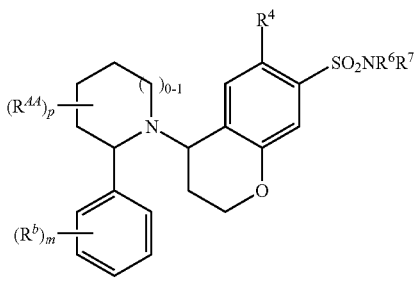

wherein m is 0, 1, 2, 3, 4 or 5; and p is 0, 1, 2, 3, 4, or 5; or a pharmaceutically acceptable salt thereof.

8. The compound of claim 1, wherein the group

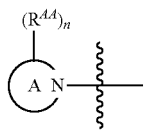

is selected from the group consisting of:

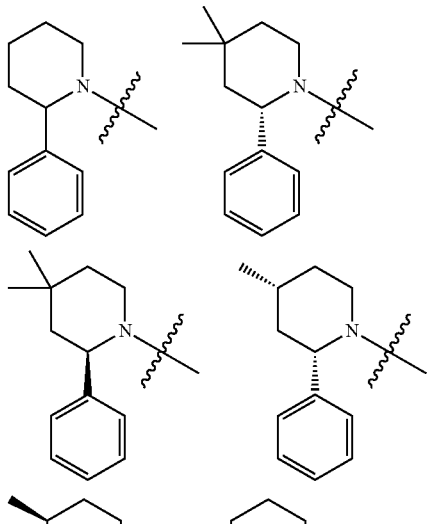

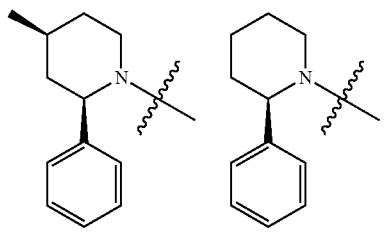

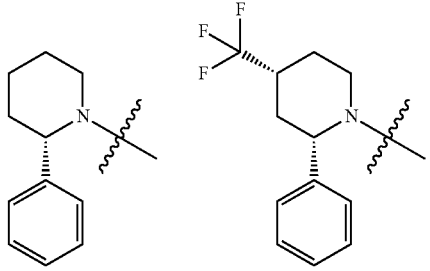

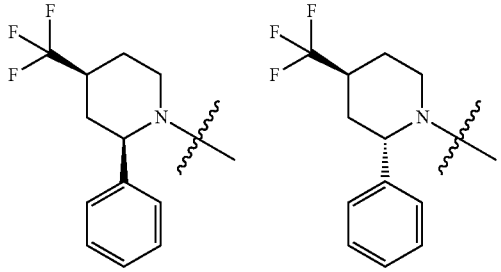

565
-continued
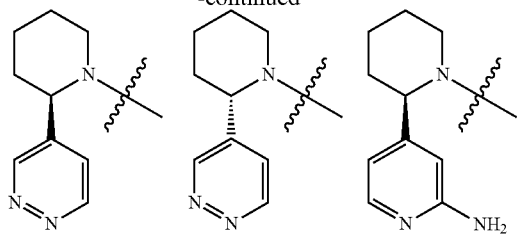
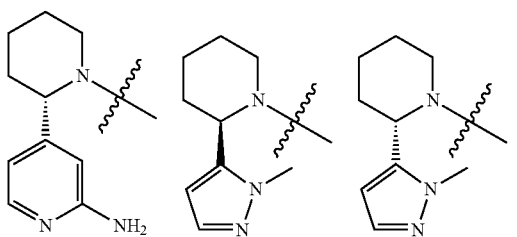
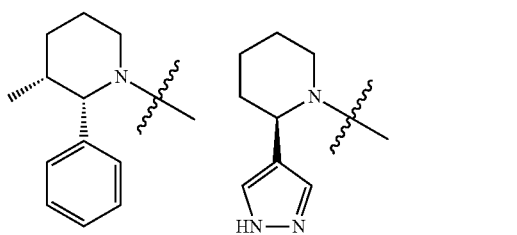
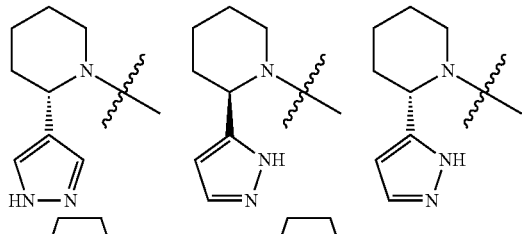
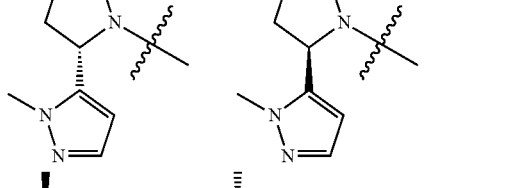
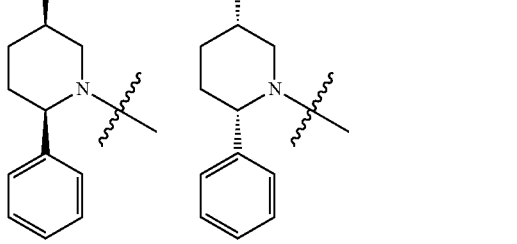
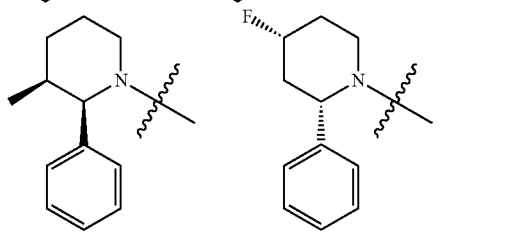
566
-continued
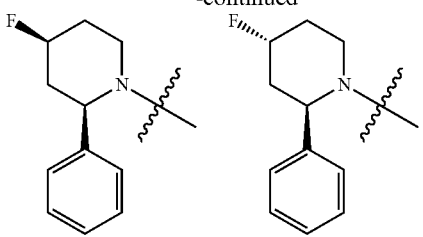
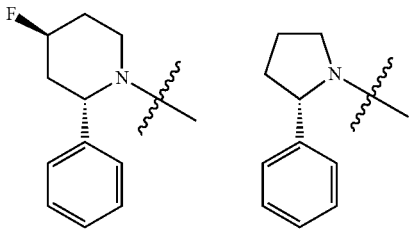
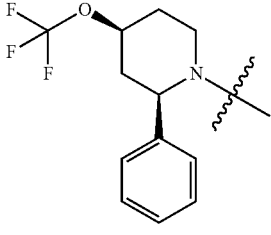
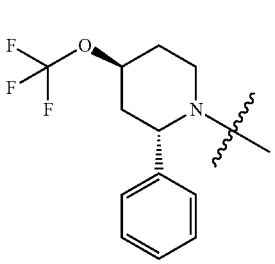
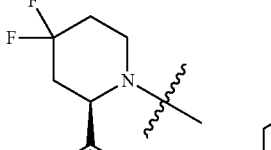
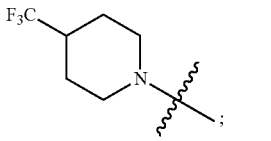
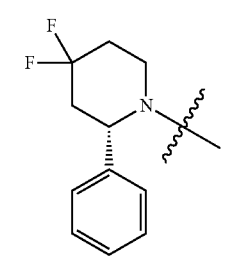
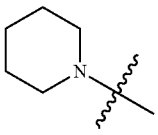
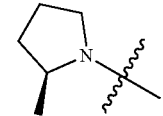
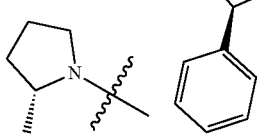
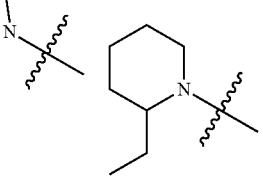

567
-continued
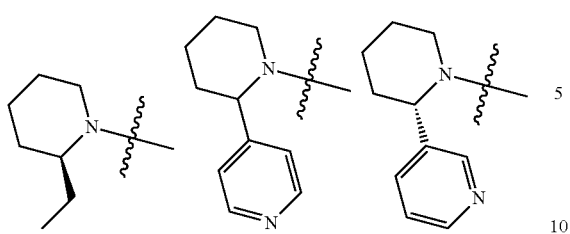
568
-continued
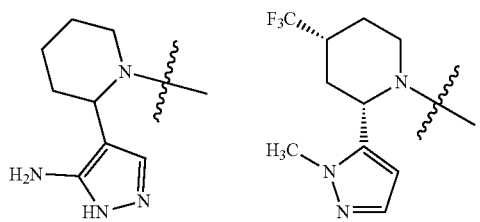
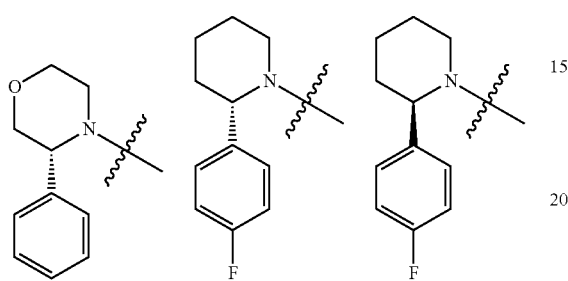
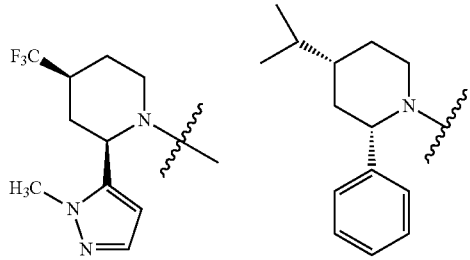
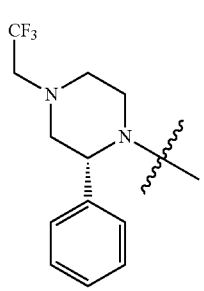
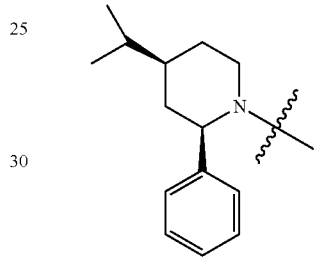
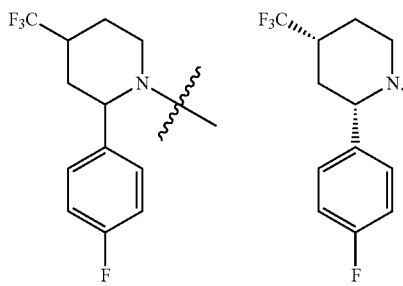
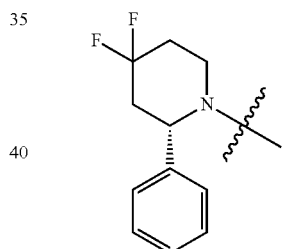
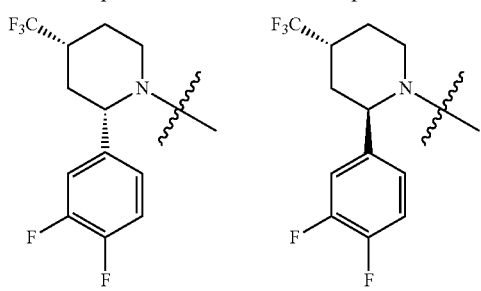
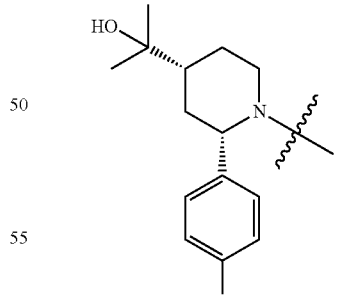
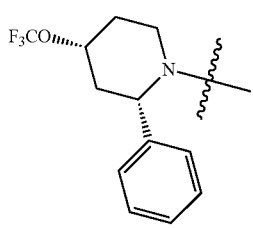
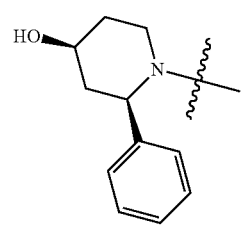
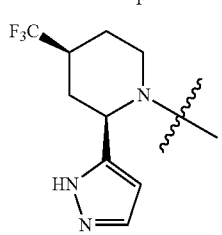
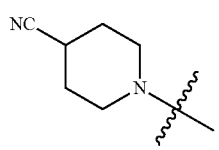

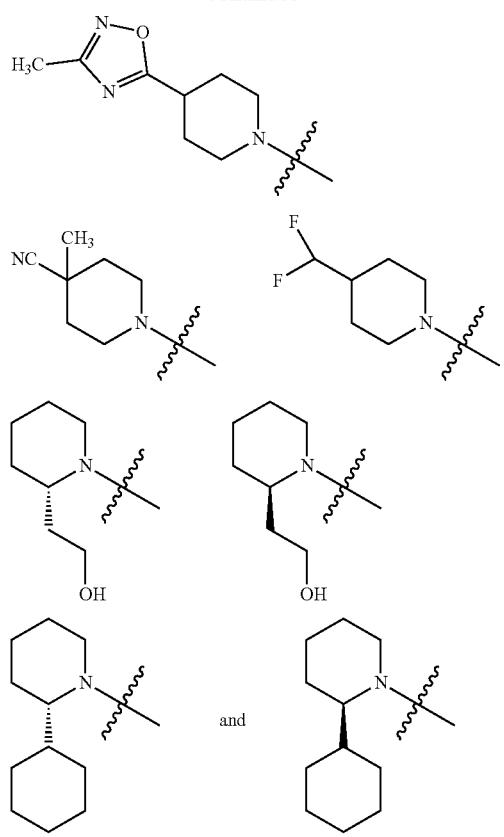
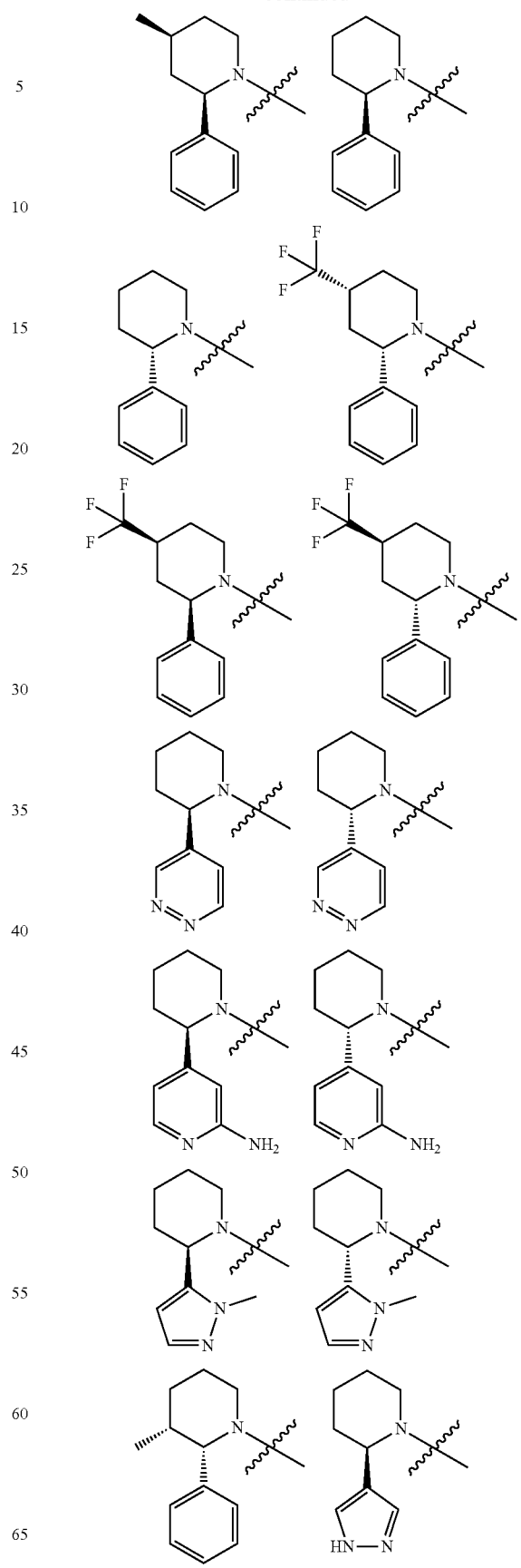
or a pharmaceutically acceptable salt thereof.
9. The compound of claim 1, wherein the group
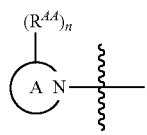
is selected from the group consisting of:
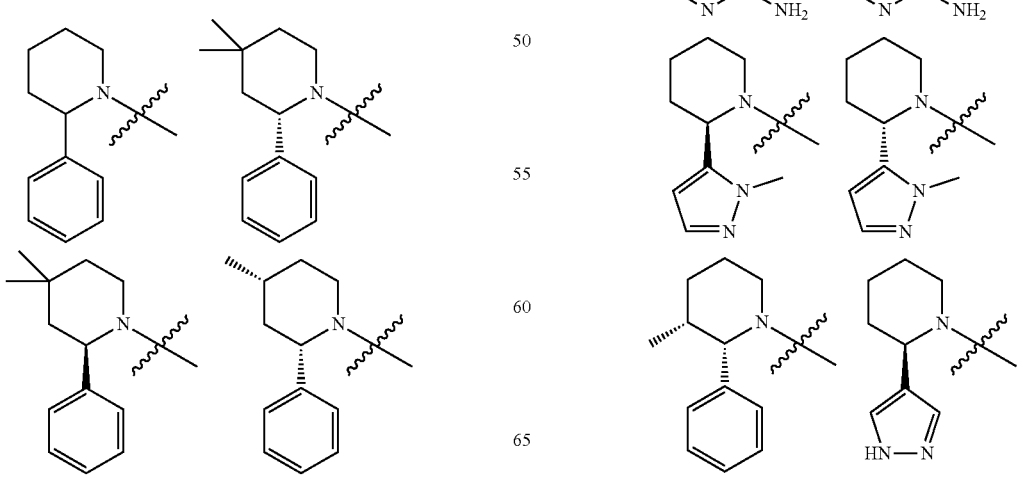

571
-continued
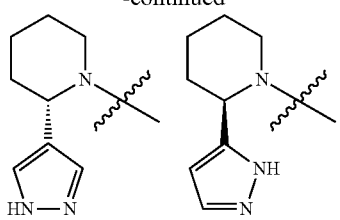
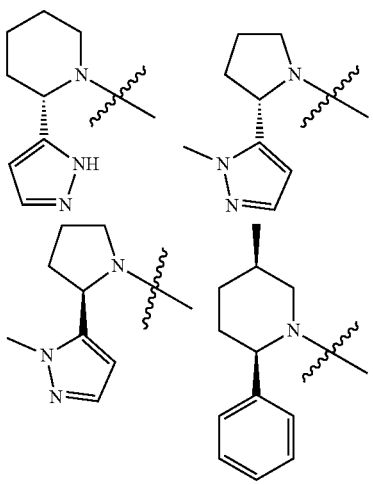
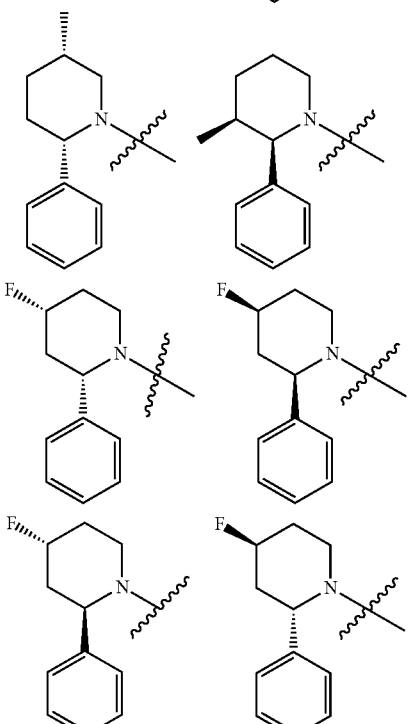
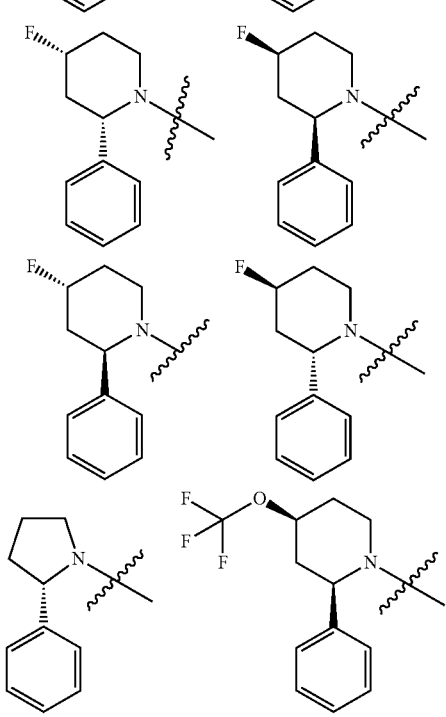
572
-continued
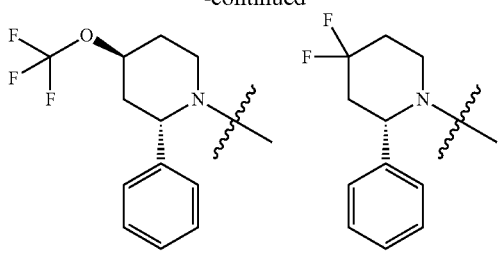
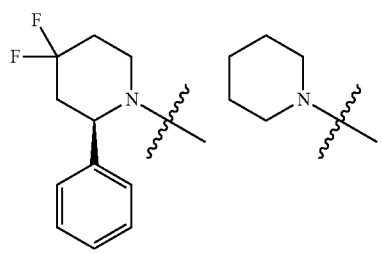
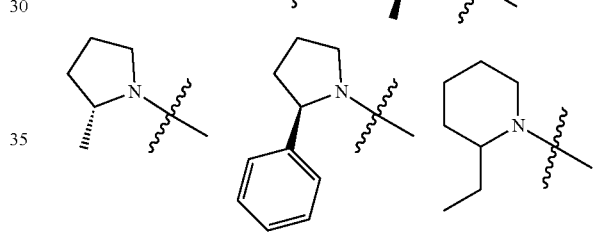
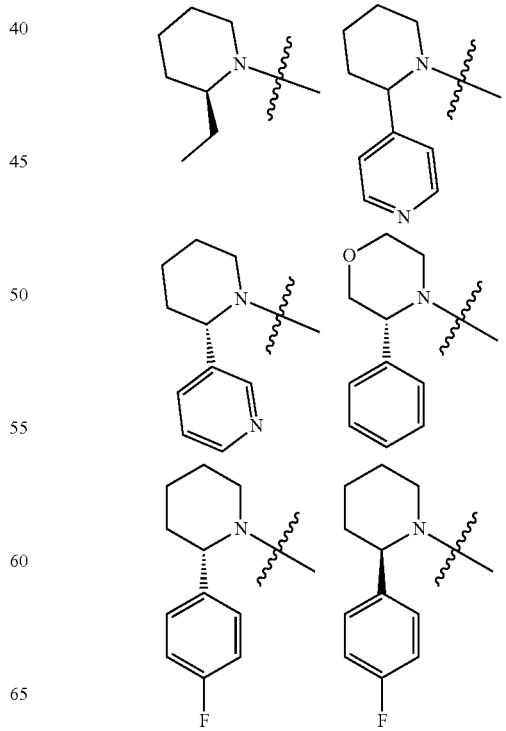

573
-continued
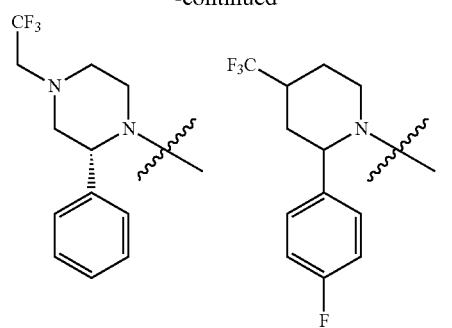
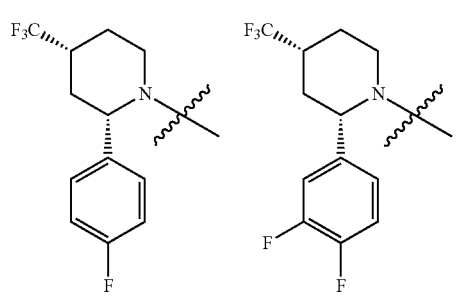
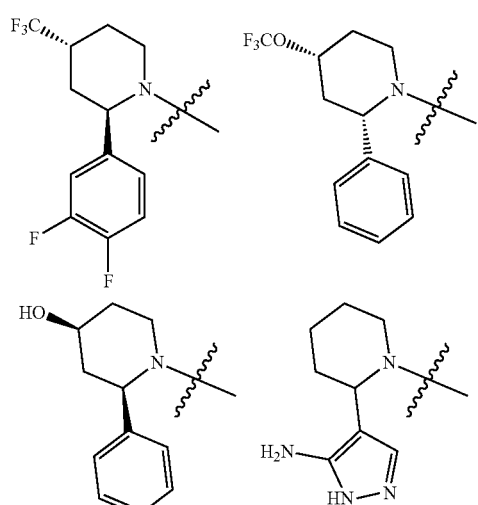
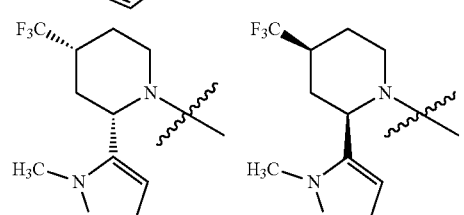
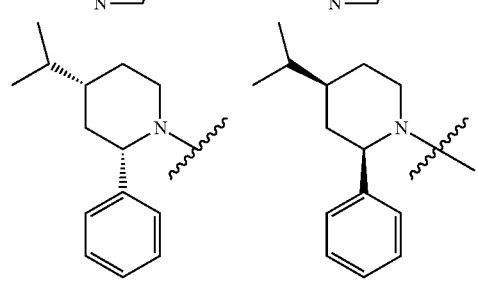
574
-continued
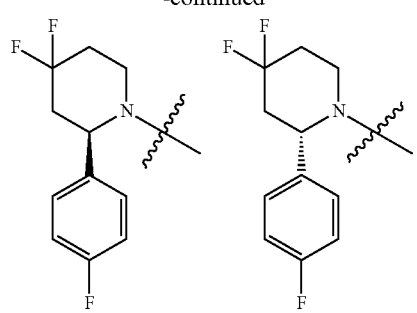
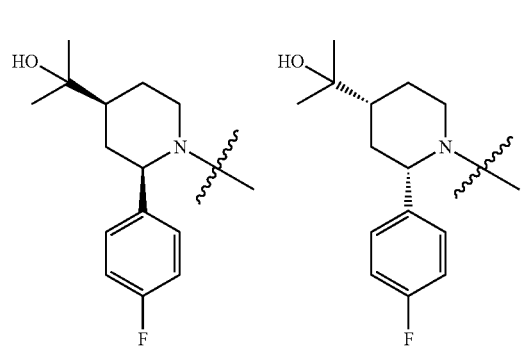
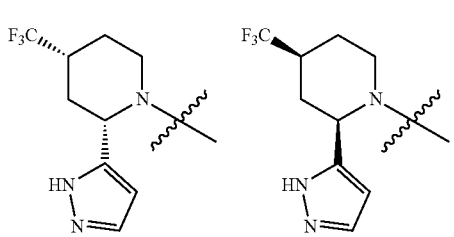
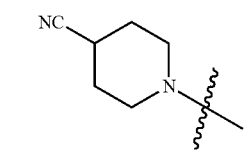
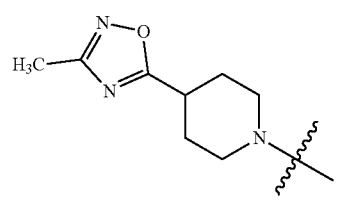
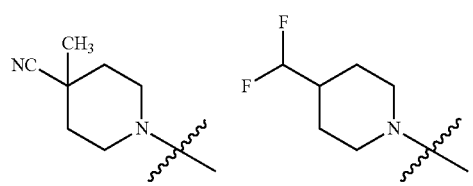
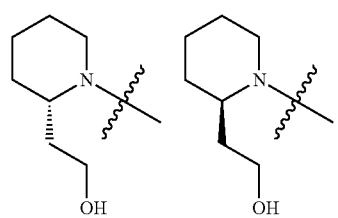

575
-continued
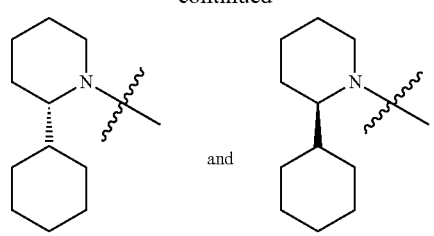
and
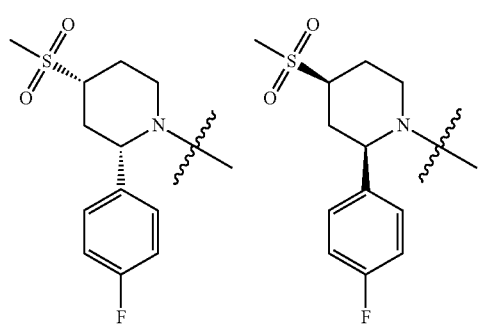
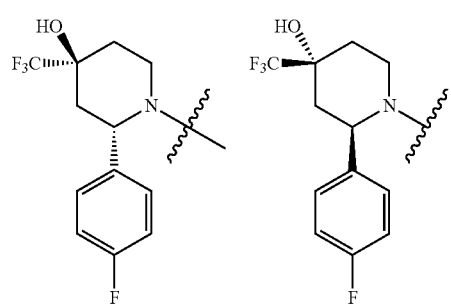
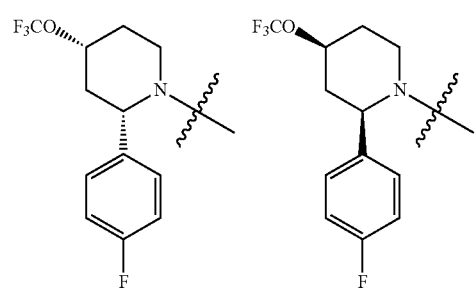
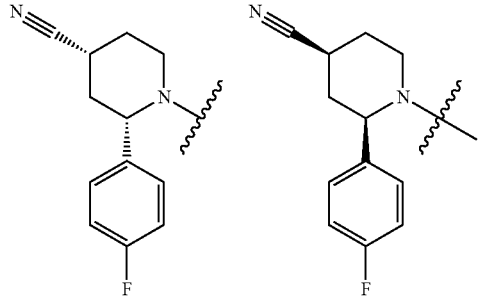
576
-continued
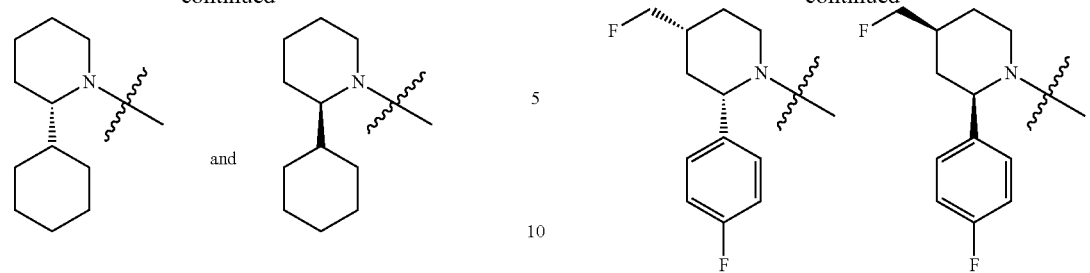
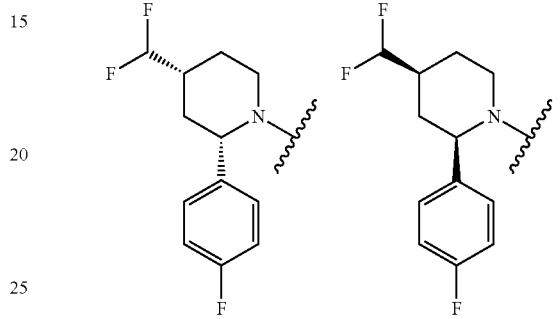
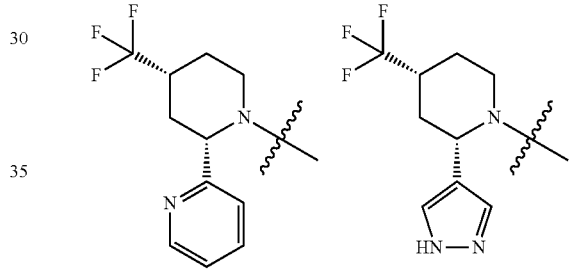
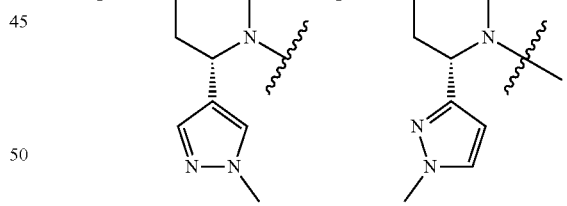
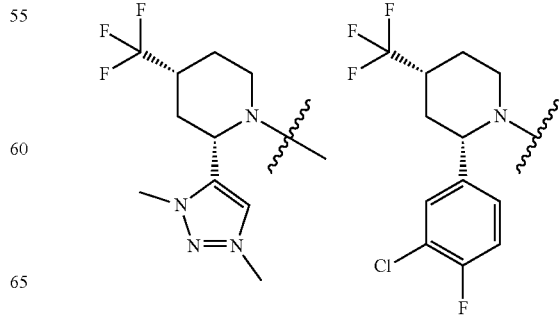

-continued
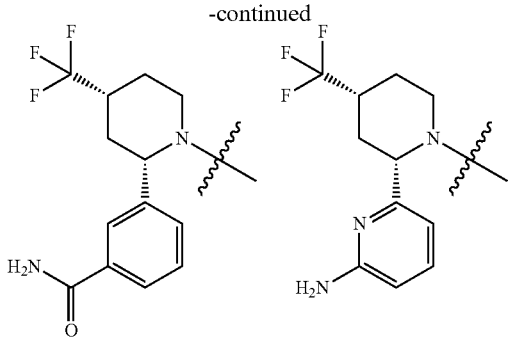
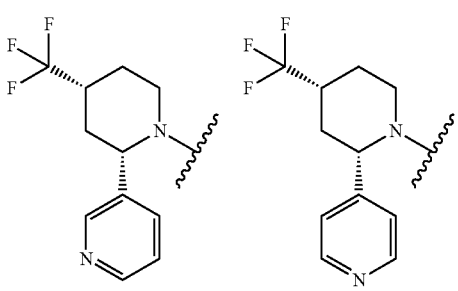
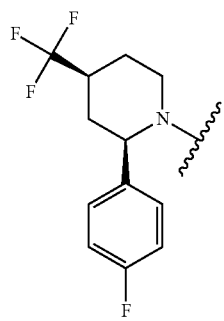
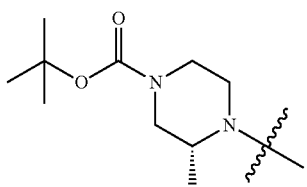
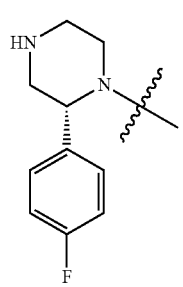
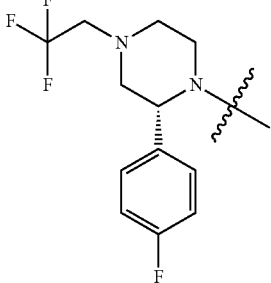
-continued
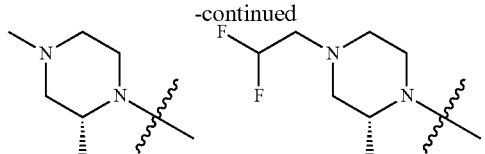
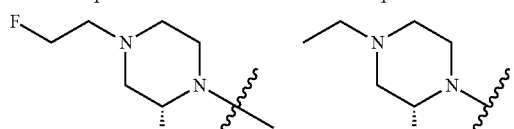
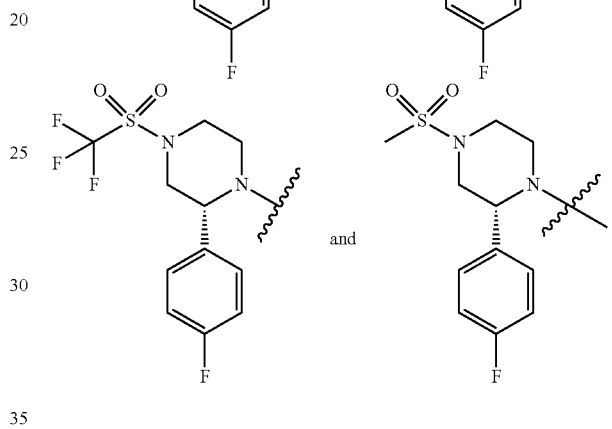
and
or a pharmaceutically acceptable salt thereof.
10. The compound of claim 1, wherein the group
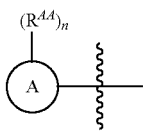
is selected from the group consisting of:
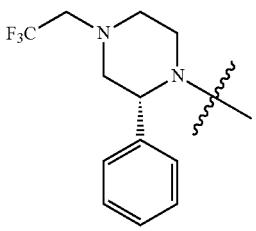
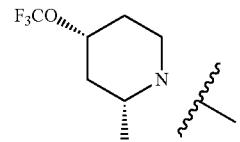
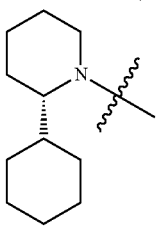
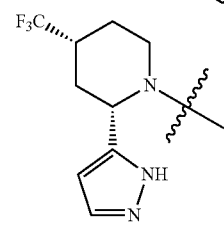

-continued

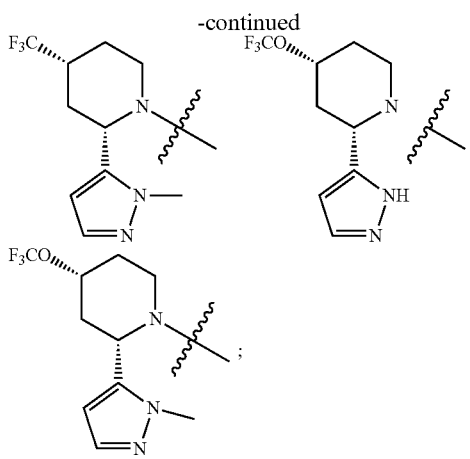

or a pharmaceutically acceptable salt thereof.

11. The compound of claim 2 which is a compound of formula Ik:

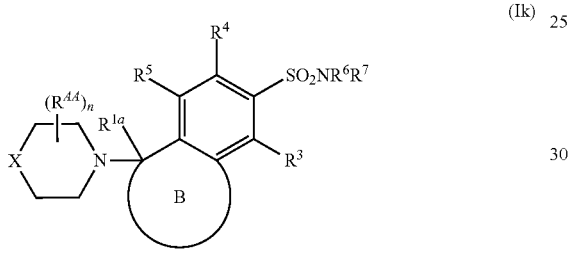

or a pharmaceutically acceptable salt thereof; wherein,
each $R^{AA}$ is independently selected from the group consisting of F, Cl, Br, I, —CN, —OR$^{A1}$, —(X$^{RA}$)-(3-15 membered carbocyclyl), —(X$^{RA}$)-(6-12 membered aryl), —(X$^{RA}$)-(5-12 membered heteroaryl), and —R$^{A2}$, wherein said (3-15 membered carbocyclyl), 6-12 membered aryl, and 5-12 membered heteroaryl of R$^{AA}$ is optionally substituted with from 1 to 5 substituents R$^b$ that are independently selected from the group consisting of F, Cl, Br, I, $C_{1-4}$ alkyl, $C_{1-4}$ haloalkyl, amino, $C_{1-4}$ alkylamino and di($C_{1-4}$alkyl)amino, and $C_{1-4}$(halo)alkoxy; R$^{A1}$ is selected from the group consisting of hydrogen, $C_{1-8}$ alkyl, $C_{2-8}$ alkenyl, $C_{1-8}$ haloalkyl, $C_{3-8}$ cycloalkyl, phenyl and benzyl;
R$^{A2}$ is selected from the group consisting of $C_{1-8}$ alkyl that is optionally substituted with one or more substituents selected from oxo, fluoro, hydroxy, amino, $C_{1-4}$ alkylamino and di($C_{1-4}$alkyl)amino; X$^{RA}$ is selected from the group consisting of absent, —C(=O)—, and $C_{1-4}$ alkylene; wherein any $C_{1-4}$ alkylene, of X$^{RA}$ is optionally substituted with 1 to 3 substituents selected from the group consisting of $C_{1-4}$ alkyl, $C_{1-4}$ haloalkyl, and phenyl that is optionally substituted with 1 to 5 substituents selected from, F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino;
ring "A" is a 5-12 membered heteroaryl, or a 3-15 membered heterocyclyl;
Ring B is a 5, 6, or 7 membered carbocyclyl or a 5, 6, or 7 membered heterocyclyl, which 5, 6, or 7 membered carbocyclyl and 5, 6, or 7 membered heterocyclyl is optionally substituted with one or more groups independently selected from $C_{1-4}$ alkyl, halo, and halo$C_{1-4}$ alkyl;
R$^{1b}$ is H or $C_{1-4}$ alkyl;
R$^3$, R$^4$, and R$^5$ are each independently selected from the group consisting of H, F, Cl, Br, I, —CN, $C_{1-8}$ alkyl, $C_{3-8}$ cycloalkyl, $C_{1-8}$ haloalkyl and $C_{1-8}$ alkoxy;
R$^6$ is selected from the group consisting of H, $C_{1-8}$ alkyl, $C_{3-8}$ cycloalkyl, aryl, and aryl($C_{1-4}$ alkyl); and R$^7$ is selected from the group consisting of $C_{1-8}$ alkyl, 3-15 membered heterocyclyl, 5-12 membered heteroaryl, —C(O)N(R$^c$)$_2$ and —C(=NCN)N(R$^c$)$_2$; or R$^6$ and R$^7$, together with the nitrogen to which they are attached, form a 3-15 membered heterocyclyl or 5-12 membered heteroaryl; wherein any $C_{1-8}$ alkyl, $C_{3-8}$ cycloalkyl, aryl, aralkyl, 3-15 membered heterocyclyl, and 5-12 membered heteroaryl is optionally substituted with one of more groups R$^d$ that are independently selected from the group consisting of F, Cl, Br, I, —NH$_2$, —OH, —CN, —NO$_2$, $C_{1-4}$ alkyl, $C_{1-4}$ haloalkyl, $C_{1-4}$ alkoxy, $C_{1-4}$(halo)alkoxy, $C_{1-4}$ alkylamino and $C_{1-4}$ dialkylamino;
each R$^c$ is independently selected from the group consisting of hydrogen, $C_{1-8}$ alkyl, $C_{3-8}$ cycloalkyl, phenyl and benzyl;
n is 0, 1, 2, 3, 4, 5, or 6; and
X is CH$_2$, NR$^{A2}$, S, or O.

12. The compound of claim 2 which is a compound of formula Im:

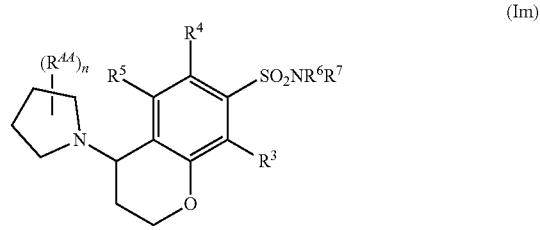

or a pharmaceutically acceptable salt thereof.

13. The compound of claim 2 which is a compound of formula Io:

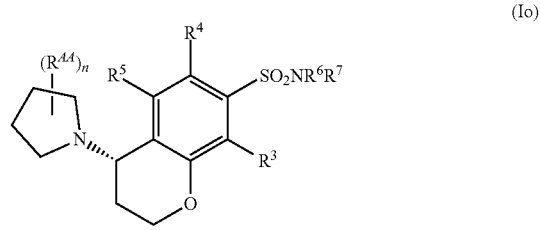

or a pharmaceutically acceptable salt thereof.

14. The compound of claim 2, which is a compound of formula Is:

581
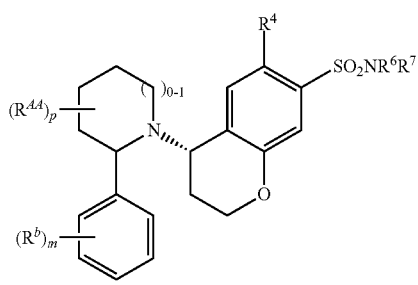
(Is)
wherein m is 0, 1, 2, 3, 4 or 5; and p is 0, 1, 2, 3, 4, or 5;
or a pharmaceutically acceptable salt thereof.
15. A compound selected from the group consisting of:
582
-continued
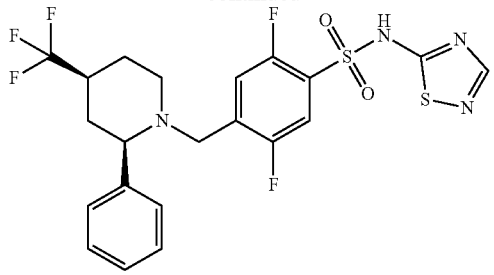
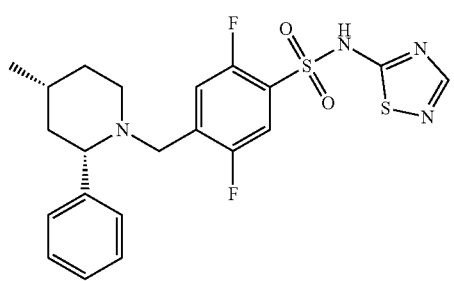
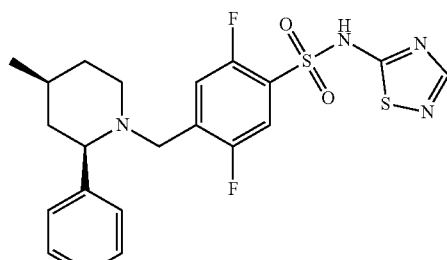
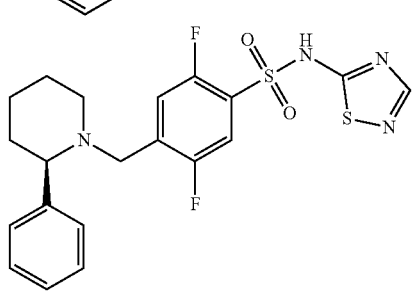
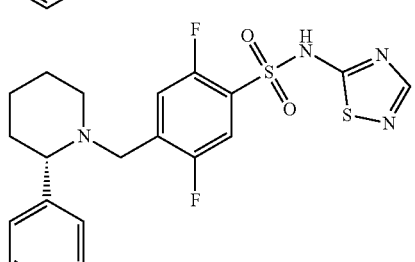
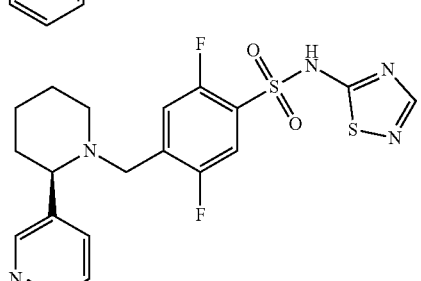

-continued
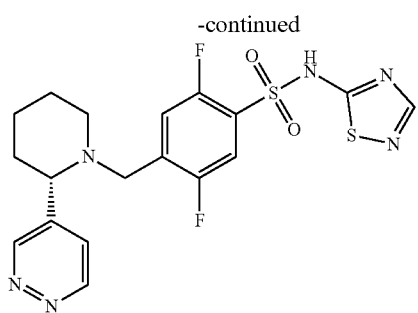
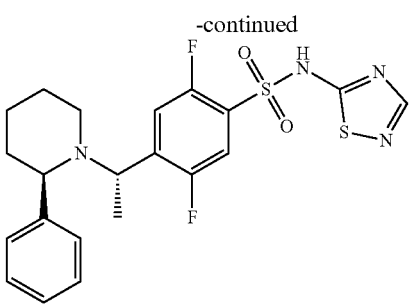
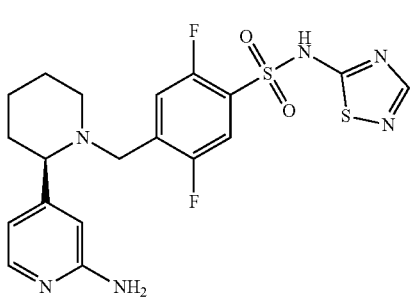
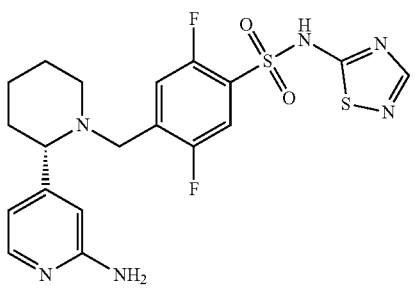
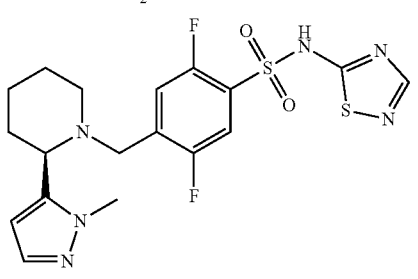
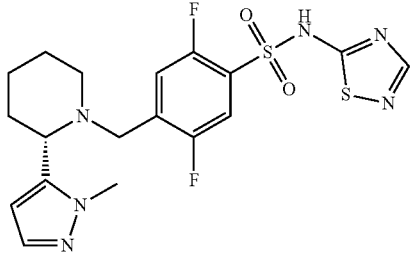
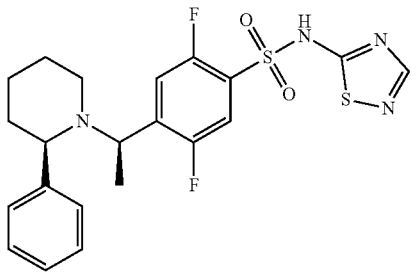

585
-continued
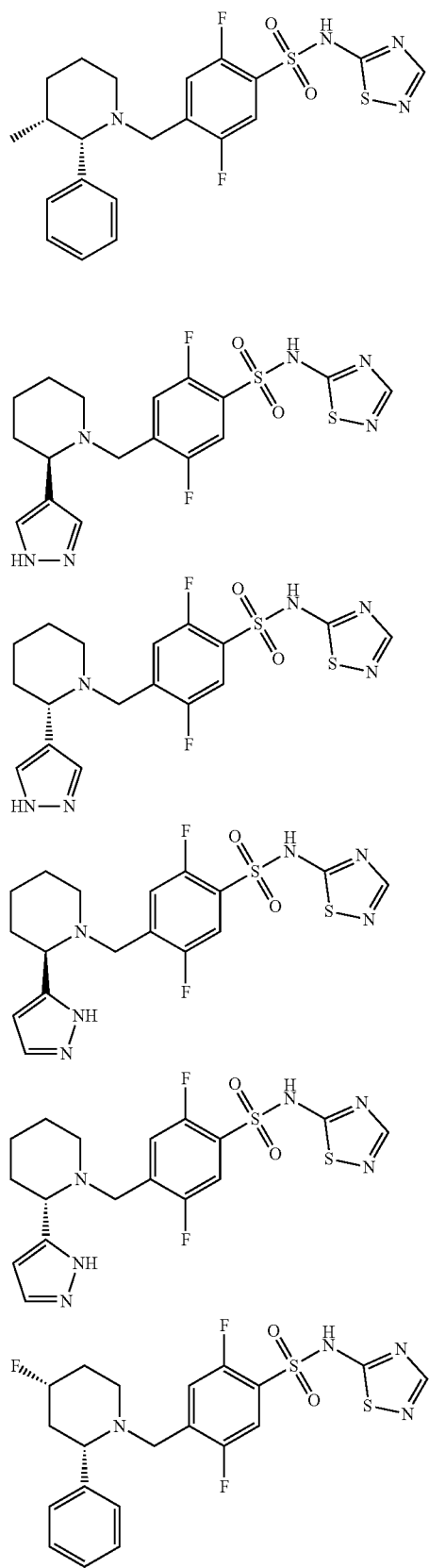
586
-continued
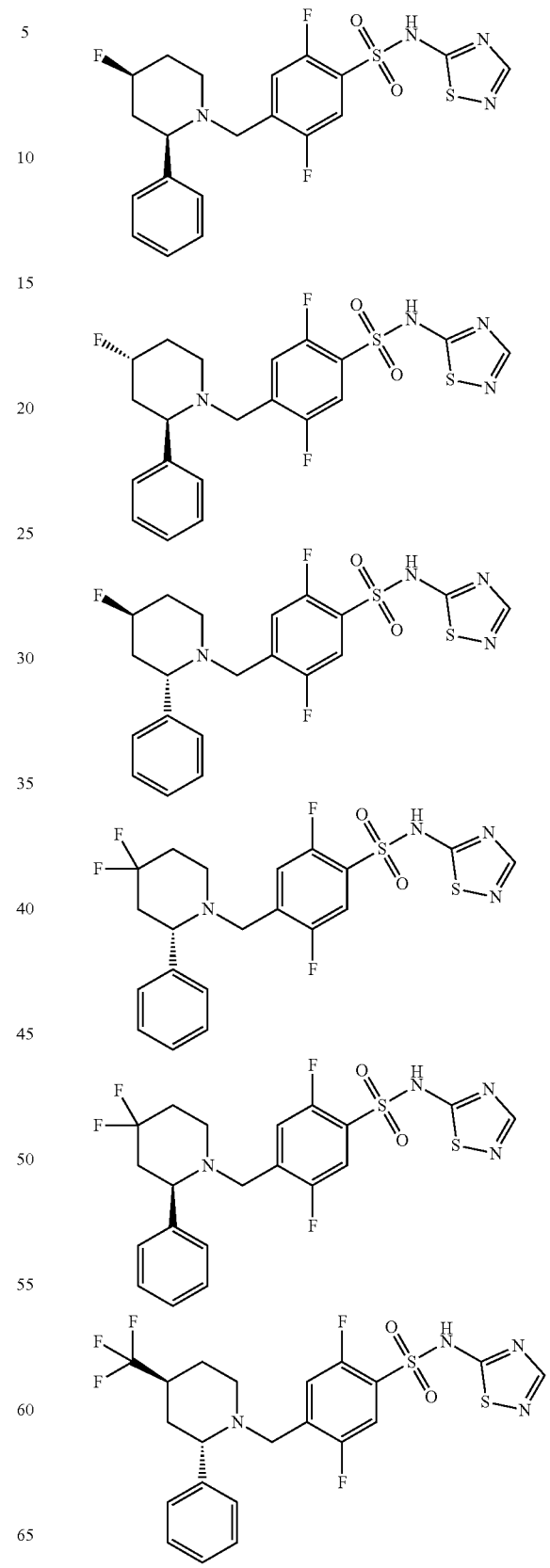

587
-continued
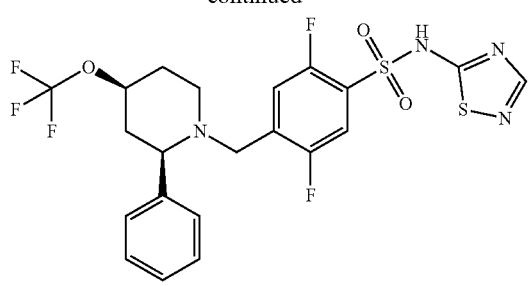
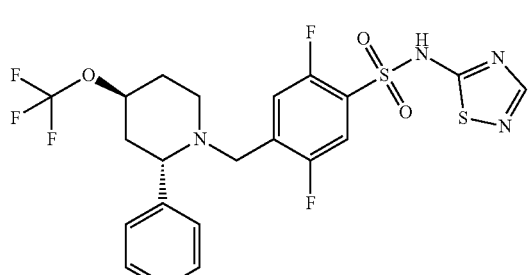
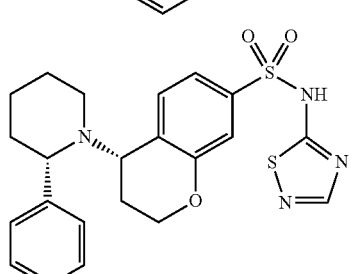
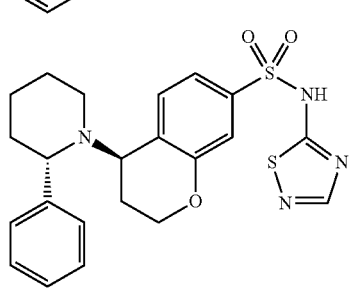
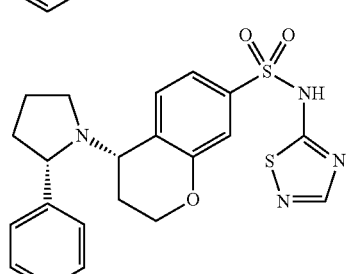
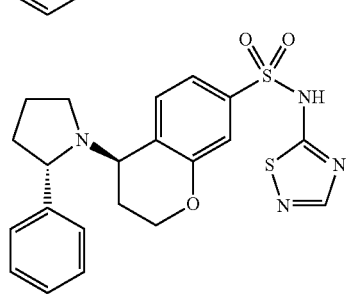
588
-continued
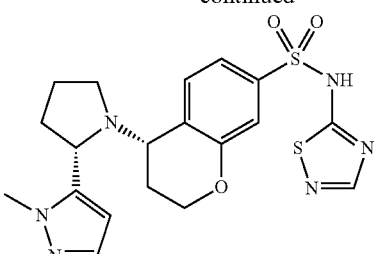
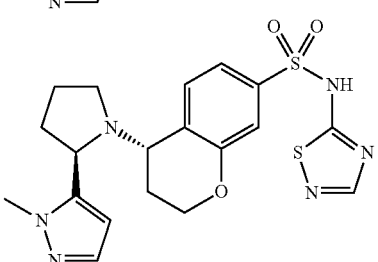
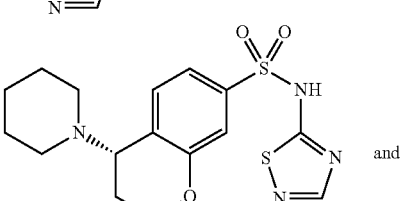
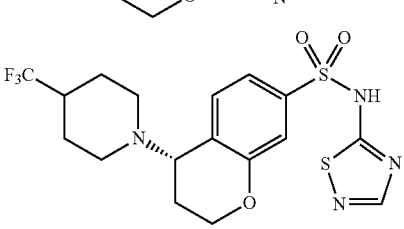
or a pharmaceutically acceptable salt thereof.
16. The compound of claim 1 selected from the group consisting of:
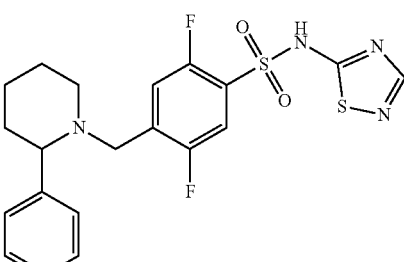
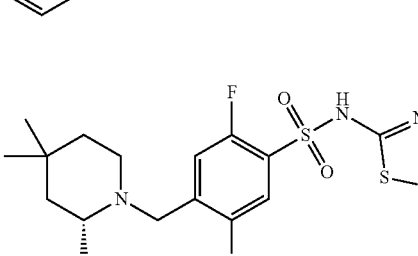

589
-continued
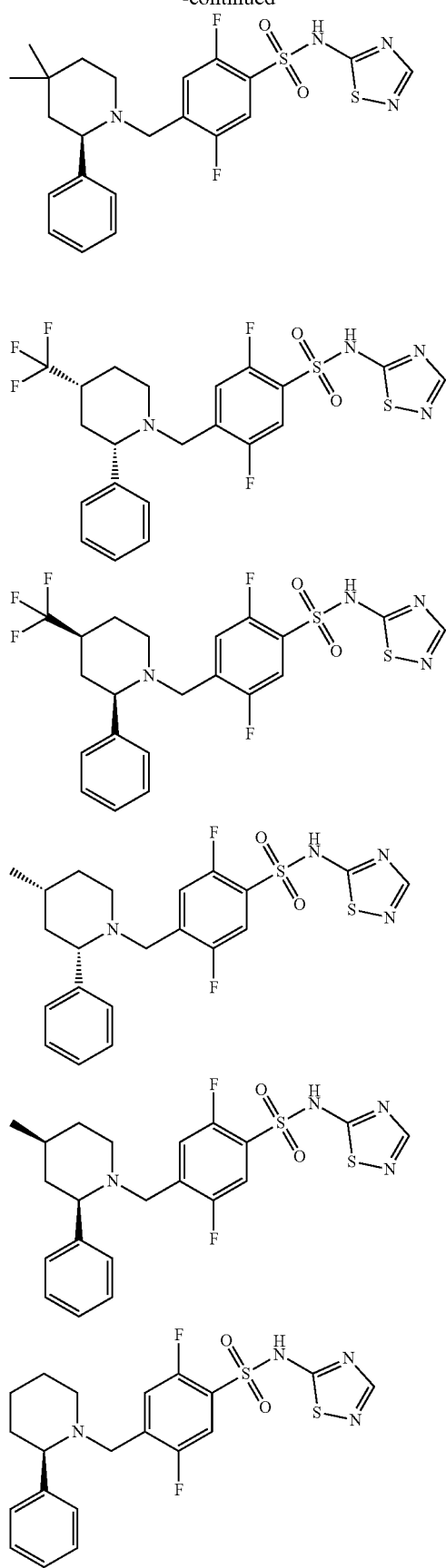
590
-continued
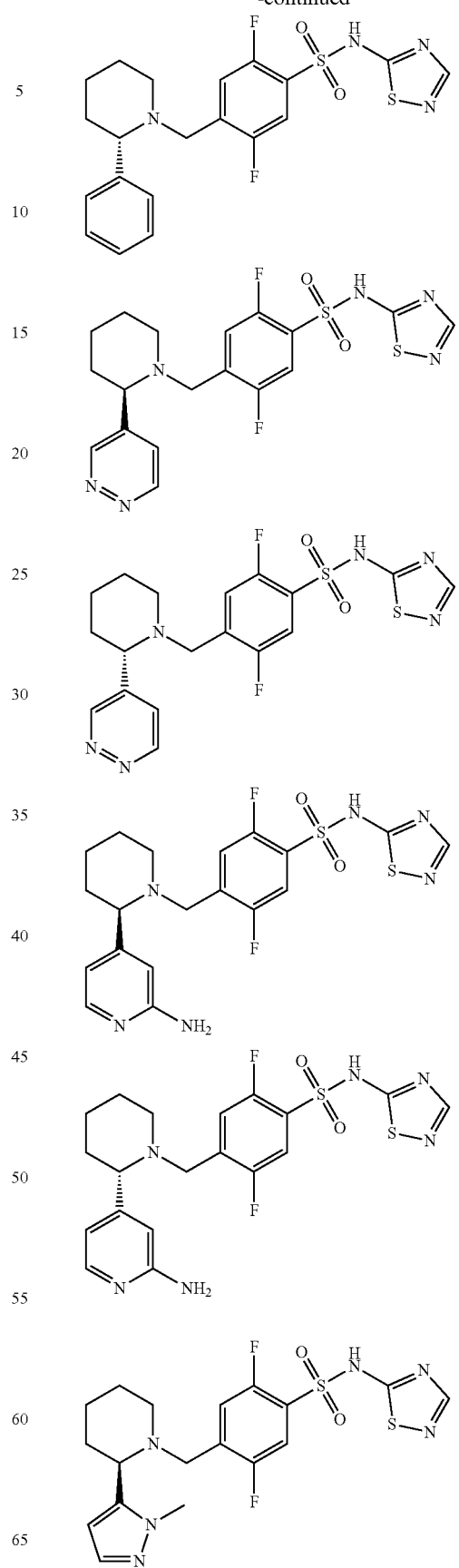

591
-continued
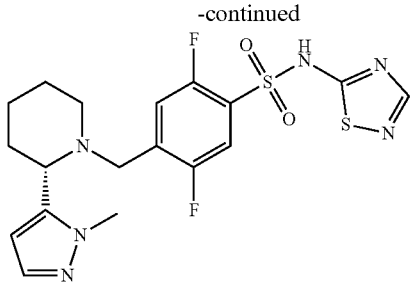
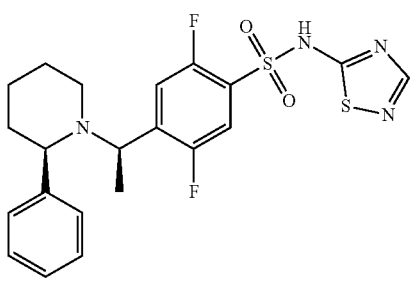
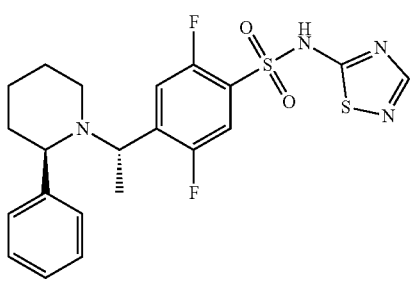
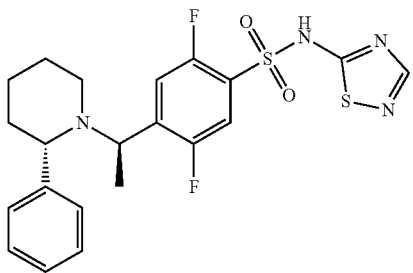
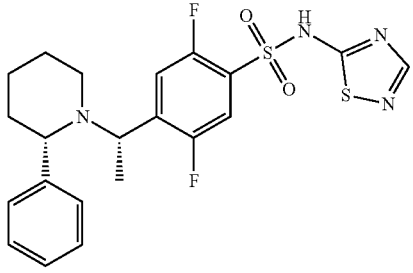
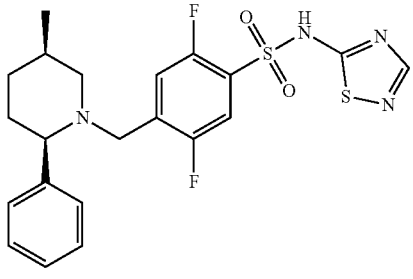
592
-continued
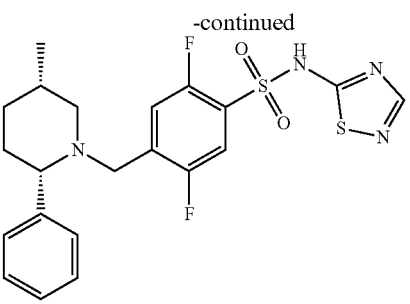
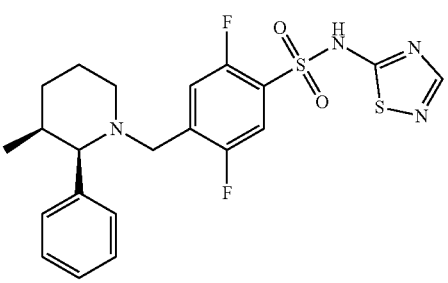
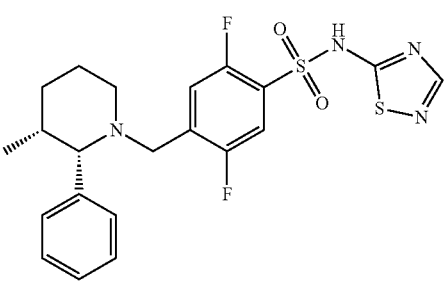
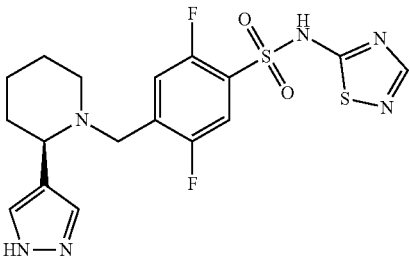
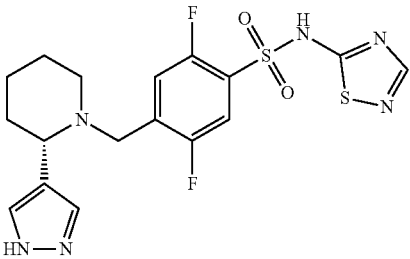
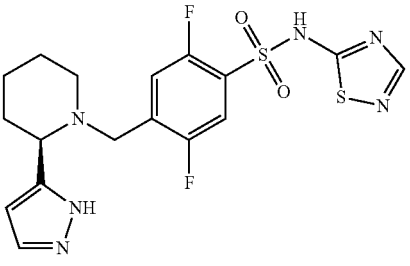

-continued
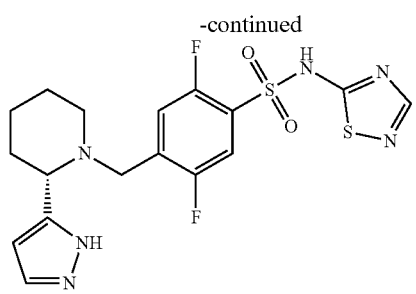
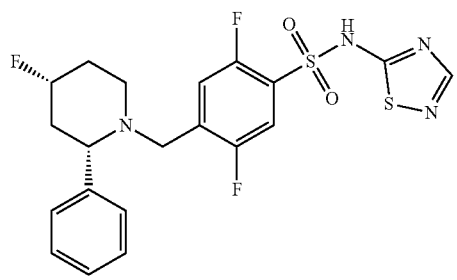
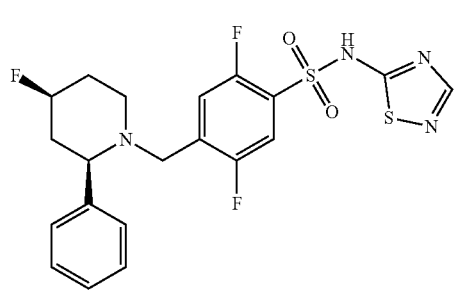
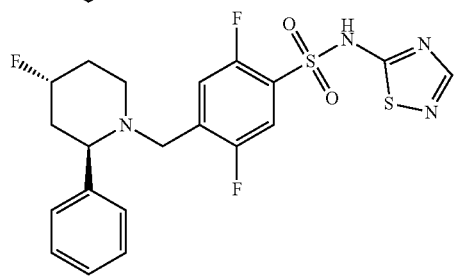
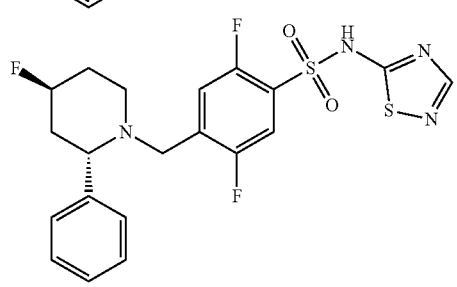
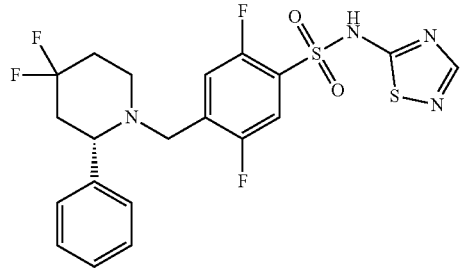
-continued
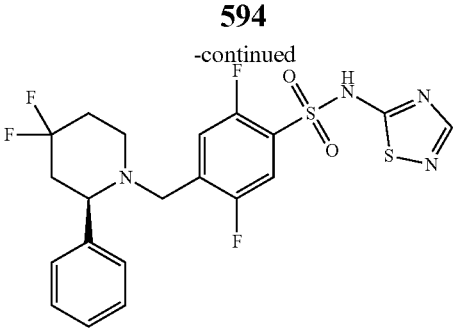
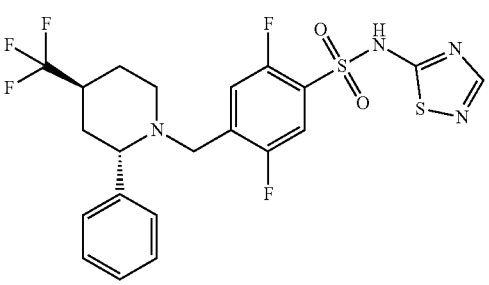
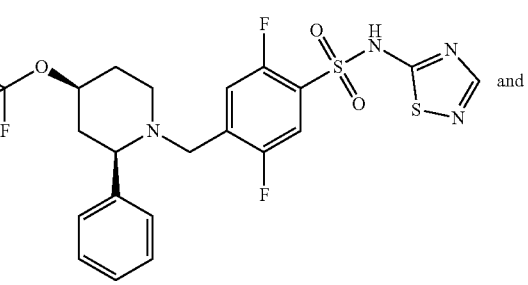
and
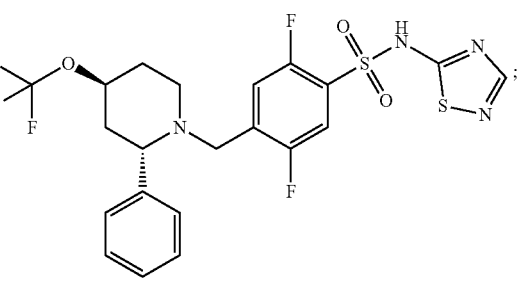
;
or a pharmaceutically acceptable salt thereof.
17. The compound of claim 2 selected from the group consisting of:
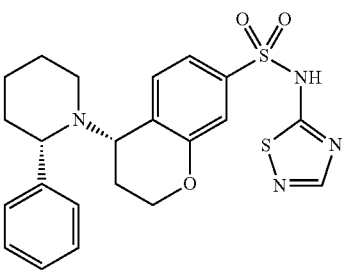

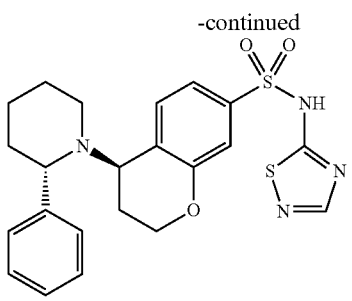
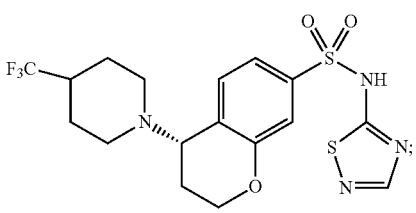
or a pharmaceutically acceptable salt thereof.
18. The compound of claim 2 selected from the group consisting of:
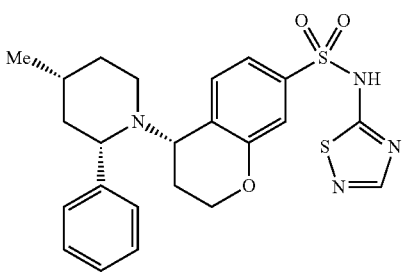
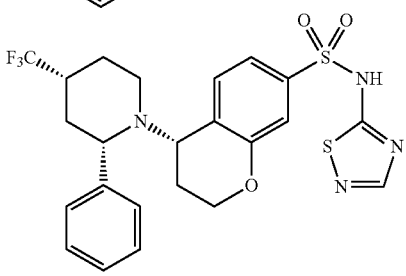
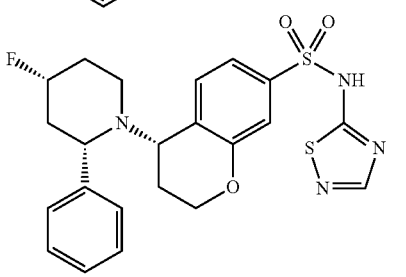
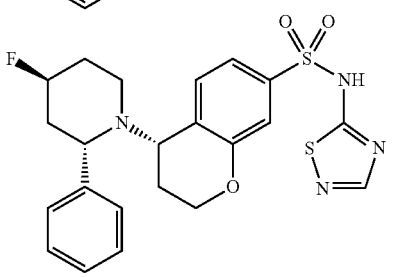
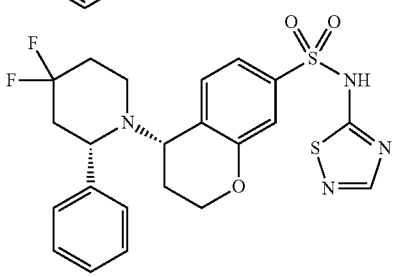

597
-continued
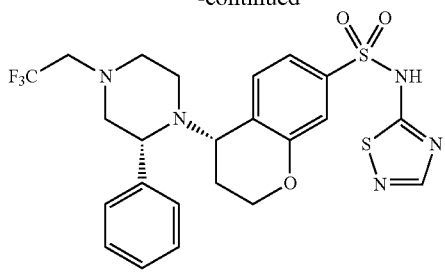
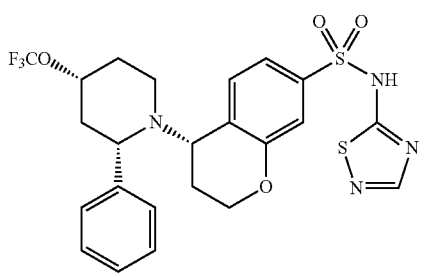
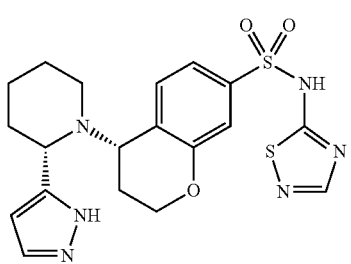
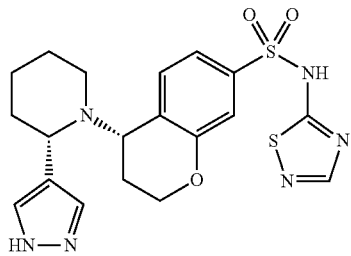
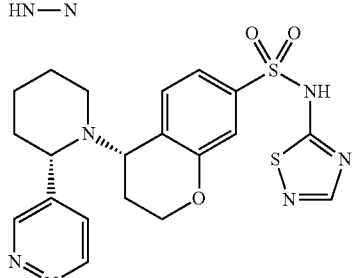
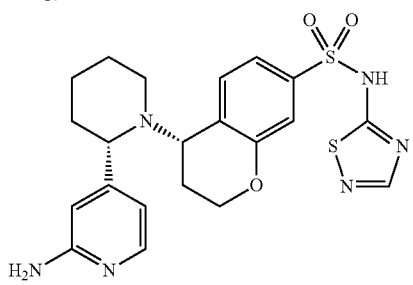
598
-continued
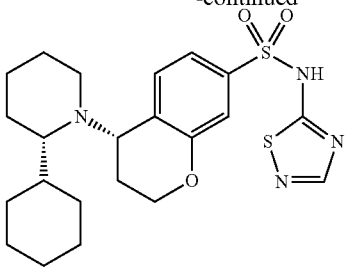
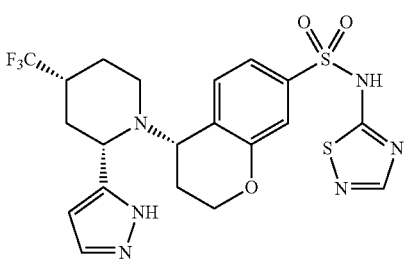
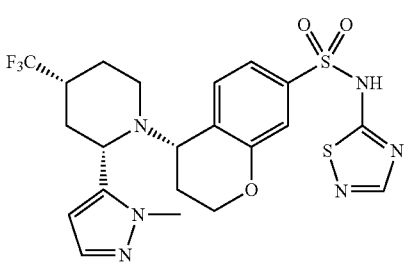
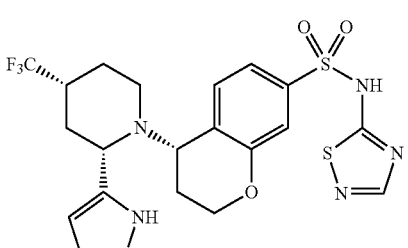
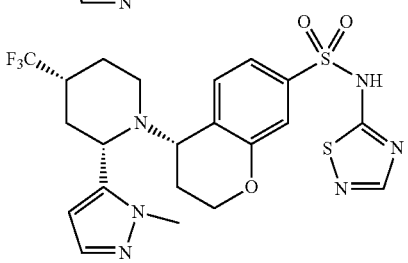
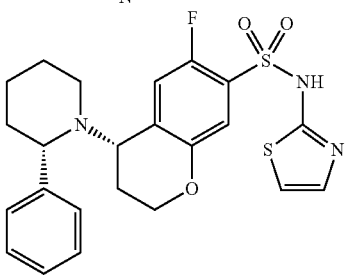

599
-continued
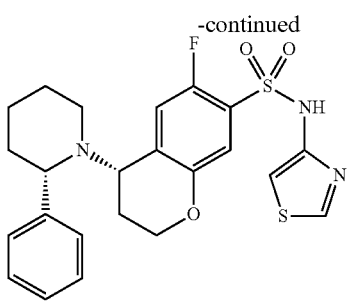
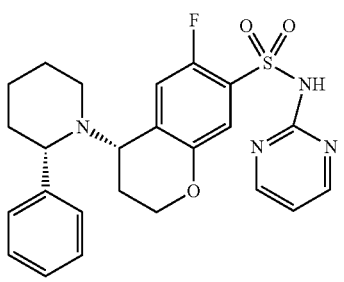
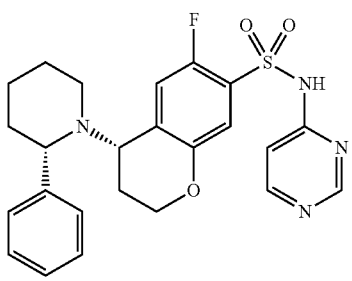
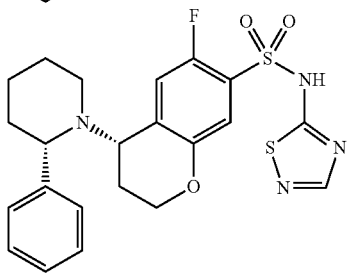
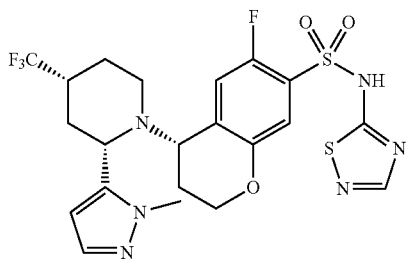
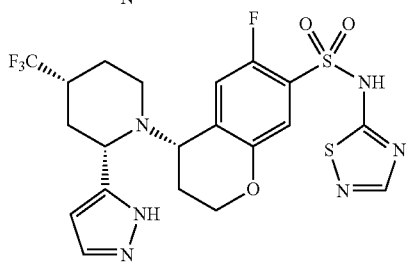
600
-continued
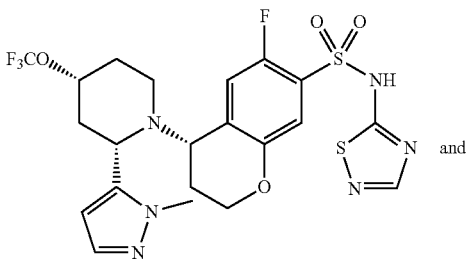 and
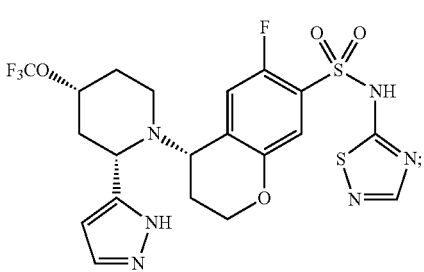
or a pharmaceutically acceptable salt thereof.
19. A compound selected from the group consisting of:
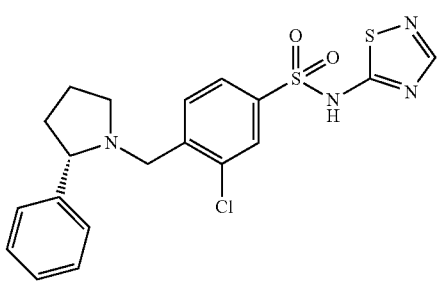
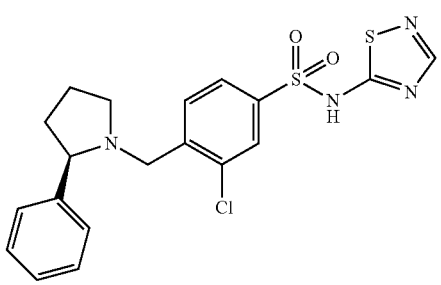
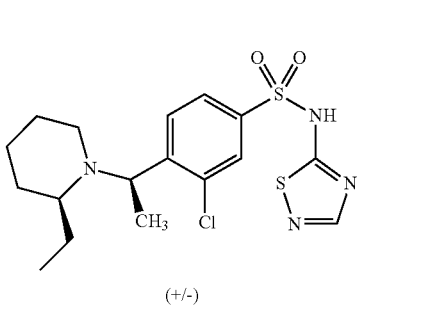
(+/−)

601
-continued
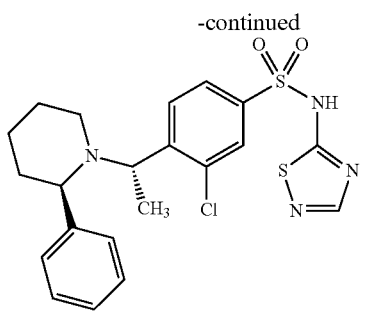
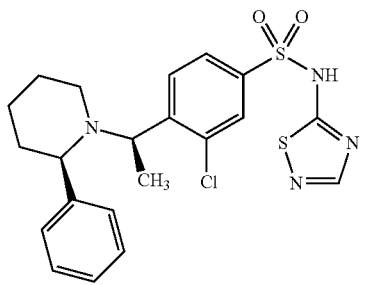
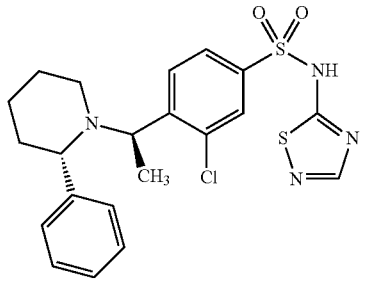
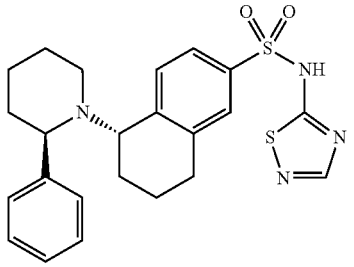
(+/-)
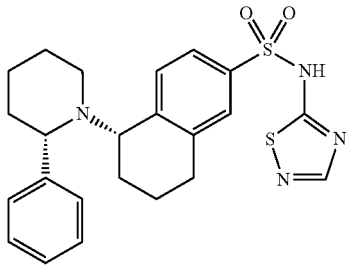
(+/-)
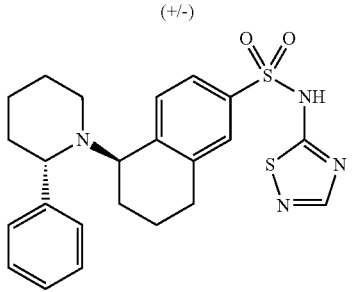
602
-continued
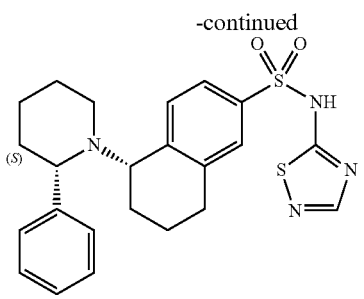
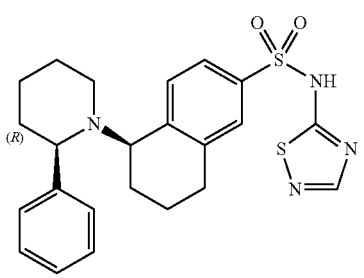
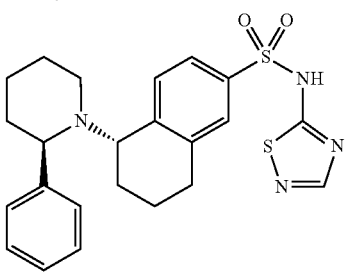
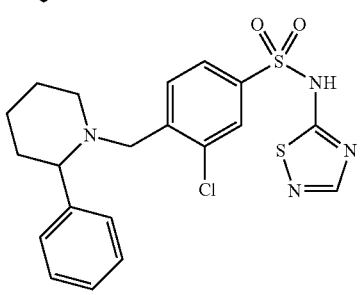
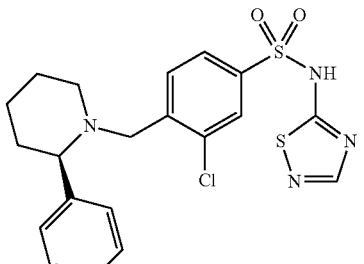
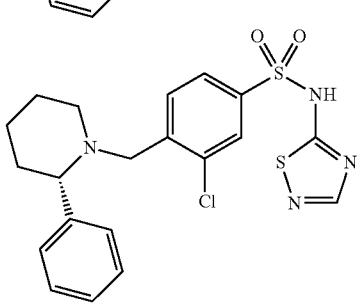

603
-continued
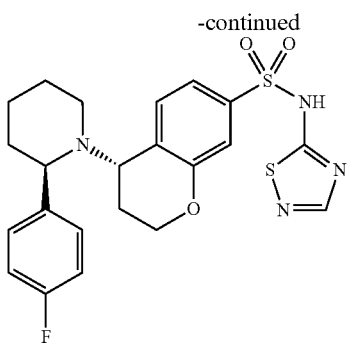
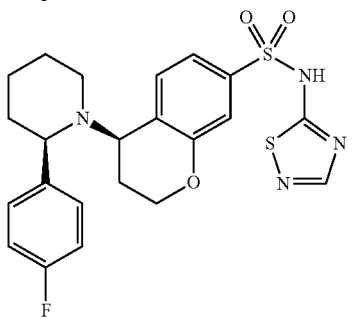
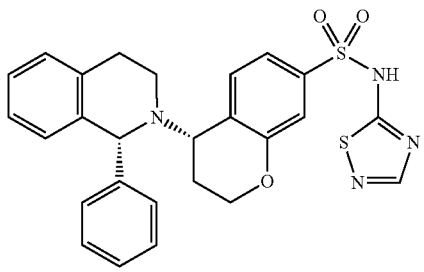
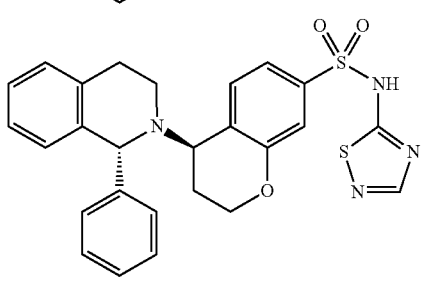
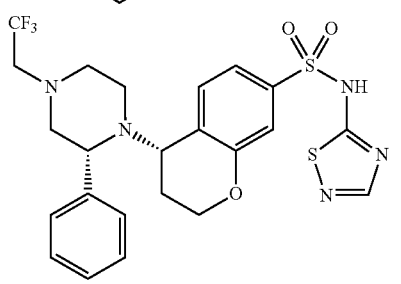
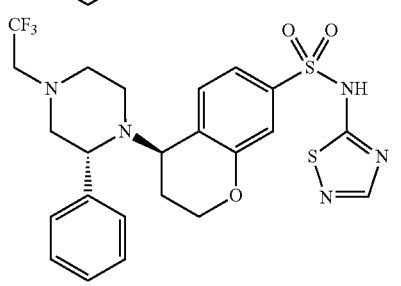
604
-continued
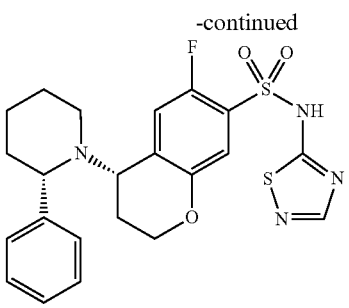
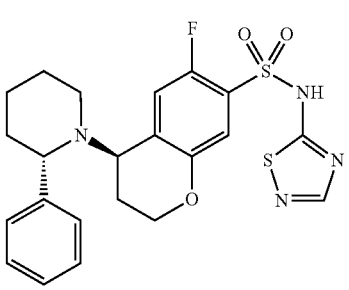
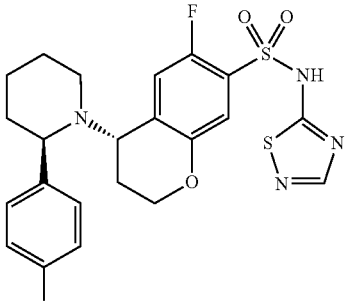
(+/-)
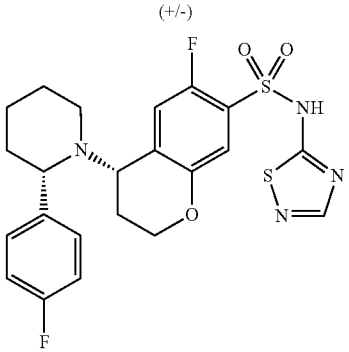
(+/-)
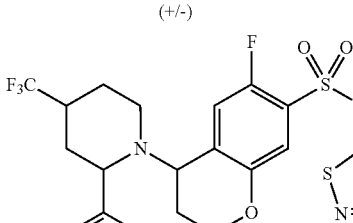
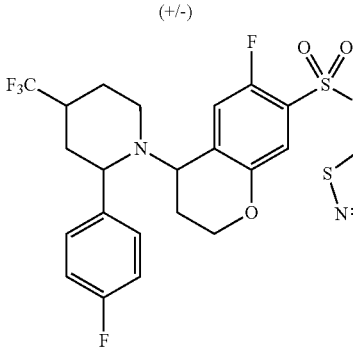

605
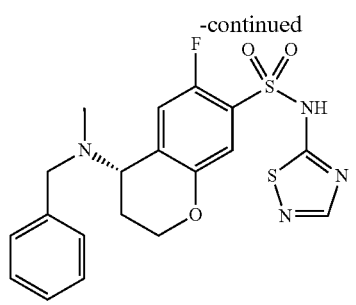
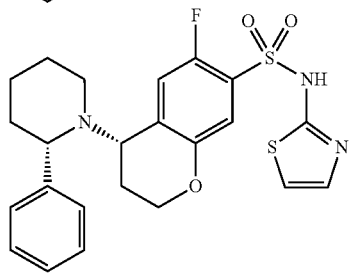
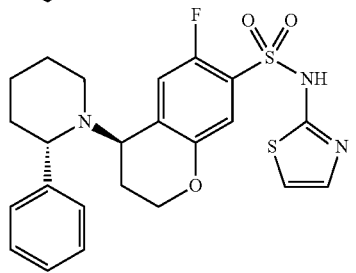
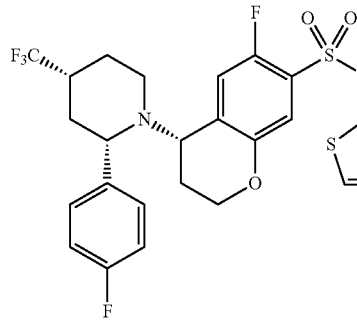
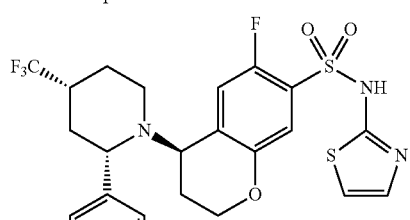
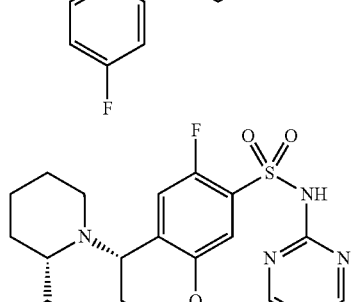
606
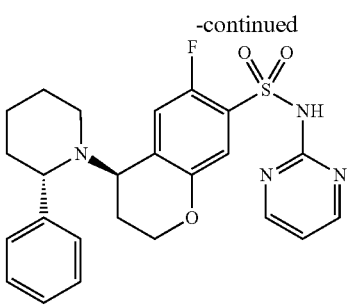
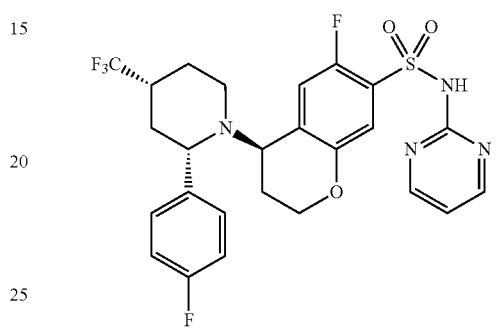
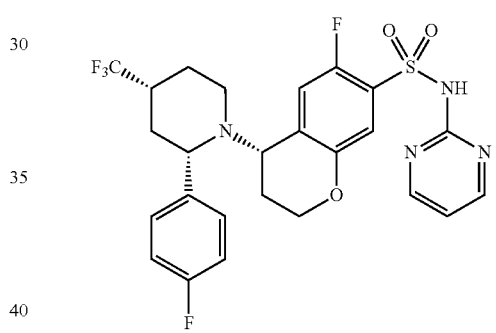
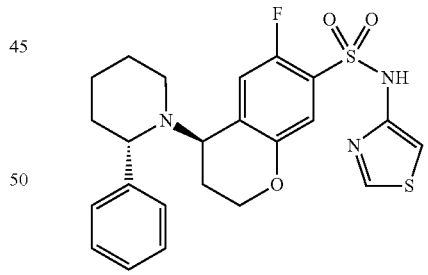
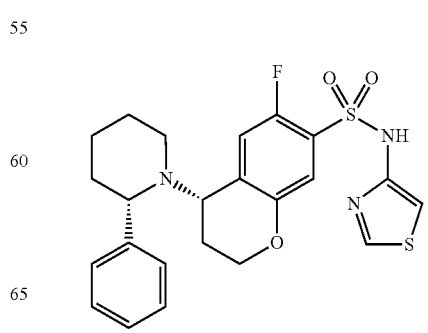

607
-continued
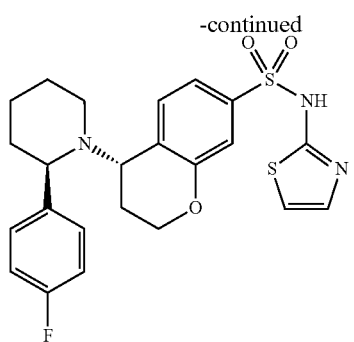
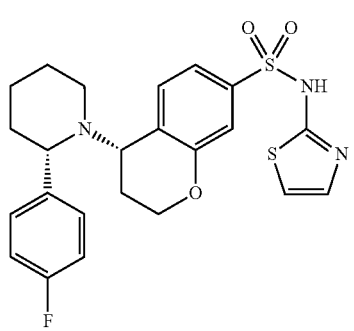
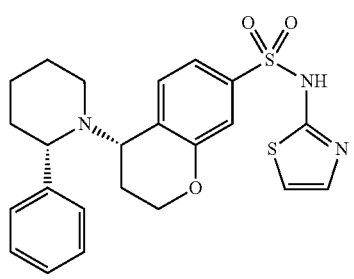
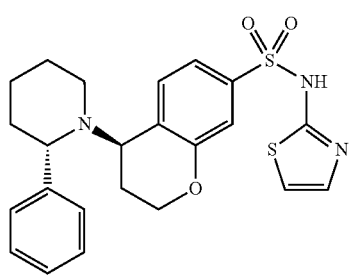
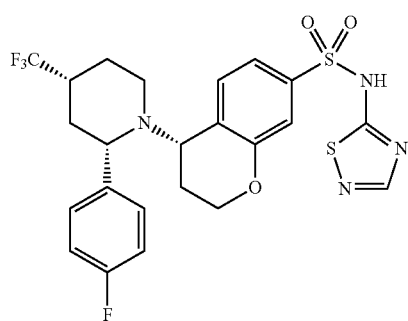
608
-continued
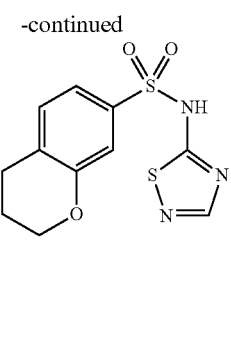
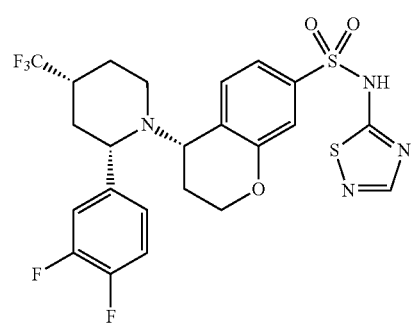
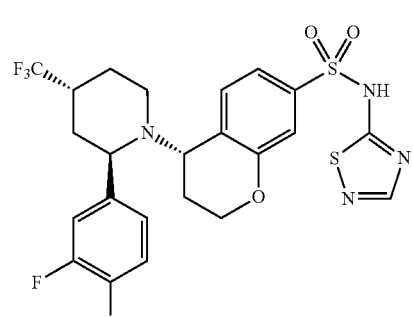
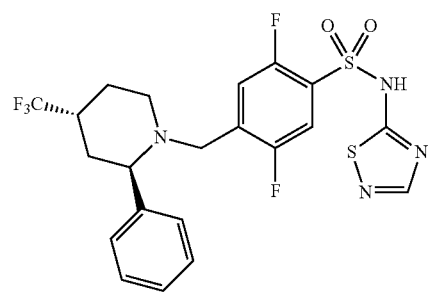
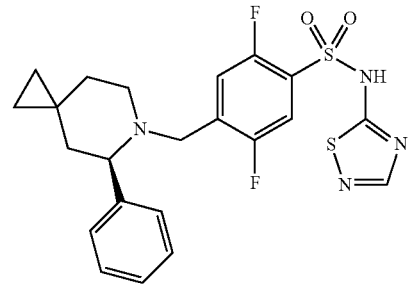

609
-continued
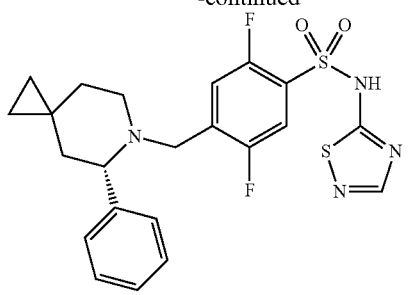
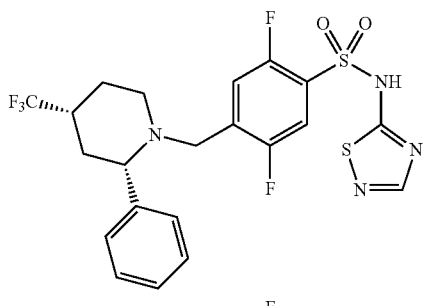
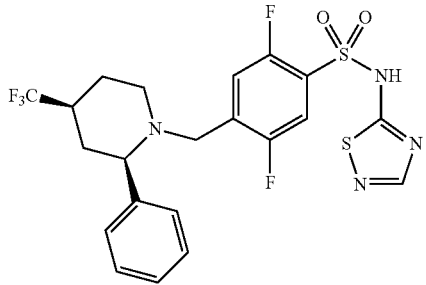
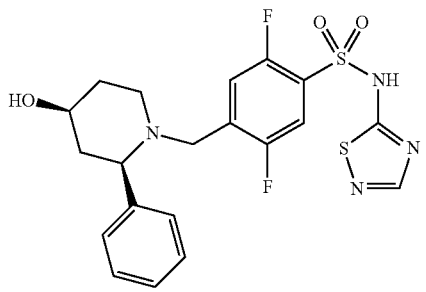
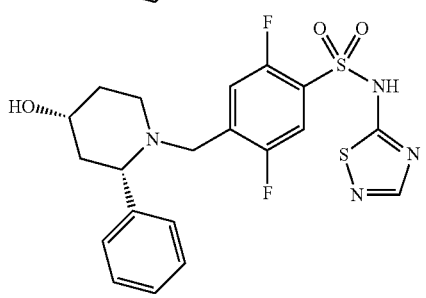
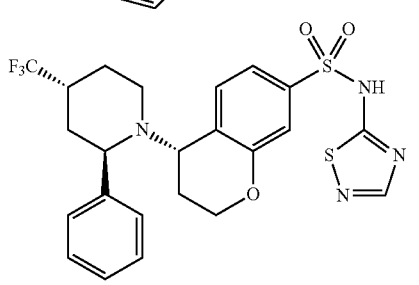
610
-continued
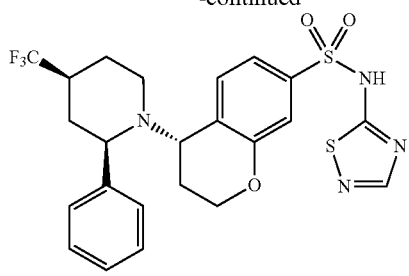
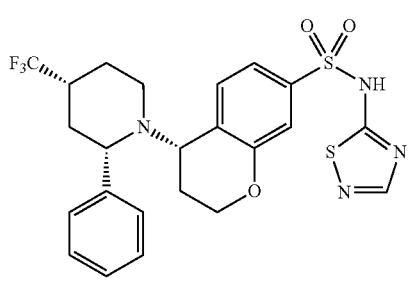
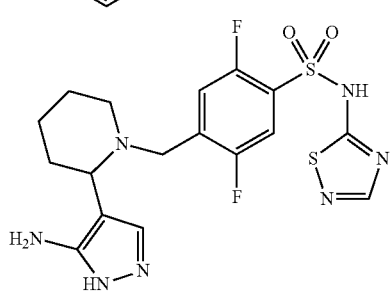
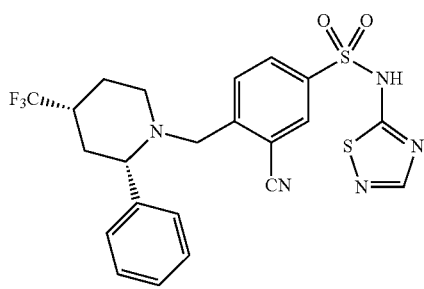
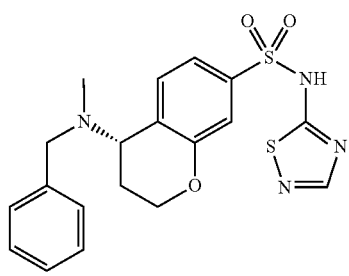
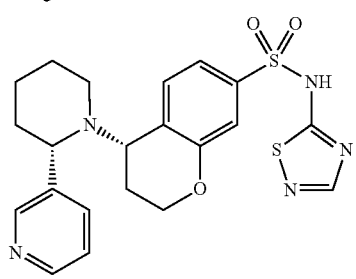

| 611 | 612 |
|---|---|
| 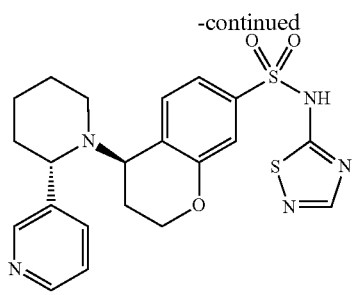 | 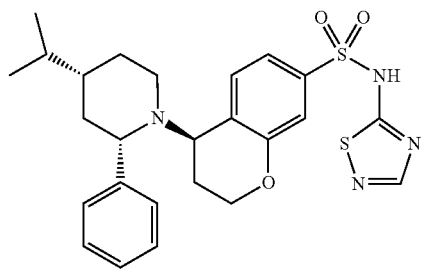 |
| 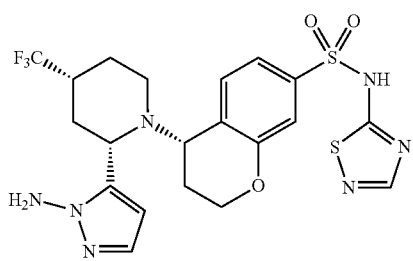 | 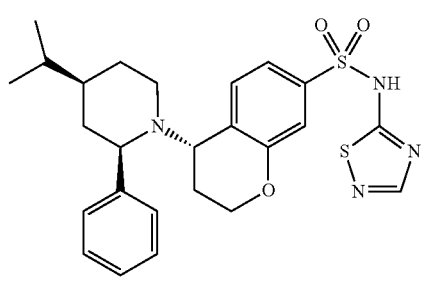 |
| 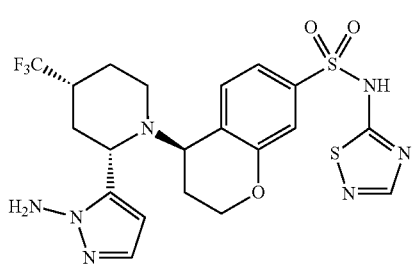 | 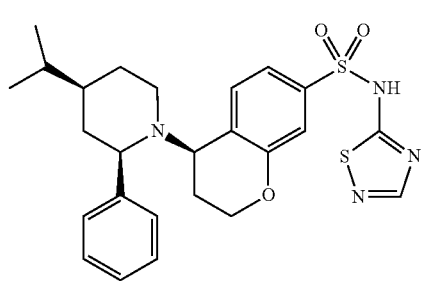 |
| 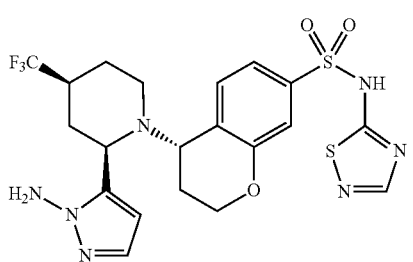 | 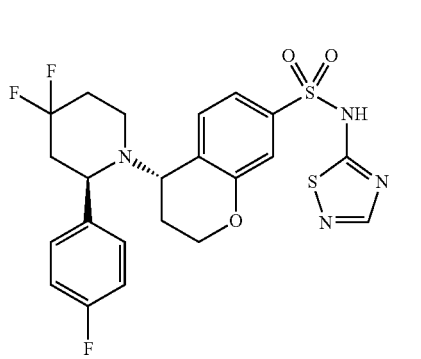 |
| 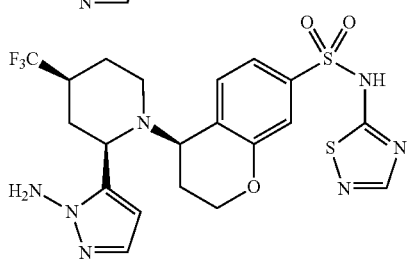 | |
| 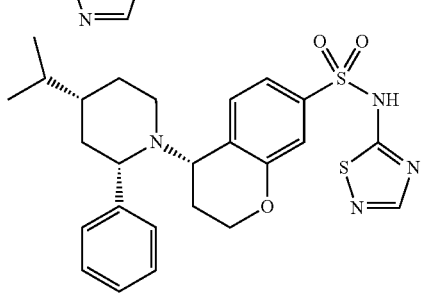 | 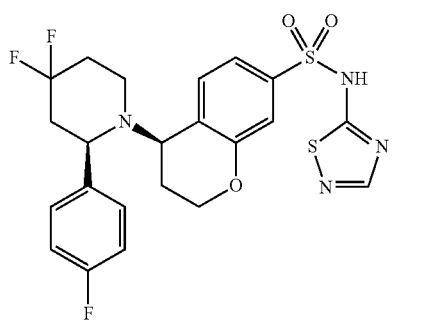 |

613
-continued
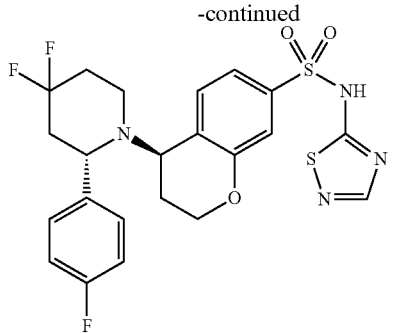
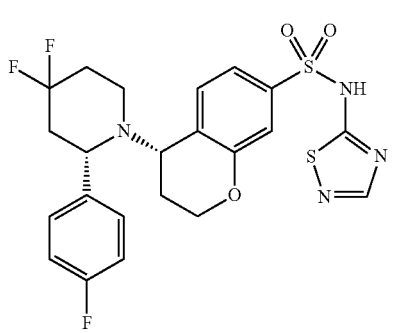
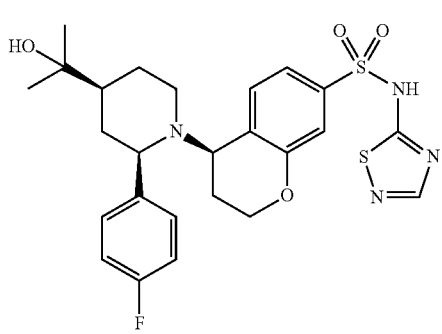
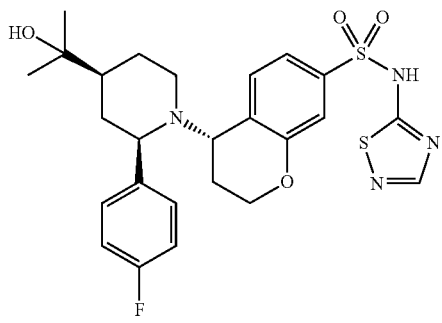
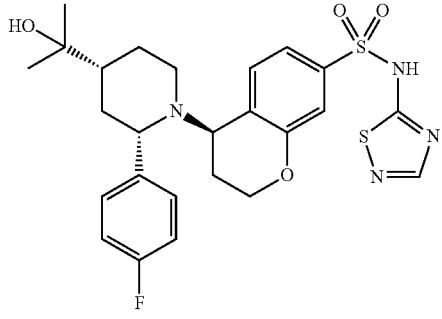
614
-continued
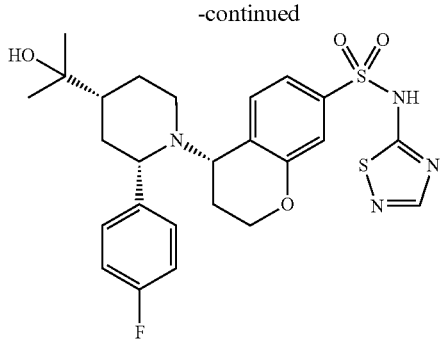
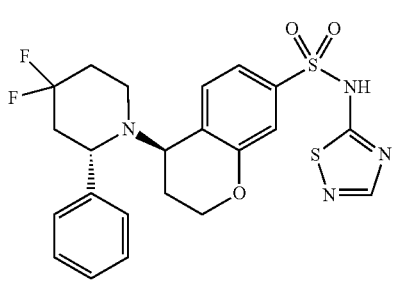
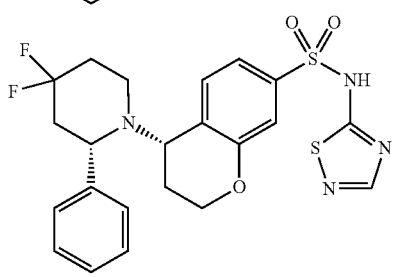
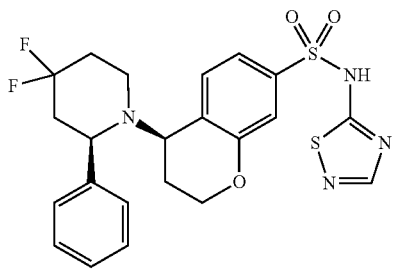
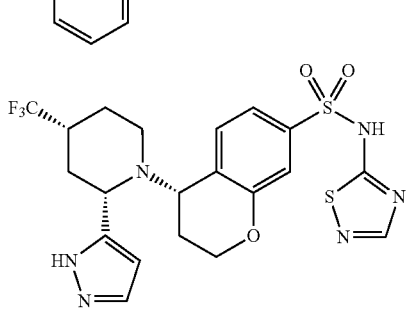

-continued
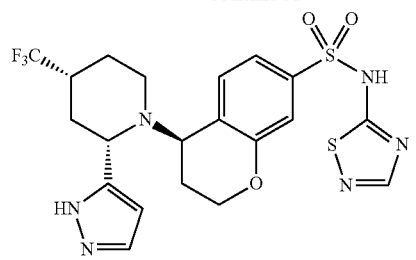
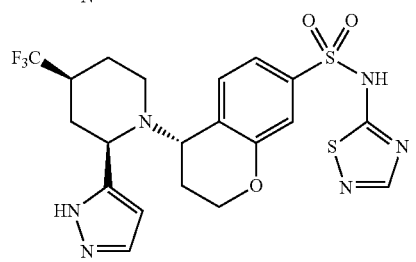
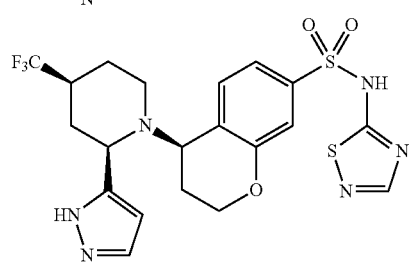
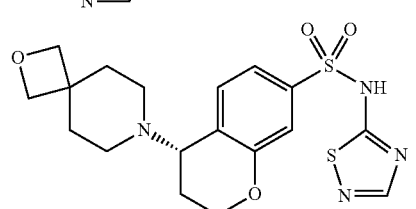
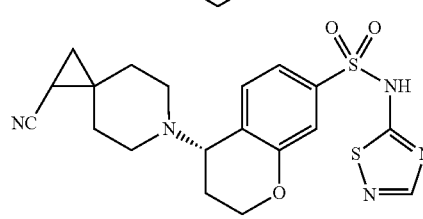
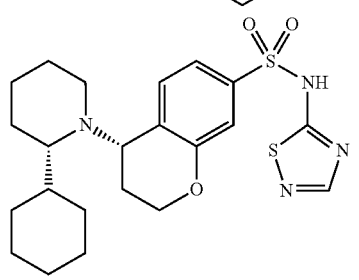
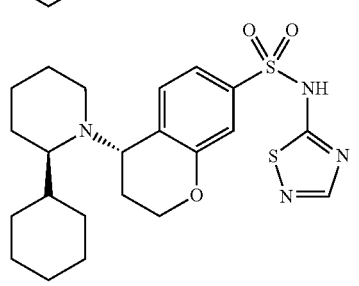
-continued
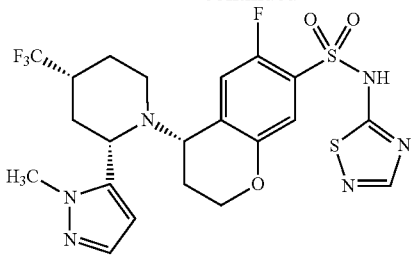
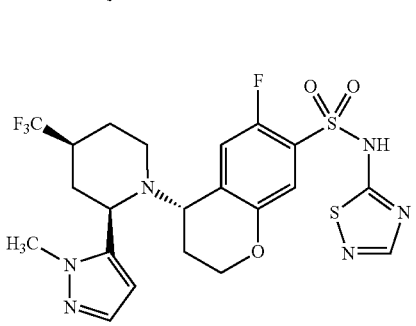
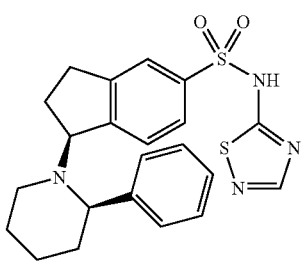
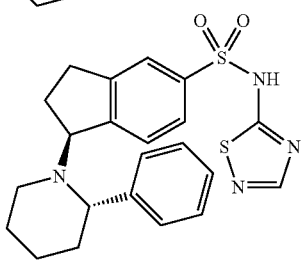
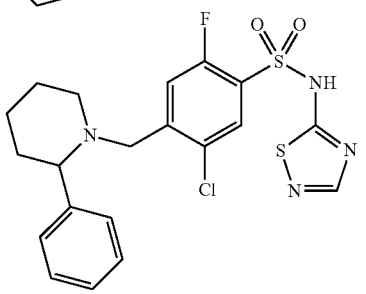
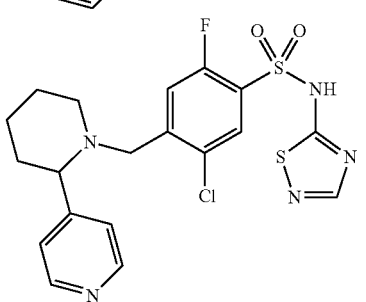

617
-continued
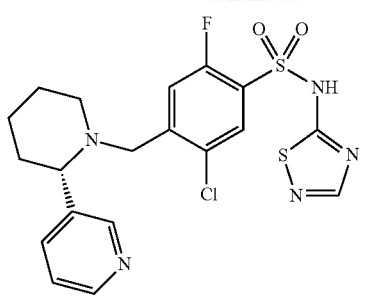
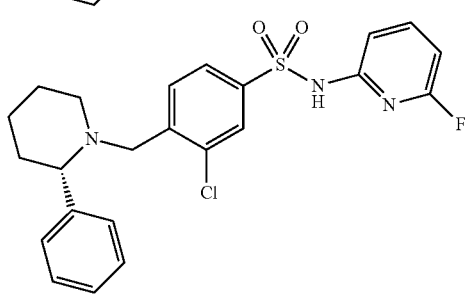
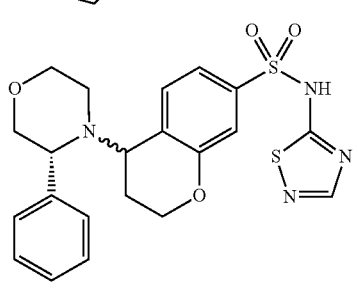
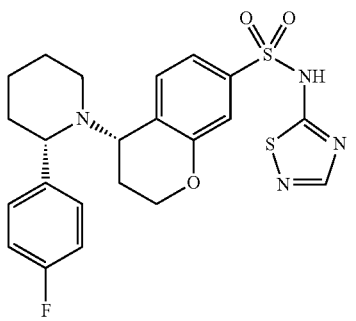
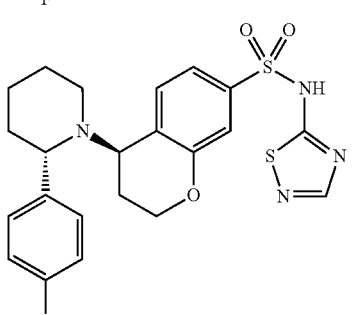
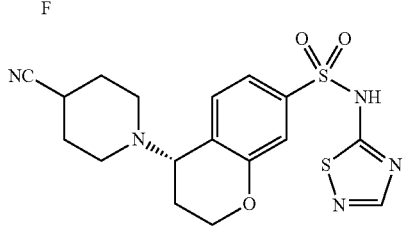
618
-continued
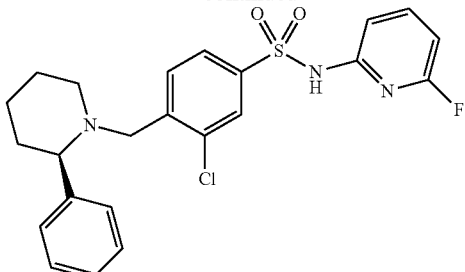
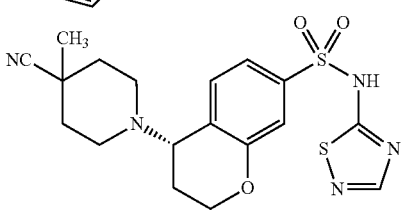
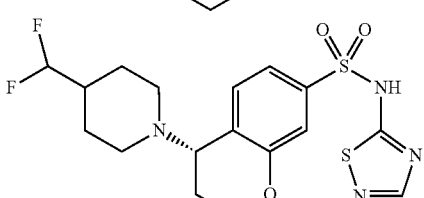
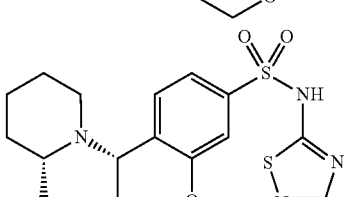
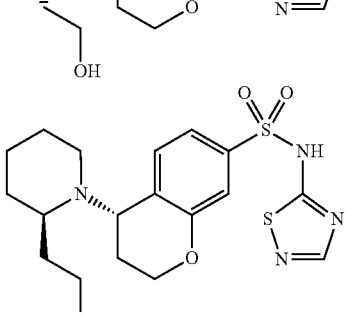
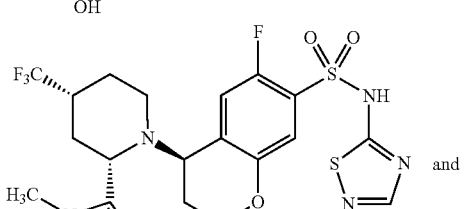
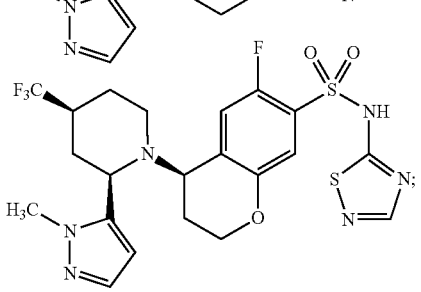
or a pharmaceutically acceptable salt thereof.

20. A compound selected from the group consisting of:
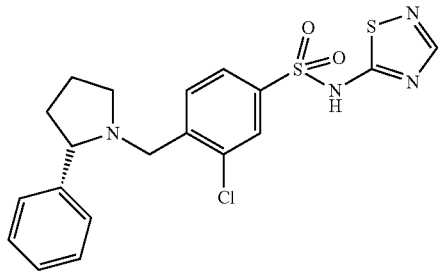
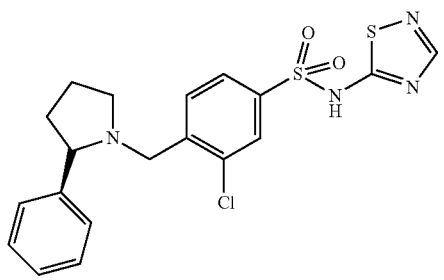
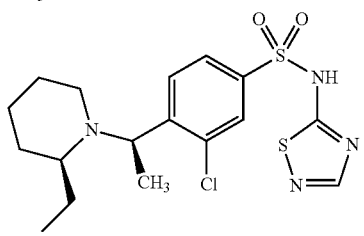
(+/-)
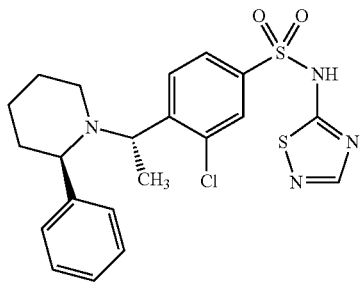
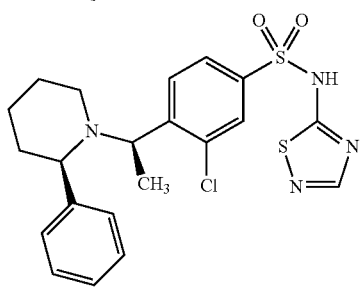
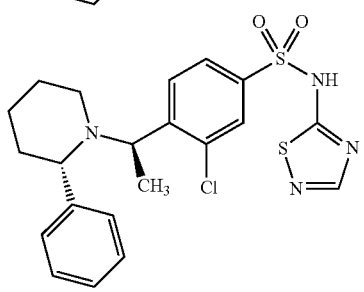
-continued
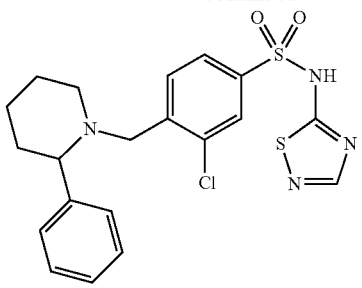
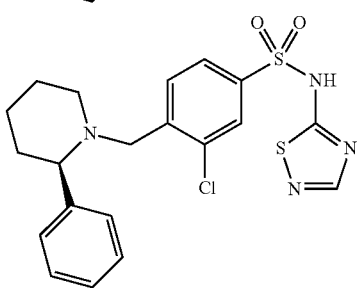
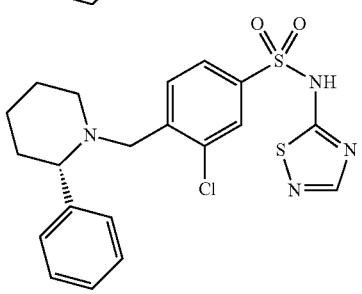
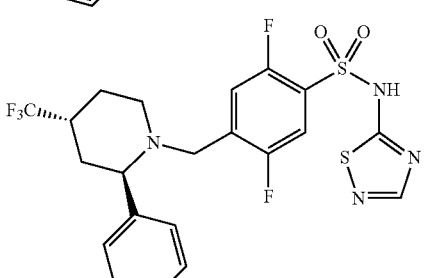
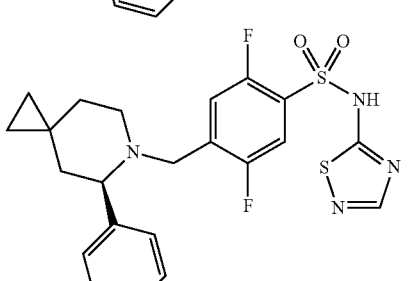
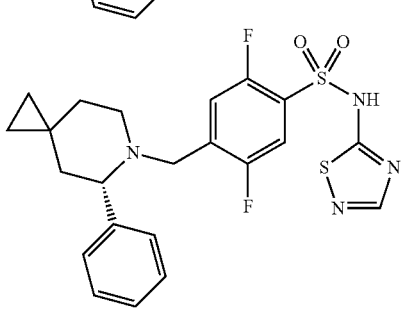

621
-continued
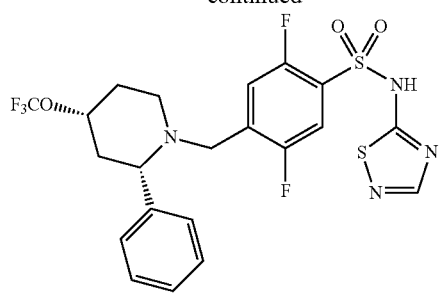
622
-continued
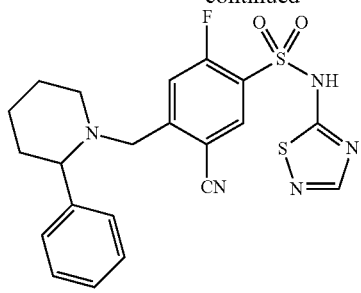
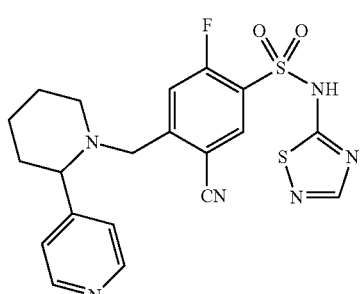
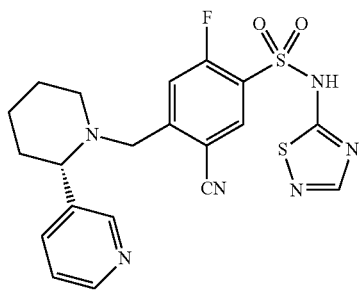
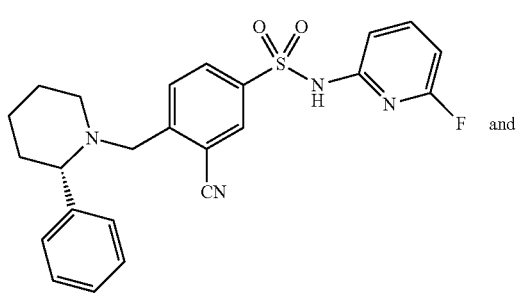
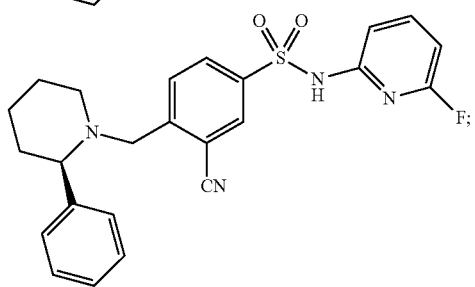
or a pharmaceutically acceptable salt thereof.
21. The compound of claim 2 selected from the group consisting of:

623
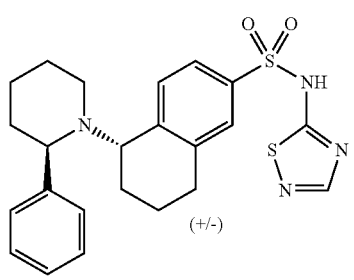
(+/-)
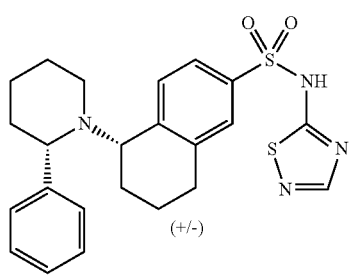
(+/-)
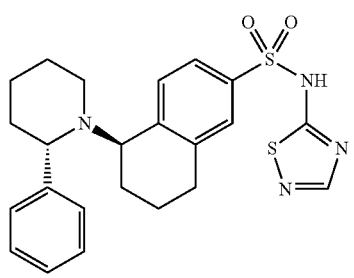
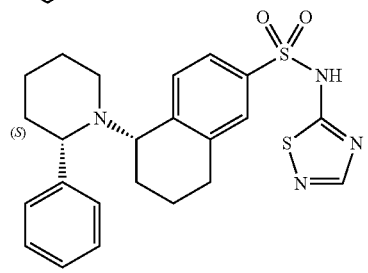
(S)
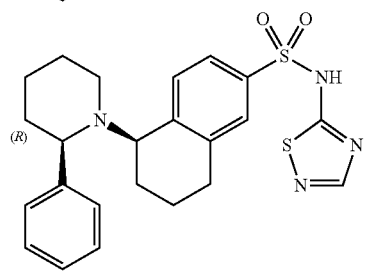
(R)
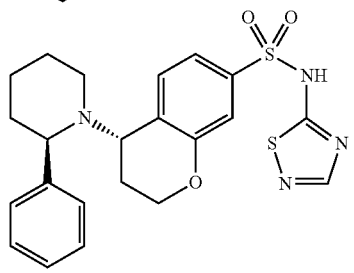
624
-continued
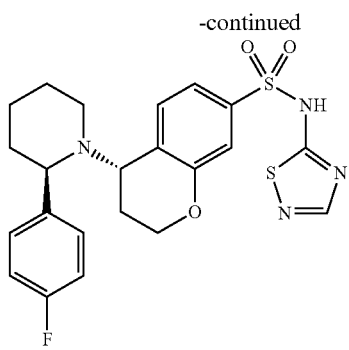
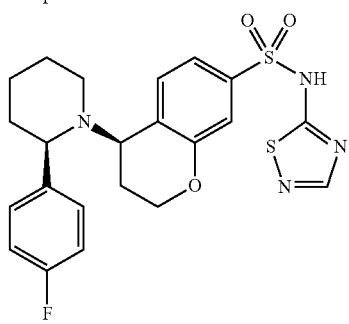
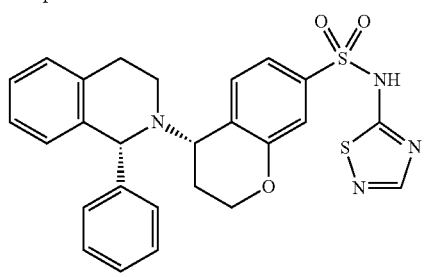
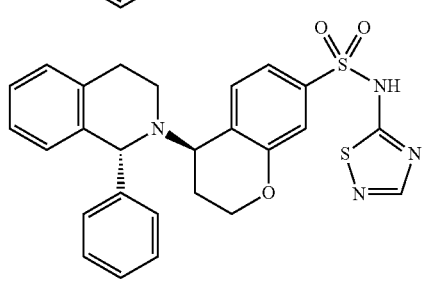
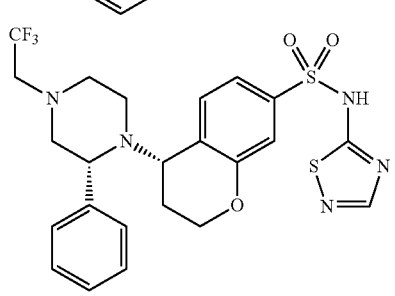
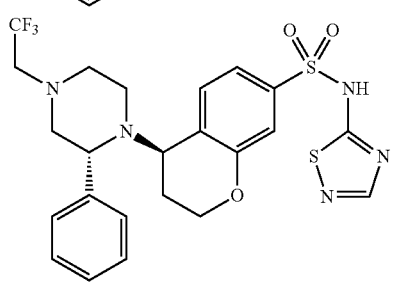

625
-continued
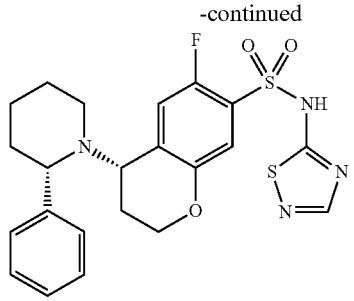
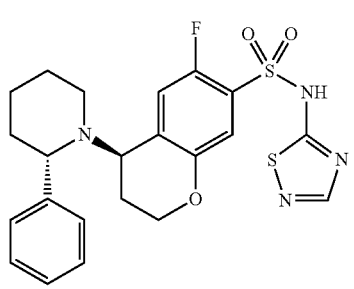
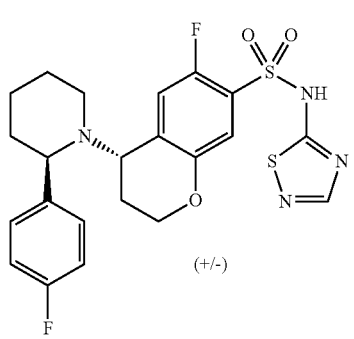
(+/−)
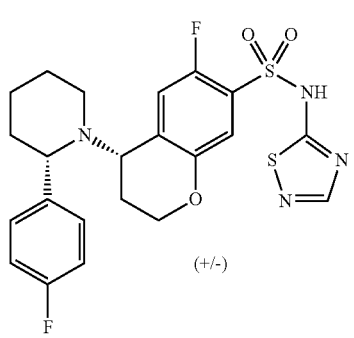
(+/−)
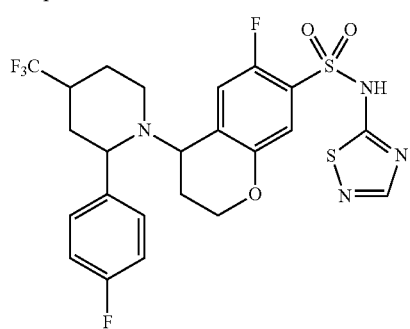
626
-continued
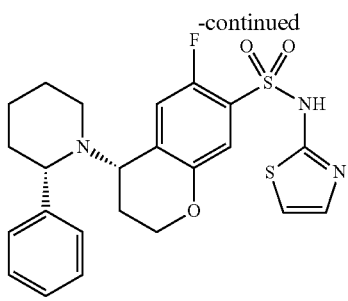
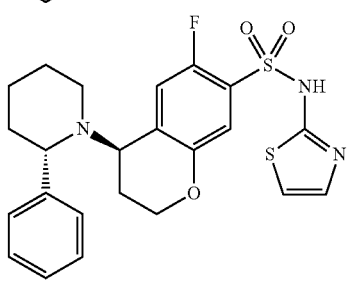
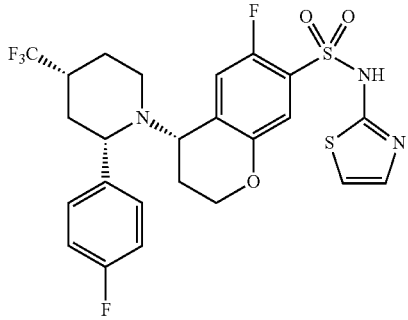
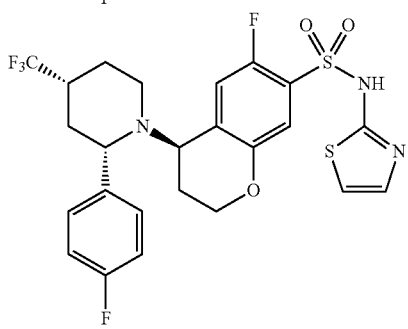
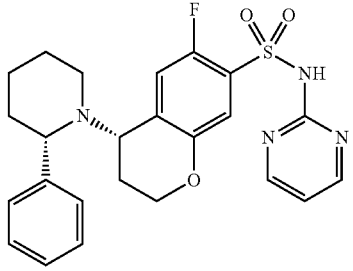
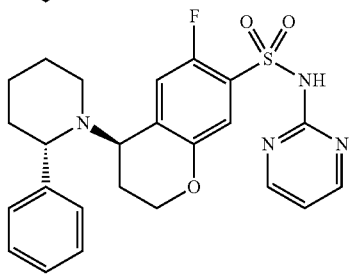

627
-continued
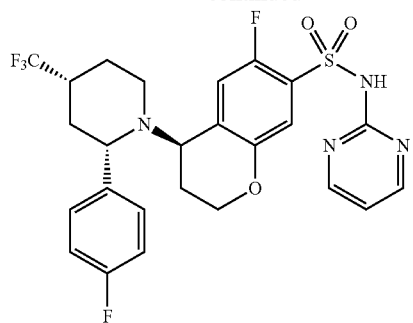
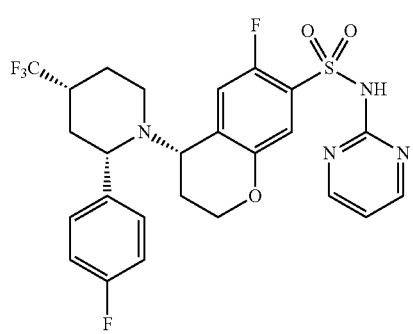
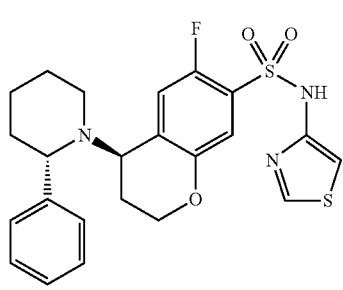
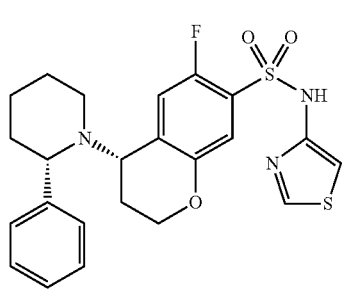
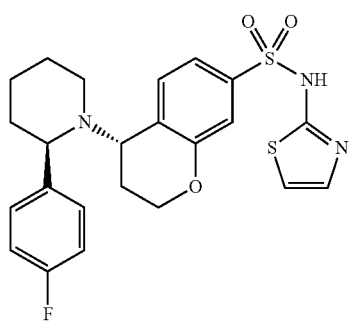
628
-continued
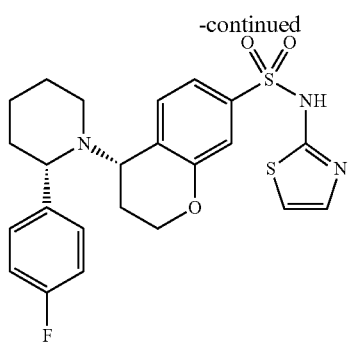
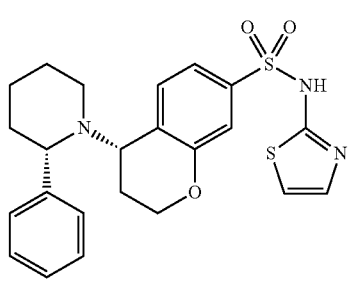
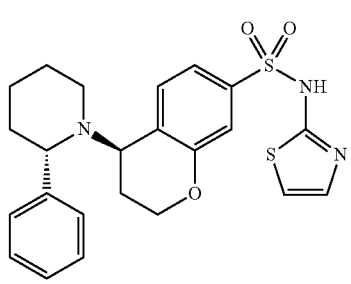
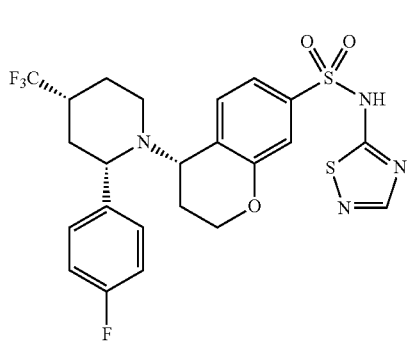
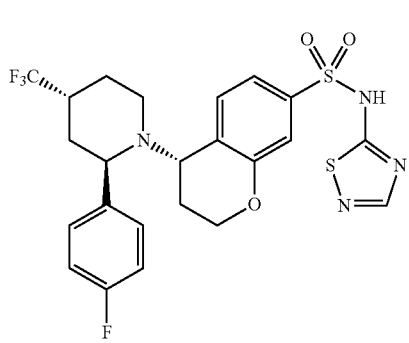

629
-continued
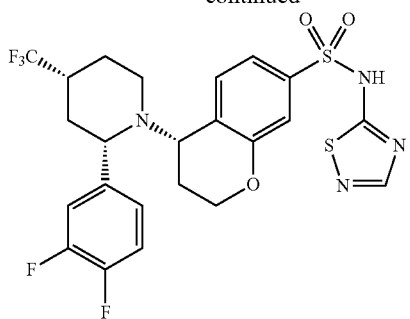
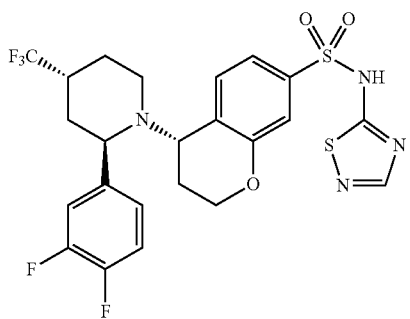
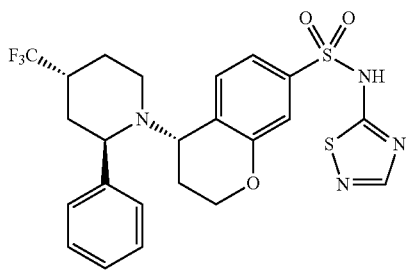
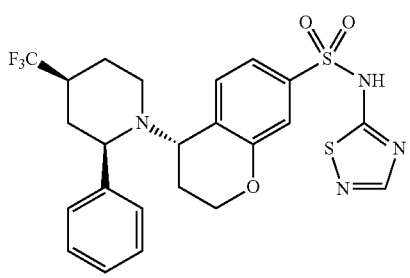
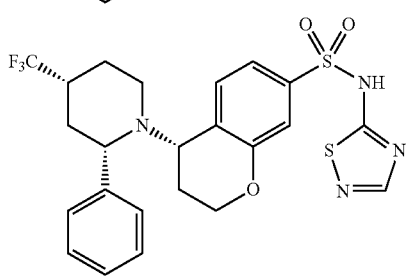
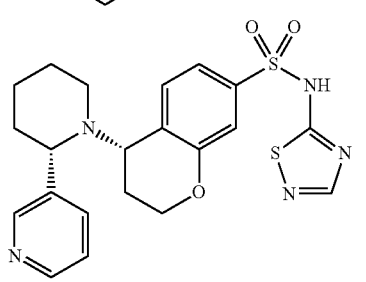
630
-continued
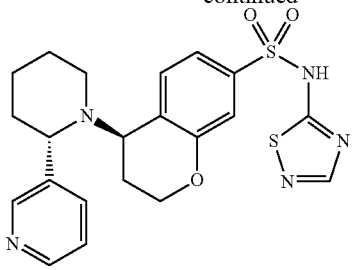
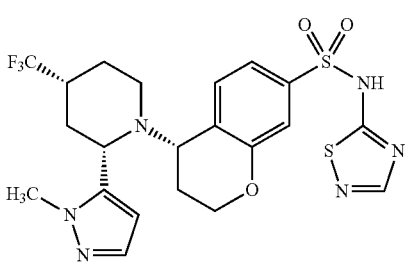
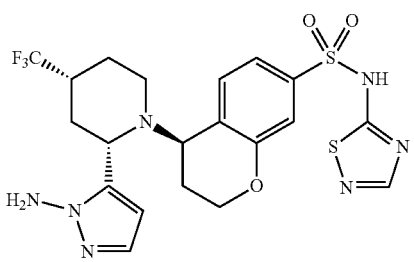
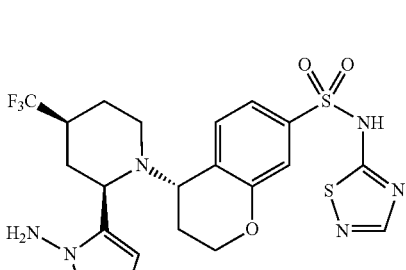
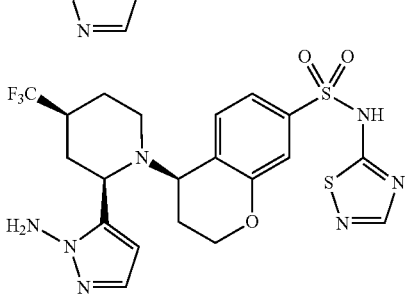
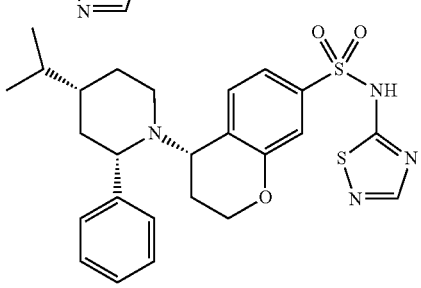

631
-continued
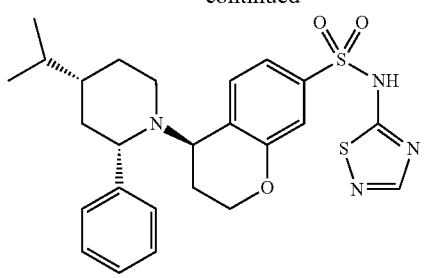
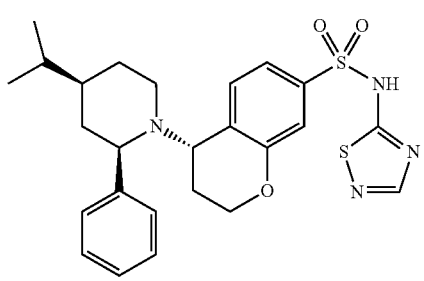
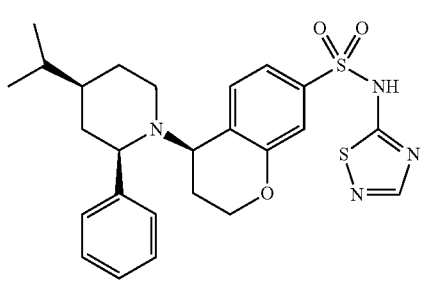
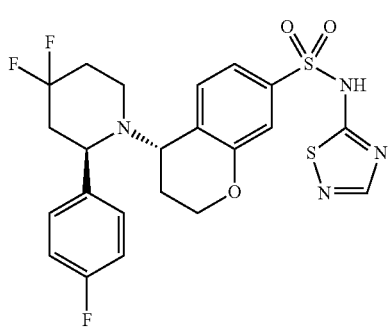
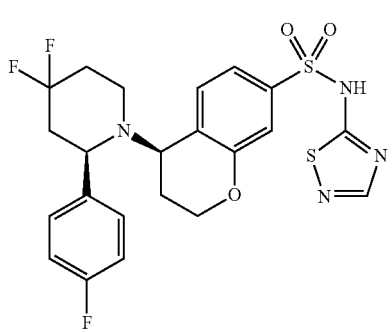
632
-continued
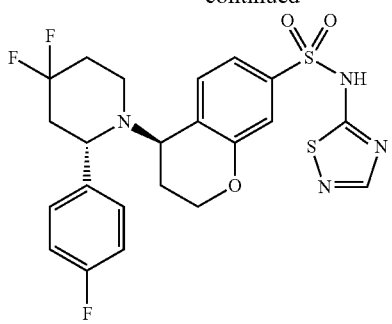
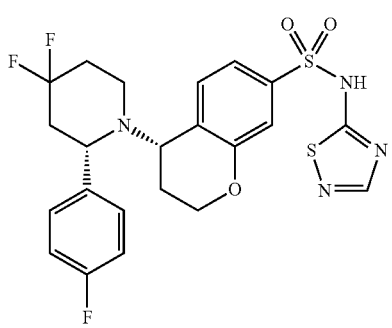
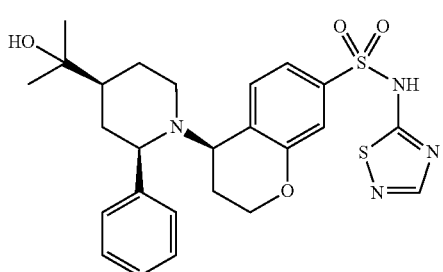
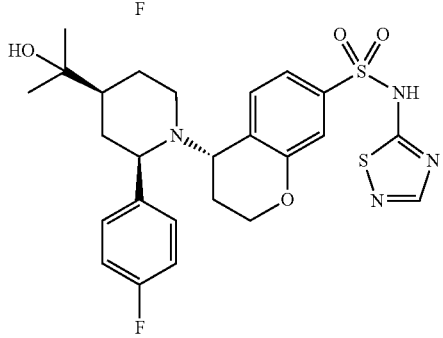
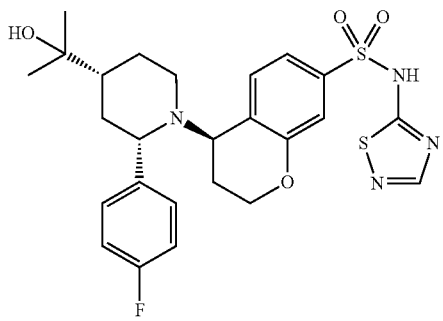

633
-continued
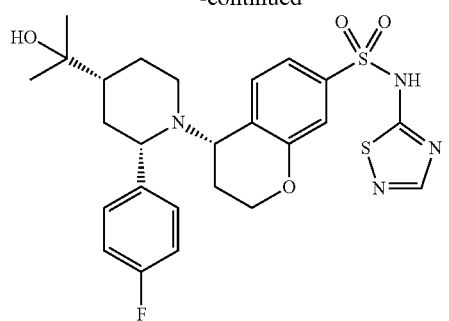
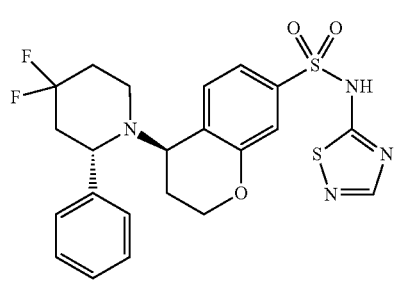
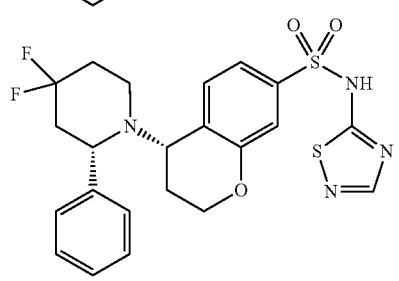
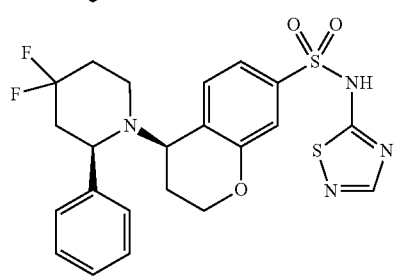
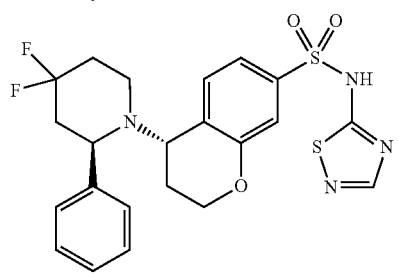
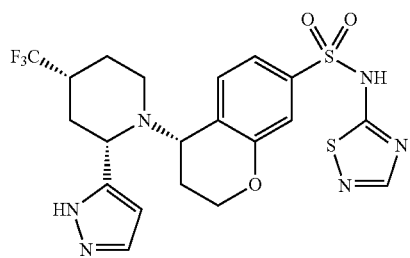
634
-continued
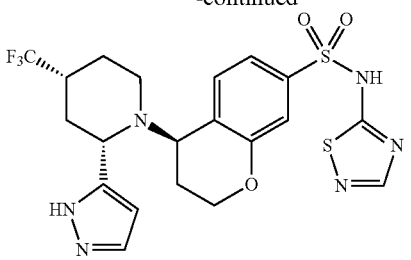
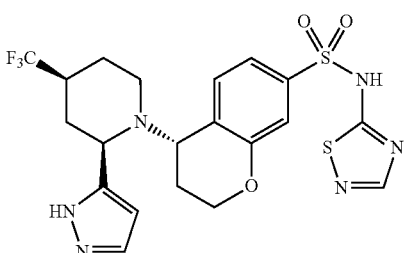
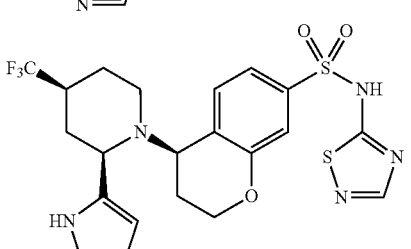
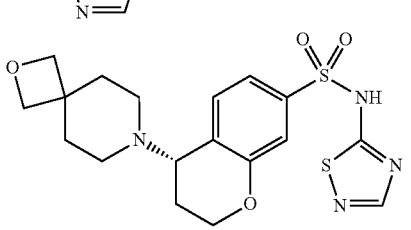
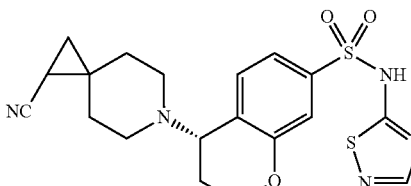
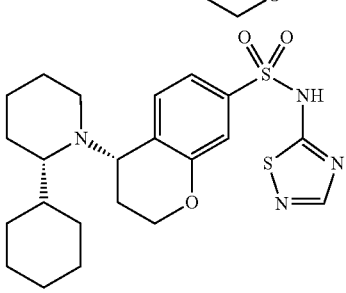
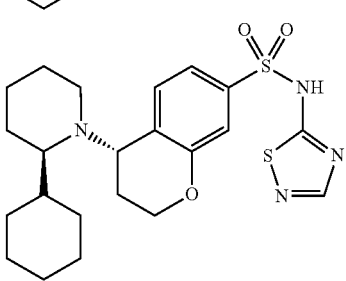

-continued
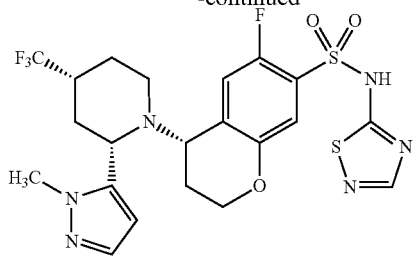
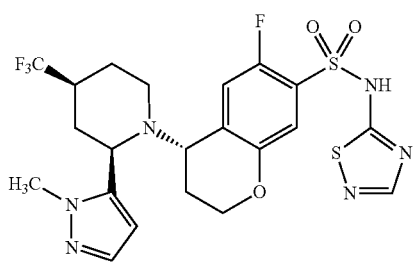
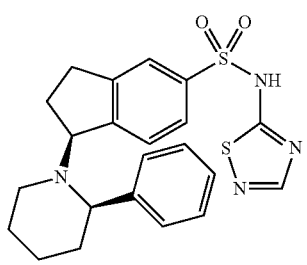
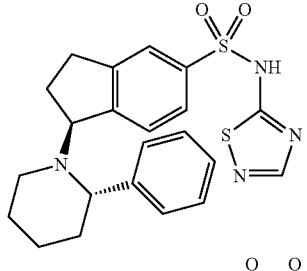
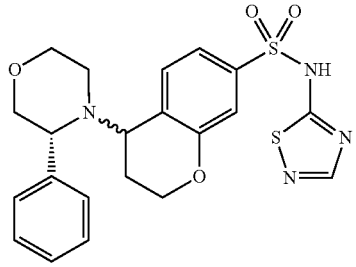
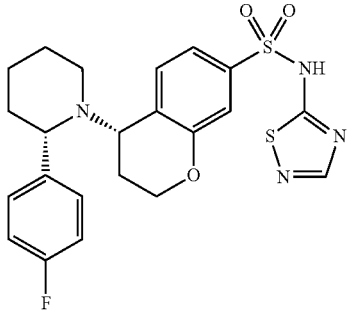
-continued
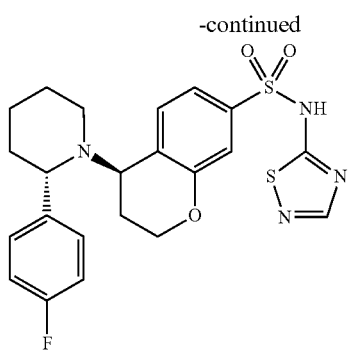
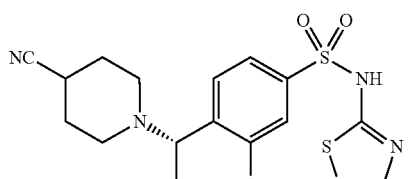
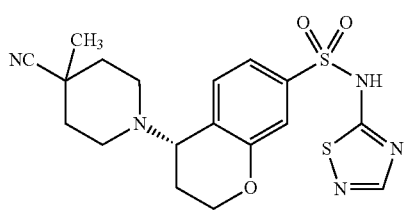
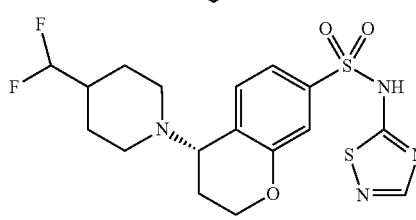
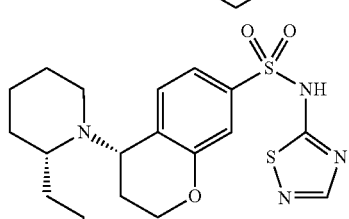
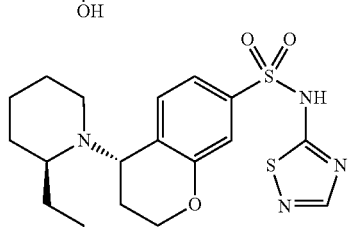
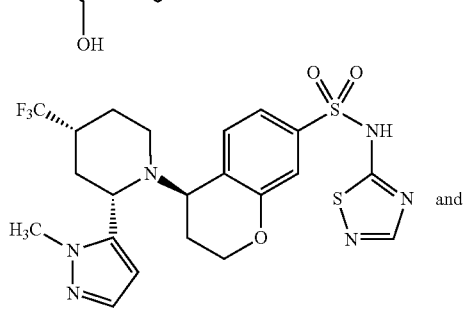
and -continued
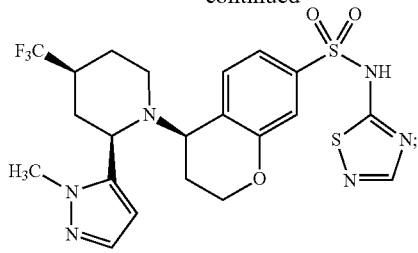
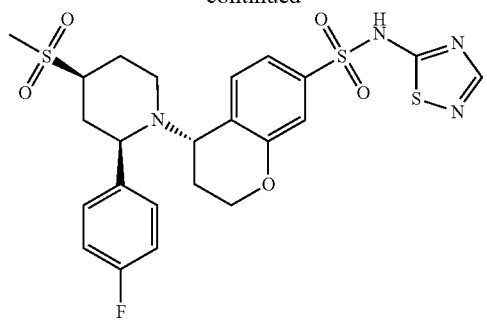
or a pharmaceutically acceptable salt thereof.
22. A compound selected from the group consisting of:
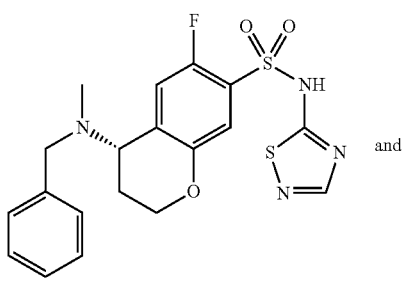
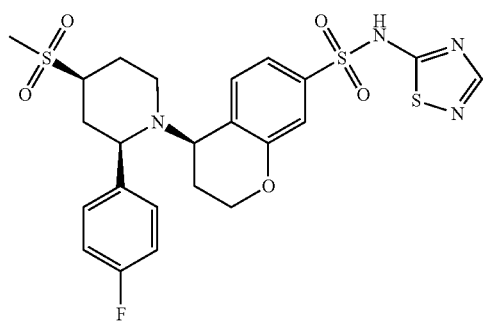
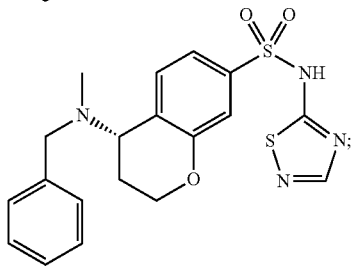
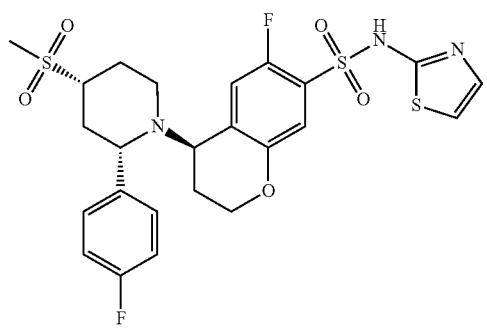
or a pharmaceutically acceptable salt thereof.
23. A compound of selected from the group consisting of:
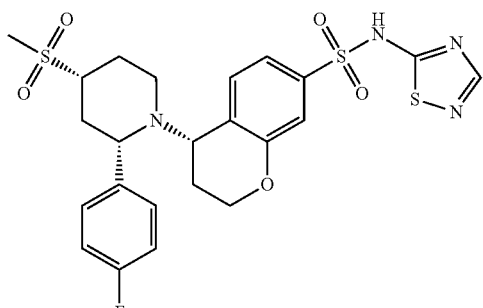
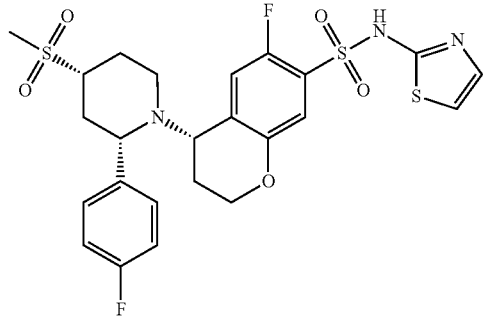
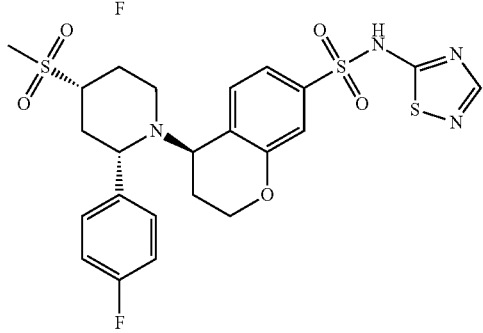
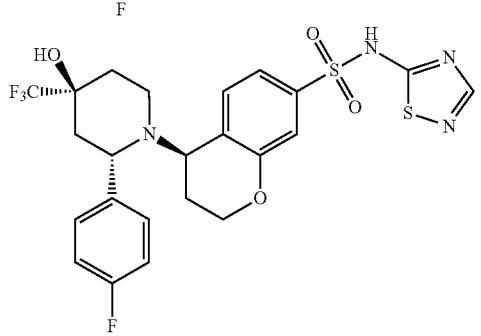

639
-continued
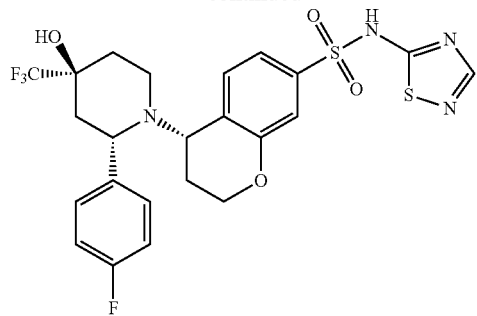
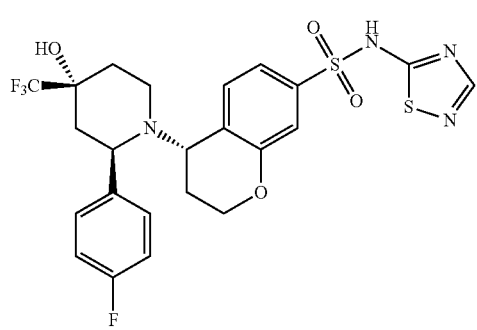
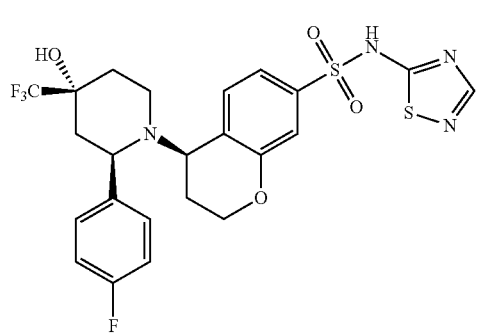
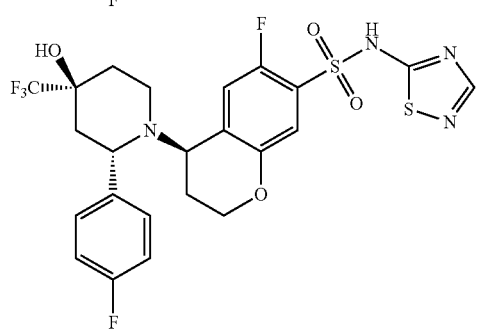
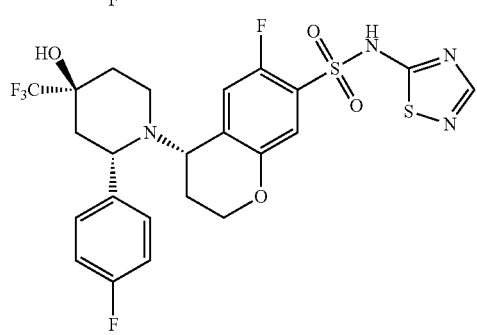
640
-continued
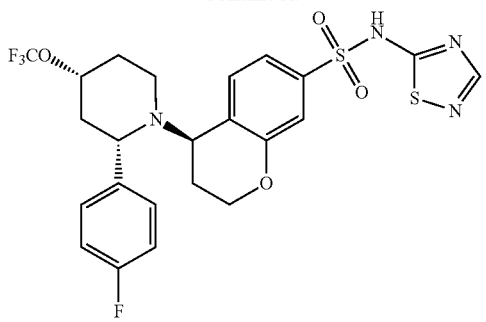
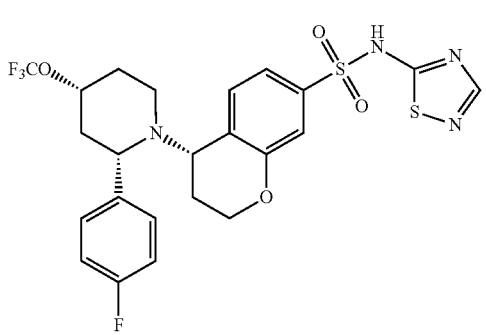
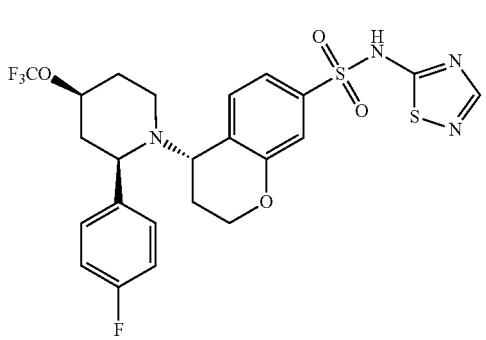
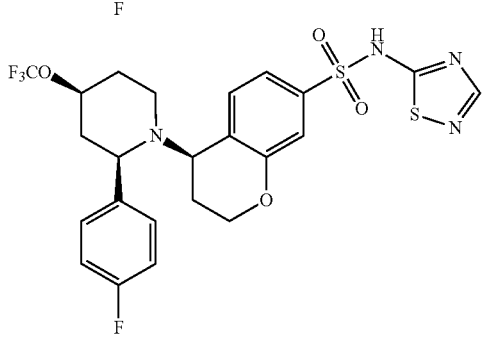
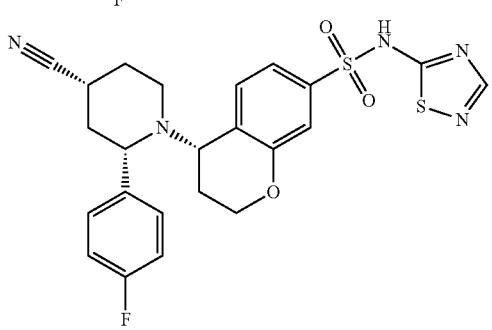

641
-continued
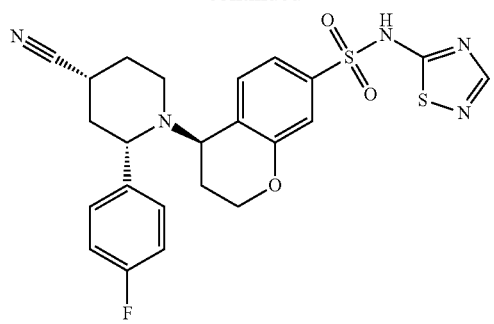
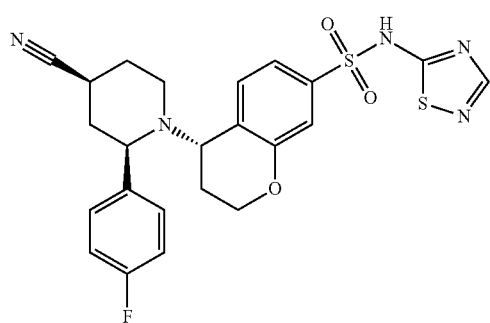
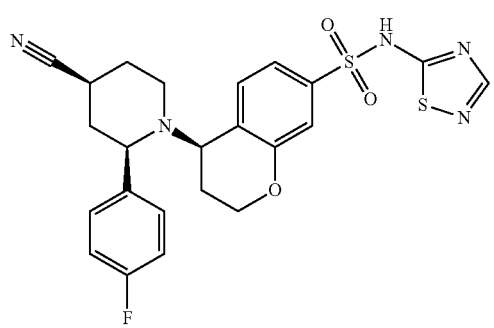
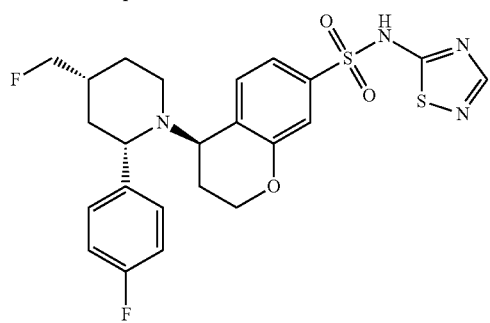
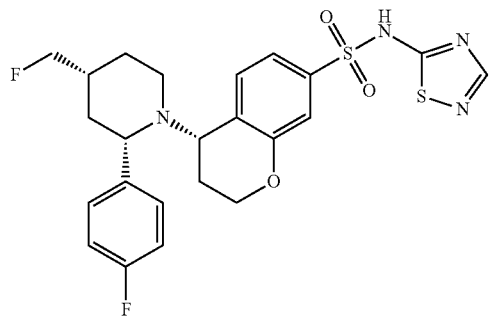
642
-continued
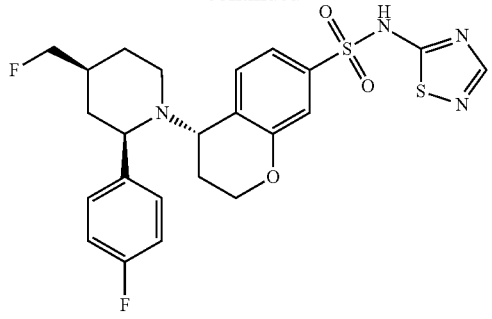
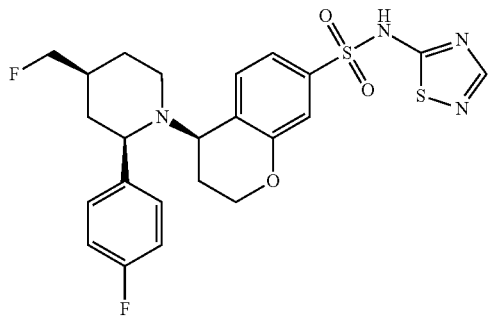
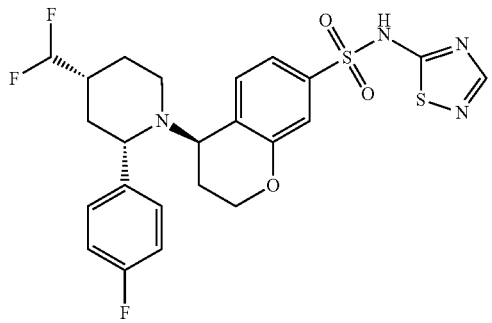
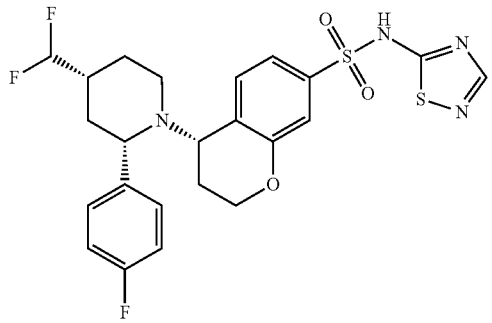
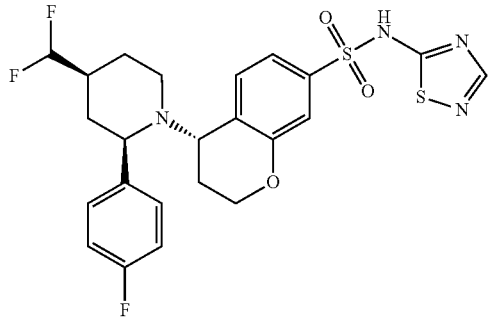

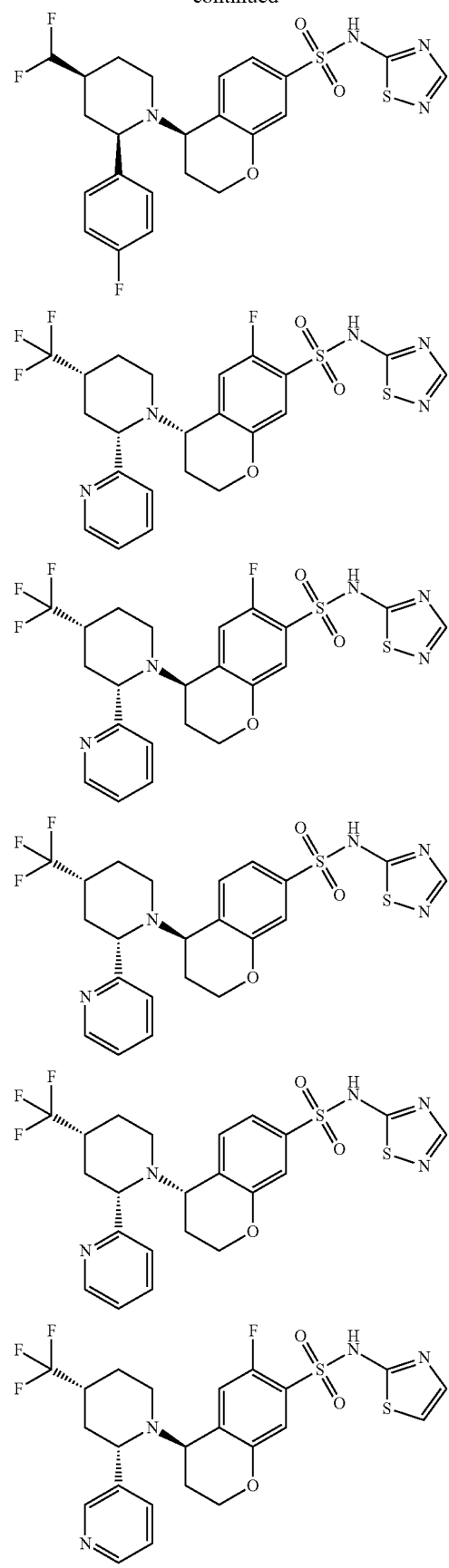
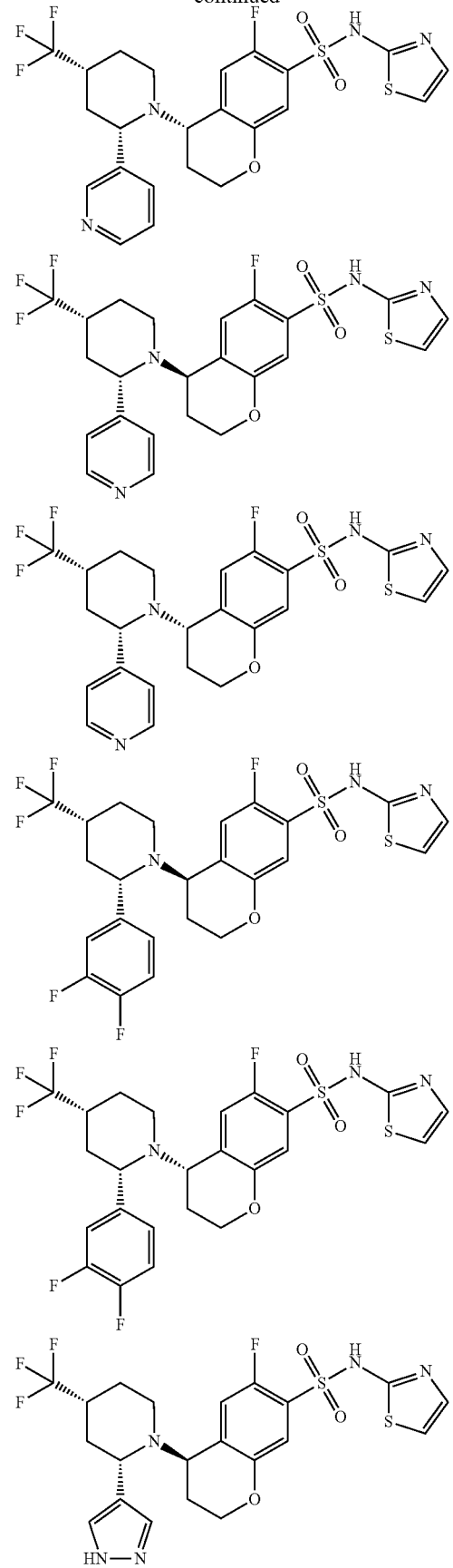

645
-continued
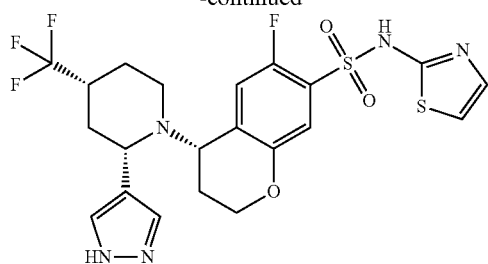
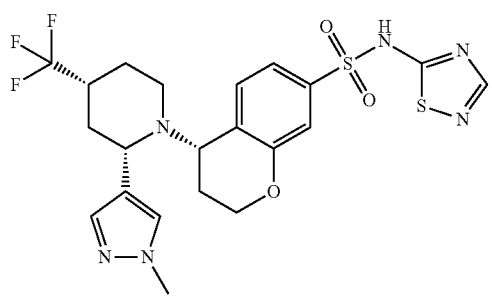
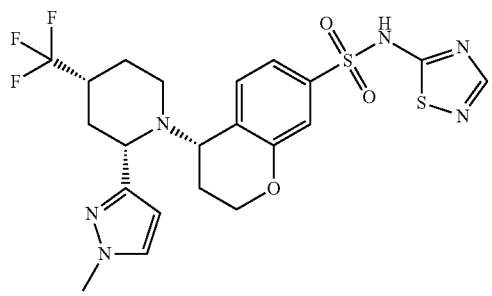
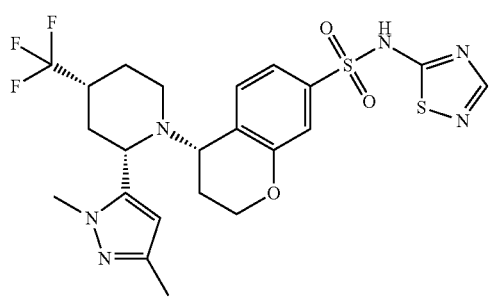
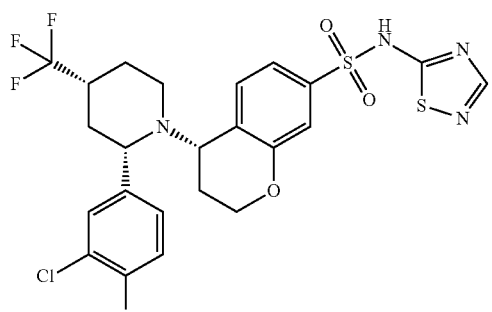
646
-continued
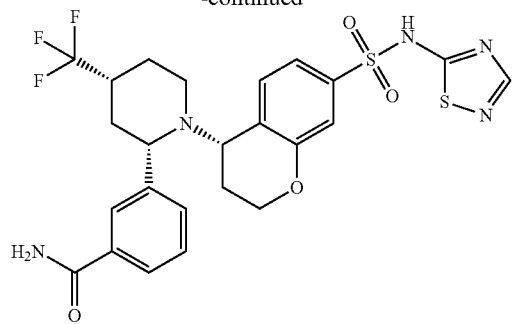
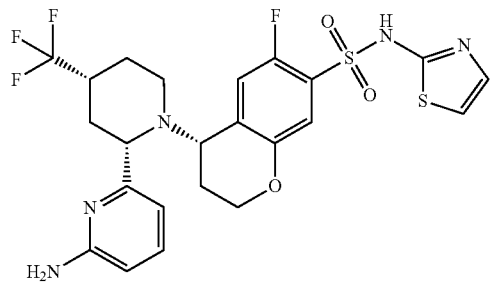
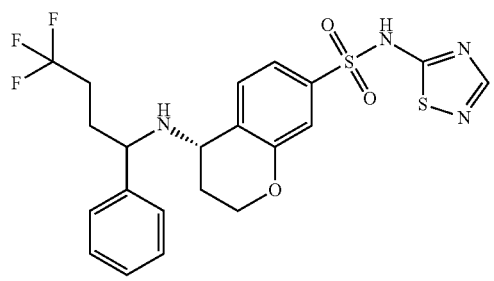
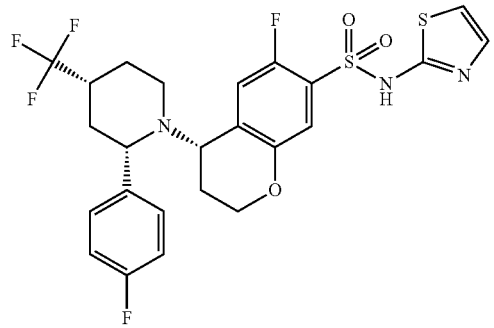
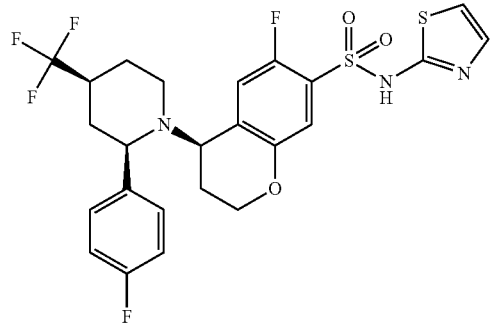

647
-continued
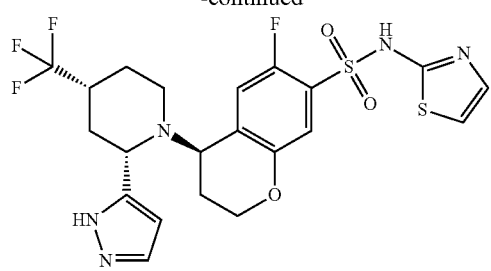
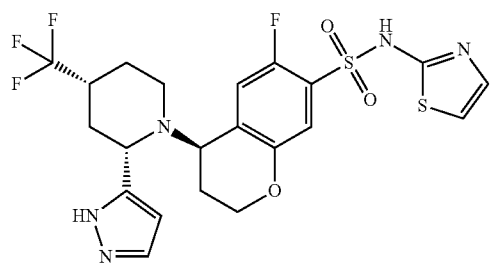
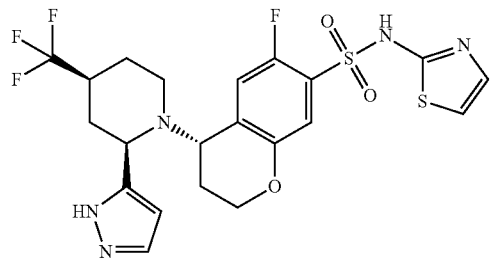
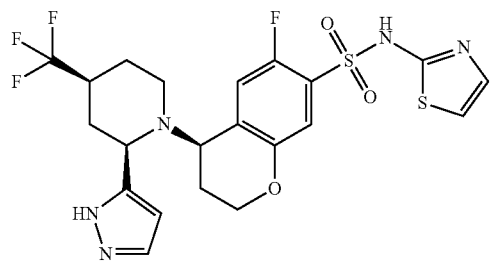
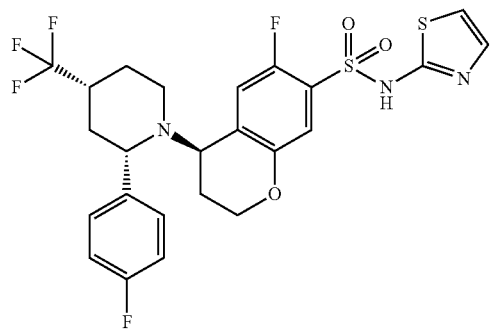
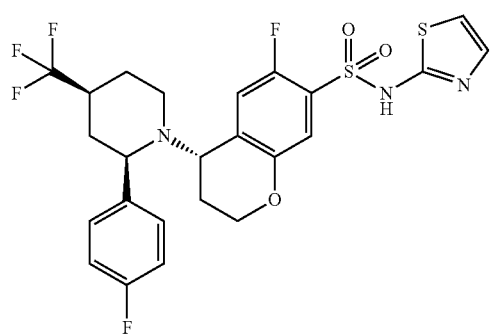
648
-continued
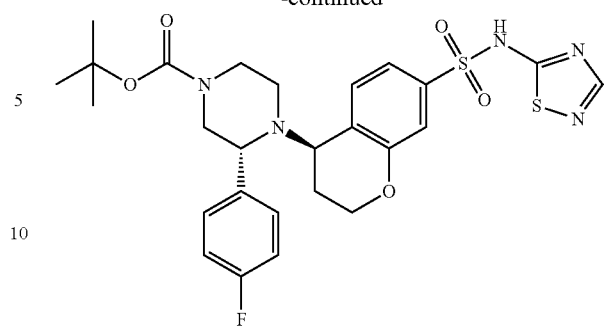
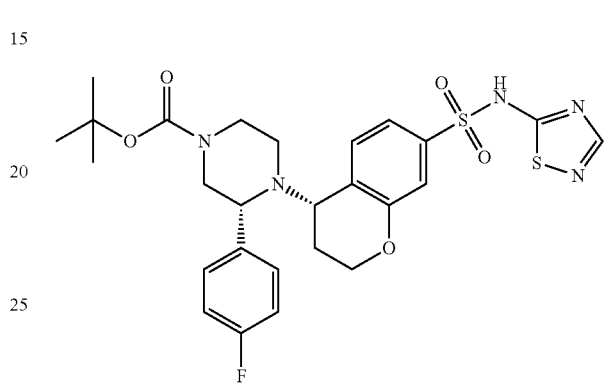
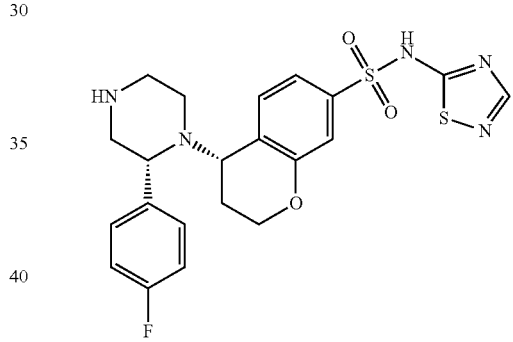
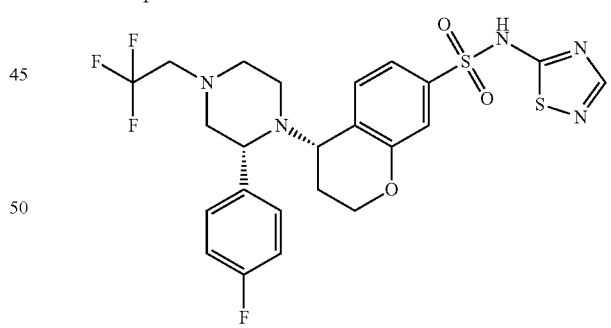
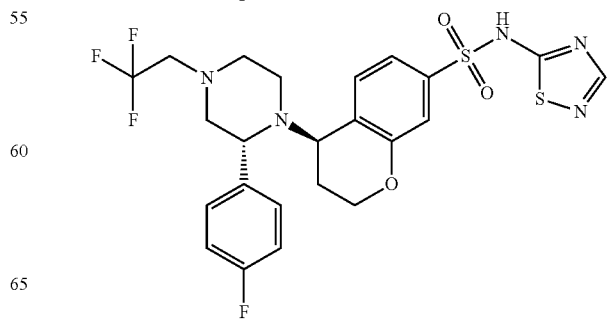

649
-continued
650
-continued
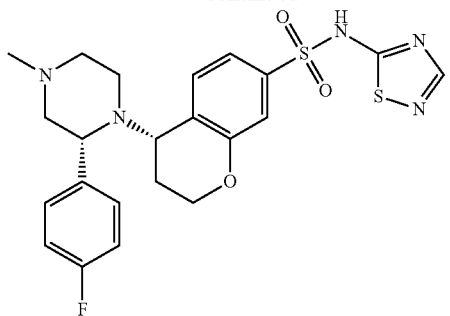
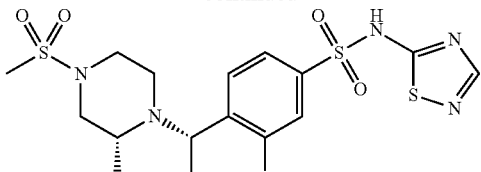
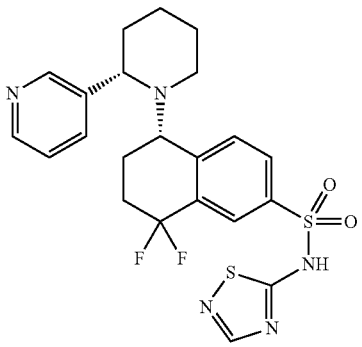
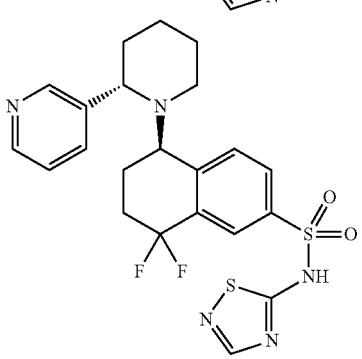
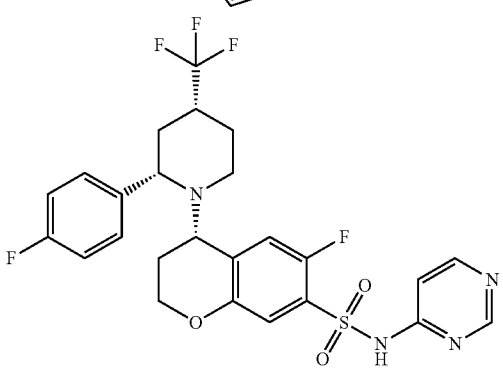
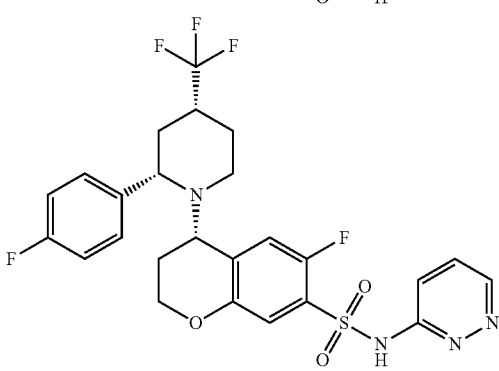

651
-continued
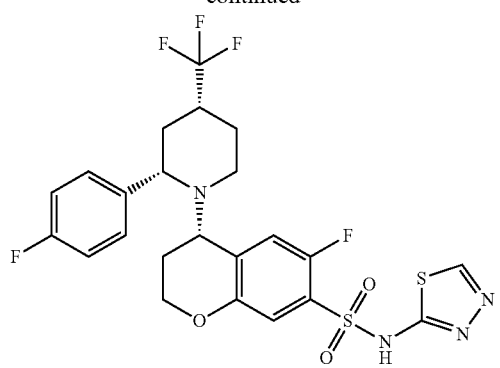
or a pharmaceutically acceptable salt thereof.
24. The compound of claim 2 selected from the group consisting of:
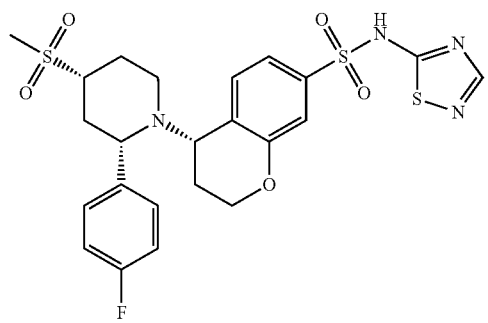
652
-continued
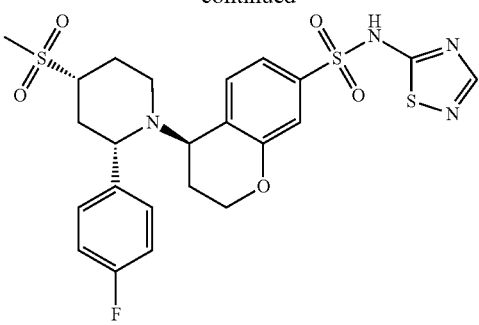

653
-continued
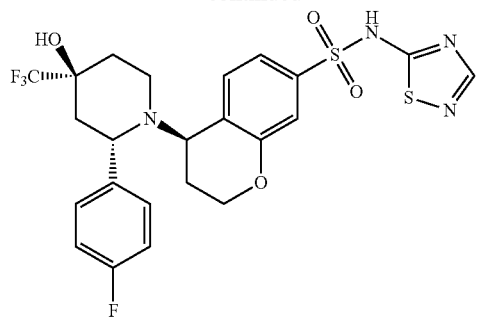
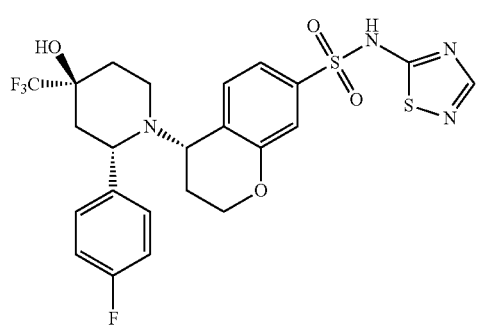
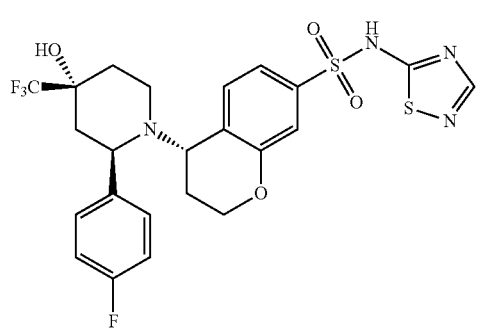
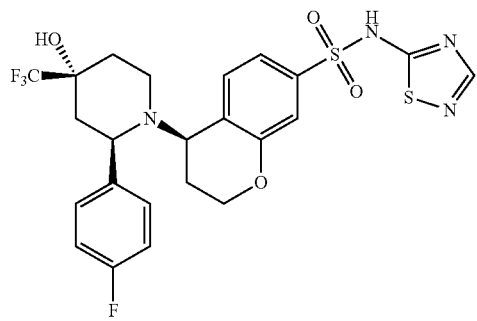
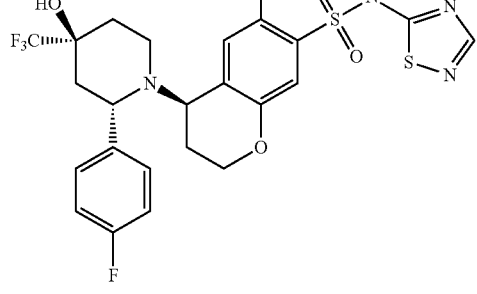
654
-continued
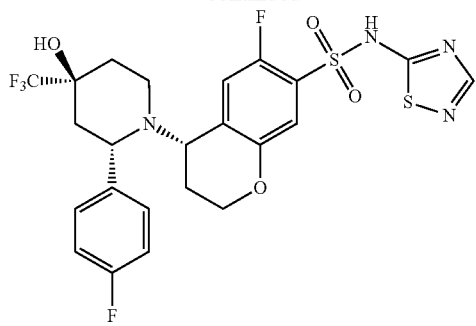
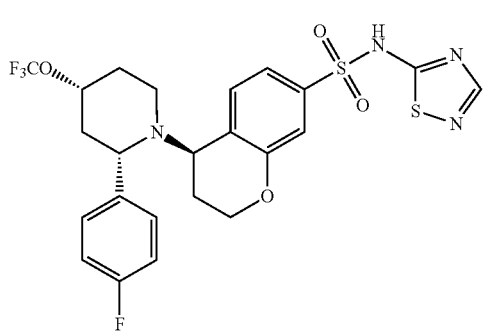
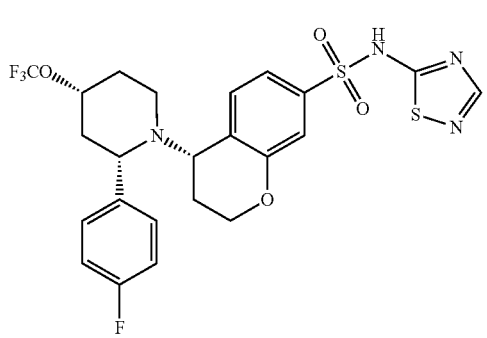
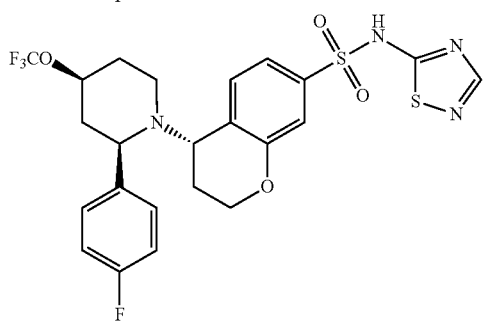
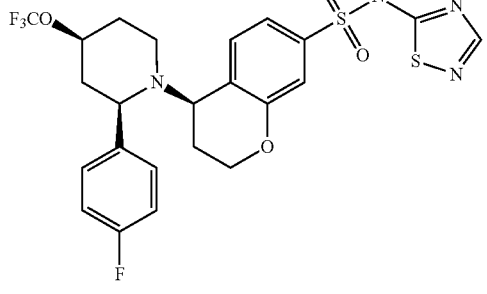

-continued
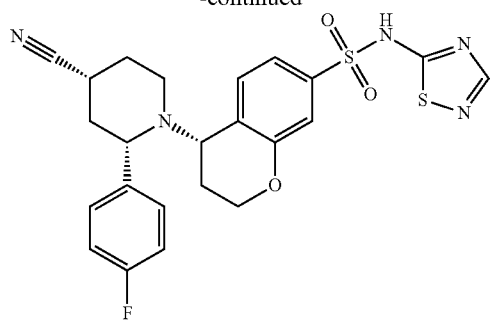
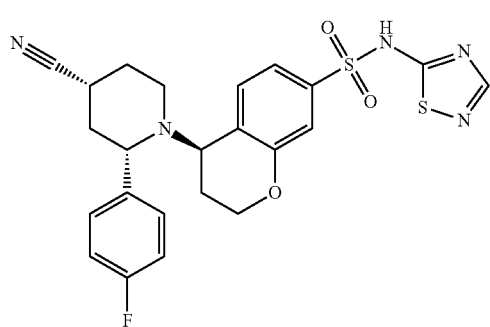
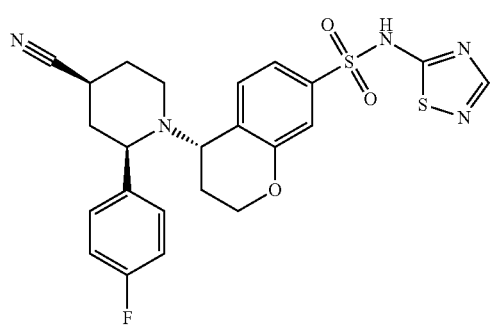
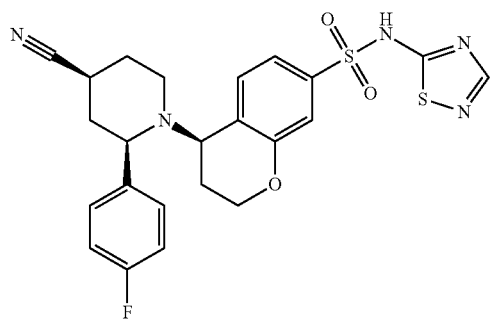
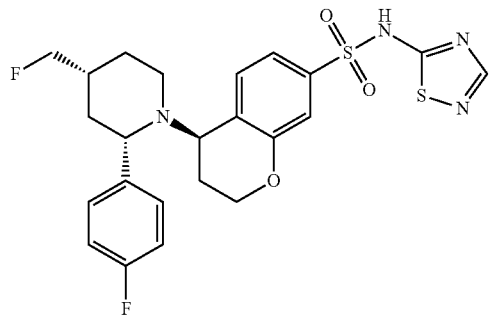
-continued
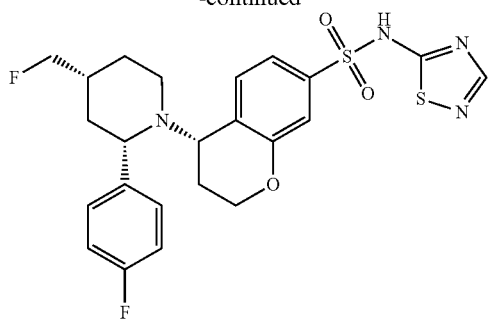
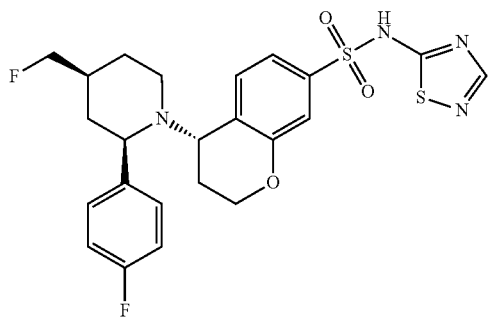
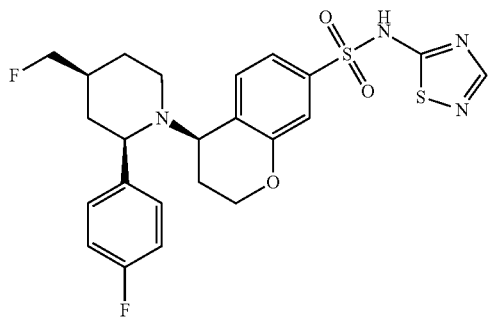
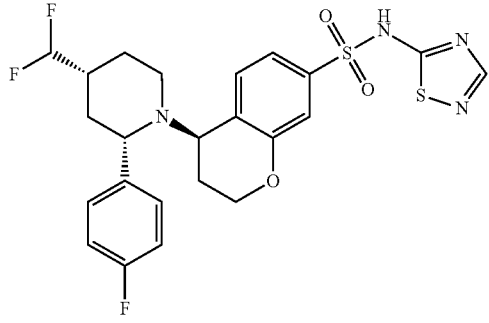
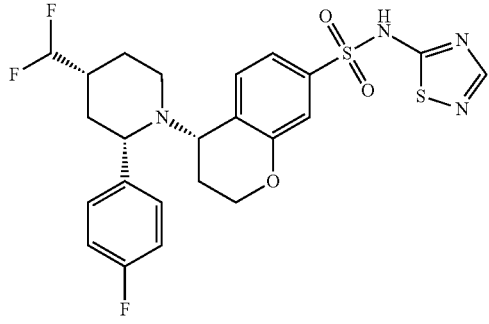

657
-continued
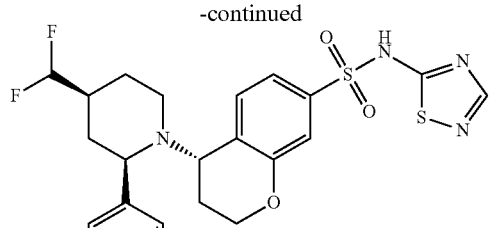
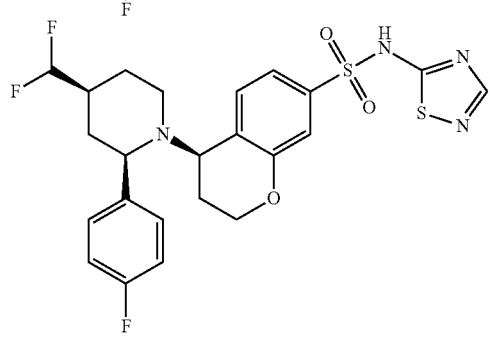
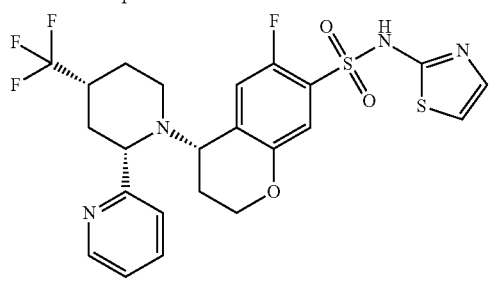
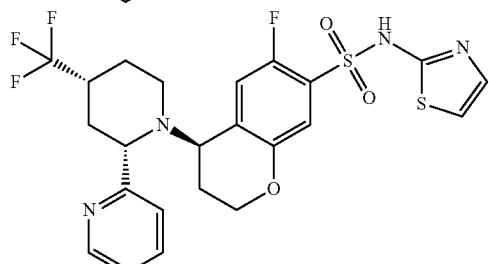
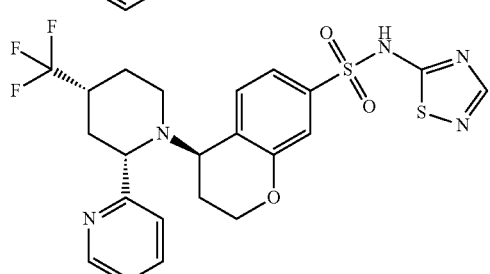
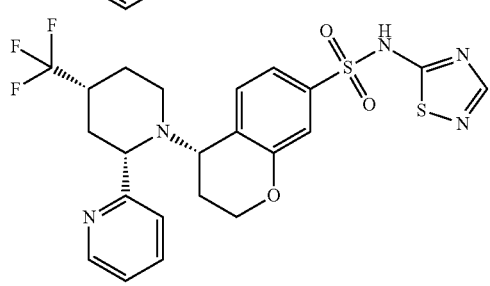
658
-continued
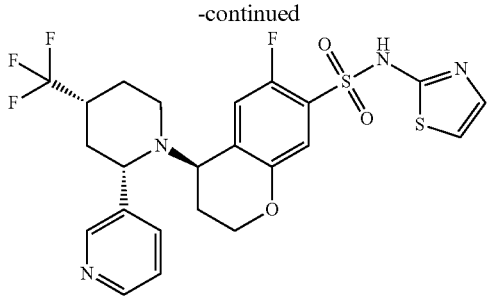
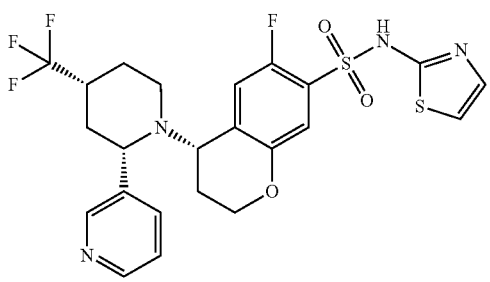
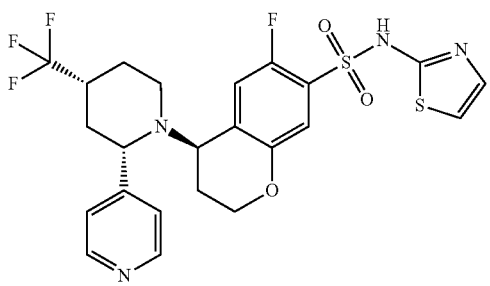
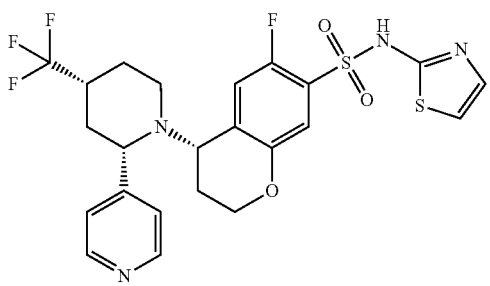
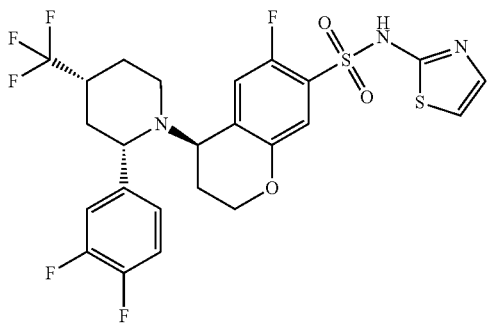

659
-continued
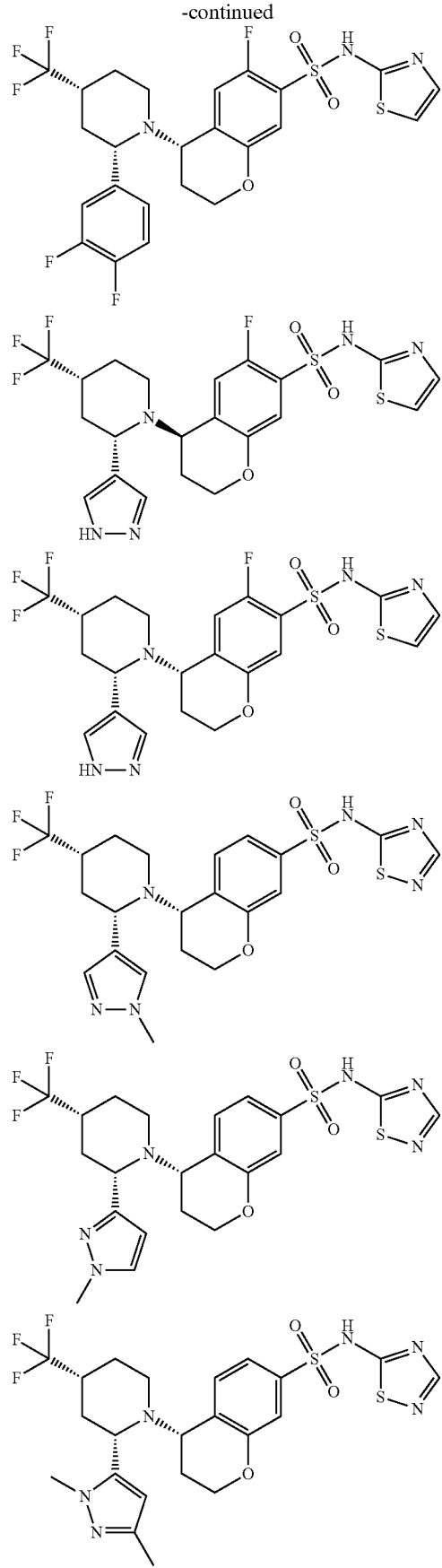
660
-continued
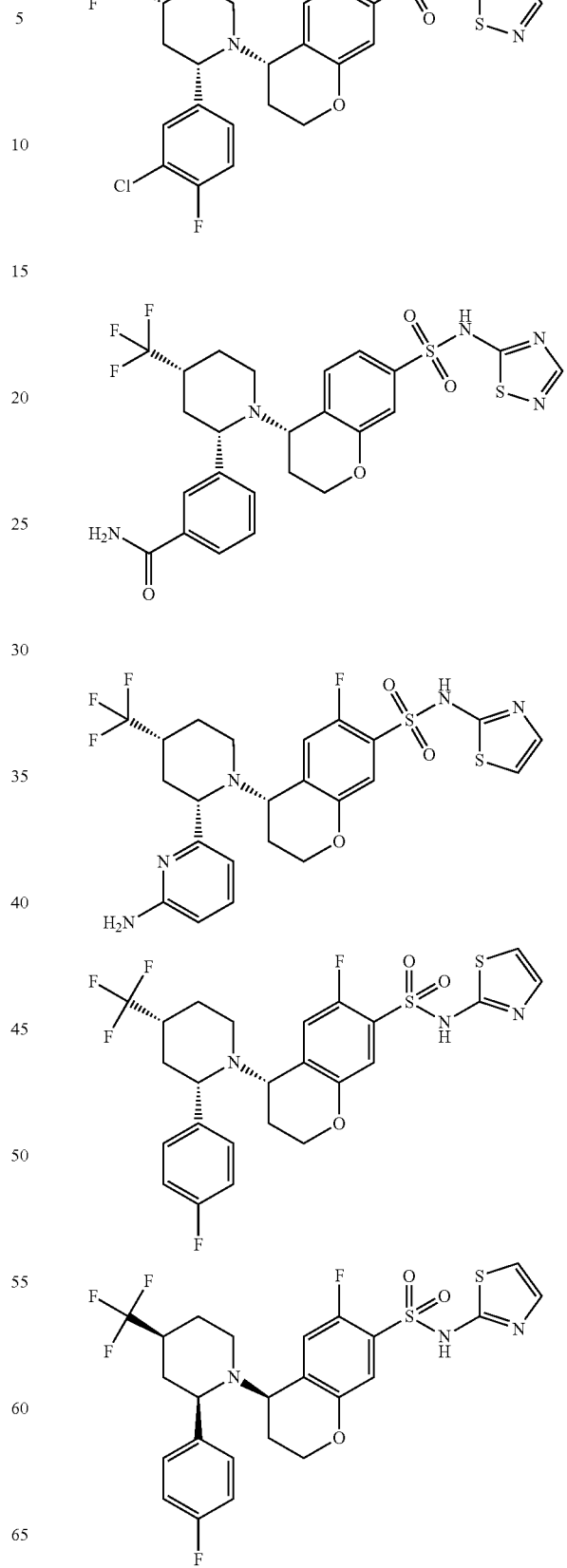

661
-continued
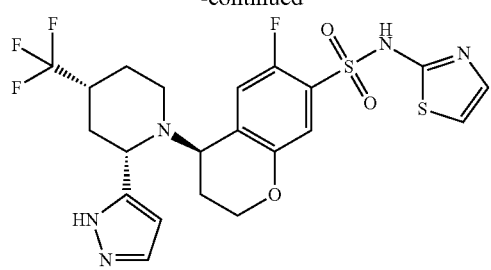
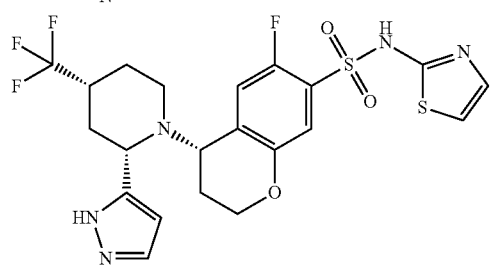
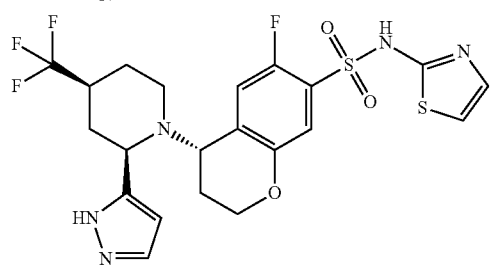
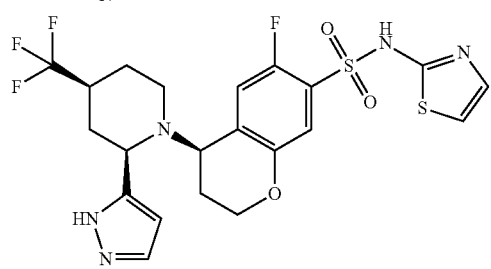
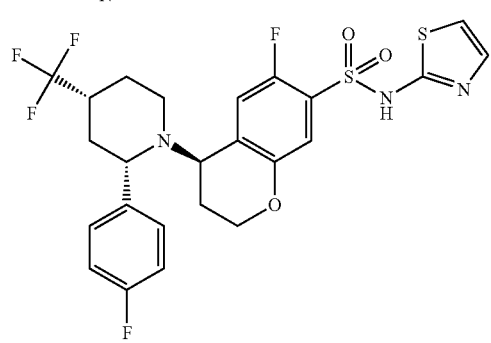
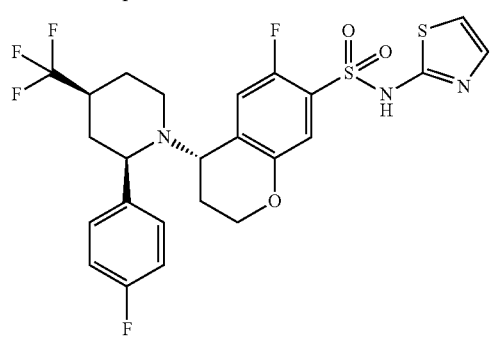
662
-continued
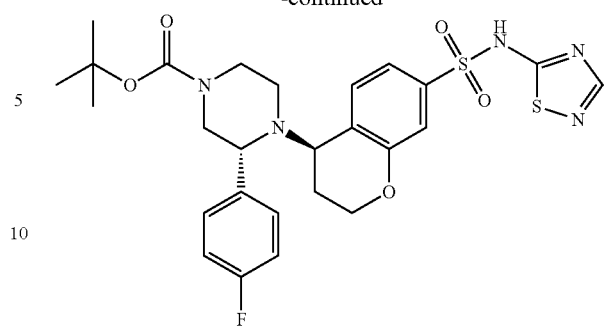
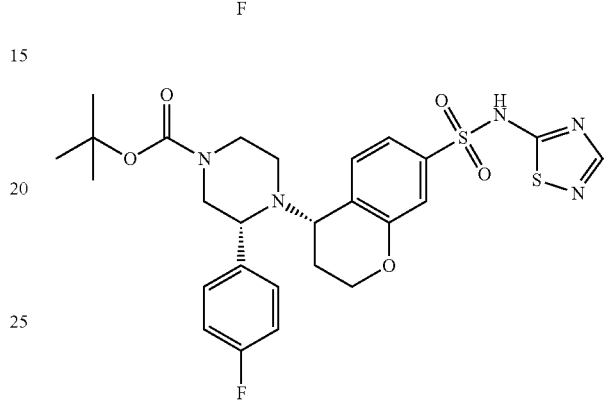
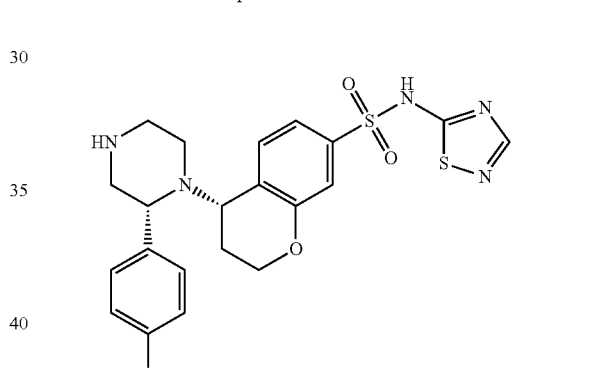
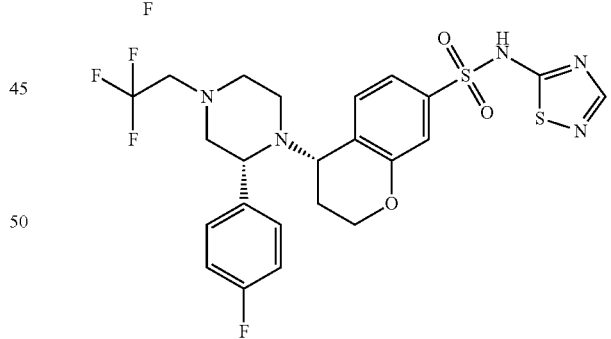
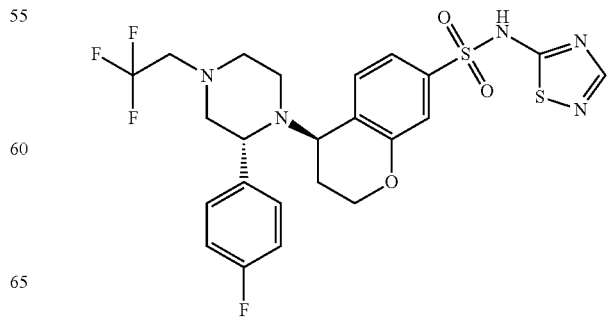

663
-continued
664
-continued
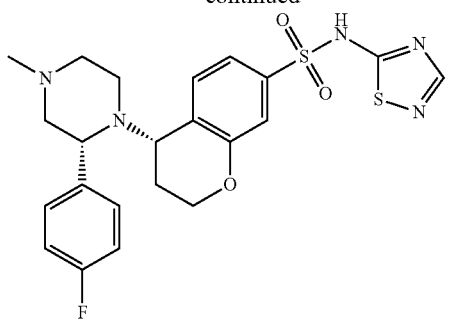
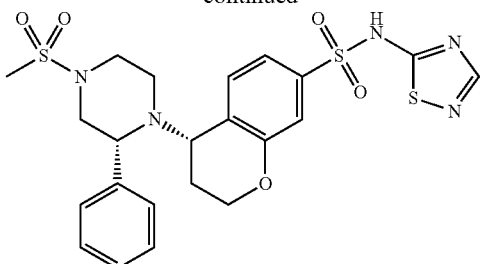
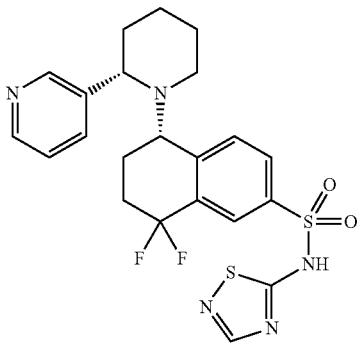
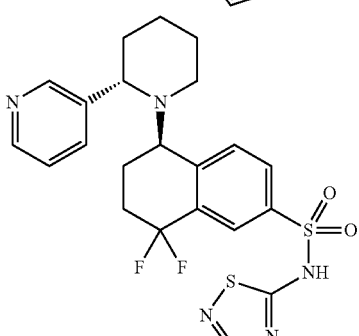
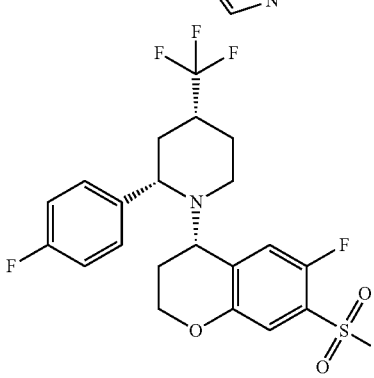
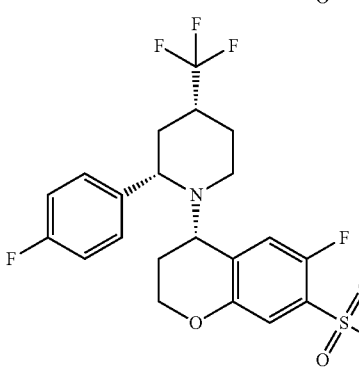

665
-continued
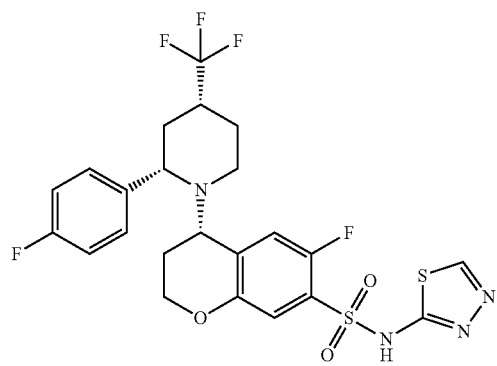
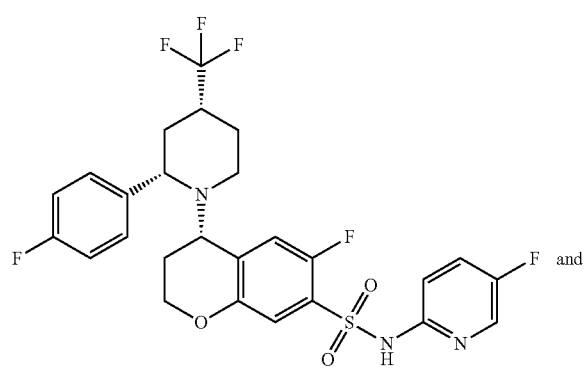
666
-continued
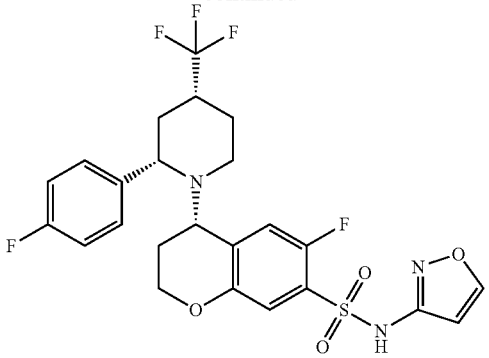
or a pharmaceutically acceptable salt thereof.
25. A compound having formula:
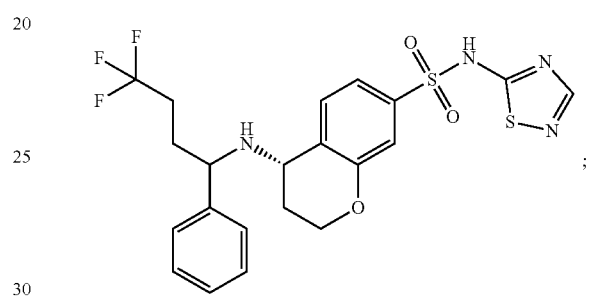
or a pharmaceutically acceptable salt thereof.
26. A pharmaceutical composition comprising a compound of claim 2, or a pharmaceutically acceptable salt thereof, and a pharmaceutically acceptable excipient.
* * * * *

UNITED STATES PATENT AND TRADEMARK OFFICE
CERTIFICATE OF CORRECTION

PATENT NO. : 10,787,446 B2  
APPLICATION NO. : 15/939112  
DATED : September 29, 2020  
INVENTOR(S) : Philippe Bergeron et al.

Page 1 of 5

It is certified that error appears in the above-identified patent and that said Letters Patent is hereby corrected as shown below:

In the Claims

Column 578, Lines 50-69, Claim 10, please delete " 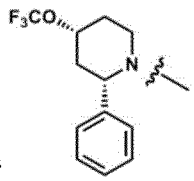 " and insert -- 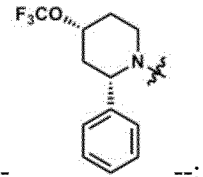 --;

Column 579, Lines 1-9, Claim 10, please delete " 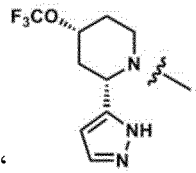 " and insert -- 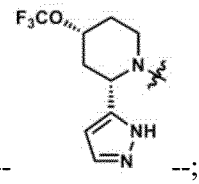 --;

Column 609, Lines 13-24, Claim 19, please delete " 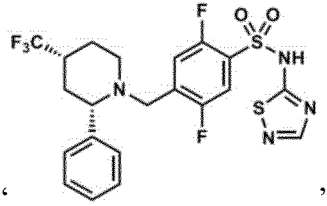 " and insert -- 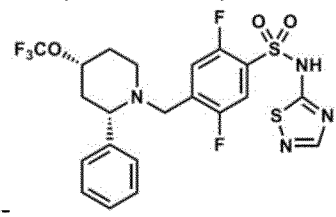 --;

Signed and Sealed this  
Ninth Day of February, 2021

Drew Hirshfeld  
*Performing the Functions and Duties of the  
Under Secretary of Commerce for Intellectual Property and  
Director of the United States Patent and Trademark Office*

Column 609, Lines 24-35, Claim 19, please delete " 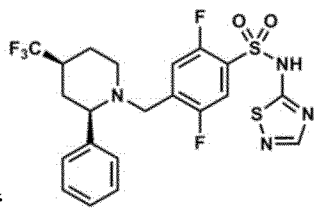 " and insert -- 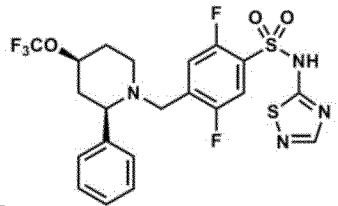 --;
Column 619, Lines 4-13, Claim 20, please delete " 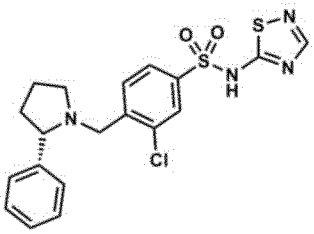 " and insert -- 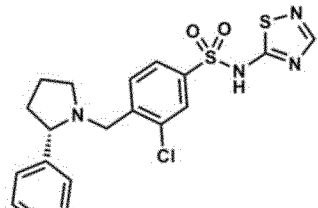 --;
Column 619, Lines 14-24, Claim 20, please delete " 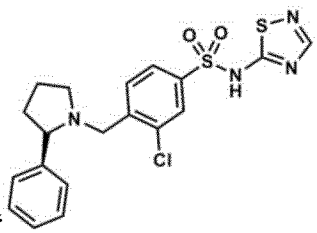 " and insert -- 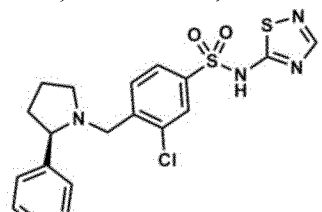 --;

CERTIFICATE OF CORRECTION (continued)
U.S. Pat. No. 10,787,446 B2

Column 622, Lines 1-12, Claim 20, please delete " 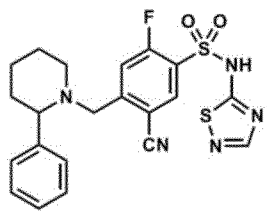 " and insert -- 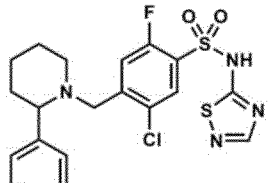 --;

Column 622, Lines 15-25, Claim 20, please delete " 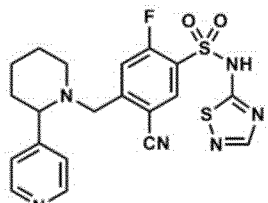 " and insert -- 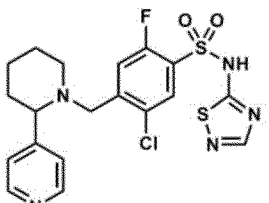 --;

Column 622, Lines 28-39, Claim 20, please delete " 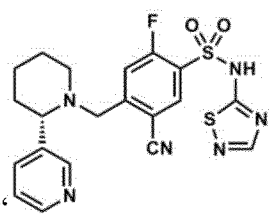 " and insert -- 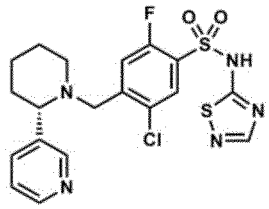 --;

Column 622, Lines 41-51, Claim 20, please delete " 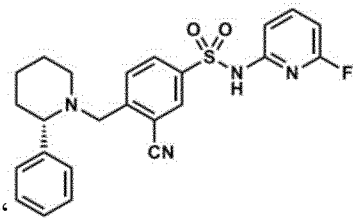 " and

CERTIFICATE OF CORRECTION (continued)
U.S. Pat. No. 10,787,446 B2 insert -- 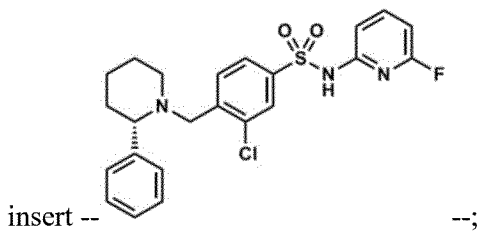 --;

Column 622, Lines 52-62, Claim 20, please delete " 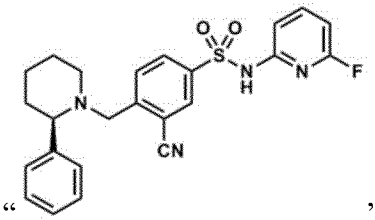 " and insert -- 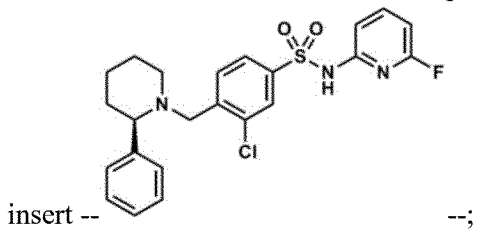 --;

Column 636, Lines 56-66, Claim 21, please delete " 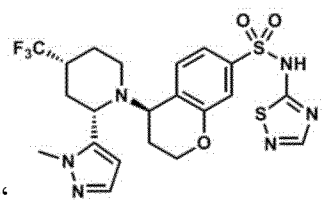 " and insert -- 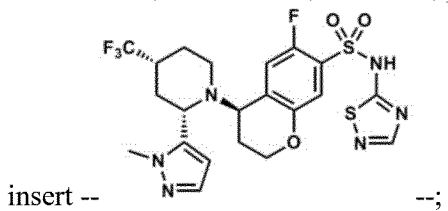 --;

Column 637, Lines 1-10, Claim 21, please delete " 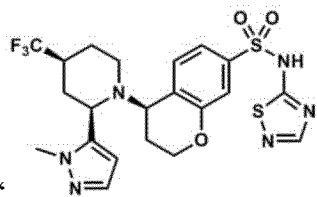 " and insert -- 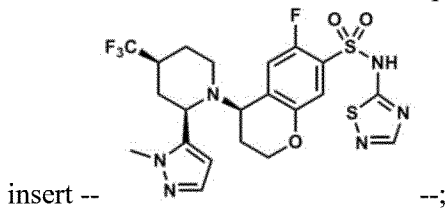 --;

CERTIFICATE OF CORRECTION (continued)
U.S. Pat. No. 10,787,446 B2

Column 643, Lines 13-23, Claim 23, please delete " 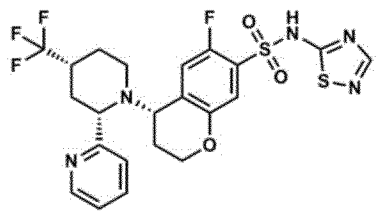 " and insert -- 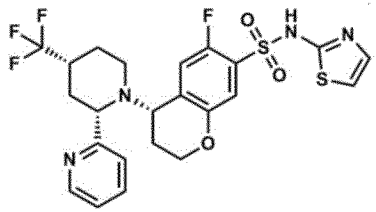 --;

Column 643, Lines 24-34, Claim 23, please delete " 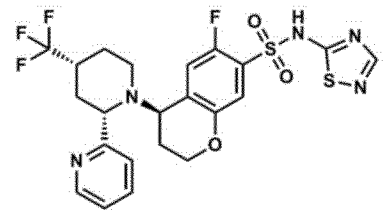 " and insert -- 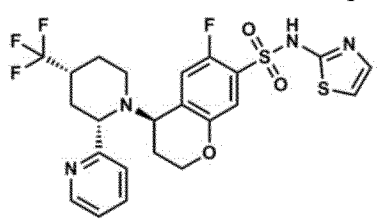 --;

Column 647, Lines 11-21, Claim 23, please delete " 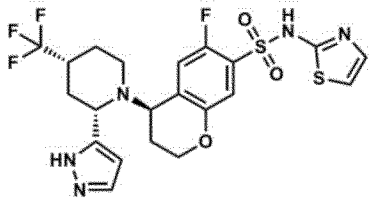 " and insert -- 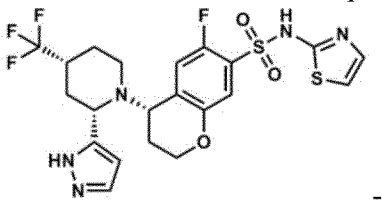 -- therefor.